US011426397B2

(12) United States Patent
Green et al.

(10) Patent No.: US 11,426,397 B2
(45) Date of Patent: Aug. 30, 2022

(54) PIPERIDINYL- AND PIPERAZINYL-SUBSTITUTED HETEROAROMATIC CARBOXAMIDES AS MODULATORS OF GPR6

(71) Applicant: TAKEDA PHARMACEUTICAL COMPANY LIMITED, Osaka (JP)

(72) Inventors: Jason Green, San Diego, CA (US); Maria Hopkins, San Diego, CA (US); Benjamin Jones, San Diego, CA (US); Andre A. Kiryanov, San Diego, CA (US); Jon Kuehler, San Diego, CA (US); Holger Monenschein, San Diego, CA (US); Sean Murphy, San Diego, CA (US); Thomas Nixey, San Diego, CA (US); Huikai Sun, San Diego, CA (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/497,967

(22) PCT Filed: Mar. 26, 2018

(86) PCT No.: PCT/US2018/024249
§ 371 (c)(1),
(2) Date: Sep. 26, 2019

(87) PCT Pub. No.: WO2018/183145
PCT Pub. Date: Oct. 4, 2018

(65) Prior Publication Data
US 2020/0375969 A1 Dec. 3, 2020

Related U.S. Application Data

(60) Provisional application No. 62/476,846, filed on Mar. 26, 2017, provisional application No. 62/476,786, filed on Mar. 26, 2017.

(51) Int. Cl.
| | | |
|---|---|---|
| *C07D 417/12* | (2006.01) | |
| *A61K 31/4545* | (2006.01) | |
| *A61K 31/198* | (2006.01) | |
| *A61K 31/451* | (2006.01) | |
| *A61K 31/4525* | (2006.01) | |
| *A61K 31/4535* | (2006.01) | |
| *A61K 31/454* | (2006.01) | |
| *A61K 31/496* | (2006.01) | |
| *A61K 31/501* | (2006.01) | |
| *A61K 31/506* | (2006.01) | |
| *A61K 31/519* | (2006.01) | |
| *A61K 31/5365* | (2006.01) | |
| *A61K 31/553* | (2006.01) | |
| *C07D 211/52* | (2006.01) | |
| *C07D 401/12* | (2006.01) | |

(Continued)

(52) U.S. Cl.
CPC ........ *A61K 31/4545* (2013.01); *A61K 31/198* (2013.01); *A61K 31/451* (2013.01); *A61K 31/454* (2013.01); *A61K 31/4525* (2013.01); *A61K 31/4535* (2013.01); *A61K 31/496* (2013.01); *A61K 31/501* (2013.01); *A61K 31/506* (2013.01); *A61K 31/519* (2013.01); *A61K 31/5365* (2013.01); *A61K 31/553* (2013.01); *C07D 211/52* (2013.01); *C07D 401/12* (2013.01); *C07D 401/14* (2013.01); *C07D 405/12* (2013.01); *C07D 409/12* (2013.01); *C07D 413/12* (2013.01); *C07D 417/12* (2013.01); *C07D 487/04* (2013.01); *C07D 498/04* (2013.01)

(58) Field of Classification Search
CPC .............. A61K 31/4545; A61K 31/519; A61K 31/496; A61K 31/553; A61K 31/4535; A61K 31/501; A61K 31/4365; C07D 401/12; C07D 401/14; C07D 211/46; C07D 487/04; C07D 405/12; C07D 498/04; C07D 413/12; C07D 409/12; C07D 417/12
See application file for complete search history.

(56) References Cited

U.S. PATENT DOCUMENTS

| | | |
|---|---|---|
| 6,106,864 A | 8/2000 | Dolan et al. |
| 2003/0060466 A1 | 3/2003 | Binggeli et al. |
| 2004/0034019 A1 | 2/2004 | Tomlinson et al. |

FOREIGN PATENT DOCUMENTS

| | | |
|---|---|---|
| EP | 2009005 A1 | 12/2008 |
| JP | 2004-536814 A | 12/2004 |

(Continued)

OTHER PUBLICATIONS

PubChem, VYPBQQVPCHOIED-UHFFFAOYSA-N. CID: 1048476, STK259519; N-[2-(4-benzoylpipe-azin-1-yl)phenyl]-2-methylbenzamide; AC1LKRN7; MolPort-022-988-750; ZINC725005; AKOS000431621. 11 pages, May 8, 2018.

(Continued)

*Primary Examiner* — Jeffrey H Murray
(74) *Attorney, Agent, or Firm* — McCarter & English, LLP; Michael J. DeGrazia

(57) ABSTRACT

Disclosed are compounds of Formula 1 and pharmaceutically acceptable salts thereof, wherein L, $R^4$, $R^5$, $R^8$, $R^{10}$, $R^{11}$, $X^1$, $X^2$, $X^3$, $X^9$, $X^{12}$, and Z are defined in the specification. This disclosure also relates to materials and methods for preparing compounds of Formula 1, to pharmaceutical compositions which contain them, and to their use for treating diseases, disorders, and conditions associated with GPR6.

17 Claims, No Drawings

(51) Int. Cl.
*C07D 401/14* (2006.01)
*C07D 405/12* (2006.01)
*C07D 409/12* (2006.01)
*C07D 413/12* (2006.01)
*C07D 487/04* (2006.01)
*C07D 498/04* (2006.01)

(56) References Cited

FOREIGN PATENT DOCUMENTS

| | | |
|---|---|---|
| JP | 2005-516903 A | 6/2005 |
| JP | 2010-508274 A | 3/2010 |
| JP | 2011-512412 A | 4/2011 |
| JP | 2015-524843 A | 8/2015 |
| WO | 1991/11172 A1 | 8/1991 |
| WO | 1994/02518 A1 | 2/1994 |
| WO | 1998/55148 A1 | 12/1998 |
| WO | 2002/098864 A1 | 12/2002 |
| WO | 2003/045393 A1 | 6/2003 |
| WO | 2007/123269 A1 | 11/2007 |
| WO | 2008/054702 A1 | 5/2008 |
| WO | 2009/105435 A1 | 8/2009 |
| WO | 2014/028479 A1 | 2/2014 |
| WO | 2015/123533 A1 | 8/2015 |
| WO | 2015/159103 A1 | 10/2015 |

OTHER PUBLICATIONS

International Search Report and Written Opinion for Application No. PCT/US2018/024249, dated Jun. 11, 2018, 7 pages.

Almarsson et al., Crystal engineering of the composition of pharmaceutical phases. Do pharmaceutical co-crystals represent a new path to improved medicines? Chem Commun. 2004;1889-1896.

Batson et al., Development of Potent, Selective SRPK1 Inhibitors as Potential Topical Therapeutics for Neovascular Eye Disease. ACS Chem Biol. Mar. 17, 2017;12(3):825-832.

Berge et al., Pharmaceutical salts. J Pharm Sci. Jan. 1977;66(1):1-19.

Duty et al., Animal models of Parkinson's disease: a source of novel treatments and clues to the cause of the disease. Br J Pharmacol. Oct. 2011;164(4):1357-91.

Finnin et al., Transdermal penetration enhancers: applications, limitations, and potential. J Pharm Sci. Oct. 1999;88 (10):955-8.

Haleblian, Characterization of habits and crystalline modification of solids and their pharmaceutical applications. J Pharm Sci. Aug. 1975;64(8):1269-88.

Liang et al., Fast-dissolving intraoral drug delivery systems. Expert Opinion on Therapeutic Patents. 2001;11(6):981-986.

PIPERIDINYL- AND PIPERAZINYL-SUBSTITUTED HETEROAROMATIC CARBOXAMIDES AS MODULATORS OF GPR6

CROSS REFERENCE TO RELATED APPLICATIONS

This application is a 35 U.S.C. § 371 national stage filing of International Application No. PCT/US2018/024249, filed Mar. 26, 2018, which claims priority to U.S. provisional patent applications 62/476,786 and 62/476,846, which were both filed on Mar. 26, 2017. Each of the aforementioned applications are incorporated by reference in their entirety.

FIELD OF THE INVENTION

This invention relates to piperidinyl- and piperazinyl-substituted aromatic or heteroaromatic carboxamides which are modulators of G protein-coupled receptor 6 (GPR6), to pharmaceutical compositions which contain them, and to their use to treat diseases, disorders, and conditions associated with GPR6, including neurological disorders such as Parkinson's disease.

BACKGROUND OF THE INVENTION

GPR6 is a member of the G protein-coupled receptor (GPCR) family of transmembrane receptors. GPR6 signals through the G protein (Gs) pathway. It is highly expressed in the central nervous system (CNS), particularly in medium spiny neurons (MSNs) of the striatum, and exhibits minimal expression in peripheral tissues. The major striatal targets of dopaminergic innervation reside in the MSNs of the striatopallidal (indirect) and stiatonigral (direct) output pathways. The MSNs of the direct output pathway express D1 dopamine receptors while those in the indirect pathway express D2 receptors. GPR6 is enriched in the D2 receptor-expressing MSNs of the striatum where GPR6 activity increases the levels of intracellular second messenger cAMP, which is functionally opposed to D2 receptor signaling. Antagonism or inverse agonism of Gs-coupled GPR6 decreases cAMP in MSNs and thus provides a functional alternative to dopamine-mediated activation of D2 receptors.

SUMMARY OF THE INVENTION

This invention provides piperidinyl- and piperazinyl-substituted aromatic or heteroaromatic carboxamides and pharmaceutical compositions which contain them. The piperidinyl- and piperazinyl-substituted aromatic or heteroaromatic carboxamides are modulators of GPR6 and may be used to treat diseases, disorders, and conditions associated with GPR6, including neurological disorders such as Parkinson's disease.

One aspect of the invention provides compounds of Formula 1:

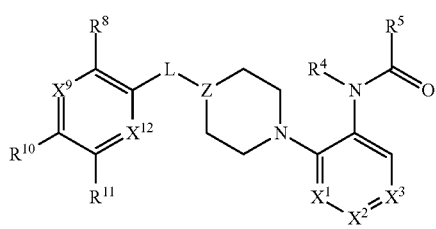

or a pharmaceutically acceptable salt thereof in which:

$X^1$ is selected from N and $CR^1$,
$X^2$ is selected from N and $CR^2$, and
$X^3$ is selected from N and $CR^3$, provided:
(a) no more than two of $X^1$, $X^2$, and $X^3$ can be N, and
(b) if $X^1$ is $CR^1$, $X^2$ is $CR^2$, $X^3$ is $CR^3$ and $R^1$, $R^2$ and $R^3$ are each hydrogen, then Z must be CH and $R^5$ cannot be 2-phenylthiazol-4-yl, and
(c) if $X^1$ is $CR^1$, $X^2$ is $CR^2$, $X^3$ is $CR^3$ and $R^1$ and $R^3$ are each hydrogen, then $R^1$ cannot be Cl, and
(d) if $X^1$ is N, $X^2$ is $CR^2$, $X^3$ is $CR^3$ and $R^2$ and $R^3$ are each hydrogen, then $R^5$ cannot be benzo[d][1,3]dioxol-5-yl;

$X^9$ is selected from N and $CR^9$, and
$X^{12}$ is selected from N and $CR^{12}$, wherein no more than one of $X^9$ and $X^{12}$ is N;
L is selected from O, S, $S(O_2)$, and $C(R^6)R^{17}$;
Z is selected from CH and N;
$R^1$ and $R^3$ are each independently selected from hydrogen, cyano, $C_{1-6}$ alkyl, $-(CH_2)_m OR^a$, $-(CH_2)_m N(R^a)R^b$, $-(CH_2)_m N(R^a)C(O)R^b$, $-(CH_2)_m NHC(O)NR^a R^b$, $-(CH_2)_m NR^a C(O)NHR^b$, $-(CH_2)_m C(O)R^a$, $-(CH_2)_m C(O)N(R^a)R^b$, $-(CH_2)_m N(R^a)S(O)_2 R^c$, $-(CH_2)_m SR^a$, $-(CH_2)_m S(O)R^c$, $-(CH_2)_m S(O)_2 R^c$, and $-(CH_2)_m S(O)_2 N(R^a)R^b$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and m is selected from 0, 1, 2, 3, and 4;
$R^2$ is selected from hydrogen, halo, cyano, $C_{1-6}$ alkyl optionally substituted with 1 to 3 halo, $-(CH_2)_n OR^d$, $-(CH_2)_2 N(R^d)R^e$, $-(CH_2)_n N(R^d)C(O)R^e$, $-(CH_2)_n NHC(O)NR^d R^e$, $-(CH_2)_n NR^d C(O)NHR^e$, $-(CH_2)_n C(O)R^d$, $-(CH_2)_n C(O)N(R^d)R^e$, $-(CH_2)_n N(R^d)S(O)_2 R^f$, $-(CH_2)_n SR^d$, $-(CH_2)_n S(O)R^f$, $-(CH_2)_n S(O)_2 R^f$, and $-(CH_2)_n S(O)_2 N(R^d)R^e$, wherein $R^d$ and $R^e$ are each independently selected from hydrogen, $C_{1-4}$ alkyl, and $C_{2-6}$ heterocyclyl, $R^f$ is selected from $C_{1-4}$ alkyl and $C_{2-6}$ heterocyclyl, and n is selected from 0, 1, 2, 3, and 4, provided if $R^2$ is halo then no more than one of $R^1$ and $R^3$ is hydrogen;
$R^4$ is selected from hydrogen and $C_{1-4}$ alkyl;
$R^5$ is selected from phenyl and $C_{1-9}$ heteroaryl, wherein phenyl is optionally substituted with from 1 to 3 substituents independently selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
  (i) from 1 to 3 substituents independently selected from halo, oxo, $C_{1-4}$ alkoxy, and amino optionally substituted with 1 or 2 $C_{1-4}$ alkyl; or
  (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
and wherein $C_{1-9}$ heteroaryl is optionally substituted with from 1 to 3 substituents independently selected from:
(a) amino optionally substituted with 1 or 2 $C_{1-4}$ alkyl;
(b) halo, hydroxy, oxo, $C_{3-6}$ cycloalkyl, and $C_{2-6}$ heterocyclyl;
(c) $C_{1-6}$ alkyl optionally substituted with:
  (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
$R^6$ and $R^7$ are each independently selected from hydrogen, halo, $C_{1-4}$ alkyl, and $C_{1-4}$ alkoxy, or together with the carbon atom to which they are attached form a carbonyl;
$R^8$, $R^9$, $R^{10}$, $R^{11}$, and $R^{12}$ are each independently selected from hydrogen, halo, cyano, $C_{1-6}$ alkyl optionally substituted with from 1 to 3 halo, and $C_{1-6}$ alkoxy optionally substituted with from 1 to 3 halo;
wherein each of the above-mentioned heteroaryl and heterocyclyl moieties independently has 1 to 3 heteroatoms as ring members, each of the heteroatoms independently selected from N, O, and S.

Another aspect of the invention provides a compound which is selected from the group of compounds described in the examples and their pharmaceutically acceptable salts.

A further aspect of the invention provides a pharmaceutical composition which includes a compound of Formula 1 or a pharmaceutically acceptable salt thereof, or any one of the compounds or pharmaceutically acceptable salts defined in the preceding paragraph; and a pharmaceutically acceptable excipient.

In some embodiments, $X^1$ is $CR^1$, $X^2$ is $CR^2$, $X^3$ is $CR^3$, and at least one of $R^1$, $R^2$ and $R^3$ is not hydrogen. In some embodiments, $X^1$ is $CR^1$, $X^2$ is $CR^2$, and $X^3$ is N. In some embodiments, $X^1$ is $CR^1$, $X^2$ is N, and $X^3$ is $CR^3$. In some embodiments, $X^1$ is N, $X^2$ is $CR^2$, and $X^3$ is $CR^3$. In some embodiments, $X^1$ is N, $X^2$ is $CR^2$, and $X^3$ is N. In some embodiments, $R^1$ is selected from hydrogen, cyano, $C_{1-6}$ alkyl, —$(CH_2)_mOR^a$, —$(CH_2)_mN(R^a)C(O)R^b$, —$(CH_2)_mC(O)N(R^a)R^b$, and —$(CH_2)_mS(O)_2R^c$, wherein and $R^b$ are each independently selected from hydrogen and $C_{1-4}$ alkyl, $R^c$ is selected from $C_{1-4}$ alkyl and $C_{2-6}$ heterocyclyl, and m is selected from 0 and 1. Alternatively, $R^1$ may be selected from hydrogen, cyano $C_{1-6}$ alkyl, —$(CH_2)_mOR^a$, —$(CH_2)_mN(R^a)C(O)R^b$, —$(CH_2)_mC(O)N(R^a)R^b$, and —$(CH_2)_mS(O)_2R^c$, wherein $R^a$ and $R^b$ may be each independently selected from hydrogen and $C_{1-4}$ alkyl, $R^c$ may be selected from $C_{1-4}$ alkyl and $C_{3-5}$ heterocyclyl, and m is selected from 0 and 1, wherein the $C_{3-5}$ heterocyclyl moiety is monocyclic, has 5 or 6 ring members in which 1 or 2 ring members are heteroatoms, and the heteroatoms are independently selected from N, O and S. In some embodiments, $R^1$ is selected from hydrogen, cyano, and $C_{1-4}$ alkyl. In some embodiments, R' is hydrogen.

In some embodiments, $R^2$ is selected from hydrogen, halo, cyano $C_{1-6}$, alkyl optionally substituted with 1 to 3 halo, —$(CH_2)_nOR^d$, —$(CH_2)_nC(O)N(R^d)R^e$, and —$(CH_2)_nS(O)_2R^f$, wherein $R^d$ and $R^e$ are each independently selected from hydrogen, $C_{1-4}$ alkyl, and $C_{2-6}$ heterocyclyl, $R^f$ is $C_{1-4}$ alkyl, and n is selected from 0 and 1. In some embodiments, $R^2$ is selected from hydrogen, halo, cyano, $C_{1-6}$ alkyl optionally substituted with 1 to 3 halo, —$(CH_2)_nOR^d$, —$(CH_2)_nC(O)N(R^d)R^e$, and —$(CH_2)_nS(O)_2R^f$, wherein $R^d$ and $R^e$ are each independently selected from hydrogen, $C_{1-4}$ alkyl, and $C_{3-5}$ heterocyclyl, $R^f$ is $C_{1-4}$ alkyl, and n is selected from 0 and 1, wherein the $C_{3-5}$ heterocyclyl moiety is monocyclic, has 5 or 6 ring members in which 1 or 2 ring members are heteroatoms, and the heteroatoms are independently, selected from N, O and S. In some embodiments, $R^2$ is selected from hydrogen, cyano. $C_{1-4}$ alkyl, —$OCH_3$, and —$C(O)N(CH_3)_2$. In some embodiments, $R^3$ is selected from hydrogen, cyano, $C_{1-6}$ alkyl, —$(CH_2)_mOR^a$, —$(CH_2)_mN(R^a)C(O)R^b$, —$(CH_2)_mC(O)N(R^a)R^b$, and —$(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and m is selected from 0 and 1. $R^3$ is selected from hydrogen, cyano, $C_{1-6}$ alkyl, —$(CH_2)_mOR^a$, —$(CH_2)_mN(R^a)C(O)R^b$, —$(CH_2)_mC(O)N(R^a)R^b$, and —$(CH_2)_mS(O)_7R^c$, wherein $R^a$ and $R^b$ are each independently selected from hydrogen and $C_{1-4}$ alkyl, $R^c$ is selected from $C_{1-4}$ alkyl and $C_{3-5}$ heterocyclyl, and in is selected from 0 and 1, wherein the $C_{3-5}$ heterocyclyl moiety is monocyclic, has 5 or 6 ring members in which 1 or 2 ring members are heteroatoms, and the heteroatoms are independently selected from N, O and S. In some embodiments, $R^3$ is selected from hydrogen, cyano, —$C(O)N(CH_3)_2$, and —$SO_2CH_3$.

In some embodiments, $R^5$ is selected from phenyl optionally substituted with from 1 to 3 substituents independently selected from: (a) amino optionally substituted with 1 or 2 $C_{1-4}$ alkyl; (b) halo, hydroxy, $C_{2-6}$ heterocyclyl, and phenyl; and (c) $C_{1-6}$ alkyl and $C_{1-6}$ alkoxy, each optionally substituted with from 1 to 3 halo. In some embodiments, $R^5$ is selected from phenyl optionally substituted with from 1 to 3 substituents independently selected from: (a) amino optionally substituted with 1 or 2 $C_{1-4}$ alkyl; (b) halo, hydroxy, $C_{3-5}$ heterocyclyl, and phenyl; and (c) $C_{1-4}$ alkyl and $C_{1-4}$ alkoxy, each optionally substituted with from 1 to 3 halo;
wherein the $C_{3-5}$ heterocyclyl moiety is monocyclic, has 5 or 6 ring members in which 1 or 2 ring members are heteroatoms, and the heteroatoms are independently selected from N, O and S. Alternatively, $R^5$ may be selected from phenyl optionally substituted with from 1 to 3 substituents independently selected from: (a) amino optionally substituted with 1 or 2 $C_{1-4}$ alkyl; (b) halo and hydroxy; and (c) $C_{1-4}$ alkyl and $C_{1-4}$ alkoxy, each optionally substituted with from 1 to 3 halo.

In some embodiments, $R^5$ is $C_{1-9}$ heteroaryl optionally substituted with from 1 to 3 substituents independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo. In some embodiments, $R^5$ is $C_{1-9}$ heteroaryl optionally substituted with from 1 to 3 substituents independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo; wherein the $C_{1-9}$ heteroaryl moiety is monocyclic or bicyclic, has 5 to 10 ring members in which 1 to 4 ring members are heteroatoms, and the heteroatoms are independently selected from N, O and S.

In some embodiments, $R^5$ is $C_{2-5}$ heteroaryl optionally substituted with from 1 to 3 substituents independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo; wherein the $C_{2-5}$ heteroaryl moiety is monocyclic, has 5 or 6 ring members in which 1 to 3 ring members are heteroatoms, and the heteroatom; are independently selected from N, O and S. In some embodiments, 115 is $C_{2-5}$ heteroaryl optionally substituted with from 1 to 3 substituents independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo; wherein the $C_{2-5}$ heteroaryl moiety is monocyclic, has ring members in which 1 to 3 ring members are heteroatoms, and the heteroatoms are each N.

In some embodiments, $R^5$ is $C_{1-9}$ heteroaryl which is selected from thienyl, pyrazolyl, imidazolyl, isoxazolyl, oxazolyl, isothiazolyl, thiazolyl, 1,2,3-triazolyl, 1,2,4-oxadiazolyl, 1,2,5-oxadiazolyl, 1,3,4-oxadiazolyl, 1,2,5-thiadiazolyl, pyridinyl, pyridazinyl pyrimidinyl, and pyrazinyl, each optionally substituted with from 1 to 3 substituents independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo. In some embodiments, $R^5$ is $C_{1-9}$ heteroaryl which is selected from pyrazolyl, pyridinyl, pyridazinyl, pyrimidinyl; and pyrazinyl, each optionally substituted with from 1 to 3 substituents independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently substituted from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo. In some embodiments, $R^5$ is $C_{1-9}$ heteroaryl which is selected from pyrazolyl and pyridinyl, each optionally substituted with from 1 to 3 substituents independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo. In some embodiments, wherein $R^5$ is $C_{1-9}$ heteroaryl which is selected from 2,3-dihydrobenzofuranyl, 2-oxo-1,2,5,6,7,8-hexahydroquinolinyl, 4-oxo-4H-pyrido[1,2-c]pyrimidinyl, 5,6,7,8-tetrahydropyrazolo[5,1-b][1,3]oxazepinyl, 5,6-dihydro-4H-pyrrolo[1,2-b]pyrazolyl; 5-oxo-5H-thiazolo[3,2-a]pyrimidinyl, 6,7-dihydro-5H-cyclopenta[b]pyridinyl, 6,7-dihydro-5H-pyrazolo[5,1-b][1,3]oxazinyl, and pyrrolo[1,2-c]pyrimidinyl, each optionally substituted with 1 or 2 substituents independently selected from: (a) amino optionally substituted with 1 or 2 $C_{1-4}$ alkyl; (b) halo, hydroxy, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo.

In some embodiments, each of the optional substituents on the $R^5$ heteroaryl moiety is independently selected from: (a) amino optionally substituted with 1 or 2 $C_{1-4}$ alkyl; (b) halo, hydroxy, oxo, $C_{3-6}$ cycloalkyl, and $C_{2-6}$ heterocyclyl; (c) $C_{1-6}$ alkyl optionally substituted with: (i) from 1 to 3 substituents independently selected from halo, oxo, $C_{1-4}$ alkoxy, and amino optionally substituted with 1 or 2 $C_{1-4}$ alkyl; or (ii) a substituent selected from phenyl and pyridinyl, each optionally substituted with from 1 to 3 halo; (d) $C_{1-6}$ alkoxy optionally substituted with from 1 to 3 halo; and (e) phenyl optionally substituted with from 1 to 3 halo, wherein the $C_{3-5}$ heterocyclyl moiety is monocyclic, has 5 or 6 ring members in which 1 or 2 ring members are heteroatoms, and the heteroatoms are independently selected from N, O and S. In some embodiments, $X^9$ is $CR^9$ and $X^{12}$ is $CR^{12}$. In some embodiments, $X^9$ is $CR^9$ and $X^{12}$ is N. In some embodiments, $X^9$ is N and $X^{12}$ is $CR^{12}$. In some embodiments, $R^8$, $R^9$, $R^{10}$, $R^{11}$, and $R^{12}$ are each independently selected from hydrogen, halo, cyano alkyl optionally substituted with from 1 to 3 halo, and $C_{1-4}$ alkoxy optionally substituted with from 1 to 3 halo. In some embodiments, $R^8$, $R^9$, $R^{10}$, $R^{11}$, and $R^{12}$ are each independently selected from hydrogen, chloro, fluoro, cyano, methyl, and methoxy optionally substituted with from 1 to 3 fluoro. In some embodiments, L is selected from O, $S(O_2)$, and $C(R^6)R^7$. In some embodiments, L is selected from O and $C(R^6)R^7$. In some embodiments, L is O or $C(R^6)R^7$. In some embodiments, L is $C(R^6)R^7$, and $R^6$ and $R^7$ are each independently selected from hydrogen, halo, $C_{1-3}$ alkyl, and $C_{1-3}$ alkoxy, or together with the carbon atom to which they are attached form a carbonyl. In some embodiments, L is $C(R^6)R^7$, and $R^6$ and $R^7$ are each independently selected from hydrogen, halo, methyl, and methoxy, or together with the carbon atom to which they are attached form a carbonyl. In some embodiments, Z is CH. In some embodiments, $R^4$ is hydrogen. In some embodiments; the compound is selected from any one of the compounds prepared in Examples 1-71, 74, 75, 78-148, 151-240, 242-257, and 261-293, and a pharmaceutically acceptable salt thereof.

Various embodiments of the invention herein provide a pharmaceutical composition comprising: a compound or pharmaceutically acceptable salt as defined herein; and a pharmaceutically acceptable excipient. In some embodiments, a compound or pharmaceutically acceptable salt described herein is provided for use as a medicament. In some embodiments, a compound or pharmaceutically acceptable salt described herein is provided for treatment of a disease, disorder or condition selected from Parkinson's disease, levodopa-induced dyskinesias, Huntington's disease, drug addiction, eating disorders, cognitive disorders, schizophrenia, bipolar disorder, epilepsy, and depression.

Various embodiments of the invention herein provide a method of treating a disease, disorder or condition in a subject, the method comprising administering to the subject a compound or pharmaceutically acceptable salt as described herein the disease, disorder or condition is selected from Parkinson's disease, levodopa-induced dyskinesias, Huntington's disease, drug addiction, eating disorders, cognitive disorders, schizophrenia, bipolar disorder, epilepsy, and depression. In some embodiments, a combination comprising a compound or pharmaceutically acceptable salt described herein and at least one additional pharmacologically active agent is provided. In some embodiments, the additional pharmacologically active agent is selected from levodopa, a DOPA decarboxylase inhibitor, a dopamine agonist, an anticholinergic, a B-selective monoamine oxidase inhibitor, and a catechol O-methyl transferase inhibitor. In some embodiments, the additional pharmacologically active agent is levodopa in combination with a DOPA decarboxylase inhibitor An additional aspect of the invention provides a compound of Formula 1 or a pharmaceutically acceptable salt thereof, or any one of the compounds and pharmaceutically acceptable salts defined in the preceding paragraphs, for use as a medicament. Another aspect of the invention provides a compound of Formula 1 or a pharmaceutically acceptable salt thereof, or any one of the compounds or pharmaceutically acceptable salts defined in the preceding paragraphs, for treatment of a disease, disorder or condition associated with GPR6.

A further aspect of the invention provides a use of a compound of Formula 1 or a pharmaceutically acceptable salt thereof, or any one of the compounds or pharmaceutically acceptable salts defined in the preceding paragraphs, for the manufacture of a medicament for the treatment of a disease, disorder or condition associated with GPR6.

An additional aspect of the invention provides a method of treating a disease, disorder or condition associated with GPR6, the method comprising administering to the subject an effective amount of a compound of Formula 1 or a pharmaceutically acceptable salt thereof, or any one of the compounds or pharmaceutically acceptable salts defined in the preceding paragraphs.

Another aspect of the invention provides a method of treating a disease, disorder or condition in a subject, the method comprising administering to the subject an effective amount of a compound of Formula 1 or a pharmaceutically acceptable salt thereof, or any one of the compounds or pharmaceutically acceptable salts defined in the preceding paragraphs, wherein the disease, disorder or condition is selected from Parkinson's disease, levodopa-induced dyskinesias, Huntington's disease, drug addiction, eating disorders, cognitive disorders, schizophrenia, bipolar disorder, epilepsy, and depression.

A further aspect of the invention provides an effective amount of a compound of Formula 1 or a pharmaceutically acceptable salt thereof, or any one of the compounds or pharmaceutically acceptable salts defined in the preceding paragraphs; and at least one additional pharmacologically active agent.

Various embodiments of the invention herein provide a method of modulating GRP6 activity in a subject comprising administering to the subject a compound of Formula 1 or pharmaceutically acceptable salt as described herein.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately." when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., C-s alkanediyl refers to an alkanediyl group having 1 to 4 (i.e., 1, 2, 3 or 4) carbon atoms, $C_{1-4}$ alkanediyl refers to an alkanediyl group having 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, I-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom, and where indicated, may optionally include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thictanyl, azetidinyl, tetrahydrofuranyl, tetrahydrothienyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. For the purposes of this disclosure, 2-pyridone and 4-pyridone, 2-quinolone and 4-quinolone, and the like, are considered to be 2-oxo- and 4-oxo-substituted derivatives of the corresponding heteroaromatic group (pyridine, quinoline, and the like).

Examples of heteroaryl groups include monocyclic groups such as pyrrolyl (e.g., pyrrol-1-yl, pyrrol-2-yl, and pyrrol-3-yl), furanyl, thienyl, pyrazolyl, imidazolyl, isoxazolyl, oxazolyl, isothiazolyl, thiazolyl, 1,2,3-triazolyl, 1,3,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4- thiadiazolyl, 1,2,5-thiadiazolyl, 1,3,4-thiadiazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothienyl, benzo[c]thienyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

Other examples of include heteroaryl groups also include bicyclic groups 2,3-dihydrobenzofuranyl, 2-oxo-1,2,5,6,7,8-hexahydroquinolinyl, 4-oxo-4H-pyrido[1,2-a]pyrimidinyl, 5,6,7,8-tetrahydropyrazolo[5,1-b][1,3]oxazepinyl, 5,6-dihydro-4H-pyrrolo[1,2-b]pyrazolyl, 5-oxo-5H-thiazolo[3,2-a]pyrimidinyl, 6,7-dihydro-5H-cyclopenta[b]pyridinyl, 6,7-dihydro-5H-pyrazolo[5,1-b][1,3]oxazinyl, and pyrrolo[1,2-c]pyrimidinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with GPR6" and similar phrases relate to a disease, disorder or condition in a subject for which modulation GPR6, including antagonism or inverse agonism of GPR6, may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); BINAP (2,2'-bis(diphenylphosphino)-1,1'-binaphthyl); Boc (tert-butoxycarbonyl); Cbz (carbobenzyloxy); dba (dibenzylideneacetone); DCC (1,3-dicyclohexylcarbodiimide); DCE (1,1-dichloroethane); DCM (dichloromethane); DIPEA (N,N-diisopropylethylamine, Hünig's Base); DMA (N,N-dimethylacetamide); DMAP (4-dimethylaminopyridine); DME (1,2-dimethoxyethane); DMF (N,N-dimethylformamide); DMSO (dimethylsulfoxide); dppf (1,1'-bis(diphenylphosphino)ferrocene); DTT (dithiothreitol); $EC_{50}$ (effective concentration at half maximal response); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOr-Bu (sodium tertiary butoxide); NMM (N-methylmorpholine); NMP (N-methyl-pyrrolidone); OTf (triflate); PE (petroleum ether); Ph (phenyl); $pEC_{50}$ ($-log_{10}$ ($EC_{50}$), where $EC_{50}$ is given in molar (M) units); $pIC_{50}$ ($-log_{10}(IC_{50})$, where $IC_{50}$ is given in molar (M) units); Pr (propyl); c-Pr (cyclopropyl), i-Pr (isopropyl); PTFE (polytetrafluoroethylene); RT (room temperature, approximately 20° C. to 25° C.); T3P (2,4,6-tripropyl-1,3,5,2,4,6-trioxatriphosphinane 2,4,6-trioxide); TCEP (tris(2-carboxyethyl) phosphine); TFA (trifluoroacetic acid); TFAA (2,2,2-trifluoroacetic anhydride); THF (tetrahydrofuran); TMEDA ($N^1$, $N^1,N^2,N^2$-tetramethylethane-1,2-diamine); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating diseases, disorders or conditions of the CNS, including Parkinson's disease, and other diseases, disorders or conditions associated with GPR6.

The compounds of Formula 1 include which (those in
$X^1$ is selected from N and $CR^1$,
$X^2$ is selected from N and $CR^2$, and
$X^3$ is selected from N and $CR^3$,
provided:
(a) no more than two of $X^1$, $X^2$, and $X^3$ can be N, and
(b) if $X^1$ is $CR^1$, $X^1$ is $CR^2$, $X^3$ is $CR^3$ and $R^1$, $R^2$ and $R^3$ are each hydrogen, then Z must be CH and $R^5$ cannot be 2-phenylthiazol-4-yl, and
(c) if $X^1$ is $CR^1$, $X^2$ is $CR^2$, $X^3$ is $CR^3$ and $R^1$ and $R^3$ are each hydrogen, then $R^2$ cannot be Cl, and
(d) if $X^1$ is N, $X^2$ is $CR^2$. $X^3$ is $CR^3$ and $R^2$ and $R^3$ are each hydrogen, then $R^5$ cannot be benzo[d][1,3] dioxol-5-yl;

$X^9$ is selected from N and $CR^9$, and
$X^{12}$ is selected from N and $CR^2$, wherein no more than one of $X^9$ and $X^{12}$ is N;
L is selected from O, S, $S(O_2)$, and $C(R^5)R^7$;
Z is selected from CH and N;
$R^1$ and $R^3$ are each independently selected from hydrogen, cyano, $C_{1-6}$alkyl, —$(CH_2)_m OR^a$, —$(CH_2)_m N(R^a)R^b$, —$(CH_2)_m N(R^a)C(O)R^b$, —$(CH_2)_m NHC(O)NR^a R^b$, —$(CH_2)_m NR^a C(O)NHR^b$, —$(CH_2)_m C(O)R^a$, —$(CH_2)_m C(O)N(R^a)R^b$, —$(CH_2)_m N(R^a)S(O)_2 R^c$, —$(CH_2)_m SR^a$, —$(CH_2)_m S(O)R^c$, —$(CH_2)_m S(O)_m R^c$, and —$(CH_2)_m S(O)_2 N(R^a)R^b$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and m is selected from 0, 1, 2, 3, and 4;
$R^2$ is selected from hydrogen, halo, cyano, $C_{1-6}$ alkyl optionally substituted with 1 to 3 halo, —$(CH_2)_n OR^d$, —$(CH_2)_n N(R^d)R^e$, —$(CH_2)_n N(R^d)C(O)R^e$, —$(CH_2)_n NHC(O)NR^d R^e$, —$(CH_2)_n NR^d C(O)NHR^e$, —$(CH_2)_n C(O)R^d$, —$(CH_2)_n C(O)N(R^d)R^e$, —$(CH_2)_n N(R^d)S(O)_2 R^f$, —$(CH_2)_n SR^d$, —$(CH_2)_n S(O)R^f$, —$(CH_2)_n S(O)_2 R^f$, and —$(CH_2)_n S(O)_2 N(R^d)R^e$, wherein $R^d$ and $R^e$ are each independently selected from hydrogen, $C_{1-4}$ alkyl, and $C_{2-6}$ heterocyclyl, $R^f$ is selected from $C_{1-4}$ alkyl and $C_{2-6}$ heterocyclyl, and n is selected from 0, 1, 2, 3, and 4, provided if $R^2$ is halo then no more than one of $R^1$ and $R^3$ is hydrogen;
$R^4$ is selected from hydrogen and $C_{1-4}$ alkyl;
$R^5$ is selected from phenyl and $C_{1-9}$ heteroaryl, wherein phenyl is optionally substituted with from 1 to 3 substituents independently selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
  (i) from 1 to 3 substituents independently selected from halo, oxo, $C_{1-4}$ alkoxy, and amino optionally substituted with 1 or 2 $C_{1-4}$ alkyl; or
  (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
and wherein $C_{1-9}$ heteroaryl is optionally substituted with from 1 to 3 substituents independently selected from:
(a) amino optionally substituted with 1 or 2 $C_{1-4}$ alkyl;
(b) halo, hydroxy, oxo, $C_{3-6}$ cycloalkyl, and $C_{2-6}$ heterocyclyl;
(c) $C_{1-6}$ alkyl optionally substituted with:
  (i) from 1 to 3 substituents independently selected from halo, oxo, $C_{1-4}$ alkoxy, and amino optionally substituted with 1 or 2 $C_{1-4}$ alkyl; or
  (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
$R^6$ and $R^7$ are each independently selected from hydrogen, halo, $C_{1-4}$ alkyl, and $C_{1-4}$ alkoxy, or together with the carbon atom to which they are attached form a carbonyl;
$R^8$, $R^9$, $R^{10}$, $R^{11}$, and $R^{12}$ are each independently selected from hydrogen, halo, cyano, $C_{1-6}$ alkyl optionally substituted with from 1 to 3 halo, and $C_{1-6}$ alkoxy optionally substituted with from 1 to 3 halo;

wherein each of the above-mentioned heteroaryl and heterocyclyl moieties independently has 1 to 3 heteroatoms as ring members, each of the heteroatoms independently selected from N, O, and S.

In addition to the specific compounds in the examples, the compounds of Formula 1 include those in which:

(2) $X^1$ is $CR^1$, $X^2$ is $CR^2$, $X^3$ is $CR^3$, and at least one of $R^1$, $R^2$ and $R^3$ is not hydrogen;
(3) $X^1$ is $CR^1$, $X^2$ is $CR^2$, and $X^3$ is N;
(4) $X^1$ is $CR^1$, $X^2$ is N, and $X^3$ is $CR^3$;
(5) $X^1$ is N, $X^2$ is $CR^2$, and $X^3$ is $CR^3$; or
(6) $X^1$ is N, $X^2$ is $CR^2$, and $X^3$ is N.

In addition, or as an alternative, to one of embodiments the preceding paragraphs, compounds of Formula 1 include those in which:

(7) $R^1$ is selected from hydrogen, cyano, $C_{1-6}$ alkyl, $-(CH_2)_mOR^a$, $-(CH_2)_mN(R)C(O)R^b$, $-(CH_2)_mC(O)N(R^a)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and in is selected from 0 and 1;

(8) $R^1$ is selected from hydrogen, cyano, $C_{1-6}$ alkyl, $-(CH_2)_mOR^a$, $-(CH_2)_mN(R^a)C(O)R^b$, $-(CH_2)_mC(O)N(R^a)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{3-5}$ heterocyclyl, and in is selected from 0 and 1, wherein the $C_{3-5}$ heterocyclyl moiety is monocyclic, has 5 or 6 ring members in which 1 or 2 ring members are heteroatoms, and the heteroatoms are independently selected from N, O and S;

(9) $R^1$ is selected from hydrogen, cyano, $C_{1-6}$ alkyl, $-(CH_2)_mOR^3$, $-(CH_2)_mN(R)C(O)R^b$, $-(CH_2)_mC(O)N(R^3)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{3-5}$ heterocyclyl, and in is selected from 0 and 1, wherein the $C_{3-5}$ heterocyclyl moiety is monocyclic, has 5 or 6 ring members in which 1 or 2 ring members are heteroatoms, one of the heteroatoms is N, and if present, the other heteroatom is selected from N, O and S;

(10) $R^1$ is selected from hydrogen, cyano, $C_{1-6}$ alkyl, $-(CH_2)_mOR^3$, $-(CH_2)_mN(R^a)C(O)R^b$, $-(CH_2)_mC(O)N(R^a)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and morpholinyl, and m is selected from 0 and 1;

(11) $R^1$ is selected from hydrogen, cyano, $C_{1-4}$ alkyl, $-CH_2NHC(O)CH_3$, $-CH_2OCH_3$, $-CH_2OH$, $-C(O)N(CH_3)_2$, $-SO_2CH_3$, and morpholin-4-ylsulfonyl;

(12) $R^1$ is selected from hydrogen, cyano, and $C_{1-4}$ alkyl; or

(13) $R^1$ is hydrogen.

In addition, or as an alternative, to one of embodiments (1) to (3), (5), and (6) in the preceding paragraphs, compounds of Formula 1 include those in which:

(14) $R^2$ is selected from hydrogen, cyano, $C_{1-6}$ alkyl optionally substituted with 1 to 3 halo, $-(CH_2)_nOR^d$, $-(CH_2)_nN(R^d)R^e$, $-(CH_2)_nN(R^d)C(O)R^e$, $-(CH_2)_nNHC(O)NR^dR^e$, $-(CH_2)_nNR^dC(O)NHR^e$, $-(CH_2)_nC(O)R^d$, $-(CH_2)_nC(O)N(R^d)R^e$, $-(CH_2)_nN(R^d)S(O)_2R^f$, $-(CH_2)_nS(O)_2R^f$, and $-(CH_2)_nS(O)_2N(R^d)R^e$, wherein $R^d$ and $R^e$ are each independently selected from hydrogen, $C_{1-4}$ alkyl, and $C_{2-6}$ heterocyclyl, $R^f$ is selected from $C_{1-4}$ alkyl and $C_{2-6}$ heterocyclyl, and n is selected from 0, 1, 2, 3, and 4;

(15) $R^2$ is selected from hydrogen, halo, cyano, $C_{1-6}$ alkyl optionally substituted with 1 to 3 halo, $-(CH_2)_nOR^d$, $-(CH_2)_nC(O)N(R^d)R^e$, and $-(CH_2)_nS(O)_2R^f$, wherein $R^d$ and $R^e$ are each independently selected from hydrogen, $C_{1-4}$ alkyl, and $C_{2-6}$ heterocyclyl, $R^f$ is $C_{1-4}$ alkyl, and n is selected from 0 and 1;

(16) $R^2$ is selected from hydrogen, halo, cyano, $C_{1-6}$ alkyl optionally substituted with 1 to 3 halo, $-(CH_2)_nOR^d$, $-(CH_2)_nC(O)N(R^d)R^e$, and $-(CH_2)_nS(O)_2R^f$, wherein $R^d$ and $R^e$ are each independently selected from hydrogen, $C_{1-4}$ alkyl, and $C_{3-5}$ heterocyclyl, $R^f$ is $C_{1-4}$ alkyl, and n is selected from 0 and 1, wherein the $C_{3-5}$ heterocyclyl moiety is monocyclic, has 5 or 6 ring members in which 1 or 2 ring members are heteroatoms, and the heteroatoms are independently selected from N, O and S;

(17) $R^2$ is selected from hydrogen, halo, cyano, $C_{1-6}$ alkyl optionally substituted with 1 to 3 halo, $-(CH_2)_nOR^d$, $-(CH_2)_nC(O)N(R^d)R^e$, and $-(CH_2)_nS(O)_2R^f$, wherein $R^d$ and $R^e$ are each independently selected from hydrogen, $C_{1-4}$ alkyl, and $C_{3-5}$ heterocyclyl, $R^f$ is $C_{1-4}$ alkyl, and n is selected from 0 and 1, wherein the $C_{3-5}$ heterocyclyl moiety is monocyclic, has 5 or 6 ring members in which 1 or 2 ring members are heteroatoms, one of the heteroatoms is O, and if present, the other heteroatom is selected from N, O and S;

(18) $R^2$ is selected from hydrogen, halo, cyano, $C_{1-6}$ alkyl optionally substituted with 1 to 3 halo, $-(CH_2)_nOR^d$, $-(CH_2)_nC(O)N(R^d)R^e$, and $-(CH_2)_nS(O)_2R^f$, wherein $R^d$ and $R^e$ are each independently selected from hydrogen, $C_{1-4}$ alkyl, and tetrahydrofuran, $R^f$ is $C_{1-4}$ alkyl, and n is selected from 0 and 1;

(19) $R^2$ is selected from hydrogen, halo, cyano, $C_{1-4}$ alkyl optionally substituted with 1 to 3 halo, $-OCH_3$, $-CH_2OCH_3$, $-C(O)NH_2$, $-C(O)NHCH_3$, $-C(O)NHCH_2CH_3$, $-C(O)NH(CH_2)_2CH_3$, $-C(O)NHCH(CH_3)_2$, $-C(O)N(CH_3)_2$, $-SO_2CH_3$, and N-(tetrahydrofuranyl)carbamoyl;

(20) $R^2$ is selected from hydrogen, cyano, alkyl, $-OCH_3$, and $-C(O)N(CH_3)_2$;

(21) $R^2$ is hydrogen, $C_{1-4}$ alkyl, and $-C(O)N(CH_3)_2$,

(22) $R^2$ is hydrogen;

(23) $R^2$ is $C_{1-4}$ alkyl;

(24) $R^2$ is methyl; or

(25) $R^2$ is $-C(O)N(CH_3)_2$.

In addition, or as an alternative, to one of embodiments (1), (2), (4), and (5) the preceding paragraphs, compounds of Formula 1 include those in which:

(26) $R^3$ is selected from hydrogen, cyano, $C_{1-6}$ alkyl, $-(CH_2)_mOR^a$, $-(CH_2)_mN(R^a)C(O)R^b$, $-(CH_2)_mC(O)N(R^a)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and m is selected from 0 and 1;

(27) $R^3$ is selected from hydrogen, cyano, $C_{1-6}$ alkyl, $-(CH_2)_mOR^a$, $-(CH_2)_mN(R^a)C(O)R^b$, $-(CH_2)_mC(O)N(R^a)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{3-5}$ heterocyclyl, and in is selected from 0 and 1, wherein the $C_{3-5}$ heterocyclyl moiety is monocyclic, has 5 or 6 ring members in which 1 or 2 ring members are heteroatoms, and the heteroatoms are independently selected from N, O and S;

(28) $R^3$ is selected from hydrogen, cyano, $C_{1-6}$ alkyl, —$(CH_2)_m OR^a$, —$(CH_2)_m N(R^a)C(O)R^b$, —$(CH_2)_m C(O)N(R^a)R^b$, and —$(CH_2)_m S(O)_2 R^c$, wherein $R^a$ and $R^b$ are each independently selected from hydrogen and $C_{1-4}$ alkyl, $R^c$ is selected from $C_{1-4}$ alkyl and $C_{3-5}$ heterocyclyl, and in is selected from 0 and 1, wherein the $C_{3-5}$ heterocyclyl moiety is monocyclic, has 5 or 6 ring members in which 1 or 2 ring members are heteroatoms, one of the heteroatoms is N, and if present, the other heteroatom is selected from N, O and S;

(29) $R^3$ is selected from hydrogen, cyano, $C_{1-6}$ alkyl, —$(CH_2)_m OR^a$, —$(CH_2)_m N(R^a)C(O)R^b$, —$(CH_2)_m C(O)N(R^a)R^b$, and —$(CH_2)_m S(O)_2 R^c$, wherein $R^a$ and $R^b$ are each independently selected from hydrogen and $C_{1-4}$ alkyl, $R^c$ is selected from $C_{1-4}$ alkyl and morpholinyl, and is selected from 0 and 1;

(30) $R^3$ is selected from hydrogen, cyano, $C_{1-4}$ alkyl, —$CH_2 NHC(O)CH_3$, —$CH_2 OCH_3$, —$CH_2 OH$, —$C(O)N(CH_3)_2$, —$SO_2 CH_3$, and morpholin-4-ylsulfonyl;

(31) $R^3$ is selected from hydrogen, cyano, —$C(O)N(CH_3)_2$, and —$SO_2 CH_3$;

(32) $R^3$ is hydrogen, cyano, and —$SO_2 CH_3$,

(33) $R^3$ is hydrogen; or

(34) $R^3$ is —$SO_2 CH_3$.

In addition, or as an alternative, to one of embodiments (1) through (34) the preceding paragraphs, compounds of Formula 1 include those in which:

(35) $R^5$ is selected from phenyl optionally substituted with from 1 to 3 substituents independently selected from:
  (a) amino optionally substituted with 1 or 2 $C_{1-4}$ alkyl;
  (b) halo, hydroxy, $C_{2-6}$ heterocyclyl, and phenyl; and
  (c) $C_{1-6}$ alkyl and $C_{1-6}$ alkoxy, each optionally substituted with from 1 to 3 halo;

(36) $R^5$ is selected from phenyl optionally substituted with from 1 to 3 substituents independently selected from:
  (a) amino optionally substituted with 1 or 2 $C_{1-4}$ alkyl;
  (b) halo, hydroxy, $C_{3-5}$ heterocyclyl, and phenyl; and
  (c) $C_{1-4}$ alkyl and $C_{1-4}$ alkoxy, each optionally substituted with from 1 to 3 halo;
  wherein the $C_{3-5}$ heterocyclyl moiety is monocyclic, has 5 or 6 ring members in which 1 or 2 ring members are heteroatoms, and the heteroatoms are independently selected from N, O and S;

(37) $R^5$ is selected from phenyl optionally substituted with from 1 to 3 substituents independently selected from:
  (a) amino optionally substituted with 1 or 2 $C_{1-4}$ alkyl;
  (b) halo, hydroxy, $C_{3-5}$ heterocyclyl, and phenyl; and
  (c) $C_{1-4}$ alkyl and $C_{1-4}$ alkoxy, each optionally substituted with from 1 to 3 halo;
  wherein the $C_{3-5}$ heterocyclyl moiety is monocyclic, has 5 or 6 ring members in which 1 or 2 ring members are heteroatoms, one of the heteroatoms is N, and if present, the other heteroatom is selected from N, O and S;

(38) $R^5$ is selected from phenyl optionally substituted with from 1 to 3 substituents independently selected from:
  (a) amino optionally substituted with 1 or 2 $C_{1-4}$ alkyl;
  (b) halo, hydroxy, morpholinyl, and phenyl; and
  (c) $C_{1-4}$ alkyl and $C_{1-4}$ alkoxy, each optionally substituted with from 1 to 3 halo;

(39) $R^5$ is selected from phenyl optionally substituted with from 1 to 3 substituents independently selected from:
  (a) amino optionally substituted with 1 or 2 $C_{1-4}$ alkyl;
  (b) halo and hydroxy; and
  (c) $C_{1-4}$ alkyl and $C_{1-4}$ alkoxy, each optionally substituted with from 1 to 3 halo; or

(40) $R^5$ is selected from phenyl optionally substituted with from 1 to 3 substituents independently selected from:
  (a) amino optionally substituted with 1 or 2 methyl;
  (b) halo and hydroxy; and
  (c) methyl and methoxy, each optionally substituted with from 1 to 3 halo.

In addition, or as an alternative, to one of embodiments (1) through (34) in the preceding paragraphs, compounds of Formula 1 include those in which:

(41) $R^5$ is $C_{1-9}$ heteroaryl optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(42) $R^5$ is $C_{1-9}$ heteroaryl optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;
  wherein the $C_{1-9}$ heteroaryl moiety is monocyclic or bicyclic, has 5 to 10 ring members in which 1 to 4 ring members are heteroatoms, and the heteroatoms are independently selected from N, O and S;

(43) $R^5$ is $C_{2-5}$ heteroaryl optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;
  wherein the $C_{2-5}$ heteroaryl moiety is monocyclic, has 5 or 6 ring members in which 1 to 3 ring members are heteroatoms, and the heteroatoms are independently selected from N, O and S;

(44) $R^5$ is $C_{2-5}$ heteroaryl optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;

(c) $C_{1-6}$ alkyl optionally substituted with:
  (i) from 1 to 3 substituents independently selected from halo, oxo, $C_{1-4}$ alkoxy, and amino optionally substituted with 1 or 2 $C_{1-4}$ alkyl; or
  (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo; wherein the $C_{2-5}$ heteroaryl moiety is monocyclic, has ring members in which 1 to 3 ring members are heteroatoms, and the heteroatoms are each N;

(45) $R^5$ is $C_{1-9}$ heteroaryl which is selected from pyrrolyl, furanyl, thienyl, pyrazolyl, imidazolyl, isoxazolyl, oxazolyl, isothiazolyl, thiazolyl, 1,2,3-triazolyl, 1,3,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, pyridinyl, pyridazinyl, pyrimidinyl, and pyrazinyl, each optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(46) $R^5$ is $C_{1-9}$ heteroaryl which is selected from thienyl, pyrazolyl, isoxazolyl, oxazolyl, isothiazolyl, 1,2,4-oxadiazolyl, 1,2,5-oxadiazolyl, 1,2,5-thiadiazolyl, pyridinyl, pyridazinyl, pyrimidinyl, and pyrazinyl, each optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(47) $R^5$ is $C_{1-9}$ heteroaryl which is selected from pyrazolyl, pyridinyl, pyridazinyl, pyrimidinyl, and pyrazinyl, each optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(48) $R^5$ is $C_{1-9}$ heteroaryl which is selected from pyrazolyl and pyridinyl, each optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(49) $R^5$ is $C_{1-9}$ heteroaryl which is pyridinyl optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(50) $R^5$ is $C_{1-9}$ heteroaryl which is selected from pyridin-2-yl and pyridin-3-yl, each optionally substituted with from 1 to 3 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(51) $R^5$ is $C_{1-9}$ heteroaryl which is selected from 2-($C_{1-6}$ alkoxy)pyridin-3-yl and 4-($C_{1-6}$ alkoxy)pyridin-3-yl, each optionally substituted with 1 or 2 substituents independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo;

(52) $R^5$ is $C_{1-9}$ heteroaryl which is selected from 2-methoxypyridin-3-yl and 4-methoxypyridin-3-yl, each optionally substituted with 1 or 2 substituents independently selected from:
(a) amino optionally substituted with 1 or 2 $C_{1-4}$ alkyl;
(b) halo, hydroxy; oxo, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, $C_{1-4}$ alkoxy, and amino optionally substituted with 1 or 2 $C_{1-4}$ alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
(53) $R^5$ is $C_{1-9}$ heteroaryl which is pyridin-2-yl optionally substituted with from 1 or 3 substituents independently selected from:
(a) amino optionally substituted with 1 or 2 $C_{1-4}$ alkyl;
(b) halo, hydroxy, oxo, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, $C_{1-4}$ alkoxy, and amino optionally substituted with 1 or 2 alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
(54) $R^5$ is $C_{1-9}$ heteroaryl which is 2-oxo-1,2-dihydropyridin-3-yl optionally substituted with 1 or 2 substituents independently selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, $C_{1-4}$ alkoxy, and amino optionally substituted with 1 or 2 $C_{1-4}$ alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
(55) $R^5$ is $C_{1-9}$ heteroaryl which is N-methyl-2-oxo-1,2-dihydropyridin-3-yl optionally substituted with a group selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, $C_{1-4}$ alkoxy, and amino optionally substituted with 1 or 2 $C_{1-4}$ alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
(56) $R^5$ is $C_{1-9}$ heteroaryl which is pyrazolyl optionally substituted with from 1 to 3 substituents independently selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, alkoxy, and amino optionally substituted with 1 or 2 $C_{1-4}$ alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
(57) $R^5$ is $C_{1-9}$ heteroaryl which is selected from 3-($C_{1-6}$ alkoxy)-1H-pyrazol-4-yl and 5-($C_{1-6}$ alkoxy)-1H-pyrazol-4-yl, each optionally substituted with 1 or 2 substituents independently selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, $C_{1-4}$ alkoxy, and amino optionally substituted with 1 or 2 $C_{1-4}$ alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
(58) $R^5$ is $C_{1-9}$ heteroaryl which is selected from 3-methoxy-1-methyl-1H-pyrazol-4-yl and 5-methoxy-1-methyl-1H-pyrazol-4-yl, each optionally substituted with a substituent selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, $C_{1-4}$ alkoxy, and amino optionally substituted with 1 or 2 $C_{1-4}$ alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo; or
(59) $R^5$ is $C_{1-9}$ heteroaryl which is selected from 2,3-dihydrobenzofuranyl, 2-oxo-1,2,5,6,7,8-hexahydroquinolinyl, 4-oxo-4H-pyrido[1,2-c]pyrimidinyl, 5,6,7,8-tetrahydropyrazolo[5,1-b][1,3]oxazepinyl, 5,6-dihydro-4H-pyrrolo[1,2-b]pyrazolyl, 5-oxo-5H-thiazolo[3,2-a]pyrimidinyl, 6,7-dihydro-5H-cyclopenta[b]pyridinyl, 6,7-dihydro-5H-pyrazolo[5,1-b][1,3]oxazinyl, and pyrrolo[1,2-c]pyrimidinyl, each optionally substituted with 1 or 2 substituents independently selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
(i) from 1 to 3 substituents independently selected from halo, oxo, $C_{1-4}$ alkoxy, and amino optionally substituted with 1 or 2 $C_{1-4}$ alkyl; or
(ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo.
In addition, or as an alternative, to one of embodiments (41) through (59) in the preceding paragraphs, compounds of Formula 1 include those in which:

(60) each of the optional substituents on the $R^5$ heteroaryl moiety is independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo. wherein the $C_{3-5}$ heterocyclyl moiety is monocyclic, has 5 or 6 ring members in which 1 or 2 ring members are heteroatoms, and the heteroatoms are independently selected from N, O and S;
(61) each of the optional substituents on the $R^5$ heteroaryl moiety is independently selected from:
  (a) amino optionally substituted with 1 or 2 $C_{1-4}$ alkyl;
  (b) halo, hydroxy, oxo, $C_{3-6}$ cycloalkyl, and $C_{2-6}$ heterocyclyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo. wherein the $C_{3-5}$ heterocyclyl moiety is monocyclic, has 5 or 6 ring members in which 1 or 2 ring members are heteroatoms, one of the heteroatoms is N, and if present, the other heteroatom is selected from N, O and S;
(62) each of the optional substituents on the IV heteroaryl moiety is independently selected from:
  (a) amino optionally substituted with 1 or 2 $C_{1-4}$ alkyl;
  (b) halo, hydroxy, oxo, $C_{3-6}$ cycloalkyl, and morpholinyl;
  (c) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo;
  (d) $C_{1-6}$ alkoxy optionally substituted with from 1 to 3 halo; and
  (e) phenyl optionally substituted with from 1 to 3 halo; or
(63) each of the optional substituents on the $R^{-5}$ heteroaryl moiety is independently selected from:
  (a) halo, hydroxy, oxo, $C_{3-6}$ cycloalkyl, morpholinyl, and phenyl;
  (b) $C_{1-6}$ alkyl optionally substituted with:
    (i) from 1 to 3 substituents independently selected from halo, oxo, $C_{1-4}$ alkoxy, and amino optionally substituted with 1 or 2 $C_{1-4}$ alkyl; or
    (ii) a substituent selected from phenyl and pyridinyl, each optionally substituted with from 1 to 3 halo; and
  (c) $C_{1-6}$ alkoxy optionally substituted with from 1 to 3 halo.

In addition, or as an alternative, to one of embodiments (1) through (63) in the preceding paragraphs, compounds of Formula 1 include those in which:
(64) $X^9$ is $CR^9$ and $X^{12}$ is $CR^{12}$;
(65) $X^9$ is $CR^9$ and $X^{12}$ is N; or
(66) $X^9$ is N and $X^{12}$ is $CR^{12}$.

In addition, or as an alternative, to one of embodiments (64) through (66) in the preceding paragraphs, compounds of Formula 1 include those in which:
(67) $R^8$, $R^9$, $R^{10}$, $R^{11}$, and $R^{12}$ are each independently selected from hydrogen, halo, cyano, $C_{1-4}$ alkyl optionally substituted with from 1 to 3 halo, and $C_{1-4}$ alkoxy optionally substituted with from 1 to 3 halo;
(68) $R^8$, $R^9$, $R^{10}$, $R^{11}$, and $R^{12}$ are each independently selected from hydrogen, halo, cyano, methyl optionally substituted with from 1 to 3 fluoro, and methoxy optionally substituted with from 1 to 3 fluoro;
(69) $R^8$, $R^9$, $R^{10}$, $R^{11}$, and $R^{12}$ are each independently selected from hydrogen, chloro, fluoro, cyano, methyl optionally substituted with from 1 to 3 fluoro, and methoxy optionally substituted with from 1 to 3 fluoro, or
(70) $R^8$, $R^9$, $R^{10}$, $R^{11}$, and $R^{12}$ are each independently selected from hydrogen, chloro, fluoro, cyano, methyl, and methoxy optionally substituted with from 1 to 3 fluoro.

In addition, or as an alternative, to one of embodiments (1) through (70) in the preceding paragraphs, compounds of Formula 1 include those in which:
(71) L is selected from O, $S(O_2)$, and $C(R^6)R^7$;
(72) L is selected from O and $C(R^6)R^7$,
(73) L is O; or
(74) L is $C(R^6)R^7$.

In addition, or as an alternative, to one of embodiments (1) through (70) in the preceding paragraphs, compounds of Formula 1 include those in which:
(75) L is $C(R^6)R^7$, and $R^6$ and $R^7$ are each independently selected from hydrogen, halo, $C_{1-3}$ alkyl, and $C_{1-3}$ alkoxy, or together with the carbon atom to which they are attached form a carbonyl;
(76) L is $C(R^6)R^7$, and $R^6$ and $R^7$ are each independently selected from hydrogen, halo, methyl, and methoxy, or together with the carbon atom to which they are attached form a carbonyl; or
(77) L is $C(R^6)R^7$, and $R^6$ and $R^7$ are each independently selected from hydrogen, fluoro, methyl, and methoxy, or together with the carbon atom to which they are attached form a carbonyl.

In addition, or as an alternative, to one of embodiments (1) through (77) in the preceding paragraphs, compounds of Formula 1 include those in which (78) Z is CH.

In addition, or as an alternative, to one of embodiments (1) through (78) in the preceding paragraphs, compounds of Formula 1 include those in which (79) $R^4$ is hydrogen.

Compounds of Formula 1 include embodiments (i) through (79) described in the preceding paragraphs and all compounds specifically named above and in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodic/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66: 1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., D20, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —$COO^-Na^+$, —$COO^-K^+$, —$SO_3^-Na^+$) or polar non-ionic moiety (such as —$N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2H$ and $^3H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{13}C$ and $^{14}C$; isotopes of iodine, such as $^{13}N$ and $^{15}N$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxyethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide. N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric tri-amide).

In the schemes, below, substituent identifiers (e.g., L, $X^1$, $X^2$, $X^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include an $R^5$ substituent having a potentially reactive amine. In such cases, R5 would include the moiety with or without, say, a Boc or Cbz group attached to the amine.

Scheme A shows a general method for preparing compounds of Formula 1. According to the method, an aromatic nitro compound (A1. $X^4$=fluoro, chloro) is reacted with a cyclic amine (A2) in the presence of a non-nucleophilic base (e.g., Et₃N, DIPEA, K₂CO₃) and a compatible aprotic solvent (e.g., DCM, DMSO, ACN) to give an ortho-substituted aromatic nitro intermediate (A3). Step 1 may be carried out at temperatures which range from 0° C. to about 80° C. The nitro group of intermediate A3 is subsequently reduced (step 2) to give an aromatic amine (A4) which is reacted (step 3) with an aromatic (or heteroaromatic) carboxylic acid derivative (A5, $X^5$=OH, Cl) to give a carboxamide (1). Though not shown in Scheme A, the carboxamide (1, $R^4$ is H) may be optionally reacted with an alkyl halide (e.g., R41, R4=C1-4 alkyl) in the presence of a strong non-nucleophilic base (e.g. NaH) and a compatible polar aprotic solvent (e.g. DMF) to give an N-alkyl carboxamide (Formula 1 when R4 is C1-4 alkyl).

The nitro reduction (step 2) may be carried out under H atmosphere at room temperature in the presence of a palladium catalyst (e.g., 10% Pd/C) and one or more compatible polar solvents (e.g. ACN, EtOAc, EtOH, MeOH, THF). Alternatively, nitro intermediate A3 may be reacted with NH₄Cl and zinc in one or more compatible polar solvents (e.g. ACN, MeOH) at a temperature of about 0° C. to room temperature.

When $X^5$ is OH, step 3 may be carried out using standard amide coupling agents, such as HATU, DCC, EDC hydrochloride, T3P, and 2-chloro-1-methylpyridin-1-ium iodide, in the presence of a non-nucleophilic base (e.g., Et₃N, DIPEA) and one or more compatible polar solvents (e.g. DCM, DMA, DMF, THF). The amide coupling may be carried out at temperatures which range from room temperature to about 80° C. HOBt may be used to facilitate the reaction. Alternatively, the aromatic amine (A4) may be reacted with A5 ($X^5$ is Cl) in the presence of a strong non-nucleophilic base (LiHMDS) to give the compound of Formula 1. The acylation may be carried out in a compatible aprotic solvent (e.g., THF, DMF) at room temperature or below Scheme A

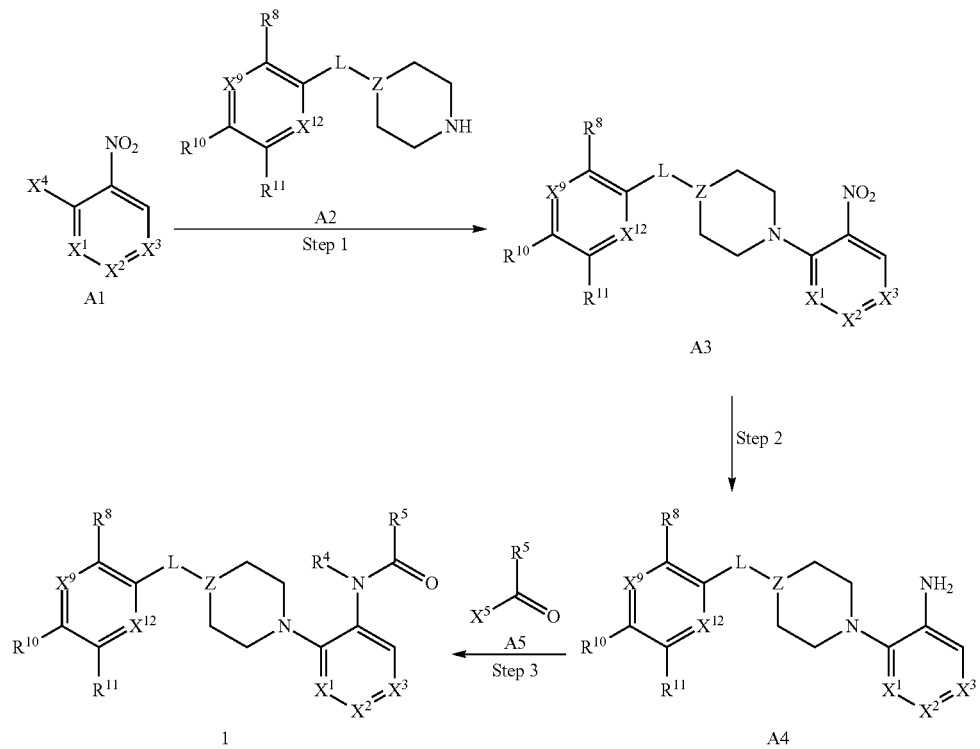

Scheme B shows a general method for preparing compounds of Formula 1 when L is O and Z is CH (Formula 1A). As in Scheme A, an aromatic nitro compound (A1, $X^4$=fluoro, chloro) is reacted (step 1) with a cyclic amine (piperidin-4-ol, B1) in the presence of a non-nucleophilic base and a compatible aprotic solvent to give an ortho-substituted aromatic nitro intermediate (B2). The nitro group of intermediate B2 is subsequently reduced (step 2) to give an aromatic amine (B3) which is reacted (step 3) with an aromatic (for example, a heteroaromatic) carboxylic acid derivative (A5, $X^5$=OH, Cl) to give a hydroxy piperidine-substituted aromatic (for example, heteroaromatic) carboxamide (B4). Though not shown in Scheme B, the carboxamide (B4, $R^4$ is H) may be optionally reacted with an alkyl halide to give an N-alkyl carboxamide (B4 when $R^4$ is $C_{1-4}$ alkyl). As indicated in Scheme B, carboxamide B4 is reacted with an aryl alcohol (B5) to give the compound of Formula 1A. The Mitsunobu reaction (step 4) is carried out in the presence of a phosphine (e.g. $PPh_3$, $P(CH_3)_3$) and an activating reagent (e.g. diethyl azodicarboxylate, diisopropyl azodicarboxylate), or a phosphorane ylide such as 2-(tributylphosphoranylidene)acetonitrile, and a compatible solvent (e.g., ACN, DCM, THF, toluene) at a temperature of about 0° C. to about 100° C.

Scheme C shows a general method for preparing compounds of Formula 1 when L is $C(R^6)R^7$ and Z is N (Formula 1B). As in Scheme A, an aromatic nitro compound (A1, $X^4$=fluoro, chloro) is reacted (step 1) with a cyclic amine (C1) in the presence of a non-nucleophilic base and a compatible aprotic solvent to give an ortho-substituted aromatic nitro intermediate (C2). A protective group ($X^6$=Boc, Cbz, etc.) is attached to one of the nitrogen ring atoms of cyclic amine C1. The nitro group of intermediate C2 is subsequently reduced (step 2) to give an aromatic amine (C3) which is reacted (step 3) with an aromatic (for example, a heteroaromatic) carboxylic acid derivative (A5, $X^5$=OH, Cl) to give a protected piperazine-substituted aromatic carboxamide (C4). Though not shown, the carboxamide (C4, $R^4$ is H) may be optionally reacted with an alkyl halide to give an N-alkyl carboxamide (C4 when $R^4$ is $C_{1-4}$ alkyl).

Following removal (step 4) of $X^6$, the de-protected piperazine derivative (C5) may be reacted (step 5) with an aryl aldehyde (C6, $X^7$=C(O)H) in the presence of a mild reducing agent, such as sodium cyanoborohydride or sodium triacetoxyborohydride, and a compatible solvent (e.g., DCM, MeOH) to give the compound of Formula 1B in which $R^6$ and $R^7$ are both H. The reductive amination may also be carried out using 5-ethyl-2-methylpyridine borane in the presence of HOAc and MeOH at elevated temperature (e.g., about 50° C.). Alternatively, the de-protected piperazine derivative (C) may be reacted with an aryl acid chloride (C6, $X^7$ is C(O)Cl) or an aryl methyl bromide (C6, $X^7$ is $CH_2Br$) to give the compound of Formula 1B in which $R^6$ and $R^7$ together represent an oxo group or are both H.

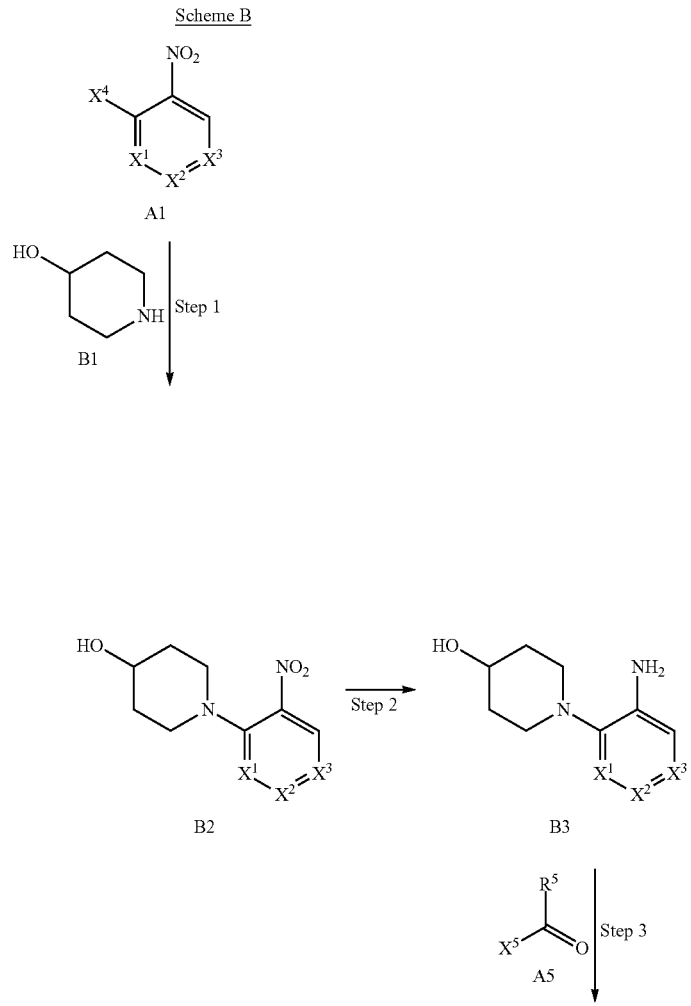

Scheme B

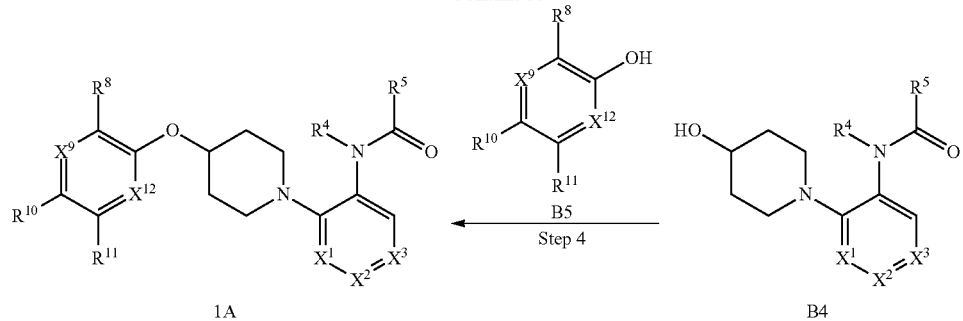

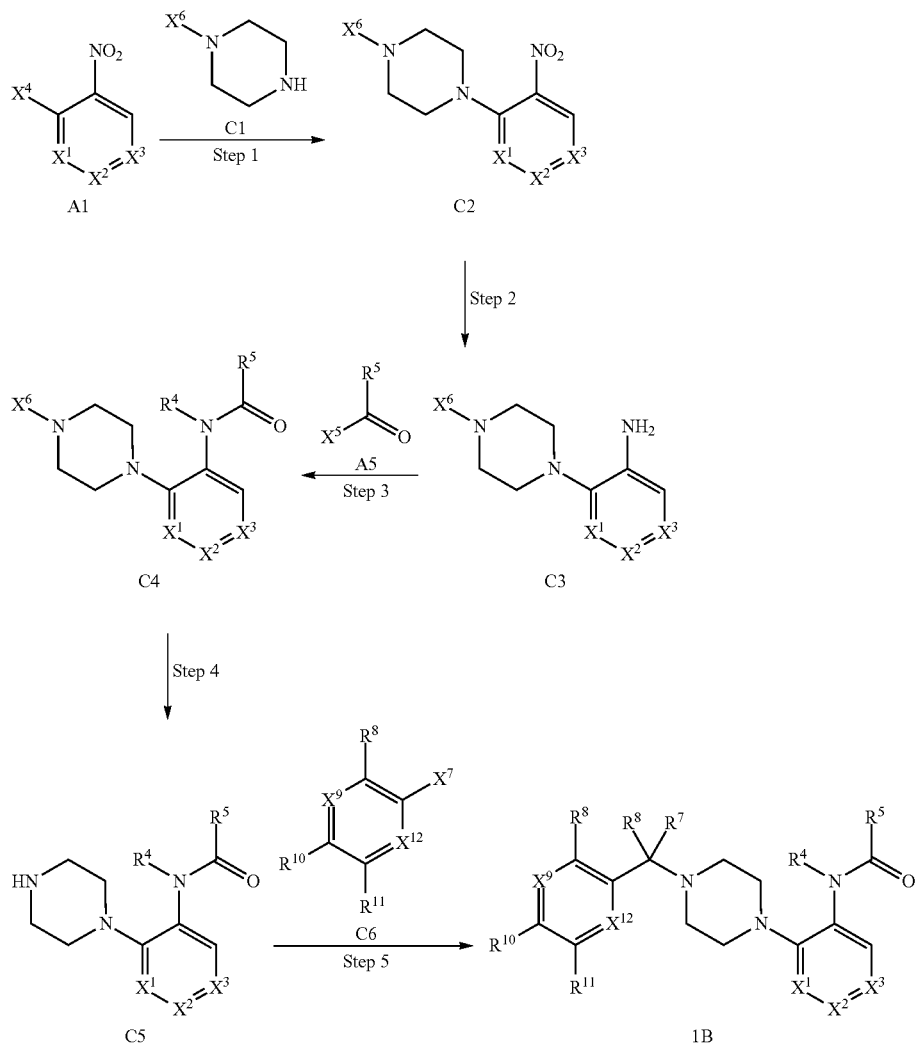

Scheme D shows an alternative method for preparing compounds of Formula 1. According to the method, a dihalo aromatic starting material (D1, $X^8$=chloro, bromo) is reacted with a cyclic amine (A2) in the presence of a non-nucleophilic base (e.g., $Et_3N$, DIPEA, $K_2CO_3$) and a compatible aprotic solvent (e.g., DCM, DMSO, ACN) to give an aryl halide intermediate (D2). Step 1 may be carried out at temperatures which range from 0° C. to about 80° C. Aryl halide (D2) is reacted (step 2) with an aromatic (for example, a heteroaromatic) amide (D3) to give the compound of Formula 1. Step 2 is carried out in the presence of a palladium catalyst with ligand (e.g. $Pd_2(dba)_3$ and Xantphos) and compatible solvent (e.g. toluene) at elevated temperature (e.g. up to reflux).

Scheme D

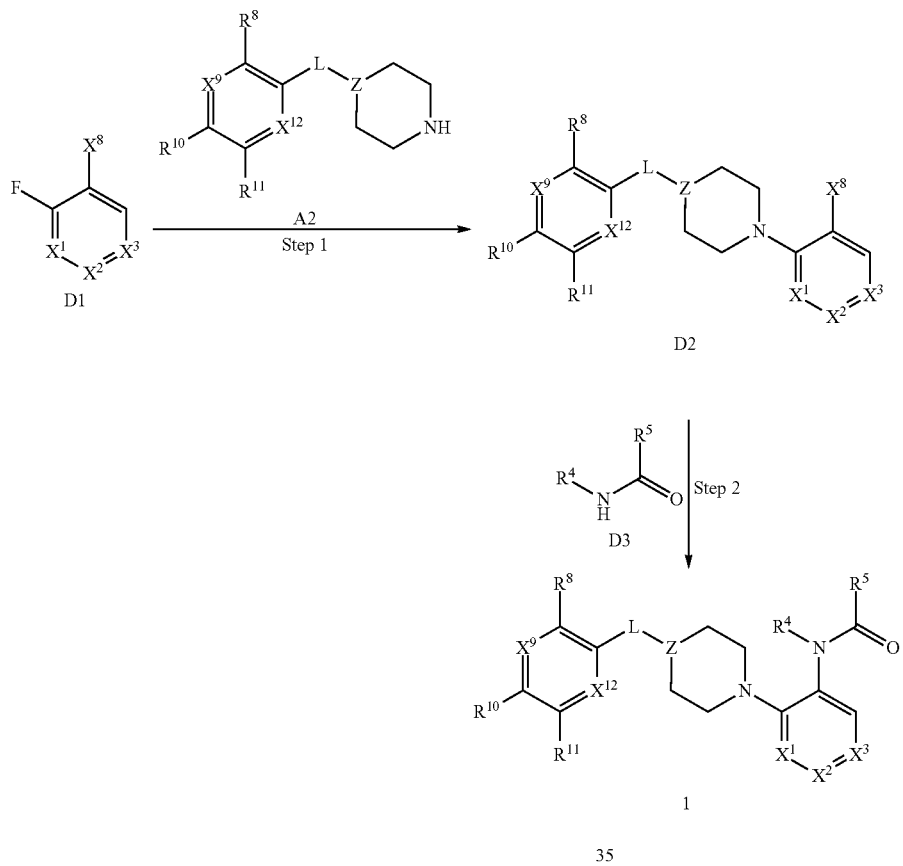

The methods depicted in the schemes may be varied as desired. For example, protecting groups may be added or removed and products (including intermediates) may be further elaborated via, for example, alkylation, acylation, hydrolysis, oxidation, reduction, amidation, sulfonation, alkynation, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), Remington: The Science and Practice of Pharmacy (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, Expert Opinion in Therapeutic Patents (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*. Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See. e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., pediatric patient) whose mass falls outside of this mass range.

The compounds of Formula 1 may be used to treat diseases, disorders, and conditions for which modulation of GPR6 is indicated. As mentioned above, antagonism or inverse agonism of Gs-coupled GPR6 provides a functional alternative to dopamine-mediated activation of D2 receptors. As such, compounds that modulate the activity of GPR6 may be useful for treating a variety of neurological and psychiatric disorders, including movement disorders such as Parkinson's disease, levodopa-induced dyskinesias, and Huntington's disease, as well as drug addiction, eating disorders, cognitive disorders, schizophrenia, bipolar disorder, epilepsy, and depression.

The pathological hallmark of Parkinson disease is neuronal cell loss within the substantia nigra. Degeneration of the nigrostriatal pathway causes reduction in the striatal concentration of dopamine which results in motor and nonmotor clinical manifestations. Many Parkinson's disease patients are treated with levodopa, a prodrug for dopamine. Levodopa has common serious side effects including induced dyskinesia (LID), impulsive control disorders (ICD), psychotic symptoms and sleep disturbances. LID is a progressive disease, with about 90% of Parkinson's disease patients developing LID within 10 years. Irreversible adaptations occur in D1 receptor signaling in MSNs in rodent models of LID, including reduced desensitization leading to hypersensitivity in the direct pathway. Genetic inactivation of D1 but not D2 receptors abolishes LID in mice. However blockade of D1 receptor signaling does not affect the antiparkinsonian efficacy of levodopa.

The claimed and disclosed compounds may be combined with one or more other pharmacologically active compounds or therapies to treat one or more diseases, disorders or conditions associated with GPR6. Such combinations may offer significant therapeutic advantages, including fewer side effects, improved ability to treat underserved patient populations, or synergistic activity. For example, compounds of Formula 1, which include compounds specifically named above, and their pharmaceutically acceptable complexes, salts, solvates and hydrates, may be administered simultaneously, sequentially or separately in combination with one or more compounds or therapies for treating movement disorders, including Parkinson's disease. These compounds include levodopa; DOPA decarboxylase inhibitors such as carbidopa, bensrazid, methyldopa, α-difluoromethyl-DOPA, and 3',4',5,7-tetrahydroxy-8-methoxyisoflavone; dopamine agonists, such as apomorphine hydrochloride, bromocriptine, rotigotine, pramipexole, and ropinirole; anticholinergics, such as trihexyphenidyl and benztropine mesylate; B-selective monoamine oxidase (MAO-B) inhibitors, such as selegiline and rasagiline; and catechol O-methyl transferase (COMT) inhibitors, such as entacapone and tolcapone.

In addition to drugs used to treat movement disorders, the compounds of Formula 1 may be combined with medications used to treat Alzheimer's disease and other diseases, disorders and conditions affecting cognition. Such medications include beta-secretase inhibitors, gamma-secretase inhibitors, HMG-CoA reductase inhibitors, nonsteroidal anti-inflammatory drugs (NSAIDs, such as apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac), vitamin E, and anti-amyloid antibodies. Specific examples of compounds used to treat Alzheimer's disease include donepezil, rivastigmine, memantine, and galantamine.

Additionally or alternatively, the compounds of Formula 1 may be combined with sedatives, hypnotics, anxiolytics, antipsychotics, tranquilizers, and other medications that are used in the treatment of neurological or psychiatric diseases. For example, the compounds of Formula 1 may be combined with one or more agents for treating depression (antidepressants) and/or schizophrenia (atypical or typical antipsychotics) including amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran, lurasidone, mirtazapine, nefazodone, nortriptyline, olanzapine, paliperidone, paroxetine, perphenazine, phenelzine, protriptyline, quetiapine, risperidone, selegiline, sertraline, tranylcypromine, trazodone, trimipramine, venlafaxine, vilazodone, and vortioxetine, and ziprasidone.

Likewise, the compounds of Formula 1 may be combined with one or more agents for treating anxiety (anxiolytics) including benzodiazepines (alprazolam, chlordiazepoxide, clobazepam, clonazepam, clorazepate, diazepam, estazolam, flurazepam, lorazepam, midazolam, oxazepam, prazepam, quazepam, temazepam, and triazolam), antihistamines (hydroxyzine), non-benzodiazepines (eszopiclone, zaleplon, zolpidem, and zopiclone) and buspirone.

The compounds of Formula 1 may also be combined with one or more agents for treating epilepsy (antiepileptics or anticonvulsants) including acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Biological Activity

The activity of compounds as GPR6 modulators may be determined by a variety of methods, including in vitro and in vivo methods.

I. In Vitro Inhibition of cAMP (EC50)

This cell based assay measures the ability of test compounds to inhibit the constitutive cAMP activity of GPR6 receptor expressed in CHO-K1 cells. CHO cells are stably expressed with GPR6 receptor, whose expression is controlled by a tetracycline inducible element. The cells were cultured in medium containing F12K, 10% FBS, 1% Penn/Strep, 200 μg/mL Hygromycin. GPR6 receptor expression is induced for 20 hours with 2 μg/mL doxycycline (Sigma D9891) in growth media. After addition of doxycycline, the cells are plated at a density of 450-750 cells per well in 96-well half-volume black tissue culture plates (Costar) and placed in an incubator (37° C., 5% $CO_2$) for 20 hours prior to cAMP assays.

Culture media is removed from the cells and they are washed with 50 μL/well of Ringer's Buffer ($MgCl_2$ 0.047 mg/mL, NaH$_2$PO$_4$ 0.18 mg/mL, Na$_2$HPO$_4$ 0.1 mg/mL, KCl 0.34 mg/mL, NaHCO$_3$ 1.26 mg/mL, D-glucose 1.8 mg/mL, NaCl 7 mg/mL; pH=7.4). The test compounds are suspended in DMSO, diluted in Ringer's Buffer containing 0.5% fatty acid free BSA plus 300 μM IBMX, and incubated on the cells for 45 minutes at 37° C. and 5% CO$_2$. After incubation, the cells are conditioned for 10 minutes at room temp with Eu-cAMP tracer solution from a Perkin Elmer Lance HTRF Ultra cAMP assay kit (TRF0263). Then ULight™-anti-cAMP solution from the Lance HTRF kit is added and incubated on a shaker at room temp for 1 hour prior to HTRF detection in a Perkin Elmer Envision plate reader. EC$_{50}$ curves are generated with a four-parameter logistic equation using GraphPad Prism 5.03.

II. In Vivo Parkinson's Disease Model Haloperidol-Induced Catalepsy

The motor symptoms of Parkinson's disease include akinesia, bradykinesia, rigidity, tremor and postural abnormalities and are associated with the loss of nigral dopaminergic cells and a decline in striatal dopamine levels. Administration of haloperidol to rodents leads to a transient Parkinsonian-like state that is reversed by the administration of levodopa and other drugs that have been clinically validated for the treatment of Parkinson's disease. See Duty, S. & Jenner, P. Br. *J. Pharmacol.* 164:1357-1391 (2011). Haloperidol antagonizes dopamine D2, and to a lesser extent, D1 receptors in medium spiny neurons that comprise the indirect and direct pathways of the motor circuit, respectively. The resultant block of striatal dopamine transmission results in abnormal downstream firing within the basal ganglia circuits that is manifest as symptoms of muscle rigidity and catalepsy. Catalepsy has been postulated to reflect the clinical features of Parkinson's disease, whereby patients experience an inability to initiate movements.

Male C57B16 mice weighing 25-35 g are used. Catalepsy is induced by the subcutaneous (sc) administration of the dopamine receptor antagonist haloperidol (0.45 mg/kg) at least 30 minutes before testing the animals on a vertical grid test. For this test, the rats or mice are placed on a wire mesh cover of a 25 cm×43 cm plexiglass cage placed at an angle of about 70 degrees with the bench table. The subject is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 seconds for rats. For mice, the front paws of the mouse is placed on a horizontal metal bar raised 2″ above a Plexiglas platform and time is recorded for up to 30 seconds per trial. The test ends when the animal's front paws return to the platform or after 30 seconds. The test is repeated three times and the average of the three trials is reported as the intensity index of catalepsy. Animals evaluated at 30 minutes after dosing are reevaluated at 60 or 90 minutes post dosing of haloperidol.

Efficacy of GPR6 modulators to reverse haloperidol induced catalepsy is measured 30 minutes, 60 minutes, and/or 90 minutes after dosing the subjects with 0.45 mg/kg ip (intraperitoneal injection) of haloperidol along with the GPR6 modulator test compound. A representative number of compounds of Formula 1 are administered in a dose range from 0.1 to 100 mg/kg (po in 0.5% methyl cellulose) in conjunction with haloperidol. The A2a antagonist SCH 420814 (preladenant) is dosed at 3 mg/kg ip as a positive control. In some embodiments, at least one of N-(4-(4-(2,4-difluorophenoxy)piperidin-1-yl)-2-methylpyrimidin-5-yl)-2-methoxynicotinamide (Example 18), 4-(4-(2,4-difluorophenoxy)piperidin-1-yl)-5-(2-methoxynicotinamido)-N,N-dimethylpicolinamide (Example 31), and 4-(4-(2,4-difluorophenoxy)piperidin-1-yl)-5-(2-methoxy-6-methylnicotinamido)-N,N-dimethylpicolinamide (Example 283) may be used to treat Parkinson's disease.

Preparations

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: CDCl$_3$ (deuterochloroform), DMSO-d$_6$ (deuterodimethylsulfoxide), CD$_3$OD (deuteromethanol), CD$_3$CN (deuteroacetonitrile), and THF-ds (deuterotetrahydrofuran). The mass spectra (m/z for [M+H]$^+$) were recorded using either electrospray ionization (ESI-MS) or atmospheric pressure chemical ionization (APCI-MS) mass spectrometry.

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Phenomenex Gemini™5p, C18, 30 mm×150 mm; Axia™, 5μ, 30 mm×75 mm) under acidic conditions ("acid mode") eluting with CH$_3$CN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM NH$_4$HCO$_3$. Preparative TLC is typically carried out on silica gel 60 F$_{234}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., H$_2$) atmosphere are typically carried out at a pressure of about 1 atmosphere (14.7 psi).

Preparation x1: methyl 3-methoxy-1H-pyrazole-4-carboxylate

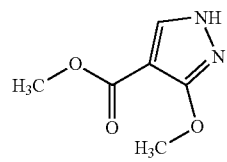

To a solution of dimethyl 2-(methoxymethylene)malonate (15.0 g, 86 mmol) dissolved in EtOH (150 mL) were added hydrazine (2.78 mL, 89 mmol) followed by HCl (2.64 mL, 86 mmol). The mixture was heated under reflux overnight. The solvent was removed and the resulting residue was dispersed in water (120 mL). The precipitate was filtered and washed with 1 N HCl (aq). The filtrate was cautiously made basic with solid K$_2$CO$_3$ and then extracted with EtOAc. The organic phase was washed with saturated (aq) NaHCO$_3$ and brine, dried over MgSO$_4$, and concentrated to give the (crude) title compound as a white semisolid (3.99 g, 29.7%). ESI-MS m/z [M+H]$^+$ 157.0.

Preparation x2: methyl 1-(2-fluoroethyl)-3-methoxy-1H-pyrazole-4-carboxylate

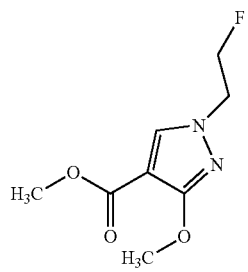

To a solution of methyl 3-methoxy-1H-pyrazole-4-carboxylate (1.01 g, 6.47 mmol) dissolved in ACN (10 mL) were added $K_2CO_3$ (1.341 g, 9.70 mmol) and 1-bromo-2-fluoroethane (0.903 g, 7.12 mmol). The reaction mixture was stirred at RT overnight. DMF (4 mL) was added to the reaction mixture and stirring was continued over the weekend. Additional 1-bromo-2-fluoroethane (0.903 g, 7.12 mmol) was added and stirring was continued for 2 days. The mixture was treated with water and extracted with EtOAc. The organic phase was washed with brine, dried over $MgSO_4$, and concentrated. The residue was purified by flash chromatography (Biotage® 120 g column) eluting with a gradient of 4:1 to 1:1 hexane/EtOAc. The product-containing fractions were collected, combined, and concentrated to give the title compound as a white solid (812 mg, 62.1%). ESI-MS m/z $[M+H]^+$ 203.1.

Preparation x3: 1-(2-fluoroethyl)-3-methoxy-1H-pyrazole-4-carboxylic acid

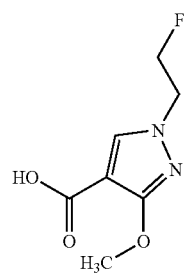

To a solution of methyl 1-(2-fluoroethyl)-3-methoxy-1H-pyrazole-4-carboxylate (0.812 g, 4.02 mmol) dissolved in dioxane (16 mL) was added 2 M LiOH (8.03 mL, 16.06 mmol). The mixture was stirred at RT over the weekend. The mixture was subsequently stirred at 50° C. for 2 hours, then acidified with 1 N HCl (aq), and extracted with EtOAc. The organic phase was dried over $MgSO_4$ and concentrated to give the (crude) title compound as a white solid (0.737 mg, 98%). ESI-MS m/z $[M+H]^+$ 189.1.

Preparation x4: methyl 1-(hydroxymethyl)-3-methoxy-1H-pyrazole-4-carboxylate

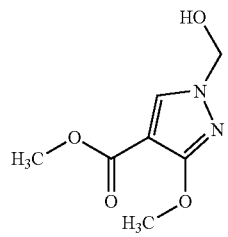

To a solution of methyl 3-methoxy-1H-pyrazole-4-carboxylate (1.030 g, 6.60 mmol) dissolved in THF (14 mL) was added formaldehyde in water (1.081 mL, 13.85 mmol). The mixture was stirred at RT over the weekend and then concentrated to dryness. The residue was treated with water and extracted with DCM (8×40 mL). The organic phase was dried over $MgSO_4$ and concentrated to give the (crude) title compound as white solid (1.28 g, 100%). ESI-MS m/z $[M+H]^+$ 187.0.

Preparation x5: methyl 1-(fluoromethyl)-3-methoxy-1H-pyrazole-4-carboxylate

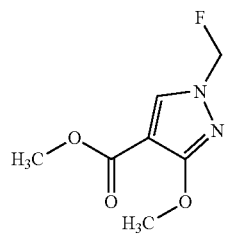

Methyl 1-(hydroxymethyl)-3-methoxy-1H-pyrazole-4-carboxylate (1.28 g, 6.88 mmol) was dissolve in THF (16 mL). The resulting solution was cooled to −78° C. and N,N-diethyl-1,1,1-trifluoro-$\lambda^4$-sulfanamine (0.908 mL, 6.88 mmol) was added dropwise. The reaction mixture was stirred at −78° C. for 5 minutes and then allowed to warm to RT over a period of 2 hours. The reaction mixture was subsequently treated with water and extracted with EtOAc. The organic phase was washed with saturated (aq) $NaHCO_3$ and brine, dried over $MgSO_4$, and concentrated to give the (crude) title compound as a white solid (1.01 g, 78%). ESI-MS m/z $[M+H]^+$ 189.1.

Preparation x6: 1-(fluoromethyl)-3-methoxy-1H-pyrazole-4-carboxylic acid

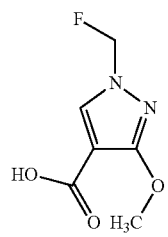

To a solution of methyl 1-(fluoromethyl)-3-methoxy-1H-pyrazole-4-carboxylate (1.015 g, 5.39 mmol) dissolved in dioxane (15 mL) was added 2 M LiOH (10.79 mL, 21.58 mmol). The reaction mixture was stirred at RT overnight and then acidified with 1 N HCl (aq) and extracted with EtOAc. The organic phase was dried over $MgSO_4$ and concentrated to give the (crude) title compound as a white solid (0.87 g, 93%). ESI-MS m/z [M+H]$^+$ 175.0.

Preparation x7: 4-(2-fluoro-4-methoxyphenoxy)-1-(4-(methylsulfonyl)-2-nitrophenyl)piperidine

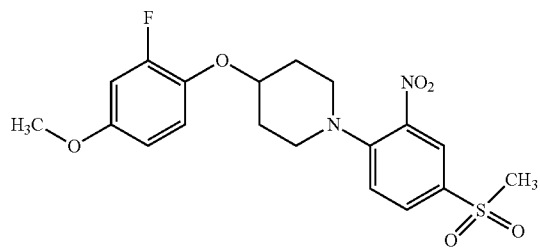 [SMILES: COc1ccc(OC2CCN(c3ccc(S(C)(=O)=O)cc3[N+](=O)[O-])CC2)c(F)c1]

To a solution of fluoro-4-(methylsulfonyl)-2-nitrobenzene (1.5 g, 6.84 mmol) dissolved in DCM (20 mL) was added $Et_3N$ (2.385 mL, 17.11 mmol). Next a solution of 4-(2-fluoro-4-methoxyphenoxy)piperidine, HCl (2.107 g, 6.84 mmol) in DCM (20 mL) was added dropwise through an addition funnel. The reaction mixture was stirred at RT overnight and then concentrated. The residue was purified by flash chromatography (Biotage® 80 g column) eluting with a gradient of 4:1 to 1:1 hexane/EtOAc. The product-containing fractions were collected and combined and then concentrated to give the title compound as a yellow solid (2.6 g, 90%).

Preparation x8: 2-(4-(2-fluoro-4-methoxyphenoxy)piperidin-1-yl)-5-(methylsulfonyl)aniline

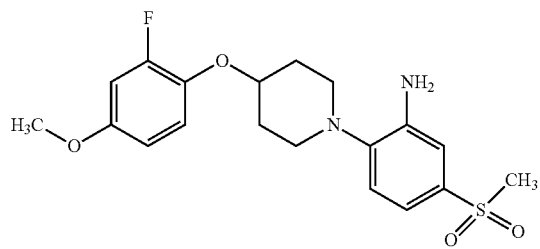

To a solution of 4-(2-fluoro-4-methoxyphenoxy)-1-(4-(methylsulfonyl)-2-nitrophenyl)piperidine (2.6 g, 6.13 mmol) dissolved in THF (30 mL) and EtOH (30.0 mL) was added palladium on activated carbon, 10%(0.652 g, 0.613 mmol). The mixture was evacuated and back-filled with hydrogen 3 times and then stirred at RT under hydrogen (balloon) overnight. The mixture was filtered. The filtrate was concentrated to give the (crude) title compound. ESI-MS m/z [M+H]$^+$ 395.3.

Preparation x9: 4-(2,4-difluorophenoxy)-1-(4-(methylsulfonyl)-2-nitrophenyl)piperidine

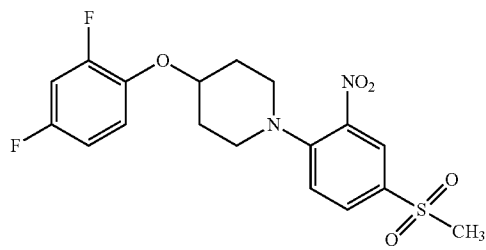 [SMILES: CS(=O)(=O)c1ccc(N2CCC(Oc3ccc(F)cc3F)CC2)c([N+](=O)[O-])c1]

To a solution of 1-fluoro-4-(methylsulfonyl)-2-nitrobenzene (1 g, 4.56 mmol) in DCM (20 mL) was added dropwise a solution of 4-(2,4-difluorophenoxy)piperidine hydrochloride (1.367 g, 5.47 mmol) and DIPEA (1.195 mL, 6.84 mmol) in DCM (10 mL). The solution stirred at 20° C. for 15 hours and then concentrated on Celite®. The product was purified by column chromatography (4 g silica gel column) eluting with a gradient of 0-70% EtOAc in heptane. The title compound was isolated as a yellow solid (1.88 g, 100%). $^1$H NMR (500 MHz, CDCl$_3$) δ ppm 1.97-2.07 (m, 2H), 2.07-2.16 (m, 2H), 3.08 (s, 3H), 3.18 (ddd, J=12.94, 6.35, 4.15 Hz, 2H), 3.52 (ddd, J=12.81, 9.15, 3.42 Hz, 2H), 4.48 (tt, J=6.22, 3.30 Hz, 1H), 6.82 (dddd, J=9.15, 7.69, 2.93, 1.71 Hz, 1H), 6.89 (ddd, J=11.23, 8.30, 2.93 Hz, H), 7.00 (td, J=9.03, 5.37 Hz, 1H), 7.22 (d, J=9.28 Hz, 1H), 7.93 (dd, J=8.79, 2.44 Hz, 1H), 8.37 (d, J=2.44 Hz, 1H); ESI-MS 413 [M+H]$^+$.

Preparation x10: 2-(4-(2,4-difluorophenoxy)piperidin-1-yl)-5-(methylsulfonyl)aniline

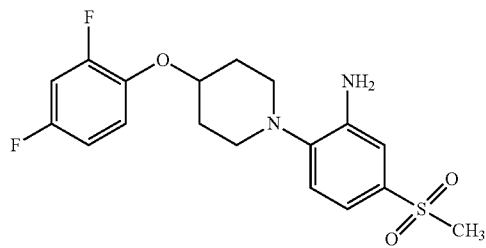

To a mixture of 4-(2,4-difluorophenoxy)-1-(4-(methylsulfonyl)-2-nitrophenyl)piperidine (575 mg, 1.394 mmol) and NH$_4$C (746 mg, 13.94 mmol) in MeOH (5 mL) and ACN (5 mL) was added zinc (638 mg, 9.76 mmol) portionwise. The reaction mixture was stirred at 20° C. for 3 days and then filtered. The solids retained on the filter were rinsed twice with MeOH. The filtrate from the first rinse yielded 0.35 g of product and the filtrate from the second rinse yielded 80 mg of product following solvent removal. The solids were combined to give the title compound as a tan solid (0.43 g, 81%). $^1$H NMR (500 MHz, DMSO-d$_6$) δ ppm 1.82-1.93 (m, 2H), 2.03-2.11 (m, 2H), 2.71-2.82 (m, 2H), 3.03-3.14 (m, 5H), 4.50 (dt, J=7.93, 4.09 Hz, 1H), 5.25 (s, 2H), 7.01 (tdd, J=8.66, 8.66, 2.93, 1.71 Hz, 1H), 7.05 (d, J=0.98 Hz, 2H), 7.18 (t, J=1.22 Hz, 1H), 7.25-7.34 (m, 2H); ESI-MS m/z [M+H]$^+$ 383.

Preparation x11: 4-(4-hydroxypiperidin-1-yl)-3-nitrobenzonitrile

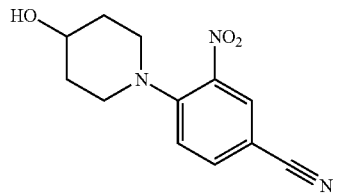 [SMILES: N#Cc1ccc(N2CCC(O)CC2)c([N+](=O)[O-])c1]

To a mixture of 4-fluoro-3-nitrobenzonitrile (1.38 g, 8.31 mmol) and DIPEA (2.176 mL, 12.46 mmol) in DCM (20 mL) was added dropwise a solution of piperidin-4-ol (1.008 g, 9.97 mmol) in DCM (5 mL). Not all of the starting materials dissolved, so a second portion of DCM (5 mL) followed by dioxane (1 mL) and MeOH (0.5 mL) were added, but a yellow solid remained undissolved. The reaction mixture was stirred at 20° C. for 2 hours and then concentrated on Celite®. The product was purified by column chromatography (40 g silica gel column) eluting with a gradient of 0-100% EtOAc in heptane to give the title compound as a yellow solid (1.96 g, 95%). $^1$H NMR (500 MHz, CDCl$_3$) δ ppm 1.69-1.79 (m, 2H), 1.99-2.09 (m, 2H), 3.02-3.15 (m, 2H), 3.37-3.48 (m, 2H), 4.02 (tt J=7.75, 3.72 Hz, 1H), 7.12 (d, J=8.79 Hz, 1H), 7.62 (dd, J=8.79, 1.95 Hz, 1H), 8.08 (d, J=2.44 Hz, 1H); ESI-MS m/z [M+H]$^+$ 248.

Preparation x12: 4-(4-((tert-butyldimethylsilyl)oxy)piperidin-1-yl)-3-nitrobenzonitrile

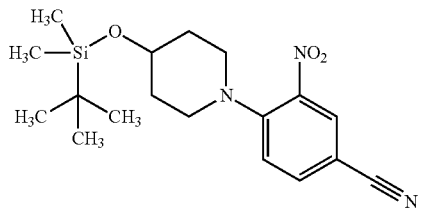 [SMILES: CC(C)(C)[Si](C)(C)OC1CCN(c2ccc(C#N)cc2N)CC1]

To a solution of 4-(4-hydroxypiperidin-1-yl)-3-nitrobenzonitrile (500 mg, 2.022 mmol) and imidazole (207 mg, 3.03 mmol) in DMF (4 mL) was added tert-butylchlorodimethylsilane (335 mg, 2.224 mmol). The solution was stirred at 20° C. for 2.5 hours and then diluted with diethyl ether (100 mL), washed with saturated (aq) NH$_4$Cl (100 mL) and brine, dried over MgSO$_4$, and concentrated in vacuo to give the title compound as a yellow solid (0.73 g, 100%). $^1$H NMR (500 MHz, CDCl$_3$) δ ppm 0.07-0.10 (m, 6H), 0.89-0.93 (m, 9H), 1.69 (dtd, J=12.69, 6.35, 6.35, 3.42 Hz, 2H), 1.91 (ddt, J=12.81, 9.15, 3.42, 3.42 Hz, 2H), 3.09 (ddd, J=12.69, 6.35, 3.91 Hz, 2H), 3.43 (ddd, J=12.69, 9.03, 3.17 Hz, 2H), 4.03 (tt, J=6.22, 3.30 Hz, 1H), 7.11 (d, J=8.79 Hz, 1H), 7.60 (dd, J=8.79, 1.95 Hz, 1H), 8.07 (d, J=1.95 Hz, 1H); ESI-MS m/z [M+H]$^+$ 362.

Preparation x13: 3-amino-4-(4-((tert-butyldimethylsilyl)oxy)piperidin-1-yl)benzonitrile

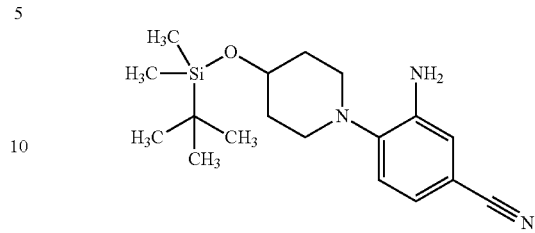

To a mixture of 4-(4-((tert-butyldimethylsilyl)oxy)piperidin-1-yl)-3-nitrobenzonitrile (500 mg, 1.383 mmol) and NH$_4$Cl (740 mg, 13.83 mmol) in MeOH (5 mL) and ACN (5.00 mL) was added zinc (633 mg, 9.68 mmol) portionwise. The reaction mixture was stirred at 20° C. for 3 days and then filtered. The solids retained on the filter were rinsed with MeOH. The filtrate was concentrated in vacuo on Celite® and purified by column chromatography (80 g silica gel column) eluting with a gradient of 0-40% EtOAc in heptane. The product-containing fractions were combined and concentrated under vacuum to give the title compound as a white solid (0.40 g, 87%). $^1$H NMR (500 MHz, DMSO-d$_6$) δ ppm 0.04-0.10 (m, 6H), 0.84-0.91 (m, 9H), 1.58-1.70 (m, 2H), 1.80-1.91 (m, 2H), 2.59-2.72 (m, 2H), 2.98-3.09 (m, 2H), 3.79-3.91 (m, 1H), 5.11 (s, 2H), 6.90-6.98 (m, 3H); ESI-MS m/z [M+H]$^+$ 332.

Preparation x14 N-(2-(4-((tert-butyldimethylsilyl)oxy)piperidin-1-yl)-5-cyanophenyl)-1-methyl-2-oxo-1,2-dihydropyridine-3-carboxamide

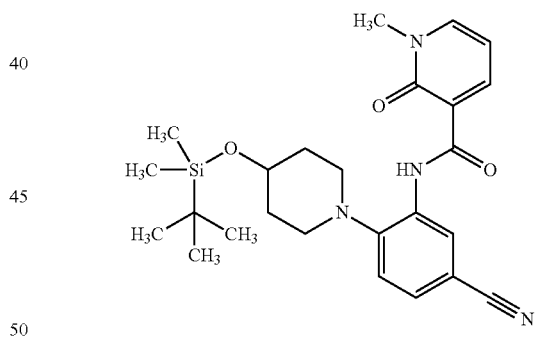

A solution of 3-amino-4-(4-((tert-butyldimethylsilyl)oxy)piperidin-1-yl)benzonitrile (400 mg, 1.207 mmol), 1-methyl-2-oxo-1,2-dihydropyridine-3-carboxylic acid (277 mg, 1.810 mmol), HATU (688 mg, 1.810 mmol) and Et$_3$N (0.336 mL, 2.413 mmol) in DMF (5 mL) was heated at 50° C. for 2 hours. The reaction mixture was then diluted with diethyl ether (250 mL) and washed with saturated (aq) NH$_4$Cl (200 mL) and brine. Ethyl acetate (20 mL) was added to dissolve some solids. The organic phase was dried over MgSO$_4$, which was rinsed with EtOAc, and concentrated in vacuo. The product was purified by column chromatography (40 g silica gel column) eluting with a gradient of 0-100% EtOAc in heptane to give the title compound as a white solid (494 mg, 88%). $^1$H NMR (500 MHz, DMSO-d$_6$) δ ppm 0.07-0.10 (m, 6H), 0.88-0.91 (m, 9H), 1.76-1.86 (m, 2H), 1.93-2.02 (m, 2H), 2.77 (ddd, J=11.59, 8.42, 2.93

Hz, 2H), 3.01-3.09 (m, 2H), 3.62 (s, 3H), 3.88-3.97 (m, 1H), 6.59 (dd, J=7.32, 6.35 Hz, 1H), 7.33 (d, J=8.30 Hz, 1H), 7.53 (dd, J=8.30, 1.95 Hz, 1H), 8.16 (dd, J=6.35, 2.44 Hz, 1H), 8.47 (dd, J=7.32, 1.95 Hz, 1H), 8.80 (d, J=1.95 Hz, H), 12.38 (s, 1H); ESI-MS m/z [M+H]+ 467.

Preparation x15: N-(5-cyano-2-(4-hydroxypiperidin-1-yl)phenyl)-1-methyl-2-oxo-1,2-dihydropyridine-3-carboxamide

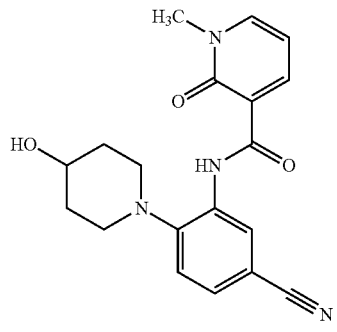 [SMILES: Cn1cccc(C(=O)Nc2cc(C#N)ccc2N2CCC(O)CC2)c1=O]

To a solution of N-(2-(4-((tert-butyldimethylsilyl)oxy)piperidin-1-yl)-5-cyanophenyl)-1-methyl-2-oxo-1,2-dihydropyridine-3-carboxamide (400 mg, 0.857 mmol) in MeOH (0.2 mL) and THF (6 mL) was added 4 N HCl in dioxane (0.8 mL, 3.20 mmol). The solution was stirred at 20° C. for 18 hours at which time LC/MS indicated the reaction was complete. The solution was concentrated in vacuo and the solids were taken up in EtOAc (100 mL) and washed with saturated (aq) NaHCO$_3$ (100 mL). The organic layer was separated (with some white solid), concentrated on Celite® and purified by column chromatography (80 g silica gel column) eluting with a gradient of 0-10% MeOH in DCM to give the title compound as a white solid (244 mg, 81%). $^1$H NMR (500 MHz, DMSO-d$_6$) δ ppm 1.73-1.84 (m, 2H), 1.87-1.96 (m, 2H), 2.72 (ddd, J=11.84, 9.15, 2.93 Hz, 2H), 3.01-3.10 (m, 2H), 3.63 (s, 3H), 3.68 (td, J=7.81, 3.91 Hz, 1H), 4.70 (d, J=3.42 Hz, 1H), 6.55-6.63 (m, 1H), 7.33 (d, J=8.30 Hz, 1H), 7.52 (dd, J=8.05, 2.20 Hz, 1H), 8.17 (dd, J=6.35, 1.95 Hz, 1H), 8.47 (dd, J=7.32, 1.95 Hz, 1H), 8.79 (d, J=1.95 Hz, 1H), 12.37 (s, 1H); ESI-MS [M+H]+ 353.

Preparation x16: 4-chloro-6-(4-(2,4-difluorophenoxy)piperidin-1-yl)-2-methyl-5-nitropyrimidine

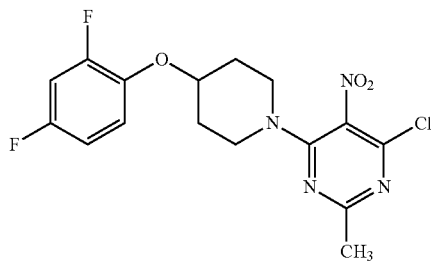 [SMILES: Cc1nc(Cl)c([N+](=O)[O-])c(N2CCC(Oc3ccc(F)cc3F)CC2)n1]

To a solution of 4,6-dichloro-2-methyl-5-nitropyrimidine (10.03 g, 48.2 mmol) and 4-(2,4-difluorophenoxy)piperidine hydrochloride (11.52 g, 46.1 mmol) in DCM (300 mL) at 0° C. was added dropwise via an addition funnel DIPEA (17.73 mL, 102 mmol) over a 1 hour period of time. The reaction mixture was stirred at 0° C. for 3 hours and then allowed to warm to 20° C. The solution was concentrated in vacuo. The crude product was taken up in EtOAc (250 mL), washed with saturated (aq) NH$_4$Cl (2×250 mL) and brine (200 mL), dried over MgSO$_4$, and concentrated in vacuo. The resulting red oil crystallized on standing under vacuum to give the (crude) title compound as an orange solid, which was used without further purification. $^1$H NMR (500 MHz, CDCl$_3$) δ ppm 1.90-2.03 (m, 4H), 2.53 (s, 3H), 3.60-3.67 (m, 2H), 3.74-3.82 (m, 2H), 4.45-4.51 (m, 1H), 6.77-6.84 (m, 1H), 6.88 (ddd, J=10.86, 8.18, 2.93 Hz, 1H), 6.98 (td, J=9.03, 5.37 Hz, 1H); ESI-MS m/z [M+H]+ 385, 387.

Preparation x17: 4-(4-(2,4-difluorophenoxy)piperidin-1-yl)-2-methylpyrimidin-5-amine

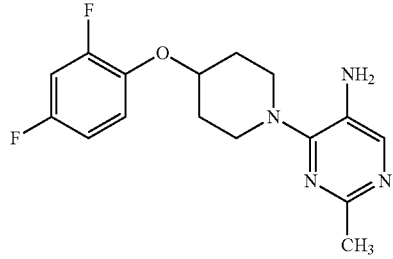 [SMILES: Cc1ncc(N)c(N2CCC(Oc3ccc(F)cc3F)CC2)n1]

To a solution of 4-chloro-6-(4-(2,4-difluorophenoxy)piperidin-1-yl)-2-methyl-5-nitropyrimidine (17.75 g, 46.1 mmol) and Et$_3$N (7.72 mL, 55.4 mmol) in MeOH (100 mL) and EtOAc (100 mL) under nitrogen was added Pd/C (Degussa, 10 wt %) (4.91 g, 4.61 mmol). The reaction mixture was stirred under an atmosphere of hydrogen for 3 days and then filtered through a pad of Celite®, rinsing with EtOH. The filtrate was concentrated in vacuo to give an orange oil, which was concentrated on Celite® and purified by column chromatography (330 g silica gel column) eluting with a gradient of 0-8% MeOH in DCM. The resulting oil was taken up in EtOAc and the mixture concentrated under vacuum to give the title compound as an off-white solid (11.9 g, 81%). $^1$H NMR (500 MHz, DMSO-d$_6$) δ ppm 1.15-1.20 (m, 1H), 1.73-1.83 (m, 2H), 1.99 (s, 1H), 2.03 (ddd, J=9.52, 5.86, 3.17 Hz, 2H), 2.33 (s, 3H), 3.04 (ddd, J=12.57, 9.40, 2.93 Hz, 2H), 3.32 (s, 1H), 3.56-3.64 (m, 2H), 4.03 (q, J=7.16 Hz, 1H), 4.52 (tt, J=8.18, 4.03 Hz, 1H), 4.59 (s, 2H), 7.01 (dddd, J=9.28, 8.05, 2.93, 1.71 Hz, 1H), 7.25-7.34 (m, 2H), 7.79 (s, 1H); ESI-MS m/z [M+H]+ 321.

Preparation x18: 6-chloro-4-(4-(2,4-difluorophenoxy)piperidin-1-yl)-5-nitropicolinic acid

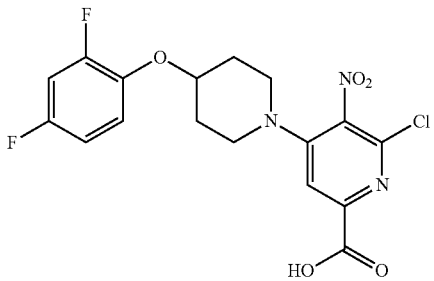 [SMILES: O=C(O)c1cc(N2CCC(Oc3ccc(F)cc3F)CC2)c([N+](=O)[O-])c(Cl)n1]

To a 500 mL 3 neck jacketed reactor were added 4,6-dichloro-5-nitropicolinic acid (4.5 g, 18.99 mmol), 4-(2,4-difluorophenoxy)piperidine hydrochloride (5.17 g, 20.70 mmol), and DCM (75 mL). While stirring, the reaction mixture was cooled to −5° C. To the reactor was added a solution of DIPEA (13.56 mL, 78 mmol) in DCM (25 mL) over a 5-minute period. The reaction mixture was allowed to warm to RT overnight and then concentrated. The concentrate was partitioned between EtOAc and water. The organic phase was separated and treated with 6N HCl (aq) (15 mL). The organics were split and held in reserve and the aqueous phase was extracted with EtOAc. The organics were combined, washed with saturated (aq) sodium chloride, dried over $Na_2SO_4$, filtered, and concentrated to give a crude yellow solid. The yellow solid was recrystallized from EtOAc to afford the title compound as a canary yellow solid (5.06 g, 64%). $^1$H NMR (400 MHz, $CDCl_3$) δ ppm 1.95-2.07 (m, 4H), 3.36 (dt, J=13.52, 4.86 Hz, 2H), 3.56-3.73 (m, 2H), 4.48 (quin, J=4.42 Hz, H), 6.77-6.84 (m, 1H), 6.88 (ddd, J=11.05, 8.27, 2.91 Hz, 1H), 6.97 (td, J=9.09, 5.56 Hz, 1H), 7.72-7.78 (m, 1H); ESI-MS m/z [M+H]$^+$ 414.1.

Preparation x19: 6-chloro-4-(4-(2,4-difluorophenoxy)piperidin-1-yl)-N-methyl-5-nitropicolinamide

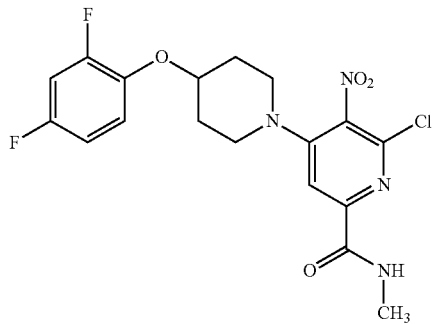 [SMILES: CNC(=O)c1cc(N2CCC(Oc3ccc(F)cc3F)CC2)c([N+](=O)[O-])c(Cl)n1]

To a mixture of 6-chloro-4-(4-(2,4-difluorophenoxy)piperidin-1-yl)-5-nitropicolinic acid (400 mg, 0.967 mmol) and HATU (551 mg, 1.450 mmol) in DMA (4 mL) was added DIPEA (0.338 mL, 1.933 mmol). The resulting solution was cooled to 0° C. and 33 wt % methanamine in EtOH (0.361 mL, 2.90 mmol) was added dropwise. The solution was stirred at 0° C. for 5 hours. The crude product was diluted with diethyl ether (100 mL) and washed with saturated (aq) $NH_4Cl$ (2×100 mL). Ethyl acetate (20 mL) was added to dissolve the solids. The solution was washed with brine (100 mL), dried over $MgSO_4$, and concentrated in vacuo. The crude product was purified by column chromatography (40 g silica gel column) eluting with a gradient of 0-70% EtOAc in heptane to give the title compound as a yellow solid (369 mg, 89%). $^1$H NMR (500 MHz, DMSO-$d_6$) δ ppm 1.67-1.79 (m, 2H), 2.03 (ddt, J=13.30, 7.08, 3.48, 3.48 Hz, 2H), 2.80 (d, J=4.88 Hz, 3H), 3.24-3.31 (m, 2H), 3.51 (ddd, J=13.06, 7.20, 3.66 Hz, 2H), 4.59 (tt, J=7.44, 3.78 Hz, 1H), 6.98-7.06 (m, 1H), 7.25-7.34 (m, 2H), 7.67 (s, 1H), 8.68 (q, J=4.56 Hz, 1H); ESI-MS m/z [M+H]$^+$ 427, 429.

Preparation x20: 5-amino-4-(4-(2,4-difluorophenoxy)piperidin-1-yl-N-methylpicolinamide

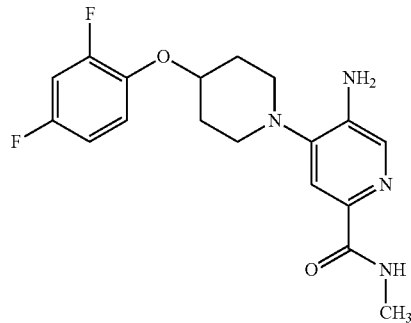 [SMILES: CNC(=O)c1cc(N2CCC(Oc3ccc(F)cc3F)CC2)c(N)cn1]

To a solution of 6-chloro-4-(4-(2,4-difluorophenoxy)piperidin-1-yl)-N-methy-5-nitropicolinamide (30 mg, 0.070 mmol) and $K_2CO_3$ (14.57 mg, 0.105 mmol) in MeOH (0.5 mL) and EtOAc (0.5 mL) under nitrogen was added Pd/C (Degussa, 10 wt %) (30 mg, 0.282 mmol). The mixture was then stirred under a hydrogen atmosphere at 20° C. for 21 hours. The reaction mixture was subsequently filtered through Celite®, rinsing with MeOH. The filtrate was concentrated in vacuo to give the title compound as a white solid that was used without further purification. $^1$H NMR (500 MHz, DMSO-$d_6$) δ ppm 1.82-1.94 (m, 2H), 2.04-2.13 (m, 2H), 2.75 (d, J=4.88 Hz, 3H), 2.77-2.84 (m, 2H), 3.14-3.19 (m, 2H), 4.51 (dt, J=7.93, 4.09 Hz, 1H), 5.36 (s, 2H), 6.98-7.07 (m, 1H), 7.26-7.36 (m, 2H), 7.47 (s, 1H), 7.92 (s, 1H), 8.31 (q, J=4.72 Hz, 1H); ESI-MS m/z [M+H]$^+$ 363.

Preparation x21: 2-chloro-4-(4-(2,4-difluorophenoxy)piperidin-1-yl)-5-nitropyridine

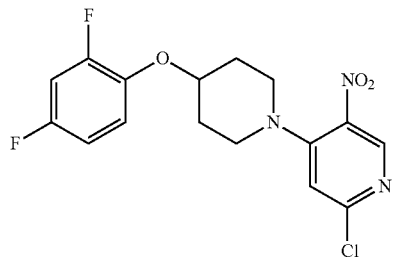 [SMILES: O=[N+]([O-])c1cnc(Cl)cc1N1CCC(Oc2ccc(F)cc2F)CC1]

To a 3 L 3 neck round bottom flask were added 4-(2,4-difluorophenoxy)piperidine hydrochloride (178 g, 712 mmol), 2,4-dichloro-5-nitropyridine (125 g, 648 mmol), and DCM (1250 mL). While stirring, the reaction mixture was cooled to −5° C. To the flask was added DIPEA (282 mL, 1619 mmol) slowly over a 45-minute period. The reaction mixture was then stirred for 1 hour and water (1000 mL) was added. The biphasic mixture was transferred to a separatory funnel and the organic layer was split and held in reserve. The aqueous phase was extracted with DCM. The organic layers were combined and washed with saturated (aq) NaCl, dried over $Na_2SO_4$, filtered, and concentrated to about one quarter of the prior volume. Isopropyl acetate (500 mL) was added and the mixture was concentrated to about one half of the prior volume. The concentrate was transferred to a separatory funnel and IPAc (1500 mL) was added. The solution was washed with (aq) 1N HCl (1 L), water (1 L), and 10% (aq) NaCl (1 L). The organic phase was dried over Na₂SO₄, filtered, and concentrated to give a yellow solid (225 g). The crude solid was slurried in isopropyl acetate (700 mL) and then heated until the solid dissolved. The yellow solution was cooled and a small amount of heptane (50 mL) was added to induce precipitation. Once cooled, a yellow solid precipitated and was filtered. The filtered solid was washed with a small amount of cold IPAc and dried in a vacuum oven to give the title compound (186 g, 78%). ¹H NMR (400 MHz, CDCl₃) δ ppm 1.93-2.17 (m, 4H), 3.12-3.25 (m, 2H), 3.52 (ddd, J=13.01, 9.22, 3.54 Hz, 2H), 4.46-4.55 (m, 1H), 6.78-6.85 (m, 1H), 6.85-6.93 (m, 2H), 6.99 (td, J=9.03, 5.43 Hz, 1H), 8.66 (s, 1H); ESI-MS m/z [M+H]⁺ 370.0.

Preparation x22: 4-(4-(2,4-difluorophenoxy)piperidin-1-yl)-2-methoxy-5-nitropyridine

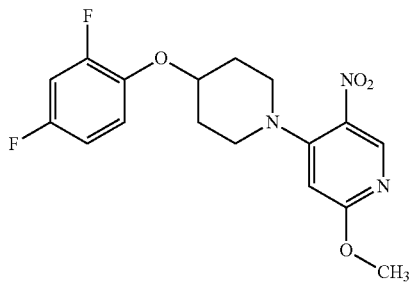 [SMILES: COc1cc(N2CCC(Oc3ccc(F)cc3F)CC2)c([N+](=O)[O-])cn1]

To a slurry of 2-chloro-4-(4-(2,4-difluorophenoxy)piperidin-1-yl)-5-nitropyridine (3.42 g, 9.25 mmol) in MeOH (30 mL) was added 0.5 M sodium methoxide in MeOH solution (27.7 mL, 13.87 mmol). The reaction mixture was stirred at 20° C. for 20 hours and then concentrated in vacuo. The concentrate was taken up in EtOAc (100 mL), washed with saturated (aq) NH₄Cl (2×100 mL) and brine (100 mL), dried over MgSO₄, and concentrated in vacuo to give the title compound as a yellow oil (3.29 g, 97%). ¹H NMR (500 MHz, CDCl₃) δ ppm 1.95-2.03 (m, 2H), 2.05-2.13 (m, 2H), 3.08 (ddd, J=12.57, 6.47, 3.91 Hz, 2H), 3.40 (ddd, J=12.57, 8.91, 3.42 Hz, 2H), 3.98 (s, 3H), 4.45 (tt, J=6.29, 3.48 Hz, 1H), 6.21 (s, 1H), 6.76-6.83 (m, 1H), 6.87 (ddd, J=11.23, 8.30, 2.93 Hz, 1H), 6.98 (td, J=9.03, 5.37 Hz, 1H), 8.68 (s, 1H); ESI-MS m/z [M+H]⁺ 366.

Preparation x23: 4-(4-(2,4-difluorophenoxy)piperidin-1-yl-6-methoxypyridin-3-amine

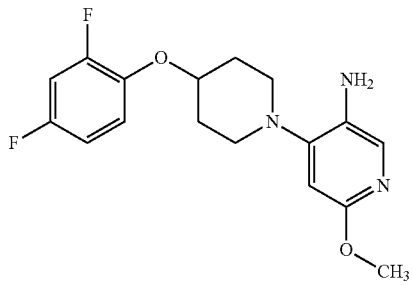 [SMILES: COc1cc(N2CCC(Oc3ccc(F)cc3F)CC2)c(N)cn1]

To a solution of 4-(4-(2,4-difluorophenoxy)piperidin-1-yl)-2-methoxy-5-nitropyridine (3.29 g, 9.01 mmol) in MeOH (30 mL) and EtOAc (30.0 mL) under nitrogen was added Pd/C (10%, Degussa) (0.958 g, 9.01 mmol). The reaction mixture was stirred under an atmosphere of hydrogen for 2 days, then filtered through Celite® (rinsing with MeOH), and concentrated in vacuo to give a tan solid (2.90 g). The crude product was taken up in EtOH (40 mL), heated to about 65° C., and then allowed to cool slowly to 20° C. The resulting crystals were collected by vacuum filtration, rinsed with a small amount of EtOH and dried under vacuum to give the title compound as tan needles (1.971 g, 65.3%). ¹H NMR (500 MHz, DMSO-d₆) δ ppm 1.78-1.88 (m, 2H), 2.05 (ddd, J=9.40, 5.98, 3.17 Hz, 2H), 2.74-2.82 (m, 2H), 3.17-3.25 (m, 2H), 3.70 (s, 3H), 4.29 (s, 2H), 4.48 (tt, J=7.99, 3.97 Hz, 1H), 6.20 (s, 1H), 7.01 (dddd, J=9.28, 8.05, 3.17, 1.46 Hz, 1H), 7.25-7.35 (m, 2H), 7.48 (s, 1H); ESI-MS m/z [M+H]⁺ 336.

Preparation x24: 4-(4-(2,4-difluorophenoxy)piperidin-1-yl)-5-nitropicolinonitrile

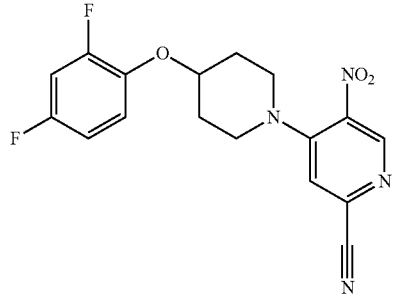 [SMILES: N#Cc1cc(N2CCC(Oc3ccc(F)cc3F)CC2)c([N+](=O)[O-])cn1]

To a 200 mL flask were added 2-chloro-4-(4-(2,4-difluorophenoxy)piperidin-1-yl)-5-nitropyridine (10.06 g, 27.2 mmol), dicyanozinc (2.076 g, 17.68 mmol), (9,9-dimethyl-9H-xanthene-4,5-diyl)bis(diphenylphosphine) (0.315 g, 0.544 mmol), and DMA (50 mL). Nitrogen was bubbled through the reaction mixture for 5 minutes and then Pd₂(dba)₃ (0.249 g, 0.272 mmol) and tetramethylethylenediamine (0.816 mL, 5.44 mmol) were added. The reaction mixture was placed under a condenser with a nitrogen line attached and was heated to 125° C. for 1 hour. The reaction mixture was passed through filter paper to give a clear amber solution, which was transferred to a 3 L flask equipped with an overhead stirrer. With agitation, water (625 mL) was slowly added to precipitate the product. After stirring an extra 60 minutes, the solids were filtered, washed with copious amounts of water, and dried in a vacuum oven at 60° C. to give the title compound as a yellow solid (9.2 g, 94%). ¹H NMR (400 MHz, CDCl₃) δ ppm 1.97-2.16 (m, 5H), 3.22-3.31 (m, 2H), 3.60 (ddd, J=13.20, 9.03, 4.04 Hz, 2H), 4.48-4.58 (m, 1H), 6.77-6.85 (m, 1H), 6.89 (ddd, J=11.05, 8.27, 2.91 Hz, 1H), 6.99 (td, J=9.09, 5.31 Hz, 1H), 7.31 (s, 1H), 8.81 (s, 1H); ESI-MS m/z [M+H]⁺ 361.1.

Preparation x25: methyl 4-(4-(2,4-difluorophenoxy)piperidin-1-yl)-5-nitropicolinate

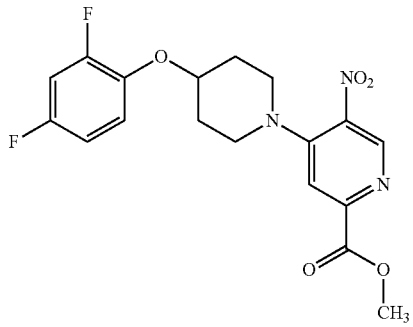 [SMILES: COC(=O)c1cc(N2CCC(Oc3ccc(F)cc3F)CC2)c([N+](=O)[O-])cn1]

To a stirring yellow suspension of 4-(4-(2,4-difluorophenoxy)piperidin-1-yl)-5-nitropicolinonitrile (0.969 g, 2.69 mmol) in MeOH (5.98 mL) was added 0.5 M sodium methoxide in MeOH solution (8.07 mL, 4.03 mmol). The reaction mixture was stirred overnight at RT. After 24 hours additional 0.5 M sodium methoxide in MeOH (2.8 mL, 1.45 mmol) was added, and the reaction mixture was stirred for an additional hour. Next, 1.5 M (aq) HCl (6.45 mL, 9.68 mmol) was added and the solids dissolved. The reaction mixture was stirred for 1 hour and during that time a solid precipitated, which was subsequently filtered, washed with water, and dried in a vacuum oven at 60° C. The solids were taken up in EtOH, and the resulting slurry was heated to 65° C. Once the material dissolved, the solution was cooled, and the resulting crystals were isolated to give the title compound as a pale yellow solid (720 mg, 68.1%). $^{1}$H NMR (400 MHz, CDCl$_3$) δ ppm 2.00-2.15 (m, 4H), 3.22-3.33 (m, 2H), 3.60 (ddd, J=13.14, 9.22, 3.66 Hz, 2H), 4.02 (s, 3H), 4.47-4.55 (m, 1H), 6.78-6.93 (m, 2H), 6.99 (td, J=9.09, 5.56 Hz, 1H), 7.79 (s, 1H), 8.88 (s, 1H); ESI-MS m/z [M+H]$^+$ 394.1.

Preparation x26: 4-(4-(2,4-difluorophenoxy)piperidin-1-yl)-5-nitropicolinic acid

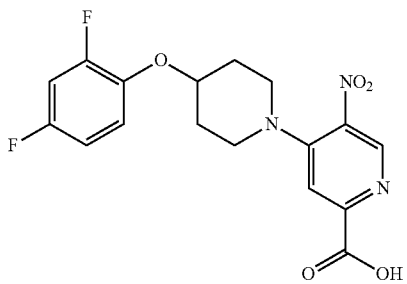 [SMILES: O=C(O)c1cc(N2CCC(Oc3ccc(F)cc3F)CC2)c([N+](=O)[O-])cn1]

To a slurry of methyl 4-(4-(2,4-difluorophenoxy)piperidin-1-yl)-5-nitropicolinate (150 mg, 0.381 mmol) in 1 N (aq) HCl (2 mL, 2 mmol) was added 4 N HCl in dioxane (0.5 mL, 2 mmol). The reaction mixture was heated at 70° C. for 40 hours and then concentrated in vacuo to give the title compound as a yellow solid which was used without further purification. ESI-MS m/z [M+H]$^+$ 380.2.

Preparation x27: 4-(4-(2,4-difluorophenoxy)piperidin-1-yl)-N,N-bis(methyl-d$_3$)-5-nitropicolinamide

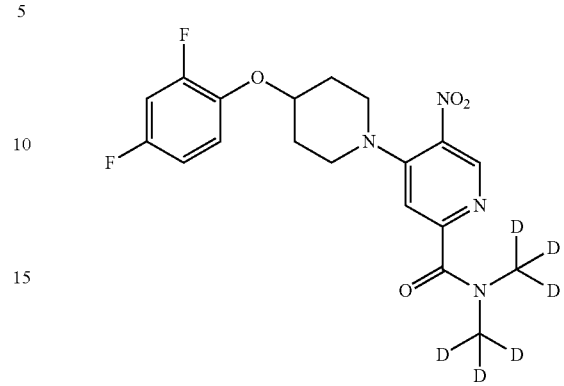

To a solution of 4-(4-(2,4-difluorophenoxy)piperidin-1-yl)-5-nitropicolinic acid (579 mg, 1.526 mmol), HATU (871 mg, 2.290 mmol) and dimethylamine-d$_6$ HCl salt (267 mg, 3.05 mmol) in DMF (6 mL) was added DIPEA (1.066 mL, 6.11 mmol). The reaction mixture was stirred at 20° C. for 2 hours. The reaction supernatant was diluted with diethyl ether (100 mL) and washed with saturated (aq) NH$_4$Cl (100 mL). The organic phase was diluted with EtOAc (15 mL) and washed with brine. The solids remaining in the reaction flask were taken up in EtOAc (30 mL) and washed with brine (30 mL). The organics were combined, dried over MgSO$_4$, and concentrated in vacuo, the crude product was purified by column chromatography (40 g silica gel column) eluting with a gradient of 0-80% EtOAc in heptane to give the title compound as a yellow oil (171 mg, 27.2%). ESI-MS m/z [M+H]$^+$ 413.

Preparation x28: 5-amino-4-(4-(2,4-difluorophenoxy)piperidin-1-yl)-N,N-bis(methyl-d$_3$)picolinamide

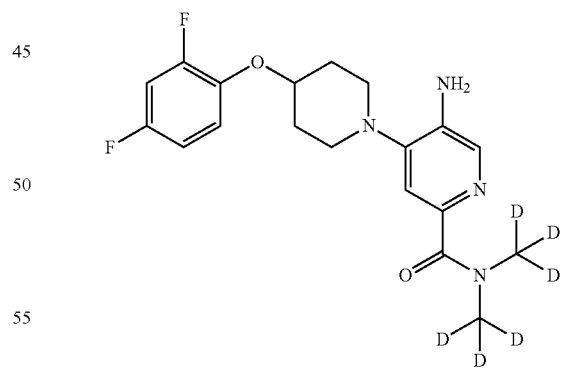

To a solution of 4-(4-(2,4-difluorophenoxy)piperidin-1-yl)-N,N-d$_6$-dimethyl-5-nitropicolinamide (170 mg, 0.412 mmol) in MeOH (3.5 mL) under nitrogen was added Pd/C (10 wt %, Degussa) (43.9 mg, 0.041 mmol). The mixture was stirred under an atmosphere of hydrogen for 3 days and then filtered through a pad of Celite®, rinsing with EtOH. The filtrate was concentrated on Celite® and purified by column chromatography (24 g silica gel column) eluting with a gradient of 0-10% MeOH in DCM to give the title compound as an off-white solid (90 mg, 57%). ¹H NMR (500 MHz, CDCl₃) δ ppm 1.92-2.02 (m, 2H), 2.07-2.16 (m, 2H), 2.88 (ddd, J=11.84, 8.66, 2.93 Hz, 2H), 3.32 (ddd, J=11.59, 7.20, 3.66 Hz, 2H), 4.35 (tt, J=7.69, 3.54 Hz, 1H), 6.81 (dddd, J=9.15, 7.69, 2.93, 1.71 Hz, 1H), 6.88 (ddd, J=11.23, 8.30, 2.93 Hz, 1H), 7.01 (td, J=9.03, 5.37 Hz, 1H), 7.34 (s, 1H), 7.98 (s, 1H); ESI-MS m/z [M+H]⁺ 383.

Preparation x29: 2-chloro-4-(4-(2,4-difluorophenoxy)piperidin-1-yl)-5-nitropyrimidine

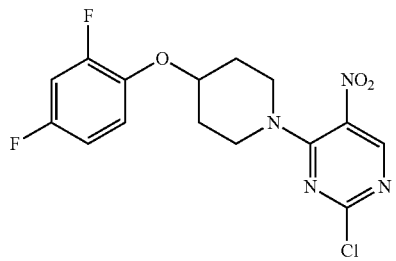 [SMILES: O=[N+]([O-])c1cnc(Cl)nc1N1CCC(Oc2ccc(F)cc2F)CC1]

To a solution of 2,4-dichloro-5-nitropyrimidine (3.5 g, 18.04 mmol) and 4-(2,4-difluorophenoxy)piperidine hydrochloride (4.96 g, 19.85 mmol) in DCM (100 mL) at 0° C. was added dropwise DIPEA (7.88 mL, 45.1 mmol). The solution was stirred at 0° C. for 3 hours and then allowed to warm slowly to 20° C. LC/MS showed nearly complete conversion of the reactants and an approximately 82:16 ratio of the desired product to a bis-addition side product. The reaction mixture was concentrated on Celite® and purified by column chromatography (120 g silica gel column) eluting with a gradient of 0-50% EtOAc in heptane to give the tile compound as a yellow oil, which crystallized while under vacuum overnight to a yellow solid (5.38 g, 80%). ¹H NMR (500 MHz, CDCl₃) δ ppm 1.98-2.12 (m, 4H), 3.66 (br s, 2H), 3.73-3.84 (m, 2H), 4.51-4.58 (m, 1H), 6.83 (dddd, J=9.15, 7.69, 2.93, 1.71 Hz, 1H), 6.90 (ddd, J=10.86, 8.18, 2.93 Hz, 1H), 7.01 (td, J=9.03, 5.37 Hz, 1H), 8.76 (s, 1H); ESI-MS m/z [M+H]⁺ 371.

Preparation x30: 4-(4-(2,4-difluorophenoxy)piperidin-1-yl)-2-methoxy-5-nitropyrimidine

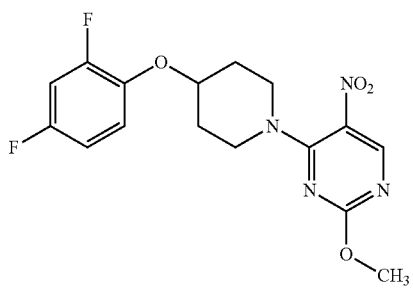 [SMILES: COc1ncc([N+](=O)[O-])c(N2CCC(Oc3ccc(F)cc3F)CC2)n1]

To a solution of 2-chloro-4-(4-(2,4-difluorophenoxy)piperidin-1-yl)-5-nitropyrimidine (1.17 g, 3.16 mmol) in THF (20 mL) was added slowly 25% sodium methoxide in MeOH solution (0.866 mL, 3.79 mmol). The solution was stirred at 20° C. for 4 hours at which time LC/MS showed the reaction was complete. The reaction mixture was subsequently concentrated in vacuo on Celite® and purified by column chromatography (80 g silica gel column) eluting with a gradient of 0-50% EtOAc in heptane to give the title compound as a yellow solid (0.669 g, 1.826 mmol, 57.9%). ¹H NMR (500 MHz, CDCl₃) δ ppm 1.95-2.13 (m, 4H), 3.60 (d, J=13.18 Hz, 2H), 3.78 (ddd, J=13.30, 9.40, 3.66 Hz, 2H), 4.02 (s, 3H), 4.49-4.56 (m, 1H), 6.78-6.85 (m, 1H), 6.90 (ddd, J=10.86, 8.18, 2.93 Hz, 1H), 7.01 (td, J=9.28, 5.37 Hz, 1H), 8.89 (s, 1H); ESI-MS m/z [M+H]⁺ 367.

Preparation x31: 4-(4-(2,4-difluorophenoxy)piperidin-1-yl)-2-methoxypyrimidin-5-amine

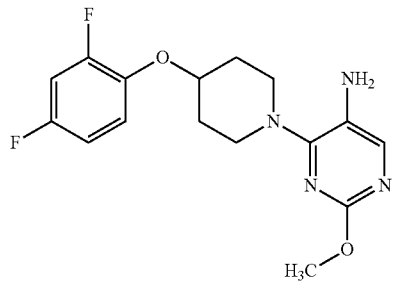 [SMILES: COc1ncc(N)c(N2CCC(Oc3ccc(F)cc3F)CC2)n1]

To a solution of 4-(4-(2,4-difluorophenoxy)piperidin-1-yl)-2-methoxy-5-nitropyrimidine (665 mg, 1.815 mmol) in MeOH (6 mL) under nitrogen was added Pd/C (10 wt %, Degussa) (386 mg, 0.363 mmol). The mixture was stirred under an atmosphere of hydrogen for 13 hours and then filtered through a pad of Celite®, rising with MeOH. The filtrate was concentrated on Celite® and purified by column chromatography (40 g silica gel column) eluting with a gradient of 0-8% MeOH in DCM to give the title compound as a white solid (584 mg, 96%). ESI-MS m/z [M+H]⁺ 337.

Preparation x32: 4-(4-(2,4-difluorophenoxy)piperidin-1-yl)-3-nitrobenzonitrile

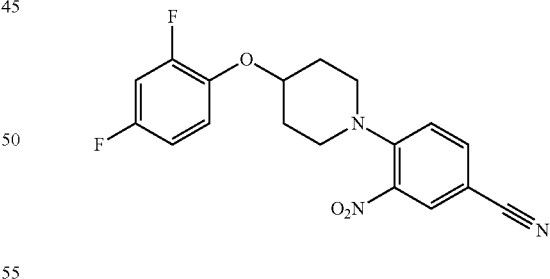

A solution of 4-(2,4-difluorophenoxy)piperidine (0.640 g, 3 mmol), 4-chloro-3-nitrobenzonitrile (0.657 g, 3.60 mmol), and K₂CO₃ (0.829 g, 6.00 mmol) in DMSO (9.09 mL) was stirred at 80° C. overnight. The reaction mixture was subsequently partitioned between EtOAc and water. The organic layer was washed twice with water and dried over anhydrous Na₂SO₄. The solvent was evaporated to give the title compound as an off-white solid, which was used without further purification. ESI-MS m/z [M+H]⁺ 360.2.

Preparation x33: 3-amino-4-(4-(2,4-difluorophenoxy)piperidin-1-yl)benzonitrile

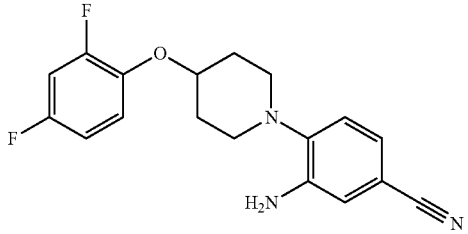 [SMILES: N#Cc1ccc(N2CCC(Oc3ccc(F)cc3F)CC2)c(N)c1]

Zinc powder (2.864 g, 43.8 mmol) was added to a solution of 4-(4-(2,4-difluorophenoxy)piperidin-1-yl)-3-nitrobenzonitrile (1.078 g, 3 mmol) in acetic acid (3 mL). The reaction mixture was stirred at RT for 72 hours and then diluted with EtOAc, filtered, and concentrated in vacuo. The crude product was purified by column chromatography (basic silica gel column) eluting with 0-100% EtOAc in heptane. The fractions were collected and concentrated in vacuo to afford the title compound as an off-white solid (381 mg, 38.6%). ESI-MS m/z [M+H]$^+$ 330.2.

Preparation x34: 4-(4-(2-fluoro-4-methoxyphenoxy)piperidin-1-yl-3-nitrobenzonitrile

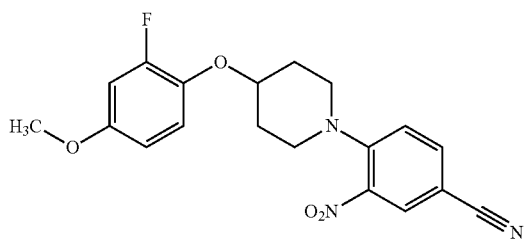

A solution of 4-(2-fluor-4-methoxyphenoxy)piperidine hydrochloride (0.785 g, 3 mmol), 4-fluoro-3-nitrobenzonitrile (0.598 g, 3.60 mmol) and K$_2$CO$_3$ (1.244 g, 9.00 mmol) in DMSO (9.09 mL) was stirred at 80° C. overnight. The reaction mixture was subsequently partitioned between EtOAc and water, and the organic layer was washed with water (2×) and dried over anhydrous Na$_2$SO$_4$. The solvent was evaporated to give the title compound as a yellow solid, which was used without further purification (1.005 g, 90%). ESI-MS m/z [M+H]$^+$ 372.3.

Preparation x35: 3-amino-4-(4-(2-fluoro-4-methoxyphenoxy)piperidin-1-yl)benzonitrile

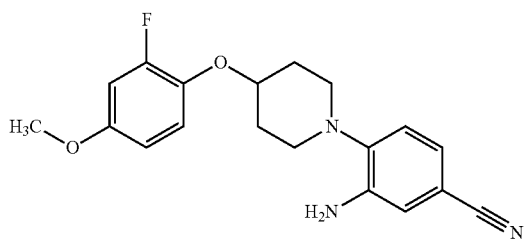 [SMILES: COc1ccc(OC2CCN(c3ccc(C#N)cc3[N+](=O)[O-])CC2)c(F)c1]

Zinc powder (2.58 g, 39.5 mmol) was added to a solution of 4-(4-(2-fluoro-4-methoxyphenoxy)piperidin-1-yl)-3-nitrobenzonitrile (1.005 g, 2.71 mmol) in acetic acid (27.1 mL). The reaction mixture was stirred at RT overnight and then heated at 60° C. overnight. The reaction mixture was cooled to 45° C. Additional zinc powder (2.58 g, 39.5 mmol) was added and the reaction mixture was again stirred at 45° C. overnight. The reaction mixture was subsequently diluted with EtOAc, filtered, and concentrated in vacuo. The crude product was purified by column chromatography (basic silica gel column) eluting with a gradient of 0-100% EtOAc in heptane. The fractions were collected and concentrated in vacuo to give the title compound as an off-white oil (392 mg, 42.4%). ESI-MS m/z [M+H]$^+$ 342.2.

Preparation x36: 4-(2,4-difluorophenoxy)-1-(5-(methylsulfonyl)-2-nitrophenyl)piperidine

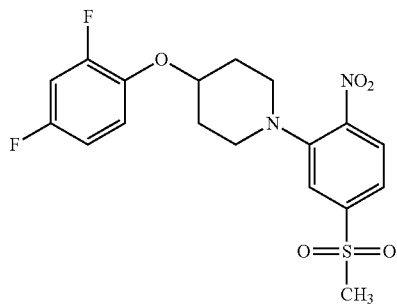

To a solution of 2-fluoro-4-(methylsulfonyl)-1-nitrobenzene (1 g, 4.56 mmol) in DCM (20.01 mL) was added dropwise a solution of 4-(2,4-difluorophenoxy)piperidine hydrochloride (1.367 g, 5.47 mmol) and DIPEA (1.195 mL, 6.84 mmol) in DCM (10.00 mL). The reaction mixture was stirred at 20° C. for 15 hours, then concentrated on Celite®, and purified by column chromatography (4 g silica gel column) eluting with a gradient of 0-70% EtOAc in heptane to give the title compound as a yellow solid (1.764 g, 94%). $^1$H NMR (500 MHz, DMSO-d$_6$) δ ppm 1.73-1.81 (m, 2H), 2.00-2.07 (m, 2H), 3.08 (ddd, J=12.33, 8.66, 3.42 Hz, 2H), 3.28-3.31 (m, 2H), 3.32 (s, 3H), 4.55 (tt, J=7.57, 3.66 Hz, H), 7.03 (dddd, J=9.15, 8.18, 3.17, 1.95 Hz, 1H), 7.27-7.35 (m, 2H), 7.55 (dd, J=8.30, 1.95 Hz, 1H), 7.74 (d, J=1.95 Hz, 1H), 8.04 (d, J=8.30 Hz, 1H); ESI-MS m/z [M+H]$^+$ 413.3.

Preparation x37: 2-(4-(2,4-difluorophenoxy)piperidin-1-yl)-4-(methylsulfonyl)aniline

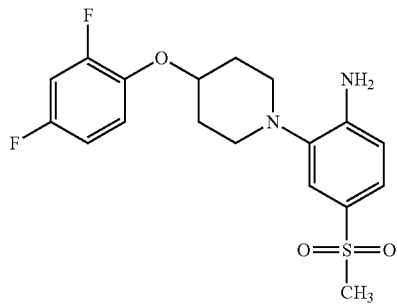 [SMILES: CS(=O)(=O)c1ccc([N+](=O)[O-])c(N2CCC(Oc3ccc(F)cc3F)CC2)c1]

To a solution of 4-(2,4-difluorophenoxy)-1-(5-(methylsulfonyl)-2-nitrophenyl)piperidine (1.764 g, 4.28 mmol) in MeOH (25.5 mL) under nitrogen was added Pd/C (10% Degussa) (0.286 g, 2.69 mmol). The slurry was stirred under an atmosphere of hydrogen overnight. Additional Pd/C (10% Degussa) (80 mg, 0.75 mmol) was added under nitrogen and the slurry was again stirred under an atmosphere of hydrogen overnight. The Pd/C was removed by filtering the reaction mixture through a syringe filter and rinsing with MeOH (200 mL). The filtrate was concentrated in vacuo to give the title compound as a light brown solid which was used without further purification (1.318 g, 81%). $^1$H NMR (500 MHz, DMSO-$d_6$) δ ppm 1.85-1.93 (m, 2H), 2.08 (d, J=12.20 Hz, 2H), 2.74 (t, J=9.03 Hz, 2H), 3.01-3.07 (m, 5H), 4.49 (br s, 1H), 5.74 (s, 2H), 6.78 (d, J=8.30 Hz, 1H), 6.99-7.06 (m, 1H), 7.27-7.35 (m, 4H); ESI-MS m/z [M+H]$^+$ 383.3.

Preparation x38: 6-chloro-4-(4-(2,4-difluorophenoxy)piperidin-1-yl)-5-nitropicolinic acid

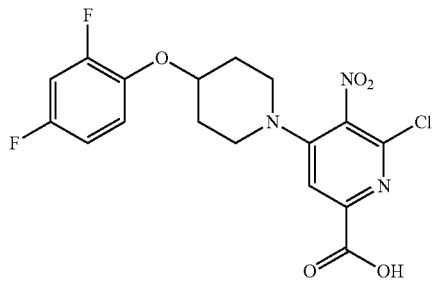 [SMILES: O=C(O)c1cc(N2CCC(Oc3ccc(F)cc3F)CC2)c([N+](=O)[O-])c(Cl)n1]

To a stirred mixture of 4,6-dichloro-5-nitropicolinic acid (9.5 g, 40.1 mmol) and 4-(2,4-difluorophenoxy)piperidine hydrochloride (10.51 g, 42.1 mmol) in THF (401 mL) was added Et$_3$N (16.76 mL, 120 mmol) at 0° C. The mixture was stirred at 20° C. for 16 hours and then poured into cold water (250 mL), extracted with EtOAc (3×350 mL) and washed with brine (150 mL). A heavy emulsion was observed. The organic phases were separated, dried over Na$_2$SO$_4$, filtered, and concentrated in vacuo to give the (crude) title compound as a yellow solid (10.494 g, 63.3%), 1H NMR (500 MHz, DMSO-$d_6$) δ ppm 1.70 (br s, 2H), 2.00 (br s, 2H), 3.16 (t, J=9.76 Hz, 2H), 3.38 (br s, 2H), 4.54 (br s, 1H), 7.01 (br s, 1H), 7.27-7.33 (m, 2H), 7.51 (s, 1H); ESI-MS m/z [M+H]$^+$ 414.3.

Preparation x39: 6-chloro-4-(4-(2,4-difluorophenoxy)piperidin-1-yl)-N,N-dimethyl-5-nitropicolinamide

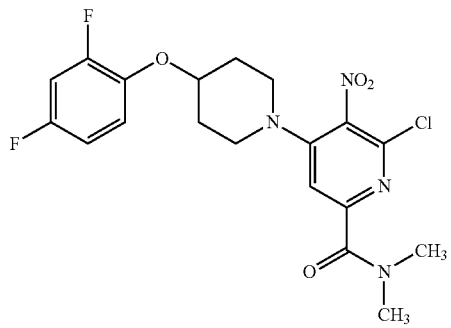 [SMILES: CN(C)C(=O)c1cc(N2CCC(Oc3ccc(F)cc3F)CC2)c([N+](=O)[O-])c(Cl)n1]

To a solution of 6-chloro-4-(4-(2,4-difluorophenoxy)piperidin-1-yl)-5-nitropicolinic acid (10.494 g, 25.4 mmol) in DCM (211 mL) was added oxalyl chloride (4.44 mL, 50.7 mmol) and DMF (0.098 mL, 1.268 mmol) at 0° C. After stirring at 20° C. for 1 hour, the mixture was concentrated in vacuo. The residue was taken up in DCM (106 mL) and added to a mixture of dimethylamine HCl (3.10 g, 38.0 mmol) and Et$_3$N (10.61 mL, 76 mmol) in DCM (317 mL). The reaction mixture was stirred at 20° C. for 1.5 hours and then concentrated in vacuo. The residue was purified by column chromatography (SiO$_2$) eluting with a gradient of 10/1 to 2/1 heptane/EtOAc to give the title compound as a yellow solid (3.358 g, 30.0%). $^1$H NMR (500 MHz, CDCl$_3$) δ ppm 1.92-2.04 (m, 4H), 3.12 (d, J=3.91 Hz, 6H), 3.22-3.29 (m, 2H), 3.56 (ddd, J=12.94, 9.03, 3.42 Hz, 2H), 4.42-4.47 (m, 1H), 6.78-6.83 (m, 1H), 6.84-6.90 (m, 1H), 6.97 (td, J=9.28, 5.37 Hz, 1H), 7.20-7.22 (m, 1H); ESI-MS m/z [M+H]$^+$ 441.3.

Preparation x40: 5-amino-4-(4-(2,4-difluorophenoxy)piperidin-1-yl)-N,N-dimethylpicolinamide

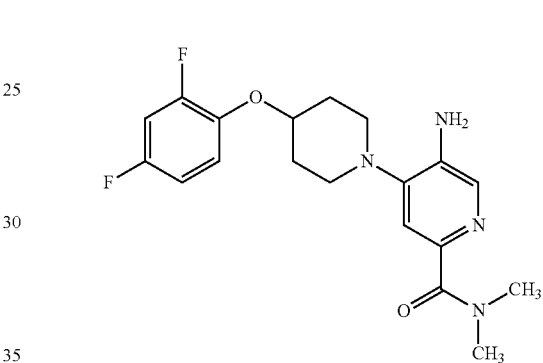

To a 250 mL round bottom flask charged with 6-chloro-4-(4-(2,4-difluorophenoxy)piperidin-1-yl)-N,N-dimethyl-5-nitropicolinamide (5.12 g, 11.61 mmol) and methanol (70 mL) was added 10% palladium on carbon (2.472 g, 1.161 mmol, Degussa® type). The flask was sealed with a septum and a balloon of hydrogen was attached. The reaction mixture was stirred for 16 hours at room temperature, then filtered through Celite® and concentrated to give an oil. The oil solidified upon sitting. The crude solid was recrystallized from EtOAc and methanol to afford a white solid (3.71 g, 85%). $^1$H NMR (400 MHz, CDCl$_3$) δ ppm 2.00-2.18 (m, 4H), 3.15 (s, 6H), 3.23-3.33 (m, 2H), 3.44-3.55 (m, 2H), 4.42-4.54 (m, 1H), 6.78-6.84 (m, 1H), 6.88 (ddd, J=11.05, 8.40, 3.03 Hz, 1H), 6.99 (td, J=9.03, 5.43 Hz, 1H), 7.16 (s, 1H), 8.68 (s, 1H); ESI-MS m/z [M+H]$^+$ 377.1.

Preparation x41: tert-butyl 4-(5-bromo-3-nitropyridin-2-yl)piperazine-1-carboxylate

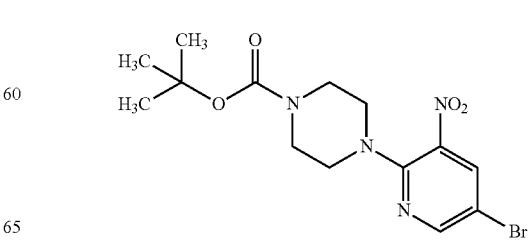

To a solution of 5-bromo-2-chloro-3-nitropyridine (10 g, 42.1 mmol) and Et₃N (8.81 mL, 63.2 mmol) in DCM (200 mL) was added portion-wise tert-butyl piperazine-1-carboxylate (9.41 g, 50.5 mmol). The solution was stirred at RT for 5.5 hours and then concentrated in vacuo. The crude was taken up in EtOAc (250 mL) and washed with saturated (aq) NH₄Cl (2×250 mL), saturated (aq) NaHCO₃ (250 mL) and brine (250 mL), dried over Na₂SO₄ and concentrated in vacuo to give the title compound as a yellow solid (15.28 g, 94%). ¹H NMR (500 MHz, DMSO-d₆) δ ppm 1.41 (s, 9H), 3.35-3.38 (m, 4H), 3.43 (d, J=5.37 Hz, 4H), 8.49 (d, J=2.44 Hz, 1H), 8.54 (d, J=2.44 Hz, 1H); ESI-MS m/z [M+H]⁺ 387.2.

Preparation x42: tert-butyl 4-(5-(methoxymethyl)-3-nitropyridin-2-yl)piperazine-1-carboxylate

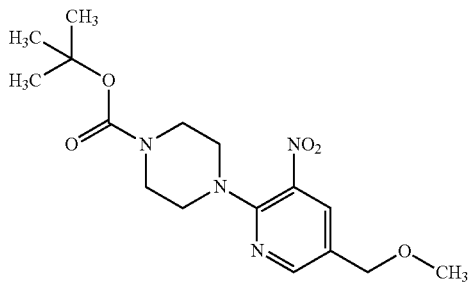 [SMILES: COCc1cnc(N2CCN(C(=O)OC(C)(C)C)CC2)c([N+](=O)[O-])c1]

Tert-butyl 4-(5-bromo-3-nitropyridin-2-yl)piperazine-1-carboxylate (5.28 g, 13.64 mmol), potassium trifluoro(methoxymethyl)borate (4.146 g, 27.3 mmol), PdCl₂(dppf) (1.996 g, 2.73 mmol) and Cs₂CO₃ (22.22 g, 68.2 mmol) were combined in dioxane (68.2 mL) and water (28 mL). The reaction mixture was heated at 100° C. for 16 hours, then cooled to RT, poured into brine (141 mL) and extracted with EtOAc (2×94 mL). The organic layers were combined, concentrated, and purified by flash column chromatography (silica gel column) eluting with a gradient of 10-40% EtOAc in heptane to give the title compound as a yellow oil (969 mg, 20.2%). ¹H NMR (500 MHz, DMSO-d₆) δ ppm 1.41 (s, 9H), 3.28 (s, 3H), 3.35-3.37 (m, 4H), 3.43-3.46 (m, 4H), 4.40 (s, 2H), 8.22 (d, J=1.95 Hz, 1H), 8.40 (d, J=1.95 Hz, 1H); ESI-MS m/z [M+H]⁺ 353.3.

Preparation x43: tert-butyl 4-(3-amino-5-(methoxymethyl)pyridin-2-yl)piperazine-1-carboxylate

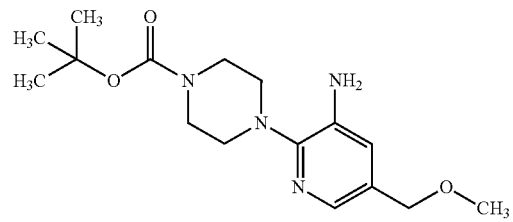 [SMILES: COCc1cnc(N2CCN(C(=O)OC(C)(C)C)CC2)c(N)c1]

To a flask containing tert-butyl 4-(5-(methoxymethyl)-3-nitropyridin-2-yl)piperazine-1-carboxylate (969 mg, 2.75 mmol) were added NH₄Cl (2206 mg, 41.2 mmol), MeOH (5.268 mL), and 2-methyltetrahydrofuran (10.5 mL). The suspension was stirred and zinc (1276 mg, 19.52 mmol) was added over a 4-minute period. The reaction mixture was stirred at RT overnight and then filtered through Celite® to remove solids. The filter pad was washed with MeOH and the filtrate concentrated. The concentrated filtrate was partitioned between EtOAc and water. The organic and aqueous phases were separated and the aqueous phase was extracted with EtOAc. The organic phases were combined, washed with saturated (aq) NaCl, dried over Na₂SO₄, filtered, and concentrated to give the title compound as a brown solid (878 mg, 99%). ¹H NMR (500 MHz, DMSO-d₆) δ ppm 1.42 (s, 9H), 2.90-2.92 (m, 4H), 3.24 (d, J=0.98 Hz, 3H), 3.48 (br s, 4H), 4.25 (s, 2H), 4.89 (s, 2H), 6.93 (s, 1H), 7.49 (s, 1H); ESI-MS m/z [M+H]⁺ 323.2.

Preparation x44: tert-butyl 4-(5-(methoxymethyl)-3-(2-methoxynicotinamido)pyridin-2-yl)piperazine-1-carboxylate

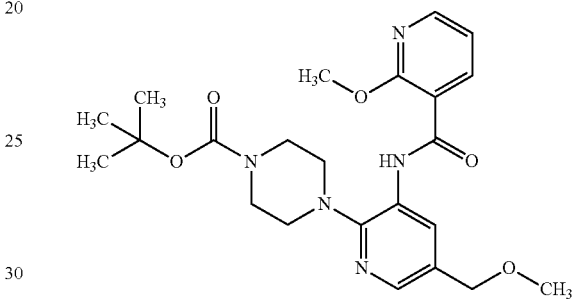

To a vial were added 2-methoxynicotinic acid (230 mg, 1.501 mmol), 2-chloro-1-methylpyridin-1-ium iodide (384 mg, 1.501 mmol), NMP (968 µL), and DIPEA (856 µL, 4.91 mmol). The mixture was stirred for 30 minutes. Tert-butyl 4-(3-amino-5-(methoxymethyl)pyridin-2-yl)piperazine-1-carboxylate (176 mg, 0.546 mmol) in NMP (968 µL) was added and the reaction mixture was heated to 65° C. After 3.5 hours, the cooled reaction mixture was slowly added to stirring water (9 mL). The mixture was extracted with EtOAc and the combined organic layers were absorbed onto Celite® and purified by flash chromatography, eluting with 40% EtOAc in heptane to give the title compound as an off-white solid (132 mg, 52.9%). ¹H NMR (500 MHz, DMSO-d₆) δ ppm 1.42 (s, 9H), 2.98-3.03 (m, 4H), 3.30 (s, 3H), 3.53 (br s, 4H), 4.15 (s, 3H), 4.42 (s, 2H), 7.28 (t, J=6.10 Hz, 1H), 8.06 (s, 1H), 8.44 (d, J=6.83 Hz, 2H), 8.62 (s, 1H), 10.29 (s, 1H); ESI-MS m/z [M+H]⁺ 458.4.

Preparation x45: 2-methoxy-N-(5-(methoxymethyl)-2-(piperazin-1-yl)pyridin-3-yl)nicotinamide

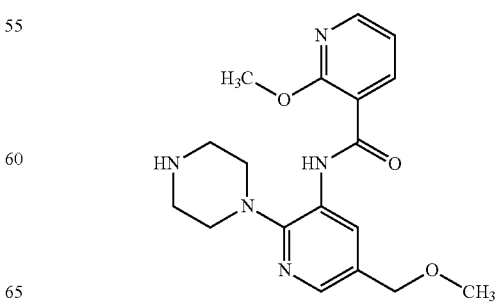

To a stirring solution of tert-butyl 4-(5-(methoxymethyl)-3-(2-methoxynicotinamido)pyridin-2-yl)piperazine-1-carboxylate (132 mg, 0.289 mmol) and DCM (2.647 mL) was added 4 M HCl in 1,4-dioxane (505 µL, 2.020 mmol). A precipitate formed quickly. The reaction mixture was stirred for 1 hour at RT. UPLC/MS indicated the reaction was complete. The solid was filtered and dried. The dried solid was slurried in water and isopropyl acetate. The mixture was made basic (~pH 10). The aqueous and organic phases were separated and the aqueous phase extracted twice with isopropyl acetate. The organic phases were combined and lyophilized to give the title compound as a solid, which was used without further purification. ESI-MS m/z [M+H]$^+$ 358.3.

Preparation x46: methyl 6-(4-(2,4-difluorophenoxy)piperidin-1-yl)-5-nitronicotinate

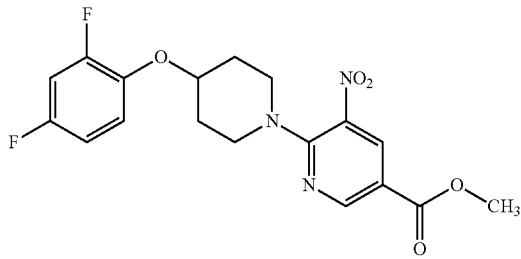

A solution of methyl 6-chloro-5-nitronicotinate (5 g, 23.09 mmol), 4-(2,4-difluorophenoxy)piperidine hydrochloride (6.92 g, 27.7 mmol) and K$_2$CO$_3$ (9.57 g, 69.3 mmol) in ACN (57.7 mL) was stirred at 80° C. for 5 hours. The reaction mixture was poured into water and extracted with EtOAc (3×250 mL). The organic layers were combined, dried over Na$_2$SO$_4$, and filtered. The filtrate was concentrated in vacuo and purified by column chromatography (ISCO column) eluting with a gradient of 0-100% EtOAc in heptane, to give the title compound as a yellow solid (6.04 g, 66.5%). $^1$H NMR (500 MHz, DMSO-d$_6$) δ ppm 1.74 (dq, J=12.88, 4.17 Hz, 2H), 2.04 (ddd, J=9.76, 6.83, 3.42 Hz, 2H), 3.45 (td, J=8.91, 4.15 Hz, 2H), 3.71-3.76 (m, 2H), 3.85 (s, 3H), 4.66 (tt, J=7.51, 3.72 Hz, 1H), 7.00-7.06 (m, 1H), 7.27-7.36 (m, 2H), 8.56 (d, J=1.46 Hz, 1H), 8.82 (d, J=1.46 Hz, 1H); ESI-MS m/z [M+H]$^+$ 394.2.

Preparation x47: methyl 5-amino-6-(4-(2,4-difluorophenoxy)piperidin-1-yl)nicotinate

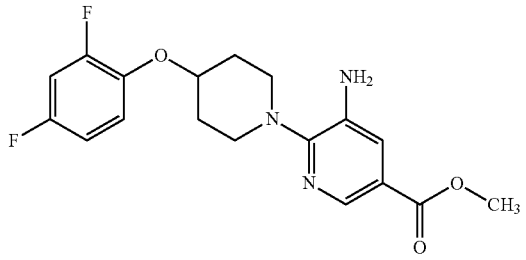 [SMILES: COC(=O)c1cnc(N2CCC(Oc3ccc(F)cc3F)CC2)c([N+](=O)[O-])c1]

To a mixture of methyl 6-(4-(2,4-difluorophenoxy)piperidin-1-yl)-5-nitronicotinate (3.65 g, 9.28 mmol) and NH$_4$Cl (4.96 g, 93 mmol) in MeOH (33.1 mL) and ACN (33.1 mL) was added zinc (4.25 g, 65.0 mmol) at 0° C. The mixture was stirred at 0° C. for 1 hour, then filtered and rinsed with MeOH. The filtrate was concentrated and purified by column chromatography (silica gel column) eluting with a gradient of 0-40% EtOAc in heptane to give the title compound as an off-white solid (1.882 g, 55.8%). $^1$H NMR (500 MHz, DMSO-d$_6$) δ ppm 1.80-1.87 (m, 2H), 2.06 (d, J=12.20 Hz, 2H), 2.97 (t, J=10.25 Hz, 2H), 3.43-3.49 (m, 2H), 3.80 (d, J=0.98 Hz, 3H), 4.52 (dt, J=7.93, 4.09 Hz, 1H), 5.06 (s, 2H), 6.98-7.05 (m, 1H), 7.26-7.35 (m, 2H), 7.44-7.47 (m, 1H), 8.12 (t, J=1.71 Hz, 1H); ESI-MS m/z [M+H]$^+$ 364.2.

Preparation x48: methyl 6-(4-(2,4-difluorophenoxy)piperidin-1-yl)-5-(2-methoxynicotinamido)nicotinate

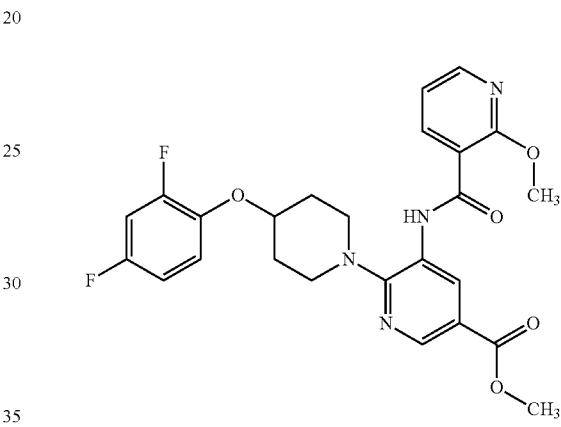

To a solution of methyl 5-amino-6-(4-(2,4-difluorophenoxy)piperidin-1-yl)nicotinate (1.172 g, 3.23 mmol) and 2-methoxynicotinic acid (0.593 g, 3.87 mmol) in NMP (11.90 mL) was added DIPEA (2.247 mL, 12.90 mmol). While stirring, 50% 2,4,6-tripropyl-1,3,5,2,4,6-trioxatriphosphinane 2,4,6-trioxide in EtOAc (4.23 mL, 7.10 mmol) was added and the reaction mixture was stirred at 60° C. overnight. The reaction was incomplete so DIPEA (2.247 mL, 12.90 mmol) was added and the reaction mixture was stirred at 60° C. for 1 hour. Next 2,4,6-tripropyl-1,3,5,2,4,6-trioxatriphosphinane 2,4,6-trioxide (50% in EtOAc) (4.23 mL, 7.10 mmol) was added and the reaction mixture was stirred at 60° C. overnight. The reaction was still incomplete so more 2,4,6-tripropyl-1,3,5,2,4,6-trioxatriphosphinane 2,4,6-trioxide (50% in EtOAc) (4.23 mL, 7.10 mmol) was added and the reaction mixture was again stirred at 60° C. overnight. Still more 2,4,6-tripropyl-1,3,5,2,4,6-trioxatriphosphinane 2,4,6-trioxide (50% in EtOAc) (4.23 mL, 7.10 mmol) was added and the reaction mixture was stirred at 60° C. overnight a fourth time. The reaction was deemed complete and was quenched with water (143 mL). The mixture became milky and a red oil formed on top. After 30 minutes of stirring a solid precipitated, which was filtered to give the title compound as a brown solid (1.419 g, 88%). ESI-MS m/z [M+H]$^+$ 499.4.

Preparation x49: 2-(4-(2,4-difluorophenoxy)piperidin-1-yl)-5-methyl-3-nitropyridine

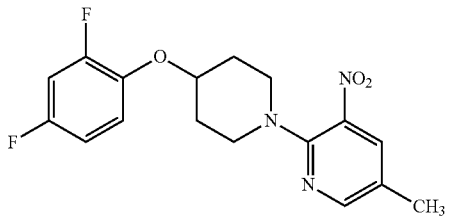 [SMILES: Cc1cnc(N2CCC(Oc3ccc(F)cc3F)CC2)c([N+](=O)[O-])c1]

A solution of 2-fluoro-5-methyl-3-nitropyridine (1 g, 6.41 mmol), 4-(2,4-difluorophenoxy)piperidine hydrochloride (1.919 g, 7.69 mmol) and K$_2$CO$_3$ (2.66 g, 19.22 mmol) in ACN (16.01 mL) was stirred at 80° C. for 5 hours. The reaction mixture was poured into water and extracted with EtOAc (3×50 mL). The organic layers were combined, dried over Na$_2$SO$_4$, and filtered. The filtrate was concentrated in vacuo and purified by flash chromatography (ISCO column) eluting with a gradient of 0-100% EtOAc in heptane to give the title compound as a yellow solid (2.21 g, 99%). $^1$H NMR (500 MHz, DMSO-d$_6$) δ ppm 1.66-1.73 (m, 2H), 2.00 (d, J=12.20 Hz, 2H), 2.25 (s, 3H), 3.19-3.25 (m, 2H), 3.52-3.57 (m, 2H), 4.58 (dt, J=7.69, 3.72 Hz, 1H), 6.98-7.04 (m, 1H), 7.26-7.34 (m, 2H), 8.11 (s, 1H), 8.28 (s, 1H); ESI-MS m/z [M+H]$^+$ 350.2.

Preparation x50: 2-(4-(2,4-difluorophenoxy)piperidin-1-yl)-5-methylpyridin-3-amine

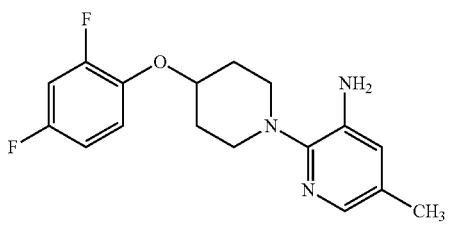

To a mixture of 2-(4-(2,4-difluorophenoxy)piperidin-1-yl)-5-methyl-3-nitropyridine (2.21 g, 6.33 mmol) and NH$_4$Cl (3.38 g, 63.3 mmol) in MeOH (22.59 mL) and ACN (22.59 mL) was added zinc (2.90 g, 44.3 mmol) at 0° C. The reaction mixture was stirred at 0° C. for 4 hours, then filtered and rinsed with MeOH. The filtrate was concentrated and purified by column chromatography (silica gel column) eluting with a gradient of 0-40% EtOAc in heptane to give the title compound as a red solid (1.23 g, 60.9%). $^1$H NMR (500 MHz, DMSO-d$_6$) δ ppm 1.80-1.86 (m, 2H), 2.02-2.06 (m, 2H), 2.10 (s, 3H), 2.77-2.82 (m, 2H), 3.18-3.23 (m, 2H), 4.46 (tt, J=8.24, 3.97 Hz, 1H), 4.75 (s, 2H), 6.77 (d, J=1.95 Hz, 1H), 7.00 (ddt, J=8.54, 7.32, 1.34, 1.34 Hz, 1H), 7.26-7.31 (m, 2H), 7.37 (dd, J=1.95, 0.98 Hz, 1H); ESI-MS m/z [M+H]$^+$ 320.5.

Preparation x51: 4-(4-(2,4-difluorophenoxy)piperidin-1-yl)-2-fluoro-5-nitrobenzonitrile

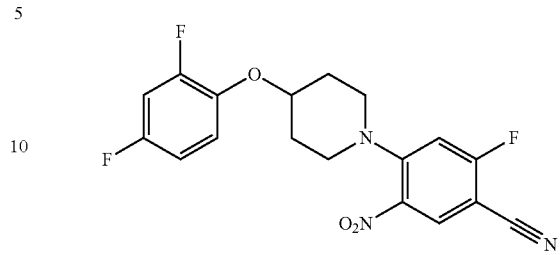

To a solution of 2,4-difluoro-5-nitrobenzonitrile (3.38 g, 18.37 mmol) in DCM (70.9 mL) was added dropwise a solution of 4-(2,4-difluorophenoxy)piperidine (4.7 g, 22.04 mmol) and DIPEA (8.02 mL, 45.9 mmol) in DCM (7.00 mL). The reaction mixture was stirred at 20° C. for 2 hours, then concentrated on Celite® and purified by column chromatography (40 g silica gel column) eluting with a gradient of 0-100% EtOAc in heptane to give the title compound as a yellow solid (1.31 g, 18.9%). ESI-MS m/z [M+H]$^+$ 378.3.

Preparation x52: 5-amino-4-(4-(2,4-difluorophenoxy)piperidin-1-yl-2-fluorobenzonitrile

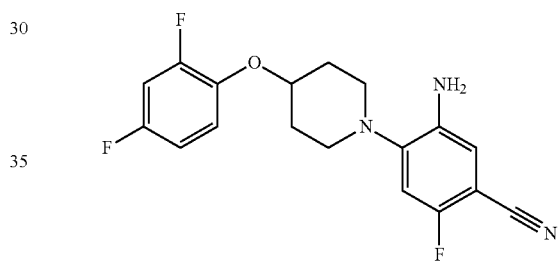

To a mixture of 4-(4-(2,4-difluorophenoxy)piperidin-1-yl)-2-fluoro-5-nitrobenzonitrile (1.31 g, 3.47 mmol) and NH$_4$Cl (1.857 g, 34.7 mmol) in MeOH (12.40 mL) and ACN (12.40 mL) was added zinc (1.589 g, 24.30 mmol). The reaction mixture was stirred at 0° C. in an ice bath, allowed to warm to 20° C., and stirred at 50° C. overnight. LCMS indicated the reaction was complete. The mixture was filtered and rinsed with MeOH. The filtrate was concentrated and purified by column chromatography (120 g silica gel column) eluting with a gradient of 0-80% EtOAc in heptane to give the title compound as a pink solid (771.3 mg, 64.0%). ESI-MS m/z [M+H]$^+$ 348.3.

Preparation x53: 1-(2-chloro-6-methyl-3-nitropyridin-4-yl)piperidin-4-ol

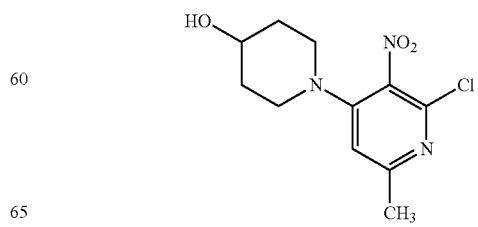

To a solution of 2,4-dichloro-6-methyl-3-nitropyridine (1.6 g, 7.73 mmol) and DIPEA (2.025 mL, 11.59 mmol) in DCM (18.62 mL) was added dropwise a solution of piperidin-4-ol (0.938 g, 9.27 mmol) in DCM (4.66 mL). The reaction mixture was stirred at 20° C. for 3 hours, then concentrated on Celite®, and purified by column chromatography (80 g silica gel column) eluting with a gradient of 0-100% EtOAc in heptane to give the title compound as a yellow solid (1.146 g, 54.6%). $^1$H NMR (500 MHz, DMSO-d$_6$) δ ppm 1.37-1.45 (m, 2H), 1.78 (ddt. J=12.69, 6.10, 3.30, 3.30 Hz, 2H), 2.37 (s, 3H), 3.04 (ddd, J=13.06, 9.40, 3.42 Hz, 2H), 3.34-3.40 (m, 2H), 3.70 (tq, J=8.15, 4.01 Hz, 1H), 4.79 (d, J=4.39 Hz, 1H), 7.08 (s, 1H); ESI-MS m/z [M+H]$^+$ 273.1. Byproduct 1-(4-chloro-6-methyl-3-nitropyridin-2-yl)piperidin-4-ol, was obtained as a yellow oil. $^1$H NMR (500 MHz, DMSO-d$_6$) δ ppm 1.35-1.42 (m, 2H), 1.75-1.80 (m, 2H), 2.38 (s, 3H), 3.09 (ddd, J=13.06, 9.64, 3.17 Hz, 2H), 3.57 (ddd, J=9.52, 8.30, 4.15 Hz, 2H), 3.67-3.73 (m, 1H), 4.76 (d, J=4.39 Hz, 1H), 6.99 (s, 1H); ESI-MS m/z [M+H]$^+$ 273.1.

Preparation x54:
1-(5-amino-2-methylpyridin-4-yl)piperidin-4-ol

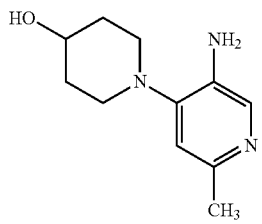

To a solution of 1-(2-chloro-6-methyl-3-nitropyridin-4-yl)piperidin-4-ol (1.146 g, 4.22 mmol) in MeOH (25.1 mL) under nitrogen was added Pd/C (10% Degussa) (0.282 g, 2.65 mmol). The resulting slurry was stirred under an atmosphere of hydrogen overnight. The solids were removed by filtering through hardened circle filter paper. The filter was rinsed with MeOH (200 mL) and the filtrate was concentrated in vacuo to give the title compound as a light brown solid which was used without further purification (1.029 g). $^1$H NMR (500 MHz, DMSO-d$_6$) δ ppm 1.54-1.63 (m, 2H), 1.83-1.90 (m, 2H), 2.45 (s, 3H), 2.97 (ddd, J=12.57, 9.64, 3.17 Hz, 2H), 3.47-3.54 (m, 2H), 3.73 (br s, 1H), 4.80 (br s, 1H), 5.34 (s, 2H), 7.05 (s, 1H), 7.73 (s, 1H); ESI-MS m/z [M+H]$^+$ 208.2.

Preparation x55: N-(4-(4-hydroxypiperidin-1-yl)-6-methylpyridin-3-yl)-2-methoxynicotinamide

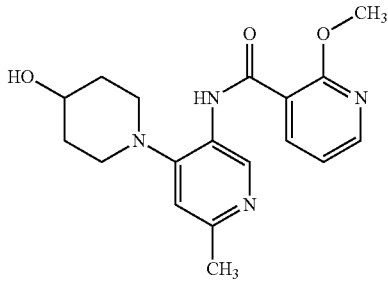 [SMILES: COc1ncccc1C(=O)Nc1cnc(C)cc1N1CCC(O)CC1]

Reactants 1-(5-amino-2-methylpyridin-4-yl)piperidin-4-ol (20.73 mg, 0.1 mmol), 2-methoxynicotinic acid (18.38 mg, 0.120 mmol), HATU (95 mg, 0.250 mmol) and DIPEA (52.4 µL, 0.300 mmol) were dissolved in DMF (1.429 mL). The reaction mixture was stirred at RT overnight and then purified by HPLC to give the title compound as an off-white solid (20 mg, 58%). $^1$H NMR (500 MHz, DMSO-d$_6$) δ ppm 1.52-1.60 (m, 2H), 1.82-1.90 (m, 2H), 2.43 (s, 3H), 2.84 (t, J=10.25 Hz, 2H), 3.20-3.29 (m, 2H), 3.68 (td, J=8.30, 4.39 Hz, 1H), 4.12 (s, 3H), 4.78 (d, J=3.91 Hz, 1H), 7.07 (s, 1H), 7.25 (dd, J=7.32, 4.88 Hz, 1H), 8.38-8.43 (m, 2H), 8.96 (s, 1H), 10.01 (s, 1H); ESI-MS m/z [M+H]$^+$ 343.3.

Preparation x56: 5-bromo-2-(4-(2,4-difluorophenoxy)piperidin-1-yl)-3-nitropyridine

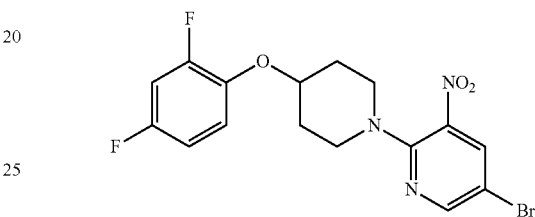

To a solution of 4-(2,4-difluorophenoxy)piperidine hydrochloride (10.52 g, 42.1 mmol) and 5-bromo-2-chloro-3-nitropyridine (10 g, 42.1 mmol) in ACN (126 mL) was added K$_2$CO$_3$ (17.46 g, 126 mmol). The reaction mixture was heated to 80° C. with a reflux condenser for 3 days, then cooled to RT, filtered through Celite®, and concentrated in vacuo. The residue was purified by flash column chromatography on silica gel (220 g SiO$_2$) eluting with a gradient of 5-30% EtOAc in heptane to give the title compound as a yellow solid (16.9 g, 97%). ESI-MS m/z [M+H]$^+$ 414.

Preparation x57: 6-(4-(2,4-difluorophenoxy)piperidin-1-yl)-5-nitronicotinonitrile

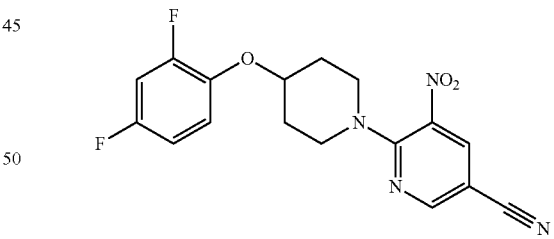

To a nitrogen-flushed suspension of 5-bromo-2-(4-(2,4-difluorophenoxy)piperidin-1-yl)-3-nitropyridine (16.9 g, 40.8 mmol) and zinc(II) cyanide (3.59 g, 30.6 mmol) in DMF (102 mL) was added Pd(Ph$_3$P)$_4$ (2.357 g, 2.040 mmol). The reaction mixture was sparged with nitrogen for 1 minute, capped, and heated to 100° C. for 2 hours. The mixture was then diluted with water (15 mL) and extracted with EtOAc (2×30 mL). The organic extracts were combined, filtered through Celite®, and purified by flash column chromatography on silica gel (two consecutive columns, 330 g SiO$_2$) eluting with a 10-30% gradient of EtOAc in heptane to give the title compound as a yellow solid (10.7 g, 72.8%). $^1$H NMR (400 MHz, CD$_3$CN) δ ppm 1.78-1.88 (m, 2H), 2.01-2.11 (m, 2H), 3.48 (ddd, J=13.64, 7.83, 3.79 Hz, 2H), 3.76 (ddd, J=13.58, 7.89, 3.79 Hz, 2H), 4.58 (dt, J=7.07, 3.54 Hz, 1H), 6.88-6.94 (m, 1H), 7.01 (ddd, J=11.37, 8.59, 3.03 Hz, 1H), 7.16 (td, J=9.22, 5.56 Hz, 1H), 8.48 (d, J=2.02 Hz, 1H), 8.55 (d, J=2.02 Hz, 1H); ESI-MS m/z [M+H]⁺ 361.

Preparation x58: 5-amino-6-(4-(2,4-difluorophenoxy)piperidin-1-yl)nicotinonitrile

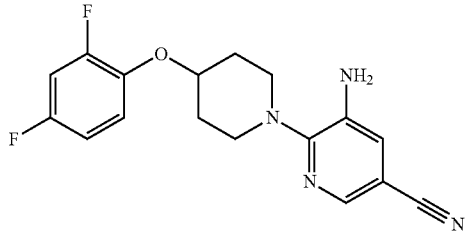

A solution of 6-(4-(2,4-difluorophenoxy)piperidin-1-yl)-5-nitronicotinonitrile (6.4 g, 17.76 mmol) dissolved in 2-methyltetrahydrofuran (67 mL) and MeOH (33 mL) was treated with NH₄Cl (14.25 g, 266 mmol) and zinc (8.13 g, 124 mmol). The reaction mixture was stirred for 1 hour, then filtered through Celite®, and concentrated in vacuo. The residue was purified by flash column chromatography (silica gel column) eluting with a gradient of 30-50% EtOAc in heptane to give the title compound (5.66 g, 96%). ¹H NMR (400 MHz, DMSO-d₆) δ ppm 1.78-1.88 (m, 2H), 1.99-2.09 (m, 2H), 2.95-3.04 (m, 2H), 3.43-3.51 (m, 2H), 4.54 (tt, J=8.02, 3.85 Hz, 1H), 5.27 (s, 2H), 6.98-7.04 (m, 1H), 7.16 (d, J=2.02 Hz, 1H), 7.26-7.34 (m, 2H), 7.95 (d, J=2.02 Hz, 1H); ESI-MS m/z [M+H]⁺ 331.

Preparation x59: 2-(4-(2,4-difluorophenoxy)piperidin-1-yl)-6-methyl-3-nitropyridine

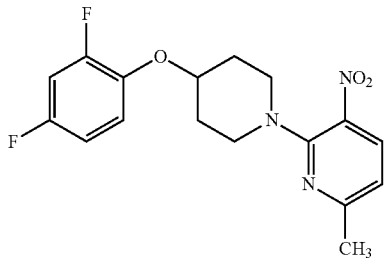 [SMILES: Cc1ccc([N+](=O)[O-])c(N2CCC(Oc3ccc(F)cc3F)CC2)n1]

To a solution of 4-(2,4-difluorophenoxy)piperidine hydrochloride (6.40 g, 25.6 mmol) and 2-fluoro-6-methyl-3-nitropyridine (4 g, 25.6 mmol) in ACN (50 mL) was added K₂CO₃ (10.62 g, 77 mmol). The reaction mixture was heated to 80° C. for 18 hours, then cooled, diluted with EtOAc (40 mL), and filtered. The filtrate was concentrated in vacuo and purified by flash column chromatography on silica gel (220 g SiO₂ column) eluting with a 0-50% gradient of EtOAc in heptane to give the title compound as a yellow oil which crystallized to a yellow solid upon standing (7.24 g, 81%).

Preparation x60: 2-(4-(2,4-difluorophenoxy)piperidin-1-yl)-6-methylpyridin-3-amine

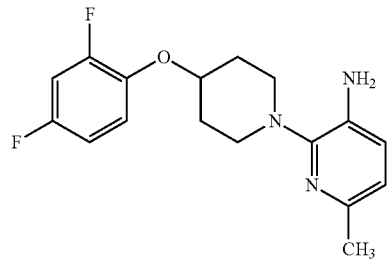 [SMILES: Cc1ccc(N)c(N2CCC(Oc3ccc(F)cc3F)CC2)n1]

A solution of 2-(4-(2,4-difluorophenoxy)piperidin-1-yl)-6-methyl-3-nitropyridine (5.23 g, 14.97 mmol) dissolved in 2-methyltetrahydrofuran (25 mL) and MeOH (12.5 mL) was treated with NH₄Cl (12.01 g, 225 mmol) and zinc (6.85 g, 105 mmol). The reaction mixture was stirred for 3 days, filtered through a plug of Celite®, and concentrated in vacuo. The residue was purified by flash column chromatography (silica gel column) eluting with a 10-50% gradient of EtOAc in heptane to afford a dark oil. The oil was purified again using identical chromatography conditions to give the title compound as a clear brown oil (3.9 g, 82%). ¹H NMR (400 MHz, DMSO-d₆) δ ppm 1.75-1.89 (m, 2H), 1.98-2.10 (m, 2H), 2.23 (s, 3H), 2.75-2.92 (m, 2H), 4.47 (dt, J=8.21, 4.23 Hz, 1H), 4.57 (s, 2H), 6.63 (d, J=7.83 Hz, 1H), 6.86 (d, J=7.58 Hz, 1H), 6.97-7.04 (m, 1H), 7.24-7.33 (m, 2H); ESI-MS m/z [M+H]⁺ 320.

Preparation x61: 2-(4-(2,4-difluorophenoxy)piperidin-1-yl)-5-(methoxymethyl)-3-nitropyridine

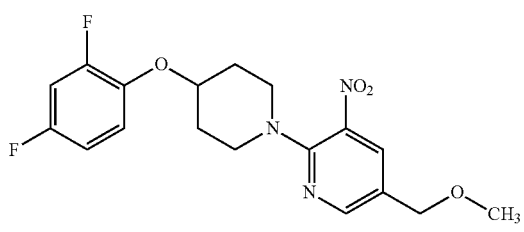

Reactants 5-bromo-2-(4-(2,4-difluorophenoxy)piperidin-1-yl)-3-nitropyridine (4 g, 9.66 mmol), PdCl₂(dppf) (1.060 g, 1.449 mmol) and Cs₂CO₃ (11.33 g, 34.8 mmol) were combined in dioxane (48.3 mL) and water (15 mL). The reaction mixture was heated at 100° C. for 16 hours, then cooled to RT, poured into brine (75 mL) and extracted with EtOAc (2×50 mL). The combined organic extracts were concentrated and purified by flash column chromatography on silica gel, eluting with a gradient of 20-70% EtOAc in heptane. The product-containing fractions were concentrated in vacuo and recrystallized from heptane-EtOAc (1:2, 5 mL) to give the title compound as a yellow solid, which was used without further purification (0.615 g, 16.8%). ESI-MS m/z [M+H]⁺ 380.2.

Preparation x62: 2-(4-(2,4-difluorophenoxy)piperidin-1-yl)-5-(methoxymethyl)pyridin-3-amine

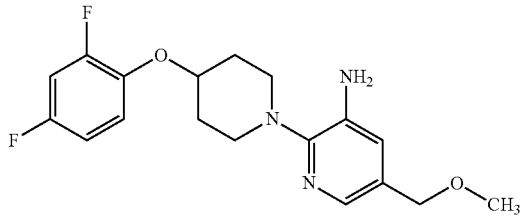 [SMILES: COCc1cnc(N2CCC(Oc3ccc(F)cc3F)CC2)c([N+](=O)[O-])c1]

A suspension of 2-(4-(2,4-difluorophenoxy)piperidin-1-yl)-5-(methoxymethyl)-3-nitropyridine (1.30 g, 3.43 mmol) in 2-methyltetrahydrofuran (2 mL) was added to a cold (5° C.) suspension of NH$_4$Cl (2.75 g, 51.4 mmol) and zinc (1.568 g, 23.99 mmol) in MeOH (5.71 mL) and 2-methyltetrahydrofuran (11.42 mL). The reaction mixture was stirred at 5° C. for 1 hour, then diluted with EtOAc (40 mL) and filtered. The filtrate was concentrated in vacuo and purified by flash column chromatography on silica gel, eluting with a gradient of 20-50% EtOAc in heptane to give the title compound as a brown oil (150 mg, 12.5%). ESI-MS m/z [M+H]$^+$ 350.2.

Preparation x63:
N-(5-cyanopyridin-3-yl)picolinamide

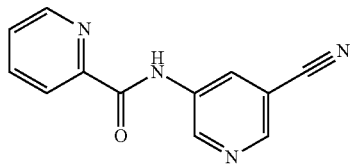 [SMILES: N#Cc1cncc(NC(=O)c2ccccn2)c1]

A solution of 5-aminonicotinonitrile (5.14 g, 43.1 mmol), HATU (19.69 g, 51.8 mmol) and picolinic acid (6.37 g, 51.8 mmol) in DMA (86 mL) was treated with DIPEA (15.03 mL, 86 mmol). The resulting mixture was heated to 80° C. for 3 hours, then diluted with brine (100 mL) and water (100 mL) and stirred for 1 hour. The solids were filtered, washed with water (3×75 mL) and dried in a vacuum oven at 70° C. for 16 hours to give the title compound as an off-white solid (8.78 g, 91%). ESI-MS m/z [M+H]$^+$ 225.1.

Preparation x64:
4-(4-benzoylpiperidin-1-yl)-3-nitrobenzonitrile

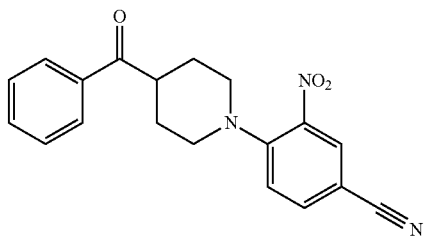

To a solution of 4-fluoro-3-nitrobenzonitrile (0.100 g, 0.600 mmol) and phenyl(piperidin-4-yl)methanone (0.114 g, 0.600 mmol) in ACN (1 mL) was added K$_2$CO$_3$ (0.249 g, 1.80 mmol). The reaction mixture was heated to 80° C. for 3 hours and then diluted with water (3 mL). The liquid phase was decanted and the solid phase was washed with water and dried in a vacuum oven at 70° C. for 4 hours to give the title compound, which was used without further purification.

Preparation x65:
3-amino-4-(4-benzoylpiperidin-1-yl)benzonitrile

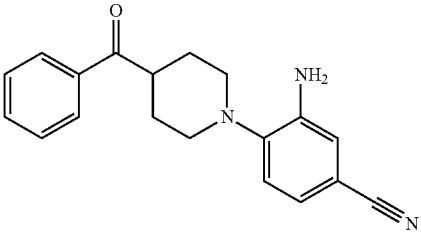 [SMILES: N#Cc1ccc(N2CCC(C(=O)c3ccccc3)CC2)c(N)c1]

To a 4 mL vial charged with 4-(4-benzoylpiperidin-1-yl)-3-nitrobenzonitrile (0.201 g, 0.600 mmol) was added zinc (0.275 g, 4.20 mmol) and NH$_4$Cl (0.385 g, 7.20 mmol). The solids were dispersed with 2-methyltetrahydrofuran (1.5 mL) and MeOH (0.8 mL). The reaction mixture was stirred vigorously at RT for 4 hours, then diluted with EtOAc (2 mL) and filtered. The filtrate was concentrated under the flow of nitrogen and dried in a vacuum oven at 70° C. for 4 hours to give the title compound, which was used without further purification.

Preparation x66: 4-(4-(2-chloro-6-fluorobenzyl)piperazin-1-yl)-3-nitrobenzonitrile

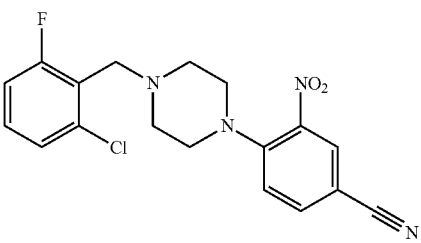 [SMILES: N#Cc1ccc(N2CCN(Cc3c(F)cccc3Cl)CC2)c([N+](=O)[O-])c1]

To a solution of 4-fluoro-3-nitrobenzonitrile (0.100 g, 0.600 mmol) and 1-(2-chloro-6-fluorobenzyl)piperazine (0.102 g, 0.446 mmol) in ACN (1 mL) was added K$_2$CO$_3$ (0.185 g, 1.338 mmol). The reaction mixture was heated to 80° C. for 3 hours and then diluted with water (3 mL). The liquid phase was decanted and the solid phase was washed with water and dried in a vacuum oven at 70° C. for 4 hours to give the title compound, which was used without further purification.

Preparation x67: 3-amino-4-(4-(2-chloro-6-fluorobenzyl)piperazin-1-yl)benzonitrile

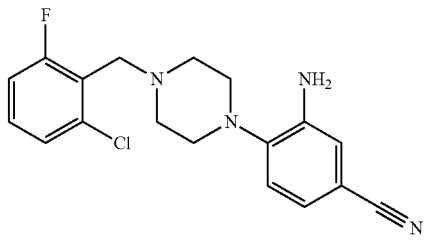 [SMILES: N#Cc1ccc(N2CCN(Cc3c(F)cccc3Cl)CC2)c(N)c1]

To a 4 mL vial charged with 4-(4-(2-chloro-6-fluorobenzyl)piperazin-1-yl)-3-nitrobenzonitrile (0.167 g, 0.446 mmol) was added zinc (0.204 g, 3.12 mmol) and NH$_4$Cl (0.286 g, 3.12 mmol). The solids were dispersed with 2-methyltetrahydrofuran (1.5 mL) and MeOH (0.8 mL). The reaction mixture was stirred vigorously at RT for 4 hours, then diluted with EtOAc (2 mL) and filtered. The filtrate was concentrated under the flow of nitrogen and dried in a vacuum oven at 70° C. for 4 hours to give the title compound, which was used without further purification.

Preparation x68: 3-nitro-4-(4-(thiophen-2-ylmethyl)piperazin-1-yl)benzonitrile

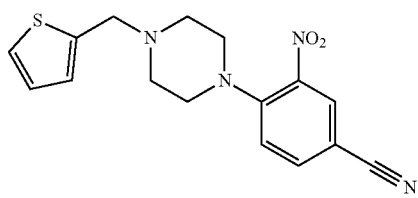

To a solution of 4-fluoro-3-nitrobenzonitrile (74.1 mg, 0.446 mmol) and 1-(thiophen-2-ylmethyl)piperazine (0.081 g, 0.446 mmol) in ACN (1 mL) was added K$_2$CO$_3$ (0.185 g, 1.338 mmol). The reaction mixture was heated to 80° C. for 3 hours and then diluted with water (3 mL). The liquid phase was decanted and the solid phase was washed with water and dried in a vacuum oven at 70° C. for 4 hours to give the title compound, which was used without further purification.

Preparation x69: 3-amino-4-(4-(thiophen-2-ylmethyl)piperazin-1-yl)benzonitrile

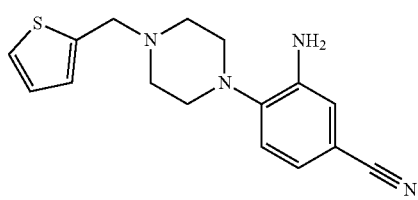 [SMILES: N#Cc1ccc(N2CCN(Cc3cccs3)CC2)c([N+](=O)[O-])c1]

To a 4 mL vial charged with 3-nitro-4-(4-(thiophen-2-ylmethyl)piperazin-1-yl)benzonitrile (0.146 g, 0.446 mmol) was added zinc (0.204 g, 3.12 mmol) and NH$_4$Cl (0.286 g, 5.35 mmol). The solids were dispersed with 2-methyltetrahydrofuran (1.5 mL) and MeOH (0.8 mL). The reaction mixture was stirred vigorously at RT for 4 hours, then diluted with EtOAc (2 mL) and filtered. The filtrate was concentrated under the flow of nitrogen and dried in a vacuum oven at 70° C. for 4 hours to give the title compound, which was used without further purification.

Preparation x70: 3-nitro-4-(4-(thiophen-3-ylmethyl)piperazin-1-yl)benzonitrile

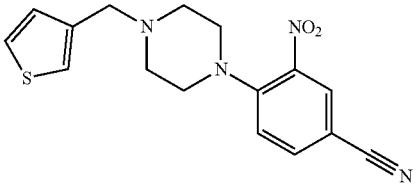 [SMILES: N#Cc1ccc(N2CCN(Cc3ccsc3)CC2)c([N+](=O)[O-])c1]

To a solution of 4-fluoro-3-nitrobenzonitrile (74.1 mg, 0.446 mmol) and 1-(thiophen-3-ylmethyl)piperazine (0.081 g, 0.446 mmol) in ACN (1 mL) was added K$_2$CO$_3$ (0.185 g, 1.338 mmol). The reaction mixture was heated to 80° C. for 3 hours and then diluted with water (3 mL). The liquid phase was decanted and the solid phase was washed with water and dried in a vacuum oven at 70° C. for 4 hours to give the title compound, which was used without further purification.

Preparation x71: 3-amino-4-(4-(thiophen-3-ylmethyl)piperazin-1-yl)benzonitrile

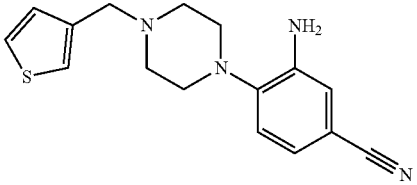 [SMILES: N#Cc1ccc(N2CCN(Cc3ccsc3)CC2)c(N)c1]

To a 4 mL vial charged with 3-nitro-4-(4-(thiophen-3-ylmethyl)piperazin-1-yl)benzonitrile (0.146 g, 0.446 mmol) was added zinc (0.204 g, 3.12 mmol) and NH$_4$Cl (0.286 g, 5.35 mmol). The solids were diluted with 2-methyltetrahydrofuran (1.5 mL) and MeOH (0.8 mL). The reaction mixture was stirred vigorously at RT for 4 hours, then diluted with EtOAc (2 mL) and filtered. The filtrate was concentrated under the flow of nitrogen and dried in a vacuum oven at 70° C. for 4 hours to give the title compound, which was used without further purification.

Preparation x72: 1-(5-bromo-3-nitropyridin-2-yl)-4-(4-fluorobenzyl)piperazine

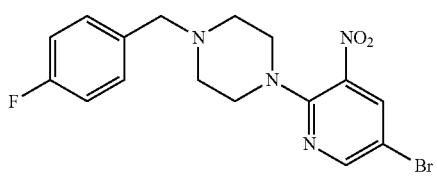 [SMILES: O=[N+]([O-])c1cc(Br)cnc1N1CCN(Cc2ccc(F)cc2)CC1]

To a solution of 1-(4-fluorobenzyl)piperazine (4.09 g, 21.06 mmol) and 5-bromo-2-chloro-3-nitropyridine (5 g, 21.06 mmol) in ACN (mL) was added K$_2$CO$_3$ (8.73 g, 63.2 mmol). The reaction mixture was heated to 80° C. with a reflux condenser for 20 hours, then cooled to RT, diluted with EtOAc (100 mL) and filtered through a plug of Celite®. The filtrate was concentrated in vacuo and dried in vacuum to give the title compound as a pink solid (8.10 g, 97%).

Preparation x73: 6-(4-(4-fluorobenzyl)piperazin-1-yl)-5-nitronicotinonitrile

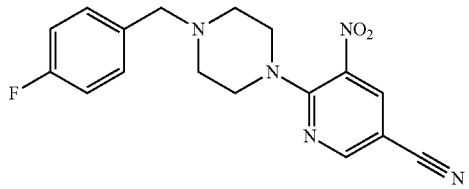 [SMILES: N#Cc1cnc(N2CCN(Cc3ccc(F)cc3)CC2)c([N+](=O)[O-])c1]

To a nitrogen-flushed suspension of 1-(5-bromo-3-nitropyridin-2-yl)-4-(4-fluorobenzyl)piperazine (8.10 g, 20.49 mmol) and zinc(II) cyanide (1.805 g, 15.37 mmol) in DMF (51.2 mL) was added Pd(Ph$_3$P)$_4$ (1.184 g, 1.025 mmol). The mixture was sparged with nitrogen for 1 minute, capped, heated to 100° C. for 2 hours, then diluted with water (150 mL) and extracted with EtOAc (2×100 mL). The organic extracts were combined, washed with water (3×50 mL) and brine (50 mL), dried over Na$_2$SO$_4$, and filtered through a short plug of Celite®. The filtrate was concentrated in vacuo. The resulting oil was purified by flash column chromatography on silica gel (330 g SiO$_2$ column) eluting with a gradient of 10-40% EtOAc in heptane to give the title compound as a yellow solid (6.7 g, 96%). ESI-MS m/z [M+H]$^+$ 342.2.

Preparation x74: 5-amino-6-(4-(4-fluorobenzyl)piperazin-1-yl)nicotinonitrile

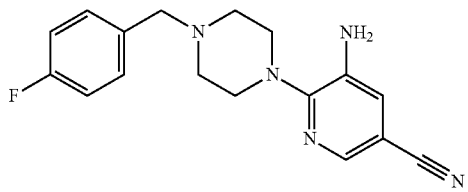 [SMILES: N#Cc1cnc(N2CCN(Cc3ccc(F)cc3)CC2)c(N)c1]

To a solution of 6-(4-(4-fluorobenzyl)piperazin-1-yl)-5-nitronicotinonitrile (6.7 g, 19.63 mmol) and NH$_4$Cl (12.60 g, 236 mmol) in 2-methyltetrahydrofuran (131 mL) and MeOH (65.4 mL) was added zinc (8.98 g, 137 mmol). The reaction mixture was stirred at RT for 2 hours, then diluted with EtOAc (150 mL) and filtered through a short plug of Celite®. The filtrate was concentrated in vacuo and dried in a vacuum oven at 70° C. for 4 hours to give the title compound as a pink solid (6.00 g, 98%). ESI-MS m/z [M+H]$^+$ 312.2.

Preparation x75: N-(1-acetyl-1H-indazol-6-yl)picolinamide

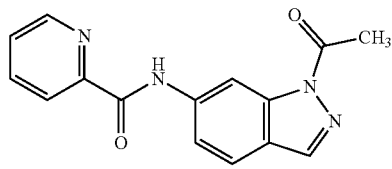 [SMILES: CC(=O)n1ncc2ccc(NC(=O)c3ccccn3)cc21]

A solution of 1-(6-amino-1H-indazol-1-yl)ethanone (0.751 g, 4.29 mmol), picolinic acid (0.792 g, 6.43 mmol) and HATU (2.445 g, 6.43 mmol) in DMA (8.57 mL) was treated with DIPEA (2.240 mL, 12.86 mmol). The reaction mixture was stirred at 80° C. for 2 hours, then diluted with water (20 mL), and stirred for 30 minutes. The resulting precipitate was filtered and dried in a vacuum oven at 80° C. to afford the title compound as an off-white solid (1.18 g, 98%). ESI-MS m/z [M+H]$^+$ 281.1.

Preparation x76: 3-amino-4-(4-(2-fluoro-4-methoxybenzoyl)piperidin-1-yl)benzonitrile

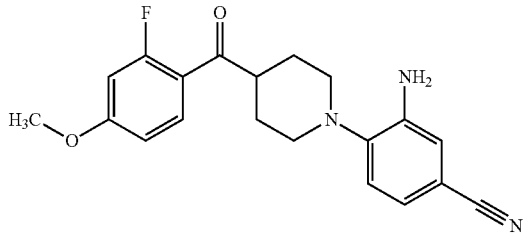 [SMILES: COc1ccc(C(=O)C2CCN(c3ccc(C#N)cc3N)CC2)c(F)c1]

A mixture of (2-fluoro-4-methoxyphenyl)(piperidin-4-yl)methanone, HCl (0.214 g, 0.782 mmol), 4-fluoro-3-nitrobenzonitrile (0.390 g, 2.345 mmol), K$_2$CO$_3$ (0.432 g, 3.13 mmol) and ACN (2.61 mL) was heated to 80° C. for 24 hours, then filtered and concentrated. The crude material was wet-loaded onto an ISCO® column using DCM and eluted with EtOAc and heptanes to afford intermediate 4-(4-(2-fluoro-4-methoxybenzoyl)piperidin-1-yl)-3-nitrobenzonitrile. The nitro-intermediate was combined with zinc (0.767 g, 11.73 mmol), NH$_4$C (0.627 g, 11.73 mmol) and a 1:1 mixture of THF and MeOH (2.61 mL). The reaction mixture was stirred at RT for 24 hours, then filtered and concentrated. The crude product was diluted with 1M (aq) NaOH, extracted with EtOAc, dried over Na$_2$SO$_4$, filtered, and concentrated in vacuo to give the title compound (0.155 g, 56.1%).

Preparation x77: 3-amino-4-(4-(2,5-difluorobenzoyl)piperidin-1-yl)benzonitrile

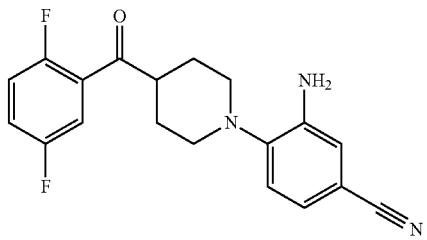 [SMILES: N#Cc1ccc(N2CCC(C(=O)c3cc(F)ccc3F)CC2)c(N)c1]

The title compound was prepared in a manner similar to Preparation x76, using (2,5-difluorophenyl)(piperidin-4-yl)methanone, HCl (0.217 g, 0.829 mmol) in place of (2-fluoro-4-methoxyphenyl)(piperidin-4-yl)methanone, HCl to afford nitro-intermediate 4-(4-(2,5-difluorobenzoyl)piperidin-1-yl)-3-nitrobenzonitrile which underwent zinc reduction to give the title compound (0.104 g, 36.7%).

Preparation x78: 3-amine-4-(4-(5-chloro-2-fluorobenzoyl)piperidin-1-yl)benzonitrile

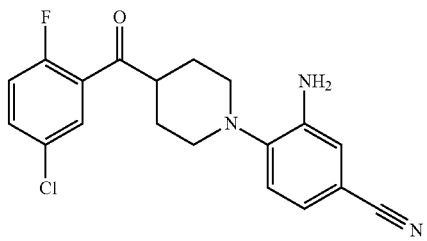 [SMILES: N#Cc1ccc(N2CCC(C(=O)c3cc(Cl)ccc3F)CC2)c(N)c1]

The title compound was prepared in a manner similar to Preparation x76, using (5-chloro-2-fluorophenyl)(piperidin-4-yl)methanone, HCl (0.209 g, 0.751 mmol) in place of (2-fluoro-4-methoxyphenyl)(piperidin-4-yl)methanone, HCl to afford nitro-intermediate 4-(4-(5-chloro-2-fluorobenzoyl)piperidin-1-yl)-3-nitrobenzonitrile which underwent zinc reduction to give the title compound (0.133 g, 49.5%).

Preparation x79: (S)-3-amino-4-(4-((2,4-difluorophenyl)fluoromethyl)piperidin-1-yl)benzonitrile

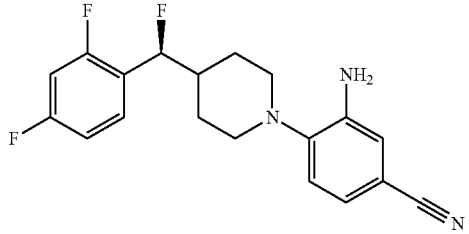 [SMILES: N#Cc1ccc(N2CCC([C@H](F)c3ccc(F)cc3F)CC2)c(N)c1]

A mixture of (S)-4-((2,4-difluorophenyl)fluoromethyl)piperidine, HCl (0.237 g, 0.892 mmol), 4-fluoro-3-nitrobenzonitrile (0.163 g, 0.981 mmol), $K_2CO_3$ (0.493 g, 3.57 mmol) and ACN (2.97 mL) was stirred at RT for 10 minutes then heated to 50° C. for 1.5 hours. The reaction mixture was diluted with water and nitro-intermediate (S)-4-(4-((2,4-difluorophenyl)fluoromethyl)piperidin-1-yl)-3-nitrobenzonitrile was isolated. Zinc (0.875 g, 13.38 mmol), $NH_4Cl$ (0.716 g, 13.38 mmol), and 1:1 mixture of THF and MeOH (2.97 mL) were added to the nitro-intermediate and the reaction mixture was heated to 50° C. for 12 hours, then filtered, and concentrated in vacuo. The concentrate was diluted with EtOAc, basified with 1 M (aq) NaOH, extracted with EtOAc, dried over $Na_2SO_4$, filtered, and concentrated in vacuo to give the title compound which was used without further purification (0.255 g, 83%).

Preparation x80: (R)-3-amino-4-(4-((2,4-difluorophenyl)fluoromethyl)piperidin-1-yl)benzonitrile

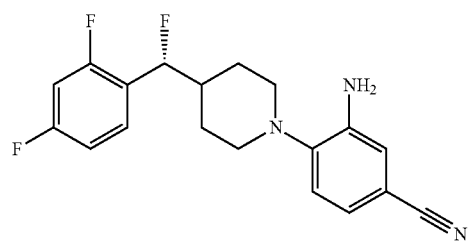 [SMILES: N#Cc1ccc(N2CCC([C@@H](F)c3ccc(F)cc3F)CC2)c(N)c1]

The title compound was prepared in a manner similar to Preparation x79, using (R)-4-((2,4-difluorophenyl)fluoromethyl)piperidine, HC (0.217 g, 0.829 mmol) in place of (S)-4-((2,4-difluorophenyl)fluoromethyl)piperidine, HCl to afford nitro-intermediate (R)-4-(4-((2,4-difluorophenyl)fluoromethyl)piperidin-1-yl)-3-nitrobenzonitrile which underwent zinc reduction to give the title compound (0.229 g, 80%).

Preparation x81: 3-amino-4-(4-((2,4-difluorophenyl)difluoromethyl)piperidin-1-yl)benzonitrile

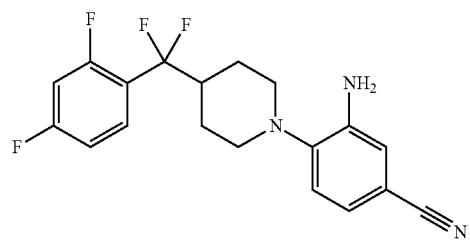 [SMILES: N#Cc1ccc(N2CCC(C(F)(F)c3ccc(F)cc3F)CC2)c(N)c1]

The title compound was prepared in a manner similar to Preparation x79, using 4-((2,4-difluorophenyl)difluoromethyl)piperidine, HCl (0.228 g, 0.804 mmol) in place of (S)-4-((2,4-difluorophenyl)fluoromethyl)piperidine, HCl to afford nitro-intermediate 4-(4-((2,4-difluorophenyl)difluoromethyl)piperidin-1-yl)-3-nitrobenzonitrile which underwent zinc reduction to give the title compound (0.627 mmol, 78%).

Preparation x82: 3-amino-4-(4-((2,5-difluorophenyl)fluoromethyl)piperidin-1-yl)benzonitrile

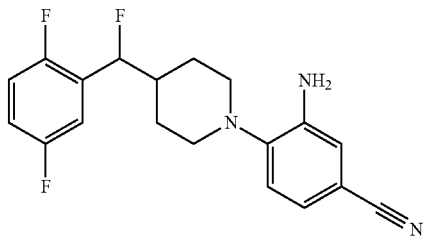 [SMILES: N#Cc1ccc(N2CCC(C(F)c3cc(F)ccc3F)CC2)c(N)c1]

The title compound was prepared in a manner similar to Preparation x79, using 4-((2,5-difluorophenyl)fluoromethyl)piperidine, HCl (0.287 g, 1.080 mmol) in place of (S)-4-((2,4-difluorophenyl)fluoromethyl)piperidine, HCl to afford nitro-intermediate 4-(4-((2,5-difluorophenyl)fluoromethyl)piperidin-1-yl)-3-nitrobenzonitrile which underwent zinc reduction to give the title compound (0.364 g, 98%).

Preparation x83: 3-amino-4-(4-((2,5-difluorophenyl)difluoromethyl)piperidin-1-yl)benzonitrile

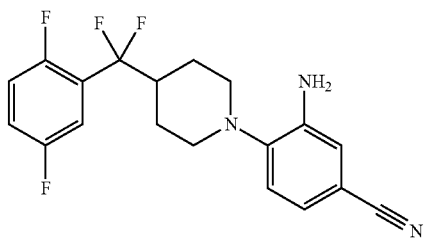 [SMILES: N#Cc1ccc(N2CCC(C(F)(F)c3cc(F)ccc3F)CC2)c(N)c1]

The title compound was prepared in a manner similar to Preparation x79, using 4-((2,5-difluorophenyl)difluoromethyl)piperidine, HCl (0.189 g, 0.666 mmol) in place of (S)-4-((2,4-difluorophenyl)fluoromethyl)piperidine, HCl to afford nitro-intermediate 4-(4-((2,5-difluorophenyl)difluoromethyl)piperidin-1-yl)-3-nitrobenzonitrile which underwent zinc reduction to give the title compound (0.206 g, 85%).

Preparation x84: 3-amino-4-(4-((5-chloro-2-fluorophenyl)difluoromethyl)piperidin-1-yl)benzonitrile

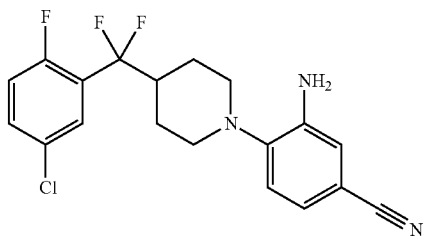 [SMILES: N#Cc1ccc(N2CCC(C(F)(F)c3cc(Cl)ccc3F)CC2)c(N)c1]

The title compound was prepared in a manner similar to Preparation x79, using 4-((5-chloro-2-fluorophenyl)difluoromethyl)piperidine, HC (0.121 g, 0.403 mmol) in place of (S)-4-((2,4-difluorophenyl)fluoromethyl)piperidine, HCl to afford nitro-intermediate 4-(4-((5-chloro-2-fluorophenyl)difluoromethyl)piperidin-1-yl)-3-nitrobenzonitrile which underwent zinc reduction to give the title compound (0.125 g, 82%).

Preparation x85: 3-amino-4-(4-(2-fluoro-4-methoxybenzyl)piperidin-1-yl)benzonitrile

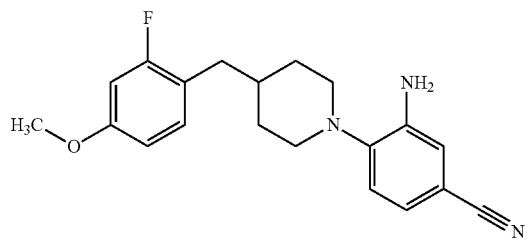 [SMILES: COc1ccc(CC2CCN(c3ccc(C#N)cc3N)CC2)c(F)c1]

The title compound was prepared in a manner similar to Preparation x79, using 4-(2-fluoro-4-methoxybenzyl)piperidine, HCl (0.156 g, 0.601) in place of (S)-4-((2,4-difluorophenyl)fluoromethyl)piperidine, HCl to afford nitro-intermediate 4-(4-(2-fluoro-4-methoxybenzyl)piperidin-1-yl)-3-nitrobenzonitrile which underwent zinc reduction to give the title compound (0.186 g, 91%).

Preparation x86: tert-butyl 4-(2-amino-4-cyanophenyl)piperazine-1-carboxylate

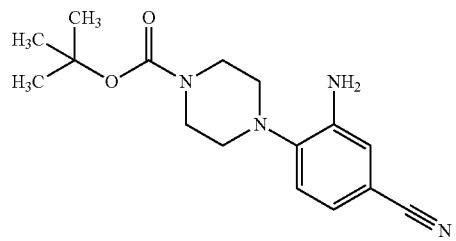 [SMILES: CC(C)(C)OC(=O)N1CCN(c2ccc(C#N)cc2N)CC1]

The title compound was prepared in a manner similar to Preparation x76, using tert-butyl piperazine-1-carboxylate (1.816 g, 9.75 mmol) in place of (2-fluoro-4-methoxyphenyl)(piperidin-4-yl)methanone, HCl to afford nitro-intermediate tert-butyl 4-(4-cyano-2-nitrophenyl)piperazine-1-carboxylate which underwent zinc reduction to give the title compound.

Preparation x87: tert-butyl 4-(4-cyano-2-(2-methoxynicotinamido)phenyl)piperazine-1-carboxylate

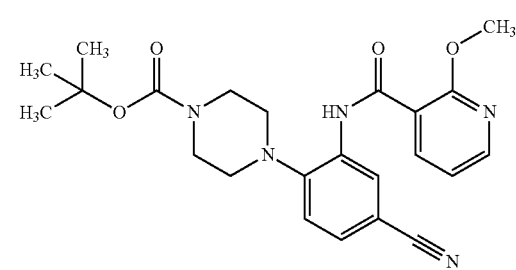 [SMILES: COc1ncccc1C(=O)Nc1cc(C#N)ccc1N1CCN(C(=O)OC(C)(C)C)CC1]

A mixture of tert-butyl 4-(2-amino-4-cyanophenyl)piperazine-1-carboxylate (3.176 g, 10.50 mmol), 2-methoxynicotinic acid (2.413 g, 15.76 mmol), 2,4,6-tripropyl-1,3,5,2,4,6-trioxatriphosphinane 2,4,6-trioxide (10.03 mL, 15.76 mmol), Et₃N (2.196 mL, 15.76 mmol) and DMF (35.0 mL) were stirred 75° C. for 48 hours. The reaction mixture was then diluted with EtOAc, washed with water (3×), dried over Na₂SO₄, filtered, and concentrated in vacuo. The crude product was purified by column chromatography to afford the title compound (1.944 g, 42.3%).

Preparation x88: N-(5-cyano-2-(piperazin-1-yl)phenyl)-2-methoxynicotinamide

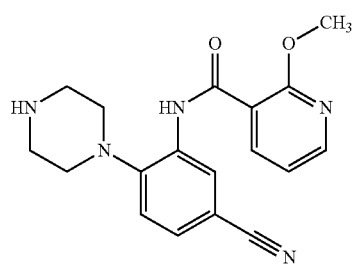 [SMILES: COc1ncccc1C(=O)Nc1cc(C#N)ccc1N1CCNCC1]

To a solution of tert-butyl 4-(4-cyano-2-(2-methoxynicotinamido)phenyl)piperazine-1-carboxylate (1.944 g, 4.44 mmol) in DCM (2 mL) and at RT was added TFA (29.6 mL). The reaction mixture was stirred for 6 hours and then concentrated in vacuo. The concentrate was diluted with EtOAc, washed with 1 M (aq) NaOH, dried over Na₂SO₄, filtered, and concentrated in vacuo to give the title compound as a white solid (1.369 g, 91% yield).

Preparation x89: 4-amino-3-(4-(2,4-difluorophenoxy)piperidin-1-yl)benzonitrile

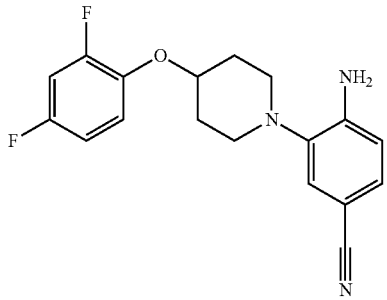 [SMILES: N#Cc1ccc(N)c(N2CCC(Oc3ccc(F)cc3F)CC2)c1]

A mixture of 3-fluoro-4-nitrobenzonitrile (2.85 g, 17.13 mmol), 4-(2,4-difluorophenoxy)piperidine, HCl (3.889 g, 15.58 mmol), and ACN (19.47 mL) was heated to 80° C. and stirred for 12 hours, then filtered and concentrated in vacuo to afford nitro-intermediate 3-(4-(2,4-difluorophenoxy)piperidin-1-yl)-4-nitrobenzonitrile. The (crude) nitro-intermediate was taken up in a 1:1 mixture of THF and MeOH (0.17 M, 90 mL). Ammonium chloride (12.50 g, 234 mmol) and zinc (15.28 g, 234 mmol) were added and the reaction mixture was stirred at RT for 2 hours, then filtered and concentrated in vacuo. The concentrate was diluted with water, basified with 1 M (aq) NaOH, extracted with EtOAc, dried over Na₂SO₄, filtered, and concentrated in vacuo to give the title compound as a viscous brown oil that solidified after 2 days (4.815 g, 94%).

Preparation x90: (4-fluoro-2-methylphenyl)(4-(4-(methylsulfonyl)-2-nitrophenyl)piperazin-1-yl)methanone

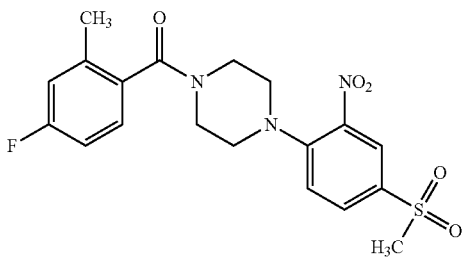

A solution of (4-fluoro-2-methylphenyl)(piperazin-1-yl)methanone hydrochloride (230 mg, 0.890 mmol), I-fluoro-4-(methylsulfonyl)-2-nitrobenzene (150 mg, 0.684 mmol) and K₂CO₃ (284 mg, 2.053 mmol) in ACN (1711 μL) was stirred on a hot plate at 80° C. for 48 hours. The reaction mixture was transferred into a separatory funnel, diluted with water and extracted with EtOAc (3×50 mL). The organic layers were combined, dried over MgSO₄, filtered with suction and the solvent removed under reduced pressure to give the title compound as a yellow oil, which was used without further purification. ESI-MS m/z [M+H]⁺ 422.2.

Preparation x91: (4-(2-amino-4-(methylsulfonyl)phenyl)piperazin-1-yl)(4-fluoro-2-methylphenyl)methanone

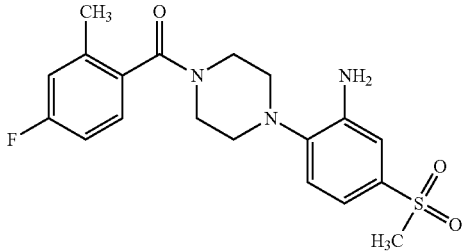 [SMILES: Cc1cc(F)ccc1C(=O)N1CCN(c2ccc(S(C)(=O)=O)cc2[N+](=O)[O-])CC1]

A solution of (4-fluoro-2-methylphenyl)(4-(4-(methylsulfonyl)-2-nitrophenyl)piperazin-1-yl)methanone (288 mg, 0.684 mmol) in MeOH (1.710 mL) and THF (1.710 mL) was treated with NH₄Cl (549 mg, 10.26 mmol) and zinc (671 mg, 10.26 mmol) portion-wise at RT. The reaction mixture was stirred for 48 hours and then filtered with suction. The solvent was removed under reduced pressure and the product purified by column chromatography (dry packing) eluting with a gradient of 0-100% EtOAc in heptanes to give the title compound as an orange solid (195 mg, 72.8). ESI-MS m/z [M+H]⁺ 392.2.

Preparation x92: tert-butyl 4-((4-fluorophenyl)(hydroxy)methyl)piperidine-1-carboxylate

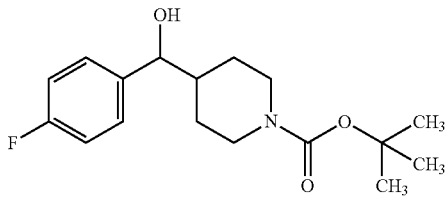 [SMILES: CC(C)(C)OC(=O)N1CCC(C(O)c2ccc(F)cc2)CC1]

A solution of (4-fluorophenyl)magnesium bromide (23.44 mL, 18.76 mmol) in ether (46.9 mL) at 0° C. under N$_2$ atmosphere was treated with a solution of tert-butyl 4-formylpiperidine-1-carboxylate (2 g, 9.38 mmol) in ether (4 mL) dropwise. Once the addition was complete the reaction mixture was allowed to warm up to RT and was stirred for 1 hour. The reaction mixture was quenched with saturated (aq) NH$_4$Cl and extracted with ether (1×150 mL) and EtOAc (1×200 mL). The organic layers were combined, dried over MgSO$_4$, filtered and the solvent removed under reduced pressure. The product was purified by column chromatography (dry packing) eluting with a gradient of 0-100% EtOAc in heptanes to give the title compound as a light yellow oil (2.37 g, 82%). ESI-MS m/z [M+H]$^+$ 310.2.

Preparation x93: tert-butyl 4-((4-fluorophenyl)(methoxy)methylpiperidine-1-carboxylate

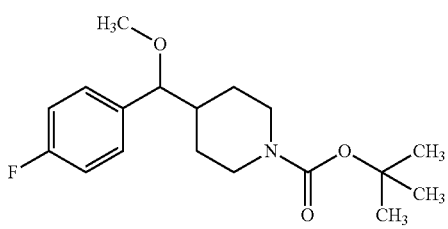 [SMILES: COC(c1ccc(F)cc1)C1CCN(C(=O)OC(C)(C)C)CC1]

Sodium hydride (101 mg, 2.52 mmol) was added to a solution of tert-butyl 4-((4-fluorophenyl)(hydroxy)methyl)piperidine-1-carboxylate (520 mg, 1.681 mmol) in THF (8.404 mL) at RT. The reaction mixture was stirred for 30 minutes and then iodomethane (1.681 mL, 3.36 mmol) was added and stirring was continued at RT for 16 hours. The reaction mixture was quenched with a few drops of water and MeOH. The solvent was removed under reduced pressure and the product purified by column chromatography (dry packing) eluting with a gradient of 0-100% EtOAc in heptanes to give the title compound as a light yellow oil (512.6 mg, 94%). ESI-MS m/z [M+H]$^+$ 324.2.

Preparation x94: 4-((4-fluorophenyl)(methoxy)methyl)piperidine hydrochloride

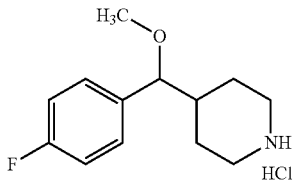 [SMILES: COC(c1ccc(F)cc1)C1CCNCC1 ; Cl]

A solution of tert-butyl 4-((4-fluorophenyl)(methoxy)methyl)piperidine-1-carboxylate (513 mg, 1.586 mmol) in dioxane (4.807 mL) and MeOH (481 µL) was treated with 4 M (aq) HCl (5.948 mL, 23.79 mmol) at RT. The resulting reaction mixture was stirred for 2 hours. The solvent was removed to give the title compound as a light yellow solid. ESI-MS m/z [M+H]$^+$ 224.2.

Preparation x95: 4-(4-((4-fluorophenyl)(methoxy)methyl)piperidin-1-yl)-3-nitrobenzonitrile

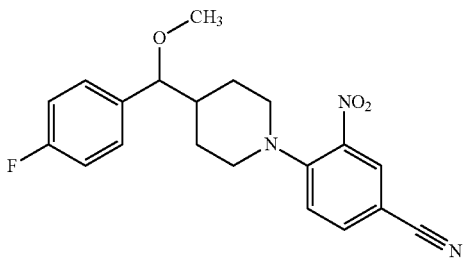

A solution of 4-((4-fluorophenyl)(methoxy)methyl)piperidine hydrochloride (0.410 g, 1.58 mmol), 4-fluoro-3-nitrobenzonitrile (0.271 g, 1.580 mmol) and K$_2$CO$_1$ (0.655 g, 4.74 mmol) in ACN (5.27 mL) was stirred on a hot plate at 80° C. for 1 hour. The reaction mixture was filtered with suction and the solvent removed under reduced pressure to afford the title compound as an orange solid. ESI-MS m/z [M+H]$^+$ 370.2.

Preparation x96: 3-amino-4-(4-((4-fluorophenyl)(methoxy)methyl)piperidin-1-yl)benzonitrile

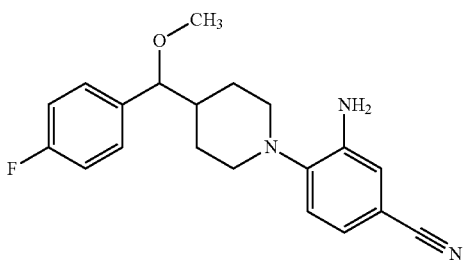 [SMILES: COC(c1ccc(F)cc1)C1CCN(c2ccc(C#N)cc2[N+](=O)[O-])CC1]

A solution of 4-(4-((4-fluorophenyl)(methoxy)methyl)piperidin-1-yl)-3-nitrobenzonitrile (584 mg, 1.58 mmol) in THF (5.267 mL) and MeOH (5.267 mL) was treated with NH$_4$Cl (845 mg, 15.80 mmol) and zinc (1033 mg, 15.80 mmol) portion-wise at RT. The resulting reaction mixture was stirred for 2 hours and then filtered with suction. The solvent removed under reduced pressure and the product purified by column chromatography (dry packing) eluting with a gradient of 0-100% EtOAc in heptanes to give the title compound as an orange oil (461.5 mg, 86%). ESI-MS m/z [M+H]$^+$ 340.2.

Preparation x97: 4-(4-((3-fluorophenyl)sulfonyl) piperidin-1-yl)-3-nitrobenzonitrile

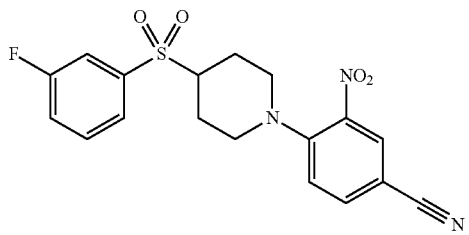 [SMILES: N#Cc1ccc(N2CCC(S(=O)(=O)c3cccc(F)c3)CC2)c([N+](=O)[O-])c1]

A solution of 4-((3-fluorophenyl)sulfonyl)piperidine hydrochloride (371 mg, 1.324 mmol), 4-fluoro-3-nitrobenzonitrile (200 mg, 1.204 mmol) and K$_2$CO$_3$ (499 mg, 3.61 mmol) in ACN (4.816 mL) was stirred on a hot plate at 80° C. for 1.5 hours and at RT overnight. The reaction mixture was filtered with suction and the solvent removed under reduced pressure to give the title compound as a brown solid, which was used without further purification. ESI-MS m/z [M+H]$^+$ 390.2.

Preparation x98: 3-amino-4-(4-((3-fluorophenyl) sulfonyl)piperidin-1-yl)benzonitrile

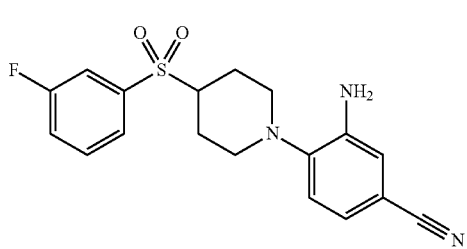

A solution of 4-(4-((3-fluorophenyl)sulfonyl)piperidin-1-yl)-3-nitrobenzonitrile (467 mg, 1.20 mmol) in MeOH (4 mL) and THF (4 mL) was treated with NH$_4$Cl (642 mg, 12 mmol) in one portion, followed by the portion-wise addition of zinc (785 mg, 12 mmol) at RT. The resulting reaction mixture was stirred at RT for 3 hours and then filtered with suction. The solvent was removed under reduced pressure and the product purified by column chromatography (dry packing) eluting with a gradient of 0-100% EtOAc in heptanes to give the title compound as an orange solid (351 mg, 81%). ESI-MS m/z [M+H]$^+$ 360.2.

Preparation x99: 4-(4-((3-methoxyphenyl)sulfonyl) piperidin-1-yl)-3-nitrobenzonitrile

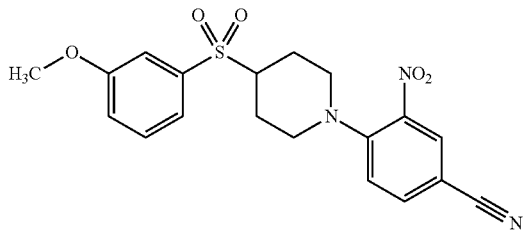

A solution of 4-((3-methoxyphenyl)sulfonyl)piperidine hydrochloride (300 mg, 1.026 mmol), 4-fluoro-3-nitrobenzonitrile (155 mg, 0.933 mmol), and K$_2$CO$_3$ (387 mg, 2.80 mmol) in ACN (3.732 mL) was stirred on a hot plate at 80° C. for 1.5 hours and at RT overnight. The reaction mixture was filtered with suction and the solvent removed under reduced pressure to give the title product which was used without further purification. ESI-MS m/z [M+H]$^+$ 402.2.

Preparation x100: 3-amino-4-(4-((3-methoxyphenyl) sulfonyl)piperidin-1-ylbenzonitrile

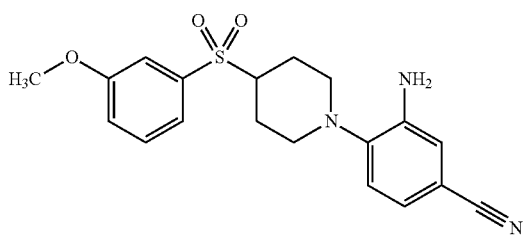 [SMILES: COc1cccc(S(=O)(=O)C2CCN(c3ccc(C#N)cc3[N+](=O)[O-])CC2)c1]

A solution of 4-(4-((3-methoxyphenyl)sulfonyl)piperidin-1-yl)-3-nitrobenzonitrile (375 mg, 0.933 mmol) in MeOH (3.110 mL) and THF (3.110 mL) was treated with NH$_4$C (499 mg, 9.33 mmol) in one portion, followed by the portion-wise addition of zinc (610 mg, 9.33 mmol) at RT. The resulting reaction mixture was stirred for 3 hours and then filtered with suction. The solvent was removed under reduced pressure and the crude product purified by column chromatography (dry packing) eluting with a gradient of 0-100% EtOAc in heptanes to give the title compound as an orange solid (301 mg, 87%). ESI-MS m/z [M+H]$^+$ 372.2.

Preparation x101: 2-chloro-4-(4-(2,4-difluorophenyl)sulfonylpiperidin-1-yl)-6-methyl-3-nitropyridine

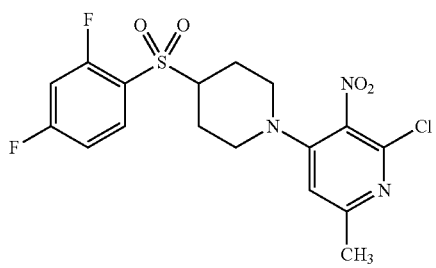 [SMILES: Cc1cc(N2CCC(S(=O)(=O)c3ccc(F)cc3F)CC2)c([N+](=O)[O-])c(Cl)n1]

A solution of 4-((2,4-difluorophenyl)sulfonyl)piperidine hydrochloride (209 mg, 0.702 mmol), 2,4-dichloro-6-methyl-3-nitropyridine (145 mg, 0.702 mmol) and K$_2$CO$_3$ (291 mg, 2.106 mmol) in ACN (2.340 yL) was stirred on a hot plate at 80° C. overnight. The reaction mixture was filtered with suction and the solvent removed under reduced pressure to give the title product which was used without further purification. ESI-MS m/z [M+H]$^+$ 432.2.

Preparation 1102: 4-(4-((2,4-difluorophenyl)sulfonyl)piperidin-1-yl)-6-methylpyridin-3-amine

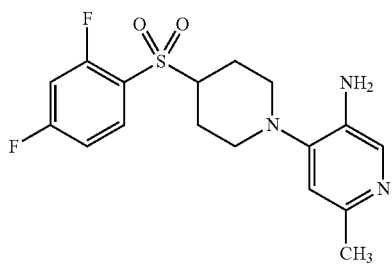 [SMILES: Cc1cc(N2CCC(S(=O)(=O)c3ccc(F)cc3F)CC2)c(N)cn1]

To a flask charged with a solution of 2-chloro-4-(4-((2,4-difluorophenyl)sulfonyl)piperidin-1-yl)-6-methyl-3-nitropyridine (303 mg, 0.702 mmol) in EtOAc (7.020 mL) was added Pd/C (112 mg, 0.105 mmol). The flask was capped with a rubber septum and evacuated to remove air. Hydrogen was added via a balloon. The resulting reaction mixture was stirred at RT overnight and then filtered through Celite®. The solvent was removed under reduced pressure and the product purified by column chromatography (dry packing) eluting with a gradient of 0-100% EtOAc in heptanes followed by a gradient of 0-30% MeOH in DCM to give the title compound as a brown-orange solid (34 mg, 13%). ESI-MS m/z [M+H]$^+$ 368.1.

Preparation x103: 1-(4-fluorobenzyl)-4-(6-methyl-3-nitropyridin-2-yl)piperazine

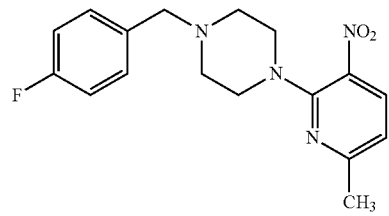 [SMILES: Cc1ccc([N+](=O)[O-])c(N2CCN(Cc3ccc(F)cc3)CC2)n1]

A solution of 1-(4-fluorobenzyl)piperazine (6.57 g, 33.1 mmol) and 2-chloro-6-methyl-3-nitropyridine (5.2 g, 30.1 mmol) in DCM (75 mL) and Et$_3$N (16.8 mL, 121 mmol) was stirred at RT overnight. The reaction mixture was poured into a separatory funnel, diluted with saturated (aq) NH$_4$C, and extracted with DCM (3×250 mL). The organic layers were combined and the solvent removed under reduced pressure. The product was purified by column chromatography (dry packing) eluting with a gradient of 0-100% EtOAc in heptanes to give the title compound as an orange oil (10 g, 100%). $^1$H NMR (400 MHz, CDCl$_3$) δ ppm 2.43-2.47 (m, 3H), 2.50-2.60 (m, 4H), 3.45-3.51 (m, 4H), 3.53 (s, 2H), 6.57 (d, J=8.08 Hz, 1H), 6.99-7.06 (m, 2H), 7.32 (dd, J=8.46, 5.68 Hz, 2H), 8.05 (d, J=8.34 Hz, 1H); ESI-MS m/z [M+H]$^+$ 331.2.

Preparation x104: 2-(4-(4-fluorobenzyl)piperazin-1-yl)-6-methylpyridin-3-amine

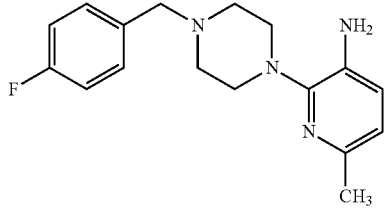 [SMILES: Cc1ccc(N)c(N2CCN(Cc3ccc(F)cc3)CC2)n1]

A solution of 1-(4-fluorobenzyl)-4-(6-methyl-3-nitropyridin-2-yl)piperazine (5.1 g, 15.44 mmol) in THF (77 mL) and MeOH (77 mL) at 0° C. was treated with NH$_4$Cl (8.26 g, 154 mmol) in one portion, followed by the portion-wise addition of zinc (10.09 g, 154 mmol). The reaction mixture was allowed to warm up slowly to RT and stirred overnight. The reaction mixture was filtered with suction and the solvent removed under reduced pressure. The product was purified by column chromatography (dry packing) eluting with a gradient of 0-100% EtOAc in heptanes to give the title compound as an orange oil (4.20 g, 91%). $^1$H NMR (400 MHz, CDCl$_3$) δ ppm 2.38 (s, 3H), 2.54-2.66 (m, 4H), 3.14 (t, J=4.67 Hz, 4H), 3.55 (s, 2H), 3.62 (s, 2H), 6.65-6.69 (m, 1H), 6.83-6.87 (m, 1H), 6.98-7.05 (m, 2H), 7.29-7.36 (m, 2H); ESI-MS m/z [M+H]$^+$ 301.2.

Preparation x105: tert-butyl 4-(5-methyl-3-nitropyridin-2-yl)piperazin-1-carboxylate

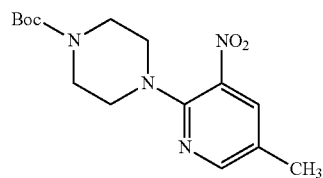

A solution of tert-butyl piperazine-1-carboxylate (7.75 g, 41.6 mmol), 2-fluoro-5-methyl-3-nitropyridine (5 g, 32.0 mmol) and K$_2$CO$_3$ (13.28 g, 96 mmol) in ACN (80 mL) was stirred at RT overnight. The reaction mixture was filtered with suction and the solvent removed under reduced pressure to give the title product which was used without further purification. ESI-MS m/z [M+H]$^+$ 323.2.

Preparation x106: tert-butyl 4-(3-amino-5-methylpyridin-2-yl)piperazine-1-carboxylate

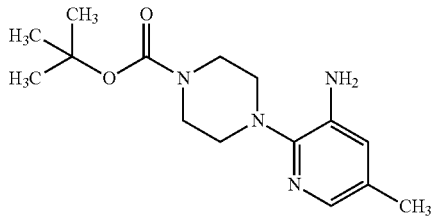 [SMILES: Cc1cnc(N2CCN(C(=O)OC(C)(C)C)CC2)c(N)c1]

A solution of tert-butyl 4-(5-methyl-3-nitropyridin-2-yl)piperazine-1-carboxylate (10.32 g, 32 mmol) in MeOH (107 mL) and THF (107 mL) was treated with NH$_4$Cl (13.69 g, 256 mmol) in one portion, followed by the portion-wise addition of zinc (16.74 g, 256 mmol) at 0° C. The reaction mixture was allowed to warm up slowly to RT and stirred overnight. The reaction mixture was filtered with suction to remove a precipitate and the solvent was removed under reduced pressure. The product was purified by column chromatography (dry packing) eluting with a gradient of 0-100% EtOAc in heptanes to give the title compound as a light purple solid (6.5 g, 70%). $^1$H NMR (400 MHz, CDCl$_3$) δ ppm 1.47-1.51 (m, 12H), 2.20-2.23 (m, 3H), 3.04 (d, J=4.55 Hz, 4H), 3.55-3.60 (m, 4H), 3.77 (br s, 2H), 6.80-6.84 (m, 1H), 7.62 (d, J=1.01 Hz, 1H); ESI-MS m/z [M+H]$^+$ 293.2.

Preparation x107: tert-butyl 4-(3-(3-methoxy-1-methyl-1H-pyrazole-4-carboxamido)-5-methylpyridin-2-yl)piperazine-1-carboxylate

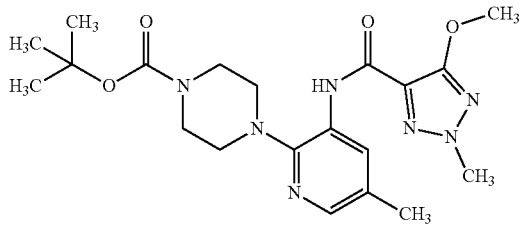 [SMILES: COc1nn(C)nc1C(=O)Nc1cc(C)cnc1N1CCN(C(=O)OC(C)(C)C)CC1]

A solution of tert-butyl 4-(3-amino-5-methylpyridin-2-yl)piperazine-1-carboxylate (1 g, 3.42 mmol), 3-methoxy-1-methyl-1H-pyrazole-4-carboxylic acid (1.068 g, 6.84 mmol), HATU (2.60 g, 6.84 mmol) and DIPEA (2.389 mL, 13.68 mmol) in DMF (8.55 mL) and THF (8.55 mL) was stirred on a hot plate at 80° C. overnight. The reaction mixture was diluted with saturated (aq) NH$_4$Cl and extracted with ether (3×150 mL). The organic layers were combined, dried over MgSO$_4$, filtered and the solvent removed under reduced pressure. The crude product was purified by column chromatography (dry packing) eluting with 50% EtOAc in heptanes to give the title compound as a light purple solid (1.07 g, 72.7%); ESI-MS m/z [M+H]$^+$ 431.3.

Preparation x108: 3-methoxy-1-methyl-N-(5-methyl-2-(piperazin-1-yl)pyridin-3-yl)-1H-pyrazole-4-carboxamide

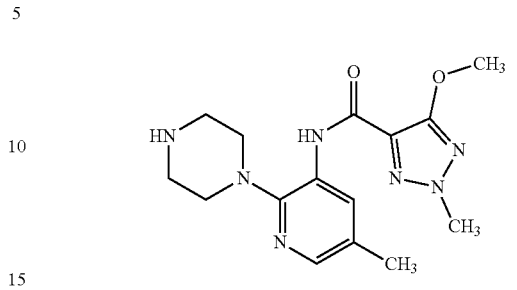

A solution of tert-butyl 4-(3-(3-methoxy-1-methyl-H-pyrazole-4-carboxamido)-5-methylpyridin-2-yl)piperazine-1-carboxylate (1 g, 2.323 mmol) in DCM (11.61 mL) and MeOH (11.61 mL) was treated with (aq) HCl (5.81 mL, 23.23 mmol) at RT and the resulting reaction mixture was stirred for 12 hours. The precipitate formed in the reaction was collected by vacuum filtration, washed with ether and dried under vacuum. The product (HCl salt) was purified by HPLC (Shimadzu) eluting with a gradient of ACN in water (basic mode) to give the title compound (free base) as an ivory solid (548 mg, 71.4%). H NMR (400 MHz, DMSO-d$_6$) δ ppm 2.24 (s, 3H), 2.80-2.85 (m, 4H), 2.87-2.93 (m, 4H), 3.75 (s, 3H), 4.06 (s, 3H), 7.86-7.89 (m, 1H), 8.14 (s, 1H), 8.47 (d, J=2.02 Hz, 1H), 9.16 (s, 1H); ESI-MS m/z [M+H]$^+$ 331.2.

Preparation x109: 6-(4-(2,4-difluorophenoxy)piperidin-1-yl)-5-nitronicotinic acid

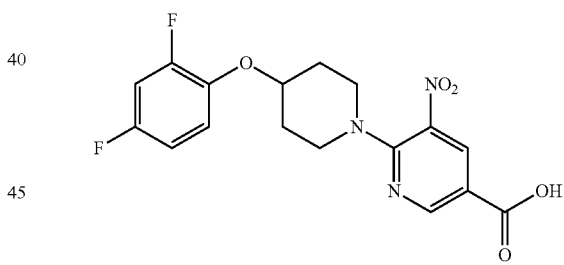

To a stirring solution of methyl 6-(4-(2,4-difluorophenoxy)piperidin-1-yl)-5-nitronicotinate (3.73 g, 9.48 mmol) in MeOH (40 mL) at 60° C. was added 5 wt % LiOH (13.52 mL, 28.4 mmol). The reaction mixture was stirred at this temperature overnight. The reaction mixture was concentrated to remove methanol and the basic aqueous phase was washed with iPAc (2×). Next, a 1.5 N HCl (aq) solution was added to adjust the pH to 3.5. After stirring for two hours, a solid precipitated from solution. The solid was isolated by filtration, washed with copious amounts of water, and dried in a vacuum oven at 65° C. overnight to give the title compound as a yellow solid (1.4 g, 40%). $^1$H NMR (400 MHz, DMSO-d$_6$) δ ppm 1.67-1.83 (m, 2H), 2.05 (ddd, J=9.66, 6.76, 3.28 Hz, 2H), 3.41-3.50 (m, 2H), 3.74 (ddd, J=13.26, 6.95, 3.79 Hz, 2H), 4.67 (tt, J=7.42, 3.69 Hz, 1H), 7.00-7.09 (m, 1H), 7.26-7.39 (m, 2H), 8.55 (d, J=2.02 Hz, 1H), 8.81 (d, J=2.02 Hz, 1H), 13.33 (br s, 1H); ESI-MS m/z [M+H]$^+$ 380.2.

Preparation x110: 6-(4-(2,4-difluorophenoxy)piperidin-1-yl)-N,N-dimethyl-5-nitronicotinamide

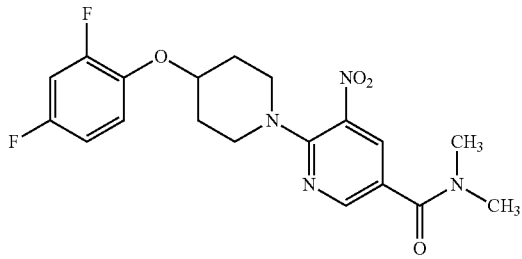 [SMILES: CN(C)C(=O)c1cnc(N2CCC(Oc3ccc(F)cc3F)CC2)c([N+](=O)[O-])c1]

To a vial was added 6-(4-(2,4-difluorophenoxy)piperidin-1-yl)-5-nitronicotinic acid (1.0 g, 2.64 mmol), HATU (1.504 g, 3.95 mmol), dimethylamine hydrochloride (0.645 g, 7.91 mmol) and DMF (6 mL). To this stirring suspension was added Et$_3$N (2.018 mL, 14.50 mmol). The vial was capped and the reaction mixture was heated to 75° C. After two hours. UPLC-MS indicated the reaction was complete. The reaction mixture was cooled to room temperature and partitioned between water and IPAc. The organic layer was separated and washed with saturated (aq) NaCl. The organic phase was dried over Na$_2$SO$_4$, filtered, and concentrated to give a crude oil which was purified by flash chromatography. The pure fractions were combined and concentrated to give the title compound as a pale yellow oil (0.995 g, 93%). H NMR (400 MHz, DMSO-d$_6$) δ ppm 1.70-1.80 (m, 2H), 2.01-2.10 (m, 2H), 3.02 (br s, 6H), 3.35-3.44 (m, 2H), 3.69 (ddd, J=13.20, 6.76, 3.79 Hz, 2H), 4.66 (tt, J=7.55, 3.69 Hz, 1H), 6.97-7.10 (m, 1H), 7.24-7.41 (m, 2H), 8.31 (d, J=2.02 Hz, 1H), 8.52 (d, J=2.27 Hz, 1H); ESI-MS m/z [M+H]$^+$ 407.1.

Preparation x111: 5-amino-6-(4-(2,4-difluorophenoxy)piperidin-1-yl)-N,N-dimethylnicotinamide

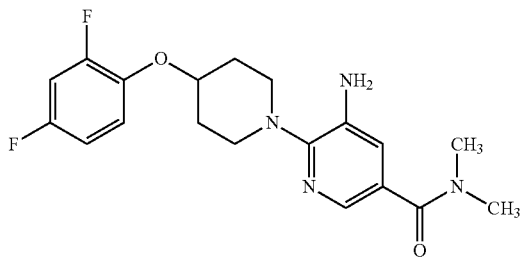 [SMILES: CN(C)C(=O)c1cnc(N2CCC(Oc3ccc(F)cc3F)CC2)c(N)c1]

To a stirring solution of 6-(4-(2,4-difluorophenoxy)piperidin-1-yl)-N,N-dimethyl-5-nitronicotinamide (0.9 g, 2.215 mmol) in 2-methyltetrahydrofuran (20 mL) and MeOH (20 mL) was added NH$_4$Cl (1.777 g, 33.2 mmol) followed by a slow addition of zinc (1.014 g, 15.50 mmol). The reaction mixture was stirred at RT for 1.5 hours and then filtered through Celite®, concentrated, and partitioned between IPAc and water. The organic layer was separated and held. The aqueous layer was extracted with IPAc. The organic layers were combined, washed with saturated (aq) NaCl, dried over Na$_2$SO$_4$, filtered, and concentrated to give the title compound as a light pink solid (0.783 g, 93.9%). $^1$H NMR (400 MHz, DMSO-d$_6$) δ ppm 1.80-1.91 (m, 2H), 2.04-2.12 (m, 2H), 2.87-2.95 (m, 2H), 2.96 (s, 6H), 3.34-3.42 (m, 2H), 4.52 (dt, J=8.15, 4.14 Hz, 1H), 4.99 (s, 2H), 6.99 (d, J=2.02 Hz, 1H), 7.03 (tdd, J=8.72, 8.72, 3.03, 1.77 Hz, 1H), 7.24-7.38 (m, 2H), 7.61 (d, J=2.27 Hz, 1H); ESI-MS m/z [M+H]$^+$ 377.2.

Preparation x112: N-(2-methyl-2H-indazol-6-yl)picolinamide

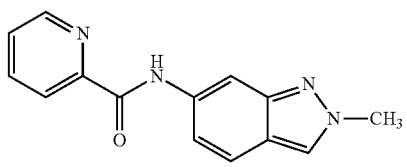 [SMILES: Cn1cc2ccc(NC(=O)c3ccccn3)cc2n1]

A solution of 2-methyl-2H-indazol-6-amine (550 mg, 3.74 mmol), picolinic acid (690 mg, 5.61 mmol) and HATU (2.131 g, 5.61 mmol) in DMA (7.474 mL) was treated with DIPEA (1.953 mL, 11.21 mmol). The reaction mixture was stirred at 80° C. for 2 hours and then diluted with water (20 mL). Sodium chloride (3 g) was added and the mixture was stirred overnight and the resulting precipitate was filtered and dried in vacuum at 80° C. to give the title compound as a gray solid (340 mg, 36.1%). $^1$H NMR (400 MHz, DMSO-d$_6$) δ ppm 4.14 (s, 3H), 7.45 (dd, J=8.84, 1.77 Hz, 1H), 7.64-7.71 (m, 2H), 8.09 (td, J=7.71, 1.77 Hz, 1H), 8.19 (dt, J=7.83, 1.01 Hz, 1H), 8.27 (s, 1H), 8.31 (s, 1H), 8.76 (d, J=4.79 Hz, 1H), 10.61 (s, 1H); ESI-MS m/z [M+H]$^+$ 253.

Preparation x113: N-(quinoxalin-6-yl)picolinamide

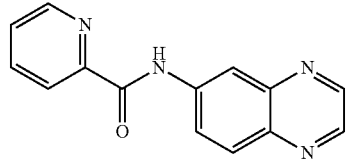 [SMILES: O=C(Nc1ccc2nccnc2c1)c1ccccn1]

A 20 mL vial was charged with picolinic acid (244 mg, 1.981 mmol), quinoxalin-6-amine (250 mg, 1.722 mmol), HATU (851 mg, 2.239 mmol), DMF (6 mL) and Et$_3$N (0.720 mL, 5.17 mmol). The reaction mixture was stirred at 70° C. for 3 hours, then water was added and a precipitate was formed. The precipitate was isolated by filtration, washed with water, and dried under vacuum overnight to give the title compound. $^1$H NMR (400 MHz, CD$_3$CN) δ ppm 7.65 (ddd, J=7.64, 4.74, 1.26 Hz, 1H), 8.05 (td, J=7.71, 1.77 Hz, 1H), 8.08-8.12 (m, 1H), 8.15-8.20 (m, 1H), 8.29 (dt, J=7.83, 1.01 Hz, 1H), 8.69 (d, J=2.27 Hz, 1H), 8.74 (d, J=4.84 Hz, 1H), 8.79 (d, J=1.77 Hz, 1H), 8.85 (d, J=1.77 Hz, 1H), 10.49 (br s, 1H).

Preparation x114: tert-butyl 4-(3-amino-5-bromopyridin-2-yl)piperazine-1-carboxylate

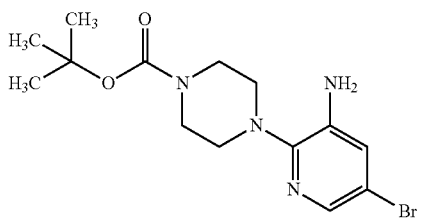 [SMILES: CC(C)(C)OC(=O)N1CCN(c2ncc(Br)cc2N)CC1]

To a 250 mL flask was added tert-butyl 4-(5-bromo-3-nitropyridin-2-yl)piperazine-1-carboxylate (5.87 g, 15.16 mmol), NH$_4$Cl (12.16 g, 227 mmol), MeOH (30 ml), and 2-methyltetrahydrofuran (60 mL). The suspension was stirred and zinc dust (6.94 g, 106 mmol) was added over a 10 minute period. The reaction mixture was stirred for 2 hours at room temperature and then filtered through Celite® to remove the solids (zinc and NH$_4$Cl). The filter pad was washed with MeOH. The filtrate was concentrated and partitioned between EtOAc and water. The phases were split and the aqueous phase extracted with EtOAc. The organic phases were combined, washed with saturated (aq) NaCl, dried over Na$_2$SO$_4$, filtered, and concentrated. The product was dried in a vacuum oven at 65° C. to give the title compound as a brown solid (4.3 g). $^1$H NMR (400 MHz, DMSO-d$_6$) δ ppm 1.43 (s, 9H), 2.84-2.96 (m, 4H), 3.45-3.54 (m, 4H), 5.23 (s, 2H), 7.13 (d, J=2.27 Hz, 1H), 7.60 (d, J=2.27 Hz, 1H); ESI-MS m/z [M+H]$^+$ 357.1.

Preparation x115: tert-butyl 4-(5-bromo-3-(3-methoxy-1-methyl-1H-pyrazole-4-carboxamido)pyridin-2-yl)piperazine-1-carboxylate

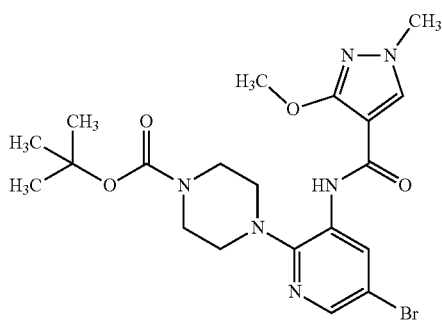 [SMILES: COc1nn(C)cc1C(=O)Nc1cc(Br)cnc1N1CCN(C(=O)OC(C)(C)C)CC1]

To a vial was added 3-methoxy-1-methyl-1H-pyrazole-4-carboxylic acid (3.03 g, 19.40 mmol), 2-chloro-1-methylpyridin-1-ium iodide (4.96 g, 19.40 mmol), NMP (25 ml), and DIPEA (11.06 ml, 63.5 mmol). After 30 minutes of stirring, tert-butyl 4-(3-amino-5-bromopyridin-2-yl)piperazine-1-carboxylate (2.52 g, 7.05 mmol) was added and the reaction mixture was heated to 65° C. and stirred for 3.5 hours. The reaction mixture was cooled and then slowly added to stirring water (110 mL) forming a precipitate. The slurry was stirred for 2 hours and filtered. The solid was washed with water and dried under vacuum and a blanket of nitrogen. The crude solid was purified by flash chromatography to give the title compound as an off-white solid (2.8 g). $^1$H NMR (400 MHz, DMSO-d$_6$) δ ppm 1.44 (s, 10H), 2.86-3.00 (m, 4H), 3.48-3.61 (m, 4H), 3.78 (s, 3H), 4.05 (s, 3H), 8.18 (d, J=2.27 Hz, 1H), 8.22 (s, 1H), 8.83 (d, J=2.27 Hz, 1H), 9.11 (s, 1H); ESI-MS m/z [M+H]$^+$ 495.2.

Preparation x116: tert-butyl 4-(5-cyano-3-(3-methoxy-1-methyl-1H-pyrazole-4-carboxamido)pyridin-2-yl)piperazine-1-carboxylate

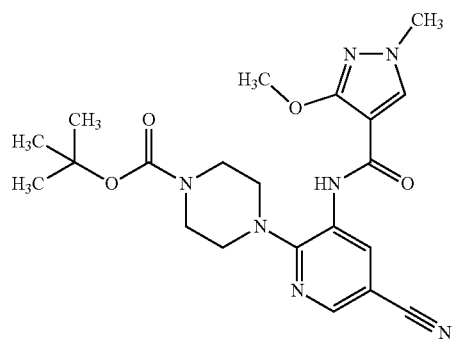 [SMILES: COc1nn(C)cc1C(=O)Nc1cc(C#N)cnc1N1CCN(C(=O)OC(C)(C)C)CC1]

To a large microwave vial were added tert-butyl 4-(5-bromo-3-(5-methoxy-1-methyl-1H-pyrazole-4-carboxamido)pyridin-2-yl)piperazine-1-carboxylate (2.8 g, 5.65 mmol), dicyanozinc (0.664 g, 5.65 mmol), Pd$_2$(dba)$_3$ (0.039 g, 0.042 mmol), XANTPHOS (0.049 g, 0.085 mmol), and DMA (11.68 mL). While under nitrogen, TMEDA (0.171 mL, 1.130 mmol) was added and the vial was capped. The reaction mixture was heated to 160° C. for 5 minutes in a microwave reactor. The reaction mixture was added to rapidly stirring water (30 mL) forming a white precipitate. The slurry was stirred for 1 hour and filtered. The solid was washed with water, dried on the filter under nitrogen, and then transferred to a vial. The solid was dried over the weekend at 65° C. in a vacuum oven to give the title compound which was used without further purification (2.41 g). $^1$H NMR (400 MHz, DMSO-d$_6$) δ ppm 1.44 (s, 9H), 3.10-3.21 (m, 4H), 3.47-3.57 (m, 4H), 3.78 (s, 3H), 4.04 (s, 3H), 8.23 (s, 1H), 8.51 (d, J=2.27 Hz, 1H), 8.74 (d, J=2.02 Hz, 1H), 8.89 (s, 1H); ESI-MS m/z [M+H]$^+$ 442.2.

Preparation x117: N-(5-cyano-2-(piperazin-1-yl)pyridin-3-yl)-3-methoxy-1-methyl-1H-pyrazole-4-carboxamide

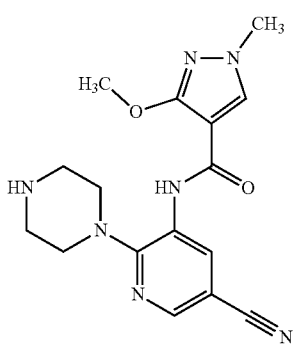 [SMILES: COc1nn(C)cc1C(=O)Nc1cc(C#N)cnc1N1CCNCC1]

To a stirring solution of tert-butyl 4-(5-cyano-3-(3-methoxy-1-methyl-1H-pyrazole-4-carboxamido)pyridin-2-yl)piperazine-1-carboxylate (2.4 g, 5.44 mmol) and DCM (50 mL) was added 4M HCl in 14-dioxane (9.51 mL, 38.1 mmol). A precipitate formed quickly and the resulting slurry was stirred for 1 hour at room temperature. The solid was filtered and dried. The dried solid was slurried in water and IPAc and made basic (~pH 10). The phases were split and the aqueous phase extracted with IPAc (2×). The organic phases were combined, washed with saturated (aq) NaCl, dried over Na$_2$SO$_4$, filtered, and concentrated to give the title compound as a solid (0.302 g). ESI-MS m/z [M+H]$^+$ 342.2.

Preparation x118: (R)-4-(4-(2,4-difluorophenoxy)piperidin-1-yl)-5-nitro-N-(tetrahydrofuran-3-yl)picolinamide

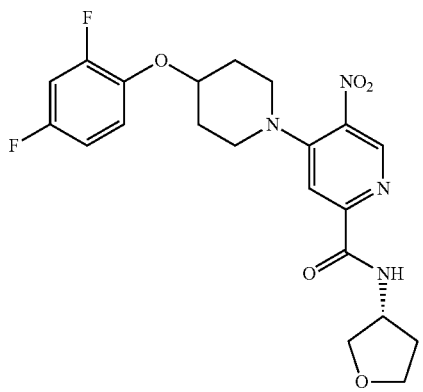 [SMILES: O=C(N[C@@H]1CCOC1)c1cc(N2CCC(Oc3ccc(F)cc3F)CC2)c([N+](=O)[O-])cn1]

To a solution of methyl 4-(4-(2,4-difluorophenoxy)piperidin-1-yl)-5-nitropicolinate (100 mg, 0.254 mmol) in DCM (847 µL) was added MgCl$_2$ (17.91 mg, 0.188 mmol) in one portion. The mixture was stirred at RT for 30 minutes and then (R)-tetrahydrofuran-3-amine (44.3 mg, 0.508 mmol) was added slowly. The resulting solution was stirred at RT for 3 hours and was subsequently purified by column chromatography to give the title compound as a bright yellow solid (82 mg, 72%). ESI-MS m/z [M+H]$^+$ 449.2.

Preparation x119: (R)-5-amino-4-(4-(2,4-difluorophenoxy)piperidin-1-yl)-N-(tetrahydrofuran-3-yl)picolinamide

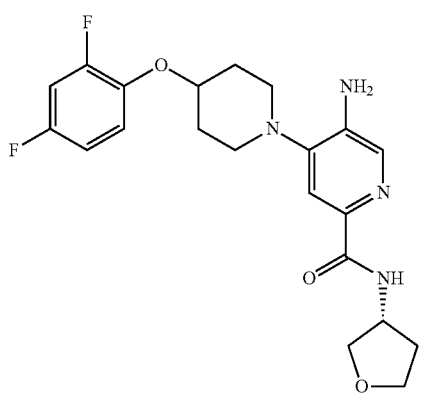

A mixture of (R)-4-(4-(2,4-difluorophenoxy)piperidin-1-yl)-5-nitro-N-(tetrahydrofuran-3-yl)picolinamide (82 mg, 0.183 mmol) and 10% Pd/C (35 mg, 0.329 mmol) in MeOH (0.35 mL) and EtOAc (0.35 mL) was stirred under H$_2$ for 6 hours. The solvent was removed to give the title compound as a white solid, which was used without further purification (62 mg, 45%). ESI-MS m/z [M+H]$^+$ 419.2.

Preparation x120: 4-(4-(2,4-difluorophenoxy)piperidin-1-yl-N-ethyl-5-nitropicolinamide

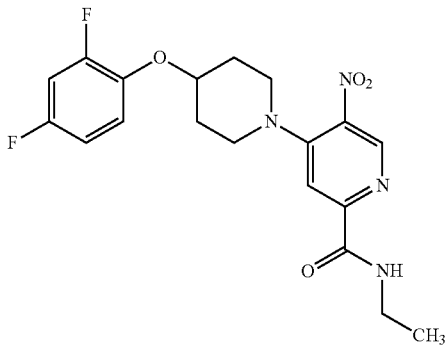

The title compound was prepared in a manner similar to Preparation x118, using ethylamine in place of (R)-tetrahydrofuran-3-amine. ESI-MS m/z [M+H]$^+$ 407.2.

Preparation x121: 5-amino-4-(4-(2,4-difluorophenoxy)piperidin-1-yl)-N-ethylpicolinamide

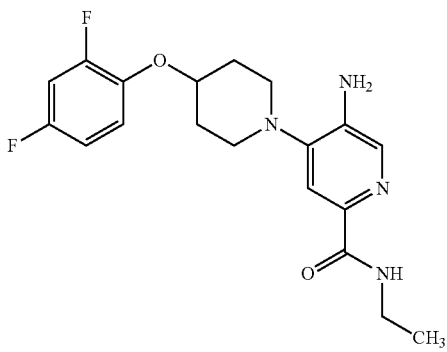 [SMILES: CCNC(=O)c1cc(N2CCC(Oc3ccc(F)cc3F)CC2)c([N+](=O)[O-])cn1]

The tide compound was prepared in a manner similar to Preparation x119, using 4-(4-(2,4-difluorophenoxy)piperidin-1-yl)-N-ethyl-5-nitropicolinamide in place of (R)-4-(4-(2,4-difluorophenoxy)piperidin-1-yl)-5-nitro-N-(tetrahydrofuran-3-yl)picolinamide. ESI-MS m/z [M+H]$^+$ 377.2.

Preparation x122: 4-(4-(2,4-difluorophenoxy)piperidin-1-yl)-N-isopropyl-5-nitropicolinamide

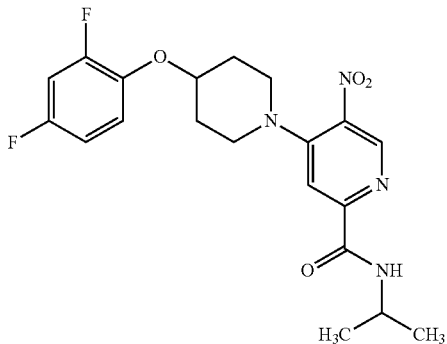 [SMILES: CC(C)NC(=O)c1cc(N2CCC(Oc3ccc(F)cc3F)CC2)c([N+](=O)[O-])cn1]

The title compound was prepared in a manner similar to Preparation x118, using isopropylamine in place of (R)-tetrahydrofuran-3-amine. ESI-MS m/z [M+H]+ 421.2.

Preparation x124: 4-(4-(2,4-difluorophenoxy)piperidin-1-yl)-5-nitro-N-propylpicolinamide

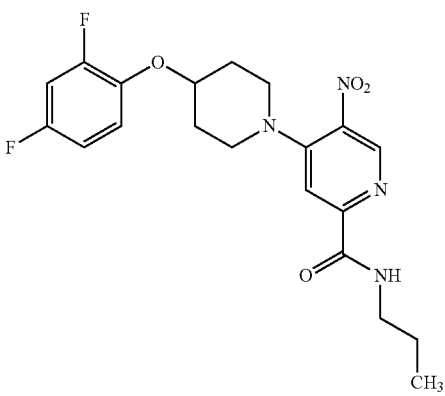 [SMILES: CCCNC(=O)c1cc(N2CCC(Oc3ccc(F)cc3F)CC2)c([N+](=O)[O-])cn1]

The title compound was prepared in a manner similar to Preparation x118, using propylamine in place of (R)-tetrahydrofuran-3-amine. ESI-MS m/z [M+H]+ 421.2.

Preparation x123: 5-amino-4-(4-(2,4-difluorophenoxy)piperidin-1-yl)-N-isopropylicolinamide

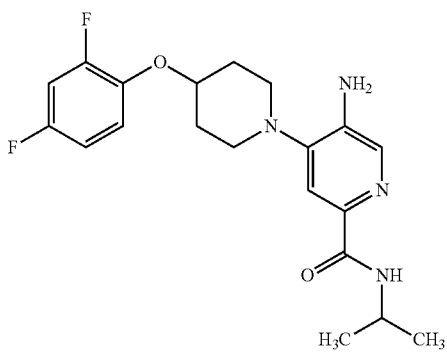

The tide compound was prepared in a manner similar to Preparation x119, using 4-(4-(2,4-difluorophenoxy)piperidin-1-yl)-N-isopropyl-5-nitropicolinamide in place of (R)-4-(4-(2,4-difluorophenoxy)piperidin-1-yl)-5-nitro-N-(tetrahydrofuran-3-yl)picolinamide. ESI-MS m/z [M+H]+ 391.2.

Preparation x125: 5-amino-4-(4-(2,4-difluorophenoxy)piperidin-1-yl)-N-propylpicolinamide

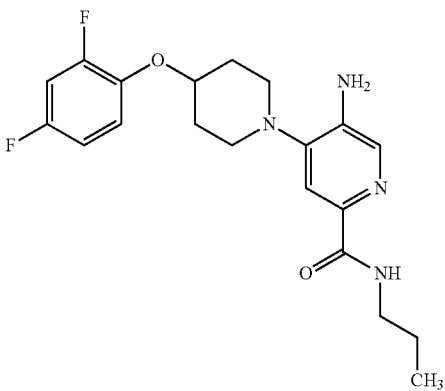

The tide compound was prepared in a manner similar to Preparation x119, using 4-(4-(2,4-difluorophenoxy)piperidin-1-yl)-5-nitro-N-propylpicolinamide in place of (R)-4-(4-(2,4-difluorophenoxy)piperidin-1-yl)-5-nitro-N-(tetrahydrofuran-3-yl)picolinamide. ESI-MS m/z [M+H]+ 391.2.

Preparation x126: 5-amino-6-(4-(2,4-difluorophenoxy)piperidin-1-yl)picolinonitrile

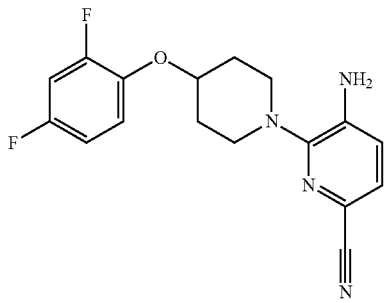

I. Step A: 6-chloro-2-(4-(2,4-difluorophenoxy)piperidin-1-yl)-3-nitropyridine

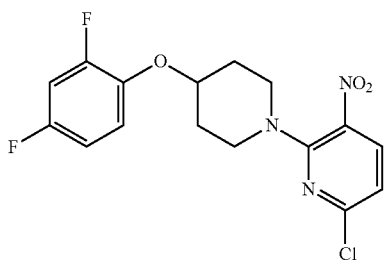 [SMILES: O=[N+]([O-])c1ccc(Cl)nc1N1CCC(Oc2ccc(F)cc2F)CC1]

To a round-bottomed flask containing 4-(2,4-difluorophenoxy)piperidine (20.0 g, 80.10 mmol, HCl), 2,6-dichloro-3-nitro-pyridine (16.23 g, 84.11 mmol), Et₃N (24.32 g, 240.30 mmol, 33.32 mL) was added THF (200.0 mL). The reaction mixture was allowed to stir at 25° C. for 1 hour under $N_2$ atmosphere. The reaction mixture was concentrated under reduced pressure to remove THF. The residue was diluted with water (800 mL) and extracted with DCM (2×1.5 L). The combined organic layers were dried over $Na_2SO_4$, filtered, concentrated under reduced pressure, and purified by flash silica gel chromatography to give the title compound as a yellow solid (25.2 g, 85%). ¹H NMR (400 MHz, CDCl₃) δ ppm 1.91-2.01 (m, 2H), 2.01-2.11 (m, 2H), 3.42 (ddd, J=13.45, 6.84, 3.97 Hz, 2H), 3.67-3.75 (m, 2H), 4.48 (tt, J=6.51, 3.42 Hz, 1H), 6.70 (d, J=8.38 Hz, 1H), 6.77-6.84 (m, 1H), 6.88 (ddd, J=10.92, 8.27, 2.87 Hz, 1H), 7.00 (td, J=9.04, 5.73 Hz, 1H), 8.11 (d, J=7.94 Hz, 1H); ESI-MS m/z [M+H]⁺ 369.9.

II. Step B: 6-(4-(2,4-difluorophenoxy)piperidin-1-yl)-5-nitropicolinonitrile

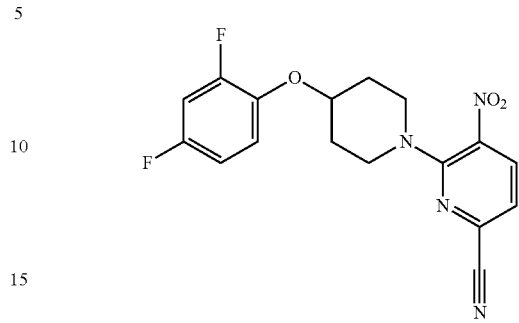

To a round-bottomed flask containing 6-chloro-2-(4-(2,4-difluorophenoxy)piperidin-1-yl)-3-nitropyridine (25.00 g, 67.61 mmol), Zn(CN)₂ (23.82 g, 202.83 mmol, 12.88 mL) and Pd(PPh₃)₄ (15.63 g, 13.52 mmol) was added DMF (200 mL). The reaction mixture was stirred at 130° C. for 16 hours under $N_2$ atmosphere. The reaction mixture was subsequently concentrated under reduced pressure to remove DMF, and the crude product purified by column chromatography, eluting with a gradient of petroleum ether/EtOAc (30:1 to 20:1), to give the title compound as a yellow solid (6.30 g, 25.1%). ¹HNMR (400 MHz, DMSO-d₆) δ ppm 1.77-1.93 (m, 2H), 1.98-2.11 (m, 2H), 2.82-2.97 (m, 2H), 3.21-3.30 (m, 1H), 3.34-3.41 (m, 1H), 4.51 (d, J=3.97 Hz, 1H), 6.90-7.06 (m, 1H), 7.25-7.34 (m, 2H), 7.35-7.54 (m, 1H), 8.71-9.10 (m, 1H); ESI-MS m/z [M+H]⁺ 360.9.

III. Step C: 5-amino-6-(4-(2,4-difluorophenoxy)piperidin-1-yl)picolinonitrile

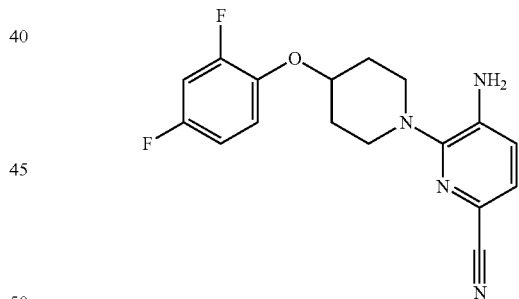

To a round-bottomed flask containing 6-(4-(2,4-difluorophenoxy)piperidin-1-yl)-5-nitropicolinonitrile (2.00 g, 5.55 mmol), Fe (3.10 g, 55.50 mmol), NH₄Cl (2.97 g, 55.50 mmol, 1.94 mL) was added MeOH (10 mL), THF (20 mL) and water (10 mL). The reaction mixture was stirred at 60° C. for 6 hours and then diluted with EtOAc (80 mL) and filtered through a pad of Celite® which was rinsed with EtOAc (3×100 mL). The combined organic layers were washed with water (100 mL), dried over anhydrous Na₂SO₄, filtered, and concentrated under reduced pressure to give the title compound as a light red solid (1.63 g, 87.1%). ¹HNMR (400 MHz, CDCl₃) δ ppm 1.88-1.99 (m, 2H), 2.09-2.18 (m, 2H), 2.94-3.02 (m, 2H), 3.38-3.46 (m, 2H), 4.26 (br s, 2H), 4.35 (tt, J=8.05, 3.86 Hz, 1H), 6.77-6.84 (m, 1H), 6.84-6.92 (m, 2H), 7.02 (td, J=9.04, 5.29 Hz, 1H), 7.25 (s, 1H); ESI-MS m/z [M+H]⁺ 331.0

Preparation x127: 5-fluoro-2-methoxynicotinoyl chloride

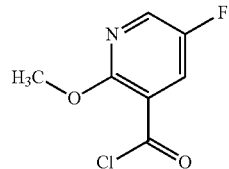

A mixture of 5-fluoro-2-methoxynicotinic acid (100 mg, 584 µmol) and DMF (4.27 mg, 58.44 µmol, 4.50 µL) in DCM (2 mL) was added oxalyl dichloride (222.52 mg, 1.75 mmol, 153.46 µL) at 0° C. The reaction mixture was stirred at 25° C. for 1.5 hours and then concentrated under reduced pressure to give the title compound as a light yellow solid, which was used without further purification (97 mg, 88%).

Preparation x128: 5-methoxy-1-methyl-1H-pyrazole-4-carbonyl chloride

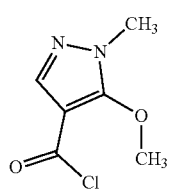

To a mixture of 5-methoxy-1-methyl-1H-pyrazole-4-carboxylic acid (120.00 mg, 768.54 µmol) and DMF (5.62 mg, 76.85 µmol, 5.92 µL) in DCM (3.00 mL) was added oxalyl dichloride (117.06 mg, 922.25 µmol, 80.73 µL) at 0° C. The reaction mixture was stirred at 25° C. for 1.5 hours and then concentrated under reduced pressure to give the title compound as a white solid, which was used without further purification (152 mg, crude).

Preparation x129: 4-(2,4-difluorophenoxy)-1-(2-nitrophenyl)piperidine

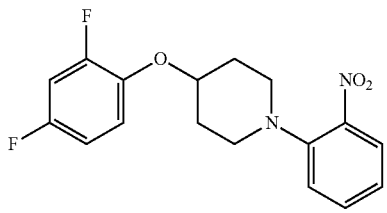 [SMILES: O=[N+]([O-])c1ccccc1N1CCC(Oc2ccc(F)cc2F)CC1]

To a solution of 1-fluoro-2-nitro-benzene (1.40 g, 9.92 mmol) in DMF (25.00 mL) was added 4-(2,4-difluorophenoxy)piperidine (3.72 g, 14.88 mmol, HCl) and $K_2CO_3$ (4.11 g, 29.76 mmol). The reaction mixture was stirred at 15° C. for 16 hours. Next saturated (aq) $NH_4Cl$ (50 mL) and water (30 mL) were added, and the mixture was extracted with EtOAc (2×20 mL). The organic phases were combined, washed with brine (50 mL), dried over anhydrous $NaSO_4$, filtered, and concentrated under vacuum to give a yellow oil. The crude product was purified by silica gel column chromatography, eluting with petroleum ether/EtOAc (20:1) to give the title compound as a yellow solid (3.10 g, 93.5%). $^1$H NMR (400 MHz, DMSO-$d_6$) δ ppm 1.66-1.86 (m, 2H), 1.92-2.09 (m, 2H), 2.88-3.04 (m, 2H), 3.10-3.27 (m, 2H), 4.51 (dt, J=7.6, 3.9 Hz, 1H), 6.96-7.06 (m, 1H), 7.11 (t, J=7.5 Hz, 1H), 7.22-7.41 (m, 3H), 7.50-7.65 (m, 1H), 7.72-7.88 (m, 1H).

Preparation x130: 2-(4-(2,4-difluorophenoxy)piperidin-1-yl)aniline

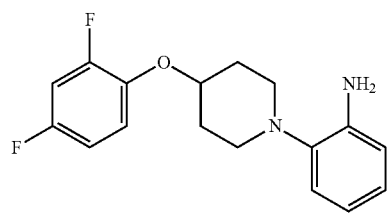 [SMILES: Nc1ccccc1N1CCC(Oc2ccc(F)cc2F)CC1]

To a solution of 4-(2,4-difluorophenoxy)-1-(2-nitrophenyl)piperidine (1.00 g, 3.00 mmol) in THF (6 mL), water (3 mL) and MeOH (3 mL) was added $NH_4Cl$ (1.60 g, 30.0 mmol). Iron powder (1.68 g, 30.0 mmol) was added in portions at 0° C. The reaction mixture was stirred at 70° C. for 2 hours and then filtered through a pad of Celite® which was rinsed with EtOAc (3×20 mL). The filtrates were combined and concentrated under vacuum to afford crude product, which was purified by silica gel column chromatography, eluting with petroleum ether/EtOAc (20:1) to give the title compound as a brown solid (680 mg, 74.5%). $^1$H NMR (400 MHz, DMSO-de) δ ppm 1.75-1.88 (m, 2H), 2.03 (d, J=11.5 Hz, 2H), 2.58-2.74 (m, 2H), 2.90-3.11 (m, 2H), 4.37-4.51 (m, 1H), 4.73 (s, 2H), 6.51 (td, J=7.5, 1.3 Hz, 1H), 6.64 (dd J=7.9, 1.3 Hz, 1H), 6.72-6.81 (m, 1H), 6.86 (d, J=7.5 Hz, 1H), 6.93-7.04 (m, 1H), 7.14-7.37 (m, 2H).

Preparation x131: (4-chlorophenyl)(4-(2-nitrophenyl)piperazin-1-yl)methanone

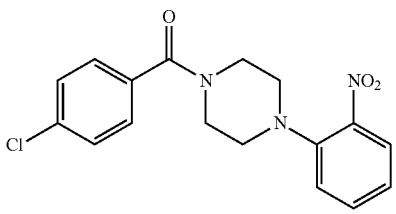

The title compound was prepared in a manner similar Preparation x129, using (4-chlorophenyl)(piperazin-1-yl)methanone (2.2 g, 8.4 mmol) in place of 4-(2,4-difluorophenoxy)piperidine to give the title compound as a yellow solid (4.0 g, yield 93%). $^1$HNMR (400 MHz, CDCl$_3$) δ ppm 2.78-3.30 (m, 4H), 3.47-4.04 (m, 4H), 7.08-7.24 (m, 2H), 7.33-7.48 (m, 4H), 7.48-7.58 (m, 1H), 7.81 (dd, J=8.16, 1.10 Hz, 1H).

Preparation x132: (4-(2-aminophenyl)piperazin-1-yl)(4-chlorophenyl)methanone

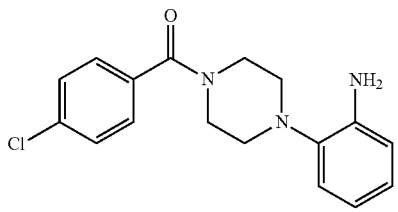 [SMILES: Nc1ccccc1N1CCN(C(=O)c2ccc(Cl)cc2)CC1]

The title compound was prepared in a manner similar to Preparation x130, using (4-chlorophenyl)(4-(2-nitrophenyl)piperazin-1-yl)methanone (3.5 g, 10 mmol) in place of 4-(2,4-difluorophenoxy)-1-(2-nitrophenyl)piperidine to give the title compound as a yellow solid (3.0 g, 82%). $^1$H NMR (400 MHz, CDCl$_3$) δ ppm 2.82-3.21 (m, 4H), 4.01-5.10 (m, 6H), 6.74-6.78 (m, 2H), 6.95-7.12 (m, 2H), 7.41-7.58 (m, 4H).

Preparation x133: 2-methoxynicotinamide

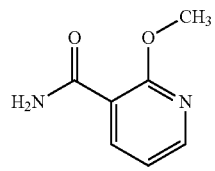

To a stirred solution of NH$_3$ (28%) in water (21.57 g, 153.87 mmol, 23.70 mL) was added a solution of 2-methoxynicotinoyl chloride (8.80 g, 51.29 mmol) in THF (40 mL). The reaction mixture was stirred at 25° C. for 0.5 hours, poured into saturated aq K$_2$CO$_3$ (250 mL), and extracted with EtOAc (3×450 mL). The organic phases were combined, washed with brine (150 mL), dried over anhydrous Na$_2$SO$_4$, filtered, and concentrated in vacuum to give the title compound as a light yellow solid (6.60 g, 84.6%).

Preparation x134: 4-bromo-5-(4-(2,4-difluorophenoxy)piperidin-1-yl)picolinonitrile

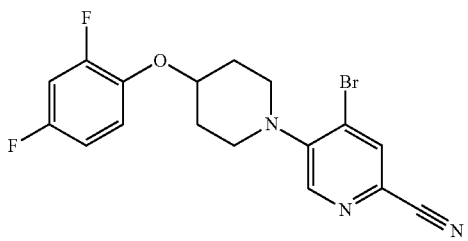 [SMILES: N#Cc1cc(Br)c(N2CCC(Oc3ccc(F)cc3F)CC2)cn1]

To a solution of 4-bromo-5-fluoropicolinonitrile (300 mg, 1.49 mmol) in NMP (5 mL) was added 4-(2,4-difluorophenoxy)piperidine (409.23 mg, 1.64 mmol, HCl) and DIPEA (963 mg, 7.45 mmol, 1.30 mL) at 25° C. The reaction mixture was stirred at 80° C. for 3 hours and then diluted with EtOAc (20 mL). The resulting mixture was washed with water (3×20 mL), dried over anhydrous Na$_2$SO$_4$, and concentrated under reduced pressure. The crude product was purified by silica gel column chromatography, eluting with EtOAc/petroleum ether (1:10) to give the title compound as a light yellow solid (489 mg, 83.3%). $^1$H NMR (400 MHz, CDCl$_3$) δ ppm 1.97-2.17 (m, 4H), 3.17 (ddd, J=11.36, 6.95, 3.75 Hz, 2H), 3.42-3.53 (m, 2H), 4.36-4.48 (m, 1H), 6.80 (t, J=7.94 Hz, 1H), 6.87 (d, J=2.65 Hz, 1H), 7.00 (td, J=9.04, 5.29 Hz, 1H), 7.83 (s, 1H), 8.30 (s, 1H).

Preparation x135: 4-methoxynicotinoyl chloride

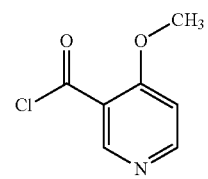

The title compound was prepared in a manner similar to Preparation x127, using 4-methoxynicotinic acid in place of 5-fluoro-2-methoxynicotinic acid to give the title compound as a light yellow solid (220.00 mg, crude).

Preparation x136: 4-methoxynicotinamide

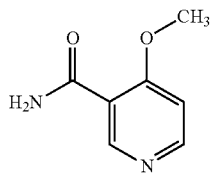

The title compound was prepared and purified in a manner similar to Preparation x133, using 4-methoxynicotinoyl chloride in place of 2-methoxynicotinoyl chloride to give the title compound as a yellow solid (150 mg, crude). $^1$H NMR (400 MHz, DMSO-d$_6$) δ ppm 3.90 (br s, 3H), 7.13-7.14 (d, J=6.0 Hz, 1H), 7.60-7.63 (d, J=12.0 Hz, 2H), 8.48-8.50 (d, J=8.0 Hz, 1H), 8.68 (s, 1H).

Preparation x137: 4-bromo-5-(4-(2,4-difluorophenoxy)piperidin-1-yl)picolinic acid

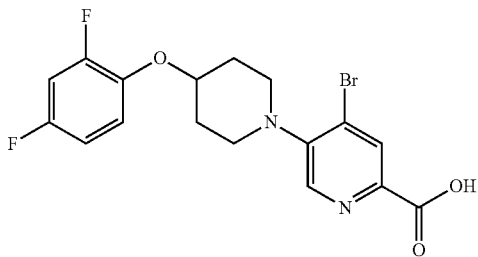 [SMILES: O=C(O)c1cc(Br)c(N2CCC(Oc3ccc(F)cc3F)CC2)cn1]

To a mixture of 4-bromo-5-(4-(2,4-difluorophenoxy)piperidin-1-yl)picolinonitrile (540 mg, 1.37 mmol) in EtOH (15 mL) was added NaOH (273.97 mg, 6.85 mmol) in H$_2$O (5 mL). The reaction mixture was stirred at 100° C. for 16 hours and then acidified to pH 5~6 by addition of 4 M HCl (aq). A precipitate was filtered and dried in vacuo to give a white solid. The filtrate was extracted with DCM (5×20 mL) and the combined organic layers were dried, filtered, and concentrated to dryness. The solids were combined to give the title compound as a yellow solid (500 mg, crude). $^1$H NMR (400 MHz, CDCl$_3$) δ ppm 1.83-2.22 (m, 4H), 2.90-3.14 (m, 2H), 3.26-3.51 (m, 2H), 4.30-4.42 (m, 1H), 6.75-6.90 (m, 2H), 6.94-7.04 (m, 1H), 8.05-8.33 (m, 2H).

Preparation x138: 4-bromo-5-(4-(2,4-difluorophenoxy)piperidin-1-yl)-N,N-dimethylpicolinamide

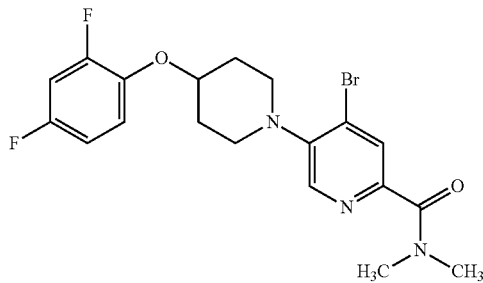

To a mixture of 4-bromo-5-(4-(2,4-difluorophenoxy)piperidin-1-yl)picolinic acid (500 mg, 1.21 mmol), NH(CH$_3$)$_2$ (118.40 mg, 1.45 mmol, 133.03 μL, HCl) and HATU (690.14 mg, 1.82 mmol) in DMF (8 mL) was added DIPEA (390.96 mg, 3.03 mmol, 528.33 μL). The reaction mixture was stirred at 20° C. for 16 hours and then diluted with water (50 mL) and extracted with EtOAc (3×20 mL). The organic layers were combined, dried over anhydrous Na$_2$SO$_4$, filtered, concentrated under reduced pressure, and purified by flash silica gel column chromatography, eluting with a gradient of 0 to 100% EtOAc in petroleum ether to give the title compound as a yellow solid (300 mg, 56.3%). $^1$H NMR (400 MHz, CDCl$_3$) δ ppm 1.99-2.19 (m, 4H), 3.04-3.16 (m, 8H), 3.37-3.48 (m, 2H), 4.37-4.46 (m, 1H), 6.77-6.84 (m, 1H), 6.85-6.92 (m, 1H), 6.98-7.05 (m, 1H), 7.89-7.92 (m, 1H), 8.20-8.24 (m, 1H).

Preparation x139: 3-amino-4-(4-(2,4-difluorophenoxy)piperidin-1-yl)-N,N-dimethylbenzamide

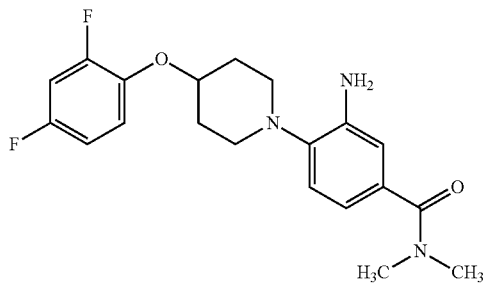

I. Step A: methyl 4-(4-(2,4-difluorophenoxy)piperidin-1-yl)-3-nitrobenzoate

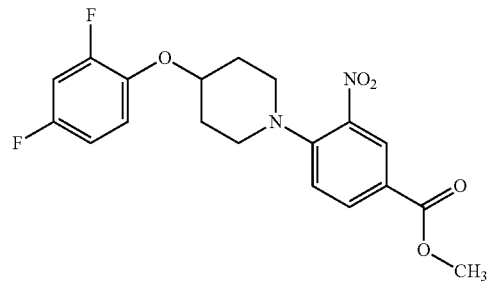 [SMILES: COC(=O)c1ccc(N2CCC(Oc3ccc(F)cc3F)CC2)c([N+](=O)[O-])c1]

To a suspension of 4-(2,4-difluorophenoxy)piperidine (1.27 g, 5.10 mmol, 1.10 eq, HCl) and methyl 4-chloro-3-nitro-benzoate (1.00 g, 4.64 mmol, 1.00 eq) in THF (20 mL) was added Et$_3$N (2.35 g, 23.20 mmol, 5.00 eq) at 20° C. The resulting mixture was stirred at 60° C. for 12 hours, then diluted with EtOAc (150 mL), and washed with water (50 mL) and brine (50 mL). The organic layer was dried over anhydrous Na$_2$SO$_4$, filtered, and concentrated in vacuo. The residue was purified by column chromatography on silica gel, eluting with petroleum ether/EtOAc (10:1 to 5:1 gradient) to give the title compound as a yellow solid (1.50 g, 82.4%). $^1$H NMR (400 MHz, CDCl$_3$) δ ppm 1.95-2.05 (m, 2H), 2.06-2.16 (m, 2H), 3.07-3.20 (m, 2H), 3.46 (ddd, J=12.6, 8.7, 3.4 Hz, 2H), 3.84-4.01 (m, 3H), 4.45 (tt, J=6.4, 3.4 Hz, 1H), 6.80 (dddd, J=9.2, 7.7, 3.0, 1.8 Hz, 1H), 6.88 (ddd, J=11.1, 8.3, 3.1 Hz, 1H), 7.00 (td, J=9.1, 5.4 Hz, 1H), 7.12 (d, J=8.8 Hz, 1H), 8.08 (dd, J=8.8, 2.0 Hz, 1H), 8.47 (d, J=2.2 Hz, 1H).

II. Step B: 4-(4-(2,4-difluorophenoxy)piperidin-1-yl)-3-nitrobenzoic acid

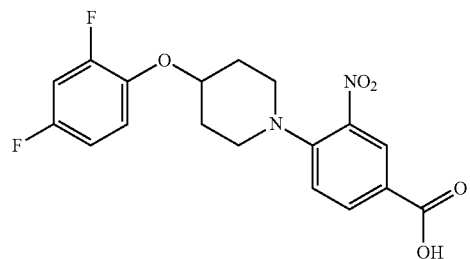 [SMILES: O=C(O)c1ccc(N2CCC(Oc3ccc(F)cc3F)CC2)c([N+](=O)[O-])c1]

To a solution of methyl 4-(4-(2,4-difluorophenoxy)piperidin-1-yl)-3-nitrobenzoate (1.50 g, 3.82 mmol, 1.00 eq) in THF (10 mL) was added aqueous NaOH (2 M, 9.55 mL, 5.00 eq) at 20° C. The resulting yellow suspension was stirred at 60° C. for 2 hours, then diluted with water (15 mL), and extracted with tert-BuOMe (20 mL). The organic layer was discarded and the aqueous layer was acidified with 2 M HCl (aq) to a pH of about 6. The mixture was extracted with DCM (2×50 mL). The organic layers were combined, washed with brine (30 mL), dried over Na$_2$SO$_4$, filtered, and concentrated in vacuo to give the title compound as a yellow solid, which was used in the next step without further purification (1.30 g, 89.0%). $^1$H NMR (400 MHz, DMSO-d$_6$) δ ppm 1.64-1.83 (m, 2H), 2.02 (ddd, J=9.5, 6.7, 3.4 Hz, 2H), 3.02-3.18 (m, 2H), 3.32-3.41 (m, 2H), 4.56 (tt, J=7.6, 3.7 Hz, 1H), 6.89-7.12 (m, 1H), 7.20-7.41 (m, 3H), 7.98 (dd, J=8.8, 2.2 Hz, 1H), 8.26 (d, J=2.0 Hz, 1H), 13.04 (br s, 1H).

III. Step C: 4-(4-(2,4-difluorophenoxy)piperidin-1-yl)-N,N-dimethyl-3-nitrobenzamide

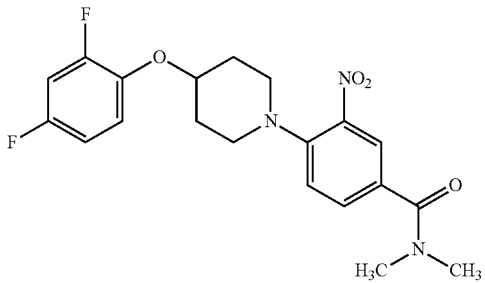

To a solution of 4-(4-(2,4-difluorophenoxy)piperidin-1-yl)-3-nitrobenzoic acid (800 mg, 2.11 mmol, 1.00 eq) and DMF (30.91 mg, 422.9 μmol, 0.20 eq) in DCM (25 mL) was added oxalyl dichloride (536.80 mg, 4.23 mmol, 2.00 eq) dropwise at 0° C. The resulting yellow solution was stirred at 20° C. for 1 hour. Dimethylamine (517.26 mg, 6.34 mmol, 3.00 eq, HCl) and Et$_3$N (1.07 g, 10.57 mmol, 5.00 eq) were added at 0° C. to the reaction mixture, which was stirred at 20° C. for 1 hour, then diluted with DCM (100 mL) and washed with saturated (aq) NaHCO$_3$ (30 mL) and brine (2×30 mL). The organic layer was dried over Na$_2$SO$_4$, filtered, and concentrated in vacuo to give the title compound as a yellow oil (730 mg, 85.3%). $^1$H NMR (400 MHz, CDCl$_3$) δ ppm 1.96-2.14 (m, 4H), 3.00-3.13 (m, 8H), 3.39 (ddd, J=12.2, 8.5, 3.3 Hz, 2H), 4.43 (tt, J=6.5, 3.4 Hz, 1H), 6.75-6.92 (m, 2H), 7.00 (td, J=9.1, 5.4 Hz, 1H), 7.16 (d, J=8.6 Hz, 1H), 7.59 (dd, J=8.5, 2.1 Hz, 1H), 7.93 (d, J=2.0 Hz, 1H); ESI-MS m/z [M+H]$^+$ 405.9.

IV. Step D: 3-amino-4-(4-(2,4-difluorophenoxy)piperidin-1-yl)-N,N-dimethylbenzamide To a solution of 4-(4-(2,4-difluorophenoxy)piperidin-1-yl)-N,N-dimethyl-3-nitrobenzamide (730 mg, 1.80 mmol, 1.00 eq) in MeOH (40 mL) was added Pd/C (10% loading, dry basis, 200 mg) under N$_2$. The resulting suspension was degassed under vacuum and purged with H$_2$ several times, and then stirred under H$_2$ (15 psi) at 20° C. for 12 hours. The reaction mixture was filtered through a pad of Celite® and the filtrate was concentrated in vacuo to give the title compound as yellow oil (630 mg, 81.1%). ESI-MS m/z [M+H]$^+$ 376.1.

Preparation x140: tert-butyl 4-(4-bromo-6-cyano-pyridin-3-yl)piperazine-1-carboxylate

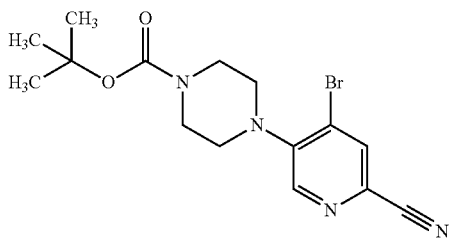 [SMILES: CC(C)(C)OC(=O)N1CCN(c2cnc(C#N)cc2Br)CC1]

A mixture of 4-bromo-5-fluoro-pyridine-2-carbonitrile (300.00 mg, 1.49 mmol, 1.00 eq), tert-butyl piperazine-1-carboxylate (333.58 mg, 1.79 mmol, 1.20 eq) and DIPEA (578.69 mg, 4.48 mmol, 782.01 μL, 3.00 eq) in NMP (15 mL) was stirred at 80° C. for 3 hours. The reaction mixture was partitioned between water (20 mL) and EtOAc (20 mL). The organic phase was separated, washed with saturated brine (3×20 mL), dried over anhydrous Na$_2$SO$_4$, filtered, concentrated under reduced pressure, and purified by column chromatography, eluting with petroleum ether/EtOAc (10:1) to give the title compound as a white solid (300 mg, 52.1%). $^1$H NMR (400 MHz, CDCl$_3$) δ ppm 1.49 (s, 9H), 3.16-3.22 (m, 4H), 3.61-3.66 (m, 4H), 7.85 (s, 1H), 8.26 (s, 1H).

Preparation x141: 3-methoxy-1-methyl-1H-pyrazole-4-carbonyl chloride

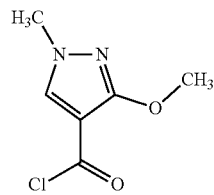

To a mixture of 3-methoxy-1-methyl-pyrazole-4-carboxylic acid (200 mg, 1.28 mmol, 1.00 eq) and DMF (9.36 mg, 128.09 μmol, 9.85 μL, 0.10 eq) in DCM (1.00 mL) was added oxalyl dichloride (195.10 mg, 1.54 mmol, 134.55 μL, 1.20 eq) at 0° C. The reaction mixture was stirred at 25° C. for 1.5 hours and then concentrated under reduced pressure to give the title compound as a yellow solid, which was used without further purification (265 mg).

Preparation x142: 3-methoxy-1-methyl-1H-pyrazole-4-carboxamide

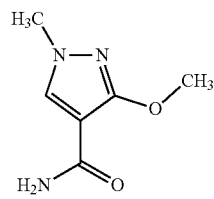

To a flask containing NH$_3$.H$_2$O (4.55 g, 36.35 mmol, 5.00 mL, 28% aq, 23.91 eq) was added 3-methoxy-1-methyl-1H-pyrazole-4-carbonyl chloride (265 mg, 1.52 mmol, 1.00 eq) in THF (1 mL) at 0° C. The reaction mixture was stirred at 0° C. for 10 minutes and then diluted with water (10 mL). The resulting mixture was extracted with DCM/MeOH (10:1) solution (10×10 mL). The organic layers were combined, dried over anhydrous Na$_2$SO$_4$, and concentrated under reduced pressure to give the title compound as yellow solid, which was used without further purification (254 mg).

Preparation x143: tert-butyl 4-(6-cyano-4-(3-methoxy-1-methyl-1H-pyrazole-4-carboxamido)pyridin-3-yl)piperazine-1-carboxylate

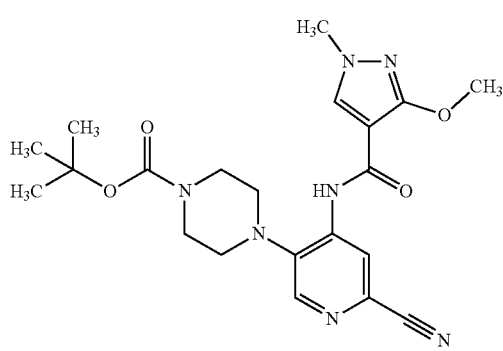 [SMILES: COc1nn(C)cc1C(=O)Nc1cc(C#N)ncc1N1CCN(C(=O)OC(C)(C)C)CC1]

The title compound was prepared in a manner similar to Example 271 using tert-butyl 4-(4-bromo-6-cyanopyridin-3-yl)piperazine-1-carboxylate (200 mg, 0.54 mmol) in place of 4-chloro-5-(4-(2,4-difluorophenoxy)piperidin-1-yl) phthalonitrile and 3-methoxy-1-methyl-H-pyrazole-4-carboxamide (127 mg, 0.82 mmol) in place of 2-methoxynicotinamide, to give the title compound (284 mg, 94.5%). $^1$H NMR (400 MHz, CDCl$_3$) δ ppm 1.49 (s, 9H), 2.94 (t, J-=4.85 Hz, 4H), 3.65 (br s, 4H), 3.80 (s, 3H), 4.10 (s, 3H), 7.85 (s, 1H), 8.36 (s, 1H), 8.89 (s, 1H), 9.49 (s, 1H); ESI-MS m/z [M+H]$^+$ 442.1.

Preparation x144: N-(2-cyano-5-(piperazin-1-yl)pyridin-4-yl)-3-methoxy-1-methyl-1H-pyrazole-4-carboxamide

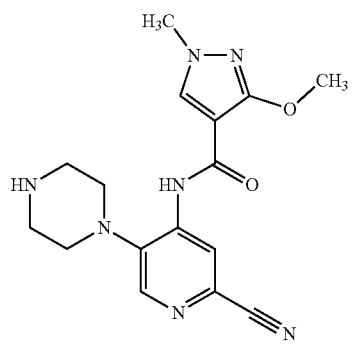 [SMILES: COc1nn(C)cc1C(=O)Nc1cc(C#N)ncc1N1CCNCC1]

To a solution of tert-butyl 4-(6-cyano-4-(3-methoxy-1-methyl-H-pyrazole-4-carboxamido)pyridin-3-yl)piperazine-1-carboxylate (50.00 mg, 113.26 μmol, 1.00 eq) in DCM (2 mL) was added HCl/EtOAc (4 M, 283.15 μL, 10.00 eq) at 20° C. The reaction mixture was stirred at 20° C. for 1 hour and then concentrated under reduced pressure to give an HCl salt of the title compound as a white solid, which was used without further purification (52 mg). ESI-MS m/z [M+H]$^+$ 342.0.

Preparation x145: 4-(4-(2,4-difluorophenoxy)piperidin-1-yl)-5-(2-methoxynicotinamido)picolinic acid

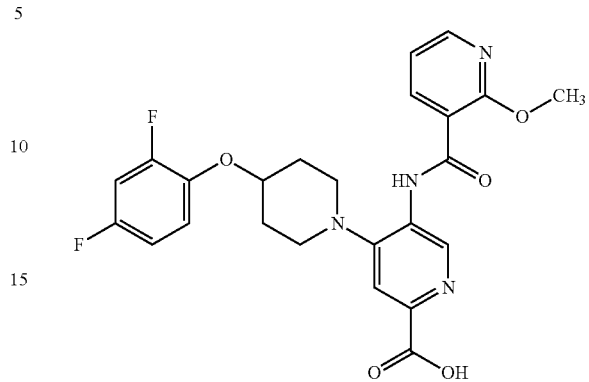

A mixture of methyl 4-(4-(2,4-difluorophenoxy)piperidin-1-yl)-5-(2-methoxynicotinamido)picolinate (660 mg, 1.32 mmol, 1.00 eq), LiOH.H$_2$O (221.55 mg, 5.28 mmol, 4.00 eq) and water (10 mL) in THF (10.00 mL) was stirred at 20° C. for 15 hours. Aqueous 2 M HCl was added to adjust the pH to 4-5. The mixture was extracted with EtOAc (2×10 mL) and the organic phases were combined, washed with brine (2×20 mL), dried over anhydrous Na$_2$SO$_4$, filtered, and concentrated in vacuo to give the title compound as a yellow solid, which was used without further purification (520 mg). ESI-MS m/z [M+H]$^+$ 485.2.

Preparation x146: 4-chloro-5-(4-(2,4-difluorophenoxy)piperidin-1-yl)phthalonitrile

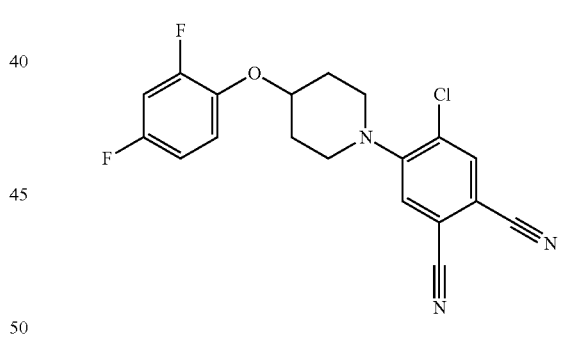

To a suspension of 4,5-dichlorophthalonitrile (2.00 g, 10.15 mmol, 1.00 eq) and 4-(2,4-difluorophenoxy)piperidine (3.04 g, 12.18 mmol, 1.20 eq, HCl) in THF (30 mL) was added Et$_3$N (3.08 g, 30.45 mmol, 3.00 eq). The resulting mixture was stirred at 70° C. for 5 hours and then concentrated in vacuo. The residue was dissolved in EtOAc (150 mL) and washed with water (50 mL) and brine (2×50 mL). The organic layer was dried over anhydrous Na$_2$SO$_4$, filtered, and concentrated in vacuo. The residue was purified by column chromatography on silica gel, eluting with petroleum ether/EtOAc (10:1 to 5:1 gradient) to give the title compound as a yellow solid (2.10 g, 55.4%). $^1$H NMR (400 MHz, CDCl$_3$) δ ppm 2.00-2.17 (m, 4H), 3.11-3.20 (m, 2H), 3.45 (ddd, J=12.0, 8.3, 3.5 Hz, 2H), 4.45 (tt, J=6.4, 3.4 Hz, 1H), 6.78-6.85 (m, 1H), 6.89 (ddd, J=11.1, 8.3, 2.9 Hz, 1H), 7.01 (td, J=9.0, 5.5 Hz, 1H), 7.34 (s, 1H), 7.73 (s, 1H).

Preparation x147: 2-methoxynicotinoyl chloride

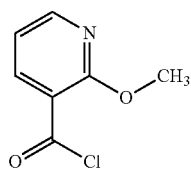

The title compound was prepared in a manner similar to Preparation x141, using 2-methoxynicotinic acid in place of 3-methoxy-1-methyl-pyrazole-4-carboxylic acid, to give the title compound.

Preparation x148: 2-methoxynicotinamide

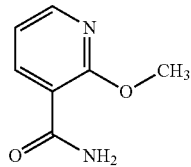

The title compound was prepared in a manner similar to Preparation x142, using 2-methoxynicotinoyl chloride in place of 3-methoxy-1-methyl-H-pyrazole-4-carbonyl chloride, to give the title compound.

Preparation x149: N-(6-(4-(2,4-difluorophenoxy)piperidin-1-yl)-1,3-dioxoisoindolin-5-yl)-2-methoxynicotinamide

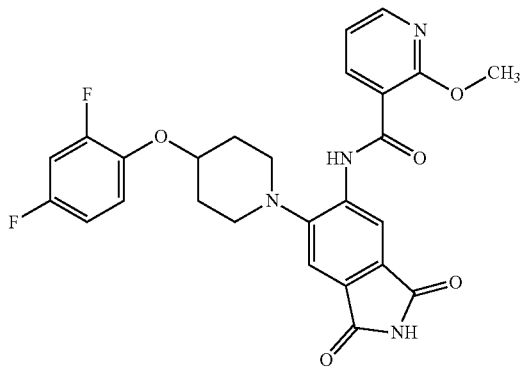 [SMILES: COc1ncccc1C(=O)Nc1cc2c(cc1N1CCC(Oc3ccc(F)cc3F)CC1)C(=O)NC2=O]

To a stirred mixture of N-(4,5-dicyano-2-(4-(2,4-difluorophenoxy)piperidin-1-yl)phenyl)-2-methoxynicotinamide (300 mg, 613 µmol, 1.00 eq) in HOAc (6 mL) was added Cu(OAc)$_2$ (11.13 mg, 61.29 µmol, 0.10 eq). The reaction mixture was stirred at 100° C. for 24 hours, then poured into saturated (aq) NaHCO$_3$ (15 mL), extracted with EtOAc (3×15 mL) and washed with brine (10 mL). The organic phases were separated, dried over anhydrous Na$_2$SO$_4$, filtered, concentrated in vacuo, and purified by column chromatography, eluting with petroleum ether/EtOAc (3:1 to 1:1 gradient) to give the title compound as a light yellow solid (50 mg). $^1$H NMR of (400 MHz, DMSO-d$_6$) δ ppm 1.82- 1.95 (m, 2H), 2.13 (d, J=11.9 Hz, 2H), 2.94 (t J=9.0 Hz, 2H), 3.10-3.21 (m, 2H), 4.14-4.26 (m, 3H), 4.57 (br s, 1H), 7.03 (t, J=8.6 Hz, 1H), 7.24-7.38 (m, 3H), 7.64 (s, 1H), 8.40-8.54 (m, 2H), 8.79 (s, 1H), 10.66 (s, 1H), 11.20 (s, 1H).

Preparation x150: 4-(4-(2,4-difluorophenoxy)piperidin-1-vi-5-(2-methoxynicotinamido)-N$^1$,N$^1$-dimethylphthalamide

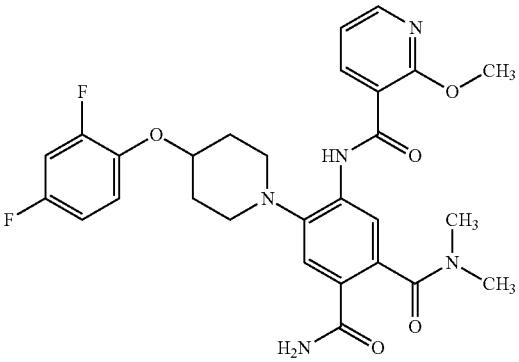 [SMILES: COc1ncccc1C(=O)Nc1cc(C(=O)N(C)C)c(C(N)=O)cc1N1CCC(Oc2ccc(F)cc2F)CC1]

5-(4-(2,4-difluorophenoxy)piperidin-1-yl)-4-(2-methoxynicotinamido)-N$^1$,N$^1$-dimethylphthalamide

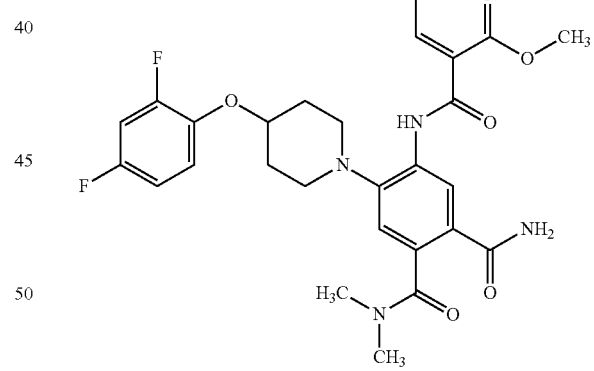

To a solution of N-(6-(4-(2,4-difluorophenoxy)piperidin-1-yl)-1,3-dioxoisoindolin-5-yl)-2-methoxynicotinamide (50.00 mg, 98.33 µmol, 1.00 eq) in DMF (1.50 mL) was added HATU (44.87 mg, 118.00 µmol, 1.20 eq) and DIPEA (63.54 mg, 491.65 µmol, 85.86 µL, 5.00 eq). The mixture was stirred at 25° C. for 12 hours, then poured into water (5 mL), extracted with EtOAc (3×5 mL) and washed with brine (5 mL). The organic phases were separated, dried over anhydrous Na$_2$SO$_4$, filtered, and concentrated in vacuo to give a mixture of the title compounds as a yellow oil (50 mg).

Preparation x151: N-(5-cyano-2-(4-(2,4-difluorophenoxy)piperidin-1-yl)phenyl)-2-methoxybenzamide

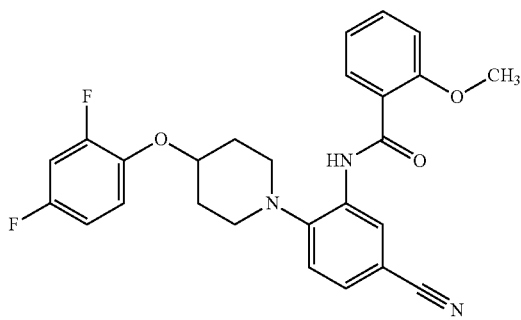 [SMILES: COc1ccccc1C(=O)Nc1cc(C#N)ccc1N1CCC(Oc2ccc(F)cc2F)CC1]

The title compound was prepared in a manner similar to Example 265, using 3-amino-4-(4-(2,4-difluorophenoxy)piperidin-1-yl)benzonitrile (50 mg, 0.15 mmol) in place of 3-amino-4-(4-(2,4-difluorophenoxy)piperidin-1-yl)-N,N-dimethylbenzamide and 2-methoxybenzoyl chloride (39 mg, 0.23 mmol) in place of 2-methoxynicotinoyl chloride, to give the title compound as a white solid (100 mg, 71%). ESI-MS m/z [M+Na]$^+$ 485.9.

Preparation x152: methyl 2-(difluoromethoxy)nicotinate and methyl 1-(difluoromethyl)-2-oxo-1,2-dihydropyridine-3-carboxylate

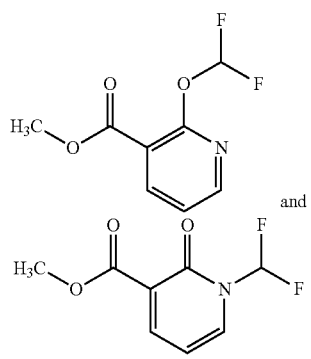

To a solution of methyl 2-hydroxynicotinate (500 mg, 3.26 mmol, 1.00 eq) in DMF (10 mL) was added Cs$_2$CO$_3$ (1.59 g, 4.89 mmol, 1.50 eq) and sodium 2-chloro-2,2-difluoroacetate (596.42 mg, 3.91 mmol, 1.20 eq). The mixture was stirred at 100° C. for 3 hours, then poured into water (5 mL), extracted with EtOAc (3×5 mL), and washed with brine (5 mL). The organic phases were separated, dried over anhydrous Na$_2$SO$_4$, filtered, concentrated in vacuo, and purified by column chromatography, eluting with petroleum ether/EtOAc (2:1) to give methyl 2-(difluoromethoxy)nicotinate as a yellow oil (200 mg, 59.8%). $^1$H NMR (400 MHz, CDCl$_3$) δ ppm 3.81-4.00 (m, 3H), 6.32-6.47 (m, 1H), 7.54-7.90 (m, 2H), 8.16-8.28 (m, 1H); ESI-MS m/z [M+H]$^+$ 203.8. A second product, methyl 1-(difluoromethyl)-2-oxo-1,2-dihydropyridine-3-carboxylate, was also obtained as a light yellow oil (40 mg, 11%). $^1$H NMR (400 MHz, CDCl$_3$) δ ppm 3.89-3.99 (m, 3H), 7.19 (dd, J=7.9, 4.9 Hz, 1H), 7.34-7.75 (m, 1H), 8.18-8.42 (m, 2H); ESI-MS m/z [M+H]$^+$ 203.8.

Preparation x153: 2-(difluoromethoxy)nicotinic acid

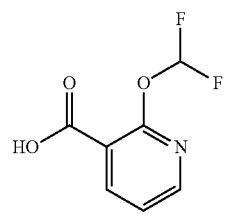 [SMILES: O=C(O)c1cccnc1OC(F)F]

To a solution of methyl 2-(difluoromethoxy)nicotinate (200 mg, 985 μmol, 1.00 eq) in THF (3 mL) was added LiOH (4 M, 1.23 mL, 5.00 eq). The mixture was stirred at 25° C. for 1 hour. Aqueous 4M HCl (2 mL) was added to quench the reaction and to adjust the pH of the mixture to about 2-3. The mixture was then extracted with EtOAc (3×5 mL) and washed with brine (3 mL). The organic phases were separated, dried over anhydrous Na$_2$SO$_4$, filtered, and concentrated in vacuo to give the title compound as a yellow solid (150 mg, 80.6%). $^1$H NMR (400 MHz, CDCl$_3$) δ ppm 6.73 (t, J=7.0 Hz, 1H), 7.61-7.95 (m, 2H), 8.63 (dd, J=7.0, 2.0 Hz, 1H), 13.08 (br s, 1H).

Preparation x154: 1-(difluoromethyl)-2-oxo-1,2-dihydropyridine-3-carboxylic acid

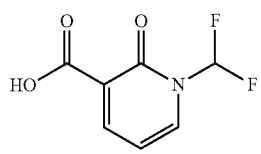 [SMILES: O=C(O)c1cccn(C(F)F)c1=O]

To a solution of methyl 1-(difluoromethyl)-2-oxo-1,2-dihydropyridine-3-carboxylate (150 mg, 738 μmol, 1.00 eq) in THF (1 mL) was added LiOH (4 M, 923.01 μL, 5.00 eq). The mixture was stirred at 25° C. for 1 h. Aqueous 4M HCl (2 mL) was added to adjust the pH of the mixture to about 2-3. The mixture was then extracted with EtOAc (3×5 mL) and washed with brine (3 mL). The organic phases were separated, dried over anhydrous Na$_2$SO$_4$, filtered, and concentrated in vacuo to give the title compound as a yellow solid (120 mg, 85.9%). $^1$H NMR (400 MHz, CDCl$_3$) δ ppm 7.24-7.29 (m, 1H), 7.40-7.82 (m, 1H), 8.34-8.52 (m, 2H).

Preparation x155: 2-(4-(2,4-difluorophenoxy)piperidin-1-yl)-5-(morpholinosulfonyl)pyridin-3-amine

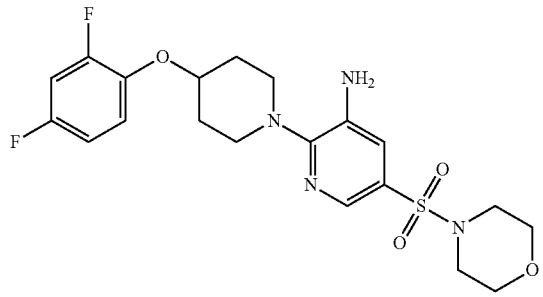 [SMILES: Nc1cc(S(=O)(=O)N2CCOCC2)cnc1N1CCC(Oc2ccc(F)cc2F)CC1]

I. Step A: 4-((5-bromo-6-chloropyridin-3-yl)sulfonyl)morpholine

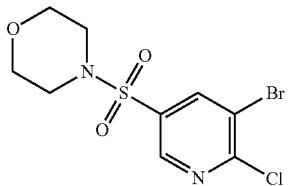 [SMILES: O=S(=O)(c1cnc(Cl)c(Br)c1)N1CCOCC1]

To a stirred mixture of 5-bromo-6-chloropyridine-3-sulfonyl chloride (10.00 g, 34.37 mmol, 1.00 eq) and Et$_3$N (5.22 g, 51.56 mmol, 1.50 eq) in dry DCM (200 mL) was added morpholine (1.50 g, 17.18 mmol, 0.50 eq) dropwise at 0° C. The mixture was stirred at 15° C. for 2 hours under nitrogen atmosphere and then diluted with DCM (200 mL) and brine (200 mL). The aqueous layers were separated and extracted with DCM (2×100 mL). The organic layers were combined, dried over anhydrous Na$_2$SO$_4$, filtered, evaporated under reduced pressure, and purified by column chromatography, eluting with petroleum ether/EtOAc (20:1 to 3:1 gradient) to give the title compound as a white solid (10.5 g, 89%). $^1$H NMR (400 MHz, CDCl$_3$) δ ppm 3.08-3.10 (m, 4H), 3.77-3.80 (m, 4H), 8.25 (s, 1H), 8.67 (s, 1H).

II. Step B: 4-((5-bromo-6-(4-(2,4-difluorophenoxy)piperidin-1-yl)pyridin-3-yl)sulfonyl)morpholine

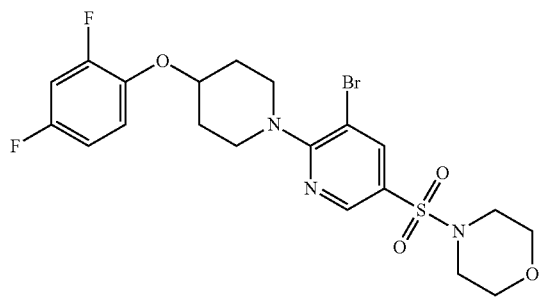 [SMILES: O=S(=O)(c1cnc(N2CCC(Oc3ccc(F)cc3F)CC2)c(Br)c1)N1CCOCC1]

To a stirred mixture of 4-((5-bromo-6-chloropyridin-3-yl)sulfonyl)morpholine (1.00 g, 2.93 mmol, 1.00 eq) and 4-(2,4-difluorophenoxy)piperidine (1.02 g, 4.10 mmol, 1.40 eq, HCl) in THF (20 mL) was added Et$_3$N (1.48 g, 14.65 mmol, 5.00 eq) at 20° C. The mixture was stirred at 20° C. for 16 hours, then diluted with EtOAc (20 mL) and washed with brine (20 mL). The aqueous layer was extracted with EtOAc (2×10 mL). The organic layers were combined, dried over anhydrous Na$_2$SO$_4$, filtered, evaporated under reduced pressure, and purified by column chromatography, eluting with petroleum ether/EtOAc (20:1 to 1:1 gradient) to give the title compound as a white solid (1.25 g, 77.4%). $^1$H NMR (400 MHz, CDCl$_3$) δ ppm 1.99-2.12 (m, 4H), 3.04-3.06 (m, 4H), 3.47-3.50 (m, 2H), 3.76-3.85 (m, 6H), 4.43-4.47 (m, 1H), 6.81-7.27 (m, 3H), 8.03 (s, 1H), 8.50 (s, 1H); ESI-MS m/z [M+H]$^+$ 519.9.

III. Step C: N-(2-(4-(2,4-difluorophenoxy)piperidin-1-yl)-5-(morpholinosulfonyl)pyridin-3-yl)-1,1-diphenylmethanimine

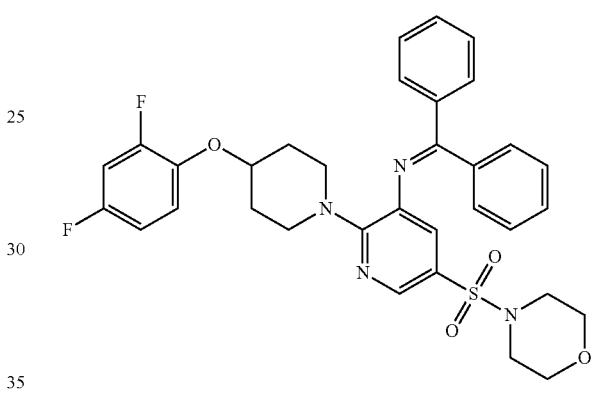

A mixture of 4-((5-bromo-6-(4-(2,4-difluorophenoxy)piperidin-1-yl)pyridin-3-yl)sulfonyl)morpholine (500 mg, 965 µmol, 1.00 eq), diphenylmethanimine (174.81 mg, 964.56 µmol, 1.00 eq), Pd$_2$(dba)$_3$ (88.33 mg, 96.46 µmol, 0.10 eq), Xantphos (111.62 mg, 192.91 µmol, 0.20 eq) and Cs$_2$CO$_3$ (628.55 mg, 1.93 mmol, 2.00 eq) in toluene (7 mL) was degassed and purged with N$_2$ (2×) and then stirred at 110° C. for 16 hours under N$_2$ atmosphere. The mixture was poured into water (20 mL), extracted with EtOAc (3×20 mL) and washed with brine (10 mL). The organic phases were separated, dried over anhydrous Na$_2$SO$_4$, filtered, concentrated in vacuo, and purified by column chromatography, eluting with petroleum ether/EtOAc (5:1 to 1:1 gradient) to give the title compound as a yellow oil (550 mg, 89.4%). ESI-MS m/z [M+H]$^+$ 619.9.

IV. Step D: 2-(4-(2,4-difluorophenoxy)piperidin-1-yl)-5-(morpholinosulfonyl)pyridin-3-amine To a stirred mixture of N-(2-(4-(2,4-difluorophenoxy)piperidin-1-yl)-5-(morpholinosulfonyl)pyridin-3-yl)-1,1-diphenylmethanimine (550 mg, 889 µmol, 1.00 eq) in THF (10 mL) was added 12 M HCl (2.00 mL, 27.00 eq) in dioxane. The mixture was stirred at 20° C. for 1 hour, then poured into 4 M NaOH aqueous solution (8 mL, pH about 8-9), extracted with EtOAc (3×20 mL) and washed with brine (10 mL). The organic phases were separated, dried over anhydrous Na$_2$SO$_4$, filtered, concentrated in vacuo, and purified by column chromatography, eluting with petroleum ether/EtOAc (3:1 to 0:1 gradient) to give the title compound as a light yellow gum (360 mg, 86.4%). $^1$H NMR (400 MHz, CDCl₃) δ ppm 1.89-2.02 (m, 2H), 2.14 (dd, J=12.8, 3.1 Hz, 2H), 2.98-3.15 (m, 4H), 3.50-3.64 (m, 2H), 3.69-3.79 (m, 4H), 3.91 (br s, 2H), 4.38 (dt, J=7.6, 3.9 Hz, 1H), 6.76-6.93 (m, 2H), 7.02 (td, J=9.0, 5.3 Hz, 1H), 7.19 (d, J=2.2 Hz, 1H), 8.12 (d, J=1.8 Hz, 1H); ESI-MS m/z [M+H]⁺ 455.1.

Preparation x156: 2-chloro-4-(4-(2,4-difluorophenoxy)piperidin-1-yl)-5-nitropyrimidine

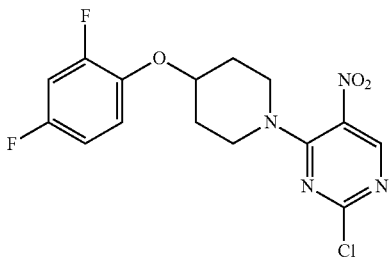 [SMILES: O=[N+]([O-])c1cnc(Cl)nc1N1CCC(Oc2ccc(F)cc2F)CC1]

A mixture of 2,4-dichloro-5-nitropyrimidine (5.00 g, 25.8 mmol, 1.00 eq), DIPEA (6.66 g, 51.55 mmol, 9.00 mL, 2.00 eq) and 4-(2,4-difluorophenoxy)piperidine (7.08 g, 28.36 mmol, 1.10 eq, HCl) in ACN (70.00 mL) was stirred at 25° C. for 1.5 hours, then diluted with EtOAc (200 mL), washed with water (3×50 mL), dried over anhydrous Na₂SO₄, and concentrated under reduced pressure. The crude product was purified by silica gel column chromatography, eluting with petroleum ether/EtOAc (5:1) to give the title compound as a yellow oil (8.00 g, 83.7%). ¹HNMR (400 MHz, CDCl₃) δ ppm 2.04 (br s, 4H), 3.62 (br dd, J=2.87, 2.21 Hz, 2H), 3.70-3.82 (m, 2H), 4.51 (t, J=4.41 Hz, 1H), 6.73-7.03 (m, 3H), 8.72 (s, 1H).

Preparation x157: 4-(4-(2,4-difluorophenoxy)piperidin-1-yl)-5-nitropyrimidine-2-carbonitrile

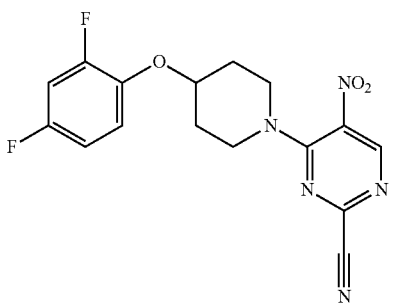 [SMILES: N#Cc1ncc([N+](=O)[O-])c(N2CCC(Oc3ccc(F)cc3F)CC2)n1]

A mixture of 2-chloro-4-(4-(2,4-difluorophenoxy)piperidin-1-yl)-5-nitropyrimidine (3.00 g, 8.09 mmol, 1.00 eq), dicyanozinc (2.85 g, 24.3 mmol, 1.54 mL, 3.00 eq) and Pd(PPh₃)₄ (4.67 g, 4.05 mmol, 0.50 eq) in DMF (50 mL) was stirred at 80° C. for 10 hours under N atmosphere. The suspension was subsequently filtered through a pad of Celite®. The pad was washed with EtOAc (3×10 mL). The combined filtrates were combined, concentrated, and purified by silica gel column chromatography, eluting with petroleum ether/EtOAc (10:1) to give the title compound as a yellow oil (1.2 g, 41%). ¹HNMR (400 MHz, CDCl₃) δ ppm 2.04 (br s, 4H), 3.62 (br dd, J=2.87, 2.21 Hz, 2H), 3.70-3.82 (m, 2H), 4.55 (t, J=4.41 Hz, 1H), 6.82-7.33 (m, 3H), 8.26 (s, 1H).

Preparation x158: 5-amino-4-(4-(2,4-difluorophenoxy)piperidin-1-yl)pyrimidine-2-carbonitrile

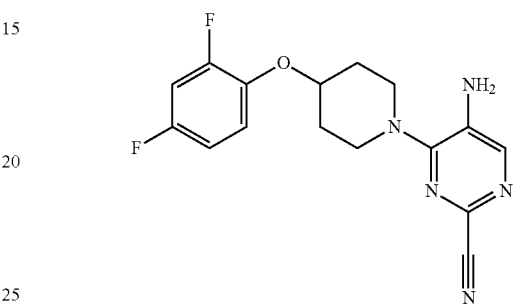

To a solution of 4-(4-(2,4-difluorophenoxy)piperidin-1-yl)-5-nitropyrimidine-2-carbonitrile (650 mg, 1.80 mmol, 1.00 eq) and NH₄Cl (962.82 mg, 18.00 mmol, 629.29 μL, 10.00 eq) in THF (8 mL), MeOH (4 mL) and water (4 mL) was added Fe (1.01 g, 18.0 mmol, 10.0 eq) at 25° C. The resulting suspension was stirred at 60° C. for 2 hours and then filtered through a pad of Celite®. The pad was washed with MeOH (3×10 mL). The combined filtrates were concentrated and then purified by silica gel column chromatography, eluting with DCM/MeOH (10:1) to give the title compound as a light-yellow solid (430 mg, 72.1%). ¹H NMR (400 MHz, CDCl₃) δ ppm 1.85-1.98 (m, 2H), 2.01-2.14 (m, 2H), 3.19-3.32 (m, 2H), 3.63-3.73 (m, 2H), 3.86 (s, 2H), 4.40 (dt, J=7.17, 3.69 Hz, 1H), 6.74-7.02 (m, 3H), 7.92 (s, 1H).

Preparation x159: 2-methoxy-6-methylnicotinoyl chloride

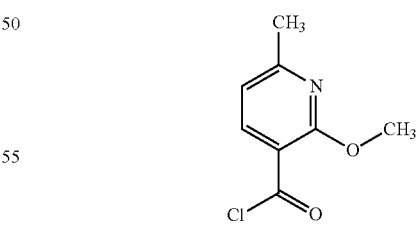

To a mixture of 2-methoxy-6-methylnicotinic acid (100 mg, 598 μmol, 1.00 eq) and DMF (4.37 mg, 59.82 μmol, 4.60 μL, 0.10 eq) in DCM (3 mL) was added oxalyl dichloride (157.10 μL, 1.79 mmol, 3.00 eq) at 0° C. The reaction mixture was stirred at 25° C. for 1.5 hours and then concentrated under reduced pressure to give the title compound as a dark brown oil, which was used without further purification (87 mg).

Preparation x160: methyl 4-(4-(2,4-difluorophenoxy)piperidin-1-yl)-5-nitropyrimidine-2-carboxylate

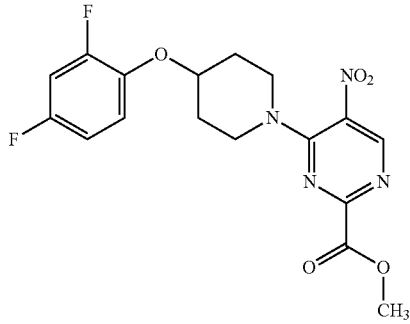 [SMILES: COC(=O)c1ncc([N+](=O)[O-])c(N2CCC(Oc3ccc(F)cc3F)CC2)n1]

A mixture of 4-(4-(2,4-difluorophenoxy)piperidin-1-yl)-5-nitropyrimidine-2-carbonitrile (1.20 g, 3.32 mmol, 1.00 eq) in 4 M HCl in MeOH (16.61 mL, 20.00 eq) was stirred at 80° C. for 3 hours and then concentrated in vacuo. The residue was dissolved in DCM (150 mL) and then washed with saturated aq NaHCO$_3$ (50 mL) and brine (50 mL). The organic layer was dried over anhydrous Na$_2$SO$_4$, filtered, and concentrated in vacuo. The residue was purified by column chromatography, eluting with petroleum ether/EtOAc (5:1 to 2:1 gradient) to give the title compound as a yellow solid (900 mg, 2.28 mmol, 68.8%). $^1$HNMR (400 MHz, CDCl$_3$) δ ppm 2.00-2.05 (m, 4H), 3.71-3.84 (m, 4H), 3.40 (s, 3H), 4.52 (br t, J=3.97 Hz, 1H), 6.76-7.02 (m, 3H), 8.91 (s, 1H).

Preparation x161: 4-(4-(2,4-difluorophenoxy)piperidin-1-yl)-5-nitropyrimidine-2-carboxylic acid

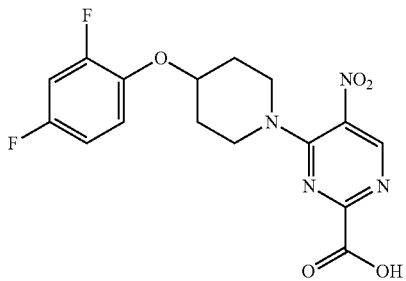 [SMILES: O=C(O)c1ncc([N+](=O)[O-])c(N2CCC(Oc3ccc(F)cc3F)CC2)n1]

The title compound was prepared in a manner similar to Preparation x145, using methyl 4-(4-(2,4-difluorophenoxy)piperidin-1-yl)-5-nitropyrimidine-2-carboxylate (350 mg, 0.888 mmol, 1.00 eq) in place of 4-(4-(2,4-difluorophenoxy)piperidin-1-yl)-5-(2-methoxynicotinamido)picolinate, to give the title compound as a dark yellow solid (300 mg, 89%). $^1$H NMR (400 MHz, DMSO-d$_6$) δ ppm 1.75-1.79 (m, 2H), 2.03-2.08 (m, 2H), 3.47-3.51 (m, 2H), 3.73-3.75 (m, 2H), 4.65-4.66 (m, 1H), 7.02-7.04 (m, 1H), 7.27-7.34 (m, 2H), 8.99 (s, 1H); ESI-MS m/z [M+H]$^+$ 380.9.

Preparation x162: 4-(4-(2,4-difluorophenoxy)piperidin-1-yl)-N,N-dimethyl-5-nitropyrimidine-2-carboxamide

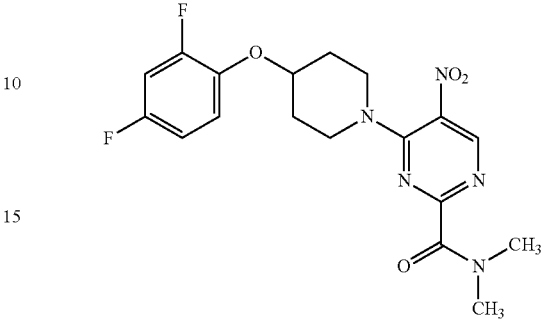

The title compound was prepared in a manner similar to Preparation x138, using 4-(4-(2,4-difluorophenoxy)piperidin-1-yl)-5-nitropyrimidine-2-carboxylic acid (200 mg, 0.53 mmol) in place of 4-bromo-5-(4-(2,4-difluorophenoxy)piperidin-1-yl)picolinic acid, to give the title compound as a yellow solid (310 mg, 96.6%). $^1$H NMR (400 MHz, DMSO-d$_6$) δ ppm 1.74-1.79 (m, 2H), 2.02-2.07 (m, 2H), 2.68-2.83 (m, 3H), 2.83-2.97 (m, 3H), 3.43-3.48 (m, 2H), 3.69-3.70 (m, 2H), 4.64-4.66 (m, 1H), 6.93-7.06 (m, 1H), 7.27-7.34 (m, 2H), 8.97 (s, 1H); ESI-MS m/z [M+H]$^+$ 408.1.

Preparation x163: 5-amino-4-(4-(2,4-difluorophenoxy)piperidin-1-yl)-N,N-dimethylpyrimidine-2-carboxamide

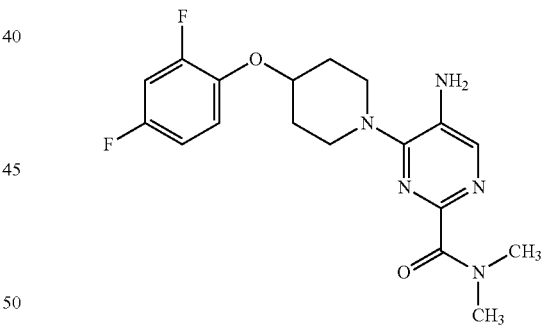

To a vessel containing 4-(4-(2,4-difluorophenoxy)piperidin-1-yl)-N,N-dimethyl-5-nitropyrimidine-2-carboxamide (310 mg, 761 μmol, 1.00 eq) in MeOH (12 mL) was added Pd/C (60.00 mg, 10 wt % loading dry basis) under N$_2$. The vessel was evacuated and refilled with H$_2$ several times and then the reaction mixture was stirred under H$_2$ (15 psi) atmosphere at 26° C. for 3 hours. Following reaction, the mixture was filtered through a pad of Celite® and concentrated in vacuo to give the title compound as a yellow solid (280 mg, 97.0%). $^1$H NMR (400 MHz, DMSO-d$_6$) δ ppm 1.71-1.83 (m, 2H), 1.97-2.07 (m, 2H), 2.79 (s, 3H), 2.92 (s, 3H), 3.00-3.10 (m, 2H), 3.54-3.62 (m, 2H), 4.52 (tt, J=7.94, 3.86 Hz, 1H), 5.08 (s, 2H), 6.95-7.03 (m, 1H), 7.22-7.33 (m, 2H), 7.87 (s, 1H); ESI-MS m/z [M+H]$^+$ 378.0.

125

Preparation x164: 6-chloro-3-(4-(2,4-difluorophenoxy)piperidin-1-yl)pyridazin-4-amine

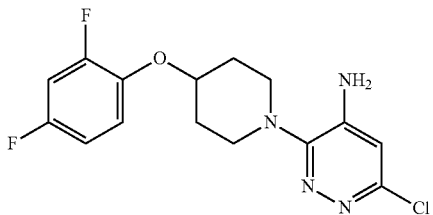 [SMILES: Nc1cc(Cl)nnc1N1CCC(Oc2ccc(F)cc2F)CC1]

To a mixture of 3,6-dichloropyridazin-4-amine (1.50 g, 9.15 mmol, 1.00 eq) and 4-(2,4-difluorophenoxy)piperidine (2.56 g, 10.25 mmol, 1.12 eq, HCl) in DMSO (15 mL) was added K$_2$CO$_3$ (6.00 g, 43.4 mmol, 4.74 eq). The resulting brown mixture was stirred at 120° C. for 16 hours and then poured into water (100 mL) and extracted with EtOAc (2×100 mL). The organic layers were combined, washed with water (100 mL), dried over anhydrous Na$_2$SO$_4$, concentrated, and purified by silica gel column chromatography, eluting with petroleum ether/EtOAc (10:1 to 2:1 gradient) to give the title compound as a light yellow solid (400 mg, 11.9%). $^1$H NMR (400 MHz, DMSO-d$_6$) δ ppm 1.82-1.93 (m, 2H), 2.02-2.13 (m, 2H), 2.88-2.98 (m, 2H), 3.26-3.33 (m, 2H), 4.49-4.58 (m, 1H), 6.29-6.43 (m, 2H), 6.62 (s, 1H), 6.97-7.05 (m, 1H), 7.24-7.36 (m, 2H); ESI-MS m/z [M+H]$^+$ 340.9.

Preparation x165: 5-amino-6-(4-(2,4-difluorophenoxy)piperidin-1-yl)pyridazine-3-carbonitrile

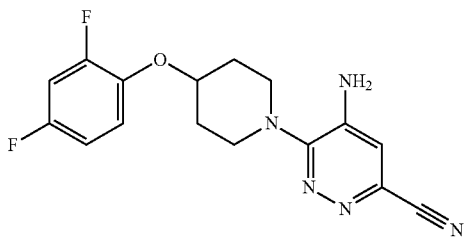 [SMILES: N#Cc1cc(N)c(N2CCC(Oc3ccc(F)cc3F)CC2)nn1]

The tide compound was prepared in a manner similar to Preparation x157, using 6-chloro-3-(4-(2,4-difluorophenoxy)piperidin-1-yl)pyridazin-4-amine (300 mg, 0.82 mmol) in place of 2-chloro-4-(4-(2,4-difluorophenoxy)piperidin-1-yl)-5-nitropyrimidine, to give the title compound as a white solid (40 mg, 13%). $^1$H NMR (400 MHz, DMSO-d$_6$) δ ppm 1.81-1.94 (m, 2H), 2.07 (br s, 2H), 3.06 (br t, J=9.48 Hz, 2H), 3.38-3.49 (m, 2H), 4.53-4.62 (m, 1H), 6.72 (br s, 2H), 6.97-7.07 (m, 2H), 7.25-7.37 (m, 2H); ESI-MS m/z [M+H]$^+$ 331.9.

EXAMPLES

Example 1: V-(2-(4-(2-fluoro-4-methoxyphenoxy)piperidin-1-yl)-5-(methylsulfonyl)phenyl)-1-(2-fluoroethyl)-3-methoxy-1H-pyrazole-4-carboxamide

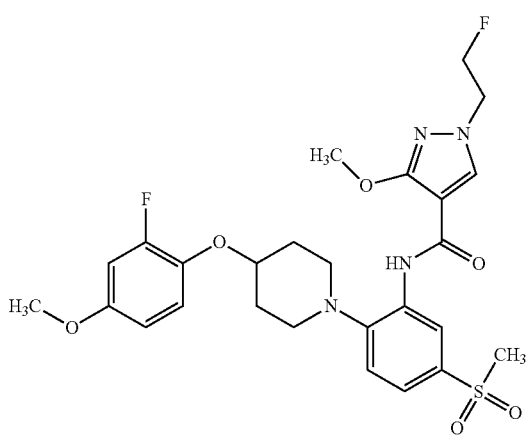 [SMILES: COc1ccc(OC2CCN(c3ccc(S(C)(=O)=O)cc3NC(=O)c3cn(CCF)nc3OC)CC2)c(F)c1]

Starting materials 2-(4-(2-fluoro-4-methoxyphenoxy)piperidin-1-yl)-5-(methylsulfonyl)aniline (0.132 g, 0.335 mmol), 1-(2-fluoroethyl)-3-methoxy-1H-pyrazole-4-carboxylic acid (0.069 g, 0.368 mmol), and pyridine (0.273 mL, 3.35 mmol) were dissolved in DMA (1.5 mL). After stirring 10 minutes, 2,4,6-tripropyl-1,3,5,2,4,6-trioxatriphosphinane 2,4,6-trioxide (0.398 mL, 0.669 mmol) was added to the reaction mixture, which was subsequently stirred at 50° C. for 5 days. Following reaction, the mixture was purified by HPLC (acid mode). The product-containing fractions were combined, concentrated, and lyophilized to give a TFA salt of the title compound as a brown solid (38.7 mg, 20.4%). $^1$H NMR (500 MHz, CDCl$_3$) δ ppm 1.98-2.10 (m, 2H), 2.15-2.22 (m, 2H), 2.74-2.90 (m, 2H), 3.08 (s, 3H), 3.14-3.29 (m, 2H), 3.78 (s, 3H), 4.19 (s, 3H), 4.23-4.39 (m, 3H), 4.68-4.78 (m, 1H), 4.78-4.88 (m, 1H), 6.55-6.64 (m, 1H), 6.66-6.78 (m, 1H), 6.92-7.07 (m, 1H), 7.26-7.29 (m, 1H), 7.59-7.71 (m, 1H), 7.97 (s, 1H), 9.01-9.12 (m, 1H), 9.44-9.53 (m, 1H); ESI-MS m/z [M+H]$^+$ 565.4.

Example 2: N-(2-(4-(2-fluoro-4-methoxyphenoxy)piperidin-1-yl)-5-(methylsulfonyl)phenyl)-1-(fluoromethyl)-3-methoxy-1H-pyrazole-4-carboxamide

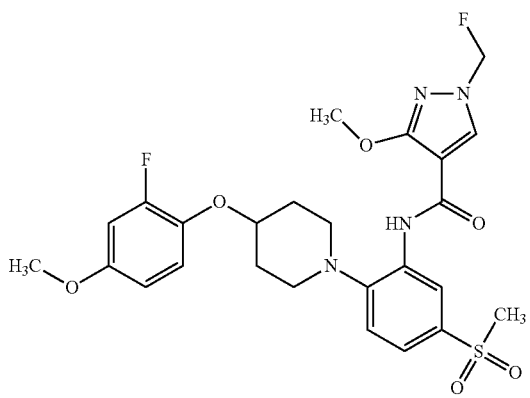 [SMILES: COc1ccc(OC2CCN(c3ccc(S(C)(=O)=O)cc3NC(=O)c3cn(CF)nc3OC)CC2)c(F)c1]

The title compound was prepared in a manner similar to Example 1, using 2-(4-(2-fluoro-4-methoxyphenoxy)piperidin-1-yl)-5-(methylsulfonyl)aniline (0.114 g, 0.289 mmol), 1-(fluoromethyl)-3-methoxy-1H-pyrazole-4-carboxylic acid (0.055 g, 0.318 mmol), pyridine (0.236 mL, 2.89 mmol), and 2,4,6-tripropyl-1,3,5,2,4,6-trioxatriphosphinane 2,4,6-trioxide (0.344 mL, 0.578 mmol) in DMA (1.5 mL), and was isolated as a colorless film (34.0 mg, 21.4%). $^1$H NMR (500 MHz, CDCl$_3$) δ ppm 1.99-2.07 (m, 2H), 2.13-2.20 (m, 2H), 2.77-2.84 (m, 2H), 3.07 (s, 3H), 3.14-3.21 (m, 2H), 3.76 (s, 3H), 3.78-3.78 (m, 1H), 3.78-3.78 (m, 1H), 4.22 (s, 3H), 4.25-4.34 (m, 1H), 5.83 (s, 1H), 5.94 (s, 1H), 6.55-6.63 (m, 1H), 6.65-6.75 (m, 1H), 6.91-7.05 (m, 1H), 7.28 (s, 1H), 7.58-7.71 (m, 1H), 8.10-8.21 (m, 1H), 9.02-9.12 (m, 1H), 9.43-9.58 (m, 1H); ESI-MS m/z [M+H]$^+$ 551.4.

Example 3: N-(2-(4-(2,4-difluorophenoxy)piperidin-1-yl)-5-(methylsulfonyl)phenyl)-1-methyl-2-oxo-1,2-dihydropyridine-3-carboxamide

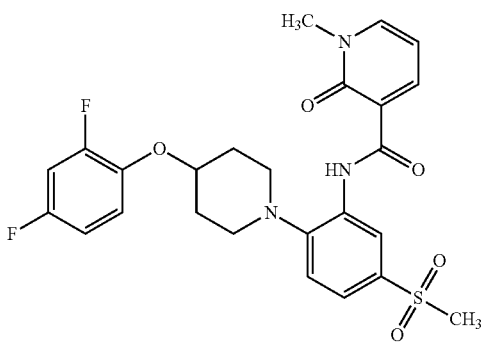 [SMILES: Cn1cccc(C(=O)Nc2cc(S(C)(=O)=O)ccc2N2CCC(Oc3ccc(F)cc3F)CC2)c1=O]

To a solution of 1-methyl-2-oxo-1,2-dihydropyridine-3-carboxylic acid (16.66 mg, 0.109 mmol), 2-(4-(2,4-difluorophenoxy)piperidin-1-yl)-5-(methylsulfonyl)aniline (32 mg, 0.084 mmol) and HATU (47.7 mg, 0.126 mmol) in DMF (0.5 mL) was added DIPEA (0.029 mL, 0.167 mmol). The solution stirred at 20° C. for 15 hours after which LC/MS indicated the reaction was complete. The solution was diluted with DMF (0.4 mL) and MeOH (0.2 mL), filtered through a syringe filter and purified by preparative HPLC, eluting with a gradient of ACN/water (acid mode) to give the title compound as a white solid (0.4 eq TFA, 31 mg, 66%). $^1$H NMR (500 MHz, DMSO-d$_6$) δ ppm 1.99-2.12 (m, 2H), 2.14-2.24 (m, 2H), 2.88 (ddd, J=11.59, 8.18, 3.17 Hz, 2H), 3.07-3.16 (m, 2H), 3.17 (s, 3H), 3.65 (s, 3H), 4.52-4.59 (m, 1H), 6.61 (dd, J=7.32, 6.35 Hz, 1H), 6.97-7.06 (m, 1H), 7.26-7.38 (m, 2H), 7.44 (d, J=8.30 Hz, 1H), 7.60-7.67 (m, 1H), 8.18 (dd, J=6.59, 2.20 Hz, 1H), 8.49 (dd, J=7.57, 2.20 Hz, 1H), 9.07 (d, J=1.95 Hz, 1H), 12.50 (s, 1H); ESI-MS m/z [M+H]$^+$ 518.

Example 4: N-(5-cyano-2-(4-(4-fluorophenoxy)piperidin-1-yl)phenyl)-1-methyl-2-oxo-1,2-dihydropyridine-3-carboxamide

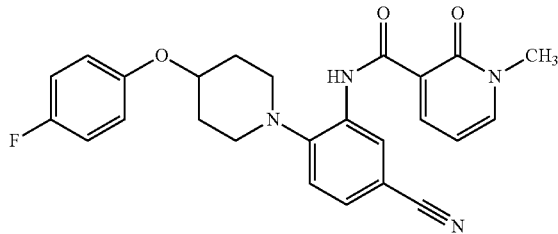 [SMILES: Cn1cccc(C(=O)Nc2cc(C#N)ccc2N2CCC(Oc3ccc(F)cc3)CC2)c1=O]

To a mixture of N-(5-cyano-2-(4-hydroxypiperidin-1-yl)phenyl)-1-methyl-2-oxo-1,2-dihydropyridine-3-carboxamide (25 mg, 0.071 mmol), 4-fluorophenol (23.86 mg, 0.213 mmol), and polymer-bound triphenylphosphine (37.2 mg, 0.142 mmol) in DMF (0.3 mL) was added diisopropyl (E)-diazene-1,2-dicarboxylate (0.021 mL, 0.106 mmol). The reaction mixture was stirred at 20° C. for 3 days, then diluted with DMF (0.5 mL) and MeOH (0.2 mL), and filtered through a large syringe filter. The product was purified by preparative HPLC, eluting with a gradient of ACN in water (basic mode) to give the title compound as an off-white solid (1.2 mg, 3.8%). $^1$H NMR (500 MHz, DMSO-d$_6$) δ ppm 1.96-2.05 (m, 2H), 2.13-2.24 (m, 2H), 2.83-2.92 (m, 2H), 3.12 (t, J=7.81 Hz, 2H), 3.64 (s, 3H), 4.55 (d, J=3.42 Hz, 1H), 6.60 (t, J=6.83 Hz, 1H), 7.00-7.08 (m, 2H), 7.08-7.16 (m, 2H), 7.38 (d, J=8.30 Hz, 1H), 7.55 (dd, J=8.30, 1.95 Hz, 1H), 8.18 (dd, J=6.59, 2.20 Hz, 1H), 8.48 (dd, J=7.32, 1.95 Hz, 1H), 8.83 (d, J=1.95 Hz, 1H), 12.44 (s, 1H); ESI-MS m/z 447 [M+H]$^+$.

Example 5: N-(2-(4-(2,4-difluorophenoxy)piperidin-1-yl)-5-(methylsulfonyl)phenyl)-2-methoxynicotinamide

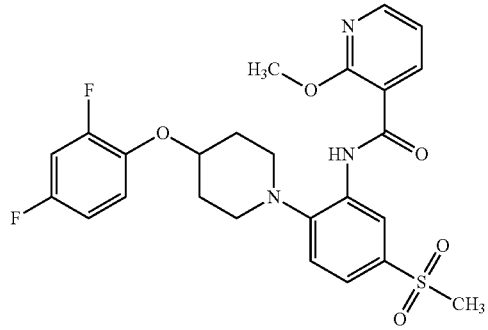 [SMILES: COc1ncccc1C(=O)Nc1cc(S(C)(=O)=O)ccc1N1CCC(Oc2ccc(F)cc2F)CC1]

To a solution of 2-methoxynicotinic acid (12.01 mg, 0.078 mmol), 2-(4-(2,4-difluorophenoxy)piperidin-1-yl)-5-(methylsulfonyl)aniline (20 mg, 0.052 mmol) and HATU (29.8 mg, 0.078 mmol) in DMF (0.4 mL) was added DIPEA (0.018 mL, 0.105 mmol). The solution was stirred at 20° C. for 2 hours and at 50° C. for 18 hours. The solution was then diluted with DMF (0.4 mL) and MeOH (0.2 mL), filtered through a syringe filter, and purified by preparative HPLC, eluting with ACN/water (basic mode) to give the title compound as a white solid (11 mg, 41%). $^1$H NMR (500 MHz, DMSO-d$_6$) δ ppm 1.84-1.96 (m, 2H), 2.08-2.18 (m, 2H), 2.90 (ddd, J=11.84, 8.91, 3.17 Hz, 2H), 3.10-3.18 (m, 2H), 3.19 (s, 3H), 4.19 (s, 3H), 4.54-4.63 (m, 1H), 6.99-7.07 (m, 1H), 7.25-7.38 (m, 3H), 7.50 (d, J=8.79 Hz, 1H), 7.69 (dd, J=8.30, 1.95 Hz, 1H), 8.46 (dd, J=4.64, 2.20 Hz, 1H), 8.49 (dd, J=7.32, 1.95 Hz, 1H), 8.93 (d, J=2.44 Hz, 1H), 10.48 (s, 1H); ESI-MS m/z [M+H]+ 518; mp 186° C. (5° C./minute gradient).

Example 6: N-(2-(4-(2,4-difluorophenoxy)piperidin-1-yl)-5-(methylsulfonyl)phenyl)-2-methoxybenzamide

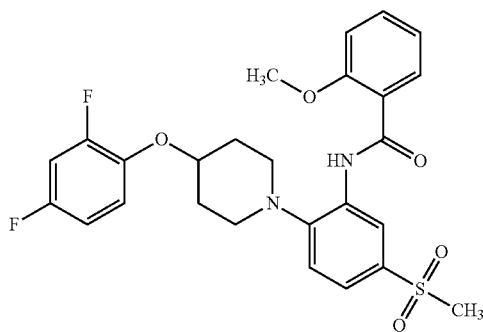 [SMILES: COc1ccccc1C(=O)Nc1cc(S(C)(=O)=O)ccc1N1CCC(Oc2ccc(F)cc2F)CC1]

To a solution of 2-methoxybenzoic acid (11.94 mg, 0.078 mmol), 2-(4-(2,4-difluorophenoxy)piperidin-1-yl)-5-(methylsulfonyl)aniline (20 mg, 0.052 mmol) and HATU (29.8 mg, 0.078 mmol) in DMF (0.4 mL) was added DIPEA (0.018 mL, 0.105 mmol). The solution was stirred at 20° C. for 2 hours and at 50° C. for 18 hours. The solution was then diluted with DMF (0.4 mL) and MeOH (0.2 mL), filtered through a syringe filter, and purified by preparative HPLC, eluting with ACN/water (basic mode) to give the title compound as a white solid (7 mg, 26%). $^1$H NMR (500 MHz, DMSO-$d_6$) δ ppm 1.82-1.95 (m, 2H), 2.08-2.16 (m, 2H), 2.85-2.94 (m, 2H), 3.10-3.17 (m, 2H), 3.18 (s, 3H), 4.11 (s, 3H), 4.57 (dt, J=7.81, 3.91 Hz, 1H), 6.98-7.06 (m, 1H), 7.19 (t, J=7.81 Hz, 1H), 7.26-7.38 (m, 3H), 7.48 (d, J=8.30 Hz, 1H), 7.59-7.70 (m, 2H), 8.11 (dd, J=7.81, 1.46 Hz, 1H), 8.95 (d, J=1.95 Hz, 1H), 10.50 (s, 1H); ESI-MS m/z [M+H]+ 517; mp 201° C. (5° C./minute gradient).

Example 7: N-(2-(4-(2,4-difluorophenoxy)piperidin-1-yl)-5-(methylsulfonyl)phenyl)-4-methoxynicotinamide

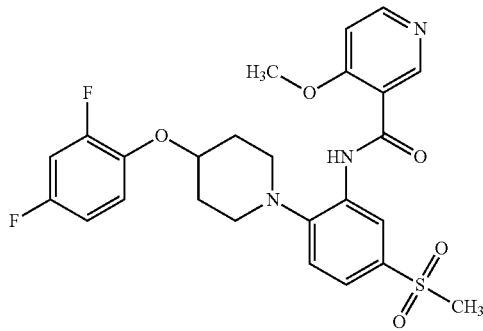

To a solution of 4-methoxynicotinic acid (12.01 mg, 0.078 mmol), 2-(4-(2,4-difluorophenoxy)piperidin-1-yl)-5-(methylsulfonyl)aniline (20 mg, 0.052 mmol) and HATU (29.8 mg, 0.078 mmol) in DMF (0.4 mL) was added DIPEA (0.018 mL, 0.105 mmol). The solution was stirred at 50° C. for 16 hours, then diluted with DMF (0.4 mL) and MeOH (0.2 mL), filtered through a syringe filter, and purified by preparative HPLC, eluting with ACN/water (basic mode) to give the title compound as a white solid (13 mg, 48%). $^1$H NMR (500 MHz, DMSO-$d_6$) δ ppm 1.81-1.92 (m, 2H), 2.05-2.16 (m, 2H), 2.85-2.94 (m, 2H), 3.11-3.17 (m, 2H), 3.19 (s, 3H), 4.16 (s, 3H), 4.56 (dt, J=7.81, 3.91 Hz, 1H), 6.99-7.07 (m, 1H), 7.25-7.37 (m, 2H), 7.39 (d, J=5.86 Hz, 1H), 7.49 (d, J=8.79 Hz, 1H), 7.69 (dd, J=8.30, 1.95 Hz, 1H), 8.66 (d, J=5.86 Hz, 1H), 8.90 (d, J=1.95 Hz, 1H), 9.04 (s, 1H), 10.20 (s, 1H); ESI-MS m/z [M+H]+ 518; mp 173° C. (5° C./minute gradient).

Example 8: N-(5-cyano-2-(4-(2-fluorophenoxy)piperidin-1-yl)phenyl-1-methyl-2-oxo-1,2-dihydropyridine-3-carboxamide

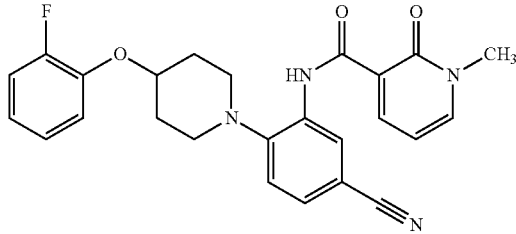 [SMILES: Cn1cccc(C(=O)Nc2cc(C#N)ccc2N2CCC(Oc3ccccc3F)CC2)c1=O]

To a mixture of N-(5-cyano-2-(4-hydroxypiperidin-1-yl)phenyl)-1-methyl-2-oxo-1,2-dihydropyridine-3-carboxamide (20 mg, 0.057 mmol), 2-fluorophenol (0.016 mL, 0.170 mmol), and polymer-bound triphenylphosphine (29.8 mg, 0.114 mmol) in DMF (0.3 mL) was added diisopropyl (E)-diazene-1,2-dicarboxylate (0.017 mL, 0.085 mmol). The reaction mixture was stirred at 20° C. for 2 hours at which time LC/MS showed the reaction was proceeding slowly. The reaction mixture was subsequently heated at 50° C. for 19 hours and then diluted with DMF (0.5 mL) and MeOH (0.2 mL), filtered through a large syringe filter, and purified by preparative HPLC, eluting with ACN/water (basic mode) to give the title compound as a white solid (6 mg, 24%). $^1$H NMR (500 MHz, DMSO-$d_6$) δ ppm 1.94-2.03 (m, 2H), 2.08-2.17 (m, 2H), 2.77-2.86 (m, 2H), 3.01-3.11 (m, 2H), 3.58 (s, 3H), 4.50-4.59 (m, 1H), 6.50-6.58 (m, 1H), 6.87-6.94 (m, 1H), 7.06 (t, J=7.81 Hz, 1H), 7.16 (ddd, J=11.72, 8.30, 1.46 Hz, 1H), 7.22 (td, J=8.42, 1.22 Hz, 1H), 7.31 (d, J=8.30 Hz, 1H), 7.49 (dd, J=8.30, 1.95 Hz, 1H), 8.11 (dd, J=6.59, 2.20 Hz, 1H), 8.42 (dd, J=7.32, 2.44 Hz, 1H), 8.76 (d, J=1.95 Hz, 1H), 12.39 (s, 1H); ESI-MS m/z [M+H]+ 447.

Example 9: N-(5-cyano-2-(4-(2,3-difluorophenoxy)piperidin-1-yl)phenyl)-1-methyl-2-oxo-1,2-dihydropyridine-3-carboxamide

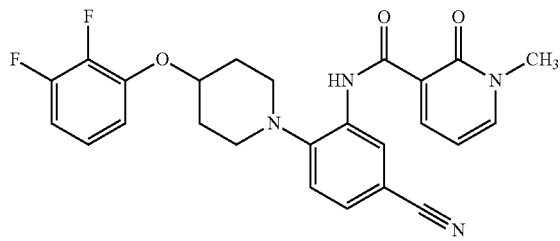 [SMILES: Cn1cccc(C(=O)Nc2cc(C#N)ccc2N2CCC(Oc3cccc(F)c3F)CC2)c1=O]

To a mixture of N-(5-cyano-2-(4-hydroxypiperidin-1-yl)phenyl)-1-methyl-2-oxo-1,2-dihydropyridine-3-carboxamide (20 mg, 0.057 mmol), 2,3-difluorophenol (22.15 mg, 0.170 mmol), and polymer-bound triphenylphosphine (29.8 mg, 0.114 mmol) in DMF (0.3 mL) was added diisopropyl (E)-diazene-1,2-dicarboxylate (0.017 mL, 0.085 mmol). The reaction mixture was stirred at 20° C. for 2 hours at which time LC/MS showed the reaction was proceeding slowly. The reaction mixture was subsequently heated at 50° C. for 19 hours and then diluted with DMF (0.5 mL) and MeOH (0.2 mL), filtered through a large syringe filter, and purified by preparative HPLC, eluting with ACN/water (basic mode) to give the title compound as a white solid (5 mg, 19%). $^1$H NMR (500 MHz, DMSO-$d_6$) δ ppm 1.95-2.05 (m, 2H), 2.10-2.19 (m, 2H), 2.83 (ddd, J=11.59, 8.18, 3.17 Hz, 2H), 3.05 (ddd, J=11.11, 7.20, 3.17 Hz, 2H), 3.58 (s, 3H), 4.63 (dt, J=7.08, 3.78 Hz, 1H), 6.51-6.57 (m, 1H), 6.90-6.98 (m, 1H), 7.03-7.13 (m, 2H), 7.31 (d, J=8.30 Hz, 1H), 7.49 (dd, J=8.30, 1.95 Hz, 1H), 8.11 (dd, J=6.59, 2.20 Hz, 1H), 8.42 (dd, J=7.32, 1.95 Hz, 1H), 8.76 (d, J=1.95 Hz, 1H), 12.40 (s, 1H); ESI-MS m/z [M+H]$^+$ 465.

Example 10: N-(2-(4-(2,4-difluorophenoxy)piperidin-1-yl-5-(methylsulfonylphenyl)-3-fluoro-2-methoxybenzamide

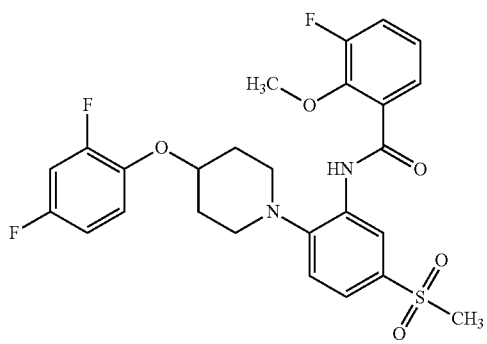 [SMILES: COc1c(F)cccc1C(=O)Nc1cc(S(C)(=O)=O)ccc1N1CCC(Oc2ccc(F)cc2F)CC1]

A solution of 2-(4-(2,4-difluorophenoxy)piperidin-1-yl)-5-(methylsulfonyl)aniline (25 mg, 0.065 mmol), 3-fluoro-2-methoxybenzoic acid (22.24 mg, 0.131 mmol), HATU (49.7 mg, 0.131 mmol) and Et$_3$N (0.023 mL, 0.163 mmol) in DMF (0.3 mL) was heated at 50° C. for 20 hours. The solution was subsequently diluted with DMF (0.5 mL) and MeOH (0.2 mL) and purified by preparative HPLC, eluting with ACN/water (basic mode) to give the title compound as a white solid (13 mg, 37%). $^1$H NMR (500 MHz, DMSO-$d_6$) δ ppm 1.85 (dtd, J=12.51, 8.27, 8.27, 3.66 Hz, 2H), 2.01-2.10 (m, 2H), 2.84 (ddd, J=11.72, 8.54, 3.17 Hz, 2H), 3.03-3.11 (m, 2H), 3.13 (s, 3H), 4.00 (d, J=1.46 Hz, 3H), 4.50 (dt, J=7.44, 3.84 Hz, 1H), 6.92-6.99 (m, 1H), 7.20-7.30 (m, 3H), 7.44 (d, J=8.30 Hz, 1H), 7.52 (ddd, J=11.47, 8.30, 1.71 Hz, 1H), 7.59-7.65 (m, 1H), 7.78 (d, J=8.30 Hz, 1H), 8.92 (d, J=2.44 Hz, 1H), 10.55 (s, 1H); ESI-MS m/z [M+H]$^+$ 535.

Example 11: N-(2-(4-(2,4-difluorophenoxy)piperidin-1-yl)-5-(methylsulfonylphenyl)-2-fluoro-6-methoxybenzamide

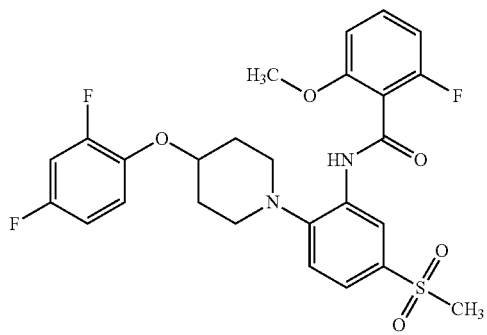 [SMILES: COc1cccc(F)c1C(=O)Nc1cc(S(C)(=O)=O)ccc1N1CCC(Oc2ccc(F)cc2F)CC1]

A solution of 2-(4-(2,4-difluorophenoxy)piperidin-1-yl)-5-(methylsulfonyl)aniline (25 mg, 0.065 mmol), 2-fluoro-6-methoxybenzoic acid (22.24 mg, 0.131 mmol), HATU (49.7 mg, 0.131 mmol) and Et$_3$N (0.023 mL, 0.163 mmol) in DMF (0.3 mL) was heated at 50° C. for 20 hours. The solution was subsequently diluted with DMF (0.5 mL) and MeOH (0.2 mL) and purified by preparative HPLC, eluting with ACN/water (basic mode) to give the title compound as a white solid (7 mg, 20%). $^1$H NMR (500 MHz, DMSO-$d_6$) δ ppm 1.74-1.85 (m, 2H), 1.97 (br s, 2H), 2.83 (t, J=8.79 Hz, 2H), 3.09-3.18 (m, 5H), 3.76 (s, 3H), 4.43 (dt, J=7.93, 4.09 Hz, 1H), 6.86 (t, J=8.54 Hz, 1H), 6.91-6.98 (m, 2H), 7.19-7.30 (m, 3H), 7.36-7.44 (m, 1H), 7.61 (dd, J=8.54, 2.20 Hz, 1H), 8.39 (d, J=1.95 Hz, 1H), 9.68 (s, 1H); ESI-MS m/z [M+H]$^+$ 535.

Example 12: N-(5-cyano-2-(4-(3-fluorophenoxy)piperidin-1-yl)phenyl)-1-methyl-2-oxo-1,2-dihydropyridine-3-carboxamide

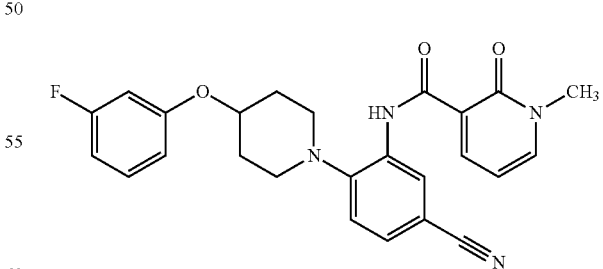

To a mixture of N-(5-cyano-2-(4-hydroxypiperidin-1-yl)phenyl)-1-methyl-2-oxo-1,2-dihydropyridine-3-carboxamide (25 mg, 0.071 mmol), 3-fluorophenol (23.86 mg, 0.213 mmol), and polymer-bound triphenylphosphine (55.8 mg, 0.213 mmol) in DMF (0.3 mL) was added diisopropyl (E)-diazene-1,2-dicarboxylate (0.041 mL, 0.213 mmol). The mixture was heated at 50° C. for 90 minutes and then diluted with DMF (0.5 mL) and MeOH (0.2 mL), filtered through a large syringe filter, and purified by preparative HPLC, eluting with ACN/water (basic mode) to give the title compound as a white solid (9 mg, 28%). $^1$H NMR (500 MHz, DMSO-d$_6$) δ ppm 1.96-2.06 (m, 2H), 2.15-2.24 (m, 2H), 2.85-2.95 (m, 2H), 3.07-3.15 (m, 2H), 3.64 (s, 3H), 4.66 (dt, J=7.44, 3.84 Hz, 1H), 6.60 (dd, J=7.32, 6.35 Hz, 1H), 6.75 (td, J=8.42, 1.71 Hz, 1H), 6.87 (dd, J=8.30, 1.95 Hz, 1H), 6.91 (dt, J=11.35, 2.38 Hz, 1H), 7.26-7.35 (m, 1H), 7.38 (d, J=8.30 Hz, 1H), 7.55 (dd, J=8.30, 1.95 Hz, 1H), 8.18 (dd, J=6.35, 1.95 Hz, 1H), 8.48 (dd, J=7.57, 2.20 Hz, 1H), 8.83 (d, J=1.95 Hz, 1H), 12.44 (s, 1H); ESI-MS m/z [M+H]$^+$ 447.

Example 13: N-(5-cyano-2-(4-(2,6-difluorophenoxy)piperidin-1-yl)phenyl)-1-methyl-2-oxo-1,2-dihydropyridine-3-carboxamide

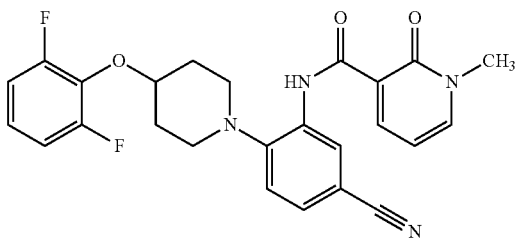 [SMILES: Cn1cccc(C(=O)Nc2cc(C#N)ccc2N2CCC(Oc3c(F)cccc3F)CC2)c1=O]

To a mixture of N-(5-cyano-2-(4-hydroxypiperidin-1-yl)phenyl)-1-methyl-2-oxo-1,2-dihydropyridine-3-carboxamide (25 mg, 0.071 mmol), 2,6-difluorophenol (27.7 mg, 0.213 mmol), and polymer-bound triphenylphosphine (55.8 mg, 0.213 mmol) in DMF (0.3 mL) was added diisopropyl (E)-diazene-1,2-dicarboxylate (0.041 mL, 0.213 mmol). The reaction mixture was stirred at 20° C. for 3 days, at 40° C. for 2 hours, and then at 50° C. for 2 hours. The mixture was subsequently diluted with DMF (0.6 mL) and MeOH (0.2 mL), filtered through a large syringe filter, and purified by preparative HPLC, eluting with ACN/water (basic mode) to give the title compound as a white solid (3 mg, 9%). $^1$H NMR (500 MHz, DMSO-d$_6$) δ ppm 2.09-2.17 (m, 4H), 2.77-2.87 (m, 2H), 3.09-3.18 (m, 2H), 3.64 (s, 3H), 4.34 (t, J=6.10 Hz, 1H), 6.60 (dd, J=7.32, 6.35 Hz, 1H), 7.12-7.20 (m, 3H), 7.35 (d, J=8.30 Hz, 1H), 7.54 (dd, J=8.30, 1.95 Hz, 1H), 8.18 (dd, J=6.59, 2.20 Hz, 1H), 8.48 (dd, J=7.32, 1.95 Hz, 1H), 8.83 (d, J=1.95 Hz, 1H), 12.49 (s, 1H); ESI-MS m/z [M+H]$^+$ 465.

Example 14: N-(5-cyano-2-(4-(3,5-difluorophenoxy)piperidin-1-yl)phenyl)-1-methyl-2-oxo-1,2-dihydropyridine-3-carboxamide

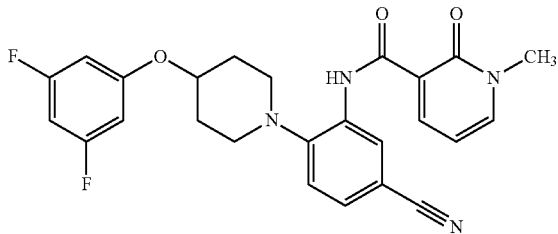 [SMILES: Cn1cccc(C(=O)Nc2cc(C#N)ccc2N2CCC(Oc3cc(F)cc(F)c3)CC2)c1=O]

To a mixture of N-(5-cyano-2-(4-hydroxypiperidin-1-yl)phenyl)-1-methyl-2-oxo-1,2-dihydropyridine-3-carboxamide (25 mg, 0.071 mmol), 3,5-difluorophenol (27.7 mg, 0.213 mmol), and polymer-bound triphenylphosphine (55.8 mg, 0.213 mmol) in DMF (0.3 mL) was added diisopropyl (E)-diazene-1,2-dicarboxylate (0.041 mL, 0.213 mmol). The reaction mixture was stirred at 20° C. for 3 days, at 40° C. for 2 hours, and then at 50° C. for 2 hours. The mixture was subsequently diluted with DMF (0.6 mL) and MeOH (0.2 mL), filtered through a large syringe filter, and purified by preparative HPLC, eluting with ACN/water (basic mode) to give the title compound as a white solid (10 mg, 30%). $^1$H NMR (500 MHz, DMSO-d$_6$) δ ppm 1.96-2.06 (m, 2H), 2.15-2.23 (m, 2H), 2.90 (ddd, J=11.59, 8.18, 3.17 Hz, 2H), 3.06-3.14 (m, 2H), 3.64 (s, 3H), 4.70 (dt, J=7.08, 3.78 Hz, 1H), 6.57-6.64 (m, 1H), 6.72-6.79 (m, 1H), 6.79-6.86 (m, 2H), 7.37 (d, J=8.30 Hz, 1H), 7.55 (dd, J=8.30, 1.95 Hz, 1H), 8.18 (dd, J=6.59, 2.20 Hz, 1H), 8.48 (dd, J=7.32, 1.95 Hz, 1H), 8.83 (d, J=1.95 Hz, 1H), 12.44 (s, 1H); ESI-MS m/z [M+H]$^+$ 465.

Example 15: N-(5-cyano-2-(4-(2,5-difluorophenoxy)piperidin-1-yl)phenyl)-1-methyl-2-oxo-1,2-dihydropyridine-3-carboxamide

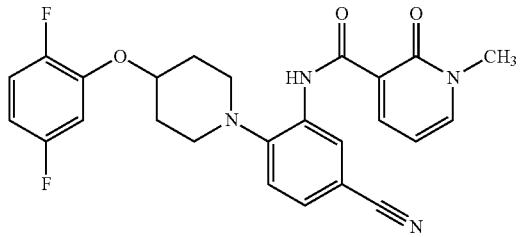 [SMILES: Cn1cccc(C(=O)Nc2cc(C#N)ccc2N2CCC(Oc3cc(F)ccc3F)CC2)c1=O]

A mixture of N-(5-cyano-2-(4-hydroxypiperidin-1-yl)phenyl)-1-methyl-2-oxo-1,2-dihydropyridine-3-carboxamide (25 mg, 0.071 mmol), 2,5-difluorophenol (18.46 mg, 0.142 mmol), and 2-(tributylphosphoranylidene)acetonitrile (0.037 mL, 0.142 mmol) in toluene (0.4 mL) was heated at 100° C. for 18 hours. The mixture was subsequently heated at 60° C. under vacuum to remove the toluene. The resulting residue was diluted with DMF (0.6 mL) and MeOH (0.2 mL), filtered through a syringe filter, and purified by preparative HPLC, eluting with ACN/water (basic mode) to give the title compound as an off-white solid (18 mg, 55%). $^1$H NMR (500 MHz, DMSO-d$_6$) δ ppm 2.00-2.07 (m, 2H), 2.16-2.25 (m, 2H), 2.90 (ddd, J=11.59, 8.18, 3.17 Hz, 2H), 3.06-3.15 (m, 2H), 3.64 (s, 3H), 4.65-4.74 (m, 1H), 6.58-6.64 (m, 1H), 6.74-6.82 (m, 1H), 7.23-7.30 (m, 2H), 7.37 (d, J=8.30 Hz, 1H), 7.55 (dd, J=8.30, 1.95 Hz, 1H), 8.18 (dd, J=6.35, 1.95 Hz, 1H), 8.48 (dd, J=7.32, 2.44 Hz, 1H), 8.83 (d, J=2.44 Hz, 1H), 12.45 (s, 1H); ESI-MS m/z [M+H]$^+$ 465.

Example 16: N-(5-cyano-2-(4-(3,4-difluorophenoxy)piperidin-1-yl)phenyl-1-methyl-2-oxo-1,2-dihydropyridine-3-carboxamide

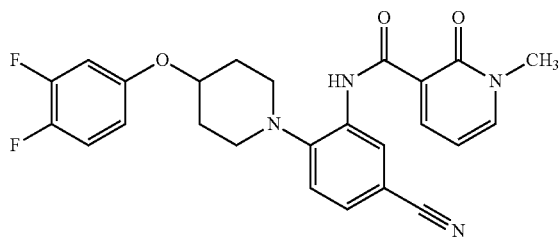 [SMILES: Cn1cccc(C(=O)Nc2cc(C#N)ccc2N2CCC(Oc3ccc(F)c(F)c3)CC2)c1=O]

A mixture of N-(5-cyano-2-(4-hydroxypiperidin-1-yl)phenyl)-1-methyl-2-oxo-1,2-dihydropyridine-3-carboxamide (25 mg, 0.071 mmol), 3,4-difluorophenol (18.46 mg, 0.142 mmol), and 2-(tributylphosphoranylidene)acetonitrile (0.037 mL, 0.142 mmol) in toluene (0.4 mL) was heated at 80° C. for 21 hours. Toluene was subsequently removed in vacuo and the resulting residue was diluted with DMF (0.6 mL) and MeOH (0.2 mL), filtered through a syringe filter, and purified by preparative HPLC, eluting with ACN/water (basic mode) to give the title compound as a white solid (19 mg, 58%). $^1$H NMR (500 MHz, DMSO-de) δ ppm 1.96-2.05 (m, 2H), 2.13-2.22 (m, 2H), 2.88 (ddd, J=11.72, 8.30, 3.42 Hz, 2H), 3.11 (ddd, J=11.23, 7.57, 3.17 Hz, 2H), 3.64 (s, 3H), 4.61 (dt, J=7.08, 3.78 Hz, 1H), 6.60 (dd, J=7.32, 6.35 Hz, 1H), 6.83-6.89 (m, 1H), 7.18 (ddd, J=12.69, 6.83, 2.93 Hz, 1H), 7.29-7.40 (m, 2H), 7.55 (dd, J=8.30, 1.95 Hz, H), 8.18 (dd, J=6.59, 2.20 Hz, 1H), 8.48 (dd, J=7.32, 2.44 Hz, 1H), 8.82 (d, J=1.95 Hz, 1H), 12.44 (s, 1H); ESI-MS m/z [M+H]$^+$ 465.

Example 17: N-(6-chloro-4-(4-(2,4-difluorophenoxy)piperidin-1-yl)pyridin-3-yl)-1-methyl-2-oxo-1,2-dihydropyridine-3-carboxamide

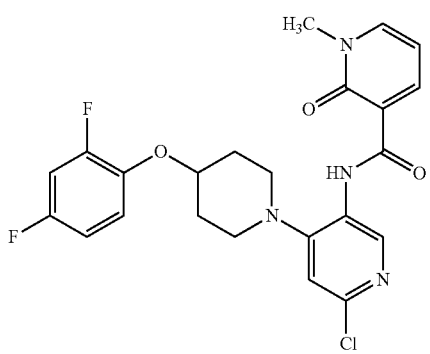 [SMILES: Cn1cccc(C(=O)Nc2cnc(Cl)cc2N2CCC(Oc3ccc(F)cc3F)CC2)c1=O]

A solution of 6-chloro-4-(4-(2,4-difluorophenoxy)piperidin-1-yl)pyridin-3-amine (25 mg, 0.074 mmol), 1-methyl-2-oxo-1,2-dihydropyridine-3-carboxylic acid (22.54 mg, 0.147 mmol), HATU (56.0 mg, 0.147 mmol) and Et$_3$N (0.026 mL, 0.184 mmol) in DMF (0.3 mL) was heated at 50° C. for 4 hours. The solution was then diluted with DMF (0.5 mL) and MeOH (0.2 mL) and purified by preparative HPLC, eluting with ACN/water (basic mode) to give the title compound as a white solid (24 mg, 69%). $^1$H NMR (500 MHz, DMSO-d$_6$) δ ppm 1.93-2.03 (m, 2H), 2.10-2.18 (m, 2H), 2.93 (ddd, J=11.96, 8.54, 2.93 Hz, 2H), 3.17-3.25 (m, 2H), 3.64 (s, 3H), 4.48-4.57 (m, 1H), 6.58-6.65 (m, 1H), 6.98-7.05 (m, 1H), 7.18 (s, 1H), 7.25-7.36 (m, 2H), 8.18 (dd, J=6.59, 2.20 Hz, 1H), 8.48 (dd, J=7.32, 1.95 Hz, 1H), 9.24 (s, 1H), 12.16 (s, 1H); ESI-MS m/z [M+H]$^+$ 475, 477.

Example 18: N-(4-(4-(2,4-difluorophenoxy)piperidin-1-yl)-2-methylpyrimidin-5-yl)-2-methoxynicotinamide

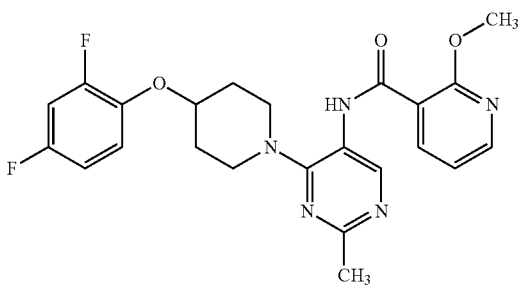 [SMILES: COc1ncccc1C(=O)Nc1cnc(C)nc1N1CCC(Oc2ccc(F)cc2F)CC1]

To a solution of 4-(4-(2,4-difluorophenoxy)piperidin-1-yl)-2-methylpyrimidin-5-amine (5.17 g, 16.14 mmol) and 2-methoxynicotinic acid (2.97 g, 19.37 mmol) in NMP (45 mL) was added DIPEA (11.24 mL, 64.6 mmol) followed by a 50% solution of 2,4,6-tripropyl-1,3,5,2,4,6-trioxatriphosphinane 2,4,6-trioxide in EtOAc (21.16 mL, 35.5 mmol). The mixture was heated at 50° C. for 21 hours. The reaction mixture was subsequently diluted with isopropyl acetate (200 mL) and washed with water (200 mL) and brine (200 mL), dried with MgSO$_4$, and concentrated in vacuo. The crude product was concentrated on Celite® and purified by column chromatography (220 g silica gel column) eluting with a gradient of 0-100% EtOAc in heptane to give an oil which crystallized after reconcentration from EtOAc. The solid product (5.00 g) was taken up in EtOH (25 mL) and heated to near reflux to dissolve the solids. The mixture was allowed to cool slowly to 20° C. and to sit covered and undisturbed for 20 hours. The resulting crystals were collected by vacuum filtration, rinsed with a small amount of ice-cold EtOH, and dried under high vacuum to give the title compound as large, yellow crystals (4.6 g, 63%). $^1$H NMR (500 MHz, DMSO-d$_6$) δ ppm 1.63-1.73 (m, 2H), 1.99 (ddd, J=9.64, 6.22, 3.17 Hz, 2H), 2.44 (s, 3H), 3.38 (ddd, J=13.06, 9.40, 3.42 Hz, 2H), 3.92-3.99 (m, 2H), 4.02 (s, 3H), 4.56 (tt, J=8.05, 3.91 Hz, 1H), 6.96-7.04 (m, 1H), 7.18 (dd, J=7.32, 4.88 Hz, 1H), 7.24-7.33 (m, 2H), 8.19 (dd, J=7.32, 1.95 Hz, 1H), 8.30 (s, 1H), 8.36 (dd, J=4.88, 1.95 Hz, 1H), 9.82 (s, 1H); ESI-MS m/z [M+H]$^+$ 456.

Example 19: 4-(4-(2,4-difluorophenoxy)piperidin-1-yl)-5-(2-methoxynicotinamido)-N-methylpicolinamide

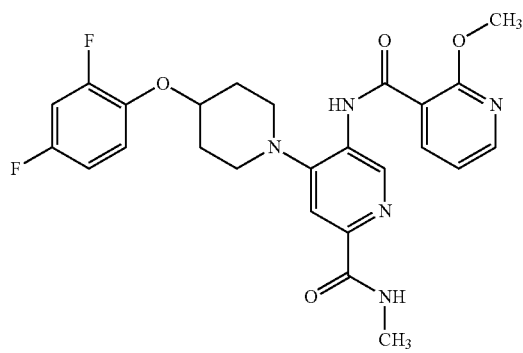 [SMILES: CNC(=O)c1cc(N2CCC(Oc3ccc(F)cc3F)CC2)c(NC(=O)c2cccnc2OC)cn1]

To a solution of 5-amino-4-(4-(2,4-difluorophenoxy)piperidin-1-yl)-N-methylpicolinamide (24 mg, 0.066 mmol) and 2-methoxynicotinic acid (20.28 mg, 0.132 mmol) in NMP (0.4 mL) were added DIPEA (0.046 mL, 0.265 mmol) and 50% 2,4,6-tripropyl-1,3,5,2,4,6-trioxatriphosphinane 2,4,6-trioxide in EtOAc (0.079 mL, 0.132 mmol). The reaction mixture was heated at 70° C. for 1.5 hours. LC/MS showed no desired product and the pH of the reaction mixture was about 4. More DIPEA (50 µL) was added (pH about 10) and the reaction mixture was heated at 70° C. for an additional 5 hours. LC/MS again showed no product (pH=10). HATU (50.4 mg, 0.132 mmol) was added and the reaction mixture was heated at 70° C. for 16 hours. LC/MS showed about 20% conversion. Additional 2-methoxynicotinic acid (20.28 mg, 0.132 mmol), HATU (50.4 mg, 0.132 mmol) and DIPEA (0.046 mL, 0.265 mmol) were added and the reaction mixture was heated at 70° C. for 5 hours at which time LC/MS showed about 35% conversion. The reaction mixture was subsequently diluted with MeOH (100 µL) and DMF (0.3 mL) and filtered through a syringe filter, rinsing with DMF (0.3 mL) and EtOH (0.1 mL). The filtrate was purified by preparative HPLC (basic mode) to give the title compound as a white solid (4.7 mg, 14%). $^1$H NMR (500 MHz, DMSO-$d_6$) δ ppm 1.80-1.94 (m, 2H), 2.07-2.16 (m, 2H), 2.81 (d, J=4.88 Hz, 3H), 2.94-3.04 (m, 2H), 3.21-3.28 (m, 2H), 4.16 (s, 3H), 4.57 (tt, J=8.05, 3.91 Hz, 1H), 6.99-7.07 (m, 1H), 7.25-7.38 (m, 3H), 7.79 (s, 1H), 8.41-8.50 (m, 2H), 8.72 (q, J=4.72 Hz, 1H), 9.34 (s, 1H), 10.24 (s, 1H); ESI-MS m/z [M+H]$^+$ 498.

Example 20: N-(4-(4-(2,4-difluorophenoxy)piperidin-1-yl)-6-methoxypyridin-3-yl)-2-methoxynicotinamide

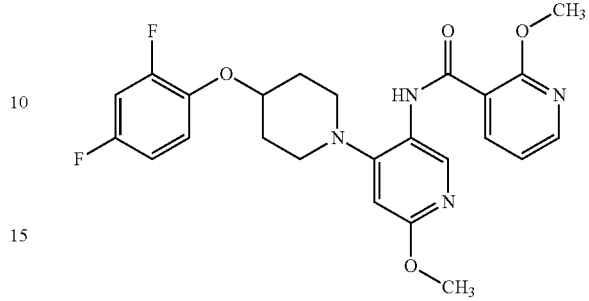

To a solution of 4-(4-(2,4-difluorophenoxy)piperidin-1-yl)-6-methoxypyridin-3-amine (1.00 g, 2.98 mmol) and 2-methoxynicotinic acid (0.548 g, 3.58 mmol) in NMP (8 mL) was added DIPEA (2.078 mL, 11.93 mmol). The mixture was stirred at RT until all of the solids were dissolved. Next, 50% 2,4,6-tripropyl-1,3,5,2,4,6-trioxatriphosphinane 2,4,6-trioxide in EtOAc (3.91 mL, 6.56 mmol) was added and the solution was heated at 50° C. for 7 hours. The reaction mixture was subsequently diluted with isopropyl acetate (100 mL) and washed with water (100 mL). The aqueous layer was extracted with isopropyl acetate (50 mL). The combined organics were washed with brine (100 mL), dried over MgSO$_4$, and concentrated in vacuo. The crude product was concentrated on Celite® and purified by column chromatography (40 g silica gel column) eluting with a gradient of 0-70% EtOAc in heptane to give a light yellow solid (1.1 g). The solids were dissolved in EtOH (10 mL) and the solution was heated to a gentle boil for about 20 minutes. The solution was allowed to cool to 20° C. and to sit undisturbed for 5 hours. The resulting crystals were collected by vacuum filtration, rinsed with cold EtOH, and dried under high vacuum to give the title compound as light yellow crystals (1.027 g, 73.2%). $^1$H NMR (500 MHz, DMSO-$d_6$) δ ppm 1.76-1.87 (m, 2H), 2.06 (ddd, J=9.52, 6.10, 3.42 Hz, 2H), 2.90 (ddd, J=11.96, 9.03, 2.93 Hz, 2H), 3.16-3.25 (m, 2H), 3.83 (s, 3H), 4.13 (s, 3H), 4.53 (tt, J=7.93, 3.78 Hz, 1H), 6.52 (s, 1H), 6.97-7.04 (m, 1H), 7.22-7.35 (m, 3H), 8.36-8.43 (m, 2H), 8.68 (s, 1H), 9.87 (s, 1H); ESI-MS m/z [M+H]$^+$ 471; mp 138° C. (2° C./minute gradient).

Example 21: N-(4-(4-(2,4-difluorophenoxy)piperidin-1-yl)-6-methoxypyridin-3-yl)-4-methoxynicotinamide

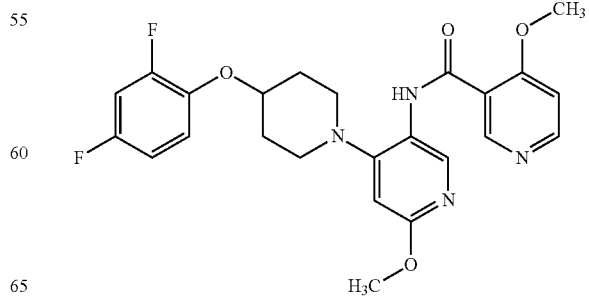

A solution of 4-(4-(2,4-difluorophenoxy)piperidin-1-yl)-6-methoxypyridin-3-amine (40 mg, 0.119 mmol), 4-methoxynicotinic acid (36.5 mg, 0.239 mmol), HATU (91 mg, 0.239 mmol) and DIPEA (0.052 mL, 0.298 mmol) in NMP (0.5 mL) was heated at 50° C. for 8 hours. More HATU (50 mg) was added and the reaction mixture was heated at 50° C. for 17 hours. The solution was diluted with DMF (0.3 mL) and MeOH (0.2 mL) and purified by preparative HPLC, eluting with ACN/water (basic mode) to give the title compound as a white solid (34 mg, 61%), 1H NMR (500 MHz, DMSO-$d_6$) δ ppm 1.74-1.84 (m, 2H), 2.04 (ddd, J=9.52, 6.35, 3.17 Hz, 2H), 2.90 (ddd, J=12.08, 8.91, 2.93 Hz, 2H), 3.19-3.27 (m, 2H), 3.83 (s, 3H), 4.07 (s, 3H), 4.51 (tt J=8.05, 3.91 Hz, 1H), 6.48 (s, 1H), 6.97-7.05 (m, 1H), 7.25-7.34 (m, 3H), 8.56 (s, 1H), 8.61 (d, J=5.86 Hz, 1H), 8.90 (s, 1H), 9.65 (s, 1H); ESI-MS m/z [M+H]$^+$ 471.

Example 22: 4-(4-(2,4-difluorophenoxy)piperidin-1-yl)-5-(2-methoxynicotinamido)-N,N-bis(methyl-$d_3$) picolinamide

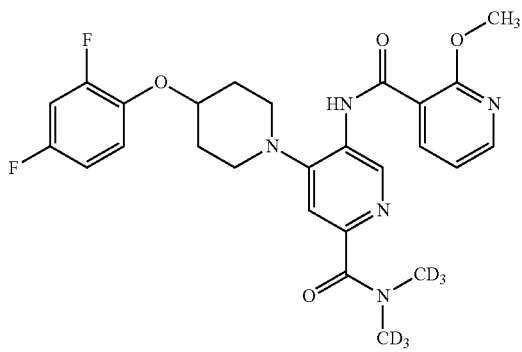 [SMILES: [2H]C([2H])([2H])N(C(=O)c1cc(N2CCC(Oc3ccc(F)cc3F)CC2)c(NC(=O)c2cccnc2OC)cn1)C([2H])([2H])[2H]]

To a solution of 5-amino-4-(4-(2,4-difluorophenoxy)piperidin-1-yl)-N,N-$d_6$-dimethylpicolinamide (90 mg, 0.235 mmol), 2-methoxynicotinic acid (72.1 mg, 0.471 mmol) and HATU (179 mg, 0.471 mmol) in NMP (1.0 mL) was added DIPEA (0.102 mL, 0.588 mmol). The solution was heated at 50° C. for 42 hours. LC/MS showed about 90% conversion. The reaction mixture was subsequently diluted with MeOH (0.1 mL), filtered through a syringe filter, rinsed with DMF (0.2 mL) and MeOH (0.1 mL), and purified by preparative HPLC (basic mode) to give the title compound as a white solid (74 mg, 61%). $^1$H NMR (500 MHz, DMSO-$d_6$) δ ppm 1.78-1.92 (m, 2H), 2.03-2.14 (m, 2H), 2.90-3.01 (m, 2H), 3.20-3.29 (m, 2H), 4.15 (s, 3H), 4.55 (dt, J=7.81, 3.91 Hz, 1H), 6.97-7.06 (m, 1H), 7.23-7.37 (m, 4H), 8.39-8.48 (m, 2H), 9.20 (s, 1H), 10.16 (s, 1H); ESI-MS m/z [M+H]$^+$ 518.

Example 23: N-(4-(4-(2,4-difluorophenoxy)piperidin-1-yl)-2-methoxypyrimidin-5-yl)-2-methoxy-6-methylnicotinamide

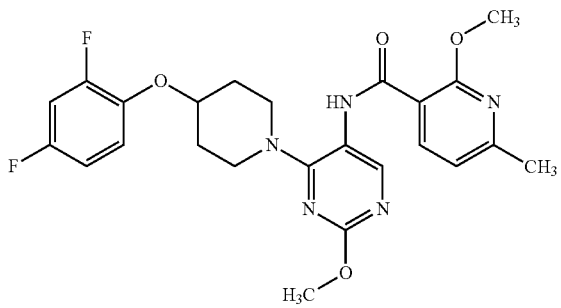 [SMILES: COc1ncc(NC(=O)c2ccc(C)nc2OC)c(N2CCC(Oc3ccc(F)cc3F)CC2)n1]

A solution of 4-(4-(2,4-difluorophenoxy)piperidin-1-yl)-2-methoxypyrimidin-5-amine (40 mg, 0.119 mmol), 2-methoxy-6-methylnicotinic acid (39.8 mg, 0.238 mmol), HATU (90 mg, 0.238 mmol) and DIPEA (0.052 mL, 0.297 mmol) in NMP (0.5 mL) was heated at 50° C. for 21 hours. LC/MS showed the reaction was complete. The solution was subsequently diluted with MeOH (0.1 mL), filtered through a syringe filter which was rinsed with DMF (0.2 mL) and MeOH (0.1 mL), and purified by basic HPLC to give N-(4-(4-(2,4-difluorophenoxy)piperidin-1-yl)-2-methoxypyrimidin-5-yl)-2-methoxy-6-methylnicotinamide (38 mg, 0.078 mmol, 65.8%) as a white solid. $^1$H NMR (500 MHz, DMSO-$d_6$) δ ppm 1.64 (dtd, J=12.75, 8.63, 8.63, 3.66 Hz, 2H), 1.97 (ddd, J=9.52, 6.35, 3.17 Hz, 2H), 2.46 (s, 3H), 3.44 (ddd, J=13.06, 9.40, 3.42 Hz, 2H), 3.83 (s, 3H), 3.99 (s, 3H), 4.00-4.08 (m, 2H), 4.55 (tt, J=7.99, 3.97 Hz, 1H), 6.96-7.04 (m, 2H), 7.24-7.33 (m, 2H), 8.02 (s, 1H), 8.08 (d, J=7.32 Hz, 1H), 9.62 (s, 1H); ESI-MS m/z [M+H]$^+$ 486.

Example 24: N-(5-cyano-2-(4-(2,4-difluorophenoxy)piperidin-1-yl)phenyl)-1,6-dimethyl-4-oxo-1,4-dihydropyridine-3-carboxamide

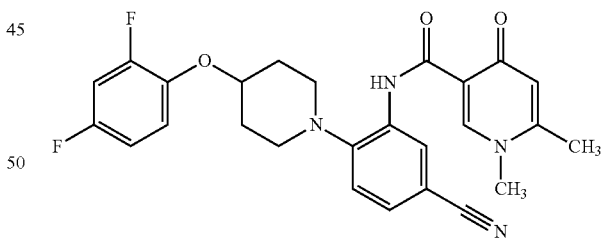

A flask was charged with 3-amino-4-(4-(2,4-difluorophenoxy)piperidin-1-yl)benzonitrile (15 mg, 0.046 mmol), 1,6-dimethyl-4-oxo-1,4-dihydropyridine-3-carboxylic acid (7.61 mg, 0.046 mmol), DIPEA (29.4 μL, 0.169 mmol), HATU (19.05 mg, 0.050 mmol), and THF (455 μL). The reaction mixture was stirred at RT for 72 hours. Methanol (2 mL) and DMF (2 mL) were added and the mixture was filtered. The solids were washed with water (4 mL) and lyophilized to give the title compound as an off-white solid (5 mg, 23%). $^1$H NMR (500 MHz, DMSO-de) δ ppm 2.04 (ddt, J=12.33, 8.18, 4.15, 4.15 Hz, 2H), 2.13-2.19 (m, 2H), 2.36 (s, 3H), 2.81-2.87 (m, 2H), 3.08-3.13 (m, 2H), 3.79 (s, 3H), 4.50-4.57 (m, 1H), 6.56 (s, 1H), 6.99-7.04 (m, 1H), 7.27-7.33 (m, 3H), 7.52 (dd, J=8.05, 2.20 Hz, 1H), 8.64 (s, 1H), 8.81 (d, J=1.95 Hz, 1H); ESI-MS m/z [M+H]⁺ 479.3.

Example 25: N-(5-cyano-2-(4-(2,4-difluorophenoxy)piperidin-1-yl)phenyl)-3-methoxyisonicotinamide

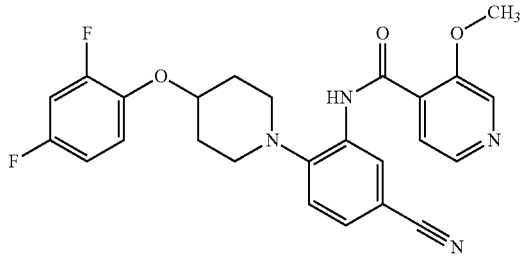 [SMILES: COc1cccnc1C(=O)Nc1cc(C#N)ccc1N1CCC(Oc2ccc(F)cc2F)CC1]

A flask was charged with 3-amino-4-(4-(2,4-difluorophenoxy)piperidin-1-yl)benzonitrile (15 mg, 0.046 mmol), 3-methoxyisonicotinic acid (6.97 mg, 0.046 mmol), DIPEA (29.4 µL, 0.169 mmol), HATU (19.05 mg, 0.050 mmol), and THF (455 µL). The reaction mixture was stirred at RT for 72 hours and was purified by HPLC to give the title compound as an off-white solid (5 mg, 24%). ¹H NMR (500 MHz, DMSO-d₆) δ ppm 1.83-1.91 (m, 2H), 2.07-2.13 (m, 2H), 2.86-2.92 (m, 2H), 3.12-3.18 (m, 2H), 4.19 (s, 3H), 4.55 (dt, J=7.81, 3.91 Hz, 1H), 6.99-7.05 (m, 1H), 7.26-7.35 (m, 2H), 7.41 (d, J=8.30 Hz, 1H), 7.62 (dd, J=8.30, 1.95 Hz, 1H), 7.89 (d, J=4.88 Hz, 1H), 8.45 (d, J=4.88 Hz, 1H), 8.62 (d, J=1.95 Hz, 1H), 8.74 (s, 1H); ESI-MS m/z [M+H]⁺ 465.3.

Example 26: N-(5-cyano-2-(4-(2,4-difluorophenoxy)piperidin-1-yl)phenyl)-3-methoxypicolinamide

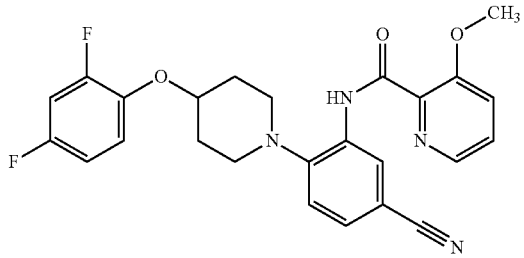

A flask was charged with 3-amino-4-(4-(2,4-difluorophenoxy)piperidin-1-yl)benzonitrile (15 mg, 0.046 mmol), 3-methoxypicolinic acid (6.97 mg, 0.046 mmol), DIPEA (29.4 µL, 0.169 mmol), HATU (19.05 mg, 0.050 mmol), and THF (455 µL). The reaction mixture was stirred at RT for 72 hours and was purified by HPLC to give the title compound as an off-white solid (5 mg, 24%). ¹H NMR (500 MHz, DMSO-d₆) δ ppm 1.91-1.98 (m, 2H), 2.12-2.18 (m, 2H), 2.89-2.94 (m, 2H), 3.14-3.19 (m, 2H), 3.92 (s, 3H), 4.56 (dt, J=7.44, 3.84 Hz, 1H), 7.00-7.05 (m, 1H), 7.28-7.35 (m, 2H), 7.37 (d, J=8.30 Hz, 1H), 7.57 (dd, J=8.30, 1.95 Hz, 1H), 7.67-7.71 (m, 1H), 7.78 (dd, J=8.79, 0.98 Hz, 1H), 8.27 (dd, J=4.39, 0.98 Hz, 1H), 8.64 (d, J=1.95 Hz, 1H); ESI-MS m/z [M+H]⁺ 465.3.

Example 27: N-(5-cyano-2-(4-(2,4-difluorophenoxy)piperidin-1-yl)phenyl)-2,3-dihydrobenzofuran-7-carboxamide

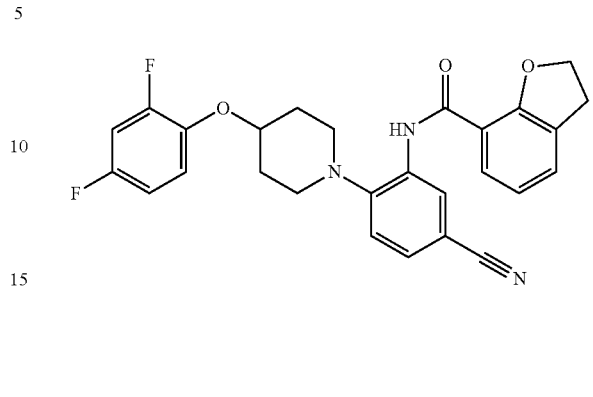

A flask was charged with 3-amino-4-(4-(2,4-difluorophenoxy)piperidin-1-yl)benzonitrile (15 mg, 0.046 mmol), 2,3-dihydrobenzofuran-7-carboxylic acid (7.48 mg, 0.046 mmol), DIPEA (29.4 µL, 0.169 mmol), HATU (19.05 mg, 0.050 mmol), and THF (455 µL). The reaction mixture was stirred at RT for 72 hours and was purified by HPLC to give the title compound as an off-white solid (1.54 mg, 7.11%). ¹H NMR (500 MHz, CD₃OD) δ ppm 2.09 (ddt, J=12.81, 8.54, 4.21, 4.21 Hz, 2H), 2.23 (br s, 2H), 2.92 (ddd, J=11.96, 9.03, 2.93 Hz, 2H), 3.18-3.22 (m, 2H), 3.41 (t, J=8.79 Hz, 2H), 4.50-4.57 (m, 1H), 4.98 (t, J=8.54 Hz, 2H), 6.89-6.95 (m, 1H), 7.00-7.10 (m, 2H), 7.24 (td, J=9.28, 5.37 Hz, 1H), 7.43-7.46 (m, 1H), 7.49-7.53 (m, 2H), 7.93-7.96 (m, 1H), 8.85 (d, J=1.95 Hz, 1H); ESI-MS m/z [M+H]⁺ 476.3.

Example 28: N-(5-cyano-2-(4-(2,4-difluorophenoxy)piperidin-1-yl)phenyl)-2-ethoxynicotinamide

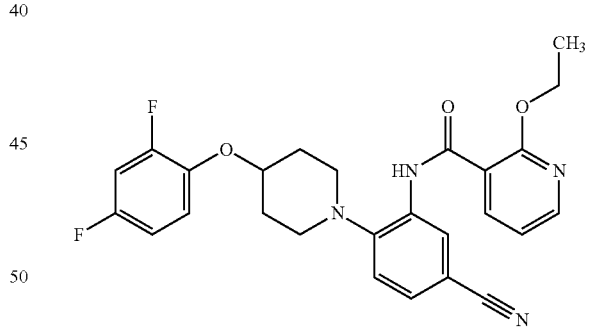

A flask was charged with 3-amino-4-(4-(2,4-difluorophenoxy)piperidin-1-yl)benzonitrile (15 mg, 0.046 mmol), 2-ethoxynicotinic acid (7.61 mg, 0.046 mmol), DIPEA (29.4 µL, 0.169 mmol), HATU (19.05 mg, 0.050 mmol), and THF (455 µL). The reaction mixture was stirred at RT for 72 hours and was purified by HPLC to give the title compound as an off-white solid (5 mg, 23%). ¹H NMR (500 MHz, DMSO-d₆) δ ppm 1.46 (t, J=7.08 Hz, 3H), 1.80-1.88 (m, 2H), 2.06-2.11 (m, 2H), 2.87-2.93 (m, 2H), 3.14-3.20 (m, 2H), 4.55 (dt, J=7.93, 4.09 Hz, 1H), 4.70 (q, J=7.00 Hz, 2H), 6.98-7.04 (m, 1H), 7.23-7.35 (m, 3H), 7.40 (d, J=8.30 Hz, 1H), 7.61 (dd, J=8.30, 1.95 Hz, 1H), 8.42-8.46 (m, 2H), 8.55 (d, J=1.46 Hz, 1H); ESI-MS m/z [M+H]⁺ 479.3.

Example 29: N-(5-cyano-2-(4-(2-fluoro-4-methoxyphenoxy)piperidin-1-yl)phenyl)-1-methyl-2-oxo-1,2-dihydropyridine-3-carboxamide

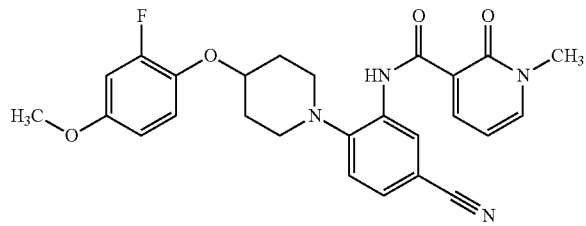

A mixture of DIPEA (119 µL, 0.682 mmol), 3-amino-4-(4-(2-fluoro-4-methoxyphenoxy)piperidin-1-yl)benzonitrile (85 mg, 0.25 mmol), 1-methyl-2-oxo-1,2-dihydropyridine-3-carboxylic acid (34.8 mg, 0.227 mmol), and DMF (2273 µL) was stirred for 10 minutes. Next, HATU (130 mg, 0.341 mmol) was added and the reaction mixture was stirred at 50° C. overnight and then at 60° C. overnight. The solution was filtered and purified by HPLC. The product-containing fractions were lyophilized to give the title compound as an off-white solid (60 mg, 55%). $^1$H NMR (500 MHz, DMSO-d$_6$) δ ppm 1.99-2.06 (m, 2H), 2.09-2.18 (m, 2H), 2.83 (ddd, J=11.72, 8.54, 3.17 Hz, 2H), 3.08-3.15 (m, 2H), 3.64 (s, 3H), 3.72 (s, 3H), 4.39 (dt, J=7.32, 3.66 Hz, 1H), 6.57-6.62 (m, 1H), 6.68-6.72 (m, 1H), 6.85-6.91 (m, 1H), 7.16-7.21 (m, 1H), 7.34-7.37 (m, 1H), 7.52-7.57 (m, 1H), 8.17 (dd, J=6.59, 2.20 Hz, 1H), 8.48 (dd, J=7.32, 2.44 Hz, 1H), 8.82 (d, J=1.95 Hz, 1H), 12.44 (s, 1H); ESI-MS m/z [M+H]$^+$ 477.4.

Example 30: N-(2-(4-(2,4-difluorophenoxy)piperidin-1-yl)-4-(methylsulfonyl)phenyl)-1-methyl-2-oxo-1,2-dihydropyridine-3-carboxamide

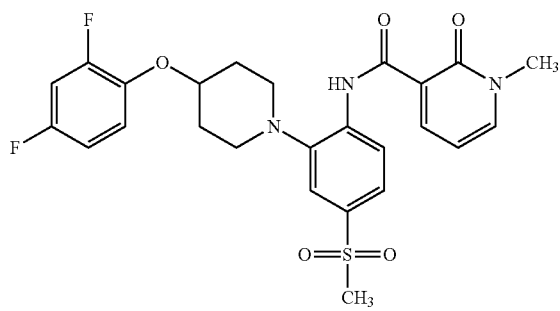 [SMILES: Cn1cccc(C(=O)Nc2ccc(S(C)(=O)=O)cc2N2CCC(Oc3ccc(F)cc3F)CC2)c1=O]

A solution of 2-(4-(2,4-difluorophenoxy)piperidin-1-yl)-4-(methylsulfonyl)aniline (30 mg, 0.078 mmol), 1-methyl-2-oxo-1,2-dihydropyridine-3-carboxylic acid (24.03 mg, 0.157 mmol), 50% 2,4,6-tripropyl-1,3,5,2,4,6-trioxatriphosphinane 2,4,6-trioxide in DMF (100 µL, 0.157 mmol) and Et$_3$N (21.87 µL, 0.157 mmol) in DMF (301 µL) was heated at 50° C. overnight. The reaction mixture was subsequently diluted with DMF (0.5 mL) and MeOH (0.2 mL) and purified by preparative HPLC, eluting with a gradient of ACN in water (basic mode) to give the title compound as an off-white solid (4.23 mg, 10.4%). $^1$H NMR (500 MHz, DMSO-d$_6$) δ ppm 2.07-2.11 (m, 2H), 2.16-2.22 (m, 2H), 2.85-2.90 (m, 2H), 3.07-3.12 (m, 2H), 3.20 (s, 3H), 3.65 (s, 3H), 4.55 (br s, 1H), 6.57-6.61 (m, 1H), 7.00-7.05 (m, 1H), 7.28-7.36 (m, 2H), 7.67-7.70 (m, 2H), 8.18 (dd, J=6.59, 2.20 Hz, 1H), 8.48 (dd, J=7.32, 2.44 Hz, 1H), 8.74-8.77 (m, 1H), 12.67 (s, 1H); ESI-MS m/z [M+H]$^+$ 518.4.

Example 31: 4-(4-(2,4-difluorophenoxy)piperidin-1-yl)-5-(2-methoxynicotinamido)-N,N-dimethylpicolinamide

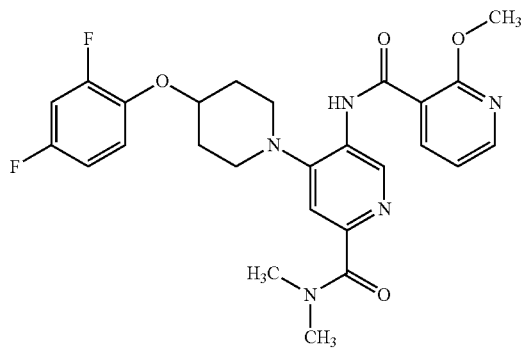 [SMILES: COc1ncccc1C(=O)Nc1cnc(C(=O)N(C)C)cc1N1CCC(Oc2ccc(F)cc2F)CC1]

A 1 L jacketed reactor was charged with 5-amino-4-(4-(2,4-difluorophenoxy)piperidin-1-yl)-N,N-dimethylpicolinamide (33.8 g, 90 mmol), 2-methoxynicotinic acid (16.50 g, 108 mmol), and NMP (330 ml). The reaction mixture was stirred and kept under a constant flow of nitrogen. To the reactor was added DIPEA (62.6 mL, 359 mmol) and stirring was continued for 30 minutes. Next 2,4,6-tripropyl-1,3,5,2,4,6-trioxatriphosphinane 2,4,6-trioxide (118 mL, 198 mmol, 50% solution in EtOAc) was added. A pre-heated circulating bath (70° C.) was attached to the reactor and the reaction mixture was stirred at 70° C. overnight. The jacket temperature was set for 10° C. Water was added (1.2 L) and the oily mixture was transferred to a 4 L separatory funnel. To the funnel was added IPAc. The phases were agitated and allowed to settle. The phases were split and the organic held in reserve. The aqueous phase was transferred to a separatory funnel. The aqueous phase was extracted with IPAc (2×). The combined organic phases were washed with 10% aqueous NaCl. The organic phase was dried over Na$_2$SO$_4$, filtered, and concentrated to give a red oil, which was crystallized from ethanol and water to give a hydrate as an off-white solid. The solid was dried under vacuum and re-crystallized from anhydrous ethanol to give the title compound as a white non-hydrated crystalline solid. $^1$H NMR (400 MHz, CDCl$_3$) δ ppm 10.24 (s, 1H), 9.53 (s, 1H), 8.65 (dd, J=7.58, 2.02 Hz, 1H), 8.37 (dd, J=4.80, 2.02 Hz, 1H), 7.49 (s, 1H), 7.16 (dd, J=7.71, 4.93 Hz, 1H), 7.00 (td, J=9.03, 5.43 Hz, 1H), 6.87 (ddd, J=10.99, 8.21, 3.03 Hz, 1H), 6.76-6.83 (m, 1H), 4.37 (dt, J=7.64, 3.88 Hz, 1H), 4.27 (s, 3H), 3.29-3.37 (m, 2H), 3.19 (s, 3H), 3.14 (s, 3H), 2.93 (t, J=8.84 Hz, 2H), 2.11-2.19 (m, 2H), 1.96-2.07 (m, 2H); ESI-MS m/z [M+H]$^+$ 512.3.

Example 32: 4-(4-(2,4-difluorophenoxy)piperidin-1-yl-5-(5-fluoro-2-methoxynicotinamido)-N,N-dimethylpicolinamide

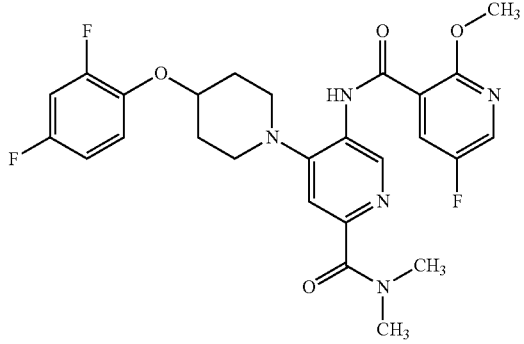 [SMILES: COc1ncc(F)cc1C(=O)Nc1cnc(C(=O)N(C)C)cc1N1CCC(Oc2ccc(F)cc2F)CC1]

To a solution of 5-fluoro-2-methoxynicotinic acid (372 mg, 2.172 mmol) in DCM (18.3 mL) was added oxalyl chloride (380 µL, 4.34 mmol) and DMF (8.41 µL, 0.109 mmol) at 0° C. After stirring at 20° C. for 1 hour, the mixture was concentrated in vacuo. The residue was taken up in THF (11 mL) and added dropwise to a mixture of 5-amino-4-(4-(2,4-difluorophenoxy)piperidin-1-yl)-N,N-dimethylpicolinamide (545 mg, 1.448 mmol) and DIPEA (759 µL, 4.34 mmol) in THF (11 mL). The reaction mixture was stirred at 60° C. for 1 hour, then cooled to RT, and filtered. The filtrate was purified by HPLC, eluting with ACN in water. The solid product was recrystallized from 3:1 MeOH/water solution and filtered. The solids were placed in a 70° C. vacuum oven overnight to give the title compound as an off-white solid (487 mg, 63.5%). $^1$H NMR (500 MHz, DMSO-d$_6$) δ ppm 1.81-1.87 (m, 2H), 2.06-2.10 (m, 2H), 2.94-2.98 (m, 2H), 2.99 (d, J=6.83 Hz, 6H), 3.27 (dd, J=11.96, 7.08 Hz, 2H), 4.12 (s, 3H), 4.55 (dt, J=7.93, 4.09 Hz, 1H), 6.99-7.05 (m, 1H), 7.27-7.34 (m, 3H), 8.25 (dd, J=8.54, 3.17 Hz, 1H), 8.46 (d, J=3.42 Hz, 1H), 9.15 (s, 1H), 10.17 (s, 1H); ESI-MS m/z [M+H]$^+$ 530.3.

Example 33: N-(2-(4-(2,4-difluorobenzyl)piperazin-1-yl)-5-(methoxymethyl)pyridin-3-yl)-2-methoxynicotinamide

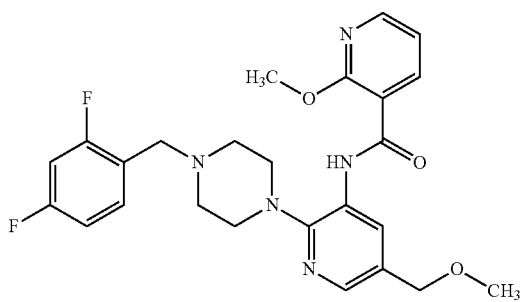 [SMILES: COCc1cnc(N2CCN(Cc3ccc(F)cc3F)CC2)c(NC(=O)c2cccnc2OC)c1]

To a 4 mL vial were added 2-methoxy-N-(5-(methoxymethyl)-2-(piperazin-1-yl)pyridin-3-yl)nicotinamide (51.5 mg, 0.144 mmol), 2,4-difluorobenzaldehyde (22.51 mg, 0.158 mmol), and DCM (1.8 mL). The reaction mixture was stirred for 30 minutes at which time sodium triacetoxyborohydride (92 mg, 0.432 mmol) was added. The reaction mixture was stirred at RT for 2.5 hours. UPLC/MS indicated the reaction was complete (significant demethylation was observed) and MeOH was added to bring the total volume 4 mL. The reaction mixture was purified by preparative HPLC (basic mode) to give the title compound as an off-white solid (4 mg, 6%). $^1$H NMR (500 MHz, CD$_3$OD) δ ppm 2.77 (br s, 4H), 3.16-3.18 (m, 4H), 3.42 (s, 3H), 3.78 (d, J=1.46 Hz, 2H), 4.10 (s, 3H), 4.48 (s, 2H), 6.98-7.02 (m, 2H), 7.23 (dd, J=7.81, 4.88 Hz, 1H), 7.48-7.53 (m, 1H), 8.07 (d, J=1.95 Hz, 1H), 8.41 (dd, J=4.88, 1.95 Hz, 1H), 8.56 (dd, J=7.81, 1.95 Hz, 1H), 8.69 (d, J=1.95 Hz, 1H); ESI-MS m/z [M+H]$^+$ 484.3.

Example 34: N-(2-(4-(2,4-difluorophenoxy)piperidin-1-yl)-5-(hydroxymethyl)pyridin-3-yl)-2-methoxynicotinamide

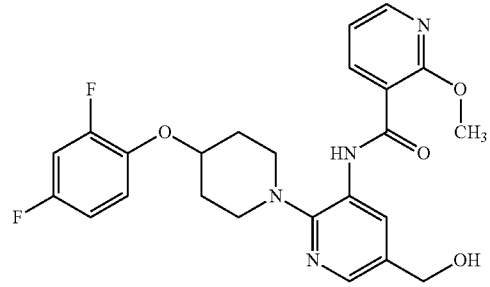 [SMILES: COc1ncccc1C(=O)Nc1cc(CO)cnc1N1CCC(Oc2ccc(F)cc2F)CC1]

Super-Hydride® or 1.0 M lithium triethylborohydride in THF solution (14.23 mL, 14.23 mmol) was added to a solution of methyl 6-(4-(2,4-difluorophenoxy)piperidin-1-yl)-5-(2-methoxynicotinamido)nicotinate (1.419 g, 2.85 mmol) in THF (28.5 mL) at −78° C. The reaction mixture was stirred for 30 minutes at −78° C. and at RT overnight. The reaction mixture was then filtered and the filtrate was purified by HPLC, eluting with ACN in water. The product was lyophilized overnight and was heated at 60° C. in a vacuum oven overnight to give the title compound as an off-white solid (810 mg, 60.5%). $^1$H NMR (500 MHz, DMSO-d$_6$) δ ppm 1.85-1.91 (m, 2H), 2.08-2.13 (m, 2H), 2.94-2.99 (m, 2H), 3.23-3.28 (m, 2H), 4.19 (s, 3H), 4.49 (d, J=5.86 Hz, 2H), 4.54-4.60 (m, 1H), 5.28 (t, J=5.61 Hz, 1H), 6.98-7.05 (m, 1H), 7.27-7.36 (m, 3H), 8.04 (d, J=1.46 Hz, 1H), 8.42-8.48 (m, 2H), 8.65 (d, J=1.95 Hz, 1H), 10.31 (s, 1H); ESI-MS m/z [M+H]$^+$ 471.4.

Example 35: N-(2-(4-(2,4-difluorophenoxy)piperidin-1-yl)-5-methylpyridin-3-yl)-4-methoxynicotinamide

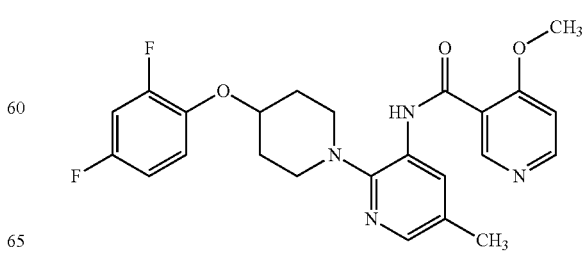

A solution of 2-(4-(2,4-difluorophenoxy)piperidin-1-yl)-5-methylpyridin-3-amine (38.0 mg, 0.119 mmol), 4-methoxynicotinic acid (36.4 mg, 0.238 mmol), HATU (90 mg, 0.238 mmol) and DIPEA (52.0 µL, 0.298 mmol) in DMF (498 µL) was heated at 50° C. for 4 days. The solution was diluted with DMF (0.3 mL) and MeOH (0.2 mL) and purified by preparative HPLC, eluting with ACN in water (basic mode) to give the title compound as an off-white solid (23 mg, 43%). $^1$H NMR (500 MHz, DMSO-$d_6$) δ ppm 1.81-1.88 (m, 2H), 2.05-2.11 (m, 2H), 2.27 (s, 3H), 2.90-2.96 (m, 2H), 3.19-3.24 (m, 2H), 4.15 (s, 3H), 4.54 (tt, J=8.05, 3.91 Hz, 1H), 6.98-7.05 (m, 1H), 7.25-7.35 (m, 2H), 7.36 (d, J=5.86 Hz, 1H), 7.94 (d, J=1.46 Hz, 1H), 8.48 (d, J=1.95 Hz, 1H), 8.64 (d, J=5.86 Hz, 1H), 9.01 (s, 1H), 10.02 (s, 1H); ESI-MS m/z [M+H]$^+$ 455.3.

Example 36: N-(2-(4-(2,4-difluorophenoxy)piperidin-1-yl)-5-methylpyridin-3-yl)-3-methoxy-1-methyl-1H-pyrazole-4-carboxamide

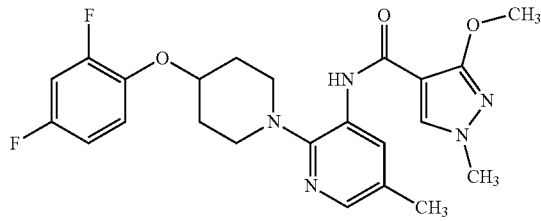 [SMILES: COc1nn(C)cc1C(=O)Nc1cc(C)cnc1N1CCC(Oc2ccc(F)cc2F)CC1]

A solution of 2-(4-(2,4-difluorophenoxy)piperidin-1-yl)-5-methylpyridin-3-amine (38.0 mg, 0.119 mmol), 3-methoxy-1-methyl-1H-pyrazole-4-carboxylic acid (37.2 mg, 0.238 mmol), HATU (90 mg, 0.238 mmol) and DIPEA (52.0 µL, 0.298 mmol) in DMF (498 µL) was heated at 50° C. for 4 days. The solution was diluted with DMF (0.3 mL) and MeOH (0.2 mL) and purified by preparative HPLC, eluting with ACN in water (basic mode) to give the title compound as an off-white solid (28 mg, 51%). $^1$H NMR (500 MHz, DMSO-$d_6$) δ ppm 1.82-1.90 (m, 2H), 2.06-2.14 (m, 2H), 2.25 (s, 3H), 2.86 (ddd, J=12.20, 9.28, 2.93 Hz, 2H), 3.07-3.15 (m, 2H), 3.76 (s, 3H), 4.06-4.10 (m, 3H), 4.55 (tt, J=8.05, 3.91 Hz, 1H), 6.98-7.05 (m, 1H), 7.25-7.37 (m, 2H), 7.85-7.91 (m, 1H), 8.13-8.17 (m, 1H), 8.47-8.51 (m, 1H), 9.18 (s, 1H); ESI-MS m/z [M+H]$^+$ 458.3.

Example 37: N-(5-cyano-2-(4-(2,4-difluorophenoxy)piperidin-1-yl)phenyl)-4-methoxypyrimidine-5-carboxamide

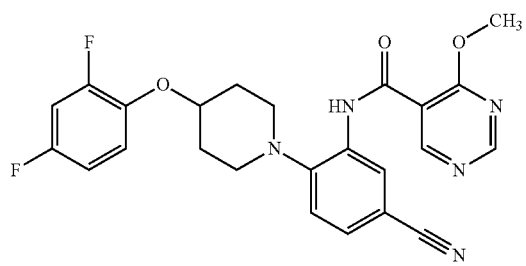 [SMILES: COc1ncncc1C(=O)Nc1cc(C#N)ccc1N1CCC(Oc2ccc(F)cc2F)CC1]

A mixture of DIPEA (101 µL, 0.580 mmol), 3-amino-4-(4-(2,4-difluorophenoxy)piperidin-1-yl)benzonitrile (70 mg, 0.213 mmol), 4-methoxypyrimidine-5-carboxylic acid (29.8 mg, 0.193 mmol), and DMF (1.932 mL) was stirred for 10 minutes. HATU (110 mg, 0.290 mmol) was added and the reaction mixture was stirred at RT for 72 hours. The mixture was filtered and purified by preparative HPLC. The product-containing fractions were collected and concentrated in vacuo to give the title compound as an off-white solid (43.67 mg, 48.6%). $^1$H NMR (500 MHz, DMSO-$d_6$) δ ppm 1.83-1.92 (m, 2H), 2.06-2.14 (m, 2H), 2.86-2.92 (m, 2H), 3.10-3.17 (m, 2H), 4.21 (s, 3H), 4.55 (tt, J=7.81, 3.91 Hz, 1H), 6.99-7.05 (m, 1H), 7.26-7.36 (m, 2H), 7.41 (d, J=8.30 Hz, 1H), 7.58-7.66 (m, 1H), 8.62 (d, J=1.46 Hz, 1H), 9.01 (s, 1H), 9.11 (s, 1H), 10.09 (s, 1H); ESI-MS m/z [M+H]$^+$ 466.4.

Example 38: N-(2-(4-(2,4-difluorophenoxy)piperidin-1-yl)-5-(methylsulfonyl)phenyl)-5,6,7,8-tetrahydropyrazolo[5,1-b][1,3]oxazepine-3-carboxamide

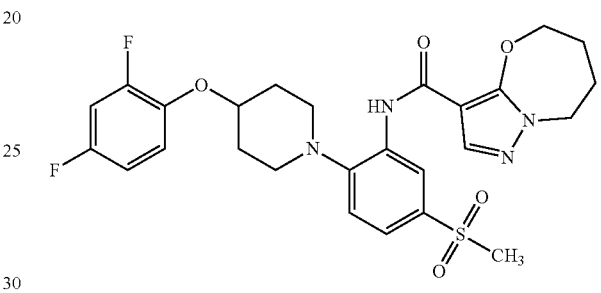

A solution of 2-(4-(2,4-difluorophenoxy)piperidin-1-yl)-5-(methylsulfonyl)aniline (60 mg, 0.157 mmol) and 5,6,7,8-tetrahydropyrazolo[5,1-b][1,3]oxazepine-3-carboxylic acid (28.6 mg, 0.157 mmol) was mixed with pyridine (127 µL, 1.569 mmol) and DMA (500 µL) and stirred for 10 minutes at RT. Next 2,4,6-tripropyl-1,3,5,2,4,6-trioxatriphosphinane 2,4,6-trioxide (50% in DMF) (200 µL, 0.314 mmol) was added and the reaction mixture was heated at 50° C. for 24 hours. The solution was then diluted with DMF (1 mL) and purified by HPLC (basic mode) to give the title compound as a white solid (2.1 mg, 2.4%). $^1$H NMR (500 MHz, DMSO-$d_6$) δ ppm 1.88-1.94 (m, 4H), 2.11-2.16 (m, 4H), 2.85-2.90 (m, 2H), 3.07-3.10 (m, 2H), 3.16-3.17 (m, 3H), 4.26-4.29 (m, 2H), 4.42-4.45 (m, 2H), 4.56-4.61 (m, 1H), 7.01-7.06 (m, 1H), 7.29-7.37 (m, 2H), 7.47-7.50 (m, 1H), 7.61 (s, 1H), 7.73 (s, 1H), 8.93-8.94 (m, 1H), 9.34-9.35 (m, 1H); ESI-MS m/z [M+H]$^+$ 547.4.

Example 39: N-(5-cyano-2-(4-(2,4-difluorophenoxy)piperidin-1-yl)-4-fluorphenyl)-2-methoxy-6-methylnicotinamide

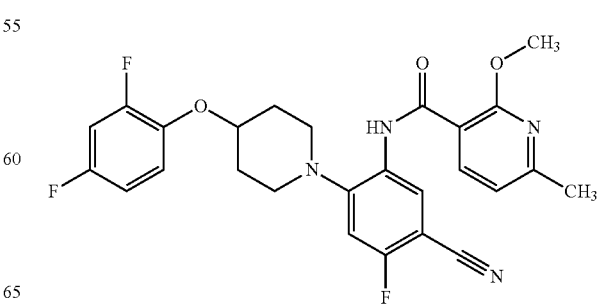

A solution of 5-amino-4-(4-(2,4-difluorophenoxy)piperidin-1-yl)-2-fluorobenzonitrile (50 mg, 0.144 mmol) and 2-methoxy-6-methylnicotinic acid (24.06 mg, 0.144 mmol) was mixed with DMA (458 μL) and pyridine (116 μL, 1.440 mmol) for 10 minutes at RT. Next 2,4,6-tripropyl-1,3,5,2,4,6-trioxatriphosphinane 2,4,6-trioxide (50% in DMF) (183 μL, 0.288 mmol) was added and the reaction mixture was heated at 50° C. for 72 hours. The solution was diluted with DMF (1 mL) and purified by HPLC (basic mode) to give the title compound as a white solid (41.2 mg, 57.6%). $^1$H NMR (500 MHz, DMSO-$d_6$) δ ppm 1.82-1.89 (m, 2H), 2.06-2.11 (m, 2H), 2.91 (br s, 2H), 3.15-3.20 (m, 2H), 4.15 (s, 3H), 4.53-4.59 (m, 1H), 6.99-7.04 (m, 1H), 7.12-7.14 (m, 1H), 7.27-7.35 (m, 2H), 7.38-7.41 (m, 1H), 8.33-8.35 (m, 1H), 8.58-8.60 (m, 1H), 10.18-10.20 (m, 1H); ESI-MS m/z [M+H]$^+$ 497.5.

Example 40: N-(4-(4-(4-cyano-2-fluorophenoxy)piperidin-1-yl)-6-methylpyridin-3-yl)-2-methoxynicotinamide

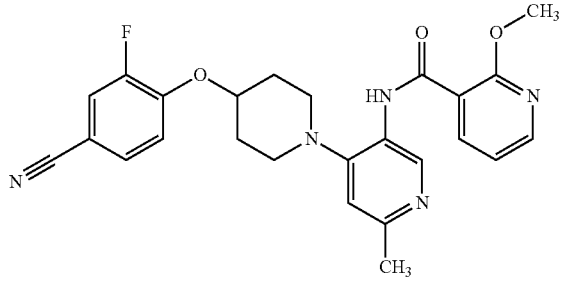 [SMILES: COc1ncccc1C(=O)Nc1cnc(C)cc1N1CCC(Oc2ccc(C#N)cc2F)CC1]

A mixture of N-(4-(4-hydroxypiperidin-1-yl)-6-methylpyridin-3-yl)-2-methoxynicotinamide (25 mg, 0.073 mmol), 3-fluoro-4-hydroxybenzonitrile (20.02 mg, 0.146 mmol) and 2-(tributylphosphoranylidene)acetonitrile (38.3 μL, 0.146 mmol) in toluene (413 μL) was heated at 100° C. overnight. The solvent was removed in vacuo (bath 60° C.). The residue was diluted with DMF (0.6 mL) and MeOH (0.2 mL), filtered through a syringe filter, and purified by preparative HPLC, eluting with ACN in water (basic mode) to give the title compound as an off-white solid (1.7 mg, 5.1%). $^1$H NMR (500 MHz, DMSO-$d_6$) δ ppm 1.88 (d, J=8.30 Hz, 2H), 1.85-1.91 (m, 1H), 2.10-2.16 (m, 2H), 2.42 (brs, 3H), 2.43 (s, 3H), 2.94 (s, 2H), 3.15-3.21 (m, 2H), 4.13 (s, 3H), 4.85-4.90 (m, 1H), 7.05-7.06 (m, 1H), 7.24-7.27 (m, 1H), 7.47-7.51 (m, 1H), 7.66-7.68 (m, 1H), 7.85-7.88 (m, 1H), 8.39-8.42 (m, 2H), 9.02-9.03 (m, 1H), 9.98-9.99 (m, 1H); ESI-MS m/z [M+H]$^+$ 462.4.

Example 41: N-(5-cyano-2-(4-(2,4-difluorophenoxy)piperidin-1-yl)phenyl)-5-methylisoxazole-3-carboxamide

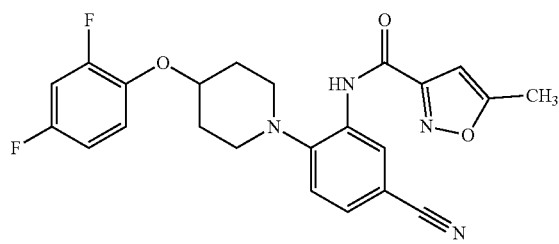 [SMILES: Cc1cc(C(=O)Nc2cc(C#N)ccc2N2CCC(Oc3ccc(F)cc3F)CC2)no1]

A solution of 3-amino-4-(4-(2,4-difluorophenoxy)piperidin-1-yl)benzonitrile (40 mg, 0.121 mmol), HATU (53.1 mg, 0.140 mmol) and DIPEA (0.063 mL, 0.364 mmol) in DMF (0.7 mL) was added to 5-methylisoxazole-3-carboxylic acid (17.0 mg, 0.134 mmol) and the resulting mixture was kept at RT for 16 hours. The mixture was diluted with water (4 mL). The solvent was decanted and the residue was washed with water (2×2 mL) and purified by HPLC, eluting with ACN in water (acid mode) to give the title compound as a tan solid (3 mg, 5.4%). ESI-MS m/z [M+H]$^+$ 439.

Example 42: N-(5-cyano-2-(4-(2,4-difluorophenoxy)piperidin-1-yl)phenyl)-1-methyl-1H-pyrazole-3-carboxamide

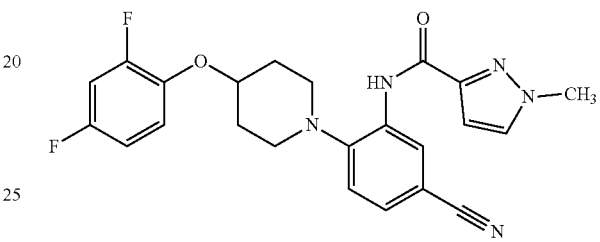

The title compound was prepared in a manner similar to Example 41, using 1-methyl-1H-pyrazole-3-carboxylic acid in place of 5-methylisoxazole-3-carboxylic acid. $^1$H NMR (400 MHz, CD$_3$CN) δ ppm 1.95-2.02 (m, 2H), 2.07-2.19 (m, 2H), 2.82 (ddd, J=11.94, 8.65, 3.16 Hz, 2H), 3.08-3.15 (m, 2H), 4.11 (s, 2H), 4.47 (tt, =7.86, 3.76 Hz, 1H), 6.86-6.96 (m, 1H), 7.02 (ddd, J=11.49, 8.72, 3.03 Hz, 1H), 7.18 (td, J=9.28, 5.43 Hz, 1H), 7.28 (d, J=8.34 Hz, 1H), 7.43 (dd, J=8.21, 1.89 Hz, 1H), 7.50-7.57 (m, 1H), 7.60 (d, J=7.83 Hz, 1H), 8.04 (td, J=7.77, 1.64 Hz, 1H), 8.49 (d, J=1.77 Hz, 1H), 8.68 (d, J=4.55 Hz, 1H), 9.36 (br s, 1H); ESI-MS m/z [M+H]$^+$ 438.

Example 43: N-(5-cyano-2-(4-(2,4-difluorophenoxy)piperidin-1-yl)phenyl)-2-methyloxazole-4-carboxamide

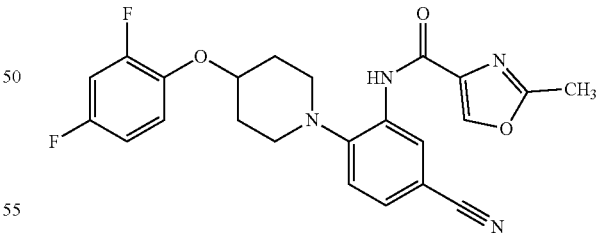

The title compound was prepared in a manner similar to Example 41, using 2-methyloxazole-4-carboxylic acid in place of 5-methylisoxazole-3-carboxylic acid. $^1$H NMR (400 MHz, CD$_3$CN) δ ppm 1.99-2.09 (m, 2H), 2.17-2.27 (m, 2H), 2.51 (s, 3H), 2.89 (ddd, J=11.94, 8.27, 3.28 Hz, 2H), 3.11-3.22 (m, 2H), 4.51 (tt, J=7.45, 3.66 Hz, 1H), 6.87-6.96 (m, 1H), 7.02 (ddd, J=11.37, 8.59, 3.03 Hz, 1H), 7.15-7.22 (m, 1H), 7.33 (d, J=8.34 Hz, 1H), 7.43-7.49 (m, 1H), 8.30 (s, 1H), 8.71 (d, J=1.77 Hz, 1H), 9.75 (br s, 1H); ESI-MS m/z [M+H]$^+$ 439.

Example 44: N-(5-cyano-2-(4-(2,4-difluorophe-noxy)piperidin-1-yl)phenyl)pyrazine-2-carboxamide

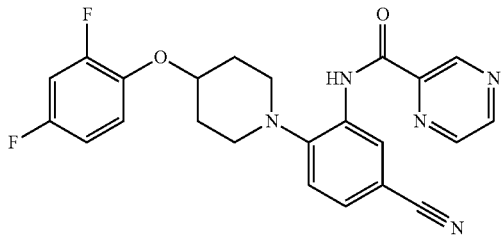 [SMILES: N#Cc1ccc(N2CCC(Oc3ccc(F)cc3F)CC2)c(NC(=O)c2cnccn2)c1]

The title compound was prepared in a manner similar to Example 41, using pyrazin-2-carboxylic acid in place of 5-methylisoxazole-3-carboxylic acid. $^1$H NMR (400 MHz, CD$_3$CN) δ ppm 1.99-2.11 (m, 2H), 2.18-2.25 (m, 2H), 2.92 (ddd, J=11.81, 8.15, 3.28 Hz, 2H), 3.20 (ddd, J=11.56, 7.52, 3.41 Hz, 2H), 4.52 (tt, J=7.42, 3.69 Hz, 1H), 6.88-6.94 (m, 1H), 7.02 (ddd, J=11.49, 8.72, 3.03 Hz, 1H), 7.19 (td, J=9.22, 5.56 Hz, 1H), 7.36 (d, J=8.08 Hz, 1H), 7.50 (dd, J=8.21, 1.89 Hz, 1H), 8.71 (dd, J=2.27, 1.52 Hz, 1H), 8.80 (d, J=2.02 Hz, 1H), 8.87 (d, J=2.27 Hz, 1H), 9.40 (d, J=1.52 Hz, 1H), 10.67 (br s, 1H); ESI-MS m/z [M+H]$^+$ 436.

Example 45: N-(5-cyano-2-(4-(2,4-difluorophe-noxy)piperidin-1-yl)phenyl)-1-methyl-1H-imida-zole-4-carboxamide

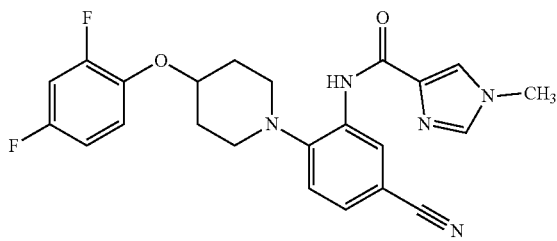 [SMILES: Cn1cnc(C(=O)Nc2cc(C#N)ccc2N2CCC(Oc3ccc(F)cc3F)CC2)c1]

The title compound was prepared in a manner similar to Example 41, using 1-methyl-1H-imidazole-4-carboxylic acid in place of 5-methylisoxazole-3-carboxylic acid. ESI-MS m/z [M+H]$^+$ 438.

Example 46: N-(5-cyano-2-(4-(2,4-difluorophe-noxy)piperidin-1-yl)phenyl)-3-methoxythiophene-2-carboxamide

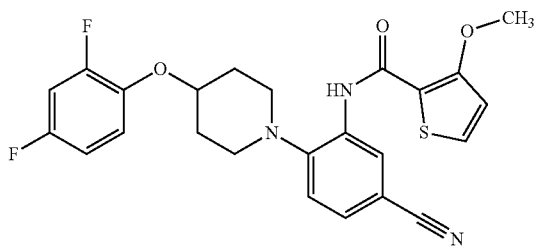 [SMILES: COc1ccsc1C(=O)Nc1cc(C#N)ccc1N1CCC(Oc2ccc(F)cc2F)CC1]

The title compound was prepared in a manner similar to Example 41, using 3-methoxythiophene-2-carboxylic acid in place of 5-methylisoxazole-3-carboxylic acid. ESI-MS m/z [M+H]$^+$ 470.

Example 47: N-(5-cyano-2-(4-(2,4-difluorophe-noxy)piperidin-1-yl)phenyl)-4-methoxythiophene-3-carboxamide

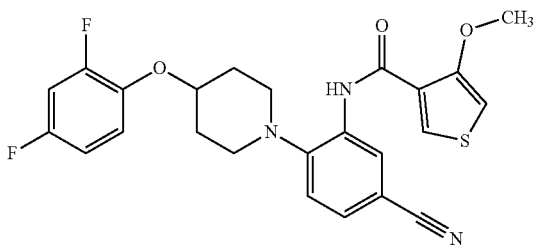 [SMILES: COc1cscc1C(=O)Nc1cc(C#N)ccc1N1CCC(Oc2ccc(F)cc2F)CC1]

The title compound was prepared in a manner similar to Example 41, using 4-methoxythiophene-3-carboxylic acid in place of 5-methylisoxazole-3-carboxylic acid. ESI-MS m/z [M+H]$^+$ 470.

Example 48: N-(5-cyano-2-(4-(2,4-difluorophe-noxy)piperidin-1-yl)phenyl)pyrrolo[1,2-c]pyrimi-dine-3-carboxamide

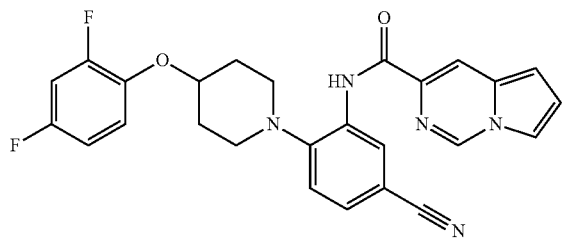 [SMILES: N#Cc1ccc(N2CCC(Oc3ccc(F)cc3F)CC2)c(NC(=O)c2cc3cccn3cn2)c1]

The title compound was prepared in a manner similar to Example 41, using pyrrolo[1,2-c]pyrimidine-3-carboxylic acid in place of 5-methylisoxazole-3-carboxylic acid. ESI-MS m/z [M+H]$^+$ 474.

Example 49: N-(5-cyano-2-(4-(2,4-difluorophe-noxy)piperidin-1-yl)phenyl)-3,5-difluoropicolina-mide

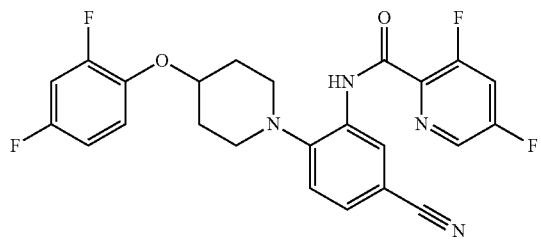 [SMILES: N#Cc1ccc(N2CCC(Oc3ccc(F)cc3F)CC2)c(NC(=O)c2ncc(F)cc2F)c1]

The title compound was prepared in a manner similar to Example 41, using 3,5-difluoropicolinic acid in place of 5-methylisoxazole-3-carboxylic acid. ESI-MS m/z [M+H]$^+$ 471.

Example 50: N-(5-cyano-2-(4-(2,4-difluorophenoxy)piperidin-1-yl)phenyl)-1-methyl-1H-imidazole-2-carboxamide

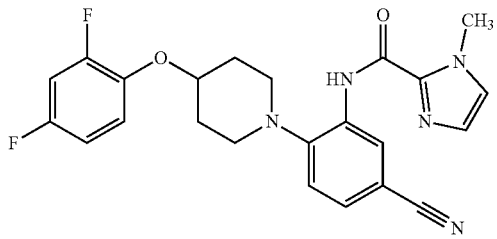 [SMILES: Cn1ccnc1C(=O)Nc1cc(C#N)ccc1N1CCC(Oc2ccc(F)cc2F)CC1]

The title compound was prepared in a manner similar to Example 41, using 1-methyl-1H-imidazole-2-carboxylic acid in place of 5-methylisoxazole-3-carboxylic acid. ESI-MS m/z [M+H]+ 438.

Example 51: N-(5-cyano-2-(4-(2,4-difluorophenoxy)piperidin-1-yl)phenyl)-4-methylthiazole-2-carboxamide

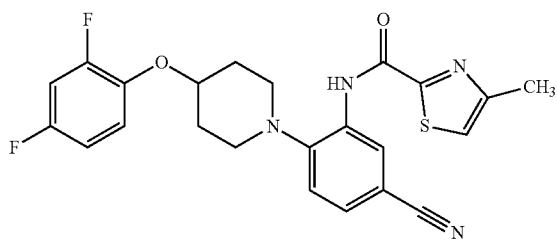 [SMILES: Cc1csc(C(=O)Nc2cc(C#N)ccc2N2CCC(Oc3ccc(F)cc3F)CC2)n1]

The title compound was prepared in a manner similar to Example 41, using 4-methylthiazole-2-carboxylic acid in place of 5-methylisoxazole-3-carboxylic acid. $^1$H NMR (400 MHz, CD$_3$CN) δ ppm 2.00-2.10 (m, 2H), 2.18-2.26 (m, 2H), 2.52 (d, J=0.76 Hz, 3H), 2.92 (s, 2H), 3.19 (br s, 2H), 4.52 (tt, J=7.55, 3.69 Hz, 1H), 6.86-6.95 (m, 1H), 7.02 (ddd, J=11.37, 8.59, 3.03 Hz, 1H), 7.19 (td, J=9.35, 5.56 Hz, 1H), 7.35 (d, J=8.08 Hz, 1H), 7.45 (d, J=1.01 Hz, 1H), 7.49 (dd, J=8.21, 1.89 Hz, 1H), 8.67 (d, J=2.02 Hz, 1H), 10.17 (br s, 1H); ESI-MS m/z [M+H]+ 455.

Example 52: N-(5-cyano-2-(4-(2,4-difluorophenoxy)piperidin-1-yl)phenyl)-6-hydroxypyridazine-3-carboxamide

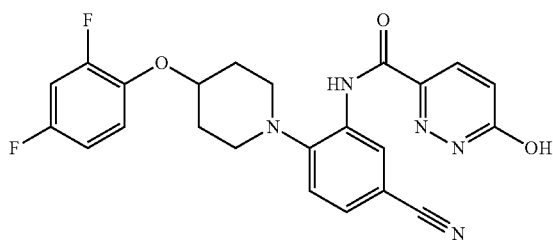 [SMILES: N#Cc1ccc(N2CCC(Oc3ccc(F)cc3F)CC2)c(NC(=O)c2ccc(O)nn2)c1]

The title compound was prepared in a manner similar to Example 41, using 6-chloropyridazine-3-carboxylic acid in place of 5-methylisoxazole-3-carboxylic acid. ESI-MS m/z [M+H]+ 452.

Example 53: N-(5-cyano-2-(4-(2,4-difluorophenoxy)piperidin-1-yl)phenyl)-6,7-dihydro-5H-pyrazolo[5,1-b][1,3]oxazine-3-carboxamide

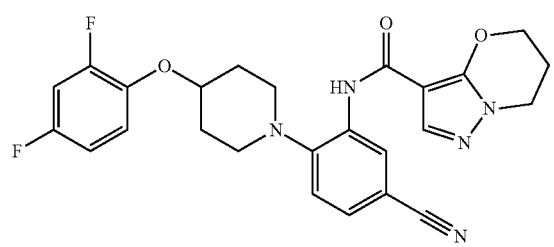 [SMILES: N#Cc1ccc(N2CCC(Oc3ccc(F)cc3F)CC2)c(NC(=O)c2cnn3c2OCCC3)c1]

The title compound was prepared in a manner similar to 41, using 6,7-dihydro-5H-pyrazolo[5,1-b][1,3]oxazine-3-carboxylic acid in place of 5-methylisoxazole-3-carboxylic acid. ESI-MS m/z [M+H]+ 480.

Example 54: N-(5-cyano-2-(4-(2,4-difluorophenoxy)piperidin-1-yl)pyridin-3-yl)-6-methylpicolinamide

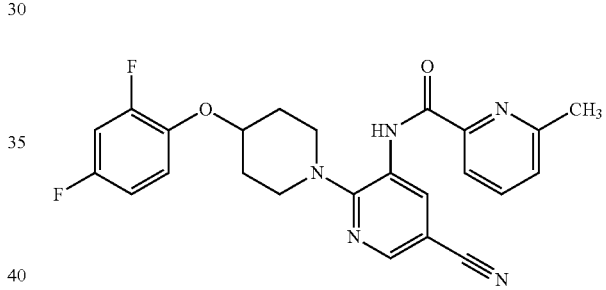

A solution of 5-amino-6-(4-(2,4-difluorophenoxy)piperidin-1-yl)nicotinonitrile (52.9 mg, 0.160 mmol), HATU (122 mg, 0.320 mmol) and DIPEA (0.103 mL, 0.590 mmol) in DMF (0.7 mL) was added to 6-methylpicolinic acid (43.9 mg, 0.320 mmol). The resulting mixture was heated at 80° C. for 16 hours and then diluted with water (4 mL). The solvent was decanted and the residue was purified by HPLC (acid mode) to give a TFA salt of the title compound as a tan solid (18 mg, 25%). ESI-MS m/z [M+H]+ 450.

Example 55: 4-chloro-V-(5-cyano-2-(4-(2,4-difluorophenoxy)piperidin-1-yl)pyridin-3-yl)picolinamide

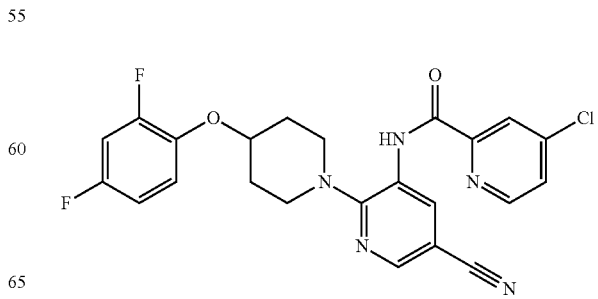

A TFA salt of the title compound was prepared in a manner similar to Example 54, using 4-chloropicolinic acid in place of 6-methylpicolinic acid. ESI-MS m/z [M+H]+ 470.

Example 56: N-(5-cyano-2-(4-(2,4-difluorobenoxy) piperidin-1-yl)pyridin-3-yl)-4-fluoro-2-methoxybenzamide

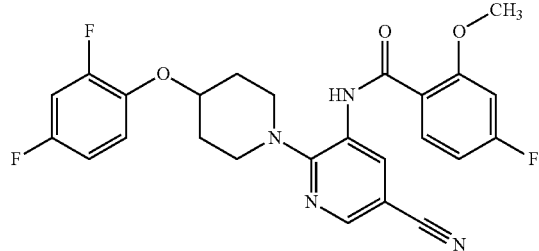 [SMILES: COc1cc(F)ccc1C(=O)Nc1cc(C#N)cnc1N1CCC(Oc2ccc(F)cc2F)CC1]

A TFA salt of the title compound was prepared in a manner similar to Example 54, using 4-fluoro-2-methoxybenzoic acid in place of 6-methylpicolinic acid. ESI-MS m/z [M+H]+ 483.

Example 57: N-(5-cyano-2-(4-(2,4-difluorophenoxy)piperidin-1-yl)pyridin-3-yl)-3-fluoro-6-methylpicolinamide

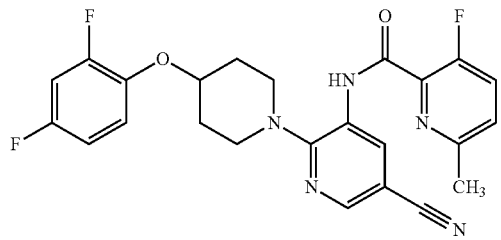 [SMILES: Cc1ccc(F)c(C(=O)Nc2cc(C#N)cnc2N2CCC(Oc3ccc(F)cc3F)CC2)n1]

A TFA salt of the title compound was prepared in a manner similar to Example 54, using 3-fluoro-6-methylpicolinic acid in place of 6-methylpicolinic acid. ESI-MS m/z [M+H]+ 468.

Example 58: N-(5-cyano-2-(4-(2,4-difluorophenoxy)piperidin-1-yl)pyridin-3-yl)-1-methyl-2-oxo-1,2-dihydropyridine-3-carboxamide

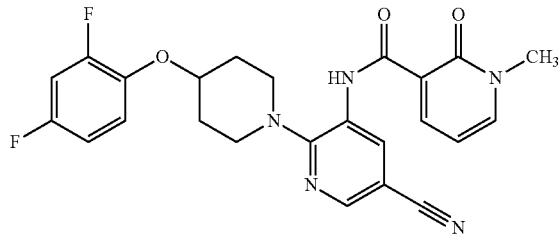

A TFA salt of the title compound was prepared in a manner similar to Example 54, using 1-methyl-2-oxo-1,2-dihydropyridine-3-carboxylic acid in place of 6-methylpicolinic acid. ESI-MS m/z [M+H]+ 466.

Example 59: N-(5-cyano-2-(4-(2,4-difluorophenoxy)piperidin-1-yl)pyridin-3-yl)-3-methylpicolinamide

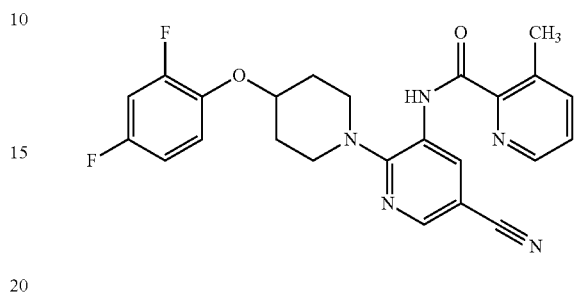

A TFA salt of the title compound was prepared in a manner similar to Example 54, using 3-methylpicolinic acid in place of 6-methylpicolinic acid. ESI-MS m/z [M+H]+ 450.

Example 60: N-(5-cyano-2-(4-(2,4-difluorophenoxy)piperidin-1-yl)pyridin-3-yl)-3-methoxy-1-methyl-1H-pyrazole-4-carboxamide

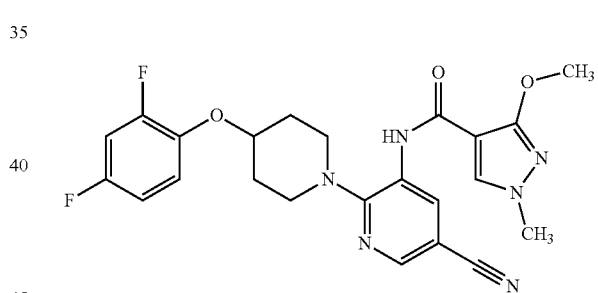

To a solution of 5-amino-6-(4-(2,4-difluorophenoxy)piperidin-1-yl)nicotinonitrile (100 mg, 0.303 mmol), 3-methoxy-1-methyl-1H-pyrazole-4-carboxylic acid (70.9 mg 454 mmol) and pyridine (0.247 mL, 3.03 mmol) in NMP (1 mL) was added 50% 2,4,6-tripropyl-1,3,5,2,4,6-trioxatriphosphinane 2,4,6-trioxide in EtOAc (0.360 mL, 0.605 mmol). The reaction mixture was stirred at 50° C. for 2 hours and then diluted with water (2-3 mL). The aqueous layer was decanted and the residue was purified by flash column chromatography on silica gel (8 g $SiO_2$ column) eluting with a 30-100% gradient of EtOAc in heptane to give the title compound as a white solid (11 mg, 8%). $^1$H NMR (400 MHz, DMSO-$d_6$) δ ppm 1.74-1.90 (m, 2H), 2.03-2.15 (m, 2H), 3.02-3.13 (m, 2H), 3.35-3.46 (m, 2H), 3.77 (s, 3H), 4.05 (s, 3H), 4.53-4.66 (m, 1H), 6.99-7.05 (m, 1H), 7.27-7.36 (m, 2H), 8.22 (s, 1H), 8.49 (d, J=2.27 Hz, 1H), 8.74 (d, J=2.27 Hz, 1H), 8.91 (s, 1H); ESI-MS m/z [M+H] 469.

Example 61: N-(5-cyano-2-(4-(2,4-difluorophenoxy)piperidin-1-yl)pyridin-3-yl-4-hydroxynicotinamide

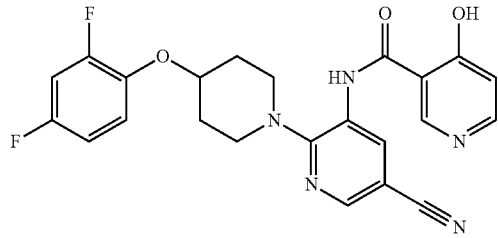 [SMILES: N#Cc1cnc(N2CCC(Oc3ccc(F)cc3F)CC2)c(NC(=O)c2cnccc2O)c1]

The title compound was prepared in a manner similar to Example 60, using 4-methoxynicotinic acid (demethylation occurs in situ) in place of 3-methoxy-1-methyl-1H-pyrazole-4-carboxylic acid. $^1$H NMR (400 MHz, DMSO-$d_6$) δ ppm 1.88-2.03 (m, 2H), 2.14 (d, J=12.63 Hz, 2H), 3.10 (t, J=9.35 Hz, 2H), 3.40-3.51 (m, 2H), 4.54-4.63 (m, 1H), 6.59 (d, J=7.33 Hz, 1H), 6.95-7.06 (m, 1H), 7.25-7.37 (m, 2H), 7.90 (dd, J=7.33, 1.77 Hz, 1H), 8.47 (d, J=2.02 Hz, 1H), 8.61 (d, J=1.52 Hz, 1H), 8.96 (d, J=2.02 Hz, 1H), 12.38 (br s, 1H), 12.96 (s, 1H); ESI-MS m/z [M+H]$^+$ 452.

Example 62: N-(2-(4-(2,4-difluorophenoxy)piperidin-1-yl)-6-methylpyridin-3-yl)-4-methoxynicotinamide

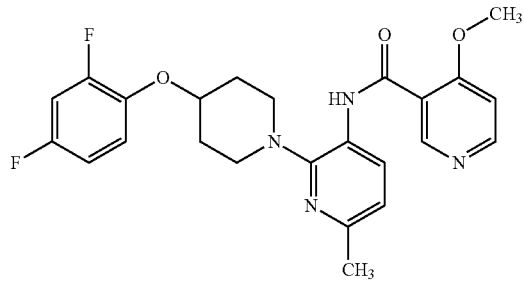 [SMILES: COc1ccncc1C(=O)Nc1ccc(C)nc1N1CCC(Oc2ccc(F)cc2F)CC1]

To a solution of 2-(4-(2,4-difluorophenoxy)piperidin-1-yl)-6-methylpyridin-3-amine (100 mg, 0.313 mmol), 4-methoxynicotinic acid (71.9 mg, 0.470 mmol) and pyridine (0.255 mL, 3.13 mmol) in NMP (1 mL) was added 50% 2,4,6-tripropyl-1,3,5,2,4,6-trioxatriphosphinane 2,4,6-trioxide in EtOAc (0.373 mL, 0.626 mmol). The mixture was stirred at 50° C. for 2 hours and then diluted with water (3 mL). The aqueous layer was decanted and the residue was purified by flash chromatography on silica gel. $^1$H NMR (400 MHz, DMSO-$d_6$) δ ppm 1.77-1.90 (m, 2H), 2.08 (s, 2H), 2.39 (s, 3H), 2.90-3.03 (m, 2H), 3.21-3.31 (m, 2H), 4.14 (s, 3H), 4.54 (dt, J=8.15, 4.14 Hz, 1H), 6.97-7.05 (m, 2H), 7.23-7.34 (m, 2H), 7.35 (d, J=5.81 Hz, 1H), 8.43 (d, J=8.08 Hz, 1H), 8.64 (d, J=5.81 Hz, 1H), 8.99 (s, 1H), 9.94 (s, 1H); ESI-MS m/z [M+H]$^+$ 455.

Example 63: N-(5-cyano-2-(4-(2,4-difluorophenoxy)piperidin-1-yl)pyridin-3-yl)-2-methoxynicotinamide

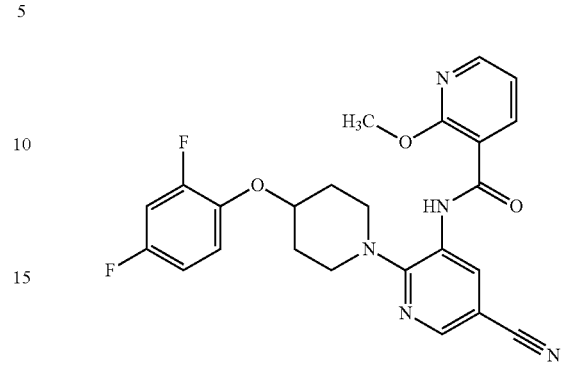

To a solution of 5-amino-6-(4-(2,4-difluorophenoxy)piperidin-1-yl)nicotinonitrile (250 mg, 0.757 mmol), 2-methoxynicotinic acid (174 mg, 1.135 mmol) and pyridine (0.617 mL, 7.57 mmol) in NMP (3 mL) was added 2,4,6-tripropyl-1,3,5,2,46-trioxatriphosphinane 2,4,6-trioxide in EtOAc (0.901 mL, 1.514 mmol). The mixture was stirred at 50° C. for 2 hours and then diluted with water (12 mL). The aqueous layer was discarded. The oily residue was rinsed with water (3 mL), dried under a flow of nitrogen, dissolved in DCM, and purified by flash column chromatography on silica gel (40 g SiO$_2$ column) eluting with a gradient of 10-30% EtOAc in heptane to give a solid mixture of product and starting material. The solid mixture was recrystallized from MeOH (5 mL) to afford a solid, containing mostly the desired product. The solid was recrystallized from MeOH (3 mL) and dried in vacuum to give the title compound as a pink solid (114 mg, 32.4%). $^1$H NMR (400 MHz, DMSO-$d_6$) δ ppm 1.72-1.87 (m, 2H), 2.05 (ddd, J=9.60, 6.19, 3.16 Hz, 2H), 3.22 (ddd, J=12.69, 9.28, 3.03 Hz, 2H), 3.57-3.68 (m, 2H), 4.11 (s, 3H), 4.59 (dt, J=7.89, 4.01 Hz, 1H), 6.96-7.05 (m, 1H), 7.23-7.35 (m, 3H), 8.35 (dd, J=7.45, 1.89 Hz, 1H), 8.42 (dd, J=4.80, 2.02 Hz, 1H), 8.53 (d, J=2.02 Hz, 1H), 8.60 (d, J=2.02 Hz, 1H), 10.11 (s, 1H).

Example 64: N-(5-(acetamidomethyl)-2-(4-(2,4-difluorophenoxy)piperidin-1-yl)pyridin-3-yl)-2-methoxynicotinamide

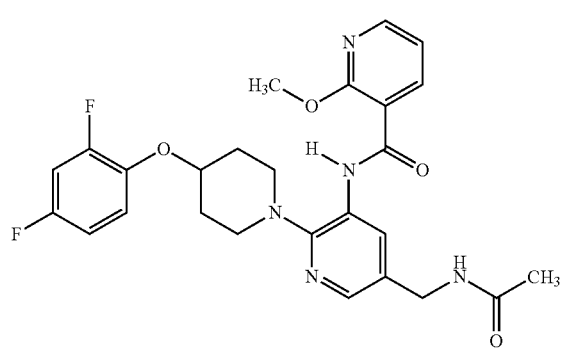 [SMILES: COc1ncccc1C(=O)Nc1cc(CNC(C)=O)cnc1N1CCC(Oc2ccc(F)cc2F)CC1]

To a suspension of N-(5-cyano-2-(4-(2,4-difluorophenoxy)piperidin-1-yl)pyridin-3-yl)-2-methoxynicotinamide (90 mg, 0.193 mmol) in acetic anhydride (5.47 mL, 58.0 mmol) was added a suspension of Raney-Ni in acetic anhydride (0.3 mL). The Raney-Ni suspension was prepared by washing Raney-Ni (Aldrich, 0.5 mL) successively with water (3×5 mL), EtOH (3×5 mL), and acetic anhydride (3×5 mL) and subsequently diluting the resulting solid with acetic anhydride (3 mL). The reaction mixture was heated in a bomb at 50° C. for 3 hours under 40 PSI of hydrogen. Following hydrogenation, acetic anhydride was removed by co-evaporation with toluene (2×10 mL). The residue was purified by flash column chromatography on silica gel (12 g SiO$_2$ column) eluting with a gradient of 70-100% EtOAc in heptane to give the title compound as white solid (29 mg, 29%). $^1$H NMR (400 MHz, DMSO-d$_6$) δ ppm 1.86 (s, 5H), 2.08 (br s, 2H), 2.91-3.01 (m, 2H), 3.19-3.28 (m, 2H), 4.18 (s, 3H), 4.23 (d, J=5.81 Hz, 2H), 4.52-4.63 (m, 1H), 6.96-7.07 (m, 1H), 7.25-7.38 (m, 3H), 8.00 (d, J=2.02 Hz, 1H), 8.35-8.49 (m, 3H), 8.58 (d, J=2.02 Hz, 1H), 10.31 (s, 1H); ESI-MS m/z [M+H]$^+$ 512.

Example 65: N-(2-(4-(2,4-difluorophenoxy)piperidin-1-yl)-5-(methoxymethyl)pyridin-3-yl)-2-methoxynicotinamide

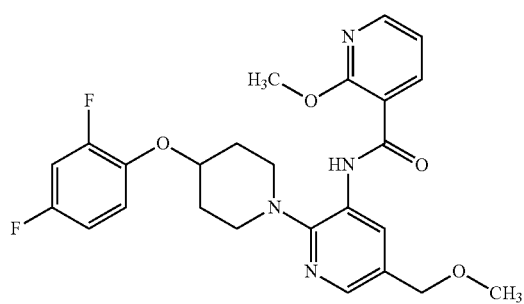

A solution of 2-(4-(2,4-difluorophenoxy)piperidin-1-yl)-5-(methoxymethyl)pyridin-3-amine (45 mg, 0.129 mmol), HATU (98 mg, 0.258 mmol) and 2-methoxynicotinic acid (39.4 mg, 0.258 mmol) in DMA (0.7 mL) was treated with DIPEA (0.090 mL, 0.515 mmol). The reaction mixture was heated to 80° C. for 2 hours and then diluted with water (3 mL). The aqueous layer was decanted. The residue was washed with water (1 mL) and recrystallized from MeOH (1.5 mL) to give a solid, which was recrystallized once more from MeOH (2.5 mL) to afford the title compound as a pink solid (40 mg, 64%). $^1$H NMR (400 MHz, DMSO-d$_6$) δ ppm 1.74-1.95 (m, 2H), 2.03-2.17 (m, 2H), 2.98 (ddd, J=12.38, 9.35, 2.78 Hz, 2H), 3.24-3.32 (m, 5H), 4.18 (s, 3H), 4.41 (s, 2H), 4.53-4.62 (m, 1H), 6.99-7.05 (m, 1H), 7.26-7.36 (m, 3H), 8.06 (d, J=2.02 Hz, 1H), 8.42-8.48 (m, 2H), 8.63 (d, J=2.02 Hz, 1H), 10.30 (s, 1H); ESI-MS m/z [M+H]$^+$ 485.

Example 66: N-(5-cyano-2-(4-(2,4-difluorophenoxy)piperidin-1-yl)pyridin-3-yl)picolinamide

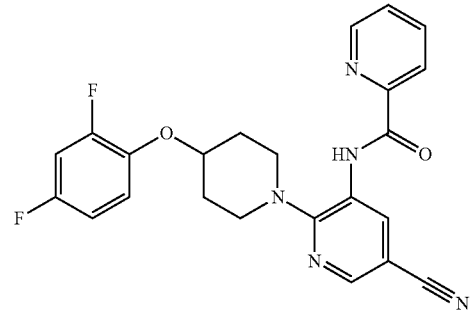 [SMILES: N#Cc1cnc(N2CCC(Oc3ccc(F)cc3F)CC2)c(NC(=O)c2ccccn2)c1]

A mixture of N-(5-cyanopyridin-3-yl)picolinamide (50 mg, 0.223 mmol), iodobenzene diacetate (144 mg, 0.446 mmol), MgCl$_2$ (4.25 mg, 0.045 mmol), copper(II) acetate hydrate (4.45 mg, 0.022 mmol), 4-(2,4-difluorophenoxy)piperidine (95 mg, 0.446 mmol), and 1,4-dioxane (1.1 mL) was briefly flushed with nitrogen and stirred at RT for 18 hours. The mixture was purified by flash column chromatography on silica gel (12 g SiO$_2$ column) eluting with a gradient of 30-100% EtOAc in heptane. The product was recrystallized from MeOH (2 mL) to give the title compound as a white solid (8 mg, 8%). $^1$H NMR (400 MHz, DMSO-d$_6$) δ ppm 1.80-1.92 (m, 2H), 2.07-2.16 (m, 2H), 3.17-3.26 (m, 2H), 3.53-3.64 (m, 2H), 4.60 (tt, J=7.71, 3.92 Hz, 1H), 6.99-7.04 (m, 1H), 7.27-7.36 (m, 2H), 7.74 (ddd, J=7.58, 4.80, 1.26 Hz, 1H), 8.12 (td, J=7.71, 1.77 Hz, 1H), 8.18-8.23 (m, 1H), 8.54 (d, J=2.27 Hz, 1H), 8.66 (d, J=2.02 Hz, 1H), 8.74-8.79 (m, 1H), 10.42 (s, 1H); ESI-MS m/z [M+H]$^+$ 436.

Example 67: N-(2-(4-benzylpiperidin-1-yl)-5-cyanopyridin-3-yl)picolinamide

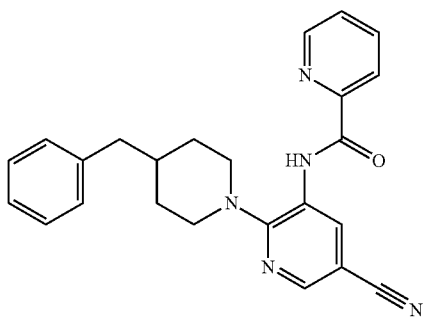 [SMILES: N#Cc1cnc(N2CCC(Cc3ccccc3)CC2)c(NC(=O)c2ccccn2)c1]

The title compound was prepared in a manner similar to Example 66, using 4-benzylpiperidine in place of 4-(2,4-difluorophenoxy)piperidine. ESI-MS m/z [M+H]$^+$ 398.

Example 68: N-(2-(4-(2-chloro-5-methylphenoxy)piperidin-1-yl)-5-cyanopyridin-3-yl)picolinamide

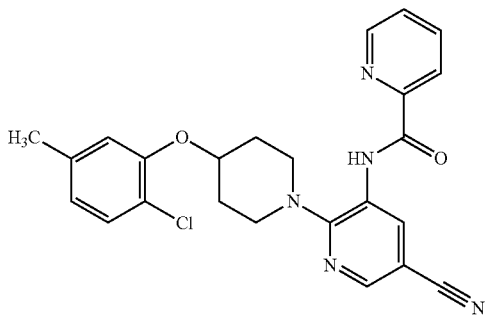 [SMILES: Cc1ccc(Cl)c(OC2CCN(c3ncc(C#N)cc3NC(=O)c3ccccn3)CC2)c1]

The title compound was prepared in a manner similar to Example 66, using 4-(2-chloro-5-methylphenoxy)piperidine in place of 4-(2,4-difluorophenoxy)piperidine. ESI-MS m/z [M+H]$^+$ 448.

Example 69: N-(5-cyano-2-(4-(p-tolylthio)piperidin-1-yl)pyridin-3-yl)picolinamide

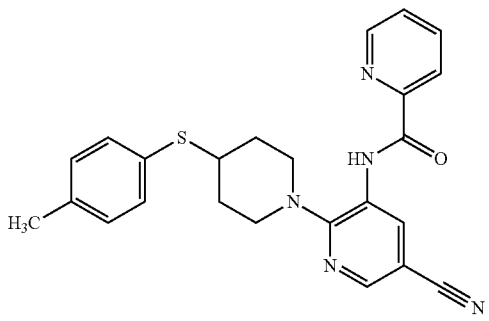 [SMILES: Cc1ccc(SC2CCN(c3ncc(C#N)cc3NC(=O)c3ccccn3)CC2)cc1]

The title compound was prepared in a manner similar to Example 66, using 4-(p-tolylthio)piperidine in place of 4-(2,4-difluorophenoxy)piperidine. ESI-MS m/z [M+H]$^+$ 430.

Example 70: N-(2-(4-benzoylpiperidin-1-yl)-5-cyanophenyl)-2-methoxynicotinamide

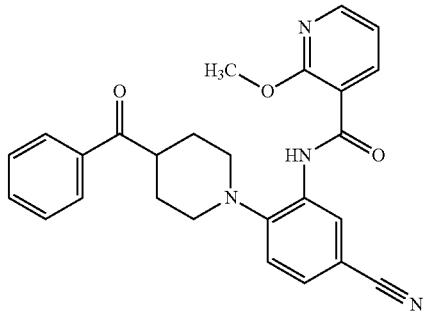 [SMILES: COc1ncccc1C(=O)Nc1cc(C#N)ccc1N1CCC(C(=O)c2ccccc2)CC1]

To a solution of 3-amino-4-(4-benzoylpiperidin-1-yl)benzonitrile (92 mg, 0.300 mmol) in DMA (0.5 mL) was added a solution of 2-methoxynicotinic acid (0.060 g, 0.390 mmol), HATU (0.148 g, 0.390 mmol) and DIPEA (0.157 mL, 0.900 mmol) in DMA (1 mL). The reaction mixture was capped and stirred at 80° C. for 2 hours, then diluted with water (3.5 mL) and spun on a centrifuge for 40 minutes. The aqueous layer was decanted and the residue was purified using supercritical fluid chromatography to give the title compound as a white solid. ESI-MS m/z [M+H]$^+$ 441.

Example 71: N-(2-(4-(2-chloro-6-fluorobenzyl)piperazin-1-yl-5-cyanophenyl)-2-methoxynicotinamide

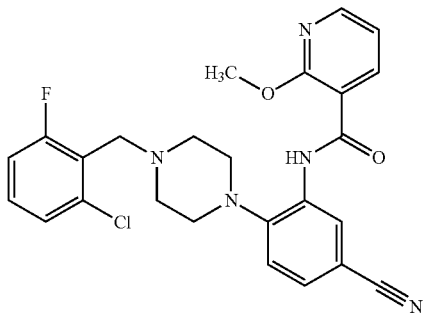 [SMILES: COc1ncccc1C(=O)Nc1cc(C#N)ccc1N1CCN(Cc2c(F)cccc2Cl)CC1]

To a solution of 3-amino-4-(4-(2-chloro-6-fluorobenzyl)piperazin-1-yl)benzonitrile (103 mg, 0.300 mmol) in DMA (1.5 mL) was added a solution of 2-methoxynicotinic acid (59.7 mg, 0.390 mmol), HATU (148 mg, 0.390 mmol) and DIPEA (0.157 mL, 0.900 mmol) in DMA (1 mL). The reaction mixture was capped and stirred at 80° C. for 2 hours, then diluted with water (3.5 mL) and spun on a centrifuge for 40 minutes. The aqueous layer was decanted and the residue was purified using supercritical fluid chromatography to give the title compound as a white solid. $^1$H NMR (400 MHz, CD$_3$OD) δ ppm 2.73-2.86 (m, 4H), 2.97 (t, J=4.67 Hz, 4H), 3.89 (d, J=2.27 Hz, 2H), 4.05 (s, 3H), 6.94-7.08 (m, 1H), 7.16 (dd, J=7.58, 5.05 Hz, 1H), 7.20-7.30 (m, 3H), 7.41 (dd, J=8.34, 2.02 Hz, 1H), 8.34 (dd, J=4.80, 2.02 Hz, 1H), 8.53 (dd, J=7.83, 2.02 Hz, 1H), 8.71 (d, J=2.02 Hz, 1H); ESI-MS m/z [M+H]$^+$ 480.

Example 72: N-(5-cyano-2-(4-(thiophen-2-ylmethyl)piperazin-1-yl)phenyl)-2-methoxynicotinamide

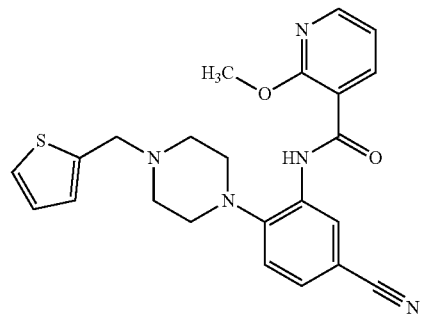 [SMILES: COc1ncccc1C(=O)Nc1cc(C#N)ccc1N1CCN(Cc2cccs2)CC1]

To a solution of 3-amino-4-(4-(thiophen-2-ylmethyl)piperazin-1-yl)benzonitrile (90 mg, 0.300 mmol) in DMA (0.5 mL) was added a solution of 2-methoxynicotinic acid (0.060 g, 0.390 mmol), HATU (0.148 g, 0.390 mmol) and DIPEA (0.157 mL, 0.900 mmol) in DMA (1 mL). The reaction mixture was capped and stirred at 80° C. for 2 hours, then diluted with water (3.5 mL) and spun on a centrifuge for 40 minutes. The aqueous layer was decanted and the residue was purified using supercritical fluid chromatography to give the title compound as a brown film. $^1$H NMR (400 MHz, CD$_3$OD) δ ppm 2.76 (br s, 4H), 3.02 (t, J=4.80 Hz, 4H), 3.93 (s, 2H), 4.01 (s, 3H), 6.94-7.02 (m, 2H), 7.16 (dd, J=7.58, 4.80 Hz, 1H), 7.27-7.32 (m, 2H), 7.44 (dd, J=8.21, 1.89 Hz, 1H), 8.34 (dd, J=4.93, 1.89 Hz, 1H), 8.53 (dd, J=7.58, 2.02 Hz, 1H), 8.71 (d, J=2.02 Hz, 1H); ESI-MS m/z [M+H]$^+$ 434.

Example 73: N-(5-cyano-2-(4-(thiophen-3-ylmethyl)piperazin-1-yl)phenyl)-2-methoxynicotinamide

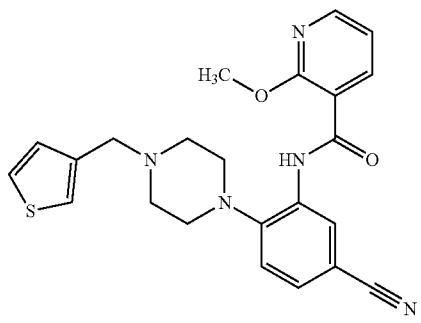 [SMILES: COc1ncccc1C(=O)Nc1cc(C#N)ccc1N1CCN(Cc2ccsc2)CC1]

To a solution of 3-amino-4-(4-(thiophen-3-ylmethyl)piperazin-1-yl)benzonitrile (90 mg, 0.300 mmol) in DMA (0.5 mL) was added a solution of 2-methoxynicotinic acid (0.060 g, 0.390 mmol), HATU (0.148 g, 0.390 mmol) and DIPEA (0.157 mL, 0.900 mmol) in DMA (1 mL). The reaction mixture was capped and stirred at 80° C. for 2 hours, then diluted with water (3.5 mL) and spun on a centrifuge for 40 minutes. The aqueous layer was decanted and the residue was purified using supercritical fluid chromatography to give the title compound as a yellow film. $^1$H NMR (400 MHz, CD$_3$OD) δ ppm 2.71 (br s, 4H), 3.01 (t, J=4.80 Hz, 4H), 3.73 (s, 2H), 4.04 (s, 3H), 7.07 (dd, J=5.05, 1.26 Hz, 1H), 7.17 (dd, J=7.71, 4.93 Hz, 1H), 7.19-7.22 (m, 1H), 7.29 (d, J=8.34 Hz, 1H), 7.33 (dd, J=4.93, 2.91 Hz, 1H), 7.44 (dd, J=8.34, 2.02 Hz, 1H), 8.35 (dd, J=4.80, 2.02 Hz, 1H), 8.54 (dd, J=7.71, 1.89 Hz, 1H), 8.72 (d, J=2.02 Hz, 1H); ESI-MS m/z [M+H]$^+$ 434.

Example 74: N-(4-(4-(2,4-difluorophenoxy)piperidin-1-yl)-2-methylpyrimidin-5-yl)-2-methoxy-6-methylnicotinamide

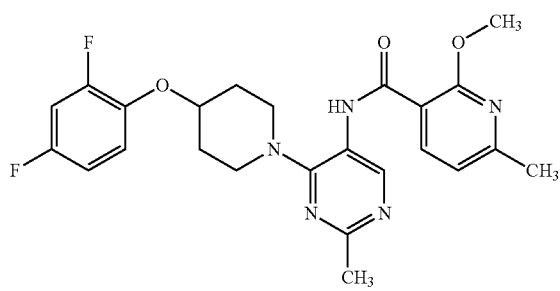 [SMILES: COc1nc(C)ccc1C(=O)Nc1cnc(C)nc1N1CCC(Oc2ccc(F)cc2F)CC1]

To a stirred solution of 2-methoxy-6-methylnicotinic acid (34.8 mg, 0.208 mmol), HATU (0.079 g, 0.208 mmol) and DIPEA (0.084 mL, 0.480 mmol) in DMA (0.3 mL) was added a solution of 4-(4-(2,4-difluorophenoxy)piperidin-1-yl)-2-methylpyrimidin-5-amine (0.051 g, 0.16 mmol) in DMA (0.4 mL). The reaction mixture was stirred at RT for 1 hour and at 80° C. for 2 hours and then diluted with water. The aqueous layer was decanted and the residue was purified by supercritical fluid chromatography to give the title compound as a yellow film. $^1$H NMR (400 MHz, CD$_3$OD) δ ppm 1.82-1.93 (m, 2H), 2.04-2.14 (m, 2H), 2.56 (d, J=4.04 Hz, 6H), 3.59-3.63 (m, 2H), 3.95-4.06 (m, 2H), 4.20 (s, 3H), 4.52-4.58 (m, 1H), 6.85-6.96 (m, 1H), 7.02 (ddd, J=11.24, 8.46, 3.03 Hz, 1H), 7.08 (d, J=7.58 Hz, 1H), 7.21 (td, J=9.22, 5.56 Hz, 1H), 7.56-7.59 (m, 1H), 8.33 (d, J=7.58 Hz, 1H), 8.43 (s, 1H); ESI-MS m/z [M+H]$^+$ 470.

Example 75: N-(5-cyano-2-(4-(4-fluorobenzyl)piperazin-1-yl)pyridin-3-yl)-2-methoxynicotinamide

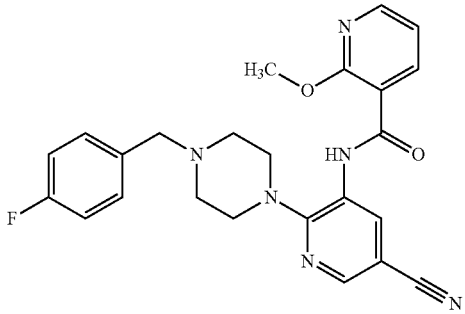 [SMILES: COc1ncccc1C(=O)Nc1cc(C#N)cnc1N1CCN(Cc2ccc(F)cc2)CC1]

A mixture of 2-methoxynicotinic acid (32.0 mg, 0.209 mmol), HATU (79 mg, 0.209 mmol) and 5-amino-6-(4-(4-fluorobenzyl)piperazin-1-yl)nicotinonitrile (50 mg, 0.161 mmol) dissolved in DMA (0.7 mL) was treated with DIPEA (0.084 mL, 0.482 mmol). The reaction mixture was stirred at 80° C. for 2 hours and then diluted with water (3.5 mL). The aqueous layer was decanted and the residue was purified using supercritical fluid chromatography to give the title compound as a clear solid (5 mg, 7%). ESI-MS m/z [M+H]$^+$ 447.

Example 76: N-(1-acetyl-7-(4-(2,4-difluorophenoxy)piperidin-1-yl)-1H-indazol-6-yl)picolinamide

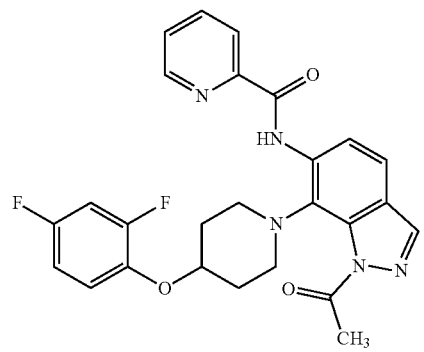 [SMILES: CC(=O)n1ncc2ccc(NC(=O)c3ccccn3)c(N3CCC(Oc4ccc(F)cc4F)CC3)c21]

Reactants N-(1-acetyl-1H-indazol-6-yl)picolinamide (0.112 g, 0.4 mmol), iodobenzene diacetate (0.258 g, 0.800 mmol), MgCl₃ (7.62 mg, 0.080 mmol), copper(II) acetate hydrate (7.99 mg, 0.040 mmol), 4-(2,4-difluorophenoxy)piperidine (0.171 g, 0.800 mmol), and 14-dioxane (2 mL) were combined. The reaction mixture was briefly flushed with nitrogen and then stirred at RT for 30 minutes. The clear solution was decanted, concentrated in vacuo, and purified by flash column chromatography on silica gel (12 g SiO₂ column) eluting with a gradient of 30-100% EtOAc in heptane to give the title compound as a white solid (20 mg, 10%). ¹H NMR (400 MHz, DMSO-d₆) δ ppm 2.03 (td, J=12.88, 7.58 Hz, 3H), 2.17-2.28 (m, 2H), 2.73 (s, 3H), 3.24-3.31 (m, 2H), 3.31 (br s, 4H), 4.65 (br s, 1H), 7.02-7.11 (m, 1H), 7.29-7.43 (m, 3H), 7.73 (ddd, J=7.39, 4.86, 0.88 Hz, 1H), 8.12 (td, J=7.71, 1.52 Hz, 1H), 8.20 (d, J=9.09 Hz, 1H), 8.23 (d, J=7.58 Hz, 1H), 8.72 (s, 1H), 8.75 (br s, 1H), 8.77 (d, J=9.60 Hz, 1H), 11.24 (s, 1H); ESI-MS m/z [M+H]⁺ 492.

Example 77: N-(7-(4-(2,4-difluorophenoxy)piperidin-1-yl)-1-methyl-1H-indazol-6-yl)picolinamide

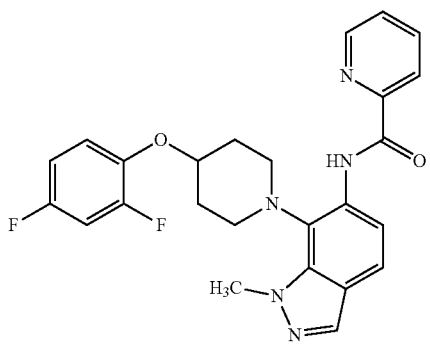 [SMILES: Cn1ncc2ccc(NC(=O)c3ccccn3)c(N3CCC(Oc4ccc(F)cc4F)CC3)c21]

Reactants N-(1-methyl-1H-indazol-6-yl)picolinamide (0.101 g, 0.4 mmol), iodobenzene diacetate (0.258 g, 0.800 mmol), MgCl₃ (7.62 mg, 0.080 mmol), copper(II) acetate hydrate (7.99 mg, 0.040 mmol), 4-(2,4-difluorophenoxy)piperidine (0.171 g, 0.800 mmol), and 1,4-dioxane (2 mL) were combined. The reaction mixture was briefly flushed with nitrogen, then stirred at RT for 30 minutes, and diluted with water (6 mL). The aqueous layer was decanted and the residue was purified by flash column chromatography on silica gel (12 g SiO₂ column) eluting with a gradient of 15-80% EtOAc in heptane to afford a red oil, which was purified again by flash column chromatography on silica gel (4 g SiO₂ column) eluting with a gradient of 15-70% EtOAc in heptane. The purified red oil was dissolved in DMSO (1 mL). Water (2 mL) was added to the solution, resulting in a solid precipitate. The solid was filtered, washed with water, and dried in a vacuum oven at 70° C. for 18 hours to give the title compound as a tan solid (20 mg, 11%). ¹H NMR (400 MHz, CDCl₃) δ ppm 1.95-2.22 (m, 3H), 2.29-2.46 (m, 2H), 3.20-3.30 (m, 2H), 3.45-3.64 (m, 2H), 4.33 (s, 1H), 4.42-4.47 (m, 2H), 4.54-4.67 (m, 1H), 6.79-6.95 (m, 2H), 7.05 (td, J=9.35, 4.80 Hz, 1H), 7.52-7.56 (m, 1H), 7.65 (dd, J=8.72, 2.65 Hz, 1H), 7.93-8.02 (m, 2H), 8.33-8.41 (m, 1H), 8.51 (d, J=8.84 Hz, 1H), 8.66 (d, J=4.94 Hz, 1H), 8.78 (d, J=4.78 Hz, 1H), 11.18 (br s, 1H), 11.46 (s, 1H); ESI-MS m/z [M+H]⁺ 464.

Example 78: N-(5-cyano-2-(4-(2,4-difluorophenoxy)piperidin-1-yl)phenyl)-2,6-dimethoxynicotinamide

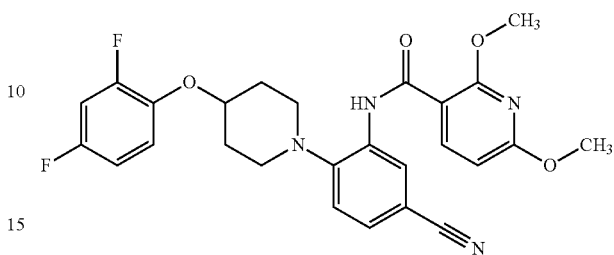

A mixture of DIPEA (0.119 mL, 0.619 mmol), 3-amino-4-(4-(2,4-difluorophenoxy)piperidin-1-yl)benzonitrile (0.082 g, 0.249 mmol), 2,6-dimethoxynicotinic acid (0.041 g, 0.226 mmol) and DMF (2.263 mL) was stirred for 10 minutes. Next HATU (0.129 g, 0.340 mmol) was added. The reaction mixture was stirred at RT for 24 hours, then diluted with DMF, filtered, and purified by HPLC to give a TFA salt of the title compound as a white solid (0.021 g, 15%). ¹H NMR (500 MHz, DMSO-d₆) δ ppm 1.76-1.95 (m, 2H), 2.04-2.23 (m, 2H), 2.79-2.92 (m, 2H), 3.03-3.19 (m, 2H), 3.99 (s, 3H), 4.22 (s, 3H), 4.48-4.65 (m, 1H), 6.65-6.67 (m, 1H), 6.97-7.09 (m, 1H), 7.23-7.37 (m, 2H), 7.37-7.46 (m, 1H), 7.54-7.63 (m, 1H), 8.39 (d, J=8.30 Hz, 1H), 8.65-8.74 (m, 1H); ESI-MS m/z [M+H]⁺ 495.2

Example 79: N-(5-cyano-2-(4-(2,4-difluorophenoxy)piperidin-1-yl)phenyl)-1,6-dimethyl-2-oxo-1,2-dihydropyridine-3-carboxamide

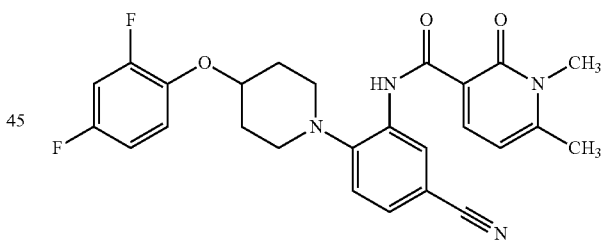

A mixture of DIPEA (0.201 mL, 1.148 mmol), 3-amino-4-(4-(2,4-difluorophenoxy)piperidin-1-yl)benzonitrile (0.104 g, 0.316 mmol), 1,6-dimethyl-2-oxo-1,2-dihydropyridine-3-carboxylic acid (0.048 g, 0.287 mmol) and DMF (0.574 mL) was stirred for 10 minutes. Next HATU (0.164 g, 0.431 mmol) was added. The reaction mixture was stirred at 55° C. for 36 hours, then diluted with DMF, filtered, and purified by HPLC to afford the title compound as a tan solid (0.0906 g, 66.0%). ¹H NMR (500 MHz, CDCl₃) δ ppm 2.13-2.23 (m, 2H), 2.23-2.34 (m, 2H), 2.50 (s, 3H), 2.84-2.86 (m, 2H), 3.18-3.22 (m, 2H), 3.67 (s, 3H), 4.33-4.48 (m, 1H), 6.37 (d, J=7.32 Hz, 1H), 6.72-6.83 (m, 1H), 6.87 (s, 1H), 7.02 (d, J=5.37 Hz, 1H), 7.17 (d, J=8.30 Hz, 1H), 7.35 (dd, J=7.81, 1.95 Hz, 1H), 8.48 (d, J=7.32 Hz, 1H), 8.96 (d, J=1.95 Hz, 1H), 12.43 (s, 1H); ESI-MS m/z [M+H]⁺ 479.3.

Example 80: N-(5-cyano-2-(4-(2,4-difluorophenoxy)piperidin-1-yl)phenyl)-2-methoxy-4,6-dimethylnicotinamide

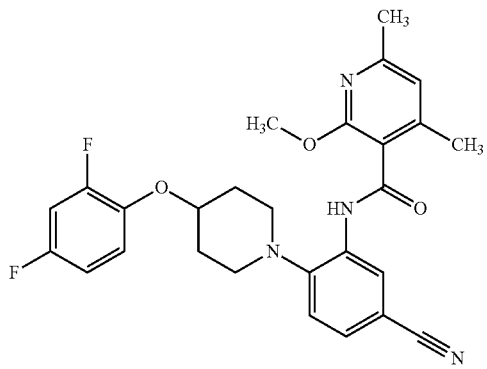 [SMILES: COc1nc(C)cc(C)c1C(=O)Nc1cc(C#N)ccc1N1CCC(Oc2ccc(F)cc2F)CC1]

A mixture of DIPEA (0.195 mL, 1.115 mmol), 3-amino-4-(4-(2,4-difluorophenoxy)piperidin-1-yl)benzonitrile (0.101 g, 0.307 mmol), 2-methoxy-4,6-dimethylnicotinic acid (0.051 g, 0.279 mmol) and DMF (0.558 mL) was stirred for 10 minutes. Next HATU (0.159 g, 0.418 mmol) was added. The reaction mixture was stirred at 55° C. for 36 hours, then diluted with DMF, filtered, and purified by HPLC to give the title compound as a light yellow solid (65.2 mg, 47.5%). $^1$H NMR (500 MHz, CDCl$_3$) δ ppm 1.91-2.01 (m, 2H), 2.03-2.12 (m, 2H), 2.46 (s, 3H), 2.47 (s, 3H), 2.78-2.90 (m, 2H), 3.15-3.29 (m, 2H), 3.93 (s, 3H), 4.28-4.41 (m, 1H), 6.73 (s, 1H), 6.76-6.85 (m, 1H), 6.85-6.93 (m, 1H), 6.94-7.03 (m, 1H), 7.24 (s, 1H), 7.35-7.44 (m, 1H), 8.90-9.03 (m, 2H); ESI-MS m/z [M+H]+ 493.3.

Example 81: N-(5-cyano-2-(4-(2-fluoro-4-methoxybenzoyl)piperidin-1-yl)phenyl)-1-methyl-2-oxo-1,2-dihydropyridine-3-carboxamide

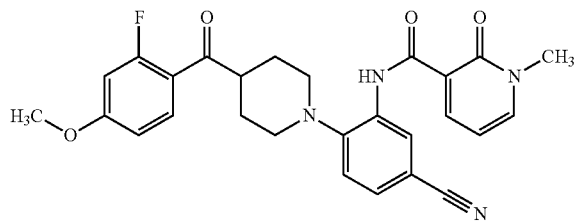

A mixture of 2-chloro-1-methylpyridin-1-ium iodide (00.112 g, 0.439 mmol), DIPEA (0.177 mL, 1.012 mmol), 1-methyl-2-oxo-1,2-dihydropyridine-3-carboxylic acid (0.052 g, 0.337 mmol), and DMA (3.75 mL) was stirred at RT for 15 minutes. Next 3-amino-4-(4-(2-fluoro-4-methoxybenzoyl)piperidin-1-yl)benzonitrile (0.155 g, 0.439 mmol) in DMA (0.5 mL) was added. The reaction mixture was heated to 80° C. for 24 hours, then diluted with DMF, filtered, and purified by HPLC to give the title compound as (0.056 g, 0.115 mmol, 34.0%). $^1$H NMR (500 MHz, CDCl$_3$) δ ppm 1.81-1.91 (m, 2H), 1.99-2.11 (m, 2H), 2.79-2.82 (m, 2H), 3.18-3.20 (m, 2H), 3.21-3.30 (m, 1H), 3.62 (s, 3H), 3.86 (s, 3H), 6.52-6.66 (m, 1H), 6.83-7.00 (m, 2H), 7.29-7.44 (m, 1H), 7.50-7.61 (m, 1H), 7.74-7.87 (m, 1H), 8.08- 8.23 (m, 1H), 8.39-8.55 (m, 1H), 8.72-8.89 (m, 1H), 12.25-12.54 (m, 1H); ESI-MS m/z [M+H]+ 489.25.

Example 82: N-(5-cyano-2-(4-(2,5-difluorobenzoyl)piperidin-1-yl)phenyl)-1-methyl-2-oxo-1,2-dihydropyridine-3-carboxamide

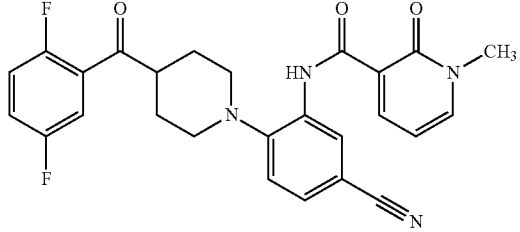

A mixture of 2-chloro-1-methylpyridin-1-ium iodide (0.078 g, 0.305 mmol), DIPEA (0.133 mL, 0.762 mmol), 1-methyl-2-oxo-1,2-dihydropyridine-3-carboxylic acid (0.039 g, 0.254 mmol) and DMA (2.82 mL) was stirred at RT for 15 minutes. Next 3-amino-4-(4-(2,5-difluorobenzoyl)piperidin-1-yl)benzonitrile (0.104 g, 0.305 mmol) in DMA (0.5 mL) was added. The reaction mixture was heated to 80° C. for 24 hours, then diluted with DMF, filtered, and purified by HPLC to give the title compound as a white solid (10 mg, 8.3%). $^1$H NMR (500 MHz, CDCl$_3$) δ ppm 1.86-1.99 (m, 2H), 1.99-2.14 (m, 2H), 2.73-2.88 (m, 2H), 3.11-3.21 (m, 2H), 3.23-3.30 (m, 1H), 3.62 (s, 3H), 6.52-6.63 (m, 1H), 7.30-7.40 (m, 1H), 7.40-7.48 (m, 1H), 7.48-7.59 (m, 2H), 7.59-7.69 (m, 1H), 8.11-8.23 (m, 1H), 8.40-8.53 (m, 1H), 8.74-8.86 (m, 1H), 12.37-12.51 (m, 1H); ESI-MS m/z [M+H]+ 477.20.

Example 83: N-(2-(4-(5-chloro-2-fluorobenzoyl)piperidin-1-yl-5-cyanophenyl)-1-methyl-2-oxo-1,2-dihydropyridine-3-carboxamide

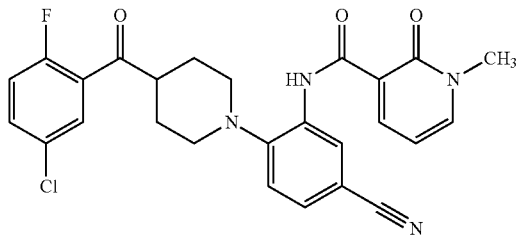 [SMILES: Cn1cccc(C(=O)Nc2cc(C#N)ccc2N2CCC(C(=O)c3cc(F)ccc3F)CC2)c1=O]

A mixture of 2-chloro-1-methylpyridin-1-ium iodide (0.095 g, 0.372 mmol), DIPEA (0.150 mL, 0.858 mmol), 1-methyl-2-oxo-1,2-dihydropyridine-3-carboxylic acid (0.044 g, 0.286 mmol), and DMA (3.18 mL) was stirred at RT for 15 minutes. Next 3-amino-4-(4-(5-chloro-2-fluorobenzoyl)piperidin-1-yl)benzonitrile (0.133 g, 0.372 mmol) in DMA (0.5 mL) was added. The reaction mixture was heated to 80° C. for 24 hours, then diluted with DMF, filtered, and purified by HPLC to give the title compound as a white solid (19 mg, 13%). $^1$H NMR (500 MHz, CDCl$_3$) δ ppm 1.86-1.97 (m, 2H), 1.99-2.08 (m, 2H), 2.74-2.89 (m, 2H), 3.11-3.15 (m, 2H), 3.23-3.31 (m, 1H), 3.63 (s, 3H), 6.54-6.64 (m, 1H), 7.30-7.39 (m, 1H), 7.40-7.48 (m, 1H), 7.51-7.58 (m, 1H), 7.67-7.75 (m, 1H), 7.79-7.87 (m, 1H), 8.12-8.20 (m, 1H), 8.42-8.50 (m, 1H), 8.75-8.83 (m, 1H), 12.45 (s, 1H); ESI-MS m/z [M+H]+ 493.20.

Example 84: (S)—N-(5-cyano-2-(4-((2,4-difluorophenyl)fluoromethyl)piperidin-1-yl)phenyl)-1-methyl-2-oxo-1,2-dihydropyridine-3-carboxamide

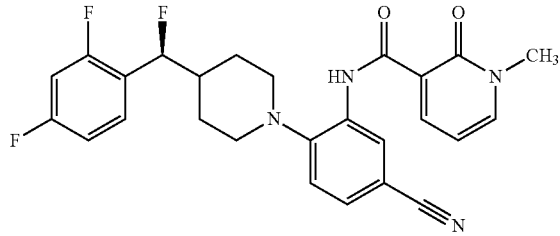 [SMILES: Cn1cccc(C(=O)Nc2cc(C#N)ccc2N2CCC([C@H](F)c3ccc(F)cc3F)CC2)c1=O]

A 0.2 M solution of 1-methyl-2-oxo-1,2-dihydropyridine-3-carboxylic acid (4.43 mL, 0.886 mmol), 2-chloro-1-methylpyridin-1-ium iodide (0.226 g, 0.886 mmol), and DIPEA (0.334 g, 2.58 mmol) was added to (S)-3-amino-4-(4-((2,4-difluorophenyl)fluoromethyl)piperidin-1-yl)benzonitrile (0.255 g, 0.738 mmol). The reaction mixture was heated to 80° C. and stirred for 12 hours, then concentrated in vacuo, and purified by HPLC (basic mode) to give the title compound as an off-white solid (67. mg, 19%). ¹H NMR (500 MHz, CDCl₃) δ ppm 1.29-1.36 (m, 1H), 1.73-1.91 (m, 3H), 1.89-2.01 (m, 1H), 2.01-2.16 (m, 1H), 2.55-2.68 (m, 1H), 2.69-2.74 (m, 1H), 3.01-3.19 (m, 2H), 3.62 (s, 3H), 5.48-5.70 (m, 1H), 6.59 (dd, J=7.32, 5.35 Hz, 1H), 7.19 (td, J=8.54, 2.44 Hz, 1H), 7.27-7.40 (m, 2H), 7.48-7.64 (m, 2H), 8.17 (dd, J=6.59, 2.20 Hz, 1H), 8.40-8.53 (m, 1H), 8.81 (d, J=1.95 Hz, 1H), 12.46 (s, 1H).

Example 85: (R)—N-(5-cyano-2-(4-((2,4-difluorophenyl)fluoromethyl)piperidin-1-yl)phenyl)-1-methyl-2-oxo-1,2-dihydropyridine-3-carboxamide

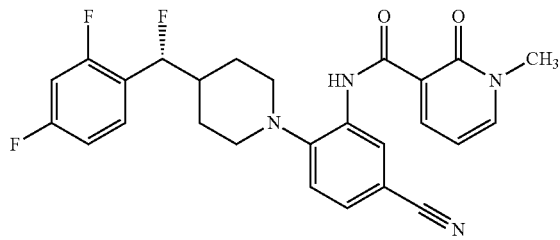 [SMILES: Cn1cccc(C(=O)Nc2cc(C#N)ccc2N2CCC([C@@H](F)c3ccc(F)cc3F)CC2)c1=O]

The title compound was prepared in a manner similar to Example 84, using (R)-3-amino-4-(4-((2,4-difluorophenyl)fluoromethyl)piperidin-1-yl)benzonitrile (0.229 g, 0.663 mmol) in place of (S)-3-amino-4-(4-((2,4-difluorophenyl)fluoromethyl)piperidin-1-yl)benzonitrile to give the title compound as a brown-orange solid (75 mg, 24%). ¹H NMR (500 MHz, CDCl₃) δ ppm 1.30-1.34 (m, 1H), 1.73-1.90 (m, 2H), 1.90-1.99 (m, 1H), 2.02-2.16 (m, 1H), 2.55-2.67 (m, 1H), 2.73 (td, J=11.72, 2.44 Hz, 1H), 3.02-3.17 (m, 2H), 3.55-3.67 (m, 3H), 5.49-5.72 (m, 1H), 6.52-6.55 (m, 1H), 7.14-7.18 (m, 1H), 7.26-7.40 (m, 2H), 7.47-7.62 (m, 2H), 8.17 (dd, J=6.59, 2.20 Hz, 1H), 8.46 (dd, J=7.32, 2.44 Hz, 1H), 8.81 (d, J=1.95 Hz, 1H), 12.46 (s, 1H); ESI-MS m/z [M+H]+ 481.20.

Example 86: N-(5-cyano-2-(4-((2,4-difluorophenyl)difluoromethyl)piperidin-1-yl)phenyl)-1-methyl-2-oxo-1,2-dihydropyridine-3-carboxamide

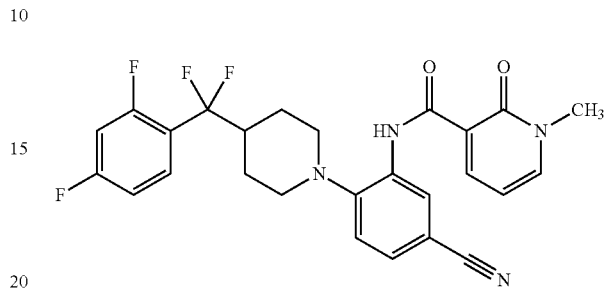

The title compound was prepared in a manner similar to Example 84, using 3-amino-4-(4-((2,4-difluorophenyl)difluoromethyl)piperidin-1-yl)benzonitrile (0.228 g, 0.627 mmol) in place of (S)-3-amino-4-(4-((2,4-difluorophenyl)fluoromethyl)piperidin-1-yl)benzonitrile to give the title compound as an off-white solid (13 mg, 4.2%). ¹H NMR (500 MHz, CDCl₃) δ ppm 1.60-1.70 (m, 2H), 1.87-2.05 (m, 2H), 2.30-2.42 (m, 1H), 2.66-2.71 (m, 2H), 3.10-3.14 (m, 2H), 3.59 (s, 3H), 6.50-6.66 (m, 1H), 7.19-7.29 (m, 1H), 7.29-7.37 (m, 1H), 7.40-7.50 (m, 1H), 7.50-7.58 (m, 1H), 7.58 7.69 (m, 1H), 8.11-8.24 (m, 1H), 8.38-8.51 (m, 1H), 8.82 (d, J=1.95 Hz, 1H), 12.38-12.57 (m, 1H); ESI-MS m/z [M+H]+ 499.2.

Example 87: N-(5-cyano-2-(4-((2,5-difluorophenyl)fluoromethyl)piperidin-1-yl)phenyl-1-methyl-2-oxo-1,2-dihydropyridine-3-carboxamide

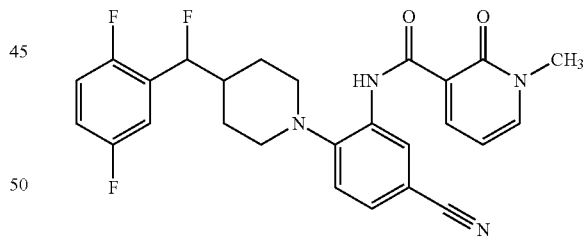

The title compound was prepared in a manner similar to Example 84, using 3-amino-4-(4-((2,5-difluorophenyl)fluoromethyl)piperidin-1-yl)benzonitrile (0.364 g, 1.054 mmol) in place of (S)-3-amino-4-(4-((2,4-difluorophenyl)fluoromethyl)piperidin-1-yl)benzonitrile to give the title compound as an orange semi-solid (0.112 g, 22%). ¹H NMR (500 MHz, CDCl₃) δ ppm 1.27-1.44 (m, 1H), 1.74-1.98 (m, 3H), 1.99-2.15 (m, 1H), 2.55-2.66 (m, 1H), 2.66-2.80 (m, 1H), 3.03-3.21 (m, 2H), 3.56-3.67 (m, 3H), 5.52-5.72 (m, 1H), 6.59 (dd, J=7.32, 6.35 Hz, 1H), 7.21-7.40 (m, 4H), 7.53 (dd, J=8.30, 1.95 Hz, 1H), 8.17 (d, J=4.39 Hz, 1H), 8.45 (dd, J=7.32, 2.44 Hz, 1H), 8.81 (d, J=1.95 Hz, 1H), 12.46 (s, 1H); ESI-MS m/z [M+H]+ 481.20.

Example 88: N-(5-cyano-2-(4-((2,5-difluorophenyl)difluoromethyl)piperidin-1-yl)phenyl)-1-methyl-2-oxo-1,2-dihydropyridine-3-carboxamide

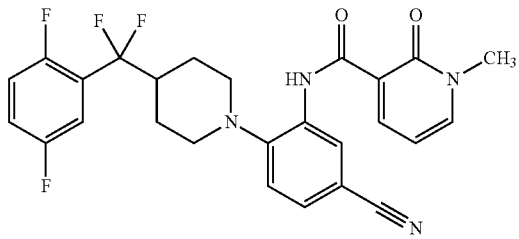 [SMILES: Cn1cccc(C(=O)Nc2cc(C#N)ccc2N2CCC(C(F)(F)c3cc(F)ccc3F)CC2)c1=O]

The title compound was prepared in a manner similar to Example 84, using 3-amino-4-(4-((2,5-difluorophenyl)difluoromethyl)piperidin-1-yl)benzonitrile (0.206 g, 0.567 mmol) in place of (S)-3-amino-4-(4-((2,4-difluorophenyl)fluoromethyl)piperidin-1-yl)benzonitrile to give the title compound as a light brown solid (53 mg, 19%). $^1$H NMR (500 MHz, CDCl$_3$) δ ppm 1.65-1.77 (m, 2H), 1.91-2.04 (m, 2H), 2.28-2.45 (m, 1H), 2.60-2.77 (m, 2H), 3.06-3.18 (m, 2H), 3.62 (s, 3H), 6.54-6.65 (m, 1H), 7.26-7.34 (m, 2H), 7.41-7.49 (m, 2H), 7.49-7.57 (m, 1H), 8.17 (dd, J=6.59, 2.20 Hz, 1H), 8.45 (dd, J=7.32, 2.44 Hz, 1H), 8.73-8.86 (m, 1H), 12.42-12.54 (m, 1H); ESI-MS m/z [M+H]$^+$ 499.25.

Example 89: N-(2-(4-((5-chloro-2-fluorophenyl)difluoromethyl)piperidin-1-yl)-5-cyanophenyl)-1-methyl-2-oxo-1,2-dihydropyridine-3-carboxamide

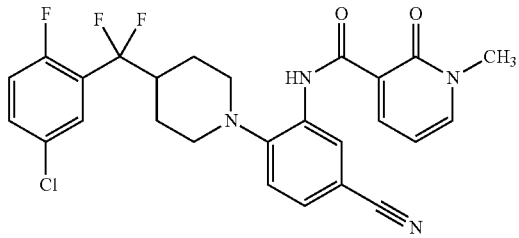 [SMILES: Cn1cccc(C(=O)Nc2cc(C#N)ccc2N2CCC(C(F)(F)c3cc(Cl)ccc3F)CC2)c1=O]

The title compound was prepared in a manner similar to Example 84, using 3-amino-4-(4-((5-chloro-2-fluorophenyl)difluoromethyl)piperidin-1-yl)benzonitrile (0.125 g, 0.329 mmol) in place of (S)-3-amino-4-(4-((2,4-difluorophenyl)fluoromethyl)piperidin-1-yl)benzonitrile to give the title compound as a light yellow solid (48 mg, 28%). $^1$H NMR (500 MHz, CDCl$_3$) δ ppm 1.64-1.72 (m, 2H), 1.91-2.05 (m, 2H), 2.31-2.46 (m, 1H), 2.70 (t, J=10.98 Hz, 2H), 3.14 (d, J=11.72 Hz, 2H), 3.59 (s, 3H), 6.58 (d, J=7.32 Hz, 1H), 7.32 (d, J=8.30 Hz, 1H), 7.40-7.50 (m, 1H), 7.50-7.58 (m, 2H), 7.64-7.73 (m, 1H), 8.12-8.19 (m, 1H), 8.41-8.48 (m, 1H), 8.82 (d, J=1.95 Hz, 1H), 12.49 (s, 1H); ESI-MS m/z [M+H]$^+$ 515.20.

Example 90: N-(5-cyano-2-(4-(2-fluoro-4-methoxybenzyl)piperidin-1-yl)phenyl)-1-methyl-2-oxo-1,2-dihydropyridine-3-carboxamide

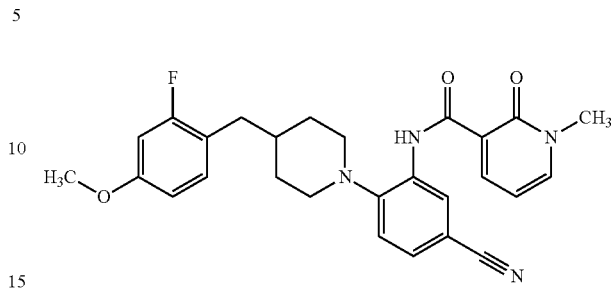

The title compound was prepared in a manner similar to Example 84, using 3-amino-4-(4-(2-fluoro-4-methoxybenzyl)piperidin-1-yl)benzonitrile (0.186 g, 0.548 mmol) in place of (S)-3-amino-4-(4-((2,4-difluorophenyl)fluoromethyl)piperidin-1-yl)benzonitrile to give the title compound as an off-white solid (81 mg, 31%). $^1$H NMR (500 MHz, CDCl$_3$) δ ppm 1.58-1.66 (m, 3H), 1.66-1.80 (m, 2H), 2.53-2.65 (m, 4H), 3.04-3.09 (m, 2H), 3.31 (s, 3H), 3.76 (s, 3H), 6.54-6.62 (m, 1H), 6.72 (dd, J=8.54, 2.68 Hz, 1H), 6.74-6.82 (m, 1H), 7.18 (t, J=8.54 Hz, 1H), 7.27-7.32 (m, 1H), 7.48-7.55 (m, 1H), 8.17 (dd, J=6.35, 2.44 Hz, 1H), 8.43-8.50 (m, 1H), 8.79 (d, J=2.44 Hz, 1H), 12.43 (s, 1H); ESI-MS m/z [M+H]$^+$ 475.30.

Example 91: N-(5-cyano-2-(4-(4-fluorobenzyl)piperazin-1-yl)phenyl)-2-methoxynicotinamide

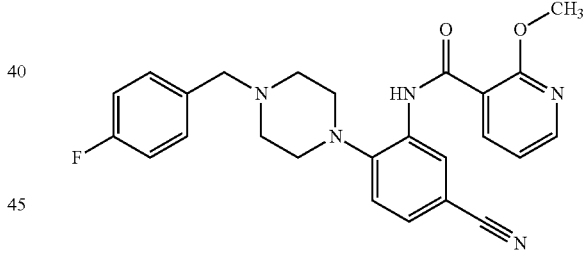

To a solution of 4-fluorobenzaldehyde (0.062 g, 0.436 mmol) and N-(5-cyano-2-(piperazin-1-yl)phenyl)-2-methoxynicotinamide (0.049 g, 0.145 mmol) in a 10:1 mixture of MeOH and HOAc (1.45 mL) was slowly added 5-ethyl-2-methylpyridine borane (0.065 mL, 0.436 mmol). The reaction mixture was heated to 50° C. for 1 hour, then quenched with 1 M (aq) HCl, stirred for 30 minutes, and basified with 1 M (aq) NaOH. The reaction mixture was extracted with EtOAc, dried over Na$_2$SO$_4$, filtered, and concentrated in vacuo. The crude residue was purified by HPLC to afford the title compound as a white solid (42 mg, 66%). $^1$H NMR (500 MHz, CDCl$_3$) δ ppm 2.50-2.73 (m, 4H), 2.80-2.93 (m, 4H), 3.46-3.66 (m, 2H), 4.08 (s, 3H), 6.59 (t, J=8.79 Hz, 2H), 7.03-7.16 (m, 2H), 7.23 (dd, J=8.30, 5.37 Hz, 2H), 7.32 (dd, J=8.30, 1.95 Hz, 1H), 8.28 (dd, J=4.88, 1.95, 1H), 8.53 (dd, J=7.32, 1.95 Hz, 1H), 8.2 (d, J=1.95 Hz, 1H), 10.23-10.43 (s, 1H); ESI-MS m/z [M+H]$^+$ 446.3.

Example 92: N-(4-cyano-2-(4-(2,4-difluorophenoxy)piperidin-1-yl)phenyl)-4-methoxynicotinamide

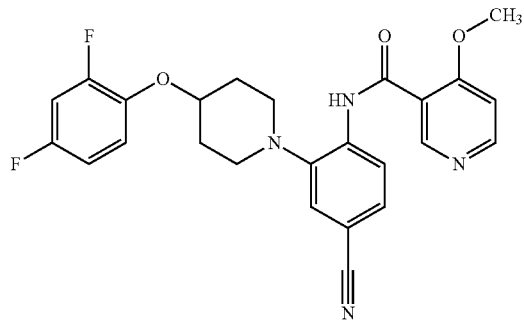 [SMILES: COc1ccncc1C(=O)Nc1ccc(C#N)cc1N1CCC(Oc2ccc(F)cc2F)CC1]

To a solution of 4-amino-3-(4-(2,4-difluorophenoxy)piperidin-1-yl)benzonitrile (58 mg, 0.176 mmol), 4-methoxynicotinic acid (40 mg, 0.264 mmol) and HATU (0.100 g, 0.264 mmol) in DMF (1.761 mL) was added DIPEA (0.062 mL, 0.352 mmol). The reaction mixture was heated to 55° C. for 24 hours, then filtered and purified by HPLC to give the title compound as a pale beige solid (13 mg, 16%). $^1$H NMR (500 MHz, CDCl$_3$) δ ppm 1.88-2.03 (m, 2H), 2.10-2.25 (m, 2H), 2.79-2.84 (m, 2H), 3.10-3.24 (m, 2H), 4.18 (s, 3H), 4.30-4.42 (m, 1H), 6.73 (dddd, J=9.15, 7.69, 2.93, 1.71 Hz, 1H), 6.90 (ddd, 11.23, 8.30, 2.93 Hz, 1H), 6.97-7.08 (m, 1H), 7.12 (d, J=5.86 Hz, 1H), 7.44-7.49 (m, 1H), 7.51 (dd, J=8.54, 1.71 Hz, 1H), 8.71 (d, J=8.30 Hz, 2H), 9.37 (s, 1H), 10.32 (s, 1H).

Example 93: N-(5-cyano-2-(4-(2,4-difluorobenzoyl)piperazin-1-yl)phenyl)-2-methoxynicotinamide

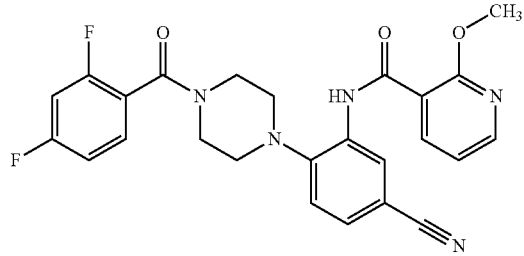 [SMILES: COc1ncccc1C(=O)Nc1cc(C#N)ccc1N1CCN(C(=O)c2ccc(F)cc2F)CC1]

To a solution of 2,4-difluorobenzoyl chloride (0.029 g, 0.165 mmol) and N-(5-cyano-2-(piperazin-1-yl)phenyl)-2-methoxynicotinamide (0.037 g, 0.110 mmol) in DMF (2.193 mL) was added DIPEA (0.043 g, 0.329 mmol). The reaction mixture was stirred for 5 hours, filtered, and purified by HPLC to afford the title compound as a white solid (30 mg, 57%). $^1$H NMR (500 MHz, CDCl$_3$) δ ppm 2.90-2.95 (m, 2H), 3.05-3.10 (m, 2H), 3.50-3.57 (m, 2H), 3.94-4.13 (m, 2H), 4.20 (s, 3H), 6.87 (td, J=9.15, 2.20 Hz, 1H), 7.00 (td, J=8.05, 2.44 Hz, 1H), 7.11-7.24 (m, 2H), 7.41-7.52 (m, 2H), 8.38 (dd, J=4.88, 1.95 Hz, 1H), 8.64 (dd, J=7.81, 1.95 Hz, 1H), 8.87 (d, J=1.95 Hz, 1H), 10.47 (s, 1H).

Example 94: N-(5-cyano-2-(4-(2,4-difluorophenoxy)piperidin-1-yl)phenyl)-3-methoxypyrazine-2-carboxamide

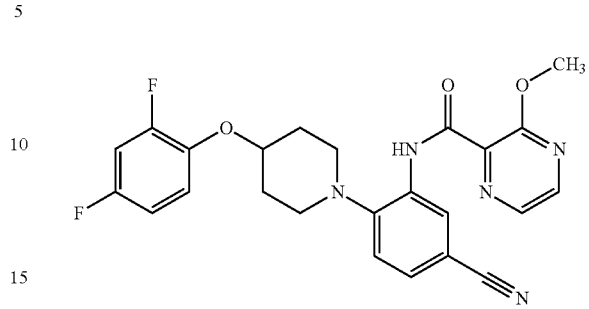

A solution of 3-amino-4-(4-(2,4-difluorophenoxy)piperidin-1-yl)benzonitrile (50 mg, 0.152 mmol), 3-methoxypyrazine-2-carboxylic acid (46.8 mg, 0.304 mmol), HATU (115 mg, 0.304 mmol) and DIPEA (106 µL, 0.607 mmol) in DMF (759 µL) was stirred on a hot plate at 80° C. overnight. The reaction mixture was filtered through a Millipore® filter, diluted with DMF and MeOH, and purified by HPLC (Shimadzu) eluting with a gradient of ACN in water (basic mode) to give the title compound as a light brown solid (68.7 mg, 97%). $^1$H NMR (400 MHz, CDCl$_3$) δ ppm 2.07-2.18 (m, 2H), 2.19-2.28 (m, 2H), 2.91 (ddd, J=11.68, 8.02, 3.28 Hz, 2H), 3.26 (ddd, J=11.62, 7.58, 3.54 Hz, 2H), 4.18 (s, 3H), 4.37-4.45 (m, 1H), 6.78-6.86 (m, 1H), 6.90 (ddd, J=11.12, 8.34, 3.03 Hz, 1H), 7.03 (td, J=9.09, 5.56 Hz, 1H), 7.23 (d, J=8.34 Hz, 1H), 7.41 (dd, J=8.34, 2.02 Hz, 1H), 8.26 (d, J=2.27 Hz, 1H), 8.41 (d, J=2.53 Hz, 1H), 8.93 (d, J=1.77 Hz, 1H), 10.62 (s, 1H); ESI-MS m/z [M+H]$^+$ 466.2.

Example 95: N-(2-(4-(4-fluoro-2-methylbenzoyl)piperazin-1-yl)-5-(methylsulfonyl)phenyl)-2-methoxynicotinamide

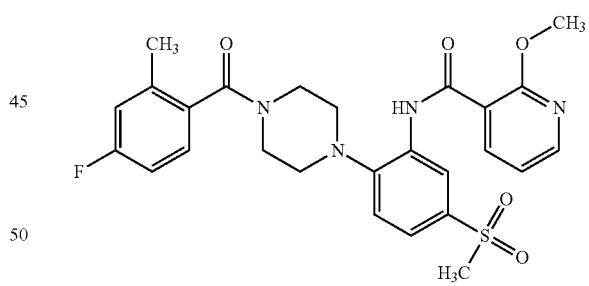

A solution of (4-(2-amino-4-(methylsulfonyl)phenyl)piperazin-1-yl)(4-fluoro-2-methylphenyl)methanone (50 mg, 0.128 mmol), 2-methoxynicotinic acid (19.56 mg, 0.128 mmol), HATU (48.6 mg, 0.128 mmol) and DIPEA (89 µL, 0.511 mmol) in DMF (639 µL) was stirred at RT overnight. The reaction mixture was filtered through a Millipore® filter, diluted with DMF and MeOH and purified by HPLC (Shimadzu) eluting with a gradient of ACN in water (basic mode) to give the title compound as a white solid (20.3 mg, 30.2%). $^1$H NMR (400 MHz, CD$_3$CN) δ ppm 2.31 (s, 3H), 2.88 (br s, 2H), 3.06 (s, 5H), 3.39 (t, J=4.67 Hz, 2H), 3.94 (br s, 2H), 4.21 (s, 3H), 6.97-7.06 (m, 2H), 7.19 (dd, J=7.58, 4.80 Hz, 1H), 7.25 (dd, J=8.34, 6.06 Hz, 1H), 7.41 (d, J=8.34 Hz, 1H), 7.67 (dd, J=8.34, 2.27 Hz, 1H), 8.38 (dd, J=4.80, 2.02 Hz, 1H), 8.56 (dd, J=7.58, 2.02 Hz, 1H), 8.99 (d, J=2.27 Hz, 1H); ESI-MS m/z [M+H]+ 527.3.

Example 96: N-(5-cyano-2-(4-((4-fluorophenyl)(methoxy)methyl)piperidin-1-yl)phenyl)-2-methoxynicotinamide

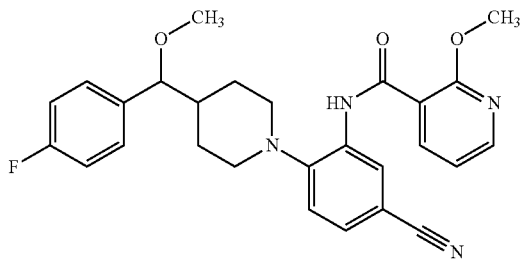 [SMILES: COc1ncccc1C(=O)Nc1cc(C#N)ccc1N1CCC(C(OC)c2ccc(F)cc2)CC1]

A solution of 3-amino-4-(4-((4-fluorophenyl)(methoxy)methyl)piperidin-1-yl)benzonitrile (60 mg, 0.177 mmol), 2-methoxynicotinic acid (54.1 mg, 0.354 mmol), HATU (134 mg, 0.354 mmol) and DIPEA (123 µL, 0.707 mmol) in DMF (884 µL) was stirred on a hot plate at 80° C. for 12 hours. The reaction mixture was filtered through a Millipore® filter, diluted with DMF and MeOH and purified by HPLC (Shimadzu) eluting with a gradient of ACN in water (basic mode). The product was re-purified by column chromatography (dry packing) eluting with 20% EtOAc in heptanes to give the title compound as a light yellow solid (53.3 mg, 63.5%). $^1$H NMR (400 MHz, CDCl$_3$) δ ppm 1.53-1.67 (m, 3H), 1.70-1.80 (m, 1H), 1.98 (d, J=12.63 Hz, 1H), 2.57-2.67 (m, 2H), 3.11-3.24 (m, 5H), 3.96-4.00 (m, 1H), 4.15 (s, 3H), 7.04-7.10 (m, 2H), 7.14-7.18 (m, 2H), 7.22-7.26 (m, 2H), 7.38 (dd, J=8.21, 1.89 Hz, 1H), 8.37 (dd, J=4.80, 2.02 Hz, 1H), 8.63 (dd, J=7.58, 2.02 Hz, 1H), 8.84 (d, J=2.02 Hz, 1H), 10.48 (s, 1H); ESI-MS m/z [M+H]+ 475.3.

Example 97: N-(5-cyano-2-(4-((3-fluorphenyl)sulfonyl)piperidin-1-yl)phenyl)-3-methoxy-1-methyl-1H-pyrazole-4-carboxamide

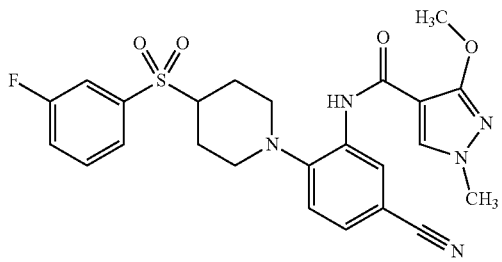 [SMILES: COc1nn(C)cc1C(=O)Nc1cc(C#N)ccc1N1CCC(S(=O)(=O)c2cccc(F)c2)CC1]

A solution of 3-amino-4-(4-((3-fluorophenyl)sulfonyl)piperidin-1-yl)benzonitrile (110 mg, 0.306 mmol), 3-methoxy-1-methyl-1H-pyrazole-4-carboxylic acid (143 mg, 0.918 mmol), HATU (349 mg, 0.918 mmol) and DIPEA (267 µL, 1.530 mmol) in DMF (1.530 mL) was stirred on a hot plate at 80° C. overnight. The reaction mixture was filtered through a Millipore® filter, diluted with DMF and MeOH and purified by HPLC (Shimadzu) eluting with a gradient of ACN in water (basic mode) to give the title compound as a white solid (17.3 mg, 11.4%). $^1$H NMR (400 MHz, CDCl$_3$) δ ppm 2.09-2.17 (m, 4H), 2.60-2.69 (m, 2H), 3.03-3.11 (m, 1H), 3.26 (d, J=12.38 Hz, 2H), 3.83 (s, 3H), 4.21 (s, 3H), 7.10 (d, J=8.34 Hz, 1H), 7.33 (dd, J=8.21, 1.89 Hz, 1H), 7.42 (tdd, J=8.24, 8.24, 2.59, 0.88 Hz, 1H), 7.59-7.67 (m, 2H), 7.72-7.76 (m, 1H), 7.85 (s, 1H), 8.86 (d, J=2.02 Hz, 1H), 9.26 (s, 1H); ESI-MS m/z [M+H]+ 498.2.

Example 98: N-(5-cyano-2-(4-((3-methoxyphenyl)sulfonyl)piperidin-1-yl)phenyl)-3-methoxy-1-methyl-1H-pyrazole-4-carboxamide

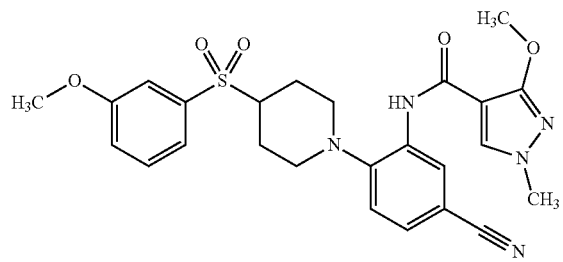 [SMILES: COc1cccc(S(=O)(=O)C2CCN(c3ccc(C#N)cc3NC(=O)c3cn(C)nc3OC)CC2)c1]

A solution of 3-amino-4-(4-((3-methoxyphenyl)sulfonyl)piperidin-1-yl)benzonitrile (100 mg, 0.269 mmol), 3-methoxy-1-methyl-1H-pyrazole-4-carboxylic acid (126 mg, 0.808 mmol), HATU (307 mg, 0.808 mmol) and DIPEA (235 µL, 1.346 mmol) in DMF (1.346 mL) was stirred on a hot plate at 80° C. overnight. The reaction mixture was filtered through a Millipore® filter, diluted with DMF and MeOH, and purified by HPLC (Shimadzu) eluting with a gradient of ACN in water (basic mode) to give the title compound as a yellow solid (88.9 mg, 64.8%). $^1$H NMR (400 MHz, CDCl$_3$) δ ppm 2.05-2.17 (m, 4H), 2.59-2.69 (m, 2H), 3.01-3.11 (m, 1H), 3.25 (d, J=12.13 Hz, 2H), 3.83 (s, 3H), 3.90 (s, 3H), 4.19-4.21 (m, 3H), 7.10 (d, J=8.34 Hz, 1H), 7.18-7.24 (m, 1H), 7.32 (dd, J=8.21, 1.89 Hz, 1H), 7.41-7.43 (m, 1H), 7.49-7.54 (m, 2H), 7.85 (s, 1H), 8.86 (d, J=1.77 Hz, 1H), 9.27 (s, 1H); ESI-MS m/z [M+H]+ 510.2.

Example 99: N-(4-(4-((2,4-difluorophenyl)sulfonyl)piperidin-1-yl)-6-methylpyridin-3-yl)-3-methoxy-1-methyl-1H-pyrazole-4-carboxamide

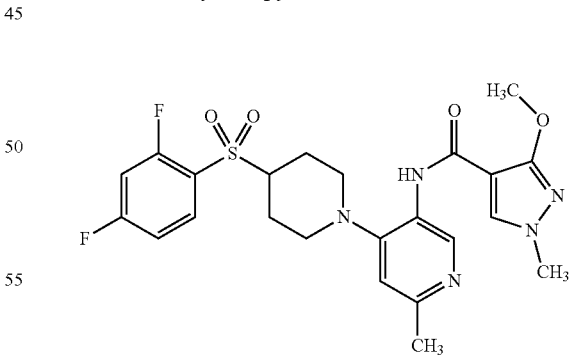

A solution of 4-(4-((2,4-difluorophenyl)sulfonyl)piperidin-1-yl)-6-methylpyridin-3-amine (34 mg, 0.093 mmol), 3-methoxy-1-methyl-1H-pyrazole-4-carboxylic acid (43.3 mg, 0.278 mmol), HATU (106 mg, 0.278 mmol) and DIPEA (64.6 µL, 0.370 mmol) in DMF (463 µL) was stirred on a hot plate at 80° C. overnight. The reaction mixture was filtered through a Millipore® filter, diluted with DMF and MeOH and purified by HPLC (Shimadzu) eluting with a gradient of ACN in water (basic mode) to give the title compound as an orange semi-solid (2.47 mg, 5.28%). ¹H NMR (400 MHz, CDCl₃) δ ppm 2.06-2.20 (m, 4H), 2.51 (s, 3H), 2.68 (td, J=11.68, 3.41 Hz, 2H), 3.29-3.39 (m, 3H), 3.81 (s, 3H), 4.21 (s, 3H), 6.79 (s, 1H), 7.00-7.15 (m, 2H), 7.83 (s, 1H), 7.97 (ddd, J=8.65, 7.89, 6.19 Hz, 1H), 8.80 (s, 1H), 9.44 (s, 1H). ESI-MS m/z [M+H]⁺ 506.2.

Example 100: 5-fluoro-N-(2-(4-(4-fluorobenzyl)piperazin-1-yl)-6-methylpyridin-3-yl)-2-methoxynicotinamide

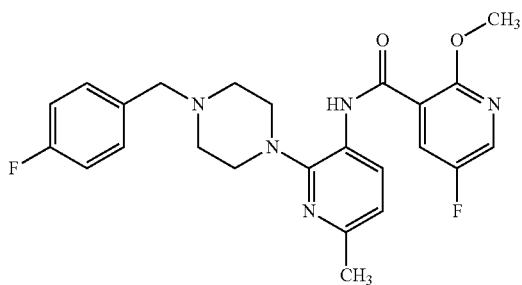 [SMILES: COc1ncc(F)cc1C(=O)Nc1ccc(C)nc1N1CCN(Cc2ccc(F)cc2)CC1]

A solution of 2-(4-(4-fluorobenzyl)piperazin-1-yl)-6-methylpyridin-3-amine (72 mg, 0.240 mmol), 5-fluoro-2-methoxynicotinic acid (123 mg, 0.719 mmol), HATU (273 mg, 0.719 mmol) and DIPEA (167 μL, 0.959 mmol) in DMF (1199 μL) was stirred on a hot plate at 80° C. overnight. The reaction mixture was filtered through a Millipore® filter, diluted with DMF and MeOH and purified by HPLC (Shimadzu) eluting with a gradient of ACN in water (basic mode) to give the title compound as a pale brown solid (64.6 mg, 59.4%). ¹H NMR (400 MHz, CDCl₃) δ ppm 2.46 (s, 3H), 2.64 (br s, 4H), 3.14 (br s, 4H), 3.60 (br s, 2H), 4.16 (s, 3H), 6.91 (d, J=8.08 Hz, 1H), 7.03 (t, J=8.59 Hz, 2H), 7.32 (br s, 2H), 8.17 (d, J=3.28 Hz, 1H), 8.36 (dd, J=8.34, 3.03 Hz, 1H), 8.55 (d, J=8.08 Hz, 1H), 10.31 (br s, 1H); ESI-MS m/z [M+H]⁺ 454.3.

Example 101: 5-fluoro-N-(2-(4-(4-fluorobenzyl)piperazin-1-yl)-6-methylpyridin-3-yl)-2-hydroxynicotinamide

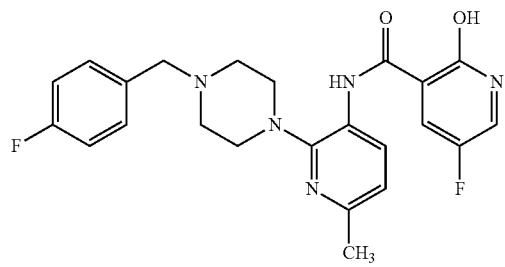 [SMILES: Cc1ccc(NC(=O)c2cc(F)cnc2O)c(N2CCN(Cc3ccc(F)cc3)CC2)n1]

The preparation of Example 100 yielded the title compound as a des-methyl side product which was recovered as an orange solid (12.4 mg, 11.8%). ¹H NMR (400 MHz, CDCl₃) δ ppm 2.40-2.47 (m, 3H), 2.82 (br s, 4H), 3.27 (br s, 6H), 6.89 (d, J=8.08 Hz, 1H), 7.03 (t, J=7.96 Hz, 2H), 7.42 (br s, 2H), 7.55 (br s, 1H), 8.53-8.64 (m, 2H), 11.69-11.88 (m, 1H); ESI-MS m/z [M+H]⁺ 440.3.

Example 102: N-(2-(4-(4-cyano-3-fluorobenzyl)piperazin-1-yl)-5-methylpyridin-3-yl)-3-methoxy-1-methyl-1H-pyrazole-4-carboxamide

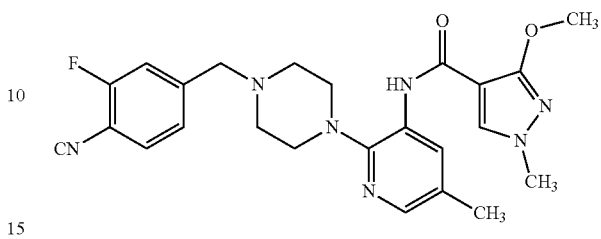

A solution of 3-methoxy-1-methyl-N-(5-methyl-2-(piperazin-1-yl)pyridin-3-yl)-1H-pyrazole-4-carboxamide (30 mg, 0.091 mmol) and 2-fluoro-4-formylbenzonitrile (27.1 mg, 0.182 mmol) in DCM (908 μL) was stirred at RT for 30 minutes. Next sodium triacetoxyhydroborate (77 mg, 0.363 mmol) was added in one portion at RT. The resulting reaction mixture was stirred at RT for 48 hours, then filtered through a Millipore® filter, diluted with DMF and MeOH and purified by HPLC (Shimadzu) eluting with a gradient of ACN in water (basic mode) to give the title compound as an ivory solid (17.7 mg, 42.1%). H NMR (400 MHz, CDCl₃) δ ppm 2.27-2.34 (m, 3H), 2.67 (br s, 4H), 3.10 (br s, 4H), 3.61-3.72 (m, 2H), 3.81 (s, 3H), 4.14 (s, 3H), 7.26-7.37 (m, 2H), 7.59 (t, J=7.20 Hz, 1H), 7.79-7.83 (m, 1H), 7.90 (d, J=1.52 Hz, 1H), 8.55 (d, J=2.02 Hz, 1H), 9.14 (br s, 1H); ESI-MS m/z [M+H]⁺ 464.3.

Example 103: N-(2-(4-(4-fluorobenzyl)piperazin-1-yl)-6-methylpyridin-3-yl)-5-methoxy-1-methyl-1H-pyrazole-4-carboxamide

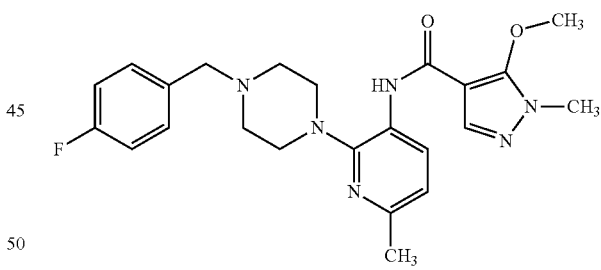

A solution of 2-(4-(4-fluorobenzyl)piperazin-1-yl)-6-methylpyridin-3-amine (68 mg, 0.226 mmol), 5-methoxy-1-methyl-1H-pyrazole-4-carboxylic acid (70.7 mg, 0.453 mmol), HATU (172 mg, 0.453 mmol) and DIPEA (158 μL, 0.906 mmol) in DMF (1.132 mL) was stirred at 80° C. for 48 hours. The reaction mixture was filtered through a Millipore® filter, diluted with DMF and MeOH and purified by HPLC (Shimadzu) eluting with a gradient of ACN in water (basic mode) to give the title compound as a white solid (13.8 mg, 13.9%). ¹H NMR (400 MHz, CDCl₃) δ ppm 2.42 (s, 3H), 2.73 (br s, 4H), 3.15 (br s, 4H), 3.53 (s, 3H), 3.56-3.72 (m, 5H), 6.83 (d, J=8.08 Hz, 1H), 7.01 (d, J=4.55 Hz, 2H), 7.36 (br s, 2H), 7.87 (s, 1H), 8.55 (d, J=8.08 Hz, 1H), 10.31 (br s, 1H); ESI-MS m/z [M+H]⁺ 439.3.

Example 104: N-(2-(4-(4-fluorobenzyl)piperazin-1-yl-6-methylpyridin-3-yl)-5-hydroxy-1-methyl-1H-pyrazole-4-carboxamide

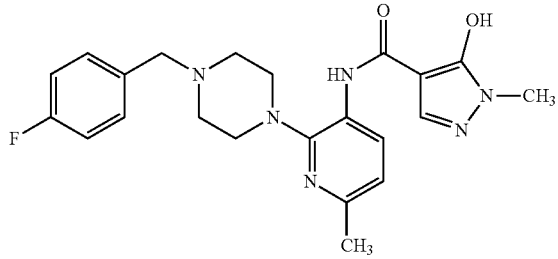 [SMILES: Cc1ccc(NC(=O)c2cnn(C)c2O)c(N2CCN(Cc3ccc(F)cc3)CC2)n1]

The preparation of Example 103 yielded the title compound as a des-methyl side product which was recovered as a brown solid (13.7 mg, 14.3%). $^1$H NMR (400 MHz, CDCl$_3$) δ ppm 2.40-2.49 (m, 3H), 2.64-2.90 (m, 4H), 3.19 (br s, 4H), 3.69 (s, 5H), 6.92 (d, J=8.08 Hz, 1H), 7.01-7.10 (m, 2H), 7.34-7.46 (m, 2H), 7.61 (br s, 1H), 8.35 (d, J=8.08 Hz, 1H); ESI-MS m/z [M+H]$^+$ 425.3.

Example 105: N-(5-cyano-2-(4-(2,4-difluorophenoxy)piperidin-1-yl)phenyl-2-methylthiazole-4-carboxamide

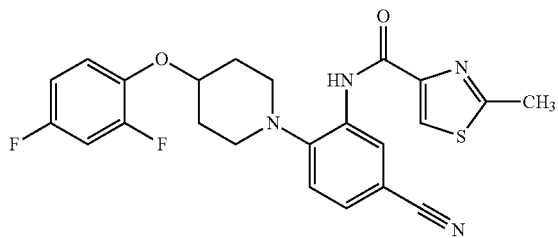 [SMILES: Cc1nc(C(=O)Nc2cc(C#N)ccc2N2CCC(Oc3ccc(F)cc3F)CC2)cs1]

To a 4 mL scintillation vial equipped with a stir bar was charged 2-methylthiazole-4-carboxylic acid (23.9 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (32.25 mg, 47%). $^1$H NMR (400 MHz, DMSO-d$_6$) δ ppm 1.92-2.07 (m, 2H), 2.12-2.24 (m, 2H), 2.77 (s, 3H), 2.85-2.95 (m, 2H), 3.08-3.17 (m, 2H), 4.48-4.68 (m, 1H), 7.03 (br s, 1H), 7.21-7.47 (m, 3H), 7.58 (dd, J=8.08, 2.02 Hz, 1H), 8.39 (s, 1H), 8.67 (d, J=2.02 Hz, 1H), 10.23 (s, 1H); ESI-MS m/z [M+H]$^+$ 455.2.

Example 106: N-(5-cyano-2-(4-(2,4-difluorophenoxy)piperidin-1-yl)phenyl)-5-fluoropicolinamide

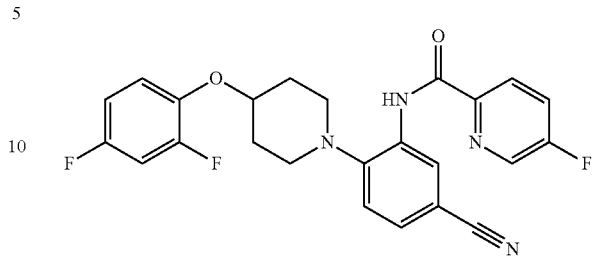

To a 4 mL scintillation vial equipped with a stir bar was charged 5-fluoropicolinic acid (23.6 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (21.30 mg, 31%). $^1$H NMR (400 MHz, DMSO-d$_6$) δ ppm 1.87-2.05 (m, 2H), 2.11-2.25 (m, 2H), 2.92 (ddd, J=11.68, 8.27, 3.03 Hz, 2H), 3.15 (dt, J=7.71, 3.98 Hz, 2H), 4.57 (dt, J=7.01, 3.69 Hz, 1H), 6.97-7.08 (m, 1H), 7.25-7.38 (m, 2H), 7.42 (d, J=8.34 Hz, 1H), 7.61 (dd, J=8.21, 1.89 Hz, 1H), 8.04 (td, J=8.59, 2.78 Hz, 1H), 8.30 (dd, J=8.59, 4.55 Hz, 1H), 8.61-8.88 (m, 2H), 10.63 (s, 1H); ESI-MS m/z [M+H]$^+$ 453.2.

Example 107: N-(5-cyano-2-(4-(2,4-difluorophenoxy)piperidin-1-yl)phenyl)-5,6-dihydro-4H-pyrrolo[1,2-b]pyrazole-2-carboxamide

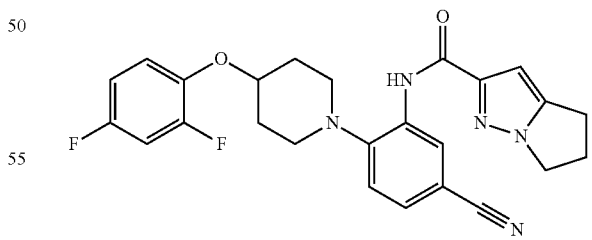

To a 4 mL scintillation vial equipped with a stir bar was charged 5,6-dihydro-4H-pyrrolo[1,2-b]pyrazole-2-carboxylic acid (25.4 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and then then sonicated and stirred at ambient temperature until a precipitate was observed. The material was filtered and the solids were washed with minimal MeOH, collected, and dried under vacuum to give the title compound as a white solid (23.42 mg, 33%). $^1$H NMR (400 MHz, DMSO-d$_6$) δ ppm 1.86-2.04 (m, 2H), 1.86-2.04 (m, 2H), 2.08-2.21 (m, 2H), 2.59 (quin, J=7.33 Hz, 2H), 2.83-2.98 (m, 4H), 3.03-3.20 (m, 2H), 4.18 (t, J=7.20 Hz, 2H), 4.56 (dt, J=7.52, 3.95 Hz, 1H), 6.57 (s, 1H), 6.97-7.08 (m, 1H), 7.26-7.42 (m, 3H), 7.55 (dd, J=8.21, 1.89 Hz, 1H), 8.61 (d, J=2.02 Hz, 1H), 9.63 (s, 1H); ESI-MS m/z [M+H]$^+$ 464.3.

Example 108: N-(5-cyano-2-(4-(2,4-difluorophenoxy)piperidin-1-yl)phenyl)-3-fluoropicolinamide

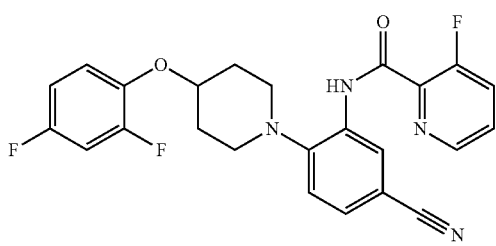 [SMILES: N#Cc1ccc(N2CCC(Oc3ccc(F)cc3F)CC2)c(NC(=O)c2ncccc2F)c1]

To a 4 mL scintillation vial equipped with a stir bar was charged 3-fluoropicolinic acid (23.6 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (29.6 mg, 43%). $^1$H NMR (400 MHz, DMSO-d$_6$) δ ppm 1.96 (ddt, J=12.44, 8.21, 4.07, 4.07 Hz, 2H), 2.10-2.26 (m, 2H), 2.84-3.00 (m, 2H), 3.07-3.26 (m, 2H), 4.57 (dt, J=7.39, 3.76 Hz, 1H), 6.95-7.12 (m, 1H), 7.23-7.47 (m, 3H), 7.60 (dd, J=8.21, 1.89 Hz, 1H), 7.83 (dt, J=8.46, 4.11 Hz, 1H), 8.01 (ddd, J=11.37, 8.59, 1.01 Hz, 1H), 8.51-8.74 (m, 2H), 10.67 (s, 1H); ESI-MS m/z [M+H]$^+$ 453.2.

Example 109: N-(5-cyano-2-(4-(2,4-difluorophenoxy)piperidin-1-yl)phenyl)-4-methoxypicolinamide

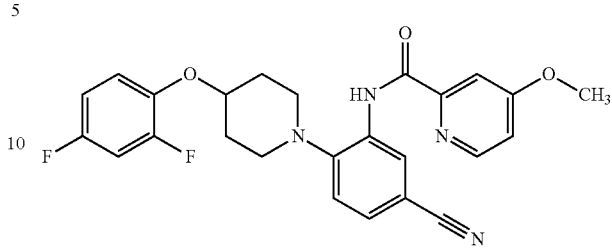

To a 4 mL scintillation vial equipped with a stir bar was charged 4-methoxypicolinic acid (25.6 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (23.1 mg, 33%). $^1$H NMR (400 MHz, DMSO-d$_6$) δ ppm 1.90-2.05 (m, 2H), 2.11-2.26 (m, 2H), 2.84-3.01 (m, 2H), 3.09-3.23 (m, 2H), 3.95 (s, 3H), 4.49-4.65 (m, 1H), 6.99-7.08 (m, 1H), 7.23-7.38 (m, 3H), 7.41 (d, J=8.34 Hz, 1H), 7.60 (dd, J=8.34, 2.02 Hz, 1H), 7.70 (d, J=2.53 Hz, 1H), 8.55 (d, J=5.56 Hz, 1H), 8.71 (d, J=2.02 Hz, 1H), 10.85 (s, 1H); ESI-MS m/z [M+H]$^+$ 465.2.

Example 110: N-(5-cyano-2-(4-(2,4-difluorophenoxy)piperidin-1-yl)phenyl)-2,5-dimethyloxazole-4-carboxamide

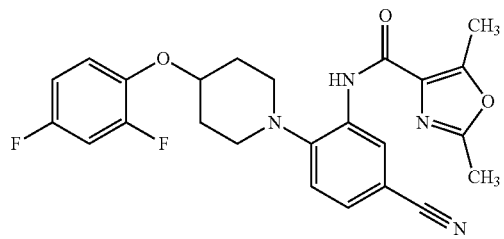 [SMILES: Cc1nc(C(=O)Nc2cc(C#N)ccc2N2CCC(Oc3ccc(F)cc3F)CC2)c(C)o1]

To a 4 mL scintillation vial equipped with a stir bar was charged 2,5-dimethyloxazole-4-carboxylic acid (23.6 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (22.1 mg, 32%). $^1$H NMR (400 MHz, DMSO-$d_6$) δ ppm 1.91-2.05 (m, 2H), 2.10-2.24 (m, 2H), 2.48 (s, 3H), 2.62 (s, 3H), 2.83-2.97 (m, 2H), 3.06-3.20 (m, 2H), 4.59 (dt, J=7.52, 3.69 Hz, 1H), 7.00-7.09 (m, 1H), 7.27-7.45 (m, 3H), 7.59 (dd, J=8.21, 1.89 Hz, 1H), 8.65 (d, J=2.02 Hz, 1H), 9.71 (s, 1H); ESI-MS m/z [M+H]$^+$ 453.2.

Example 111: N-(5-cyano-2-(4-(2,4-difluorophenoxy)piperidin-1-yl)phenyl-5-cycloproyloxazole-4-carboxamide

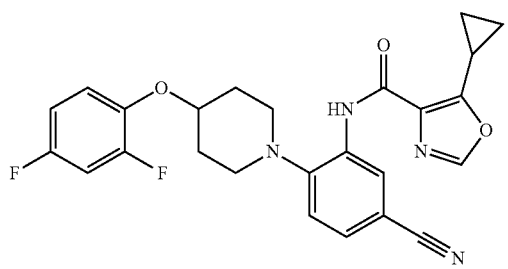 [SMILES: N#Cc1ccc(N2CCC(Oc3ccc(F)cc3F)CC2)c(NC(=O)c2ncoc2C2CC2)c1]

To a 4 mL scintillation vial equipped with a stir bar was charged 5-cyclopropyloxazole-4-carboxylic acid (25.6 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (21.7 mg, 31%). $^1$H NMR (400 MHz, DMSO-$d_6$) δ ppm 0.94-1.02 (m, 2H), 1.09-1.17 (m, 2H), 1.78-1.94 (m, 2H), 2.02-2.15 (m, 2H), 2.72-2.91 (m, 3H), 2.98-3.14 (m, 2H), 4.49 (dt, J=7.71, 3.98 Hz, 1H), 6.89-7.03 (m, 1H), 7.18-7.41 (m, 3H), 7.52 (dd, J=8.34, 2.02 Hz, 1H), 8.36 (s, 1H), 8.60 (d, J=1.77 Hz, 1H), 9.57 (s, 1H); ESI-MS m/z [M+H]$^+$ 465.2.

Example 112: N-(5-cyano-2-(4-(2,4-difluorophenoxy)piperidin-1-yl)phenyl)thiazole-4-carboxamide

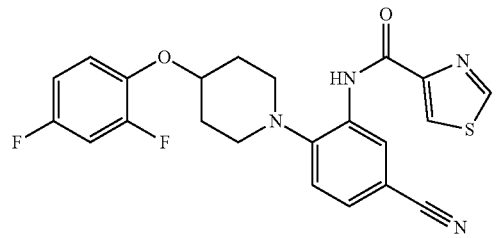 [SMILES: N#Cc1ccc(N2CCC(Oc3ccc(F)cc3F)CC2)c(NC(=O)c2cscn2)c1]

To a 4 mL scintillation vial equipped with a stir bar was charged thiazole-4-carboxylic acid (21.6 mg, 0.167 mmol), DMF (0.5 mL), HATU (66.4 mg, 0.174 mmol) and DIPEA (0.08 mL, 0.455 mmol). The mixture was stirred 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight then cooled to ambient temperature, and diluted with water (2 mL). The mixture was sonicated and stirred until a residue was observed around the inside of the vessel. The liquids were decanted, leaving an oily residue to which was added MeOH (1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (29.8 mg, 45%). $^1$H NMR (400 MHz, DMSO-de) δ ppm 1.78-1.97 (m, 2H), 2.02-2.19 (m, 2H), 2.84 (ddd, J=11.75, 8.59, 2.91 Hz, 2H), 3.01-3.16 (m, 2H), 4.50 (dt, J=7.45, 3.85 Hz, 1H), 6.90-7.01 (m, 1H), 7.17-7.43 (m, 3H), 7.54 (dd, J=8.34, 2.02 Hz, 1H), 8.49-8.69 (m, 2H), 9.27 (d, J=1.77 Hz, 1H), 10.07 (s, 1H); ESI-MS m/z [M+H]$^+$ 441.2.

Example 113: N-(5-cyano-2-(4-(2,4-difluorophenoxy)piperidin-1-yl)phenyl)-1,5-dimethyl-1H-pyrazole-3-carboxamide

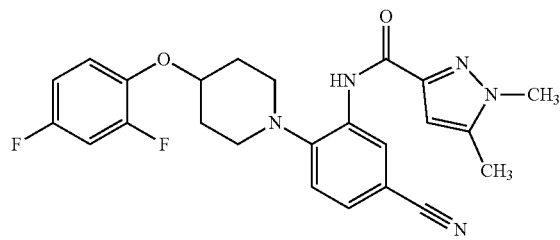 [SMILES: Cc1cc(C(=O)Nc2cc(C#N)ccc2N2CCC(Oc3ccc(F)cc3F)CC2)nn1C]

To a 4 mL scintillation vial equipped with a stir bar was charged 1,5-dimethyl-1H-pyrazole-3-carboxylic acid (23.4 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (14.4 mg, 21%); ESI-MS m/z [M+H]$^+$ 452.3.

Example 114: N-(5-cyano-2-(4-(2,4-difluorophenoxy)piperidin-1-yl)phenyl)-3,5-dimethylpyrazine-2-carboxamide

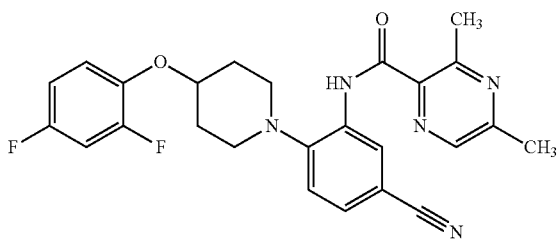 [SMILES: Cc1cnc(C(=O)Nc2cc(C#N)ccc2N2CCC(Oc3ccc(F)cc3F)CC2)c(C)n1]

To a 4 mL scintillation vial equipped with a stir bar was charged 3,5-dimethylpyrazine-2-carboxylic acid (23.4 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (25.7 mg, 37%). $^1$H NMR (400 MHz, DMSO-d$_6$) δ ppm 1.88-2.02 (m, 2H), 2.10-2.24 (m, 2H), 2.59 (s, 3H), 2.85-3.00 (m, 5H), 3.10-3.22 (m, 2H), 4.47-4.64 (m, 1H), 6.97-7.09 (m, 1H), 7.27-7.45 (m, 3H), 7.60 (dd, J=8.34, 2.02 Hz, 1H), 8.55 (s, 1H), 8.70 (d, J=1.77 Hz, 1H), 10.71 (s, 1H); ESI-MS m/z [M+H]$^+$ 464.2.

Example 115: N-(5-cyano-2-(4-(2,4-difluorophenoxy)piperidin-1-yl)phenyl)-3-methylpyrazine-2-carboxamide

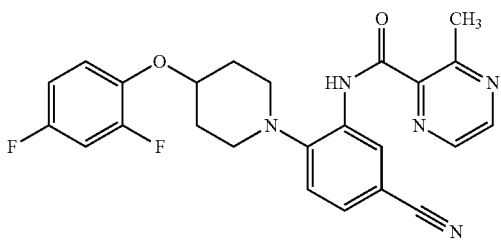 [SMILES: Cc1nccnc1C(=O)Nc1cc(C#N)ccc1N1CCC(Oc2ccc(F)cc2F)CC1]

To a 4 mL scintillation vial equipped with a stir bar was charged 3-methylpyrazine-2-carboxylic acid (23.1 mg, 0.167 mmol), DMF (0.5 mL), HATU (66.4 mg, 0.174 mmol) and DIPEA (0.08 mL, 0.455 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (32.25 mg, 47%). $^1$H NMR (400 MHz, DMSO-d$_6$) δ ppm 1.92-2.07 (m, 2H), 2.12-2.24 (m, 2H), 2.77 (s, 3H), 2.85-2.95 (m, 2H), 3.08-3.17 (m, 2H), 4.48-4.68 (m, 1H), 7.03 (br s, 1H), 7.21-7.47 (m, 3H), 7.58 (dd, J=8.08, 2.02 Hz, 1H), 8.39 (s, 1H), 8.67 (d, J=2.02 Hz, 1H), 10.23 (s, 1H); ESI-MS m/z [M+H]$^+$ 450.2.

Example 116: N-(5-cyano-2-(4-(2,4-difluorophenoxy)piperidin-1-yl)phenyl)-1,2,3-thiadiazole-4-carboxamide

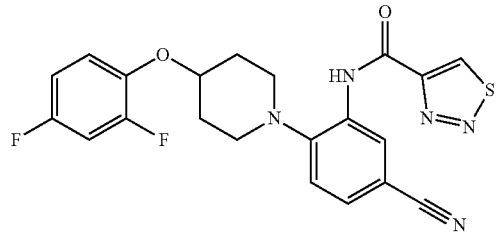 [SMILES: N#Cc1ccc(N2CCC(Oc3ccc(F)cc3F)CC2)c(NC(=O)c2csnn2)c1]

To a 4 mL scintillation vial equipped with a stir bar was charged 1,2,3-thiadiazole-4-carboxylic acid (21.7 mg, 0.167 mmol), DMF (0.5 mL), 2,4,6-tripropyl-1,3,5,2,4,6-trioxatriphosphinane 2,4,6-trioxide (0.186 mL, 0.304 mmol) and pyridine (0.05 mL, 0.607 mmol). The mixture was stirred for 5 minutes at ambient temperature and then a solution of 3-amino-4-(4-(2,4-difluorophenoxy)piperidin-1-yl)benzonitrile (50 mg, 0.152 mmol) in DMF (0.5 mL) was added in a single portion. The reaction mixture was stirred at 70° C. overnight, then cooled to ambient temperature, and diluted with water (2 mL). The mixture was sonicated and stirred until a residue was observed around the inside of the vessel. The liquids were decanted, leaving an oily residue to which was added MeOH (~1 mL). The mixture was heated until it became a translucent solution and was then sonicated and stirred at ambient temperature until a precipitate was observed. The material was filtered and the solids were washed with minimal MeOH, collected, and dried under vacuum to give the title compound as a white solid (2.1 mg, 3%). $^1$H NMR (400 MHz, DMSO-d$_6$) δ ppm 1.98-2.07 (m, 2H), 2.20-2.26 (m, 2H), 2.93 (ddd, J=11.87, 8.34, 3.28 Hz, 2H), 3.21 (ddd, J=11.68, 7.01, 4.04 Hz, 2H), 4.53 (dt, J=7.77, 3.82 Hz, 1H), 6.86-6.95 (m, 1H), 7.02 (ddd, J=11.49, 8.72, 3.03 Hz, 1H), 7.18 (td, J=9.22, 5.56 Hz, 1H), 7.39 (d, J=8.34 Hz, 1H), 7.52 (dd, J=8.21, 1.89 Hz, 1H), 8.78 (d, J=2.02 Hz, 1H), 9.51 (s, 1H), 10.39 (br s, 1H); ESI-MS m/z [M+H]$^+$ 442.2.

Example 117: N-(5-cyano-2-(4-(2,4-difluorophenoxy)piperidin-1-yl)phenyl)isoxazole-3-carboxamide

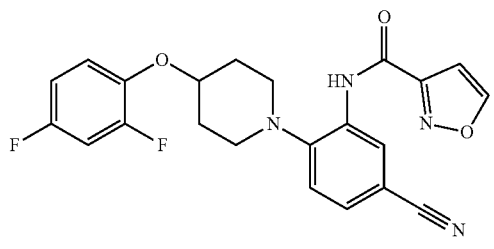 [SMILES: N#Cc1ccc(N2CCC(Oc3ccc(F)cc3F)CC2)c(NC(=O)c2ccon2)c1]

To a 4 mL scintillation vial equipped with a stir bar was charged isoxazole-3-carboxylic acid (19.74 mg, 0.175 mmol), DMF (1 mL), HATU (75 mg, 0.197 mmol) and Et$_3$N (0.063 mL, 0.455 mmol). The mixture was stirred for 5 minutes at ambient temperature and then 3-amino-4-(4-(2,4-difluorophenoxy)piperidin-1-yl)benzonitrile (50 mg, 0.152 mmol) was added. The reaction mixture was stirred at 70° C. overnight, then cooled to RT, and diluted with MeOH (~3 mL). The product was purified by preparative HPLC (Shimadzu, basic mode) and dried under vacuum to give the title compound as a white solid (6.3 mg, 9.7%). $^1$H NMR (400 MHz, CD$_3$CN) δ ppm 2.17-2.25 (m, 2H), 2.84-2.98 (m, 2H), 3.09-3.28 (m, 2H), 4.51 (dt, J=7.33, 3.66 Hz, 1H), 6.86-7.06 (m, 3H), 7.18 (td, J=9.28, 5.43 Hz, 1H), 7.37 (d, J=8.34 Hz, 1H), 7.52 (dd, J=8.08, 1.77 Hz, 1H), 8.67 (d, J=1.77 Hz, 1H), 8.78 (d, J=1.52 Hz, 1H), 9.66 (br s, 1H); ESI-MS m/z [M+H]$^+$ 425.2.

Example 118: N-(5-cyano-2-(4-(2,4-difluorophenoxy)piperidin-1-yl)phenyl)-5-ethylisoxazole-3-carboxamide

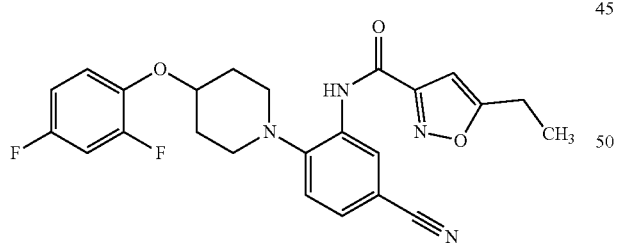

To a 4 mL scintillation vial equipped with a stir bar was charged 5-ethylisoxazole-3-carboxylic acid (24.64 mg, 0.175 mmol), DMF (1 mL), HATU (75 mg, 0.197 mmol) and Et$_3$N (0.063 mL, 0.455 mmol). The mixture was stirred for 5 minutes at ambient temperature and then 3-amino-4-(4-(2,4-difluorophenoxy)piperidin-1-yl)benzonitrile (50 mg, 0.152 mmol) was added. The reaction mixture was stirred at 70° C. overnight, then cooled to RT, and diluted with MeOH (~3 mL). The product was purified by preparative HPLC (Shimadzu, basic mode) and dried under vacuum to give the title compound as an off-white solid (9.4 mg, 13.7%). $^1$H NMR (400 MHz, CD$_3$CN) δ ppm 1.29 (t, J=7.58 Hz, 3H), 1.89-1.92 (m, 1H), 1.96-2.00 (m, 1H), 2.14 (ddt, 2H), 2.81-2.90 (m, 4H), 3.09-3.16 (m, 2H), 4.47 (dt, J=7.77, 3.82 Hz, 1H), 6.57 (t, J=0.88 Hz, 1H), 6.85-6.91 (m, 1H), 6.99 (ddd, J=11.49, 8.72, 3.03 Hz, 1H), 7.14 (td, J=9.35, 5.56 Hz, 1H), 7.32 (d, J=8.08 Hz, 1H), 7.46 (dd, J=8.34, 2.02 Hz, 1H), 8.62 (d, J=1.77 Hz, 1H), 9.57 (br s, 1H); ESI-MS m/z [M+H]$^+$ 453.2.

Example 119: N-(5-cyano-2-(4-(2,4-difluorophenoxy)piperidin-1-yl)phenyl)-4-methyl-1,2,5-oxadiazole-3-carboxamide

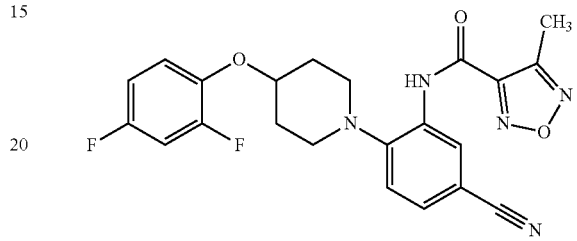

To a 4 mL scintillation vial equipped with a stir bar was charged 4-methyl-1,2,5-oxadiazole-3-carboxylic acid (22.36 mg, 0.175 mmol), DMF (1 mL), HATU (75 mg, 0.197 mmol) and Et$_3$N (0.063 mL, 0.455 mmol). The mixture was stirred for 5 minutes at ambient temperature and then 3-amino-4-(4-(2,4-difluorophenoxy)piperidin-1-yl)benzonitrile (50 mg, 0.152 mmol) was added. The reaction mixture was stirred at 70° C. overnight, then cooled to RT, and diluted with MeOH (3 mL). The product was purified by preparative HPLC (Shimadzu, basic mode) and dried under vacuum to give the title compound as a white solid (19.7 mg, 29.5%). $^1$H NMR (400 MHz, CD$_3$CN) δ ppm 1.95-2.02 (m, 2H), 2.16-2.20 (m, 2H), 2.63 (s, 3H), 2.89 (ddd, J=11.87, 8.34, 3.28 Hz, 2H), 3.10-3.22 (m, 2H), 4.46-4.54 (m, 1H), 6.87-6.94 (m, 1H), 7.01 (ddd, J=11.43, 8.53, 3.03 Hz, 1H), 7.17 (td, J=9.28, 5.43 Hz, 1H), 7.37 (d, J=8.34 Hz, 1H), 7.53 (dd, J=8.21, 1.89 Hz, 1H), 8.59 (d, J=1.77 Hz, 1H), 9.61 (br s, 1H); ESI-MS m/z [M+H]$^+$ 440.2.

Example 120: N-(5-cyano-2-(4-(2,4-difluorophenoxy)piperidin-1-yl)pyridin-3-yl)-1-ethyl-5-methoxy-1H-pyrazole-4-carboxamide

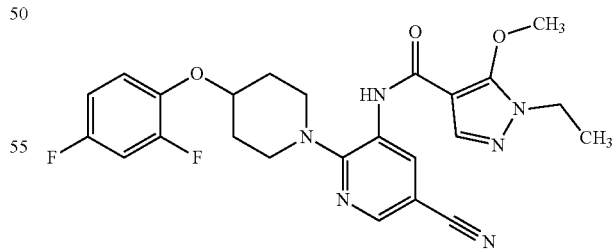

To a 4 mL scintillation vial equipped with a stir bar was charged 1-ethyl-5-methoxy-1H-pyrazole-4-carboxylic acid (29.7 mg, 0.175 mmol), 3-amino-4-(4-(2,4-difluorophenoxy)piperidin-1-yl)benzonitrile (50 mg, 0.152 mmol) and pyridine (0.049 mL, 0.607 mmol). The mixture was stirred for 5 minutes at ambient temperature and then 2,4,6-tripropyl-1,3,5,2,4,6-trioxatriphosphinane 2,4,6-trioxide (0.186 mL, 0.304 mmol) was added. The reaction mixture was stirred at 60° C. overnight and then cooled to RT. The product was purified by flash chromatography and dried under vacuum to give the title compound as a white solid (1.2 mg, 1.9%). ¹H NMR (400 MHz, CD₃CN) δ ppm 1.44 (t, J=7.33 Hz, 4H), 2.13 (d, J=2.27 Hz, 2H), 3.08 (ddd, J=12.76, 9.09, 3.16 Hz, 3H), 3.39-3.50 (m, 2H), 4.00-4.16 (m, 6H), 4.48-4.58 (m, 1H), 6.88-6.97 (m, 1H), 7.03 (ddd, J=11.49, 8.72, 3.03 Hz, 1H), 7.20 (td, J=9.22, 5.56 Hz, 1H), 7.96 (s, 1H), 8.35 (d, J=2.02 Hz, 1H), 8.88 (d, J=2.02 Hz, 1H), 8.98 (s, 1H); ESI-MS m/z [M+H]⁺ 483.2.

Example 121: N-(5-cyano-2-(4-(2,4-difluorophenoxy)piperidin-1-yl)pyridin-3-yl)-5-ethoxy-1-methyl-1H-pyrazole-4-carboxamide

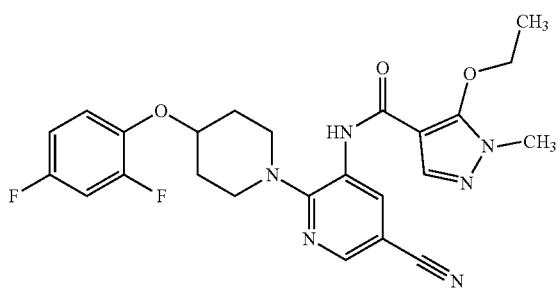 [SMILES: CCOc1c(C(=O)Nc2cc(C#N)cnc2N2CCC(Oc3ccc(F)cc3F)CC2)cnn1C]

To a 4 mL scintillation vial equipped with a stir bar was charged 5-ethoxy-1-methyl-1H-pyrazole-4-carboxylic acid (29.7 mg, 0.175 mmol), 3-amino-4-(4-(2,4-difluorophenoxy)piperidin-1-yl)benzonitrile (50 mg, 0.152 mmol) and pyridine (0.049 mL, 0.607 mmol). The mixture was stirred for 5 minutes at ambient temperature and then 2,4,6-tripropyl-1,3,5,2,4,6-trioxatriphosphinane 2,4,6-trioxide (0.186 mL, 0.304 mmol) was added. The reaction mixture was stirred at 60° C. overnight and then cooled to RT. The product was purified by flash chromatography and dried under vacuum to give the title compound as a white solid (1.7 mg, 2.3%). ¹H NMR (400 MHz, CD₃CN) δ ppm 1.51 (t, J=7.07 Hz, 3H), 1.83-1.93 (m, 2H), 2.01-2.13 (m, 2H), 3.13 (ddd, J=12.88, 9.22, 3.16 Hz, 2H), 3.44-3.60 (m, 2H), 3.74 (s, 3H), 4.39-4.63 (m, 3H), 6.80-6.96 (m, 1H), 7.01 (ddd, J=11.49, 8.72, 3.03 Hz, 1H), 7.17 (td, J=9.35, 5.56 Hz, 1H), 7.88 (s, 1H), 8.28-8.41 (m, 1H), 8.69-8.84 (m, 2H); ESI-MS m/z [M+H]⁺ 483.4.

Example 122: N-(5-cyano-2-(4-(2,4-difluorophenoxy)piperidin-1-yl)phenyl)oxazole-4-carboxamide

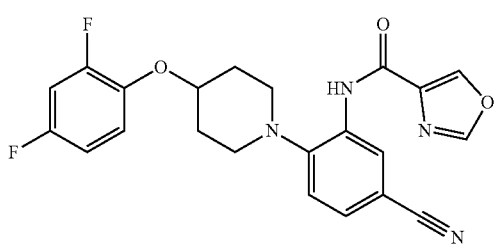 [SMILES: N#Cc1ccc(N2CCC(Oc3ccc(F)cc3F)CC2)c(NC(=O)c2cocn2)c1]

To a 4 mL vial was added 3-amino-4-(4-(2,4-difluorophenoxy)piperidin-1-yl)benzonitrile (50 mg, 0.152 mmol), HATU (66.4 mg, 0.175 mmol), DMF (1.00 mL) and DIPEA (0.079 mL, 0.455 mmol). The contents of the vial were thoroughly mixed and oxazole-4-carboxylic acid (18.88 mg, 0.167 mmol) was added. The vial was capped and the reaction mixture was stirred at 70° C. overnight. The reaction was subsequently quenched with water (3 mL). The mixture was vortexed for 2 minutes and the supernatant was removed. Methanol (2 mL) was added to the residue and the resulting mixture was stirred and heated until all the material was dissolved. A solid precipitated upon cooling. The solid was isolated by filtration, washed with a small amount of cold methanol, and dried to afford the title compound as an off-white solid (11.1 mg, 17.2%). ¹H NMR (400 MHz, DMSO-d₆) δ ppm 1.89-2.05 (m, 2H), 2.11-2.25 (m, 2H), 2.83-2.99 (m, 2H), 3.09-3.21 (m, 2H), 4.58 (dt, J=7.58, 4.04 Hz, 1H), 6.99-7.11 (m, 1H), 7.29-7.39 (m, 2H), 7.43 (d, J=8.34 Hz, 1H), 7.63 (dd, J=8.21, 1.89 Hz, 1H), 8.65 (d, J=2.02 Hz, 1H), 8.74 (d, J=0.76 Hz, 1H), 8.97 (d, J=1.01 Hz, 1H), 9.71 (s, 1H); ESI-MS m/z [M+H]⁺ 425.2.

Example 123: N-(5-cyano-2-(4-(2,4-difluorophenoxy)piperidin-1-yl)phenyl)-5-methylpyrazine-2-carboxamide

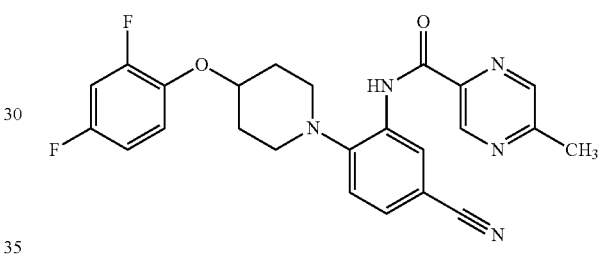

The title compound was prepared in a manner similar to Example 122, using 5-methylpyrazine-2-carboxylic acid (23.07 mg, 0.167 mmol, 1.1 eq) in place of oxazole-4-carboxylic acid to give the title compound as a white solid (23.3 mg, 34.1%). ¹H NMR (400 MHz, DMSO-d₆) δ ppm 1.88-2.03 (m, 2H), 2.10-2.25 (m, 2H), 2.65 (s, 3H), 2.87-2.98 (m, 2H), 3.10-3.22 (m, 2H), 4.56 (dt, J=7.45, 3.85 Hz, 1H), 6.98-7.10 (m, 1H), 7.29-7.38 (m, 2H), 7.43 (d, J=8.34 Hz, 1H), 7.63 (dd, J=8.34, 2.02 Hz, 1H), 8.70 (d, J=2.02 Hz, 1H), 8.74 (d, J=1.01 Hz, 1H), 9.23 (d, J=1.26 Hz, 1H), 10.52 (s, 1H); ESI-MS m/z [M+H]⁺ 450.2.

Example 124: N-(5-cyano-2-(4-(2,4-difluorophenoxy)piperidin-1-yl)phenyl)-5-methylpicolinamide

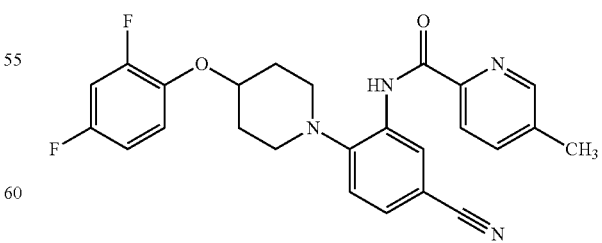

The title compound was prepared in a manner similar to Example 122, using 5-methylpicolinic acid (23.07 mg, 0.167 mmol, 1.1 eq) in place of oxazole-4-carboxylic acid to give the title compound as a white solid (12 mg, 18%). ¹H NMR (400 MHz, DMSO-d$_6$) δ ppm 1.93-2.08 (m, 2H), 2.17-2.25 (m, 2H), 2.46 (s, 3H), 2.89-2.99 (m, 2H), 3.13-3.22 (m, 2H), 4.54-4.65 (m, 1H), 7.00-7.10 (m, 1H), 7.30-7.40 (m, 2H), 7.43 (d, J=8.34 Hz, 1H), 7.62 (dd, J=8.34, 2.02 Hz, 1H), 7.92-7.98 (m, 1H), 8.13 (d, J=8.08 Hz, 1H), 8.59-8.64 (m, 1H), 8.75 (d, J=1.77 Hz, 1H), 10.82 (s, 1H); ESI-MS m/z [M+H]$^+$ 449.2.

Example 125: N-(5-cyano-2-(4-(2,4-difluorophenoxy)piperidin-1-yl)phenyl)-5-cyclopropylisoxazole-3-carboxamide

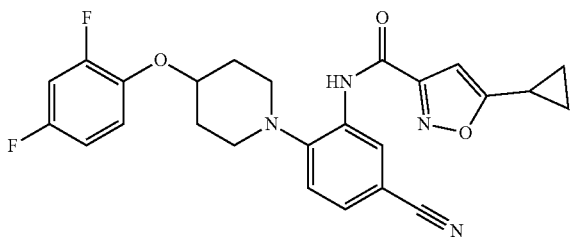 [SMILES: N#Cc1ccc(N2CCC(Oc3ccc(F)cc3F)CC2)c(NC(=O)c2cc(C3CC3)on2)c1]

The title compound was prepared in a manner similar to Example 122, using 5-cyclopropylisoxazole-3-carboxylic acid (25.6 mg, 0.167 mmol, 1.1 eq) in place of oxazole-4-carboxylic acid to give the title compound as a white solid (11.5 mg, 16.3%). $^1$H NMR (400 MHz, DMSO-d$_6$) δ ppm 0.92-0.97 (m, 2H), 1.04-1.10 (m, 2H), 1.73-1.91 (m, 2H), 2.04 (d, J=12.63 Hz, 2H), 2.14-2.23 (m, 1H), 2.76-2.91 (m, 2H), 3.02-3.14 (m, 2H), 4.49 (dt, J=7.89, 4.01 Hz, 1H), 6.67 (s, 1H), 6.91-7.01 (m, 1H), 7.21-7.30 (m, 2H), 7.33 (d, J=8.34 Hz, 1H), 7.57 (dd, J=8.34, 2.02 Hz, 1H), 8.37 (d, J=1.77 Hz, 1H), 9.61 (s, 1H); ESI-MS m/z [M+H]$^+$ 465.2.

Example 126: N-(5-cyano-2-(4-(2,4-difluorophenoxy)piperidin-1-yl)phenyl)pyridazine-3-carboxamide

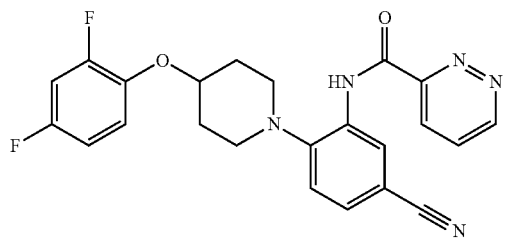 [SMILES: N#Cc1ccc(N2CCC(Oc3ccc(F)cc3F)CC2)c(NC(=O)c2cccnn2)c1]

The title compound was prepared in a manner similar to Example 122, using pyridazine-3-carboxylic acid (20.72 mg, 0.167 mmol, 1.1 eq) in place of oxazole-4-carboxylic acid to give the title compound as a white solid (19.8 mg, 30.0%). $^1$H NMR (400 MHz, DMSO-d$_6$) δ ppm 1.99 (ddt, J=12.63, 8.40, 4.14, 4.14 Hz, 1H), 2.20 (dd, J=12.51, 3.16 Hz, 1H), 2.90-3.05 (m, 1H), 3.14-3.29 (m, 1H), 4.61 (dt, J=7.89, 4.01 Hz, 1H), 6.98-7.10 (m, 1H), 7.26-7.41 (m, 1H), 7.46 (d, J=8.34 Hz, 1H), 7.67 (dd, J=8.34, 2.02 Hz, 1H), 8.05 (dd, J=8.34, 5.05 Hz, 1H), 8.43 (dd, J=8.46, 1.64 Hz, 1H), 8.72 (d, J=2.02 Hz, 1H), 9.52 (dd, J=5.10, 1.80 Hz, 1H), 10.92 (s, 1H); ESI-MS m/z [M+H]$^+$ 436.2.

Example 127: N-(5-cyano-2-(4-(2,4-difluorophenoxy)piperidin-1-yl)phenyl)-5-methyloxazole-4-carboxamide

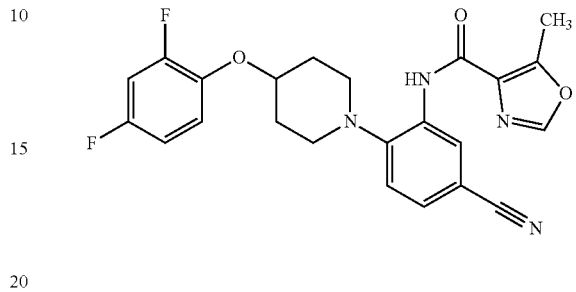

The title compound was prepared in a manner similar to Example 122, using 5-methyloxazole-4-carboxylic acid (80 mg, 0.629 mmol, 3.77 eq) in place of oxazole-4-carboxylic acid to give the title compound as a white solid (56.5 mg, 77%). $^1$H NMR (400 MHz, DMSO-d$_6$) δ ppm 1.87-2.00 (m, 2H), 2.15 (d, J=12.38 Hz, 2H), 2.67 (s, 3H), 2.84-2.96 (m, 2H), 3.06-3.18 (m, 2H), 4.56 (dt, J=7.77, 3.82 Hz, 1H), 6.97-7.09 (m, 1H), 7.27-7.37 (m, 2H), 7.40 (d, J=8.34 Hz, 1H), 7.59 (dd, J=8.21, 1.89 Hz, 1H), 8.54 (s, 1H), 8.65 (d, J=1.77 Hz, 1H), 9.67 (s, 1H); ESI-MS m/z [M+H]$^+$ 439.2.

Example 128: N-(5-cyano-2-(4-(2,4-difluorophenoxy)piperidin-1-yl)phenyl)isothiazole-3-carboxamide

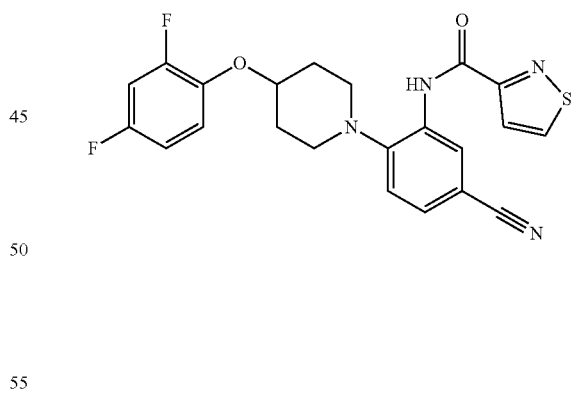

The title compound was prepared in a manner similar to Example 122, using isothiazole-3-carboxylic acid (77 mg, 0.596 mmol, 3.64 eq) in place of oxazole-4-carboxylic acid to give the title compound as a tan solid (51.9 mg, 71.9%). $^1$H NMR (400 MHz, DMSO-d$_6$) δ ppm 1.89-2.03 (m, 2H), 2.10-2.23 (m, 2H), 2.89-3.00 (m, 2H), 3.12-3.23 (m, 2H), 4.59 (dt, J=7.33, 3.92 Hz, 1H), 6.99-7.10 (m, 1H), 7.29-7.40 (m, 2H), 7.44 (d, J=8.34 Hz, 1H), 7.64 (dd, J=8.34, 2.02 Hz, 1H), 7.97 (d, J=4.80 Hz, 1H), 8.62 (d, J=2.02 Hz, 1H), 9.30 (d, J=4.55 Hz, 1H), 10.07 (s, 1H); ESI-MS m/z [M+H]$^+$ 441.2.

Example 129: N-(5-cyano-2-(4-(2,4-difluorophenoxy)piperidin-1-yl)phenyl)-6-methoxypyrazine-2-carboxamide

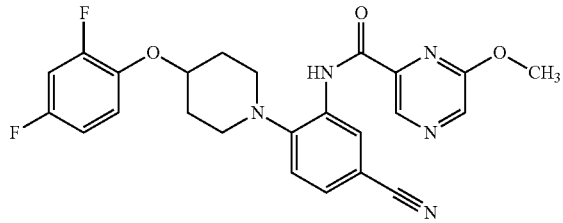 [SMILES: COc1cncc(C(=O)Nc2cc(C#N)ccc2N2CCC(Oc3ccc(F)cc3F)CC2)n1]

The title compound was prepared in a manner similar to Example 122, using 6-methoxypyrazine-2-carboxylic acid (46.8 mg, 0.304 mmol, 2 eq) in place of oxazole-4-carboxylic acid to give the title compound as an off-white solid (55.9 mg, 79%). $^1$H NMR (400 MHz, DMSO-$d_6$) δ ppm 1.81-1.97 (m, 2H), 2.08-2.22 (m, 2H), 2.87-2.97 (m, 2H), 3.09-3.19 (m, 2H), 4.19 (s, 3H), 4.58 (dt, J=8.34, 4.17 Hz, 1H), 6.99-7.09 (m, 1H), 7.28-7.41 (m, 2H), 7.49 (d, J=8.34 Hz, 1H), 7.67 (dd, J=8.34, 2.02 Hz, 1H), 8.68 (s, 1H), 8.70 (d, J=2.02 Hz, 1H), 8.95 (s, 1H), 10.39 (s, 1H); ESI-MS m/z [M+H]$^+$ 466.2.

Example 130: N-(5-cyano-2-(4-(2,4-difluorophenoxy)piperidin-1-yl)phenyl)-6-methylpyrazine-2-carboxamide

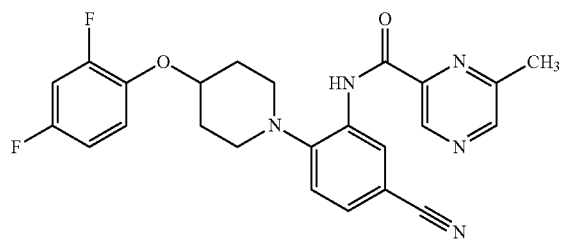 [SMILES: Cc1cncc(C(=O)Nc2cc(C#N)ccc2N2CCC(Oc3ccc(F)cc3F)CC2)n1]

The title compound was prepared in a manner similar to Example 122, using 6-methylpyrazine-2-carboxylic acid (41.9 mg, 0.304 mmol, 2 eq) in place of oxazole-4-carboxylic acid to give the title compound as an off-white solid (53.1 mg, 78%). $^1$H NMR (400 MHz, DMSO-$d_6$) δ ppm 1.94-2.10 (m, 2H), 2.14-2.29 (m, 2H), 2.70 (s, 3H), 2.87-3.01 (m, 2H), 3.10-3.23 (m, 2H), 4.62 (dt, J=7.77, 4.07 Hz, 1H), 6.99-7.11 (m, 1H), 7.26-7.43 (m, 2H), 7.47 (d, J=8.34 Hz, 1H), 7.65 (dd, J=8.21, 1.89 Hz, 1H), 8.75 (d, J=2.02 Hz, 1H), 8.92 (s, 1H), 9.18 (s, 1H), 10.76 (s, 1H); ESI-MS m/z [M+H]$^+$ 450.2.

Example 131: N-(5-cyano-2-(4-(2,4-difluorophenoxy)piperidin-1-yl)phenyl)-4,5-dimethylisoxazole-3-carboxamide

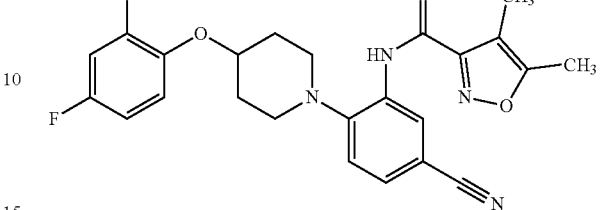

The title compound was prepared in a manner similar to Example 122, using 4,5-dimethylisoxazole-3-carboxylic acid (42.9 mg, 0.304 mmol, 2 eq) in place of oxazole-4-carboxylic acid to give the title compound as a white solid (20.6 mg, 30.0%). $^1$H NMR (400 MHz, DMSO-$d_6$) δ ppm 1.90 (td, J=8.46, 4.55 Hz, 2H), 2.08-2.22 (m, 5H), 2.45 (s, 3H), 2.87-2.99 (m, 2H), 3.09-3.22 (m, 2H), 4.58 (dt, J=7.89, 4.01 Hz, 1H), 6.96-7.12 (m, 1H), 7.29-7.38 (m, 2H), 7.41 (d, J=8.34 Hz, 1H), 7.65 (dd, J=8.34, 2.02 Hz, 1H), 8.48 (d, J=1.77 Hz, 1H), 9.70 (s, 1H); ESI-MS m/z [M+H]$^+$ 453.2.

Example 132: N-(5-cyano-2-(4-(2,4-difluorophenoxy)piperidin-1-yl)phenyl)-5-methyl-1,3,4-oxadiazole-2-carboxamide

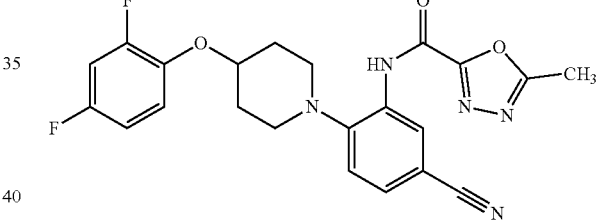

The title compound was prepared in a manner similar to Example 122, using 5-methyl-1,3,4-oxadiazole-2-carboxylic acid (38.9 mg, 0.304 mmol, 2 eq) in place of oxazole-4-carboxylic acid to give the title compound as a white solid (46.7 mg, 70.0%). $^1$H NMR (400 MHz, DMSO-$d_6$) δ ppm 1.82-1.97 (m, 2H), 2.12 (d, J=12.63 Hz, 2H), 2.66 (s, 3H), 2.95 (t, J=8.84 Hz, 2H), 3.16-3.27 (m, 2H), 4.58 (dt, J=7.64, 3.88 Hz, 1H), 6.99-7.09 (m, 1H), 7.29-7.38 (m, 2H), 7.41 (d, J=8.34 Hz, 1H), 7.70 (dd, J=8.34, 2.02 Hz, 1H), 8.35 (d, J=1.52 Hz, 1H), 10.04 (s, 1H); ESI-MS m/z [M+H]$^+$ 440.2.

Example 133: N-(5-cyano-2-(4-(2,4-difluorophenoxy)piperidin-1-yl)phenyl)-5-methoxypicolinamide

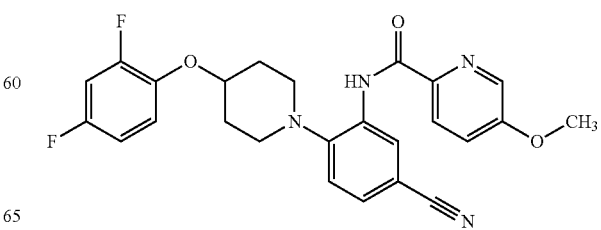

The title compound was prepared in a manner similar to Example 122, using 5-methoxypicolinic acid (46.5 mg, 0.304 mmol, 2 eq) in place of oxazole-4-carboxylic acid to give the title compound as a white solid (49.5 mg, 70.2%). $^1$H NMR (400 MHz, DMSO-d$_6$) δ ppm 1.91-2.06 (m, 2H), 2.12-2.28 (m, 2H), 2.86-2.99 (m, 2H), 3.09-3.23 (m, 2H), 3.97 (s, 3H), 4.59 (d, J=3.28 Hz, 1H), 6.99-7.11 (m, 1H), 7.30-7.40 (m, 2H), 7.42 (d, J=8.34 Hz, 1H), 7.60 (dd, J=8.34, 2.02 Hz, 1H), 7.67 (dd, J=8.72, 2.91 Hz, 1H), 8.20 (d, J=8.59 Hz, 1H), 8.43 (d, J=2.78 Hz, 1H), 8.74 (d, J=2.02 Hz, 1H), 10.65 (s, 1H); ESI-MS m/z [M+H]$^+$ 465.2.

Example 134: N-(5-cyano-2-(4-(2,4-difluorophenoxy)piperidin-1-yl)phenyl)-1,2,5-thiadiazole-3-carboxamide

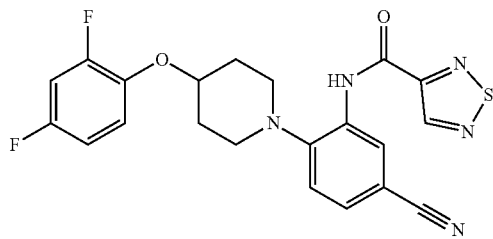 [SMILES: N#Cc1ccc(N2CCC(Oc3ccc(F)cc3F)CC2)c(NC(=O)c2cnsn2)c1]

The title compound was prepared in a manner similar to Example 122, using 1,2,5-thiadiazole-3-carboxylic acid (39.5 mg, 0.304 mmol, 2 eq) in place of oxazole-4-carboxylic acid to give the title compound as an off-white solid (43.3 mg, 64.6%). $^1$H NMR (400 MHz, DMSO-d$_6$) δ ppm 1.87-2.04 (m, 2H), 2.09-2.23 (m, 2H), 2.89-3.02 (m, 2H), 3.13-3.25 (m, 2H), 4.58 (dt, J=7.58, 3.79 Hz, 1H), 6.98-7.10 (m, 1H), 7.27-7.39 (m, 2H), 7.44 (d, J=8.34 Hz, 1H), 7.67 (dd, J=8.34, 2.02 Hz, 1H), 8.55 (d, J=2.02 Hz, 1H), 9.41 (s, 1H), 9.92 (s, 1H); ESI-MS m/z [M+H]$^+$ 442.2.

Example 135: N-(5-cyano-2-(4-(2,4-difluorophenoxy)piperidin-1-yl)phenyl)-2,6-dimethylpyrimidine-4-carboxamide

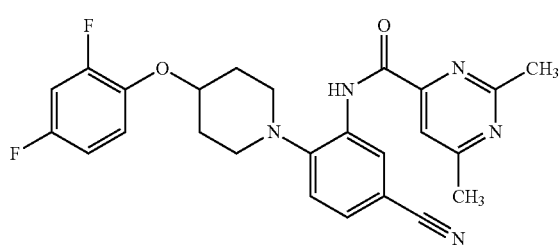 [SMILES: Cc1cc(C(=O)Nc2cc(C#N)ccc2N2CCC(Oc3ccc(F)cc3F)CC2)nc(C)n1]

The title compound was prepared in a manner similar to Example 122, using 2,6-dimethylpyrimidine-4-carboxylic acid (46.2 mg, 0.304 mmol, 2 eq) in place of oxazole-4-carboxylic acid to give the title compound as a brown solid (44.1 mg, 62.7%). $^1$H NMR (400 MHz, DMSO-d$_6$) δ ppm 1.98-2.08 (m, 2H), 2.22 (d, J=12.88 Hz, 2H), 2.61 (s, 3H), 2.77 (s, 3H), 2.89-2.99 (m, 2H), 3.17 (dd, J=10.48, 5.43 Hz, 2H), 4.56-4.68 (m, 1H), 7.00-7.10 (m, 1H), 7.26-7.43 (m, 2H), 7.47 (d, J=8.34 Hz, 1H), 7.65 (dd, J=8.21, 1.89 Hz, 1H), 7.93 (s, 1H), 8.74 (d, J=2.02 Hz, 1H), 10.92 (s, 1H); ESI-MS m/z [M+H]$^+$ 464.2.

Example 136: N-(5-cyano-2-(4-(2,4-difluorophenoxy)piperidin-1-yl)phenyl)-6-methoxypyridazine-3-carboxamide

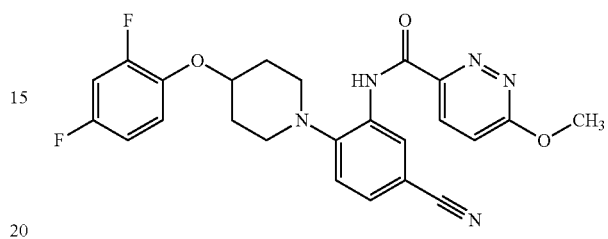

The title compound was prepared in a manner similar to Example 122, using 6-methoxypyridazine-3carboxylic acid (46.8 mg, 0.304 mmol, 2 eq) in place of oxazole-4-carboxylic acid to give the title compound as a grey solid (60.2 mg, 85%). $^1$H NMR (400 MHz, DMSO-de) δ ppm 1.91-2.05 (m, 2H), 2.12-2.23 (m, 2H), 2.89-3.02 (m, 2H), 3.13-3.25 (m, 2H), 4.19 (s, 3H), 4.61 (dt, J=7.64, 3.88 Hz, 1H), 6.99-7.11 (m, 1H), 7.29-7.41 (m, 2H), 7.45 (d, J=8.34 Hz, 1H), 7.51 (d, J=9.09 Hz, 1H), 7.65 (dd, J=8.21, 1.89 Hz, 1H), 8.30 (d, J=9.09 Hz, 1H), 8.70 (d, J=2.02 Hz, 1H); ESI-MS m/z [M+H]$^+$ 466.2.

Example 137: N-(5-cyano-2-(4-(2,4-difluorophenoxy)piperidin-1-yl)phenyl)-5-fluoro-6-methylpicolinamide

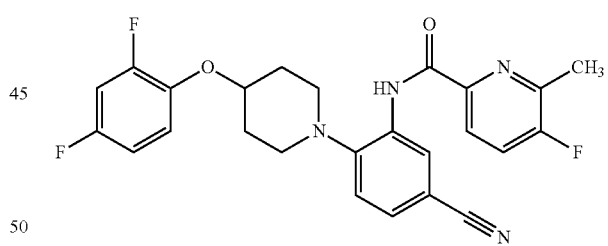

The title compound was prepared in a manner similar to Example 122, using 5-fluoro-6-methylpicolinic acid (47.1 mg, 0.304 mmol, 2 eq) in place of oxazole-4-carboxylic acid to give the title compound as an off-white solid (54.2 mg, 77%). $^1$H NMR (400 MHz, DMSO-de) δ ppm 1.96-2.08 (m, 2H), 2.21 (d, J=11.12 Hz, 2H), 2.63 (d, J=2.78 Hz, 3H), 2.92 (t, J=9.22 Hz, 2H), 3.11-3.19 (m, 2H), 4.54-4.69 (m, 1H), 7.00-7.09 (m, 1H), 7.28-7.41 (m, 2H), 7.45 (d, J=8.34 Hz, 1H), 7.61 (dd, J=8.34, 2.02 Hz, 1H), 7.94 (t, J=8.97 Hz, 1H), 8.13 (dd, J=8.46, 3.92 Hz, 1H), 8.75 (d, J=1.77 Hz, 1H), 10.82 (s, 1H); ESI-MS m/z [M+H]$^+$ 467.2.

Example 138: N-(5-cyano-2-(4-(2,4-difluorophenoxy)piperidin-1-yl)phenyl)-4-methoxypyrimidine-2-carboxamide

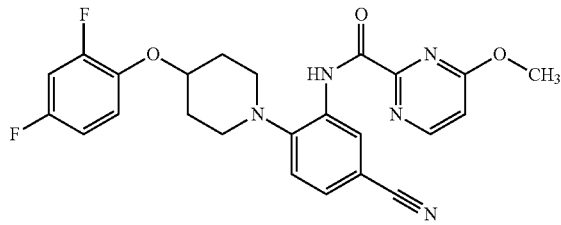 [SMILES: COc1ccnc(C(=O)Nc2cc(C#N)ccc2N2CCC(Oc3ccc(F)cc3F)CC2)n1]

To a stirring solution of 4-methoxypyrimidine-2-carboxylic acid (37 mg, 0.240 mmol), 3-amino-4-(4-(2,4-difluorophenoxy)piperidin-1-yl)benzonitrile (87 mg, 0.264 mmol) and pyridine (0.064 mL, 0.792 mmol) in DMF (0.2 mL) was added 2,4,6-tripropyl-1,3,5,2,4,6-trioxatriphosphinane 2,4,6-trioxide (299 mg, 0.470 mmol, 50% solution in DMF). The reaction mixture was heated to 50° C. After 1.5 hours the reaction was complete. The reaction mixture was diluted with water (3 mL) and agitated. The solids were filtered, washed with water, and returned to the vial. Methanol (1.5 mL) was added and the suspension was heated for 10 minutes at 65° C. The dissolved material crystallized upon cooling. The solids were isolated by filtration, washed with a small amount of MeOH, and dried to give the title compound as a white solid (38.1 mg, 34.1%). $^1$H NMR (400 MHz, DMSO-d$_6$) δ ppm 1.88-2.00 (m, 2H), 2.16 (dd J=12.88, 3.03 Hz, 2H), 2.87-2.98 (m, 2H), 3.09-3.21 (m, 2H), 4.09 (s, 3H), 4.56 (dt, J=7.71, 3.98 Hz, 1H), 6.96-7.09 (m, 1H), 7.22 (d, J=5.56 Hz, 1H), 7.27-7.38 (m, 2H), 7.43 (d, J=8.34 Hz, 1H), 7.63 (dd, J=8.21, 1.89 Hz, 1H), 8.69 (d, J=2.02 Hz, 1H), 8.75 (d, J=5.81 Hz, 1H), 10.69 (s, 1H); ESI-MS m/z [M+H]$^+$ 466.2.

Example 139: N-(5-cyano-2-(4-(2,4-difluorophenoxy)piperidin-1-yl)phenyl)-1,2,5-oxadiazole-3-carboxamide

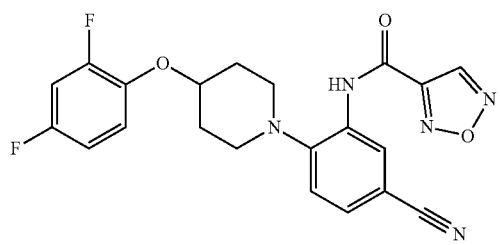 [SMILES: N#Cc1ccc(N2CCC(Oc3ccc(F)cc3F)CC2)c(NC(=O)c2cnon2)c1]

The title compound was prepared in a manner similar to Example 138, using 1,2,5-oxadiazole-3-carboxylic acid (20.42 mg, 0.179 mmol, 1.0 eq) in place of 4-methoxypyrimidine-2-carboxylic acid to give the title compound as a pale green solid (29.9 mg, 39.3%). $^1$H NMR (400 MHz, DMSO-d$_6$) δ ppm 1.77-1.92 (m, 2H), 2.02-2.17 (m, 2H), 2.80-2.95 (m, 2H), 3.05-3.20 (m, 2H), 4.50 (dt, J=7.96, 4.11 Hz, 1H), 6.99-7.06 (m, 1H), 7.25-7.42 (m, 3H), 7.64 (dd, J=8.34, 2.02 Hz, 1H), 8.39 (d, J=1.52 Hz, 1H), 9.50 (s, 1H); ESI-MS m/z [M+H]$^+$ 426.2.

Example 140: N-(5-cyano-2-(4-(2,4-difluorophenoxy)piperidin-1-yl)phenyl)-5-methyl-1,2,4-oxadiazole-3-carboxamide

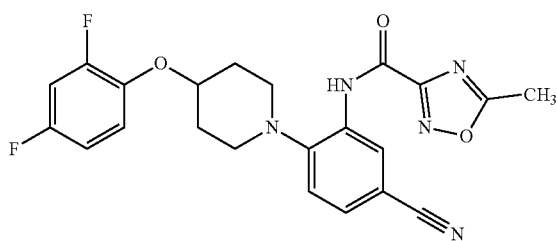 [SMILES: Cc1nc(C(=O)Nc2cc(C#N)ccc2N2CCC(Oc3ccc(F)cc3F)CC2)no1]

The title compound was prepared in a manner similar to Example 138, using 5-methyl-1,2,4-oxadiazole-3-carboxylic acid (22.93 mg, 0.179 mmol, 1.0 eq) in place of 4-methoxypyrimidine-2-carboxylic acid to give the title compound as a white solid (37.2 mg, 47.3%). $^1$H NMR (400 MHz, DMSO-d$_6$) δ ppm 1.85-1.98 (m, 2H), 2.09-2.19 (m, 2H), 2.75 (s, 3H), 2.89-2.99 (m, 2H), 3.14-3.23 (m, 2H), 4.57 (dt, J=7.71, 3.98 Hz, 1H), 6.99-7.11 (m, 1H), 7.29-7.39 (m, 2H), 7.43 (d, J=8.34 Hz, 1H), 7.69 (dd, J=8.34, 2.02 Hz, 1H), 8.45 (d, J=1.77 Hz, 1H), 9.97 (s, 1H); ESI-MS m/z [M+H]$^+$ 440.2.

Example 141: N-(5-cyano-2-(4-(2,4-difluorophenoxy)piperidin-1-yl)phenyl)-2-methylpyrimidine-4-carboxamide

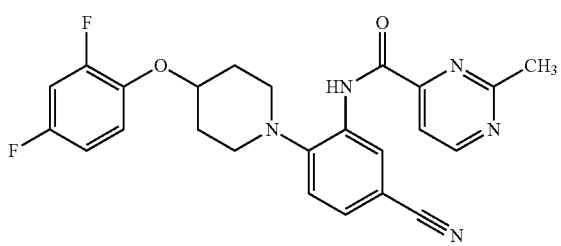 [SMILES: Cc1nccc(C(=O)Nc2cc(C#N)ccc2N2CCC(Oc3ccc(F)cc3F)CC2)n1]

The title compound was prepared in a manner similar to Example 138, using 2-methylpyrimidine-4-carboxylic acid (24.72 mg, 0.179 mmol, 1.0 eq) in place of 4-methoxypyrimidine-2-carboxylic acid to give the title compound as a white solid (60.1 mg, 74.7%). $^1$H NMR (400 MHz, DMSO-d$_6$) δ ppm 1.98-2.11 (m, 2H), 2.15-2.29 (m, 2H), 2.83 (s, 3H), 2.89-3.02 (m, 2H), 3.10-3.24 (m, 2H), 4.62 (dt, J=7.96, 3.85 Hz, 1H), 7.00-7.12 (m, 1H), 7.29-7.41 (m, 2H), 7.47 (d, J=8.34 Hz, 1H), 7.66 (dd, J=8.08, 2.02 Hz, 1H), 8.02 (d, J=5.05 Hz, 1H), 8.74 (d, J=1.77 Hz, 1H), 9.09 (d, J=5.05 Hz, 1H), 10.92 (s, 1H); ESI-MS m/z [M+H]$^+$ 450.2.

Example 142: N-(4-(4-(2,4-difluorophenoxy)piperidin-1-yl)-6-methylpyridin-3-yl)-5-methoxypyrazine-2-carboxamide

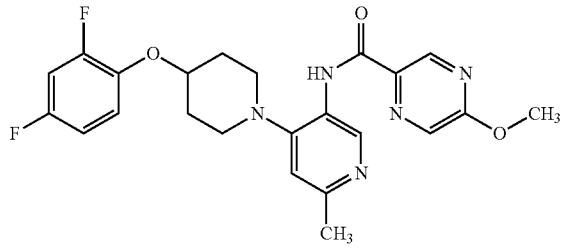 [SMILES: COc1cnc(C(=O)Nc2cnc(C)cc2N2CCC(Oc3ccc(F)cc3F)CC2)cn1]

To a stirring solution of 5-methoxypyrazine-2-carboxylic acid (29.9 mg, 0.194 mmol), 4-(4-(2,4-difluorophenoxy)piperidin-1-yl)-6-methylpyridin-3-amine (65 mg, 0.204 mmol) and pyridine (0.065 mL, 0.776 mmol) in DMF (0.6 mL) was added 2,4,6-tripropyl-1,3,5,2,4,6-trioxatriphosphinane 2,4,6-trioxide (0.238 mL, 0.388 mmol, 50% solution in DMF). The reaction mixture was heated to 50° C. until UPLC-MS indicated the reaction was complete. The solids were filtered and recrystallized from MeOH to give the title compound as a white solid (19.0 mg, 21.5%). $^1$H NMR (400 MHz, DMSO-$d_6$) δ ppm 1.83-1.96 (m, 2H), 2.06-2.18 (m, 2H), 2.44 (s, 3H), 2.93 (ddd, J=11.87, 8.46, 2.91 Hz, 2H), 3.16-3.26 (m, 2H), 4.04 (s, 3H), 4.55 (dt, J=7.33, 3.66 Hz, 1H), 7.00-7.06 (m, 1H), 7.07 (s, 1H), 7.29-7.37 (m, 2H), 8.46 (d, J=1.26 Hz, 1H), 8.94 (d, J=1.52 Hz, 1H), 9.11 (s, 1H), 9.90 (s, 1H); ESI-MS m/z [M+H]$^+$ 456.3.

Example 143: N-(5-cyano-2-(4-(2,4-difluorophenoxy)piperidin-1-yl)phenyl)-1-ethyl-5-methyl-1H-pyrazole-3-carboxamide

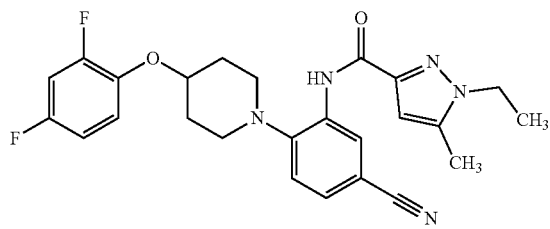 [SMILES: CCn1nc(C(=O)Nc2cc(C#N)ccc2N2CCC(Oc3ccc(F)cc3F)CC2)cc1C]

To a stirring solution of 1-ethyl-5-methyl-1H-pyrazole-3-carboxylic acid (26 mg, 0.169 mmol), 3-amino-4-(4-(2,4-difluorophenoxy)piperidin-1-yl)benzonitrile (61 mg, 0.186 mmol) and Et$_3$N (0.094 mL, 0.675 mmol) in DMA (0.6 mL) was added 2,4,6-tripropyl-1,3,5,2,4,6-trioxatriphosphinane 2,4,6-trioxide (215 mg, 0.337 mmol, 50% solution in EtOAc). The reaction was heated to 50° C. After 1.5 hour the reaction was complete. The reaction mixture was diluted with water (3 mL) and agitated. The solids were filtered, washed with water, and returned to the vial. Methanol (1.5 mL) was added and the suspension was heated for 10 minutes at 65° C. The dissolved material crystallized upon cooling. The solids were isolated by filtration, washed with a small amount of MeOH, and dried to give the title compound as a white solid (19.0 mg, 24.1%). $^1$H NMR (400 MHz, DMSO-$d_6$) δ ppm 1.43 (t, J=7.20 Hz, 3H), 1.94-2.04 (m, 2H), 2.15-2.23 (m, 2H), 2.35 (s, 3H), 2.86-2.95 (m, 2H), 3.09-3.18 (m, 2H), 4.17 (q, J=7.24 Hz, 2H), 4.59 (dt, J=8.02, 3.95 Hz, 1H), 6.62 (s, 1H), 7.04 (tdd, J=8.72, 8.72, 3.03, 1.77 Hz, 1H), 7.29-7.39 (m, 2H), 7.41 (d, J=8.34 Hz, 1H), 7.57 (dd, J=8.34, 2.02 Hz, 1H), 8.64 (d, J=2.02 Hz, 1H), 9.78 (s, 1H); ESI-MS m/z [M+H]$^+$ 466.2.

Example 144: N-(5-cyano-2-(4-(2,4-difluorophenoxy)piperidin-1-yl)phenyl-2-methoxypyrimidine-4-carboxamide

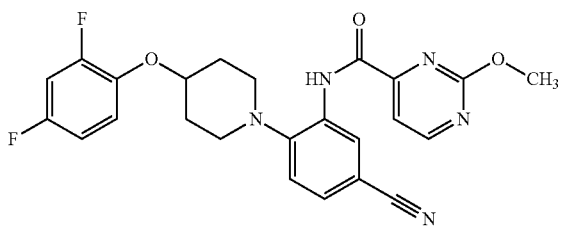

The title compound was prepared in a manner similar to Example 143, using 2-methoxypyrimidine-4-carboxylic acid (0.029 g, 0.188 mmol, 1.0 eq) in place of 1-ethyl-5-methyl-1H-pyrazole-3-carboxylic acid to give the title compound as a tan solid (38.8 mg, 44.1). $^1$H NMR (400 MHz, DMSO-$d_6$) δ ppm 1.81-1.93 (m, 2H), 2.03-2.14 (m, 2H), 2.79-2.89 (m, 2H), 3.07 (dt, J=7.83, 3.92 Hz, 2H), 3.97 (s, 3H), 4.49 (dt, J=7.26, 3.57 Hz, 1H), 6.93-7.00 (m, 1H), 7.21-7.31 (m, 2H), 7.35 (d, J=8.34 Hz, H), 7.54 (dd, J=8.08, 2.02 Hz, 1H), 8.38 (d, J=1.26 Hz, 1H), 8.62 (d, J=2.02 Hz, 1H), 8.89 (d, J=1.52 Hz, 1H), 10.28 (s, 1H); ESI-MS m/z [M+H]$^+$ 466.3.

Example 145: N-(5-cyano-2-(4-(2,4-difluorophenoxy)piperidin-1-yl)phenyl)-1-methyl-1H-1,2,3-triazole-4-carboxamide

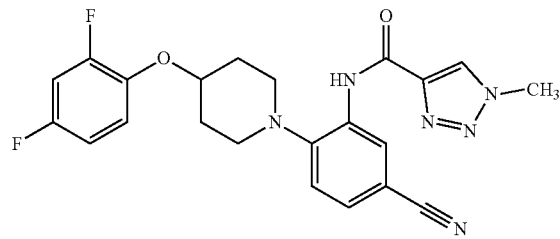 [SMILES: Cn1cc(C(=O)Nc2cc(C#N)ccc2N2CCC(Oc3ccc(F)cc3F)CC2)nn1]

The title compound was prepared in a manner similar to Example 143, using 1-methyl-1H-1,2,3-triazole-4-carboxylic acid (19 mg, 0.152 mmol, 1.0 eq) in place of 1-ethyl-5-methyl-1H-pyrazole-3-carboxylic acid to give the title compound as an off-white solid (31.8 mg, 47.5%). $^1$H NMR (400 MHz, DMSO-$d_6$) δ ppm 1.81-1.96 (m, 2H), 2.02-2.16 (m, 2H), 2.78-2.92 (m, 2H), 3.01-3.14 (m, 2H), 4.08 (s, 3H), 4.52 (dt, J=7.58, 3.79 Hz, 1H), 6.92-6.99 (m, 1H), 7.20-7.31 (m, 2H), 7.35 (d, J=8.34 Hz, 1H), 7.54 (dd, J=8.08, 2.02 Hz, 1H), 8.53 (d, J=2.02 Hz, 1H), 8.74 (s, 1H), 9.80 (s, 1H); ESI-MS m/z [M+H]$^+$ 439.3.

Example 146: N-(5-cyano-2-(4-(2,4-difluorophenoxy)piperidin-1-yl)phenyl)-6-methylpyridazine-3-carboxamide

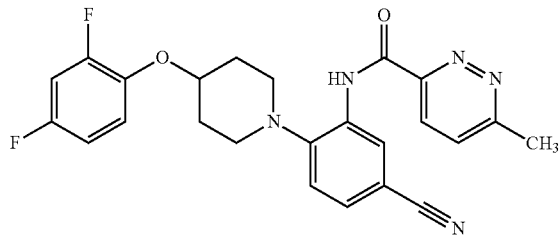 [SMILES: Cc1ccc(C(=O)Nc2cc(C#N)ccc2N2CCC(Oc3ccc(F)cc3F)CC2)nn1]

The title compound was prepared in a manner similar to Example 143, using 6-methylpyridazine-3-carboxylic acid (21 mg, 0.152 mmol, 1.0 eq) in place of 1-ethyl-5-methyl-1H-pyrazole-3-carboxylic acid to give the title compound as an off-white solid (27.7 mg, 40.7%). $^1$H NMR (400 MHz, DMSO-d$_6$) δ ppm 1.84-1.96 (m, 2H), 2.06-2.16 (m, 2H), 2.71 (s, 3H), 2.88 (ddd, J=11.81, 8.53, 2.91 Hz, 2H), 3.07-3.16 (m, 2H), 4.54 (dt, J=7.58, 3.79 Hz, 1H), 6.92-7.00 (m, 1H), 7.20-7.32 (m, 2H), 7.37 (d, J=8.34 Hz, 1H), 7.57 (dd, J=8.08, 2.02 Hz, 1H), 7.82 (d, J=8.84 Hz, 1H), 8.22 (d, J=8.59 Hz, 1H), 8.65 (d, J=2.02 Hz, 1H), 10.78 (s, 1H); ESI-MS m/z [M+H]$^+$ 450.2.

Example 147: 6-(4-(2,4-difluorophenoxy)piperidin-1-yl)-5-(2-methoxy-5-methylnicotinamido)-N,N-dimethylnicotinamide

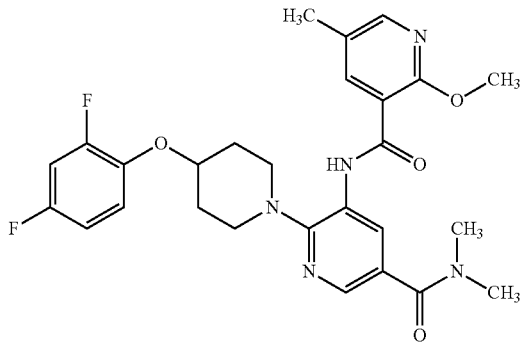 [SMILES: COc1ncc(C)cc1C(=O)Nc1cc(C(=O)N(C)C)cnc1N1CCC(Oc2ccc(F)cc2F)CC1]

To a 20 mL vial was added 5-amino-6-(4-(2,4-difluorophenoxy)piperidin-1-yl)-N,N-dimethylnicotinamide (0.150 g, 0.399 mmol), 2-methoxy-5-methylnicotinic acid (0.080 g, 0.478 mmol), NMP (2.0 mL) and DIPEA (0.278 mL, 1.594 mmol). While stirring, 2,4,6-tripropyl-1,3,5,2,4,6-trioxatriphosphinane 2,4,6-trioxide (0.522 mL, 0.877 mmol) was added and the reaction mixture stirred at 60° C. overnight. The reaction was quenched with water (12 mL). The aqueous mixture was extracted twice with IPAc. The organic extracts were combined and washed with saturated (aq) NaCl, dried over Na$_2$SO$_4$, filtered, and concentrated. The concentrated red oil was taken up in EtOH (10 mL) and to this was added a few drops of water. The milky-red mixture was heated to 74° C. and the mixture became homogeneous. Upon cooling a solid crystallized out of solution. After stirring for 2 hours, the solid was filtered and washed with 20% EtOH in water. The solid was de-liquored on the filter, transferred to a vial, and dried overnight at 60° C. in a vacuum oven to give the title compound as a white solid (131.7 mg, 63.0%). $^1$H NMR (400 MHz, DMSO-d$_6$) δ ppm 1.07 (t, J=6.95 Hz, 1H), 1.80-1.93 (m, 2H), 2.04-2.16 (m, 2H), 2.34 (s, 3H), 2.92-3.04 (m, 8H), 3.20-3.29 (m, 2H), 4.14 (s, 3H), 4.57 (dq, J=7.93, 3.93 Hz, 1H), 6.95-7.12 (m, 1H), 7.24-7.40 (m, 3H), 8.28 (s, 2H), 9.24 (s, 1H), 10.19 (s, 1H); ESI-MS m/z [M+H]$^+$ 526.2.

Example 148: 6-(4-(2,4-difluorophenoxy)piperidin-1-yl)-5-(2-methoxynicotinamido)-N,N-dimethylnicotinamide

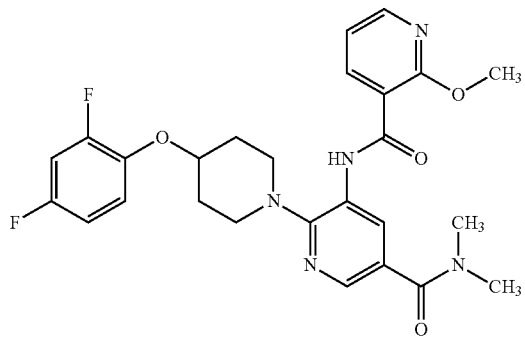 [SMILES: COc1ncccc1C(=O)Nc1cc(C(=O)N(C)C)cnc1N1CCC(Oc2ccc(F)cc2F)CC1]

The title compound was prepared in a manner similar to Example 147, using 2-methoxynicotinic acid (50 mg, 0.325 mmol, 1.2 eq) in place of 2-methoxy-5-methylnicotinic acid to give the title compound as a light pink solid. $^1$H NMR (400 MHz, CDCl$_3$) δ ppm 1.94-2.06 (m, 2H), 2.12-2.25 (m, 2H), 3.01-3.17 (m, 8H), 3.41-3.51 (m, 2H), 4.28 (s, 3H), 4.38 (tt, J=8.24, 4.01 Hz, 1H), 6.76-6.83 (m, 1H), 6.87 (ddd, J=11.05, 8.40, 3.03 Hz, 1H), 7.02 (td, J=9.03, 5.43 Hz, 1H), 7.15 (dd, J=7.58, 4.80 Hz, 1H), 7.12-7.19 (m, 1H), 8.24 (d, J=2.02 Hz, 1H), 8.37 (dd, J=4.80, 2.02 Hz, 1H), 8.61 (dd, J=7.58, 2.02 Hz, 1H), 8.83 (d, J=2.02 Hz, 1H), 10.35 (s, 1H); ESI-MS m/z [M+H]$^+$ 512.2.

Example 149: N-(7-(4-(2,4-difluorophenoxy)piperidin-1-yl)-2-methyl-2H-indazol-6-yl)picolinamide

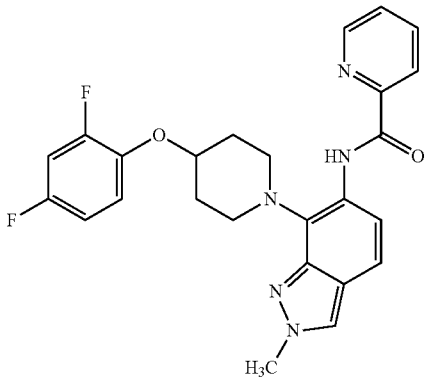 [SMILES: Cn1cc2ccc(NC(=O)c3ccccn3)c(N3CCC(Oc4ccc(F)cc4F)CC3)c2n1]

To a 4 mL vial was added N-(2-methyl-2H-indazol-6-yl)picolinamide (64 mg, 0.254 mmol), diacetoxyiodobenzene (163 mg, 0.507 mmol), MgCl$_2$ (4.83 mg, 0.051 mmol) and copper(II) acetate hydrate (5.07 mg, 0.025 mmol). While the vial was kept under a flow of nitrogen, 1,4-dioxane (2 mL) and 4-(2,4-difluorophenoxy)piperidine (108 mg, 0.507 mmol) were added. The vial was capped and after 2 minutes of stirring the reaction mixture turned a dark brownish-green color. The reaction mixture was stirred for 16 hours and then diluted with EtOAc. The mixture was filtered to remove undissolved solids and washed with water and saturated (aq) NaCl. The organic phase was dried over $Na_2SO_4$, filtered, and concentrated. The concentrated material was dissolved in MeOH (1.5 mL) and DCM (0.5 mL) and subsequently purified to give the title compound as a brown film (11 mg, 9.4%). $^1$H NMR (400 MHz, CD$_3$OD) δ ppm 2.04-2.20 (m, 2H), 2.20-2.34 (m, 2H), 3.54 (t, J=10.23 Hz, 2H), 4.21 (s, 3H), 4.47-4.58 (m, 1H), 6.87-6.94 (m, 1H), 7.02 (ddd, J=11.37, 8.59, 3.03 Hz, 1H), 7.25 (td, J=9.22, 5.56 Hz, 1H), 7.55 (d, J=9.09 Hz, 1H), 7.63 (ddd, J=7.64, 4.74, 1.26 Hz, 1H), 8.04 (td, J=7.71, 1.77 Hz, 1H), 8.16 (s, 1H), 8.24 (dt, J=7.83, 1.01 Hz, 1H), 8.37 (d, J=8.84 Hz, 1H), 8.73-8.81 (m, 1H); ESI-MS m/z [M+H]$^+$ 464.3.

Example 150: N-(5-(4-(2,4-difluorophenoxy)piperidin-1-yl)quinoxalin-6-yl)picolinamide

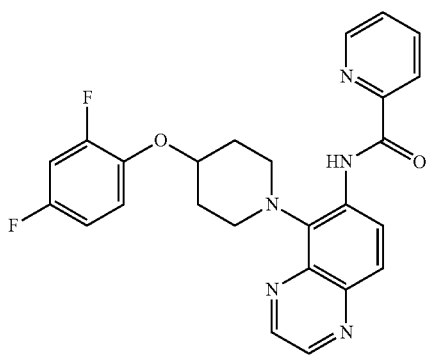 [SMILES: O=C(Nc1ccc2nccnc2c1N1CCC(Oc2ccc(F)cc2F)CC1)c1ccccn1]

The title compound was prepared in a manner similar to Example 149, using N-(quinoxalin-6-yl)picolinamide (64 mg, 0.256 mmol, 1.0 eq) in place of N-(2-methyl-2H-indazol-6-yl)picolinamide to give the title compound as a yellow solid (23.6 mg, 20%). $^1$H NMR (400 MHz, CD$_3$OD) δ ppm 2.06-2.41 (m, 3H), 2.99-3.16 (m, 1H), 4.01 (br s, 1H), 4.45 (br s, 1H), 6.86 (tdd, J=8.49, 8.49, 2.97, 1.77 Hz, 1H), 6.94 (ddd, J=11.18, 8.40, 2.91 Hz, 1H), 7.18 (td, J=9.16, 5.43 Hz, 1H), 7.62 (dd, J=6.69, 4.93 Hz, 1H), 7.91-8.07 (m, 2H), 8.27 (d, J=7.83 Hz, 1H), 8.70 (d, J=1.77 Hz, 1H), 8.79 (br s, 1H), 8.84 (br s, 1H), 9.15 (d, J=9.35 Hz, 1H); ESI-MS m/z [M+H]$^+$ 462.3.

Example 151: N-(5-cyano-2-(4-(5-cyano-2-fluorobenzyl)piperazin-1-yl)pyridin-3-yl)-3-methoxy-1-methyl-1H-pyrazole-4-carboxamide

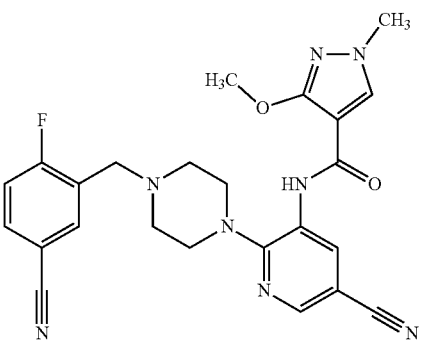 [SMILES: COc1nn(C)cc1C(=O)Nc1cc(C#N)cnc1N1CCN(Cc2cc(C#N)ccc2F)CC1]

To a 4 mL vial was added N-(5-cyano-2-(piperazin-1-yl)pyridin-3-yl)-3-methoxy-1-methyl-1H-pyrazole-4-carboxamide (25 mg, 0.073 mmol), 4-fluoro-3-formylbenzonitrile (12.01 mg, 0.081 mmol) and DCM (0.75 mL). The mixture was stirred for 30 minutes at which time sodium triacetoxyborohydride (46.6 mg, 0.220 mmol) was added. The vial was capped and the reaction was stirred for 4 hours and then quenched with methanol. The reaction mixture was purified by preparative HPLC (Phenomenex Gemini-NX™ C18, 5 μm, 150 mm×30 mm column). The pure fractions were combined and concentrated to give the title compound as a white solid (6.7 mg, 19%). $^1$H NMR (400 MHz, DMSO-d$_6$) δ ppm 2.63 (br s, 4H), 3.17 (d, J=4.80 Hz, 4H), 3.73 (s, 2H), 3.78 (s, 3H), 3.94 (s, 3H), 7.46-7.52 (m, 1H), 7.91 (ddd, J=8.53, 4.86, 2.27 Hz, 1H), 8.00 (dd, J=6.69, 2.15 Hz, 1H), 8.22 (s, 1H), 8.50 (d, J=2.02 Hz, 1H), 8.74 (d, J=2.02 Hz, 1H), 8.83 (s, 1H); ESI-MS m/z [M+H]$^+$ 475.3.

Example 152: N-(5-cyano-2-(4-(2-fluoro-4-methoxybenzyl)piperazin-1-yl)pyridin-3-yl)-3-methoxy-1-methyl-1H-pyrazole-4-carboxamide

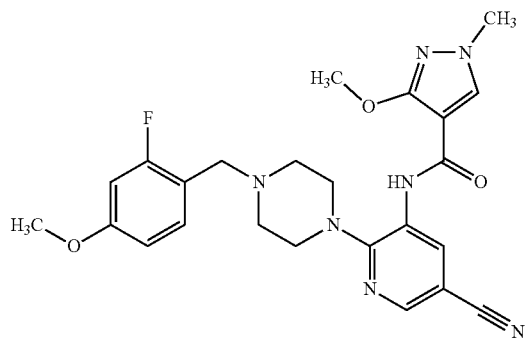 [SMILES: COc1ccc(CN2CCN(c3ncc(C#N)cc3NC(=O)c3cn(C)nc3OC)CC2)c(F)c1]

The title compound was prepared in a manner similar to Example 151, using 2-fluoro-4-methoxybenzaldehyde (12.42 mg, 0.081 mmol, 1.1 eq) in place of 4-fluoro-3-formylbenzonitrile to give the title compound as a white solid (19.6 mg, 55.8%). $^1$H NMR (400 MHz, CD$_3$OD) δ ppm 2.06-2.41 (m, 3H), 2.99-3.16 (m, 1H), 4.01 (br s, 1H), 4.45 (br s, 1H), 6.86 (tdd, J=8.49, 8.49, 2.97, 1.77 Hz, 1H), 6.94 (ddd, J=11.18, 8.40, 2.91 Hz, 1H), 7.18 (td, J=9.16, 5.43 Hz, 1H), 7.62 (dd, J=6.69, 4.93 Hz, 1H), 7.91-8.07 (m, 2H), 8.27 (d, J=7.83 Hz, 1H), 8.70 (d, J=1.77 Hz, 1H), 8.79 (br s, 1H), 8.84 (br s, 1H), 9.15 (d, J=9.35 Hz, 1H); ESI-MS m/z [M+H]+ 480.3.

Example 153: N-(5-cyano-2-(4-(4-cyanobenzyl) piperazin-1-yl)pyridin-3-yl)-3-methoxy-1-methyl-1H-pyrazole-4-carboxamide

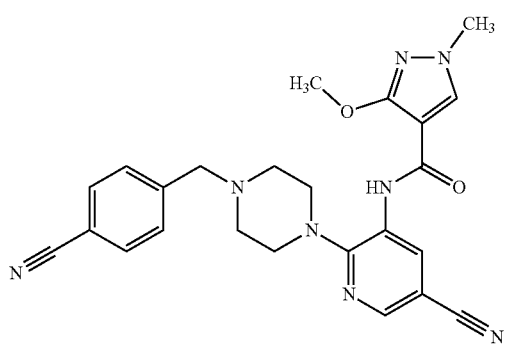 [SMILES: COc1nn(C)cc1C(=O)Nc1cc(C#N)cnc1N1CCN(Cc2ccc(C#N)cc2)CC1]

The title compound was prepared in a manner similar to Example 151, using 4-formylbenzonitrile (10.56 mg, 0.081 mmol, 1.1 eq) in place of 4-fluoro-3-formylbenzonitrile to give the title compound as a white solid (11.7 mg, 35.0%). ¹H NMR (400 MHz, DMSO-d₆) δ ppm 2.60 (d, J=4.04 Hz, 4H), 3.19 (br s, 4H), 3.70 (s, 2H), 3.78 (s, 3H), 3.99 (s, 3H), 7.58 (d, J=8.34 Hz, 2H), 7.84 (d, J=8.34 Hz, 2H), 8.22 (s, 1H), 8.50 (d, J=2.02 Hz, 1H), 8.74 (d, J=2.02 Hz, 1H), 8.84 (s, 1H); ESI-MS m/z [M+H]+ 457.4.

Example 154: N-(5-cyano-2-(4-(3-cyano-4-fluorobenzyl)piperazin-1-yl)pyridin-3-yl)-3-methoxy-1-methyl-1H-pyrazole-4-carbonamide

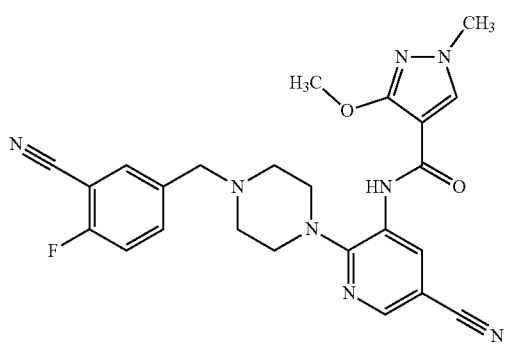 [SMILES: COc1nn(C)cc1C(=O)Nc1cc(C#N)cnc1N1CCN(Cc2ccc(F)c(C#N)c2)CC1]

The title compound was prepared in a manner similar to Example 151, using 2-fluoro-5-formylbenzonitrile (12.01 mg, 0.081 mmol, 1.1 eq) in place of 4-fluoro-3-formylbenzonitrile to give the title compound as a white solid (6.2 mg, 18%). ¹H NMR (400 MHz, DMSO-d₆) δ ppm 2.59 (br s, 4H), 3.15-3.22 (m, 4H), 3.64 (s, 2H), 3.78 (s, 3H), 4.02 (s, 3H), 7.53 (t, J=8.97 Hz, 1H), 7.76-7.82 (m, 1H), 7.91 (dd, J=6.32, 2.02 Hz, 1H), 8.22 (s, 1H), 8.50 (d, J=2.02 Hz, 1H), 8.74 (d, J=2.27 Hz, 1H), 8.85 (s, 1H); ESI-MS m/z [M+H]+ 475.3.

Example 155: N-(5-cyano-2-(4-(4-fluoro-2-methoxybenzyl)piperazin-1-yl)pyridin-3-yl)-3-methoxy-1-methyl-1H-pyrazole-4-carboxamide

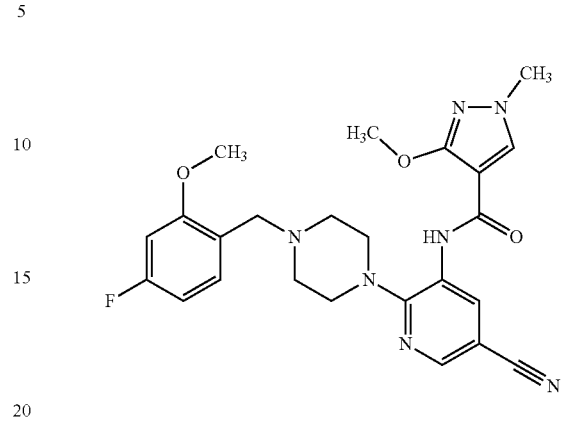

The title compound was prepared in a manner similar to Example 151, using 4-fluoro-2-methoxybenzaldehyde (10.93 mg, 0.071 mmol, 1.1 eq) in place of 4-fluoro-3-formylbenzonitrile to give the title compound as a white solid (17.2 mg, 55.7%). ¹H NMR (400 MHz, DMSO-d₆) δ ppm 2.66 (br s, 4H), 3.14 (br s, 4H), 3.78 (s, 3H), 3.80 (d, J=2.53 Hz, 2H), 3.94 (s, 3H), 7.98 (td, J=9.41, 2.40 Hz, 1H), 8.23 (s, 1H), 8.49 (d, J=2.02 Hz, 1H), 8.53 (d, J=2.53 Hz, 1H), 8.73 (d, J=2.02 Hz, 1H), 8.81 (s, 1H); ESI-MS m/z [M+H]+ 480.3.

Example 156: N-(5-cyano-2-(4-(3-methoxybenzyl) piperazin-1-yl)pyridin-3-yl)-3-methoxy-1-methyl-1H-pyrazole-4-carboxamide

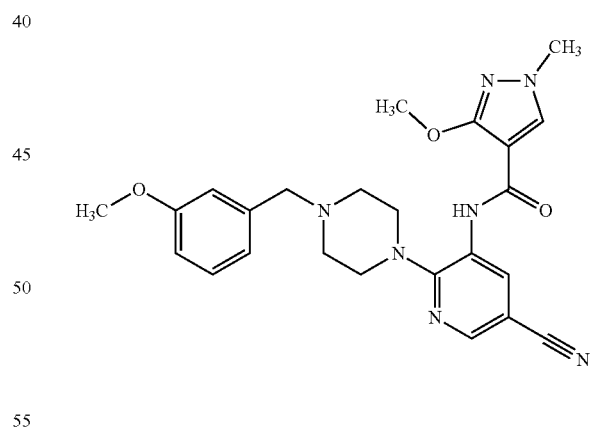

The title compound was prepared in a manner similar to Example 151, using 3-methoxybenzaldehyde (10.97 mg, 0.081 mmol, 1.1 eq) in place of 4-fluoro-3-formylbenzonitrile to give the title compound as a white solid (20.3 mg, 60.1%). ¹H NMR (400 MHz, DMSO-d₆) δ ppm 2.59 (br s, 4H), 3.17 (br s, 4H), 3.59 (s, 2H), 3.76 (s, 3H), 3.77 (s, 3H), 3.96 (s, 3H), 6.83-6.87 (m, 1H), 6.91-6.95 (m, 2H), 7.27 (t, J=7.96 Hz, 1H), 8.22 (s, 1H), 8.50 (d, J=2.02 Hz, 1H), 8.75 (d 0.1=2.27 Hz, 1H), 8.84 (s, 1H); ESI-MS m/z [M+H]+ 462.3.

Example 157: N-(5-cyano-2-(4-(4-methoxybenzyl)piperazin-1-yl)pyridin-3-yl)-3-methoxy-1-methyl-1H-pyrazole-4-carboxamide

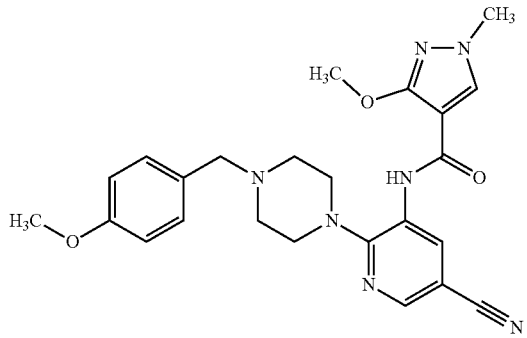 [SMILES: COc1ccc(CN2CCN(c3ncc(C#N)cc3NC(=O)c3cn(C)nc3OC)CC2)cc1]

The title compound was prepared in a manner similar to Example 151, using 4-methoxybenzaldehyde (10.97 mg, 0.081 mmol, 1.1 eq) in place of 4-fluoro-3-formylbenzonitrile to give the title compound as a white solid (19.5 mg, 57.7%). H NMR (400 MHz, DMSO-$d_6$) δ ppm 2.56 (br s, 4H), 3.14 (d, J=4.55 Hz, 4H), 3.54 (s, 2H), 3.75 (s, 3H), 3.77 (s, 3H), 3.95 (s, 3H), 6.86-6.97 (m, 2H), 7.26 (d, J=8.59 Hz, 2H), 8.22 (s, 1H), 8.49 (d, J=2.02 Hz, 1H), 8.74 (d, J=2.02 Hz, 1H), 8.83 (s, 1H); ESI-MS m/z [M+H]$^+$ 462.3.

Example 158: N-(5-cyano-2-(4-(4-fluoro-3-methoxybenzyl)piperazin-1-yl)pyridin-3-yl)-3-methoxy-1-methyl-1H-pyrazole-4-carboxamide

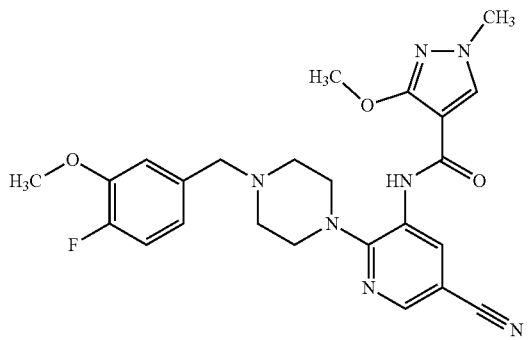 [SMILES: COc1cc(CN2CCN(c3ncc(C#N)cc3NC(=O)c3cn(C)nc3OC)CC2)ccc1F]

The title compound was prepared in a manner similar to Example 151, using 4-fluoro-3-methoxybenzaldehyde (12.42 mg, 0.081 mmol, 1.1 eq) in place of 4-fluoro-3-formylbenzonitrile to give the title compound as a white solid (19.4 mg, 55.2%). H NMR (400 MHz, DMSO-$d_6$) δ ppm 2.59 (br s, 4H), 3.18 (t, J=5.56 Hz, 4H), 3.58 (s, 2H), 3.78 (s, 3H), 3.85 (s, 3H), 3.99 (s, 3H), 6.91 (ddd, J=8.21, 4.42, 1.77 Hz, 1H), 7.09-7.21 (m, 2H), 8.22 (s, 1H), 8.50 (d, J=2.27 Hz, 1H), 8.75 (d, J=2.02 Hz, 1H), 8.85 (s, 1H); ESI-MS m/z [M+H]$^+$ 480.3.

Example 159: N-(5-cyano-2-(4-(3-fluoro-5-methoxybenzyl)piperazin-1-yl)pyridin-3-yl)-3-methoxy-1-methyl-1H-pyrazole-4-carboxamide

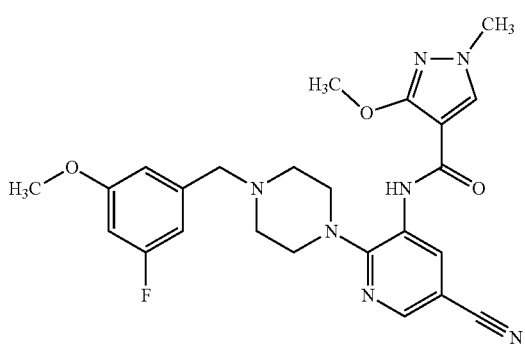 [SMILES: COc1cc(F)cc(CN2CCN(c3ncc(C#N)cc3NC(=O)c3cn(C)nc3OC)CC2)c1]

The title compound was prepared in a manner similar to Example 151, using 3-fluoro-5-methoxybenzaldehyde (12.42 mg, 0.081 mmol, 1.1 eq) in place of 4-fluoro-3-formylbenzonitrile to give the title compound as a white solid (22.7 mg, 64.6%). $^1$H NMR (400 MHz, DMSO-$d_6$) δ ppm 2.59 (br s, 4H), 3.17 (d, J=4.55 Hz, 4H), 3.59 (s, 2H), 3.78 (d, J=1.77 Hz, 6H), 3.99 (s, 3H), 6.69-6.83 (m, 3H), 8.22 (s, 1H), 8.50 (d, J=2.02 Hz, 1H), 8.74 (d, J=2.27 Hz, 1H), 8.84 (s, 1H); ESI-MS m/z [M+H]$^+$ 480.3.

Example 160: N-(5-cyano-2-(4-(3-fluoro-2-methoxybenzyl)piperazin-1-yl)pyridin-3-yl)-3-methoxy-1-methyl-1H-pyrazole-4-carboxamide

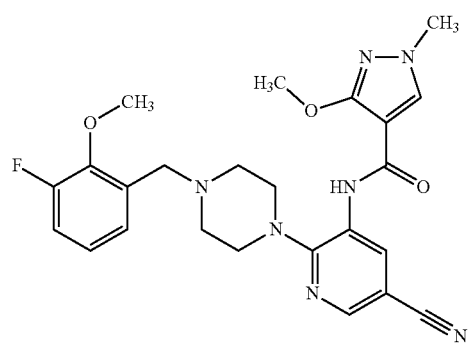 [SMILES: COc1nn(C)cc1C(=O)Nc1cc(C#N)cnc1N1CCN(Cc2cccc(F)c2OC)CC1]

The title compound was prepared in a manner similar to Example 151, using 3-fluoro-2-methoxybenzaldehyde (12.42 mg, 0.081 mmol, 1.1 eq) in place of 4-fluoro-3-formylbenzonitrile to give the title compound as a white solid (19.7 mg, 56.1%). H NMR (400 MHz, DMSO-$d_6$) δ ppm 2.61 (br s, 4H), 3.15 (d, J=4.55 Hz, 4H), 3.65 (s, 2H), 3.78 (s, 3H), 3.86 (d, J=1.26 Hz, 3H), 3.98 (s, 3H), 7.08-7.14 (m, 1H), 7.17-7.24 (m, 2H), 8.23 (s, 1H), 8.50 (d, J=2.02 Hz, 1H), 8.75 (d, J=2.02 Hz, 1H), 8.85 (s, 1H); ESI-MS m/z [M+H]$^+$ 480.3.

Example 161: N-(5-cyano-2-(4-(5-fluoro-2-methoxybenzyl)piperazin-1-yl)pyridin-3-yl)-3-methoxy-1-methyl-1H-pyrazole-4-carboxamide

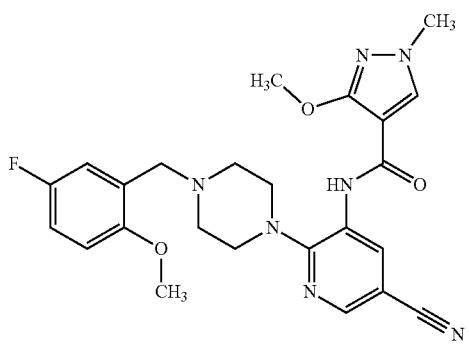 [SMILES: COc1ccc(F)cc1CN1CCN(c2ncc(C#N)cc2NC(=O)c2cn(C)nc2OC)CC1]

The title compound was prepared in a manner similar to Example 151, using 5-fluoro-2-methoxybenzaldehyde (12.42 mg, 0.081 mmol, 1.1 eq) in place of 4-fluoro-3-formylbenzonitrile to give the title compound as a white solid (23.5 mg, 66.9%). $^1$H NMR (400 MHz, DMSO-d$_6$) δ ppm 2.62 (brs, 4H), 3.13-3.23 (m, 4H), 3.62 (s, 2H), 3.77 (s, 3H), 3.79 (s, 3H), 3.95 (s, 3H), 7.00-7.04 (m, 1H), 7.05-7.12 (m, 1H), 7.19 (dd, J=9.35, 3.03 Hz, 1H), 8.22 (s, 1H), 8.50 (d, J=2.27 Hz, 1H), 8.75 (d, J=2.27 Hz, 1H), 8.84 (s, 1H); ESI-MS m/z [M+H]$^+$ 480.3.

Example 162: N-(5-cyano-2-(4-(4-(difluoromethoxy)benzyl)piperazin-1-yl)pyridin-3-yl)-3-methoxy-1-methyl-1H-pyrazole-4-carboxamide

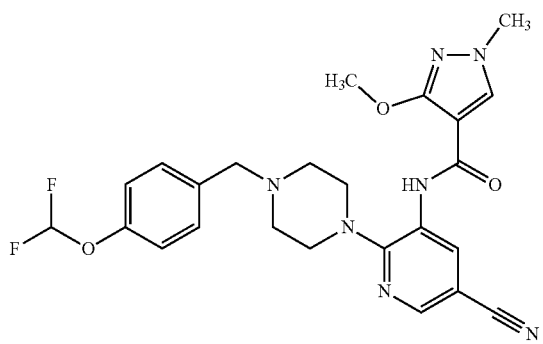 [SMILES: COc1nn(C)cc1C(=O)Nc1cc(C#N)cnc1N1CCN(Cc2ccc(OC(F)F)cc2)CC1]

The title compound was prepared in a manner similar to Example 151, using 4-(difluoromethoxy)benzaldehyde (13.87 mg, 0.081 mmol, 1.1 eq) in place of 4-fluoro-3-formylbenzonitrile to give the title compound as a white solid (21.4 mg, 58.7%). $^1$H NMR (400 MHz, DMSO-d$_6$) δ ppm 2.58 (br s, 4H), 3.15 (d, J=4.29 Hz, 4H), 3.61 (s, 2H), 3.77 (s, 3H), 3.95-3.99 (m, 3H), 7.04-7.44 (m, 5H), 8.22 (s, 1H), 8.50 (d, J=2.02 Hz, 1H), 8.74 (d, J=2.27 Hz, 1H), 8.83 (s, 1H); ESI-MS m/z [M+H]$^+$ 498.3.

Example 163: N-(5-cyano-2-(4-(2-(difluoromethoxy)benzyl)piperazin-1-yl)pyridin-3-yl)-3-methoxy-1-methyl-1H-pyrazole-4-carboxamide

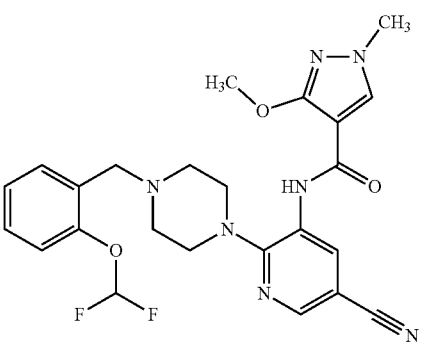 [SMILES: COc1nn(C)cc1C(=O)Nc1cc(C#N)cnc1N1CCN(Cc2ccccc2OC(F)F)CC1]

The title compound was prepared in a manner similar to Example 151, using 2-(difluoromethoxy)benzaldehyde (13.87 mg, 0.081 mmol, 1.1 eq) in place of 4-fluoro-3-formylbenzonitrile to give the title compound as a white solid (22.4 mg, 61.5%). $^1$H NMR (400 MHz, DMSO-d$_6$) δ ppm 2.61 (br s, 4H), 3.16 (br s, 4H), 3.65 (s, 2H), 3.78 (s, 3H), 3.97 (s, 3H), 6.98-7.42 (m, 4H), 7.50 (dd, J=7.45, 1.64 Hz, 1H), 8.22 (s, 1H), 8.50 (d, J=2.02 Hz, 1H), 8.76 (d, J=2.27 Hz, 1H), 8.85 (s, 1H), ESI-MS m/z [M+H]$^+$ 498.3.

Example 164: N-(5-cyano-2-(4-(3-(difluoromethoxy)benzyl)piperazin-1-yl)pyridin-3-yl)-3-methoxy-1-methyl-1H-pyrazole-4-carboxamide

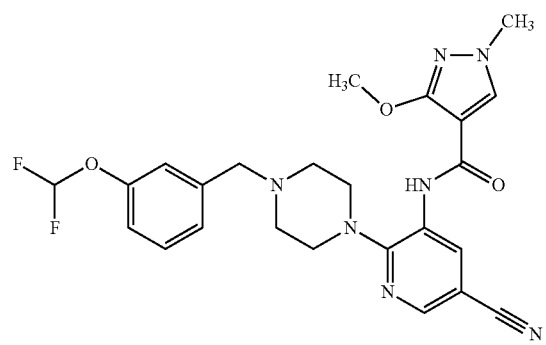 [SMILES: COc1nn(C)cc1C(=O)Nc1cc(C#N)cnc1N1CCN(Cc2cccc(OC(F)F)c2)CC1]

The title compound was prepared in a manner similar to Example 151, using 3-(difluoromethoxy)benzaldehyde (13.87 mg, 0.081 mmol, 1.1 eq) in place of 4-fluoro-3-formylbenzonitrile to give the title compound as a white solid (22.1 mg, 60.7%). $^1$H NMR (400 MHz, DMSO-d$_6$) δ ppm 2.60 (br s, 4H), 3.17 (br s, 4H), 3.64 (s, 2H), 3.77 (s, 3H), 3.97 (s, 3H), 7.05-7.46 (m, 5H), 8.22 (s, 1H), 8.50 (d, J=2.02 Hz, 1H), 8.75 (d, J=2.27 Hz, 1H), 8.85 (s, 1H); ESI-MS m/z [M+H]$^+$ 498.3.

Example 165: N-(5-cyano-2-(4-(3-(trifluoromethoxy)benzyl)piperazin-1-yl)pyridin-3-yl)-3-methoxy-1-methyl-1H-pyrazole-4-carboxamide

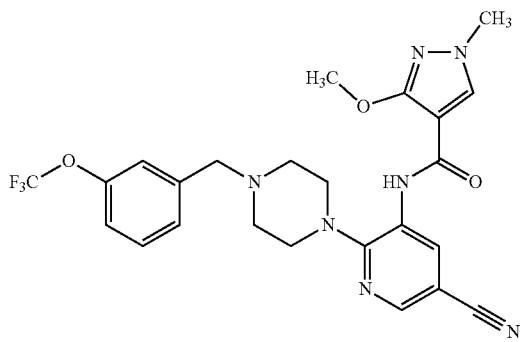 [SMILES: COc1nn(C)cc1C(=O)Nc1cc(C#N)cnc1N1CCN(Cc2cccc(OC(F)(F)F)c2)CC1]

The title compound was prepared in a manner similar to Example 151, using 3-(trifluoromethoxy)benzaldehyde (15.32 mg, 0.081 mmol, 1.1 eq) in place of 4-fluoro-3-formylbenzonitrile to give the title compound as a white solid (24.0 mg, 63.6%). $^1$H NMR (400 MHz, DMSO-$d_6$) δ ppm 2.60 (br s, 4H), 3.17 (d, J=4.80 Hz, 4H), 3.68 (s, 2H), 3.77 (s, 3H), 3.96 (s, 3H), 7.29 (d, J=8.34 Hz, 1H), 7.36 (s, 1H), 7.41 (d, J=7.83 Hz, 1H), 7.47-7.54 (m, 1H), 8.22 (s, 1H), 8.50 (d, J=2.27 Hz, 1H), 8.75 (d, J=2.27 Hz, 1H), 8.85 (s, 1H); ESI-MS m/z [M+H]$^+$ 516.2.

Example 166: N-(5-cyano-2-(4-(4-(trifluoromethoxy)benzyl)piperazin-1-yl)pyridin-3-yl)-3-methoxy-1-methyl-1H-pyrazole-4-carboxamide

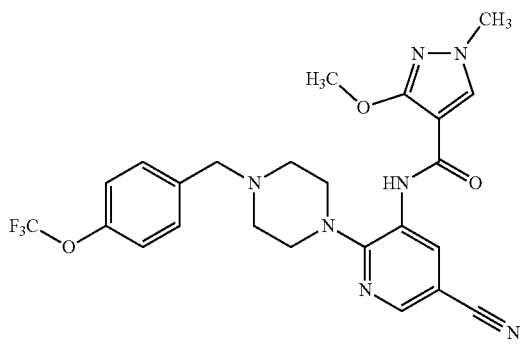 [SMILES: COc1nn(C)cc1C(=O)Nc1cc(C#N)cnc1N1CCN(Cc2ccc(OC(F)(F)F)cc2)CC1]

The title compound was prepared in a manner similar to Example 151, using 4-(trifluoromethoxy)benzaldehyde (15.32 mg, 0.081 mmol, 1.1 eq) in place of 4-fluoro-3-formylbenzonitrile to give the title compound as a white solid (24.1 mg, 63.8%). $^1$H NMR (400 MHz, DMSO-$d_6$) δ ppm 2.59 (br s, 4H), 3.17 (br s, 4H), 3.65 (s, 2H), 3.77 (s, 3H), 3.96 (s, 3H), 7.36 (d, J=7.83 Hz, 2H), 7.49 (d, J=8.59 Hz, 2H), 8.22 (s, 1H), 8.50 (d, J=2.02 Hz, 1H), 8.75 (d, J=2.02 Hz, 1H), 8.84 (s, 1H); ESI-MS m/z [M+H]$^+$ 516.2.

Example 167: N-(5-cyano-2-(4-(2-(trifluoromethoxy)benzyl)piperazin-1-yl)pyridin-3-yl)-3-methoxy-1-methyl-1H-pyrazole-4-carboxamide

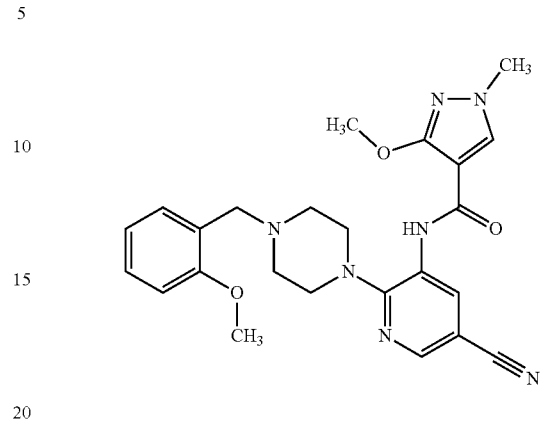

The title compound was prepared in a manner similar to Example 151, using 2-(trifluoromethoxy)benzaldehyde (15.32 mg, 0.081 mmol, 1.1 eq) in place of 4-fluoro-3-formylbenzonitrile to give the title compound as a white solid (22.2 mg, 58.8%). $^1$H NMR (400 MHz, DMSO-$d_6$) δ ppm 2.61 (br s, 4H), 3.16 (br s, 4H), 3.68 (s, 2H), 3.77 (s, 3H), 3.97 (s, 3H), 7.35-7.41 (m, 1H), 7.41-7.48 (m, 2H), 7.61 (dd, J=7.07, 2.27 Hz, 1H), 8.22 (s, 1H), 8.50 (d, J=2.02 Hz, 1H), 8.75 (d, J=2.02 Hz, 1H), 8.85 (s, 1H); ESI-MS m/z [M+H]$^+$ 516.3.

Example 168: N-(5-cyano-2-(4-(3-fluoro-4-methoxybenzyl)piperazin-1-yl)pyridin-3-yl)-3-methoxy-1-methyl-1H-pyrazole-4-carboxamide

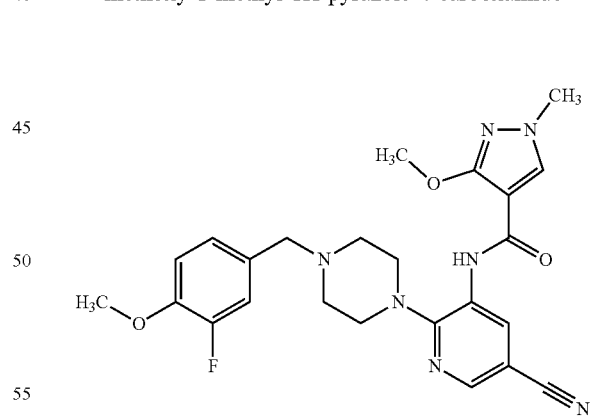

The title compound was prepared in a manner similar to Example 151, using 3-fluoro-4-methoxybenzaldehyde (13.41 mg, 0.087 mmol, 1.1 eq) in place of 4-fluoro-3-formylbenzonitrile to give the title compound as a white solid (16.8 mg, 44.3%). $^1$H NMR (400 MHz, DMSO-$d_6$) δ ppm 2.57 (br s, 4H), 3.16 (br s, 4H), 3.55 (s, 2H), 3.78 (s, 3H), 3.83 (s, 3H), 3.97 (s, 3H), 7.08-7.17 (m, 2H), 7.17-7.22 (m, 1H), 8.22 (s, 1H), 8.50 (d, J=2.02 Hz, 1H), 8.74 (d, J=2.27 Hz, 1H), 8.84 (s, 1H); ESI-MS m/z [M+H]$^+$ 480.3.

Example 169: N-(5-cyano-2-(4-(3,5-difluorobenzyl)piperazin-1-yl)pyridin-3-yl)-3-methoxy-1-methyl-1H-pyrazole-4-carboxamide

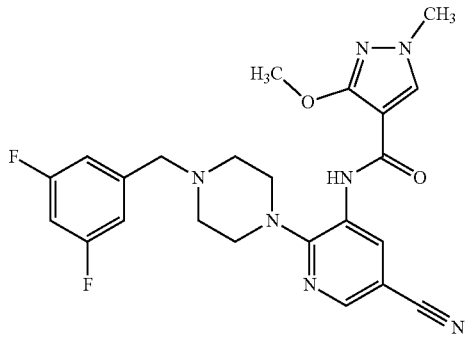 [SMILES: COc1nn(C)cc1C(=O)Nc1cc(C#N)cnc1N1CCN(Cc2cc(F)cc(F)c2)CC1]

The title compound was prepared in a manner similar to Example 151, using 3,5-difluorobenzaldehyde (15.11 mg, 0.106 mmol, 1.1 eq) in place of 4-fluoro-3-formylbenzonitrile to give the title compound as a white solid (13.6 mg, 30.1%). $^1$H NMR (400 MHz, DMSO-$d_6$) δ ppm 2.60 (br s, 4H), 3.12-3.24 (m, 4H), 3.65 (s, 2H), 3.77 (s, 3H), 4.00 (s, 3H), 7.04-7.23 (m, 3H), 8.22 (s, 1H), 8.50 (d, J=2.02 Hz, 1H), 8.74 (d, J=2.02 Hz, 1H), 8.84 (s, 1H); ESI-MS m/z [M+H]$^+$ 468.3.

Example 170: N-(5-cyano-2-(4-(4,5-difluoro-2-methoxybenzyl)piperazin-1-yl)pyridin-3-yl)-3-methoxy-1-methyl-1H-pyrazole-4-carboxamide

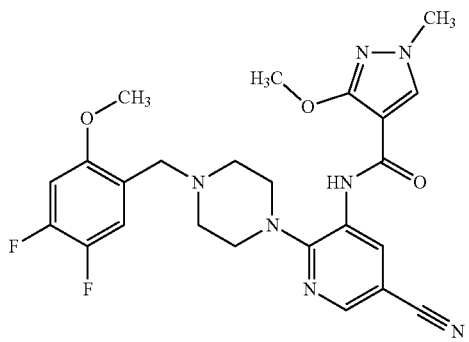 [SMILES: COc1cc(F)c(F)cc1CN1CCN(c2ncc(C#N)cc2NC(=O)c2cn(C)nc2OC)CC1]

The title compound was prepared in a manner similar to Example 151, using 4,5-difluoro-2-methoxybenzaldehyde (19.97 mg, 0.116 mmol, 1.1 eq) in place of 4-fluoro-3-formylbenzonitrile to give the title compound as a white solid (14.1 mg, 26.9%). $^1$H NMR (400 MHz, DMSO-$d_6$) δ ppm 2.61 (br s, 4H), 3.10-3.24 (m, 4H), 3.57 (s, 2H), 3.78 (s, 3H), 3.80 (s, 3H), 3.98 (s, 3H), 7.17 (dd, J=12.88, 6.82 Hz, 1H), 7.39 (dd, J=11.37, 9.60 Hz, 1H), 8.23 (s, 1H), 8.50 (d, J=2.02 Hz, 1H), 8.75 (d, J=2.27 Hz, 1H), 8.84 (s, 1H); ESI-MS m/z [M+H]$^+$ 498.3.

Example 171: N-(5-cyano-2-(4-(2,4,6-trifluoro-3-methoxybenzyl)piperazin-1-yl)pyridin-3-yl)-3-methoxy-1-methyl-1H-pyrazole-4-carboxamide

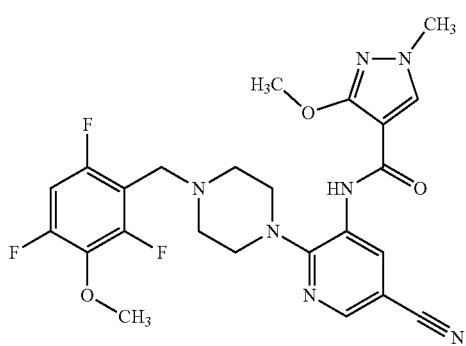 [SMILES: COc1nn(C)cc1C(=O)Nc1cc(C#N)cnc1N1CCN(Cc2c(F)cc(F)c(OC)c2F)CC1]

The title compound was prepared in a manner similar to Example 151, using 2,4,6-trifluoro-3-methoxybenzaldehyde (18.99 mg, 0.100 mmol, 1.1 eq) in place of 4-fluoro-3-formylbenzonitrile to give the title compound as an off-white solid (28.1 mg, 60.0%). $^1$H NMR (400 MHz, DMSO-$d_6$) δ ppm 2.61 (br s, 4H), 3.14 (br s, 4H), 3.71 (s, 2H), 3.78 (s, 3H), 3.88 (s, 3H), 3.91 (s, 3H), 7.35 (t, J=9.73 Hz, 1H), 8.22 (s, 1H), 8.49 (d, J=1.77 Hz, 1H), 8.74 (d, J=1.77 Hz, 1H), 8.80 (s, 1H); ESI-MS m/z [M+H]$^+$ 516.2.

Example 172: N-(2-(4-(4-chloro-2-fluorobenzyl)piperazin-1-yl)-5-cyanopyridin-3-yl)-3-methoxy-1-methyl-1H-pyrazole-4-carboxamide

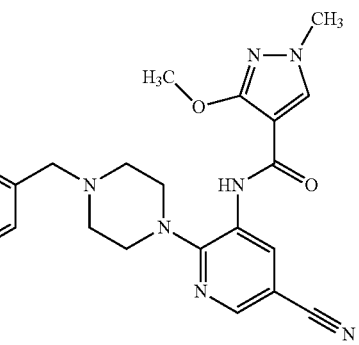

The title compound was prepared in a manner similar to Example 151, using 4-chloro-2-fluorobenzaldehyde (13.79 mg, 0.087 mmol, 1.1 eq) in place of 4-fluoro-3-formylbenzonitrile to give the title compound as a white solid (20.1 mg, 52.5%). $^1$H NMR (400 MHz, DMSO-$d_6$) δ ppm 2.60 (br s, 4H), 3.15 (br s, 4H), 3.68 (s, 2H), 3.78 (s, 3H), 3.91 (s, 3H), 7.32 (dd, J=8.34, 1.77 Hz, 1H), 7.41-7.55 (m, 2H), 8.22 (s, 1H), 8.50 (d, J=2.02 Hz, 1H), 8.75 (d, J=2.02 Hz, 1H), 8.82 (s, 1H).

Example 173: N-(5-cyano-2-(4-(2,4,6-trifluorobenzyl)piperazin-1-yl)pyridin-3-yl)-3-methoxy-1-methyl-1H-pyrazole-4-carboxamide

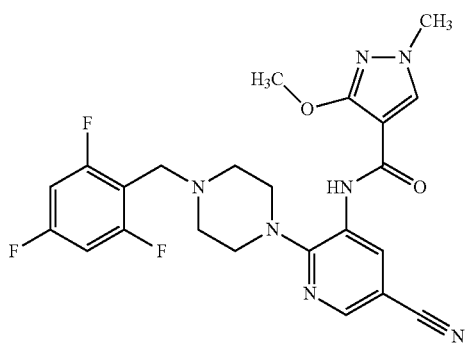 [SMILES: COc1nn(C)cc1C(=O)Nc1cc(C#N)cnc1N1CCN(Cc2c(F)cc(F)cc2F)CC1]

The title compound was prepared in a manner similar to Example 151, using 2,4,6-trifluorobenzaldehyde (14.96 mg, 0.093 mmol, 1.1 eq) in place of 4-fluoro-3-formylbenzonitrile to give the title compound as an off-white solid (14.1 mg, 34.2%). $^1$H NMR (400 MHz, DMSO-$d_6$) δ ppm 2.61 (brs, 4H), 3.14-3.21 (m, 4H), 3.65 (s, 2H), 3.78 (s, 3H), 3.96 (s, 3H), 7.51-7.66 (m, 2H), 8.23 (s, 1H), 8.50 (d, J=2.02 Hz, 1H), 8.74 (d, J=2.02 Hz, 1H), 8.82 (s, 1H); ESI-MS m/z [M+H]$^+$ 486.2.

Example 174: N-(2-(4-(4-chloro-2,6-difluorobenzyl)piperazin-1-yl)-5-cyanopyridin-3-yl)-3-methoxy-1-methyl-1H-pyrazole-4-carboxamide

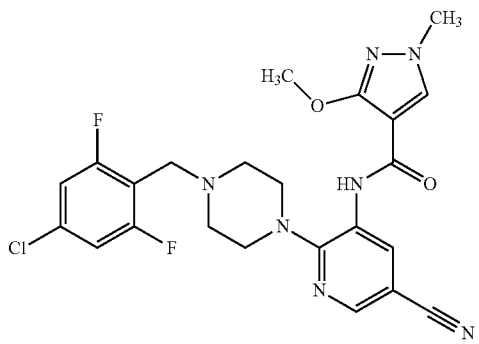 [SMILES: COc1nn(C)cc1C(=O)Nc1cc(C#N)cnc1N1CCN(Cc2c(F)cc(Cl)cc2F)CC1]

The title compound was prepared in a manner similar to Example 151, using 4-chloro-2,6-difluorobenzaldehyde (15.93 mg, 0.090 mmol, 1.1 eq) in place of 4-fluoro-3-formylbenzonitrile to give the title compound as an off-white solid (4.0 mg, 9.8%). $^1$H NMR (400 MHz, DMSO-$d_6$) δ ppm 2.61 (br s, 4H), 3.13 (br s, 4H), 3.72 (s, 2H), 3.78 (s, 3H), 3.86 (s, 3H), 7.44 (d, J=7.07 Hz, 2H), 8.22 (s, 1H), 8.49 (d, J=2.02 Hz, 1H), 8.75 (d, J=2.02 Hz, 1H), 8.79 (s, 1H); ESI-MS m/z [M+H]$^+$ 502.2.

Compounds in Examples 175 through 238 were prepared in accordance with Scheme E.

Scheme E

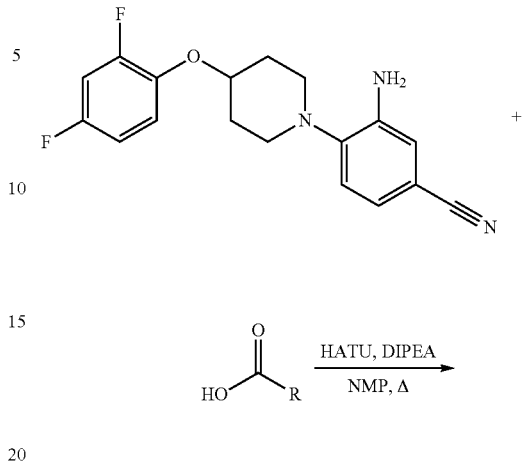

For Examples 175 through 238, a solution of HATU (0.057 g, 0.150 mmol) and DIPEA (0.052 mL, 0.300 mmol) in NMP (0.5 mL) was added to the requisite carboxylic acid R—COOH (0.150 mmol) in a 4 mL vial equipped with a stir bar. After stirring for 5-10 minutes, a solution of 3-amino-4-(4-(2,4-difluorophenoxy)piperidin-1-yl)benzonitrile (0.033 g, 0.1 mmol) in NMP (0.5 mL) was added and the resulting solution was stirred for an additional 30-60 minutes at 100-140° C. The product was purified by preparative HPLC (Phenomenex Gemini-NX™ C18.5 µm, 150 mm×30 mm column) eluting with a gradient of 45-100% acetonitrile in water (acid mode) to give each of the title compounds as a TFA salt. The compound in Example 210 was re-dissolved in CH$_3$CN, treated with Si-carbonate, filtered and evaporated to give the title compound as the free form.

Example 175: N-(5-cyano-2-(4-(2,4-difluorophenoxy)piperidin-1-yl)phenyl)-6-methoxypicolinamide

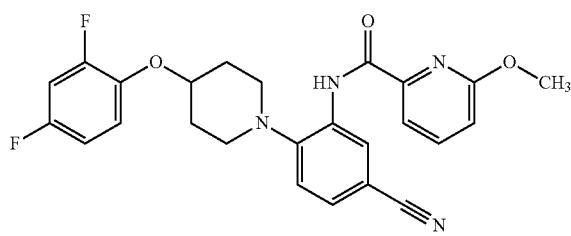 [SMILES: COc1cccc(C(=O)Nc2cc(C#N)ccc2N2CCC(Oc3ccc(F)cc3F)CC2)n1]

ESI-MS m/z [M+H]$^+$ 465.

Example 176: N-(5-cyano-2-(4-(2,4-difluorophenoxy)piperidin-1-yl)phenyl)-1,4,6-trimethyl-2-oxo-1,2-dihydropyridine-3-carboxamide

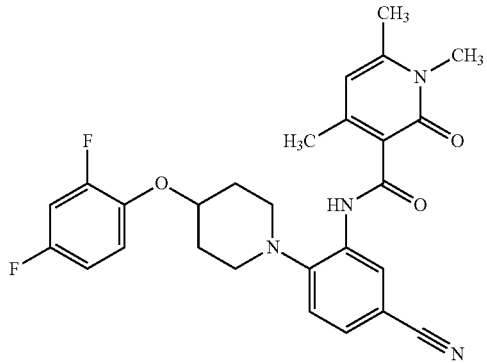 [SMILES: Cc1cc(C)n(C)c(=O)c1C(=O)Nc1cc(C#N)ccc1N1CCC(Oc2ccc(F)cc2F)CC1]

ESI-MS m/z [M+H]$^+$ 493.

Example 177: 1-benzyl-N-(5-cyano-2-(4-(2,4-difluorophenoxy)piperidin-1-yl)phenyl)-2-oxo-1,2-dihydropyridine-3-carboxamide

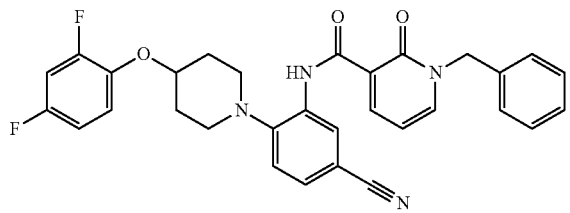

ESI-MS m/z [M+H]$^+$ 541.

Example 178: N-(5-cyano-2-(4-(2,4-difluorophenoxy)piperidin-1-yl)phenyl)-4-oxo-4H-pyrido[1,2-a]pyrimidine-3-carboxamide

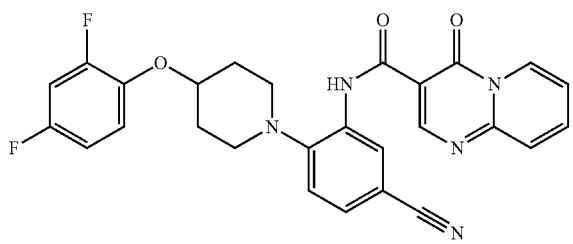 [SMILES: N#Cc1ccc(N2CCC(Oc3ccc(F)cc3F)CC2)c(NC(=O)c2cnc3ccccn3c2=O)c1]

ESI-MS m/z [M+H]$^+$ 502.

Example 179: 1-butyl-N-(5-cyano-2-(4-(2,4-difluorophenoxy)piperidin-1-yl)phenyl)-2-oxo-1,2-dihydropyridine-3-carboxamide

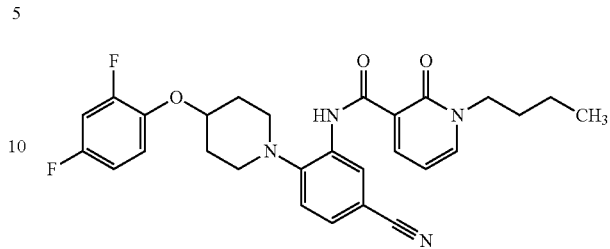

ESI-MS m/z [M+H]$^+$ 507.

Example 180: N-(5-cyano-2-(4-(2,4-difluorophenoxy)piperidin-1-yl)phenyl)-1-cyclohexyl-2-oxo-1,2-dihydropyridine-3-carboxamide

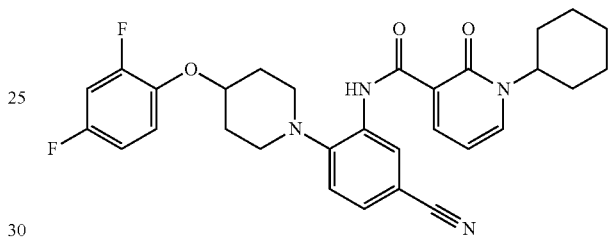

ESI-MS m/z [M+H]$^+$ 533.

Example 181: N-(5-cyano-2-(4-(2,4-difluorophenoxy)piperidin-1-yl)phenyl)-1-isopropyl-2-oxo-1,2-dihydropyridine-3-carboxamide

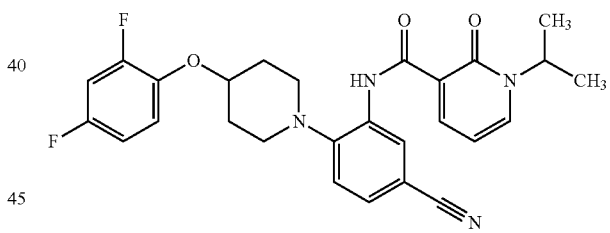

ESI-MS m/z [M+H]$^+$ 493.

Example 182: 5-bromo-N-(5-cyano-2-(4-(2,4-difluorophenoxy)piperidin-1-yl)phenyl)-1-isopropyl-2-oxo-1,2-dihydropyridine-3-carboxamide

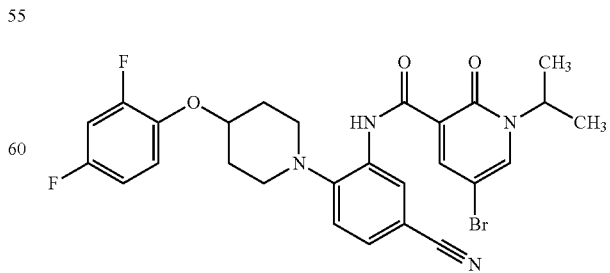

ESI-MS m/z [M+H]$^+$ 571.

Example 183: N-(5-cyano-2-(4-(2,4-difluorophenoxy)piperidin-1-yl)phenyl)-1-methyl-6-oxo-2-phenyl-1,6-dihydropyrimidine-5-carboxamide

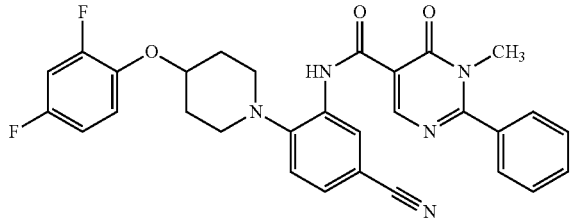 [SMILES: Cn1c(-c2ccccc2)ncc(C(=O)Nc2cc(C#N)ccc2N2CCC(Oc3ccc(F)cc3F)CC2)c1=O]

ESI-MS m/z [M+H]$^+$ 542.

Example 184: N-(5-cyano-2-(4-(2,4-difluorophenoxy)piperidin-1-yl)phenyl)-1,5,6-trimethyl-2-oxo-1,2-dihydropyridine-3-carboxamide

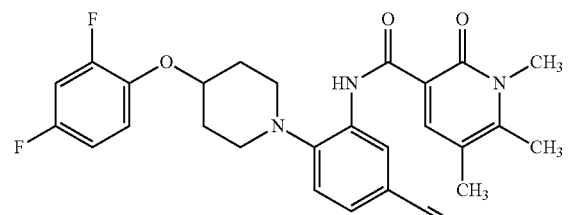

ESI-MS m/z [M+H]$^+$ 493.

Example 185: N-(5-cyano-2-(4-(2,4-difluorophenoxy)piperidin-1-yl)phenyl-1-methyl-2-oxo-1,2,5,6,7,8-hexahydroquinoline-3-carboxamide

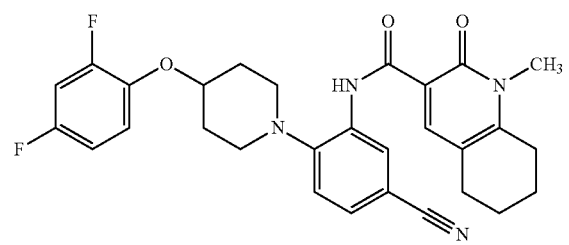 [SMILES: Cn1c2c(cc(C(=O)Nc3cc(C#N)ccc3N3CCC(Oc4ccc(F)cc4F)CC3)c1=O)CCCC2]

ESI-MS m/z [M+H]$^+$ 519.

Example 186: N-(5-cyano-2-(4-(2,4-difluorophenoxy)piperidin-1-yl)phenyl-6-isopropyl-1-methyl-2-oxo-1,2-dihydropyridine-3-carboxamide

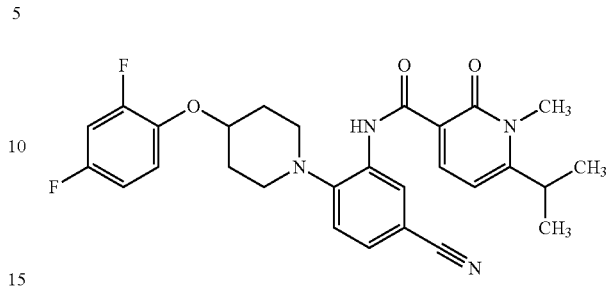

$^1$H NMR (500 MHz, CD$_3$CN) δ ppm 1.29-1.35 (m, 6H), 2.09-2.17 (m, 2H), 2.20-2.29 (m, 2H), 2.85-2.91 (m, 2H), 3.19 (m, 2H), 3.22-3.30 (m, 1H), 3.70-3.72 (s, 3H), 4.46-4.53 (m, 1H), 6.50-6.54 (m, 1H), 6.90-6.96 (m, 1H), 7.00-7.06 (m, 1H), 7.16-7.23 (m, 1H), 7.29-7.32 (m, 1H), 7.40-7.44 (m, 1H), 8.45-8.49 (m, 1H), 8.89-8.92 (m, 1H), 12.52-12.57 (s, 1H); ESI-MS m/z [M+H]$^+$ 507.

Example 187: N-(5-cyano-2-(4-(2,4-difluorophenoxy)piperidin-1-yl)phenyl)-6-methyl-4-oxo-4H-pyrido[1,2-a]pyrimidine-3-carboxamide

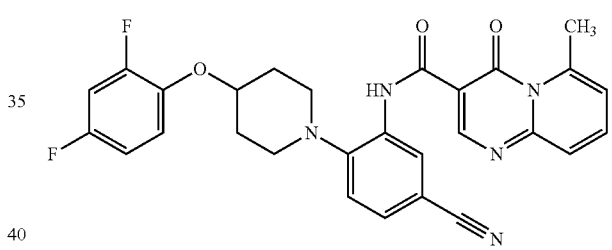

ESI-MS m/z [M+H]$^+$ 516.

Example 188: N-(5-cyano-2-(4-(2,4-difluorophenoxy)piperidin-1-yl)phenyl)-4-(dimethylamino)-2-methoxybenzamide

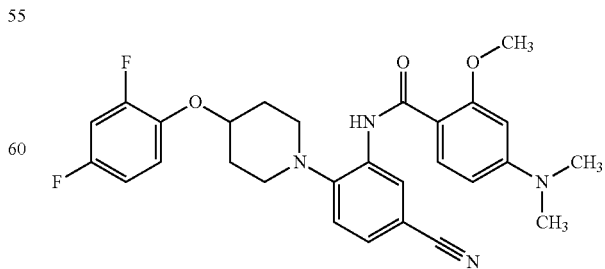

ESI-MS m/z [M+H]$^+$ 507.

Example 189: N-(5-cyano-2-(4-(2,4-difluorophe-noxy)piperidin-1-yl)phenyl)-3,6-difluoro-2-methoxybenzamide

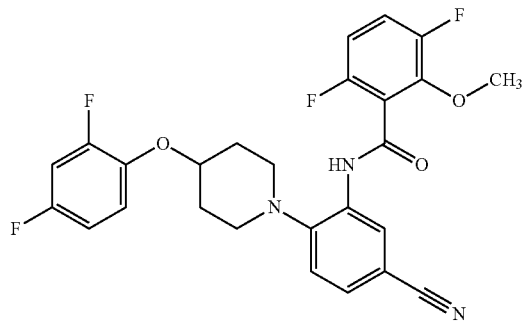 [SMILES: COc1c(F)ccc(F)c1C(=O)Nc1cc(C#N)ccc1N1CCC(Oc2ccc(F)cc2F)CC1]

ESI-MS m/z [M+H]$^+$ 500.

Example 190: 4,5-dichloro-N-(5-cyano-2-(4-(2,4-difluorophenoxy)piperidin-1-yl)phenyl)-2-methoxy-benzamide

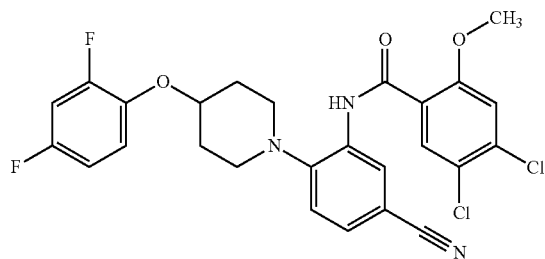

ESI-MS m/z [M+H]$^+$ 532.

Example 191: 6-chloro-N-(5-cyano-2-(4-(2,4-difluo-rophenoxy)piperidin-1-yl)phenyl)-2-methoxynicoti-namide

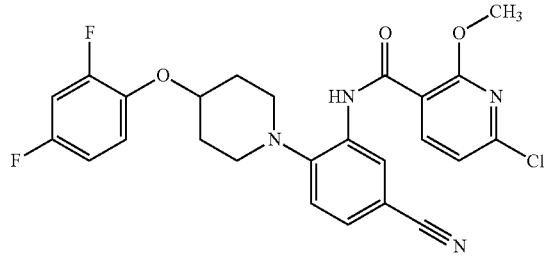 [SMILES: COc1nc(Cl)ccc1C(=O)Nc1cc(C#N)ccc1N1CCC(Oc2ccc(F)cc2F)CC1]

ESI-MS m/z [M+H]$^+$ 499.

Example 192: N-(5-cyano-2-(4-(2,4-difluorophe-noxy)piperidin-1-yl)phenyl)-2,3-difluoro-6-methoxybenzamide

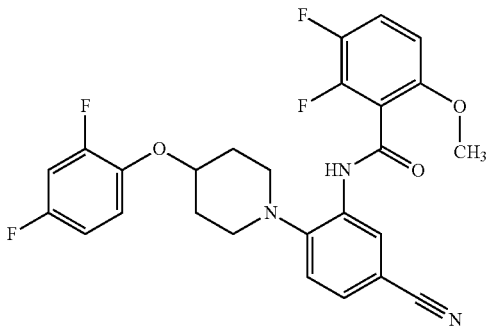 [SMILES: COc1ccc(F)c(F)c1C(=O)Nc1cc(C#N)ccc1N1CCC(Oc2ccc(F)cc2F)CC1]

ESI-MS m/z [M+H]$^+$ 500.

Example 193: 5-chloro-N-(5-cyano-2-(4-(2,4-difluo-rophenoxy)piperidin-1-yl)phenyl)-2-methoxynicoti-namide

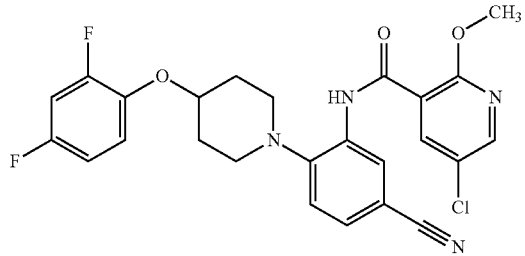 [SMILES: COc1ncc(Cl)cc1C(=O)Nc1cc(C#N)ccc1N1CCC(Oc2ccc(F)cc2F)CC1]

ESI-MS m/z [M+H]$^+$ 499.

Example 194: N-(5-cyano-2-(4-(2,4-difluorophe-noxy)piperidin-1-yl)phenyl)-2-methoxy-4-(trifluo-romethyl)benzamide

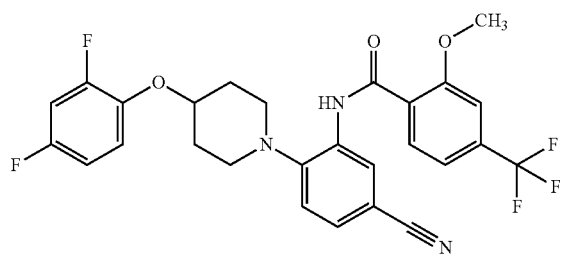 [SMILES: COc1cc(C(F)(F)F)ccc1C(=O)Nc1cc(C#N)ccc1N1CCC(Oc2ccc(F)cc2F)CC1]

ESI-MS m/z [M+H]$^+$ 532.

Example 195: 5-chloro-N-(5-cyano-2-(4-(2,4-difluorophenoxy)piperidin-1-yl)phenyl-2-methoxy-3-methylbenzamide

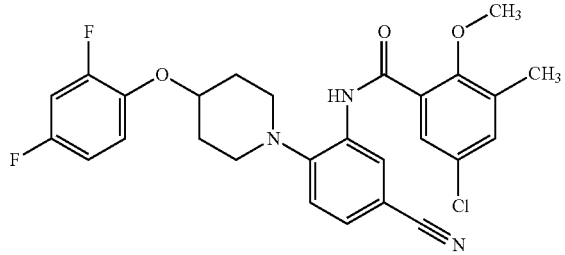 [SMILES: COc1c(C)cc(Cl)cc1C(=O)Nc1cc(C#N)ccc1N1CCC(Oc2ccc(F)cc2F)CC1]

ESI-MS m/z [M+H]$^+$ 512.

Example 196: N-(5-cyano-2-(4-(2,4-difluorophenoxy)piperidin-1-yl)phenyl)-2-methoxy-6,7-dihydro-5H-cyclopenta[b]pyridine-3-carboxamide

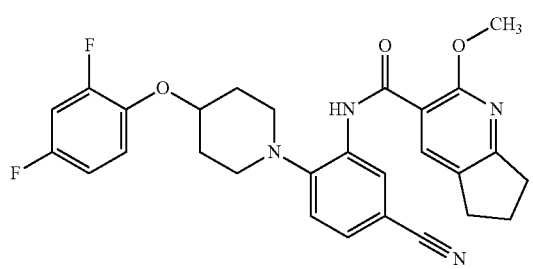 [SMILES: COc1nc2c(cc1C(=O)Nc1cc(C#N)ccc1N1CCC(Oc3ccc(F)cc3F)CC1)CCC2]

ESI-MS m/z [M+H]$^+$ 505.

Example 197: N-(5-cyano-2-(4-(2,4-difluorophenoxy)piperidin-1-yl)phenyl)-9-methyl-4-oxo-4H-pyrido[1,2-a]pyrimidine-3-carboxamide

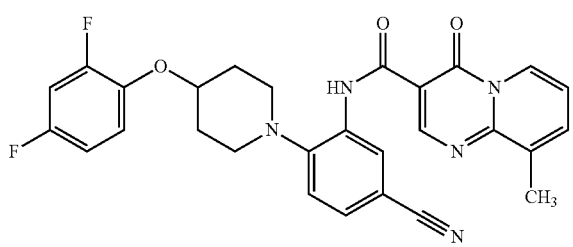 [SMILES: Cc1cccn2c(=O)c(C(=O)Nc3cc(C#N)ccc3N3CCC(Oc4ccc(F)cc4F)CC3)cnc12]

ESI-MS m/z [M+H]$^+$ 516.

Example 198: N-(5-cyano-2-(4-(2,4-difluorophenoxy)piperidin-1-yl)phenyl)-2,3-dimethyl-5-oxo-5H-thiazolo[3,2-a]pyrimidine-6-carboxamide

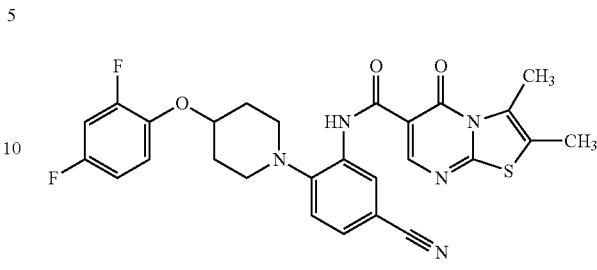

ESI-MS m/z [M+H]$^+$ 536.

Example 199: N-(5-cyano-2-(4-(2,4-difluorophenoxy)piperidin-1-yl)phenyl)-1-(3-methoxypropyl-2-oxo-1,2-dihydropyridine-3-carboxamide

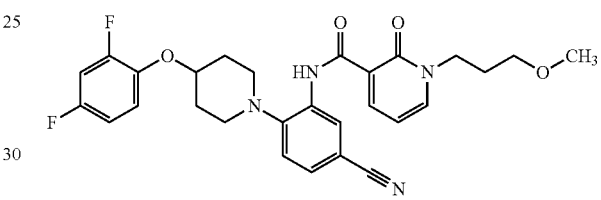

ESI-MS m/z [M+H]$^+$ 523.

Example 200: N-(5-cyano-2-(4-(2,4-difluorophenoxy)piperidin-1-yl)phenyl)-5-oxo-5H-thiazolo[3,2-a]pyrimidine-6-carboxamide

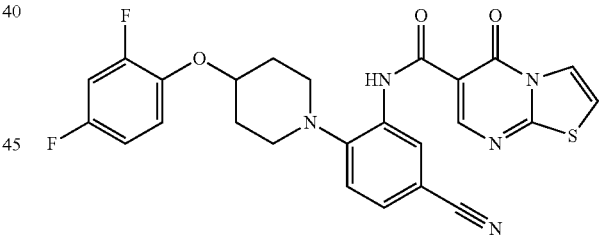

ESI-MS m/z [M+H]$^+$ 508.

Example 201: N-(5-cyano-2-(4-(2,4-difluorophenoxy)piperidin-1-yl)phenyl-7-methyl-4-oxo-4H-pyrido[1,2-a]pyrimidine-3-carboxamide

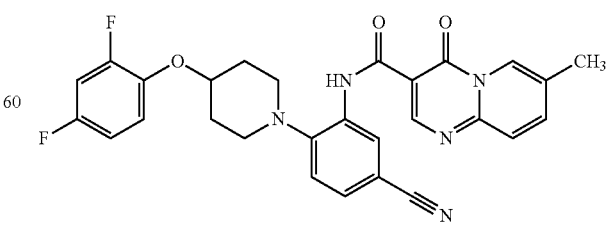

ESI-MS m/z [M+H]$^+$ 516.

Example 202: N-(5-cyano-2-(4-(2,4-difluorophenoxy)piperidin-1-yl)phenyl-1-ethyl-4,6-dimethyl-2-oxo-1,2-dihydropyridine-3-carboxamide

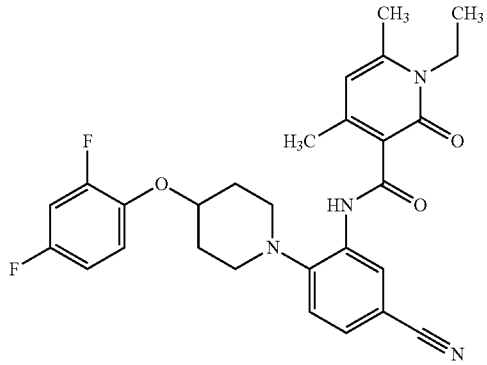 [SMILES: CCn1c(C)cc(C)c(C(=O)Nc2cc(C#N)ccc2N2CCC(Oc3ccc(F)cc3F)CC2)c1=O]

ESI-MS m/z [M+H]$^+$ 507.

Example 203: N-(5-cyano-2-(4-(2,4-difluorophenoxy)piperidin-1-yl)phenyl)-2-oxo-1-(pyridin-2-ylmethyl)-1,2-dihydropyridine-3-carboxamide

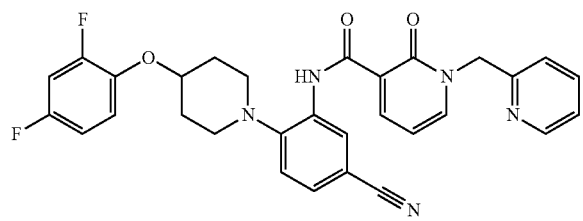 [SMILES: N#Cc1ccc(N2CCC(Oc3ccc(F)cc3F)CC2)c(NC(=O)c2cccn(Cc3ccccn3)c2=O)c1]

ESI-MS m/z [M+H]$^+$ 542.

Example 204: N-(5-cyano-2-(4-(2,4-difluorophenoxy)piperidin-1-yl)phenyl)-1-(2-(dimethylamino)-2-oxoethyl)-2-oxo-1,2-dihydropyridine-3-carboxamide

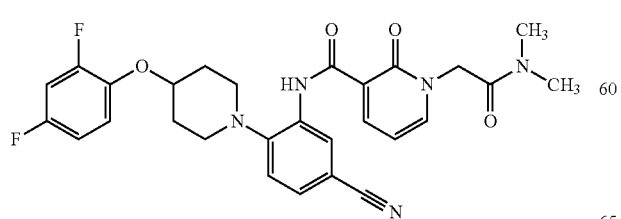

ESI-MS m/z [M+H]$^+$ 536.

Example 205: N-(5-cyano-2-(4-(2,4-difluorophenoxy)piperidin-1-yl)phenyl)-2,5-dimethoxybenzamide

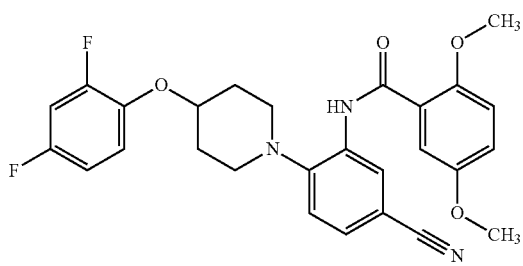 [SMILES: COc1ccc(OC)c(C(=O)Nc2cc(C#N)ccc2N2CCC(Oc3ccc(F)cc3F)CC2)c1]

ESI-MS m/z [M+H]$^+$ 494.

Example 206: 3,6-dichloro-N-(5-cyano-2-(4-(2,4-difluorophenoxy)piperidin-1-yl)phenyl)-2-methoxybenzamide

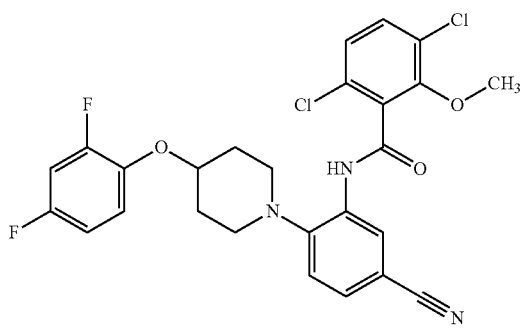 [SMILES: COc1c(Cl)ccc(Cl)c1C(=O)Nc1cc(C#N)ccc1N1CCC(Oc2ccc(F)cc2F)CC1]

ESI-MS m/z [M+H]$^+$ 532.

Example 207: N-(5-cyano-2-(4-(2,4-difluorophenoxy)piperidin-1-yl)phenyl)-3,5-difluoro-2-methoxybenzamide

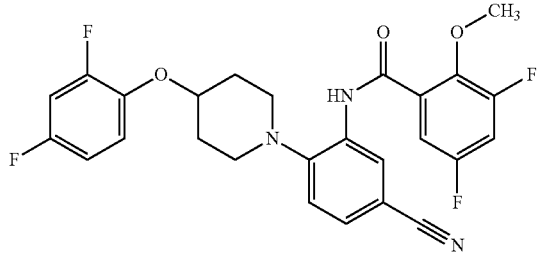 [SMILES: COc1c(F)cc(F)cc1C(=O)Nc1cc(C#N)ccc1N1CCC(Oc2ccc(F)cc2F)CC1]

ESI-MS m/z [M+H]$^+$ 500.

Example 208: N-(5-cyano-2-(4-(2,4-difluorophenoxy)piperidin-1-yl)phenyl)-2-methoxy-5-(trifluoromethyl)benzamide

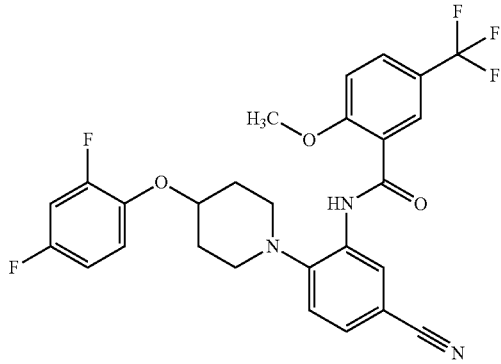 [SMILES: COc1ccc(C(F)(F)F)cc1C(=O)Nc1cc(C#N)ccc1N1CCC(Oc2ccc(F)cc2F)CC1]

ESI-MS m/z [M+H]$^+$ 532.

Example 209: 5-(tert-butyl)-N-(5-cyano-2-(4-(2,4-difluorophenoxy)piperidin-1-yl)phenyl)-2-methoxybenzamide

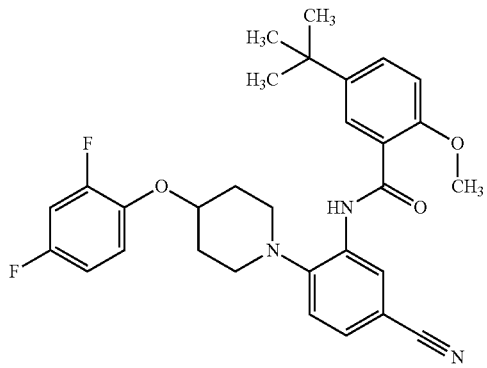 [SMILES: COc1ccc(C(C)(C)C)cc1C(=O)Nc1cc(C#N)ccc1N1CCC(Oc2ccc(F)cc2F)CC1]

ESI-MS m/z [M+H]$^+$ 520.

Example 210: N-(5-cyano-2-(4-(2,4-difluorophenoxy)piperidin-1-yl)phenyl)-5-fluoro-2-methoxybenzamide

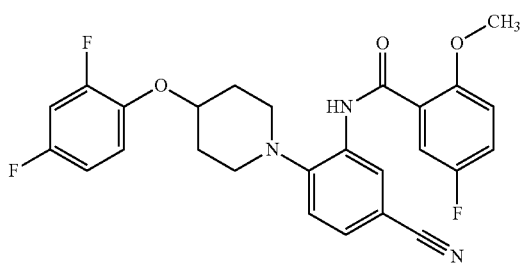 [SMILES: COc1ccc(F)cc1C(=O)Nc1cc(C#N)ccc1N1CCC(Oc2ccc(F)cc2F)CC1]

ESI-MS m/z [M+H]$^+$ 482.

Example 211: 5-chloro-N-(5-cyano-2-(4-(2,4-difluorophenoxy)piperidin-1-yl)phenyl)-2-methoxybenzamide

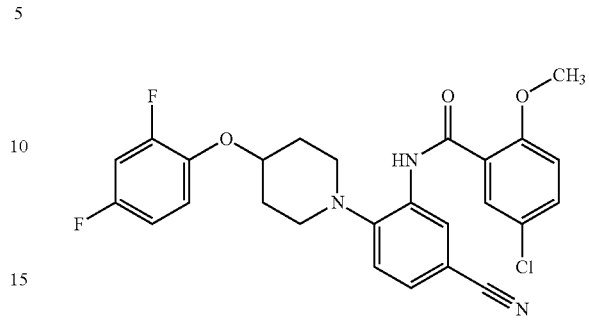

ESI-MS m/z [M+H]$^+$ 498.

Example 212: 3-chloro-N-(5-cyano-2-(4-(2,4-difluorophenoxy)piperidin-1-yl)phenyl)-2,6-dimethoxybenzamide

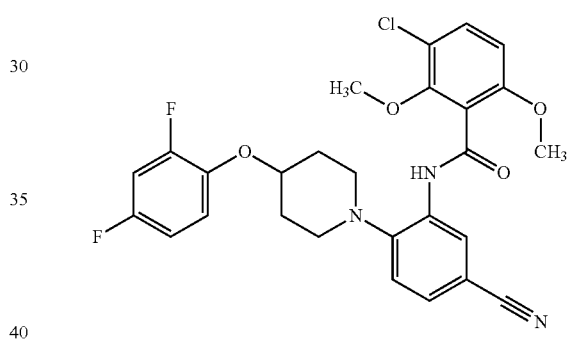

ESI-MS m/z [M+H]$^+$ 528.

Example 213: N-(5-cyano-2-(4-(2,4-difluorophenoxy)piperidin-1-yl)phenyl-2-methoxy-6-(trifluoromethyl)nicotinamide

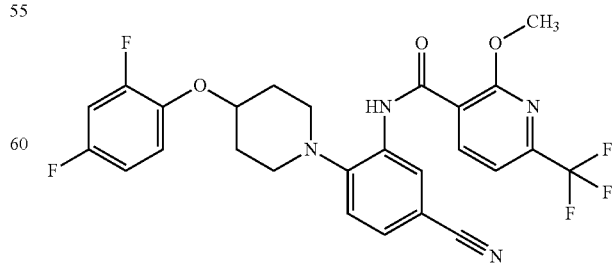

ESI-MS m/z [M+H]$^+$ 533.

Example 214: N-(5-cyano-2-(4-(2,4-difluorophenoxy)piperidin-1-yl)phenyl)-2-methoxy-3,6-dimethylbenzamide

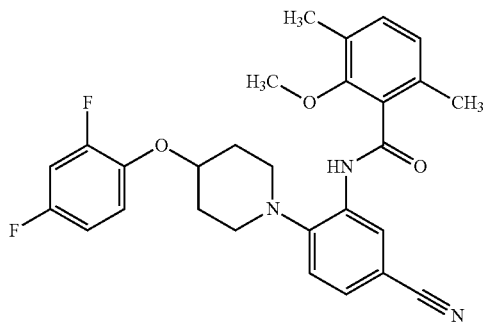 [SMILES: COc1c(C)ccc(C)c1C(=O)Nc1cc(C#N)ccc1N1CCC(Oc2ccc(F)cc2F)CC1]

ESI-MS m/z [M+H]+ 492.

Example 215: N-(5-cyano-2-(4-(2,4-difluorophenoxy)piperidin-1-yl)phenyl)-2-methoxy-5-morpholinobenzamide

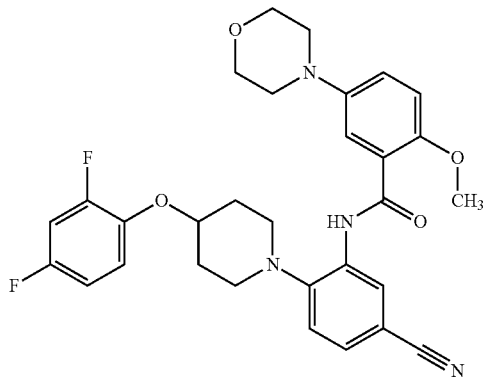 [SMILES: COc1ccc(N2CCOCC2)cc1C(=O)Nc1cc(C#N)ccc1N1CCC(Oc2ccc(F)cc2F)CC1]

ESI-MS m/z [M+H]+ 549.

Example 216: 4-(tert-butyl)-N-(5-cyano-2-(4-(2,4-difluorophenoxy)piperidin-1-yl)phenyl)-2-methoxybenzamide

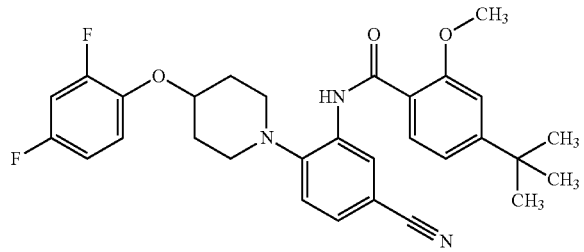 [SMILES: COc1cc(C(C)(C)C)ccc1C(=O)Nc1cc(C#N)ccc1N1CCC(Oc2ccc(F)cc2F)CC1]

ESI-MS m/z [M+H]+ 520.

Example 217: N-(5-cyano-2-(4-(2,4-difluorophenoxy)piperidin-1-yl)phenyl)-2-methyl-5-oxo-5H-thiazolo[3,2-a]pyrimidine-6-carboxamide

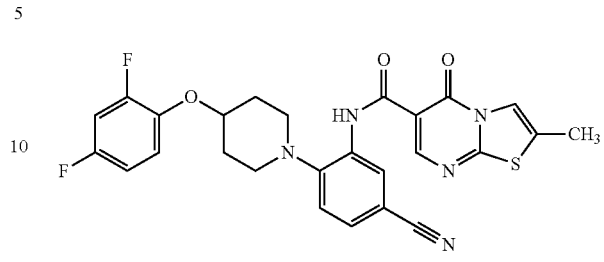

ESI-MS m/z [M+H]+ 522.

Example 218: N-(5-cyano-2-(4-(2,4-difluorophenoxy)piperidin-1-yl)phenyl)-3-methyl-5-oxo-5H-thiazolo[3,2-a]pyrimidine-6-carboxamide

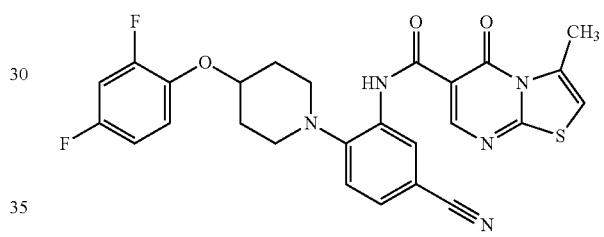

ESI-MS m/z [M+H]+ 522.

Example 219: N-(5-cyano-2-(4-(2,4-difluorophenoxy)piperidin-1-yl)phenyl)-4-methoxy-1-phenyl-1H-pyrazole-3-carboxamide

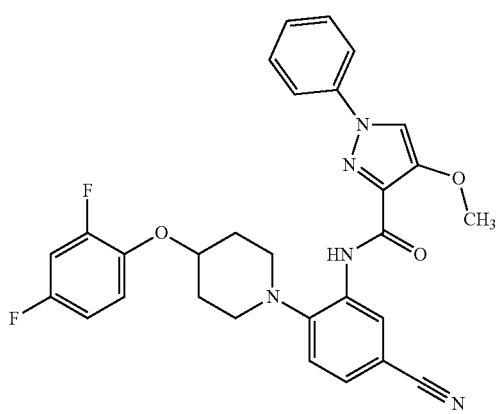 [SMILES: COc1cn(-c2ccccc2)nc1C(=O)Nc1cc(C#N)ccc1N1CCC(Oc2ccc(F)cc2F)CC1]

ESI-MS m/z [M+H]+ 530.

Example 220: 1-benzyl-N-(5-cyano-2-(4-(2,4-difluorophenoxy)piperidin-1-yl)phenyl)-5-methoxy-1H-1,2,3-triazole-4-carboxamide

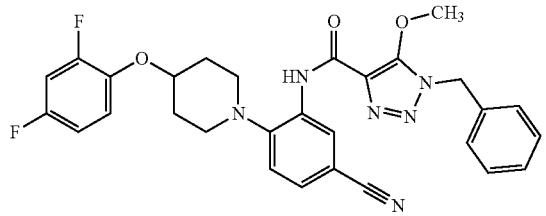 [SMILES: COc1c(C(=O)Nc2cc(C#N)ccc2N2CCC(Oc3ccc(F)cc3F)CC2)nnn1Cc1ccccc1]

ESI-MS m/z [M+H]$^+$ 545.

Example 221: 1-(2-chlorobenzyl)-N-(5-cyano-2-(4-(2,4-difluorophenoxy)piperidin-1-yl)phenyl)-5-methoxy-1H-1,2,3-triazole-4-carboxamide

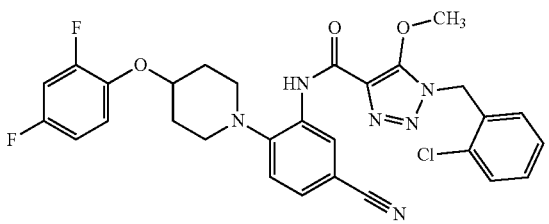 [SMILES: COc1c(C(=O)Nc2cc(C#N)ccc2N2CCC(Oc3ccc(F)cc3F)CC2)nnn1Cc1ccccc1Cl]

ESI-MS m/z [M+H]$^+$ 579.

Example 222: 3-chloro-N-(5-cyano-2-(4-(2,4-difluorophenoxy)piperidin-1-yl)phenyl)-2-methoxybenzamide

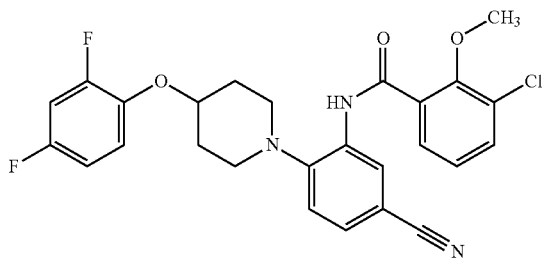

ESI-MS m/z [M+H]$^+$ 498.

Example 223: 4-chloro-N-(5-cyano-2-(4-(2,4-difluorophenoxy)piperidin-1-yl)phenyl)-2-methoxynicotinamide

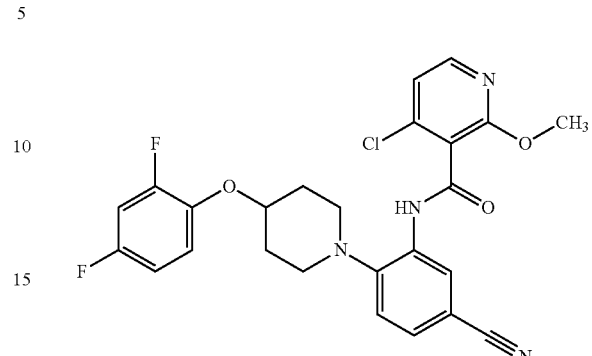

ESI-MS m/z [M+H]$^+$ 499.

Example 224: N-(5-cyano-2-(4-(2,4-difluorophenoxy)piperidin-1-yl)phenyl)-5-fluoro-2-methoxynicotinamide

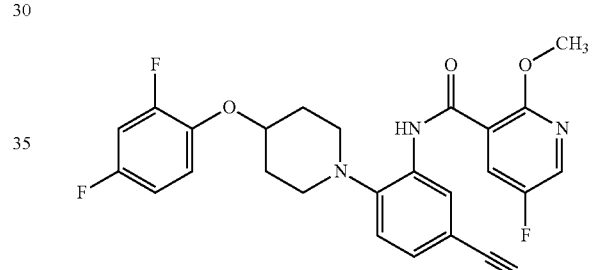

ESI-MS m/z [M+H]$^+$ 483.

Example 225: 5-bromo-N-(5-cyano-2-(4-(2,4-difluorophenoxy)piperidin-1-yl)phenyl)-2-methoxybenzamide

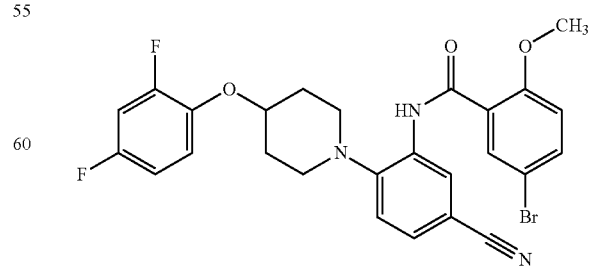

ESI-MS m/z [M+H]$^+$ 542.

Example 226: 4-bromo-N-(5-cyano-2-(4-(2,4-difluorophenoxy)piperidin-1-yl)phenyl)-2-methoxybenzamide

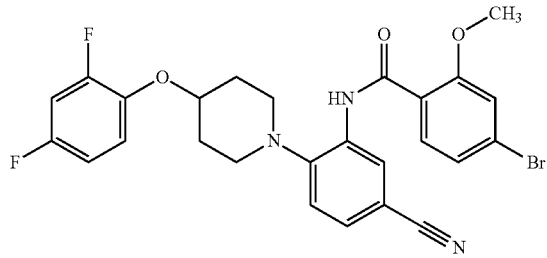 [SMILES: COc1cc(Br)ccc1C(=O)Nc1cc(C#N)ccc1N1CCC(Oc2ccc(F)cc2F)CC1]

ESI-MS m/z [M+H]$^+$ 542.

Example 227: N-(5-cyano-2-(4-(2,4-difluorophenoxy)piperidin-1-yl)phenyl)-2-methoxy-6-methylbenzamide

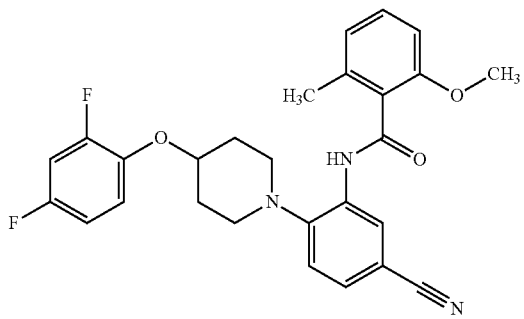 [SMILES: COc1cccc(C)c1C(=O)Nc1cc(C#N)ccc1N1CCC(Oc2ccc(F)cc2F)CC1]

ESI-MS m/z [M+H]$^+$ 478.

Example 228: 4-chloro-N-(5-cyano-2-(4-(2,4-difluorophenoxy)piperidin-1-yl)phenyl)-2-methoxybenzamide

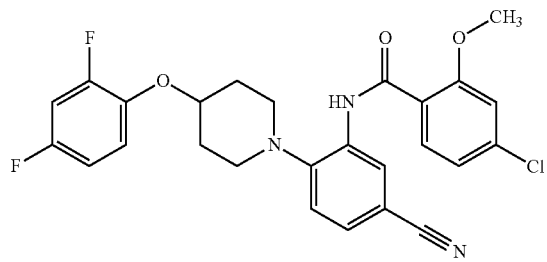

ESI-MS m/z [M+H]$^+$ 498.

Example 229: N-(5-cyano-2-(4-(2,4-difluorophenoxy)piperidin-1-yl)phenyl-4,5-difluoro-2-methoxybenzamide

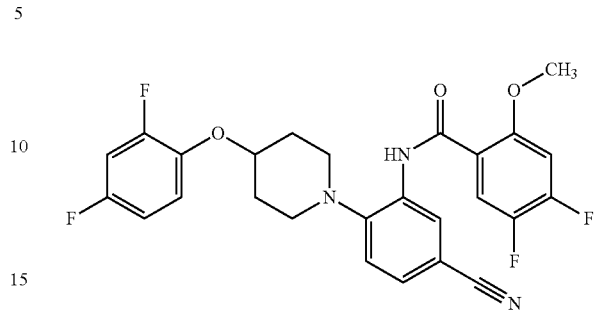

ESI-MS m/z [M+H]$^+$ 500.

Example 230: N-(5-cyano-2-(4-(2,4-difluorophenoxy)piperidin-1-yl)phenyl-2,3-dimethoxybenzamide

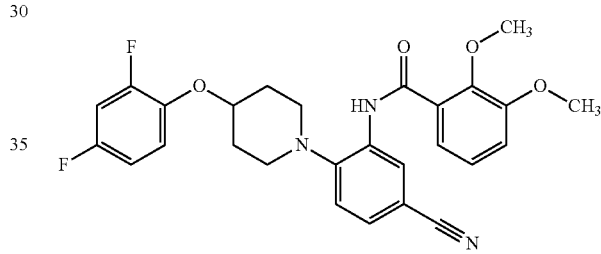

ESI-MS m/z [M+H]$^+$ 494.

Example 231: N-(5-cyano-2-(4-(2,4-difluorophenoxy)piperidin-1-yl)phenyl)-2-methoxy-5-(trifluoromethoxy)benzamide

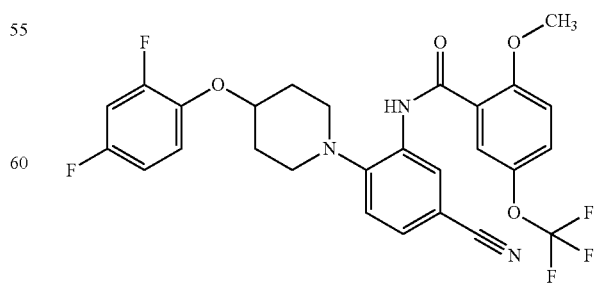

ESI-MS m/z [M+H]$^+$ 548.

Example 232: N-(5-cyano-2-(4-(2,4-difluorophenoxy)piperidin-1-yl)phenyl)-2-methoxy-3-methylbenzamide

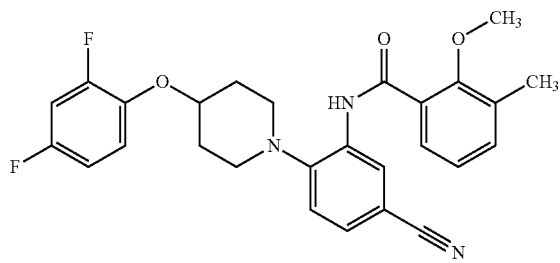 [SMILES: COc1c(C)cccc1C(=O)Nc1cc(C#N)ccc1N1CCC(Oc2ccc(F)cc2F)CC1]

ESI-MS m/z [M+H]$^+$ 478.

Example 233: N-(5-cyano-2-(4-(2,4-difluorophenoxy)piperidin-1-yl)phenyl)-3,4-difluoro-2-methoxybenzamide

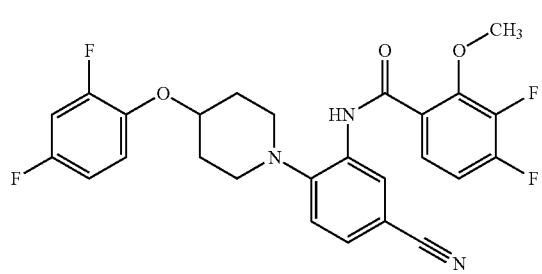 [SMILES: COc1c(C(=O)Nc2cc(C#N)ccc2N2CCC(Oc3ccc(F)cc3F)CC2)ccc(F)c1F]

ESI-MS m/z [M+H]$^+$ 500.

Example 234: 3,5-dichloro-N-(5-cyano-2-(4-(2,4-difluorophenoxy)piperidin-1-yl)phenyl)-2-methoxybenzamide

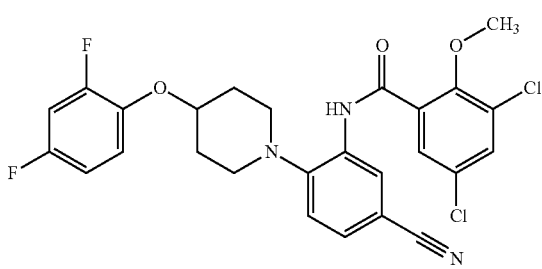 [SMILES: COc1c(Cl)cc(Cl)cc1C(=O)Nc1cc(C#N)ccc1N1CCC(Oc2ccc(F)cc2F)CC1]

ESI-MS m/z [M+H]$^+$ 532.

Example 235: N-(5-cyano-2-(4-(2,4-difluorophenoxy)piperidin-1-yl)phenyl)-2,4-dimethoxybenzamide

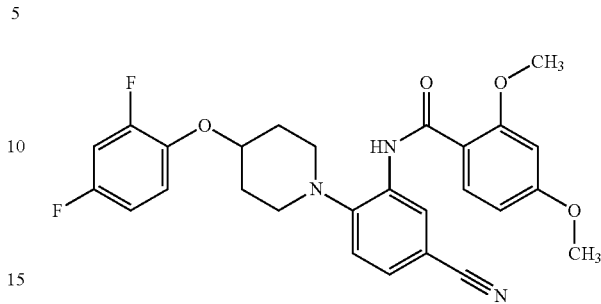

ESI-MS m/z [M+H]$^+$ 494.

Example 236: N-(5-cyano-2-(4-(2,4-difluorophenoxy)piperidin-1-yl)phenyl)-2-methoxy-4-methylbenzamide

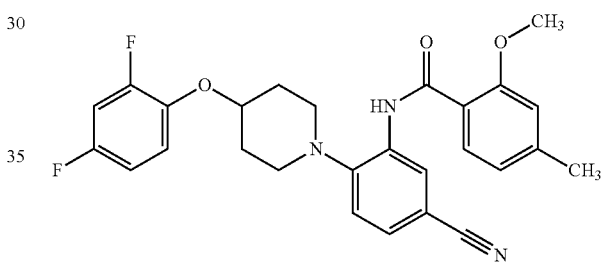

ESI-MS m/z [M+H]$^+$ 478.

Example 237: N-(5-cyano-2-(4-(2,4-difluorophenoxy)piperidin-1-yl)phenyl)-2-methoxy-5-methylbenzamide

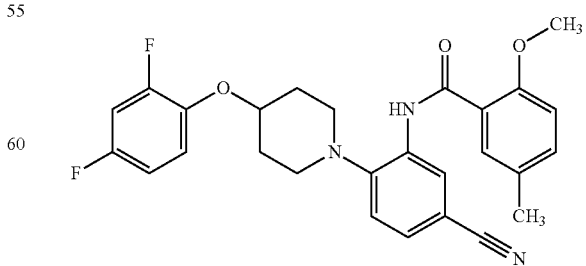

ESI-MS m/z [M+H]$^+$ 478.

Example 238: N-(5-cyano-2-(4-(2,4-difluorophenoxy)piperidin-1-yl)phenyl)-2,6-dimethoxybenzamide

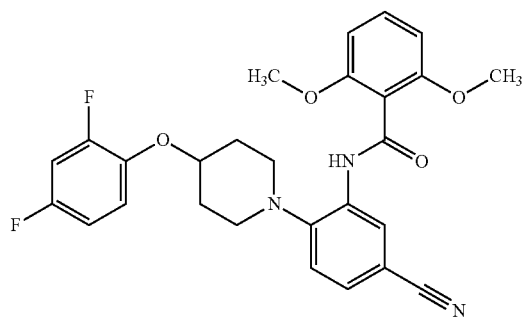 [SMILES: COc1cccc(OC)c1C(=O)Nc1cc(C#N)ccc1N1CCC(Oc2ccc(F)cc2F)CC1]

ESI-MS m/z [M+H]$^+$ 494.

Compounds in Examples 239 through 250 were prepared in accordance with Scheme F.

Scheme F

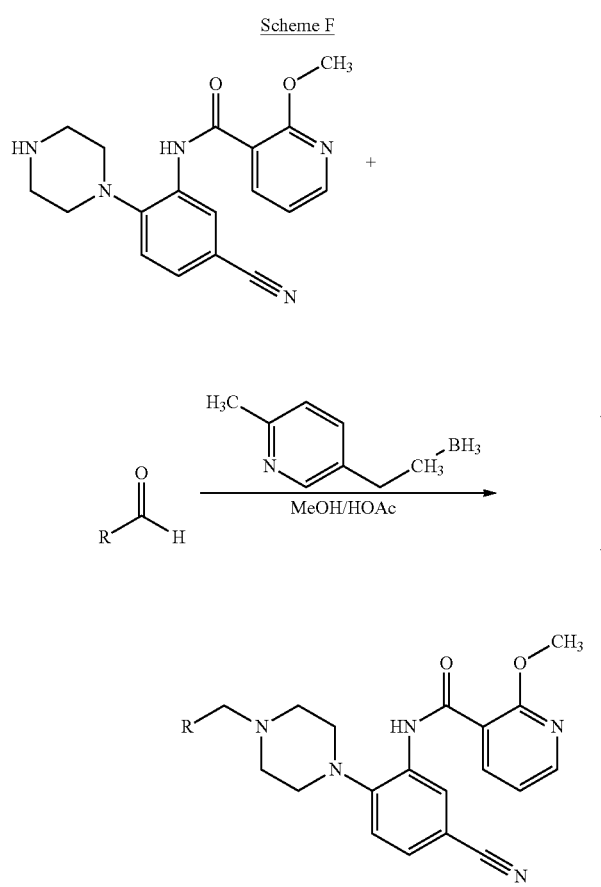

For Examples 239 through 250, a solution of N-(5-cyano-2-(piperazin-1-yl)phenyl)-2-methoxynicotinamide (0.017 g, 0.05 mmol) and an aldehyde R—C(O)H (0.200 mmol) in 10% HOAc/MeOH (v/v, 0.5 mL) was stirred for 15 minutes at room temperature. Next, 5-ethyl-2-methylpyridine borane (0.030 mL, 0.200 mmol) was added and the resulting solution was heated at 50° C. for 15 minutes. Following reaction, the product was purified by preparative HPLC, eluting with a gradient of 5-50% acetonitrile in water (acid mode) to give each of the title compounds as a TFA salt. Compounds in Examples 240 and 247 were re-purified by preparative HPLC, eluting with a gradient of 10-70% acetonitrile in water (basic mode) to give the title compound as the free form.

Example 239: N-(5-cyano-2-(4-(2-fluorobenzyl)piperazin-1-yl)phenyl)-2-methoxynicotinamide

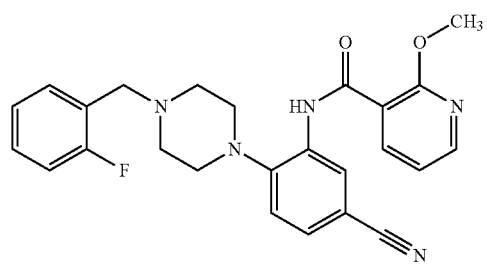 [SMILES: COc1ncccc1C(=O)Nc1cc(C#N)ccc1N1CCN(Cc2ccccc2F)CC1]

ESI-MS m/z [M+H]$^+$ 446.

Example 240: N-(5-cyano-2-(4-(3-fluorobenzyl)piperazin-1-yl)phenyl)-2-methoxynicotinamide

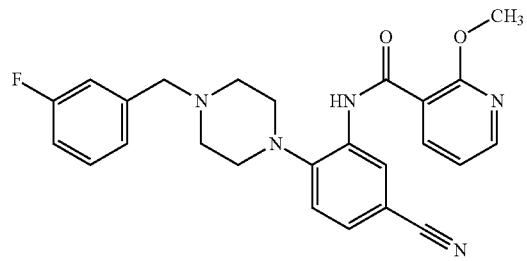 [SMILES: COc1ncccc1C(=O)Nc1cc(C#N)ccc1N1CCN(Cc2cccc(F)c2)CC1]

$^1$H NMR (500 MHz, CD$_3$OD), δ ppm 2.69-2.83 (m, 4H), 3.04-3.09 (m, 4H), 3.74-3.77 (m, 2H), 4.17-4.20 (m, 3H), 7.07-7.13 (m, 1H), 7.19-7.30 (m, 3H), 7.40-7.46 (m, 2H), 7.55-7.59 (m, 1H), 8.44-8.47 (m, 1H), 8.58-8.62 (m, 1H), 8.75-8.78 (m, 1H); ESI-MS m/z [M+H]$^+$ 446.

Example 241: N-(5-cyano-2-(4-(thiazol-4-ylmethyl)piperazin-1-yl)phenyl)-2-methoxynicotinamide

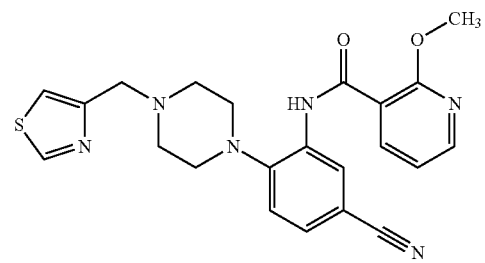 [SMILES: COc1ncccc1C(=O)Nc1cc(C#N)ccc1N1CCN(Cc2cscn2)CC1]

ESI-MS m/z [M+H]$^+$ 435.

Example 242: N-(5-cyano-2-(4-(2-fluoro-5-methoxybenzyl)piperazin-1-yl)phenyl)-2-methoxynicotinamide

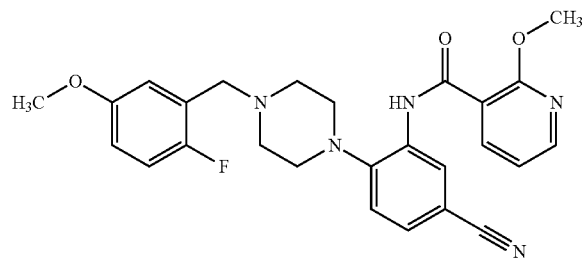

ESI-MS m/z [M+H]$^+$ 476.

Example 243: N-(5-cyano-2-(4-(2,3-difluorobenzyl)piperazin-1-yl)phenyl)-2-methoxynicotinamide

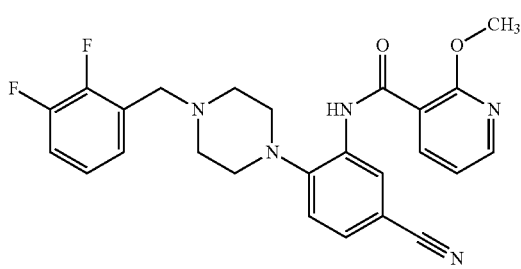 [SMILES: COc1ncccc1C(=O)Nc1cc(C#N)ccc1N1CCN(Cc2cccc(F)c2F)CC1]

ESI-MS m/z [M+H]$^+$ 464.

Example 244: N-(5-cyano-2-(4-((5-fluoropyridin-2-yl)methylpiperazin-1-yl)phenyl)-2-methoxynicotinamide

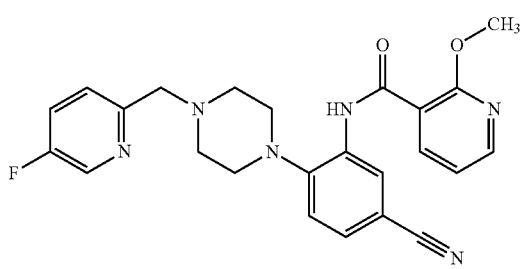 [SMILES: COc1ncccc1C(=O)Nc1cc(C#N)ccc1N1CCN(Cc2ccc(F)cn2)CC1]

ESI-MS m/z [M+H]$^+$ 447.

Example 245: N-(5-cyano-2-(4-(2-cyanobenzyl)piperazin-1-yl)phenyl)-2-methoxynicotinamide

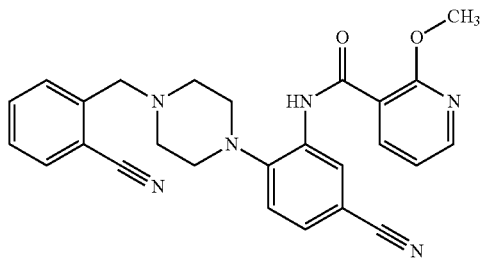 [SMILES: COc1ncccc1C(=O)Nc1cc(C#N)ccc1N1CCN(Cc2ccccc2C#N)CC1]

ESI-MS m/z [M+H]$^+$ 453.

Example 246: N-(5-cyano-2-(4-(3,4-difluorobenzyl)piperazin-1-yl)phenyl)-2-methoxynicotinamide

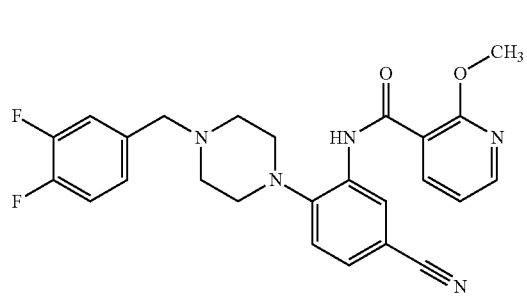 [SMILES: COc1ncccc1C(=O)Nc1cc(C#N)ccc1N1CCN(Cc2ccc(F)c(F)c2)CC1]

ESI-MS m/z [M+H]$^+$ 464.

Example 247: N-(5-cyano-2-(4-(2-methoxybenzyl)piperazin-1-yl)phenyl)-2-methoxynicotinamide

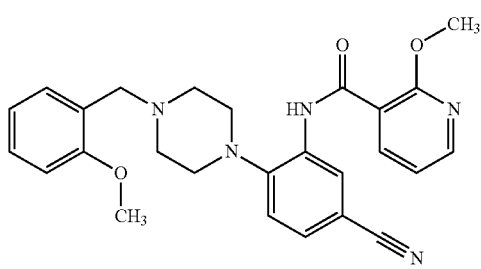 [SMILES: COc1ccccc1CN1CCN(c2ccc(C#N)cc2NC(=O)c2cccnc2OC)CC1]

ESI-MS m/z [M+H]$^+$ 458.

Example 248: N-(5-cyano-2-(4-(3-cyanobenzyl)piperazin-1-yl)phenyl)-2-methoxynicotinamide

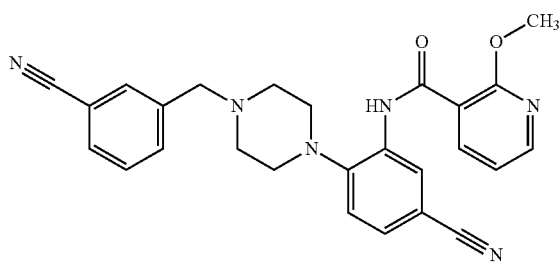 [SMILES: COc1ncccc1C(=O)Nc1cc(C#N)ccc1N1CCN(Cc2cccc(C#N)c2)CC1]

ESI-MS m/z [M+H]+ 453.

Example 249: N-(5-cyano-2-(4-(2,6-difluorobenzyl)piperazin-1-yl)phenyl-2-methoxynicotinamide

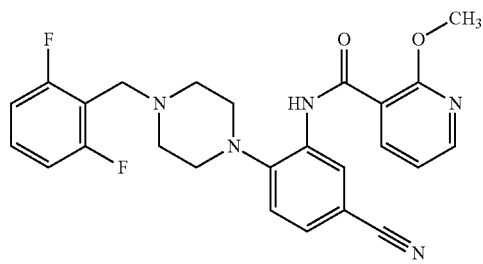 [SMILES: COc1ncccc1C(=O)Nc1cc(C#N)ccc1N1CCN(Cc2c(F)cccc2F)CC1]

ESI-MS m/z [M+H]+ 464.

Example 250: N-(5-cyano-2-(4-((5-methoxypyridin-2-yl)methyl)piperazin-1-yl)phenyl)-2-methoxynicotinamide

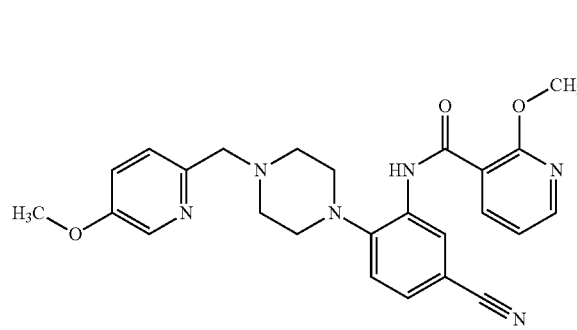

ESI-MS m/z [M+H]+ 459.

Example 251: (R)-4-(4-(2,4-difluorophenoxy)piperidin-1-yl)-5-(2-methoxynicotinamido)-N-(tetrahydrofuran-3-yl)picolinamide

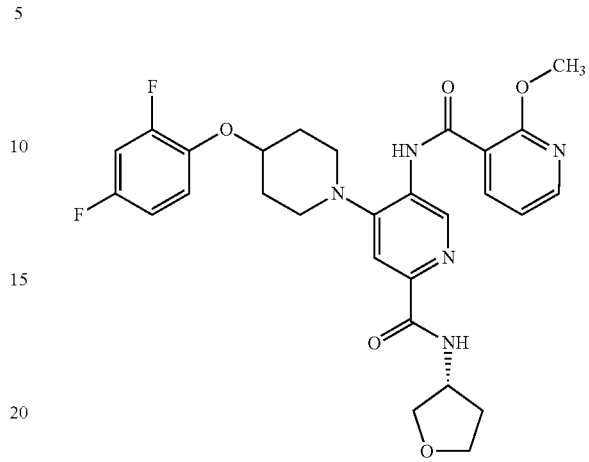

To a solution of (R)-5-amino-4-(4-(2,4-difluorophenoxy)piperidin-1-yl)-N-(tetrahydrofuran-3-yl)picolinamide (31 mg, 0.074 mmol) in toluene (494 µL) was added 2-methoxynicotinic acid (13.61 mg, 0.089 mmol) and DIPEA (51.8 µL, 0.296 mmol), followed by 2,4,6-tripropyl-1,3,5,2,4,6-trioxatriphosphinane 2,4,6-trioxide (97 µL, 0.163 mmol) (50% solution in EtOAc). The resulting solution was heated at 110° C. for 8 hours and then purified by preparative HPLC (acidic conditions) to give a TFA salt of the title compound as a yellow solid (26 mg, 53%). $^1$H NMR (500 MHz, CD$_3$OD) δ ppm 2.02-2.11 (m, 4H), 2.16-2.26 (m, 2H), 2.33-2.43 (m, 1H), 3.13-3.25 (m, 2H), 3.42-3.57 (m, 2H), 3.79 (dd, J=9.03, 3.66 Hz, 1H), 3.85-3.92 (m, 1H), 3.98 (dd, J=9.28, 5.86 Hz, 1H), 4.00-4.06 (m, 1H), 4.27 (s, 3H), 4.52-4.59 (m, 1H), 4.63 (ddt, J=7.63, 6.04, 3.91, 3.91 Hz, 1H), 6.90 (ddq, J=9.76, 7.32, 1.46, 1.46, 1.46 Hz, 1H), 7.01 (ddd, J=11.35, 8.42, 3.17 Hz, 1H), 7.16-7.26 (m, 2H), 7.96 (s, 1H), 8.43 (dd, J=4.88, 1.95 Hz, 1H), 8.55 (dd, J=7.81, 1.95 Hz, 1H), 9.28 (s, 1H); ESI-MS m/z [M+H]+ 554.3.

Example 252: 4-(4-(2,4-difluorophenoxy)piperidin-1-yl)-N-ethyl-5-(2-methoxynicotinamido)picolinamide

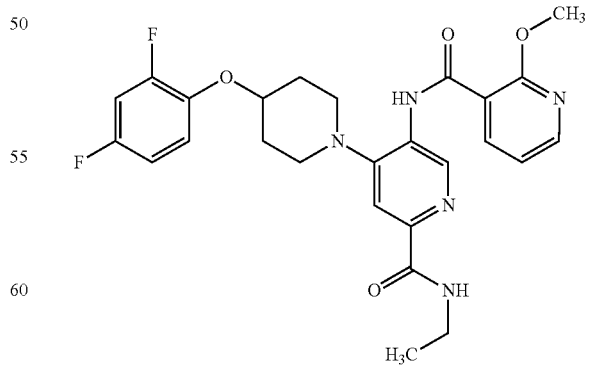

The title compound was prepared in a manner similar to Example 251, using 5-amino-4-(4-(2,4-difluorophenoxy)piperidin-1-yl)-N-ethylpicolinamide (32 mg, 0.085 mmol, 1 eq) in place of (R)-5-amino-4-(4-(2,4-difluorophenoxy)piperidin-1-yl)-N-(tetrahydrofuran-3-yl)picolinamide to give a TFA salt of the title compound as a yellow solid (29 mg, 55%). ¹H NMR (500 MHz, CD₃OD) δ ppm 1.26-1.30 (m, 3H), 2.02-2.09 (m, 2H), 2.20 (ddt, J=13.42, 7.08, 3.42, 3.42 Hz, 2H), 3.12-3.21 (m, 2H), 3.43-3.54 (m, 5H), 3.45-3.51 (m, 4H), 4.27 (s, 3H), 4.56 (tt, J=7.44, 3.78 Hz, 1H), 6.90 (dddd, J=9.34, 7.87, 3.05, 1.71 Hz, 1H), 7.01 (ddd, J=1.23, 8.54, 3.17 Hz, 1H), 7.15-7.30 (m, 2H), 7.94 (s, 1H), 8.42 (dd, J=4.88, 1.95 Hz, 1H), 8.56 (dd, J=7.32, 1.95 Hz, 1H), 9.30 (s, 1H); ESI-MS m/z [M+H]⁺ 512.3.

Example 253: 4-(4-(2,4-difluorophenoxy)piperidin-1-yl)-N-isopropyl-5-(2-methoxynicotinamido)picolinamide

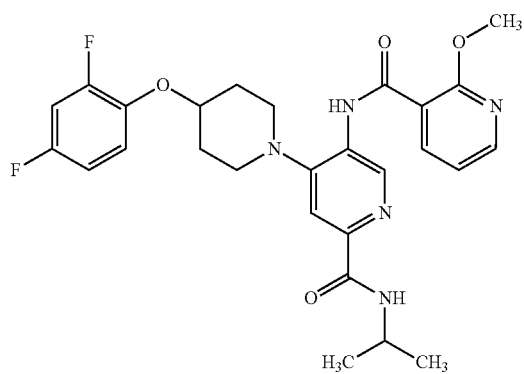 [SMILES: COc1ncccc1C(=O)Nc1cnc(C(=O)NC(C)C)cc1N1CCC(Oc2ccc(F)cc2F)CC1]

The title compound was prepared in a manner similar to Example 251, using 5-amino-4-(4-(2,4-difluorophenoxy)piperidin-1-yl)-N-isopropylpicolinamide (32 mg, 0.082 mmol, 1 eq) in place of (R)-5-amino-4-(4-(2,4-difluorophenoxy)piperidin-1-yl)-N-(tetrahydrofuran-3-yl)picolinamide to give a TFA salt of the title compound as a yellow film (8 mg, 15%). ¹H NMR (500 MHz, CD₃OD) δ ppm 1.30 (d, J=6.83 Hz, 6H), 2.00-2.10 (m, 2H), 2.15-2.25 (m, 2H), 3.19 (ddd, J=12.08, 8.42, 3.42 Hz, 2H), 3.45-3.53 (m, 2H), 4.16-4.25 (m, 1H), 4.27 (s, 3H), 4.56 (tt, J=7.44, 3.54 Hz, 1H), 6.85-6.95 (m, 1H), 7.00 (ddd, J=11.23, 8.54, 3.17 Hz, 1H), 7.17-7.29 (m, 2H), 7.94 (s, 1H), 8.42 (dd, J=4.88, 1.95 Hz, 1H), 8.54 (dd, J=7.32, 1.95 Hz, 1H), 9.27 (s, 1H); ESI-MS m/z [M+H]⁺ 526.25.

Example 254: 4-(4-(2,4-difluorophenoxy)piperidin-1-yl)-5-(2-methoxynicotinamido)-N-propylpicolinamide

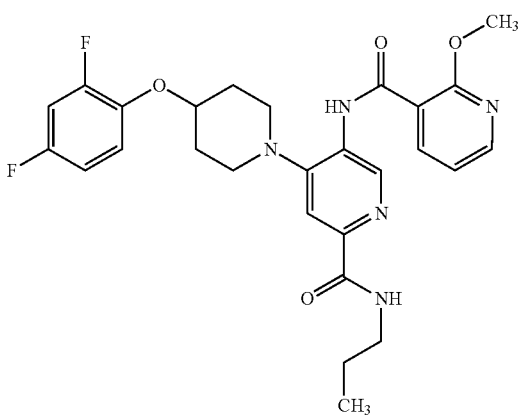 [SMILES: CCCNC(=O)c1cc(N2CCC(Oc3ccc(F)cc3F)CC2)c(NC(=O)c2cccnc2OC)cn1]

The title compound was prepared in a manner similar to Example 251, using 5-amino-4-(4-(2,4-difluorophenoxy)piperidin-1-yl)-N-propylpicolinamide (38 mg, 0.097 mmol, 1 eq) in place of (R)-5-amino-4-(4-(2,4-difluorophenoxy)piperidin-1-yl)-N-(tetrahydrofuran-3-yl)picolinamide to give a TFA salt of the title compound as a light yellow solid (33 mg, 53%). ¹H NMR (500 MHz, CD₃OD) δ ppm 1.00 (t, J=7.57 Hz, 3H), 1.68 (sxt, J=7.32 Hz, 2H), 2.01-2.10 (m, 2H), 2.15-2.27 (m, 2H), 3.14 (ddd, J=11.96, 8.54, 2.93 Hz, 2H), 3.39-3.51 (m, 4H), 4.28 (s, 3H), 4.56 (tt, J=7.57, 3.66 Hz, 1H), 6.83-6.94 (m, 1H), 7.01 (ddd, J=11.23, 8.54, 3.17 Hz, 1H), 7.14-7.29 (m, 2H), 7.94 (s, 1H), 8.42 (dd, J=4.88, 1.95 Hz, 1H), 8.56 (dd, J=7.81, 1.95 Hz, 1H), 9.33 (s, 1H); ESI-MS m/z [M+H]⁺ 526.3.

Example 255: N-(6-cyano-2-(4-(2,4-difluorophenoxy)piperidin-1-yl)pyridin-3-yl)-5-fluoro-2-methoxynicotinamide

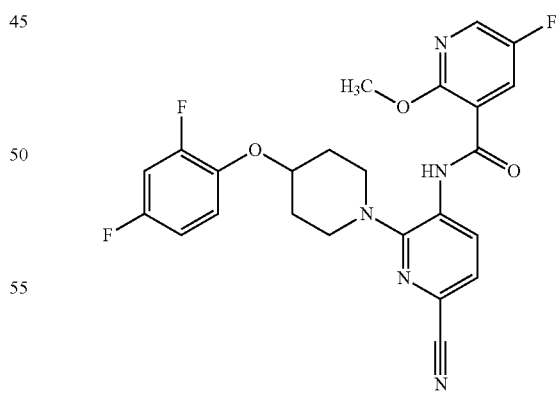

To a solution of 5-amino-6-(4-(2,4-difluorophenoxy)piperidin-1-yl)picolinonitrile (60.00 mg, 181.64 µmol) and 5-fluoro-2-methoxynicotinoyl chloride (51.65 mg, 272.46 µmol) in THF (2 mL) was added LiHMDS (1 M, 544.91 L) at 25° C. The reaction mixture was stirred at 25° C. for 0.5 hours and then diluted with water (5 mL) and extracted with DCM (3×5 mL). The organic layers were combined, dried over anhydrous Na₂SO₄, and concentrated under reduced pressure. The crude product was purified by preparative HPLC (basic conditions) to give the title compound as a white solid (23.5 mg, 26.8%). ¹HNMR (400 MHz, CDCl₃) δ ppm 1.98 (td, J=8.49, 4.19 Hz, 2H), 2.13-2.24 (m, 2H), 2.98-3.12 (m, 2H), 3.35-3.49 (m, 2H), 4.26 (s, 3H), 4.33-4.47 (m, 1H), 6.80 (td, J=8.38, 1.76 Hz, 1H), 6.83-6.92 (m, 1H), 7.01 (td, J=9.04, 5.73 Hz, 1H), 7.47 (d, J=7.94 Hz, 1H), 8.22 (d, J=3.09 Hz, 1H), 8.34 (dd, J=7.94, 3.09 Hz, 1H), 8.86 (d, J=8.38 Hz, 1H), 10.57 (s, 1H); ESI-MS m/z [M+H]⁺ 484.1.

Example 256: N-(6-cyano-2-(4-(2,4-difluorophenoxy)piperidin-1-yl)pyridin-3-yl)-5-methoxy-1-methyl-H-pyrazole-4-carboxamide

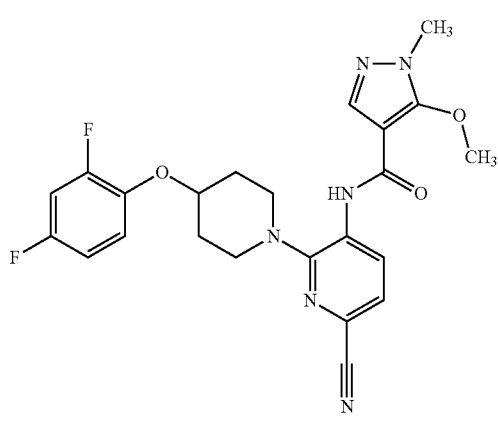 [SMILES: COc1c(C(=O)Nc2ccc(C#N)nc2N2CCC(Oc3ccc(F)cc3F)CC2)cnn1C]

The title compound was prepared in a manner similar to Example 255, using 5-methoxy-1-methyl-1H-pyrazole-4-carbonyl chloride (40 mg, 0.23 mmol) in place of 5-fluoro-2-methoxynicotinoyl chloride to give the title compound as a white solid (11.1 mg, 15.2%). ¹HNMR (400 MHz, CDCl₃) δ ppm 1.96-2.04 (m, 2H), 2.18 (br s, 2H), 3.01 (t, J=9.48 Hz, 2H), 3.25-3.37 (m, 2H), 3.81 (s, 3H), 4.15 (s, 3H), 4.36 (d, J=3.97 Hz, 1H), 6.78-6.92 (m, 2H), 7.03 (td, J=9.15, 5.51 Hz, 1H), 7.48 (d, J=8.38 Hz, 1H), 7.85 (s, 1H), 8.87 (d, J=8.38 Hz, 1H), 8.93 (s, 1H); ESI-MS m/z [M+H]⁺ 469.1.

Example 257: N-(2-(4-(2,4-difluorophenoxy)piperidin-1-yl)phenyl)-1-methyl-2-oxo-1,2-dihydropyridine-3-carboxamide

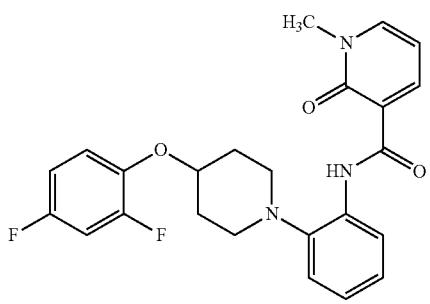 [SMILES: Cn1cccc(C(=O)Nc2ccccc2N2CCC(Oc3ccc(F)cc3F)CC2)c1=O]

To a round bottomed flask containing 2-(4-(2,4-difluorophenoxy)piperidin-1-yl)aniline (100 mg, 329 μmol), 1-methyl-2-oxo-2-dihydropyridine-3-carboxylic acid (55.35 mg, 361.5 μmol), HATU (187.41 mg, 492.89 μmol) and DIPEA (127.40 mg, 985.77 μmol) was added DCM (2 mL). The reaction mixture was stirred at 15° C. for 16 hours. The reaction was quenched with water (20 mL) and the resulting mixture was extracted with DCM (2×30 mL). The organic layers were combined, dried over anhydrous Na₂SO₄, and concentrated under vacuum to give a crude product, which was purified by preparative HPLC (Phenomenex® Gemini, 5 μm, 150 mm×25 mm column) eluting with a gradient of 10-100% ACN in water (0.05% NH₄₀H) to give the title compound as a light yellow solid (76.5 mg, 52.5%). ¹H NMR (400 MHz, CDCl₃) δ ppm 2.16-2.29 (m, 4H), 2.83 (ddd, J=11.36, 7.39, 4.19 Hz, 2H), 3.15-3.23 (m, 2H), 3.71 (s, 3H), 4.39 (br s, 1H), 6.43 (t, J=6.84 Hz, 1H), 6.75-6.83 (m, 1H), 6.88 (ddd, J=11.03, 8.38, 3.09 Hz, 1H), 7.00-7.11 (m, 2H), 7.12-7.17 (m, 1H), 7.20 (d, J=7.94 Hz, 1H), 7.57 (dd, J=6.40, 1.98 Hz, 1H), 8.57-8.66 (m, 2H); ESI-MS m/z [M+H]⁺ 440.1.

Example 258: N-(2-(4-(4-chlorobenzoyl)piperazin-1-yl)phenyl)pyrimidine-2-carboxamide

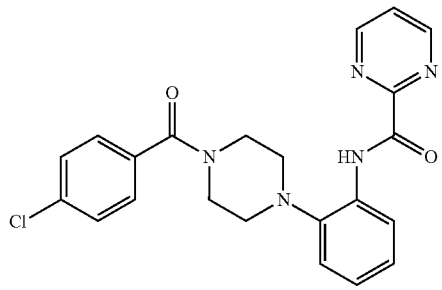 [SMILES: O=C(Nc1ccccc1N1CCN(C(=O)c2ccc(Cl)cc2)CC1)c1ncccn1]

To a round-bottomed flask containing (4-(2-aminophenyl)piperazin-1-yl)(4-chlorophenyl)methanone (30 mg, 95 μmol), pyrimidine-2-carboxylic acid (14.15 mg, 114.0 μmol) and HATU (54.18 mg, 142.5 μmol) in DCM (2 mL) was added DIPEA (36.83 mg, 285.00 μmol). The reaction mixture was stirred at 14° C. for 16 hours and then quenched with water (15 mL) and extracted with DCM (2×30 mL). The organic layers were combined, dried over anhydrous Na₂SO₄, and concentrated under vacuum. The crude product was purified by flash silica gel column chromatography, eluting with a gradient of 0 to 50% EtOAc in petroleum ether to give the title compound as a light yellow solid (31.3 mg, 77.3%). ¹H NMR (400 MHz, DMSO-d₆) δ ppm 2.91 (br s, 4H), 3.58 (br s, 2H), 3.88 (br s, 2H), 7.10-7.17 (m, 1H), 7.18-7.24 (m, 1H), 7.31 (d, J=7.94 Hz, 1H), 7.46-7.56 (m, 4H), 7.76 (t, J=4.85 Hz, 1H), 8.41-8.46 (m, 1H), 9.09 (d, J=4.85 Hz, 2H), 11.08 (s, 1H); ESI-MS m/z [M+Na]⁺ 444.0.

Example 259: N-(2-(4-(4-chlorobenzoyl)piperazin-1-yl)phenyl)pyrimidine-4-carboxamide

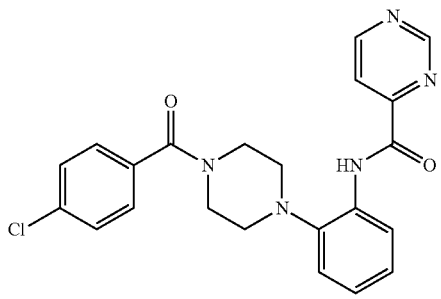 [SMILES: O=C(Nc1ccccc1N1CCN(C(=O)c2ccc(Cl)cc2)CC1)c1ccncn1]

The title compound was prepared in a manner similar to Example 258, using pyrimidine-4-carboxylic acid (14 mg, 0.11 mmol) in place of pyrimidine-2-carboxylic acid to give the title compound as a light yellow solid (11.2 mg, 66.4%). $^1$H NMR (400 MHz, DMSO-$d_6$) δ ppm 2.82-3.00 (m, 4H), 3.59 (br s, 2H), 3.90 (br s, 2H), 7.13-7.25 (m, 2H), 7.33 (d, J=7.50 Hz, 1H), 7.43-7.61 (m, 4H), 8.17 (dd, J=5.29, 1.32 Hz, 1H), 8.39-8.45 (m, 1H), 9.15 (d, J=5.29 Hz, 1H), 9.50 (d, J=1.32 Hz, 1H), 11.04 (s, 1H); ESI-MS m/z [M+Na]$^+$ 444.0.

Example 260: N-(2-(4-(4-chlorobenzoyl)piperazin-1-ylphenyl)-2-hydroxy-N-methylbenzamide

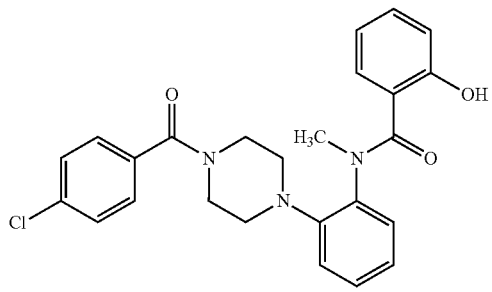 [SMILES: CN(C(=O)c1ccccc1O)c1ccccc1N1CCN(C(=O)c2ccc(Cl)cc2)CC1]

I. Step A: N-(2-(4-(4-chlorobenzoyl)piperazin-1-yl)phenyl)-2-methoxybenzamide

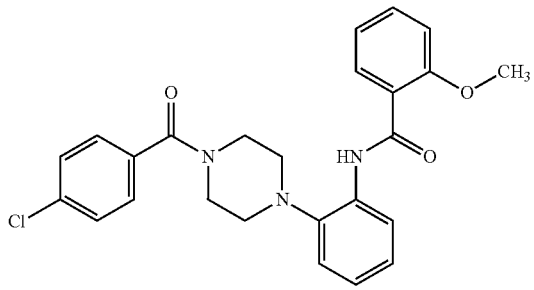 [SMILES: COc1ccccc1C(=O)Nc1ccccc1N1CCN(C(=O)c2ccc(Cl)cc2)CC1]

The title compound was prepared and purified in a manner similar to Example 258, using 2-methoxybenzoic acid in place of pyrimidine-2-carboxylic acid to give the title compound as a white solid (300 mg). ESI-MS m/z [M+H]$^+$ 450.0.

II. Step B: N-(2-(4-(4-chlorobenzoyl)piperazin-1-yl)phenyl-2-methoxy-N-methylbenzamide

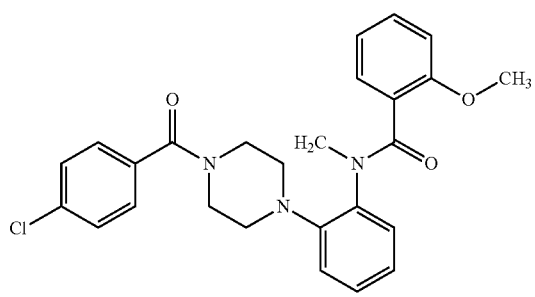 [SMILES: COc1ccccc1C(=O)N(C)c1ccccc1N1CCN(C(=O)c2ccc(Cl)cc2)CC1]

To a solution of N-(2-(4-(4-chlorobenzoyl)piperazin-1-yl)phenyl)-2-methoxybenzamide (200 mg, 445 μmol) in THF (2 mL) was added NaH (17.78 mg, 444.51 μmol, 60% in mineral oil) at 0° C. Next iodomethane (69.40 mg, 488.96 μmol, 1.10 eq) was added and the resulting mixture was stirred at 18° C. for 2 hours. The reaction mixture was poured into NH$_4$Cl solution (20 mL) and extracted with DCM (3×30 mL). The organic phases were combined, washed with brine (30 mL), dried over anhydrous Na$_2$SO$_4$, filtered, and concentrated under reduced pressure to give the title compound (200.00 mg, crude). ESI-MS m/z [M+H]$^+$ 464.1.

III. Step C: N-(2-(4-(4-chlorobenzoyl)piperazin-1-yl)phenyl)-2-hydroxy-N-methylbenzamide To a solution of N-(2-(4-(4-chlorobenzol)piperazin-1-yl)phenyl)-2-methoxy-N-methylbenzamide (100.00 mg, 215.54 μmol) in DCM (2 mL) was added dropwise a solution of BBr$_3$ (107.99 mg, 431.08 μmol) in DCM (1 mL) at −60° C. The reaction mixture was stirred at −60° C. for 1 hour. The reaction was then quenched with NH$_4$Cl solution (10 mL) and the mixture diluted with water (10 mL) and extracted with DCM (3×10 mL). The organic layers were combined, washed with brine (20 mL), dried over anhydrous Na$_2$SO$_4$, filtered, and concentrated under reduced pressure. The resulting residue was purified by preparative HPLC to give the title compound as a white solid (23.5 mg, 24.2%). $^1$H NMR (400 MHz, CD$_3$OD) δ ppm 2.88 (br s, 4H), 3.41 (br s, 3H), 3.50 (br s, 2H), 3.81 (br s, 2H), 6.51 (br s, 1H), 6.82 (d, J=8.4 Hz, 1H), 6.90-7.11 (m, 2H), 7.16-7.31 (m, 3H), 7.40-7.52 (m, 5H); ESI-MS m/z [M+H]$^+$ 450.1.

Example 261: N-(2-cyano-5-(4-(2,4-difluorophenoxy)piperidin-1-yl)pyridin-4-yl)-2-methoxynicotinamide

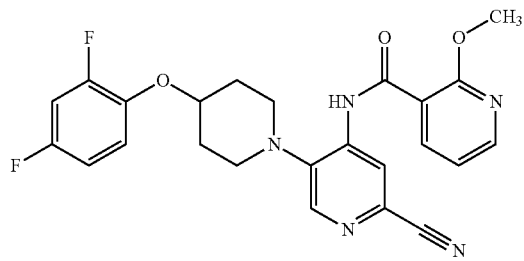 [SMILES: COc1ncccc1C(=O)Nc1cc(C#N)ncc1N1CCC(Oc2ccc(F)cc2F)CC1]

A mixture of 4-bromo-5-(4-(2,4-difluorophenoxy)piperidin-1-yl)picolinonitrile (480 mg, 1.22 mmol), 2-methoxynicotinamide (278.43 mg, 1.83 mmol), Pd$_2$(dba)$_3$ (111.72 mg, 122.00 µmol), Xantphos (141.18 mg, 244.00 µmol) and Cs$_2$CO$_3$ (1.19 g, 3.66 mmol) in toluene (8 mL) was stirred at 100° C. for 10 hours. The reaction mixture was subsequently filtered through a pad of Celite® which was rinsed with EtOAc (3×20 mL). The combined filtrates were concentrated and purified by silica gel column chromatography, eluting with DCM/MeOH (1:0 to 50:1 gradient), followed by preparative HPLC to give the title compound as a white solid (183.5 mg, 32.3%). $^1$H NMR (400 MHz, CDCl$_3$) δ ppm 1.99-2.10 (m, 2H), 2.17 (d, J=2.65 Hz, 2H), 2.95 (br s, 2H), 3.30 (d, J=4.85 Hz, 2H), 4.28 (s, 3H), 4.36-4.45 (m, 1H), 6.76-6.84 (m, 1H), 6.84-6.92 (m, 1H), 7.01 (d, J=5.73 Hz, 1H), 7.18 (dd, J=7.50, 4.85 Hz, 1H), 8.40 (dd, J=4.63, 1.98 Hz, 1H), 8.47 (s, 1H), 8.61 (dd, J=7.50, 1.76 Hz, 1H), 8.93 (s, 1H), 10.64 (br s, 1H); ESI-MS m/z [M+H]$^+$ 466.1.

Example 262: 5-(4-(2,4-difluorophenoxy)piperidin-1-yl)-4-(4-methoxynicotinamido)-N,N-dimethylpicolinamide

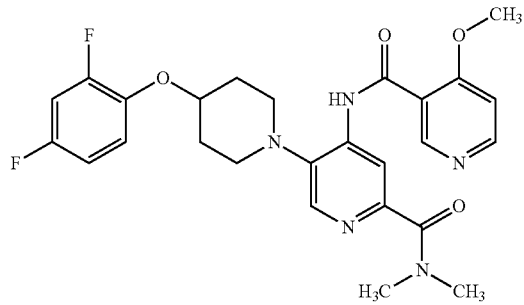 [SMILES: COc1ccncc1C(=O)Nc1cc(C(=O)N(C)C)ncc1N1CCC(Oc2ccc(F)cc2F)CC1]

The title compound was prepared and purified in a manner similar to Example 261 using 4-bromo-5-(4-(2,4-difluorophenoxy)piperidin-1-yl)-N,N-dimethylpicolinamide (70 mg, 0.16 mmol) and 4-methoxynicotinamide (36 mg, 0.24 mmol) in place of 4-bromo-5-(4-(2,4-difluorophenoxy)piperidin-1-yl)picolinonitrile and 2-methoxynicotinamide, respectively, to give the title compound as a white solid (13.5 mg, 16.1%). $^1$H NMR (400 MHz, CDCl$_3$) δ ppm 1.92-2.03 (m, 2H), 2.19 (d, J=9.70 Hz, 2H), 2.87-2.98 (m, 2H), 3.05 (s, 3H), 3.13 (s, 3H), 3.20-3.30 (m, 2H), 4.22 (s, 3H), 4.36 (dt, J=8.05, 4.13 Hz, 1H), 6.79-6.85 (m, 1H), 6.89 (ddd, J=11.03, 8.38, 2.65 Hz, 1H), 6.99-7.06 (m, 2H), 8.40 (s, 1H), 8.68 (d, J=5.73 Hz, 1H), 8.72 (s, 1H), 9.31 (s, 1H), 10.26 (br s, H); ESI-MS m/z [M+H]$^+$ 512.1.

Example 263: N-(4-(4-(2,4-difluorophenoxy)piperidin-1-yl)-6-methylpyridin-3-yl-4-methoxynicotinamide

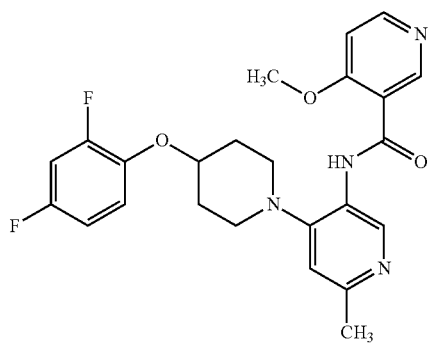 [SMILES: COc1ccncc1C(=O)Nc1cnc(C)cc1N1CCC(Oc2ccc(F)cc2F)CC1]

I. Step A: 2-chloro-4-(4-(2,4-difluorophenoxy)piperidin-1-yl)-6-methyl-3-nitropyridine

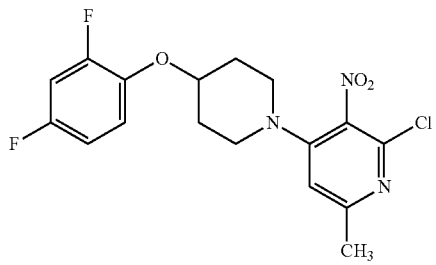 [SMILES: Cc1cc(N2CCC(Oc3ccc(F)cc3F)CC2)c([N+](=O)[O-])c(Cl)n1]

To a suspension of 4-(2,4-difluorophenoxy)piperidine (13.27 g, 53.14 mmol, 1.10 eq, HCl) and 2,4-dichloro-6-methyl-3-nitro-pyridine (10.00 g, 48.31 mmol, 1.00 eq) in THF (200 mL) was added Et$_3$N (24.44 g, 241.55 mmol, 33.48 mL, 5.00 eq) at 0° C. The resulting mixture was stirred at 25° C. for 16 hours, then diluted with EtOAc (200 mL, and washed with water (100 mL) and brine (100 mL). The organic layer was dried over anhydrous Na$_2$SO$_4$, filtered, and concentrated in vacuo. The residue was purified by column chromatography on silica gel, eluting with petroleum ether/EtOAc (20:1 to 5:1 gradient) to give the title compound as a yellow solid (11.00 g, 58.14%), 1H NMR (400 MHz, CDCl$_3$) δ ppm 1.89-2.04 (m, 4H), 2.48 (s, 3H), 3.11-3.20 (m, 2H), 3.43-3.52 (m, 2H), 4.34-4.49 (m, 1H), 6.69 (s, 1H), 6.75-7.01 (m, 3H); ESI-MS m/z [M+H]$^+$ 383.8.

II. Step B: 4-(4-(2,4-difluorophenoxy)piperidin-1-yl)-6-methylpyridin-3-amine

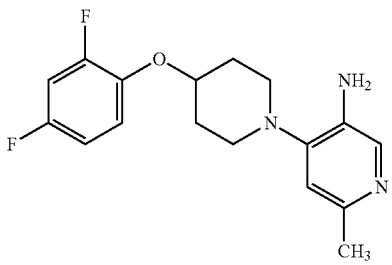 [SMILES: Cc1cc(N2CCC(Oc3ccc(F)cc3F)CC2)c(N)cn1]

To a solution of 2-chloro-4-(4-(2,4-difluorophenoxy)piperidin-1-yl)-6-methyl-3-nitropyridine (8.00 g, 20.85 mmol, 1.00 eq) in MeOH (300 mL) was added Pd/C (10% loading dry basis, 800.00 mg) under $N_2$. The resulting suspension was degassed under vacuum and purged with $H_2$ several times, and then stirred under $H_2$ (30 psi) at 25° C. for 18 hours. The reaction mixture was filtered and the filtrate was concentrated in vacuo to give the title compound as an off-white solid (6.00 g, 88.3%). $^1$H NMR (400 MHz, $CD_3OD$) δ ppm 1.95-2.05 (m, 2H), 2.13-2.22 (m, 2H), 2.54 (s, 3H), 3.31 (d, J=1.3 Hz, 2H), 3.55-3.63 (m, 2H), 4.53-4.60 (m, 1H), 6.86-6.93 (m, 1H), 6.96-7.03 (m, 1H), 7.08-7.13 (m, 1H), 7.17-7.25 (m, 1H), 7.76 (s, 1H); ESI-MS m/z [M+H]$^+$ 319.9.

III. Step C: N-(4-(4-(2,4-difluorophenoxy)piperidin-1-yl)-6-methylpyridin-3-yl)-4-methoxynicotinamide To a round-bottomed flask containing 4-(4-(2,4-difluorophenoxy)piperidin-1-yl)-6-methylpyridin-3-amine (30.00 mg, 93.94 μmol, 1.00 eq), 4-methoxynicotinic acid (17.26 mg, 112.73 μmol, 1.20 eq), HATU (42.86 mg, 112.73 μmol, 1.20 eq) and DIPEA (30.35 mg, 234.85 μmol, 41.01 μL, 2.50 eq) was added DMF (1 mL). The reaction mixture was stirred at 20° C. for 16 hours and then poured into water (20 mL). The aqueous phase was extracted with DCM (2×20 mL), and the combined organic layers were washed with water (2×20 mL), dried over anhydrous $Na_2SO_4$, and concentrated in vacuo. The residue was purified by preparative HPLC, eluting with water (0.05% $NH_4OH$) in ACN to give the title compound as white solid (17.2 mg, 40.3%). $^1$H NMR (400 MHz, $CDCl_3$) δ ppm 1.90-1.99 (m, 2H), 2.14 (d, J=11.03 Hz, 2H), 2.54 (s, 3H), 2.85 (t, J=9.26 Hz, 2H), 3.23-3.30 (m, 2H), 4.19 (s, 3H), 4.30-4.37 (m, 1H), 6.78-6.91 (m, 3H), 6.97-7.04 (m, 2H), 8.67 (d, J=5.73 Hz, 1H), 9.40 (d, J=7.50 Hz, 2H), 9.68 (br s, 1H); ESI-MS m/z [M+H]$^+$ 455.1.

Example 264: N-(4-(4-(2,4-difluorophenoxy)piperidin-1-yl)piperidin-3-yl)-2-methoxynicotinamide

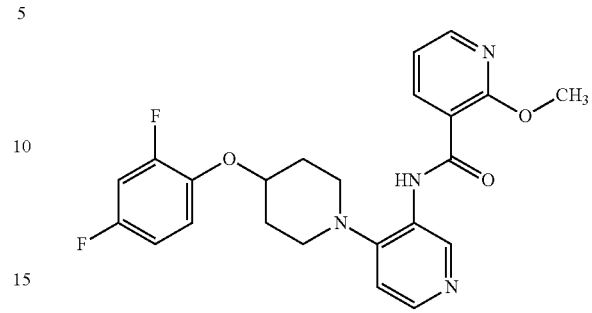

I. Step A: 4-(4-(2,4-difluorophenoxy)piperidin-1-yl)-3-nitropyridine

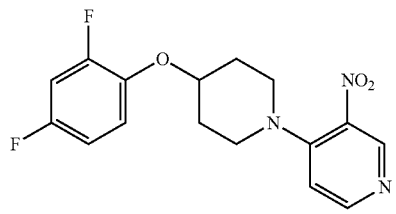 [SMILES: O=[N+]([O-])c1cnccc1N1CCC(Oc2ccc(F)cc2F)CC1]

To a suspension of 4-(2,4-difluorophenoxy)piperidine (943.79 mg, 3.78 mmol, 1.20 eq, HCl) and 4-chloro-3-nitropyridine (500.00 mg, 3.15 mmol, 1.00 eq) in THF (15 mL) was added $Et_3N$ (956.25 mg, 9.45 mmol, 3.00 eq) dropwise at 0° C. The resulting mixture was stirred at 20° C. for 3 hours, then diluted with EtOAc (100 mL), and washed with water (50 mL) and brine (50 mL). The organic layer was dried over anhydrous $Na_2SO_4$, filtered, and concentrated in vacuo. The residue was purified by column chromatography on silica gel eluting with petroleum ether/EtOAc (3:1 to 1:1) to give the title compound as a yellow solid (850.00 mg, 80.48%). $^1$H NMR (400 MHz, $CDCl_3$) δ ppm 1.89-2.21 (m, 4H), 3.19 (ddd, J=13.1, 6.1, 4.2 Hz, 2H), 3.52 (ddd, J=12.9, 9.0, 3.4 Hz, 2H), 4.49 (tt, J=6.1, 3.2 Hz, 1H), 6.72-6.94 (m, 2H), 6.93-6.95 (m, 1H), 6.99 (td, J=9.1, 5.4 Hz, 1H), 8.38 (d, J=6.0 Hz, 1H), 8.86 (s, 1H).

II. Step B: 4-(4-(2,4-difluorophenoxy)piperidin-1-yl)pyridin-3-amine

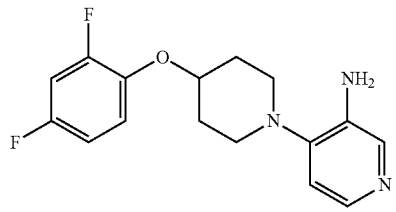 [SMILES: Nc1cnccc1N1CCC(Oc2ccc(F)cc2F)CC1]

To a solution of 4-(4-(2,4-difluorophenoxy)piperidin-1-yl)-3-nitropyridine (500 mg, 1.49 mmol, 1.00 eq) in MeOH (30.00 mL) was added Pd/C (10% loading dry basis, 100.00 mg) under N₂. The resulting suspension was degassed under vacuum and purged with H₂ several times, and then stirred under H₂ (15 psi) at 20° C. for 12 hours. A black suspension was observed. The reaction mixture was filtered through a pad of Celite® and the filtrate was concentrated in vacuo to give the title compound as a yellow oil, which was used in the next step without further purification (460 mg, 79.9%). ESI-MS m/z [M+H]⁺ 306.0.

III. Step C: N-(4-(4-(2,4-difluorophenoxy)piperidin-1-yl)pyridin-3-yl)-2-methoxynicotinamide A mixture of 4-(4-(2,4-difluorophenoxy)piperidin-1-yl)pyridin-3-amine (150 mg, 368 μmol, 1.00 eq), 2-methoxynicotinic acid (73.36 mg, 479.01 μmol, 1.30 eq), HATU (168.12 mg, 442.16 μmol, 1.20 eq) and DIPEA (142.86 mg, 1.11 mmol, 3.00 eq) in DMF (8 mL) was stirred at 20° C. for 12 hours. A light yellow solution was observed. The reaction mixture was subsequently diluted with EtOAc (100 mL) and washed with saturated (aq) Na₂CO₃ (30 mL) and brine (30 mL). The organic layer was dried over anhydrous Na₂SO₄, filtered, and concentrated in vacuo. The residue was purified by preparative HPLC (neutral conditions) to give the title compound as a white solid (3.4 mg, 2.1%). H NMR (400 MHz, CDCl₃) δ ppm 2.02 (d, J=7.5 Hz, 2H), 2.14 (br s, 2H), 2.90 (d, J=8.4 Hz, 2H), 3.29 (br s, 2H), 4.26 (s, 3H), 4.38 (br s, 1H), 6.69-6.93 (m, 2H), 6.94-7.09 (m, 2H), 7.16 (br s, 1H), 8.35 (br s, 2H), 8.67 (d, J=7.1 Hz, 1H), 9.56 (br s, 1H), 10.18 (br s, 1H); ESI-MS m/z [M+H]⁺ 440.9.

Example 265: N-(2-(4-(2,4-difluorophenoxy)piperidin-1-yl-5-(dimethylcarbamoyl)phenyl)-2-methoxynicotinamide

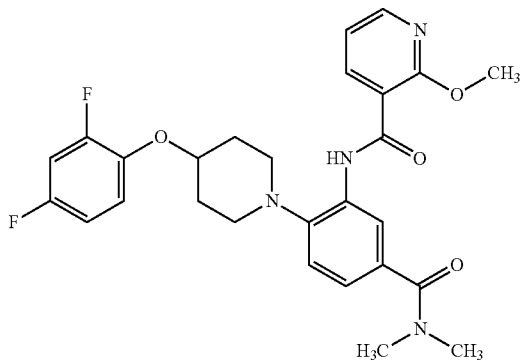 [SMILES: COc1ncccc1C(=O)Nc1cc(C(=O)N(C)C)ccc1N1CCC(Oc2ccc(F)cc2F)CC1]

To a solution of 3-amino-4-(4-(2,4-difluorophenoxy)piperidin-1-yl)-N,N-dimethylbenzamide (200 mg, 463.49 μmol, 1.00 eq) in DCM (10 mL) was added Et₃N (234.5 mg, 2.32 mmol, 5.00 eq) and 2-methoxynicotinoyl chloride (146.82 mg, 556.19 μmol, 1.20 eq) at 0° C. The resulting mixture was stirred at 20° C. for 12 hours. A light yellow solution was observed. The reaction mixture was then diluted with DCM (100 mL) and washed with saturated (aq) Na₂CO₃ (30 mL) and brine (30 mL). The organic layer was dried over anhydrous Na₂SO₄, filtered, and concentrated in vacuo. The residue was purified by column chromatography on silica gel, eluting with petroleum ether/EtOAc (1:1 to 1:5 gradient). The crude product was further purified by preparative TLC eluting with petroleum ether/EtOAc (1:5) to give the title compound as a white solid (50 mg, 21%). ¹H NMR (400 MHz, CDCl₃) δ ppm 1.99-2.08 (m, 2H), 2.15 (br s, 2H), 2.79-2.88 (m, 2H), 3.10 (br s, 6H), 3.17-3.24 (m, 2H), 4.28 (s, 3H), 4.33-4.41 (m, 1H), 6.76-6.83 (m, 1H), 6.88 (ddd, J=10.9, 8.3, 2.9 Hz, 1H), 7.02 (td, J=9.0, 5.3 Hz, 1H), 7.14 (dd, J=7.5, 4.9 Hz, 1H), 7.20-7.26 (m, 2H), 8.35 (dd, J=4.9, 2.2 Hz, 1H), 8.56-8.66 (m, 2H), 10.57 (s, 1H); ESI-MS m/z [M+H]⁺ 511.1.

Example 266: N-(2-cyano-5-(4-(2,3,4-trifluorobenzyl)piperazin-1-yl)pyridin-4-yl)-3-methoxy-1-methyl-1H-pyrazole-4-carboxamide

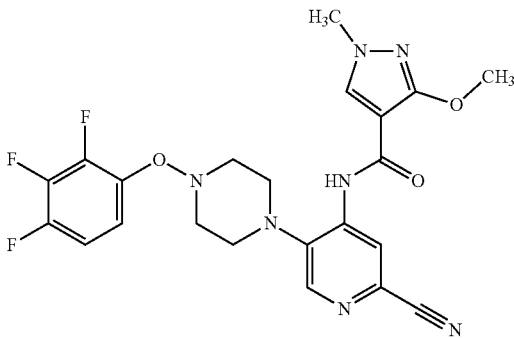 [SMILES: COc1nn(C)cc1C(=O)Nc1cc(C#N)ncc1N1CCN(Oc2ccc(F)c(F)c2F)CC1]

To a suspension of N-(2-cyano-5-(piperazin-1-yl)pyridin-4-yl)-3-methoxy-1-methyl-1H-pyrazole-4-carboxamide HCl (52.00 mg, 137.6 μmol, 1.00 eq) and 1-(bromomethyl)-2,3,4-trifluoro-benzene (27.87 mg, 123.87 μmol, 0.90 eq) in THF (3.00 mL) was added Et₃N (69.63 mg, 688.14 μmol, 95.39 μL, 5.00 eq) at 20° C. The reaction mixture was stirred at 65° C. for 6 hours, then concentrated under reduced pressure, and purified by preparative HPLC (Waters Xbridge Prep OBD C18.5 μm, 150 mm×30 mm column) eluting with a gradient of 40-70% water in ACN (basic mode) to give the title compound as a white solid (26.5 mg, 39.7%). ¹H NMR (400 MHz, CDCl₃) δ ppm 2.70 (br s, 4H), 3.03 (br s, 4H), 3.70 (s, 2H), 3.81 (s, 3H), 4.05 (s, 3H), 6.98 (d, J=8.82 Hz, 1H), 7.13 (br s, 1H), 7.84 (s, 1H), 8.39 (s, 1H), 8.87 (s, 1H), 9.41 (br s, 1H); ESI-MS m/z [M+H]⁺ 486.1.

Example 267: N-(2-cyano-5-(4-(3,4,5-trifluorobenzyl)piperazin-1-yl)pyridin-4-yl)-3-methoxy-1-methyl-1H-pyrazole-4-carboxamide

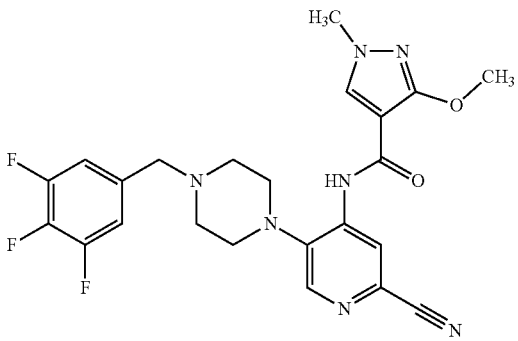 [SMILES: COc1nn(C)cc1C(=O)Nc1cc(C#N)ncc1N1CCN(Cc2cc(F)c(F)c(F)c2)CC1]

The title compound was prepared in a manner similar to Example 266, using N-(2-cyano-5-(piperazin-1-yl)pyridin-4-yl)-3-methoxy-1-methyl-1H-pyrazole-4-carboxamide (50 mg, 0.13 mmol) in place of N-(2-cyano-5-(piperazin-1-yl)

pyridin-4-yl)-3-methoxy-1-methyl-1H-pyrazole-4-carboxamide HCl and 5-(chloromethyl)-1,2,3-trifluorobenzene (21.5 mg, 0.12 mmol) in place of 1-(bromomethyl)-2,3,4-trifluoro-benzene, to give the title compound as a white solid (6.80 mg, 10.3%). $^1$H NMR (400 MHz, CDCl$_3$) δ ppm 2.67 (br s, 4H), 3.05 (t, J=4.52 Hz, 4H), 3.55 (s, 2H), 3.82 (s, 3H), 4.14 (s, 3H), 6.96-7.06 (m, 2H), 7.85 (s, 1H), 8.42 (s, 1H), 8.88 (s, 1H), 9.42 (s, 1H); ESI-MS m/z [M+H]$^+$ 486.1.

Example 268: N-(4-(4-(2,4-difluorophenoxy)piperidin-1-yl-6-(methoxymethyl)pyridin-3-yl)-2-methoxynicotinamide

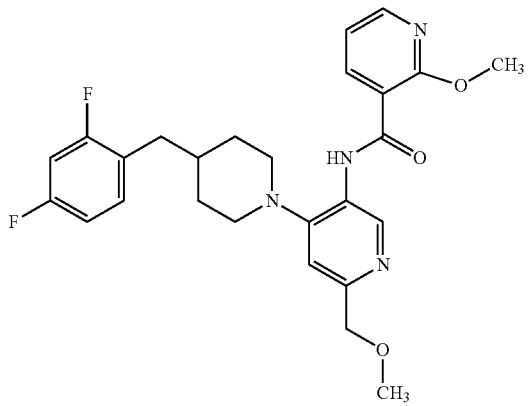 [SMILES: COCc1cc(N2CCC(Cc3ccc(F)cc3F)CC2)c(NC(=O)c2cccnc2OC)cn1]

I. Step A: 4,6-dichloro-5-nitropicolinic acid

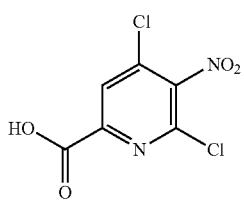 [SMILES: O=C(O)c1cc(Cl)c([N+](=O)[O-])c(Cl)n1]

To a stirred mixture of 2,4-dichloro-6-methyl-3-nitropyridine (10.00 g, 48.31 mmol, 1.00 eq) in H$_2$SO$_4$ (18 M, 48.71 mL, 18.15 eq) was added CrO$_3$ (14.01 g, 140.09 mmol, 2.90 eq) at 20° C. The mixture was stirred at 60° C. for 2.5 hours. Cold water (100 mL) was added to the mixture and subsequently filtered. The filter cake was slurried in EtOAc (400 mL) and cold water (200 mL). The resulting mixture was extracted with EtOAc (3×500 mL). The combined organics were washed with brine (150 mL, dried over anhydrous Na$_2$SO$_4$, filtered, and concentrated in vacuo to give the title compound, which was used without further purification (9.50 g, 83.0%). $^1$H NMR (400 MHz, DMSO-d$_6$) δ ppm 8.45 (s, 1H), 14.36 (br s, 1H).

II. Step B: 6-chloro-4-(4-(2,4-difluorophenoxy)piperidin-1-yl)-5-nitropicolinic acid

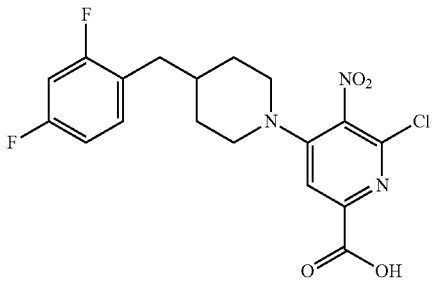 [SMILES: O=C(O)c1cc(N2CCC(Cc3ccc(F)cc3F)CC2)c([N+](=O)[O-])c(Cl)n1]

To a stirred mixture of 4,6-dichloro-5-nitropicolinic acid (8.50 g, 35.86 mmol, 1.00 eq) and 4-(2,4-difluorophenoxy)piperidine (9.40 g, 37.65 mmol, 1.05 eq, HCl) in THF (350 mL) was added Et$_3$N (10.89 g, 107.58 mmol, 3.00 eq) at 0° C. The reaction mixture was stirred at 20° C. for 16 hours, then poured into cold water (250 mL) and extracted with EtOAc (3×350 mL). The combined organics were washed with brine (150 mL), dried over anhydrous Na$_2$SO$_4$, filtered, and concentrated in vacuo to give the title compound, which was used without further purification (8.00 g). $^1$H NMR (400 MHz, DMSO-d$_6$) δ ppm 1.64-1.77 (m, 2H), 1.97-2.07 (m, 2H), 3.22-3.32 (m, 2H), 3.44-3.56 (m, 2H), 4.57 (dt, J=7.4, 3.6 Hz, 1H), 6.93-7.04 (m, 1H), 7.22-7.35 (m, 2H), 7.69 (s, 1H); ESI-MS m/z [M+H]$^+$ 413.8.

III. Step C: methyl 6-chloro-4-(4-(2,4-difluorophenoxy)piperidin-1-yl)-5-nitropicolinate

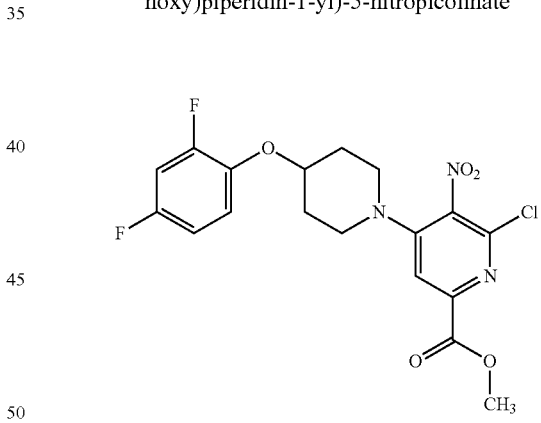

To a solution of 6-chloro-4-(4-(2,4-difluorophenoxy)piperidin-1-yl)-5-nitropicolinic acid (2.00 g, 4.83 mmol, 1.00 eq) in DCM (30 mL) was added (COCl)$_2$ (1.23 g, 9.66 mmol, 845.62 µL, 2.00 eq) and DMF (17.65 mg, 241.50 µmol, 18.58 µL, 0.05 eq) at 0° C. The mixture was stirred at 20° C. for 0.5 h and then concentrated in vacuo. The residue was taken up in DCM (10 mL) and then added to a solution of DIPEA (1.87 g, 14.49 mmol, 2.53 mL, 3.00 eq) in MeOH (15.00 mL). The mixture was stirred at 20° C. for 1 hour and then purified by column chromatography, eluting with petroleum ether/EtOAc (15:1 to 3:1 gradient) to give the title compound as a yellow solid (2.1 g, 100%). $^1$H NMR (400 MHz, CDCl$_3$) δ ppm 1.91-2.09 (m, 4H), 3.31 (dt, J=13.3, 4.9 Hz, 2H), 3.60 (ddd, J=13.1, 8.7, 4.1 Hz, 2H), 4.00 (s, 3H), 4.46 (br t, J=4.0 Hz, 1H), 6.80 (dddd, J=9.2, 7.7, 2.9, 1.7 Hz, 1H), 6.88 (ddd, J=11.0, 8.3, 3.0 Hz, 1H), 6.97 (td, J=9.1, 5.4 Hz, 1H), 7.69 (s, 1H); ESI-MS m/z [M+H]⁺ 428.0.

IV. Step D: methyl 5-amino-4-(4-(2,4-difluorophenoxy)piperidin-1-yl)picolinate

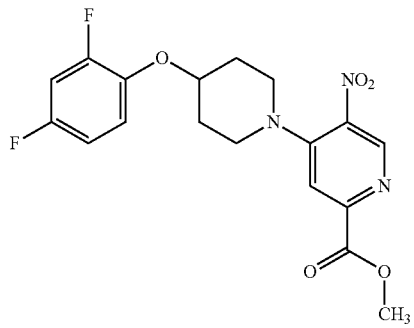

A mixture of methyl 6-chloro-4-(4-(2,4-difluorophenoxy)piperidin-1-yl)-5-nitropicolinate (2.10 g, 4.91 mmol, 1.00 eq) and Pd/C (200 mg, 10% loading wet basis) in MeOH (10 mL) was stirred at 20° C. for 15 hours under H₂ at atmospheric pressure. The mixture was filtered, and the filtrate was concentrated in vacuo to give the title compound as a yellow solid, which was used without further purification (2.00 g). ESI-MS m/z [M+H]⁺ 364.0.

V. Step E: methyl 4-(4-(2,4-difluorophenoxy)piperidin-1-yl)-5-(2-methoxynicotinamido)picolinate

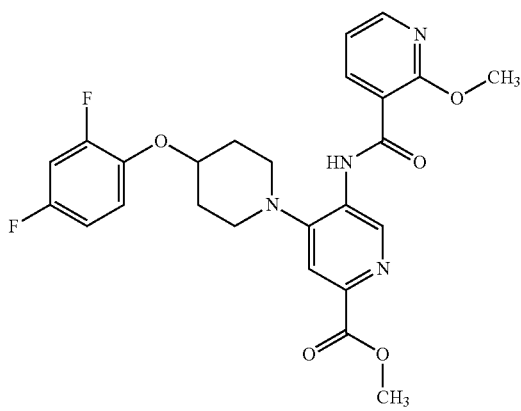 [SMILES: COC(=O)c1cc(N2CCC(Oc3ccc(F)cc3F)CC2)c(NC(=O)c2cccnc2OC)cn1]

To a solution of methyl 5-amino-4-(4-(2,4-difluorophenoxy)piperidin-1-yl)picolinate (1.00 g, 2.75 mmol, 1.00 eq) and DIPEA (1.07 g, 8.25 mmol, 1.44 mL, 3.00 eq) in THF (20 mL) was added a solution of 2-methoxynicotinoyl chloride (708.31 mg, 4.13 mmol, 1.50 eq) in THF (10 mL) dropwise at 60° C. The mixture was stirred at 60° C. for 1 hour and then concentrated in vacuo. The residue was diluted with EtOAc (20 mL), washed with brine (3×20 mL), dried over anhydrous Na₂SO₄, filtered, and concentrated in vacuo. The residue was purified by column chromatography, eluting with petroleum ether/EtOAc (10:1 to 1:1 gradient) to give the title compound as a yellow solid (580 mg, 42.2%). ¹H NMR (400 MHz, CDCl₃) δ ppm 1.94-2.10 (m, 2H), 2.12-2.24 (m, 2H), 2.94 (ddd, J=12.0, 8.7, 3.2 Hz, 2H), 3.27-3.37 (m, 2H), 4.01 (s, 3H), 4.27 (s, 3H), 4.40 (dt, J=7.8, 3.7 Hz, 1H), 6.75-6.84 (m, 1H), 6.88 (ddd, J=11.1, 8.3, 3.1 Hz, 1H), 7.01 (td, J=9.1, 5.4 Hz, 1H), 7.17 (dd, J=7.5, 4.9 Hz, 1H), 7.93 (s, 1H), 8.33-8.39 (m, 1H), 8.66 (dd, J=7.7, 2.0 Hz, 1H), 9.75 (s, 1H), 10.37 (s, 1H); ESI-MS m/z [M+H]⁺ 499.1.

VI. Step F: N-(4-(4-(2,4-difluorophenoxy)piperidin-1-yl)-6-(hydroxymethyl)pyridin-3-yl)-2-methoxynicotinamide

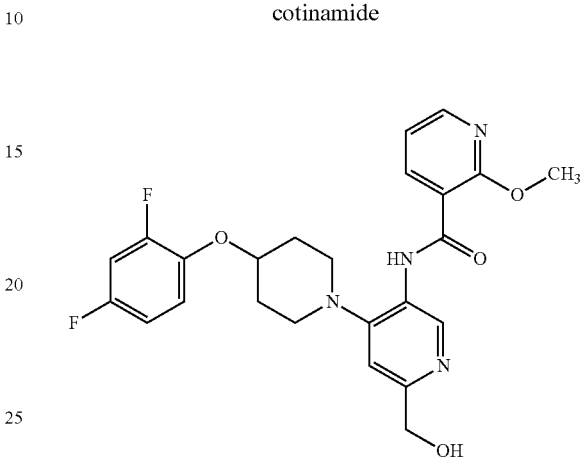

To a solution of methyl 4-(4-(2,4-difluorophenoxy)piperidin-1-yl)-5-(2-methoxynicotinamido)picolinate (250 mg, 502 μmol, 1.00 eq) in THF (10 mL) was added LiBH₄ (32.77 mg, 1.50 mmol, 3.00 eq) at 0° C. The reaction mixture was stirred at 20° C. for 1.5 hours, then quenched with (aq) NH₄Cl (10 mL), and extracted with EtOAc (3×15 mL). The organic layers were combined, washed with brine (2×30 mL), dried with anhydrous Na₂SO₄, filtered, and concentrated in vacuo to give the title compound as a light yellow solid, which was used without further purification (220 mg). ESI-MS m/z [M+H]⁺ 471.1.

VII. Step G: N-(4-(4-(2,4-difluorophenoxy)piperidin-1-yl)-6-(methoxymethyl)pyridin-3-yl)-2-methoxynicotinamide To a solution of N-(4-(4-(2,4-difluorophenoxy)piperidin-1-yl)-6-(hydroxymethyl)pyridin-3-yl)-2-methoxynicotinamide (200 mg, 425 μmol, 1.00 eq) in DCM (10 mL) was added SOCl₂ (75.86 mg, 637.7 μmol, 46.26 μL, 1.50 eq) at 20° C. The mixture was stirred at 20° C. for 1 hour and then concentrated in vacuo. The residue was diluted with MeOH (10 mL) and NaOMe (22.96 mg, 425.11 μmol, 1.00 eq) was added. The reaction mixture was stirred at 75° C. for 13 hours and subsequently diluted with EtOAc (20 mL), washed with brine (20 mL), dried over anhydrous Na₂SO₄, filtered, and concentrated in vacuo. The residue was purified by preparative TLC, eluting with EtOAc, followed by preparative HPLC, eluting with acetonitrile/water (0.05% ammonia hydroxide) to give the title compound as a white solid (3.9 mg, 1.9%). ¹H NMR (400 MHz, CDCl₃) δ ppm 1.90-1.97 (m, 2H), 2.04-2.14 (m, 2H), 2.79-2.89 (m, 2H), 3.19-3.31 (m, 2H), 3.42 (s, 3H), 4.19 (s, 3H), 4.30 (dt, J=7.7, 3.9 Hz, 1H), 4.50 (s, 2H), 6.68-6.76 (m, 1H), 6.80 (ddd, J=11.1, 8.3, 2.9 Hz, 1H), 6.93 (td, J=9.1, 5.4 Hz, 1H), 7.08 (dd, J=7.5, 4.9 Hz, 1H), 7.12 (s, 1H), 8.28 (dd, J=4.9, 2.0 Hz, 1H), 8.59 (dd, J=7.5, 2.0 Hz, 1H), 9.40 (s, 1H), 10.08 (s, 1H); ESI-MS m/z [M+H]⁺ 485.1.

Example 269: 4-(4-(2,4-difluorophenoxy)piperidin-1-yl)-5-(2-methoxynicotinamido)picolinamide

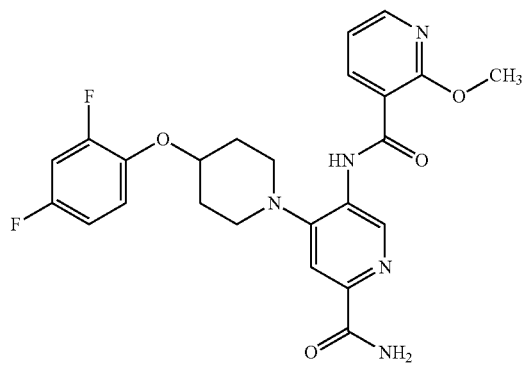 [SMILES: COc1ncccc1C(=O)Nc1cnc(C(N)=O)cc1N1CCC(Oc2ccc(F)cc2F)CC1]

The title compound was prepared in a manner similar to Preparation x138, using 4-(4-(2,4-difluorophenoxy)piperidin-1-yl)-5-(2-methoxynicotinamido)picolinic acid (420 mg, 0.87 mmol) in place of 4-bromo-5-(4-(2,4-difluorophenoxy)piperidin-1-yl)picolinic acid and NH$_4$Cl (93 mg, 1.7 mmol) in place of NH(CH$_3$)$_2$, to give the title compound as a white solid (12.30 mg, 38.4%). $^1$H NMR (400 MHz, DMSO-d$_6$) δ ppm 1.79-1.89 (m, 2H), 2.04-2.13 (m, 2H), 2.91-3.00 (m, 2H), 3.21-3.26 (m, 2H), 4.14 (s, 3H), 4.51-4.59 (m, 1H), 6.97-7.04 (m, 1H), 7.24-7.35 (m, 3H), 7.57 (br s, 1H), 7.78 (s, 1H), 8.08 (br s, 1H), 8.40-8.46 (m, 2H), 9.32 (s, 1H), 10.24 (s, 1H); ESI-MS m/z [M+H]$^+$ 484.1.

Example 270: N-(6-cyano-4-(4-(2,4-difluorophenoxy)piperidin-1-yl)pyridin-3-yl)-2-methoxynicotinamide

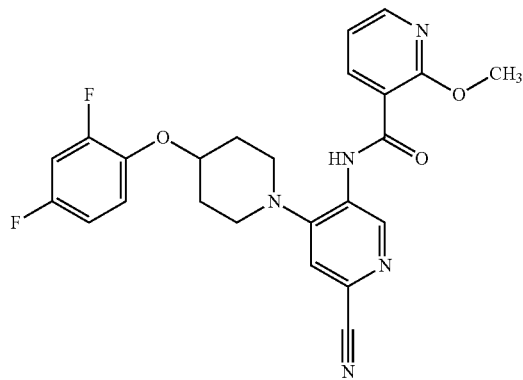 [SMILES: COc1ncccc1C(=O)Nc1cnc(C#N)cc1N1CCC(Oc2ccc(F)cc2F)CC1]

The title compound was prepared in a manner similar to Examples 272 and 273, using 4-(4-(2,4-difluorophenoxy)piperidin-1-yl)-5-(2-methoxynicotinamido)picolinamide (100 mg, 0.21 mmol) in place of 4-(4-(2,4-difluorophenoxy)piperidin-1-yl)-5-(2-methoxynicotinamido)-N,N-dimethylphthalamide and 5-(4-(2,4-difluorophenoxy)piperidin-1-yl)-4-(2-methoxynicotinamido)-N',N'-dimethylphthalamide, to give the title compound as a white solid (52.2 mg, 36.1%). $^1$H NMR (400 MHz, CDCl$_3$) δ ppm 2.01-2.10 (m, 2H), 2.11-2.22 (m, 2H), 2.93 (ddd, J=11.9, 8.1, 3.4 Hz, 2H), 3.27-3.36 (m, 2H), 4.25-4.30 (m, 3H), 4.42 (dt, =7.4, 3.6 Hz, 1H), 6.78-6.93 (m, 2H), 7.02 (td, J=9.0, 5.5 Hz, 1H), 7.15-7.22 (m, 1H), 7.43 (s, 1H), 8.40 (dd, J=4.9, 2.0 Hz, 1H), 8.65 (dd, J=7.6, 2.1 Hz, 1H), 9.72 (s, 1H), 10.33 (s, 1H); ESI-MS m/z [M+H]$^+$ 466.1.

Example 271: N-(4,5-dicyano-2-(4-(2,4-difluorophenoxy)piperidin-1-yl)phenyl-2-methoxynicotinamide

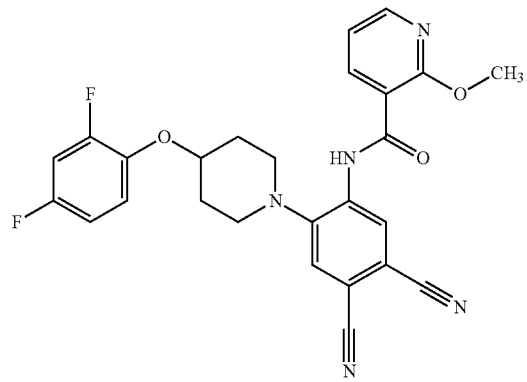 [SMILES: COc1ncccc1C(=O)Nc1cc(C#N)c(C#N)cc1N1CCC(Oc2ccc(F)cc2F)CC1]

A mixture of 4-chloro-5-(4-(2,4-difluorophenoxy)piperidin-1-yl)phthalonitrile (150 mg, 401 μmol, 1.00 eq), 2-methoxynicotinamide (73.27 mg, 481.6 μmol, 1.20 eq), Pd$_2$(dba)$_3$ (18.37 mg, 20.07 μmol, 0.05 eq), Xantphos (23.22 mg, 40.13 μmol, 0.10 eq) and Cs$_2$CO$_3$ (261.51 mg, 802.62 μmol, 2.00 eq) in toluene (2 mL) was degassed and purged with N$_2$ three times. The mixture was subsequently stirred at 110° C. for 16 hours under N$_2$ atmosphere, then poured into water (5 mL), extracted with EtOAc (3×5 mL) and washed with brine (5 mL). The organic phases were separated, dried over anhydrous Na$_2$SO$_4$, filtered, and concentrated in vacuo. The crude residue was purified by column chromatography, eluting with petroleum ether/EtOAc (3:1) to give the title compound as a yellow solid (26.50 mg, 13%). $^1$HNMR (400 MHz, CDCl$_3$) δ ppm 2.03-2.13 (m, 2H), 2.13-2.25 (m, 2H), 2.83-2.94 (m, 2H), 3.20-3.31 (m, 2H), 4.28 (s, 3H), 4.37-4.49 (m, 1H), 6.76-6.93 (m, 2H), 6.97-7.06 (m, 1H), 7.19 (dd, J=7.5, 5.0 Hz, 1H), 7.47-7.54 (m, 1H), 8.40 (dd, J=4.8, 1.8 Hz, 1H), 8.61 (dd, J=7.5, 2.0 Hz, 1H), 9.06 (s, 1H), 10.66 (s, 1H); ESI-MS m/z [M+H]$^+$ 490.1.

Example 272: N-(4-cyano-2-(4-(2,4-difluorophenoxy)piperidin-1-yl-5-(dimethylcarbamoyl)phenyl)-2-methoxynicotinamide

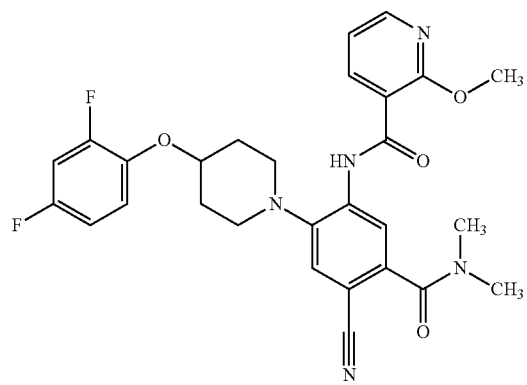 [SMILES: COc1ncccc1C(=O)Nc1cc(C(=O)N(C)C)c(C#N)cc1N1CCC(Oc2ccc(F)cc2F)CC1]

Example 273: N-(5-cyano-2-(4-(2,4-difluorophenoxy)piperidin-1-yl)-4-(dimethylcarbamoyl)phenyl)-2-methoxynicotinamide

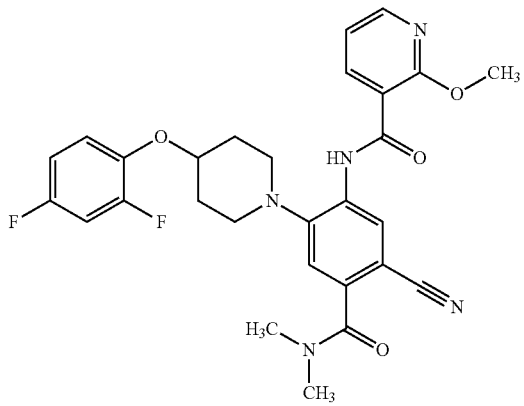 [SMILES: COc1ncccc1C(=O)Nc1cc(C#N)c(C(=O)N(C)C)cc1N1CCC(Oc2ccc(F)cc2F)CC1]

To a stirred mixture of 4-(4-(2,4-difluorophenoxy)piperidin-1-yl)-5-(2-methoxynicotinamido)-N¹,N¹-dimethylphthalamide and 5-(4-(2,4-difluorophenoxy)piperidin-1-yl)-4-(2-methoxynicotinamido)-N',N-dimethylphthalamide (50 mg) in DCM (1 mL) was added TFAA (37.94 mg, 180.64 μmol, 25.13 μL, 2.00 eq) and Et₃N (36.56 mg, 361.28 μmol, 50.08 μL, 4.00 eq). The reaction mixture was stirred at 25° C. for 5 hours, then poured into water (5 mL), extracted with EtOAc (3×5 mL) and washed with brine (5 mL). The organic phases were separated, dried over anhydrous Na₂SO₄, filtered, concentrated in vacuo, and purified by preparative TLC, eluting with petroleum ether/EtOAc (1:1) to give N-(4-cyano-2-(4-(2,4-difluorophenoxy)piperidin-1-yl)-5-(dimethylcarbamoyl)phenyl)-2-methoxynicotinamide (10.5 mg, 42.1%) and N-(5-cyano-2-(4-(2,4-difluorophenoxy)piperidin-1-yl)-4-(dimethylcarbamoyl)phenyl)-2-methoxynicotinamide (5.20 mg, 20.6%) each as a yellow oil. ¹H NMR (400 MHz, CDCl₃) δ ppm 1.98-2.09 (m, 2H), 2.13-2.24 (m, 2H), 2.77-2.89 (m, 2H), 3.00-3.23 (m, 8H), 4.28 (s, 3H), 4.39 (d, J=3.5 Hz, 1H), 6.76-6.84 (m, 1H), 6.89 (ddd, J=11.2, 8.4, 3.0 Hz, 1H), 7.02 (td, J=9.0, 5.5 Hz, 1H), 7.16 (dd, J=7.5, 5.0 Hz, 1H), 7.48 (s, 1H), 8.38 (dd, J=4.8, 1.8 Hz, 1H), 8.59 (dd, J=7.5, 2.0 Hz, 1H), 8.74 (s, 1H), 10.72 (s, 1H) ESI-MS m/z [M+H]⁺ 536.1 (Example 272); and ¹H NMR (400 MHz, CDCl₃) δ ppm 1.98-2.10 (m, 2H), 2.11-2.22 (m, 2H), 2.83-2.93 (m, 2H), 2.98-3.19 (m, 6H), 3.25 (td, J=7.4, 3.3 Hz, 2H), 4.21-4.31 (m, 3H), 4.32-4.43 (m, 1H), 6.76-6.84 (m, 1H), 6.88 (ddd, J=11.0, 8.3, 2.8 Hz, 1H), 7.00 (td, J=9.0, 5.5 Hz, 1H), 7.17 (dd, J=7.8, 4.8 Hz, 1H), 7.26 (s, 1H), 8.38 (dd, J=4.5, 2.0 Hz, 1H), 8.59-8.69 (m, 1H), 8.89 (s, 1H), 10.50 (s, 1H); ESI-MS m/z [M+H]⁺ 536.1 (Example 273).

Example 274: N-(5-cyano-2-(4-(2,4-difluorophenoxy)piperidin-1-yl)phenyl-2-oxo-1,2-dihydropyridine-3-carboxamide

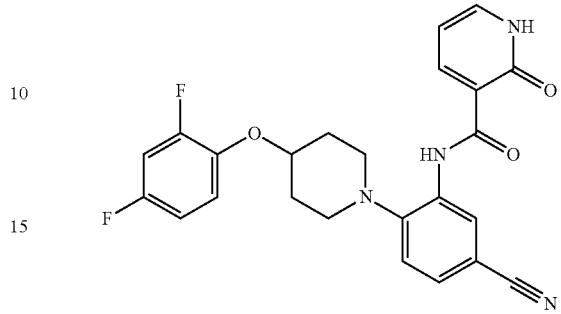

To a round bottom flask containing 3-amino-4-(4-(2,4-difluorophenoxy)piperidin-1-yl)benzonitrile (20.00 mg, 60.73 μmol, 1.00 eq), 2-oxo-1,2-dihydropyridine-3-carboxylic acid (10.14 mg, 72.88 μmol, 1.20 eq), HATU (34.64 mg, 91.10 μmol, 1.50 eq) and DIPEA (23.55 mg, 182.19 μmol, 31.82 μL, 3.00 eq) was added DMF (2 mL). The reaction mixture was stirred at 18° C. for 16 hours and then heated to 80° C. for 24 hours. The reaction mixture was diluted with water (30 mL) and extracted with DCM (2×30 mL). The organic layers were combined, dried over anhydrous Na₂SO₄, filtered, concentrated under reduced pressure, and purified by preparative HPLC (Phenomenex® Gemini, 5 μm, 150 mm×25 mm column) eluting with a gradient of 10-100% ACN in water (0.05% NH₄₀H) to give the title compound as a light yellow solid (5.10 mg, 18.5%). ¹H NMR (400 MHz, CDCl₃) δ ppm 2.09-2.28 (m, 4H), 2.86 (br s, 2H), 3.25 (br s, 2H), 4.35 (br s, 1H), 6.60 (d, J=6.17 Hz, 1H), 6.75-6.90 (m, 2H), 6.97 (dd, J=8.82, 3.53 Hz, 1H), 7.20 (d, J=4.85 Hz, 1H), 7.26-7.32 (m, 1H), 7.39 (d, J=2.21 Hz, 1H), 7.65 (br s, 1H), 8.73 (br s, 1H), 8.91 (d, J=3.09 Hz, 1H), 11.98 (br s, 1H); ESI-MS m/z [M+H]⁺ 451.0.

Example 275: N-(5-cyano-2-(4-(2,4-difluorophenoxy)piperidin-1-yl)phenyl)-2-hydroxybenzamide

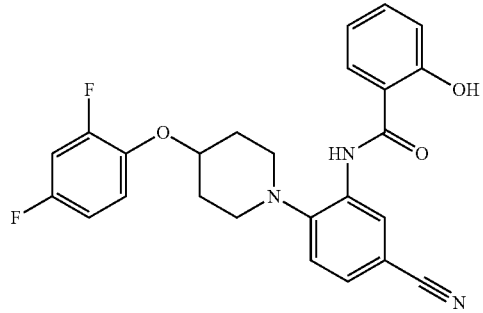 [SMILES: N#Cc1ccc(N2CCC(Oc3ccc(F)cc3F)CC2)c(NC(=O)c2ccccc2O)c1]

To a round-bottomed flask containing N-(5-cyano-2-(4-(2,4-difluorophenoxy)piperidin-1-yl)phenyl)-2-methoxybenzamide (70.00 mg, 151.03 μmol, 1.00 eq) was added DCM (2 mL), followed by BBr₃ (75.67 mg, 302.06 μmol, 29.10 μL, 2.00 eq) drop-wise at −78° C. The reaction mixture was warmed to 20° C. for 16 hours and then quenched with water (20 mL). The aqueous phase was extracted with DCM (2×20 mL). The organic layers were combined, washed with water (2×10 mL), dried over anhydrous Na₂SO₄, concentrated, and purified by preparative TLC, eluting with petroleum ether/EtOAc (1:1), followed by preparative HPLC to give the title compound as a white solid (11.70 mg, 17.2%). ¹H NMR (400 MHz, CDCl₃) δ ppm 2.03-2.18 (m, 4H), 2.88 (ddd, J=11.58, 7.61, 3.75 Hz, 2H), 3.20-3.27 (m, 2H), 4.43 (br s, 1H), 6.82 (t, J=8.60 Hz, 1H), 6.90 (ddd, J=10.92, 8.27, 2.87 Hz, 1H), 6.97-7.06 (m, 2H), 7.09 (d, J=8.38 Hz, 1H), 7.32 (d, J=8.38 Hz, 1H), 7.43-7.55 (m, 3H), 8.80 (d, J=1.76 Hz, 1H), 9.39 (br s, 1H), 11.96 (s, 1H); ESI-MS m/z [M+H]⁺ 450.1.

Example 276: N-(5-cyano-2-(4-(2,4-difluorophenoxy)piperidin-1-yl)phenyl)-2-(difluoromethoxy)nicotinamide

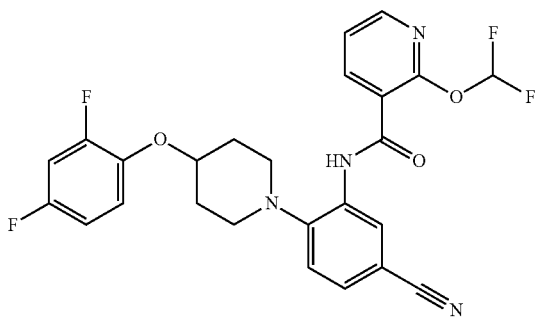 [SMILES: N#Cc1ccc(N2CCC(Oc3ccc(F)cc3F)CC2)c(NC(=O)c2cccnc2OC(F)F)c1]

To a stirred mixture of 2-(difluoromethoxy)nicotinic acid (50.00 mg, 264.38 μmol, 1.00 eq) and 3-amino-4-(4-(2,4-difluorophenoxy)piperidin-1-yl)benzonitrile (104.49 mg, 317.26 μmol, 1.20 eq) in DMF (1.50 mL) was added HATU (120.63 mg, 317.26 μmol, 1.20 eq) and DIPEA (170.84 mg, 1.32 mmol, 230.86 μL, 5.00 eq). The mixture was stirred at 25° C. for 12 hours, then quenched with water (5 mL), extracted with EtOAc (3×5 mL) and washed with brine (3 mL). The organic phases were separated, dried over anhydrous NaSO₄, filtered, concentrated in vacuo, and purified by preparative HPLC (aqueous HCl) to give the title compound as a yellow solid (42.5 mg, 31.8%). ¹H NMR (400 MHz, CDCl₃) δ ppm 2.08-2.29 (m, 4H), 2.79-2.92 (m, 2H), 3.15-3.27 (m, 2H), 4.42 (br s, 1H), 6.66 (t, J=7.1 Hz, 1H), 6.76-6.93 (m, 2H), 7.03 (td, J=9.0, 5.7 Hz, 1H), 7.24 (d, J=7.9 Hz, 1H), 7.41 (dd, J=8.2, 2.0 Hz, 1H), 7.68-8.02 (m, 2H), 8.73 (dd, J=7.1, 1.8 Hz, 1H), 8.94 (d, J=1.8 Hz, 1H), 11.85 (br s, 1H); ESI-MS m/z [M+H]⁺ 501.1.

Example 277: N-(5-cyano-2-(4-(2,4-difluorophenoxy)piperidin-1-yl)phenyl)-1-(difluoromethyl)-2-oxo-1,2-dihydropyridine-3-carboxamide

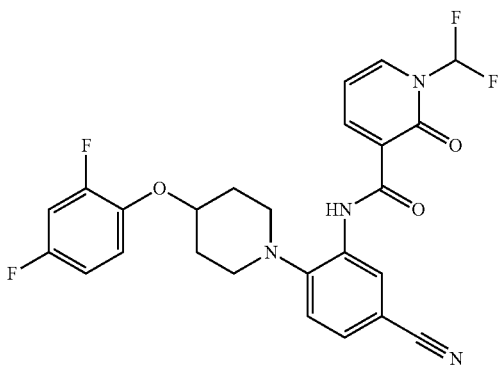 [SMILES: N#Cc1ccc(N2CCC(Oc3ccc(F)cc3F)CC2)c(NC(=O)c2cccn(C(F)F)c2=O)c1]

The title compound was prepared in a manner similar to Example 276, using 1-(difluoromethyl)-2-oxo-2-dihydropyridine-3-carboxylic acid (50 mg, 0.26 mmol) in place of 2-(difluoromethoxy)nicotinic acid, to give the title compound as a white solid (11.5 mg, 8.61%). ¹HNMR (400 MHz, CDCl₃) δ ppm 2.01-2.20 (m, 4H), 2.82-2.94 (m, 2H), 3.16-3.27 (m, 2H), 4.43 (br s, 1H), 6.75-6.83 (m, 1H), 6.87 (ddd, J=11.0, 8.4, 3.1 Hz, 1H), 7.00 (td, J=9.0, 5.7 Hz, 1H), 7.30 (d, J=8.4 Hz, 1H), 7.38 (dd, J=7.5, 4.9 Hz, 1H), 7.45 (dd 0.1=8.2, 1.5 Hz, 1H), 7.55-7.98 (m, 1H), 8.39 (dd, J=4.9, 1.8 Hz, 1H), 8.72 (dd, J=7.7, 1.5 Hz, 1H), 8.83 (d, J=1.3 Hz, 1H), 9.96 (br s, 1H); ESI-MS m/z [M+H]⁺ 501.0.

Example 278: N-(5-cyano-2-(4-(2,4-difluorophenoxy)piperidin-1-yl)phenyl-4-methoxy-2-methylpyrimidine-5-carboxamide

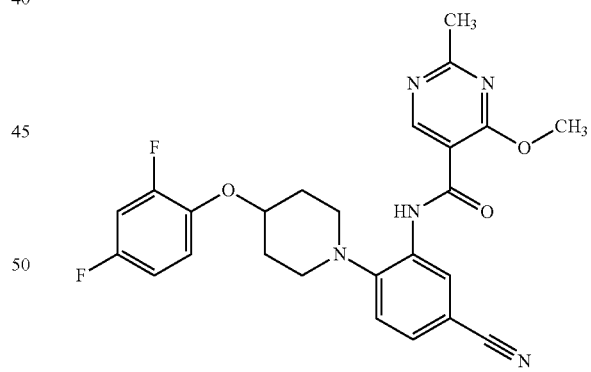

The title compound was prepared in a manner similar to Example 276, using 4-methoxy-2-methylpyrimidine-5-carboxylic acid (250 mg, 1.49 mmol) in place of 2-(difluoromethoxy)nicotinic acid, to give the title compound as a white solid (101 mg, 14%). ¹H NMR (400 MHz, CDCl₃) δ ppm 1.95-2.07 (m, 2H), 2.17 (d, J=11.91 Hz, 2H), 2.73 (s, 3H), 2.79-2.89 (m, 2H), 3.16-3.27 (m, 2H), 4.32 (s, 3H), 4.37 (dd, J=7.50, 3.97 Hz, 1H), 6.76-6.84 (m, 1H), 6.88 (ddd, J=1.03, 8.38, 2.65 Hz, 1H), 7.01 (td, J=9.04, 5.73 Hz, 1H), 7.24 (d, J=7.94 Hz, 1H), 7.41 (dd, J=8.16, 1.54 Hz, 1H), 8.84 (d, J=1.32 Hz, 1H), 9.29 (s, 1H), 10.13 (s, 1H); ESI-MS m/z [M+H]⁺ 480.1.

Example 279: N-(2-(4-(2,4-difluorophenoxy)piperidin-1-yl)-5-(morpholinosulfonyl)pyridin-3-yl)-1-methyl-2-oxo-1,2-dihydropyridine-3-carboxamide

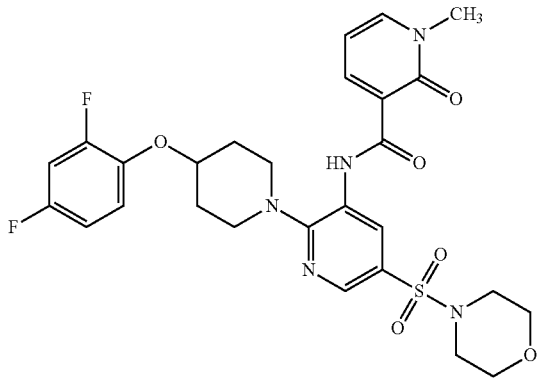 [SMILES: Cn1cccc(C(=O)Nc2cc(S(=O)(=O)N3CCOCC3)cnc2N2CCC(Oc3ccc(F)cc3F)CC2)c1=O]

To a solution of 2-(4-(2,4-difluorophenoxy)piperidin-1-yl)-5-(morpholinosulfonyl)pyridin-3-amine (50.00 mg, 110.0 µmol, 1.00 eq) and 1-methyl-2-oxo-1,2-dihydropyridine-3-carboxylic acid (20.22 mg, 132.0 µmol, 1.20 eq) in DMF (2 mL) was added HATU (62.75 mg, 165.02 µmol, 1.50 eq) and DIPEA (42.65 mg, 330.0 µmol, 57.64 µL, 3.00 eq). The resulting mixture was stirred at 25° C. for 12 hours, then diluted with EtOAc (50 mL) and washed with saturated aq Na$_2$CO$_3$ (20 mL) and brine (20 mL). The organic layers were dried over anhydrous Na$_2$SO$_4$, filtered, concentrated in vacuo, and purified by preparative HPLC (basic mode) to give the title compound as a white solid (18 mg, 27%). $^1$H NMR (400 MHz, CDCl$_3$) δ ppm 2.09-2.27 (m, 4H), 3.01-3.15 (m, 4H), 3.15-3.24 (m, 2H), 3.54-3.63 (m, 2H), 3.72 (s, 3H), 3.75-3.85 (m, 4H), 4.42 (dt, J=7.1, 3.5 Hz, 1H), 6.49 (t, J=7.1 Hz, 1H), 6.74-6.83 (m, 1H), 6.87 (ddd, J=11.0, 8.4, 3.1 Hz, 1H), 7.03 (td, J=9.2, 5.5 Hz, 1H), 7.64 (dd, J=6.6, 1.8 Hz, 1H), 8.43 (d, J=2.2 Hz, 1H), 8.60 (dd, J=7.3, 2.0 Hz, 1H), 9.07 (d, J=2.2 Hz, 1H), 12.23 (s, 1H); ESI-MS m/z [M+H]$^+$ 590.0.

Example 280: N-(2-cyano-4-(4-(2,4-difluorophenoxy)piperidin-1-yl)pyrimidin-5-yl)-2-methoxy-6-methylnicotinamide

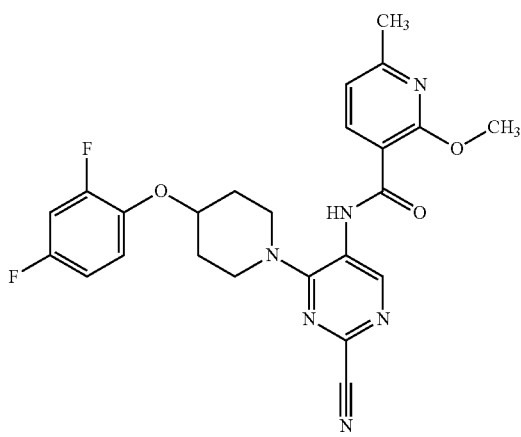 [SMILES: COc1nc(C)ccc1C(=O)Nc1cnc(C#N)nc1N1CCC(Oc2ccc(F)cc2F)CC1]

To a solution of 5-amino-4-(4-(2,4-difluorophenoxy)piperidin-1-yl)pyrimidine-2-carbonitrile (60 mg, 181 µmol, 1.00 eq) and 2-methoxy-6-methylnicotinoyl chloride (50.42 mg, 271.6 µmol, 1.50 eq) in THF (2 mL) was added LiHMDS (1 M, 543.27 µL, 3.00 eq) at 25° C. The mixture was stirred at 25° C. for 3 hours. The reaction mixture was quenched with water (5 mL) and then extracted with DCM (3×5 mL). The organic layers were combined, dried over anhydrous Na$_2$SO$_4$, concentrated under reduced pressure, and purified by preparative HPLC (0.1% aq NH$_4$HCO$_3$ additive) to give the title compound as a white solid (8.0 mg, 9.2%). $^1$HNMR (400 MHz, CDCl$_3$) δ ppm 1.90-1.99 (m, 2H), 2.04-2.13 (m, 2H), 2.54 (s, 3H), 3.38-3.46 (m, 2H), 3.73 (d, J=4.41 Hz, 2H), 4.21 (s, 3H), 4.40-4.48 (m, 1H), 6.73-6.90 (m, 2H), 6.96-7.02 (m, 2H), 8.45 (d, J=7.94 Hz, 1H), 9.37 (s, 1H), 9.85 (s, 1H); ESI-MS m/z [M+H]$^+$ 481.1.

Example 281: 4-(4-(2,4-difluorophenoxy)piperidin-1-yl)-5-(2-methoxynicotinamido)-N,N-dimethylpyrimidine-2-carboxamide

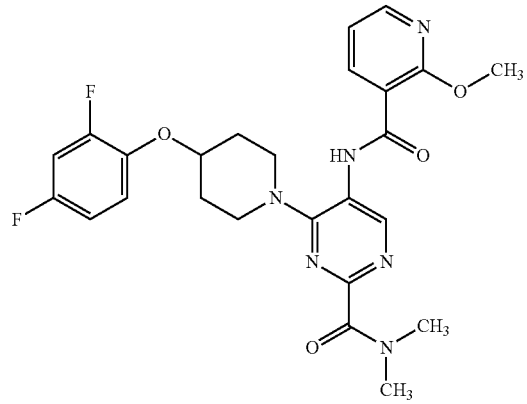 [SMILES: COc1ncccc1C(=O)Nc1cnc(C(=O)N(C)C)nc1N1CCC(Oc2ccc(F)cc2F)CC1]

To a solution of 5-amino-4-(4-(2,4-difluorophenoxy)piperidin-1-yl)-N,N-dimethylpyrimidine-2-carboxamide (60.0 mg, 159 µmol, 1.00 eq) in THF (2 mL) was added LiHMDS (1 M, 476.96 µL, 3.00 eq) at 0° C. The reaction mixture was warmed to 25° C. for 0.5 hours. A solution of 2-methoxynicotinoyl chloride (81.84 mg, 477.0 µmol, 3.00 eq) in THF was added at 25° C. The reaction mixture was stirred at 25° C. for 1 hour and then was quenched with water (10 mL) and extracted with EtOAc (3×5 mL). The organic layers were combined, dried over anhydrous Na$_2$SO$_4$, concentrated under reduced pressure, and purified by preparative HPLC to give the title compound as a white solid (2.30 mg, 2.79%). $^1$HNMR (400 MHz, CDCl$_3$) δ ppm 1.93 (br s, 2H), 2.07 (d, J=3.53 Hz, 2H), 2.99 (s, 3H), 3.13 (s, 3H), 3.33-3.43 (m, 2H), 3.70-3.81 (m, 2H), 4.23 (s, 3H), 4.40 (d, J=3.09 Hz, 1H), 6.74-6.91 (m, 2H), 6.98 (td, J=9.04, 5.73 Hz, 1H), 7.16 (dd, J=7.50, 4.85 Hz, 1H), 8.37 (d, J=3.53 Hz, 1H), 8.61 (d, J=7.50 Hz, 1H), 9.22 (s, 1H), 9.73 (s, 1H); ESI-MS m/z [M+H]$^+$ 513.1.

Example 282: N-(6-cyano-3-(4-(2,4-difluorophenoxy)piperidin-1-yl)pyridazin-4-yl)-2-methoxynicotinamide

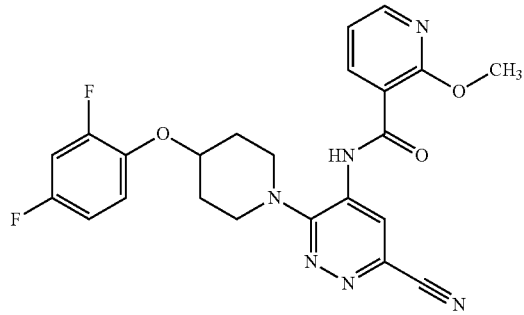 [SMILES: COc1ncccc1C(=O)Nc1cc(C#N)nnc1N1CCC(Oc2ccc(F)cc2F)CC1]

To a mixture of 5-amino-6-(4-(2,4-difluorophenoxy)piperidin-1-yl)pyridazine-3-carbonitrile (40.00 mg, 120.7 µmol, 1.00 eq) in THF (2 mL) was added LiHMDS in THF (400.0 µL, 1 M 3.31 eq) at 0° C. The light yellow mixture was stirred at 20° C. for 0.5 hours and then 2-methoxynicotinoyl chloride (100.00 mg, 582.82 µmol, 4.83 eq) was added. The reaction mixture was stirred at 20° C. for 0.5 hours, then poured into water (50 mL) and extracted with EtOAc (2×50 mL). The organic layers were combined, washed with water (50 mL), dried over anhydrous $Na_2SO_4$, concentrated, and purified by preparative HPLC (Boston Analytics Green ODS 5µ, 150 mm×30 mm column) eluting with a gradient of 60-90% EtOAc in water (0.05% HCl) to give an HCl salt of the title compound as a white solid (3.40 mg, 5.4%). $^1$H NMR (400 MHz, DMSO-$d_6$) δ ppm 1.81-1.96 (m, 2H), 2.11 (br s, 2H), 3.31 (t, J=9.70 Hz, 2H), 3.64 (d, J=13.23 Hz, 2H), 4.14 (s, 3H), 4.66 (br s, 1H), 7.03 (t, J=8.38 Hz, 1H), 7.24-7.39 (m, 3H), 8.34-8.41 (m, 1H), 8.47 (d, J=3.09 Hz, 1H), 8.74 (s, 1H), 10.36 (s, 1H); ESI-MS m/z [M+H]$^+$ 467.0.

Compounds in Examples 283 through 293 are prepared in a manner similar to the above examples.

Example 283: 4-(4-(2,4-difluorophenoxy)piperidin-1-yl)-5-(2-methoxy-6-methylnicotinamido)-N,N-dimethylpicolinamide

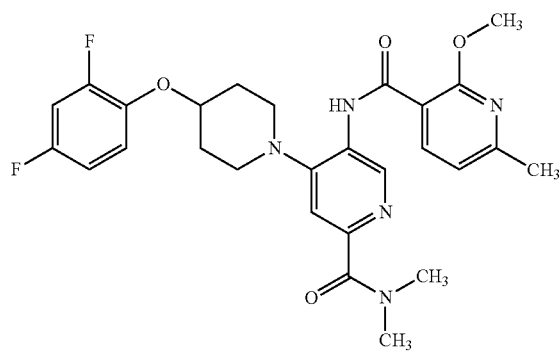 [SMILES: COc1nc(C)ccc1C(=O)Nc1cnc(C(=O)N(C)C)cc1N1CCC(Oc2ccc(F)cc2F)CC1]

ESI-MS m/z [M+H]$^+$ 526.5.

Example 284: N-(5-cyano-2-(4-(2-fluoro-4-methoxybenzoyl)piperazin-1-yl)phenyl)-2-methoxynicotinamide

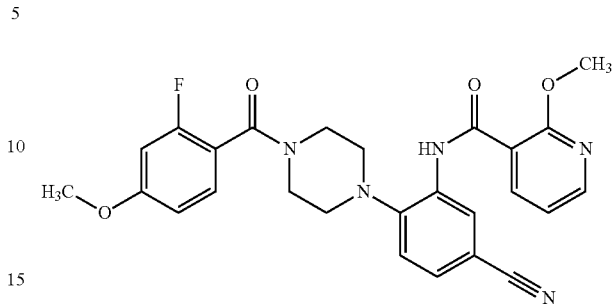

$^1$H NMR (500 MHz, CDCl$_3$) δ ppm 2.81-2.98 (m, 2H), 2.98-3.15 (m, 2H) 3.45-3.66 (m, 2H), 3.82 (s, 3H), 3.92-4.10 (m, 2H), 4.24 (s, 3H), 6.56-6.66 (m, 1H), 6.74-6.83 (m, 1H), 7.11-7.22 (m, 2H), 7.34-7.47 (m, 2H), 8.37 (dd, J=4.88, 2.44 Hz, 1H), 8.58-8.72 (m, 1H), 8.80-8.91 (m, 1H), 10.48 (s, 1H).

Example 285: N-(2-(4-(4-chlorobenzoyl)piperazin-1-yl)-5-cyanophenyl)-2-methoxynicotinamide

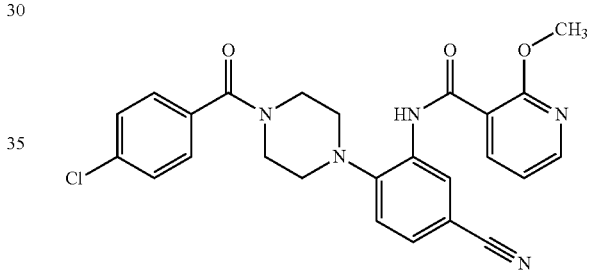

$^1$H NMR (500 MHz, CDCl$_3$) δ ppm 3.00 (br s, 4H), 3.49-4.15 (m, 4H), 4.25 (s, 3H), 7.13-7.23 (m, 2H), 7.33-7.49 (m, 5H), 8.37 (dd, J=4.88, 1.95 Hz, 1H), 8.55-8.71 (m, 1H), 8.85 (d, J=1.95 Hz, 1H), 10.44 (s, 1H).

Example 286: N-(5-cyano-2-(4-(4-fluorobenzoyl)piperazin-1-yl)phenyl)-2-methoxynicotinamide

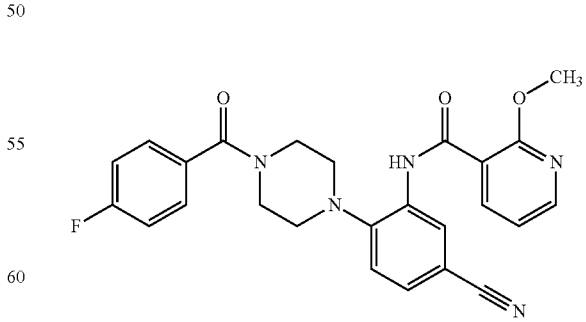

$^1$H NMR (500 MHz, CDCl$_3$) δ ppm 3.00 (br s, 4H), 3.83 (br s, 4H), 4.25 (s, 3H), 7.05-7.24 (m, 4H), 7.38-7.53 (m, 3H), 8.37 (dd, J=4.88, 1.95 Hz, 1H), 8.56-8.70 (m, 1H), 8.85 (d, J=1.95 Hz, 1H), 10.45 (s, 1H).

Example 287: N-(5-cyano-2-(4-((4-fluorophenyl)sulfonyl)piperazin-1-yl)phenyl)-2-methoxynicotinamide

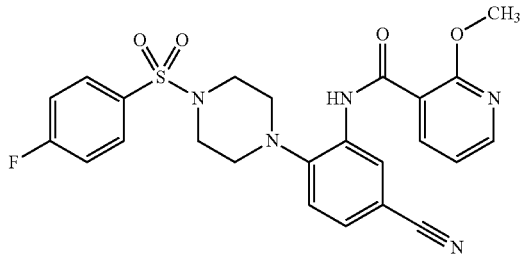 [SMILES: COc1ncccc1C(=O)Nc1cc(C#N)ccc1N1CCN(S(=O)(=O)c2ccc(F)cc2)CC1]

¹H NMR (500 MHz, CDCl₃) δ ppm 3.07 (s, 4H), 3.17-3.33 (m, 4H), 3.56 (s, 3H), 7.10-7.23 (m, 2H), 7.28-7.35 (m, 2H), 7.42 (dd, J=8.30, 1.95 Hz, 1H), 7.79-7.92 (m, 2H), 8.25-8.38 (m, 1H), 8.53-8.66 (m, 1H), 8.83 (d, J=1.95 Hz, 1H), 10.25 (s, 1H).

Example 289: N-(4-(4-(2,4-difluorophenoxy)piperidin-1-yl-6-(trifluoromethyl)pyridin-3-yl)-2-methoxynicotinamide

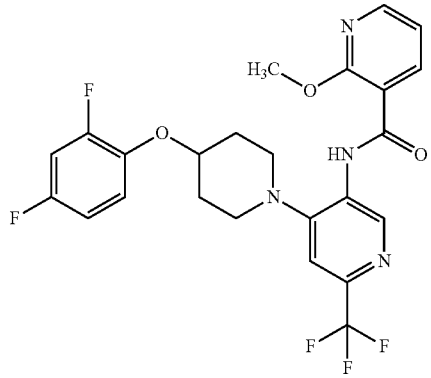

¹H NMR (500 MHz, CDCl₃) δ ppm 1.92-2.03 (m, 3H), 2.06-2.15 (m, 2H), 2.88 (ddd, J=11.96, 8.30, 3.17 Hz, 2H), 3.19-3.32 (m, 2H), 4.16-4.21 (m, 3H), 4.33 (tt, J=7.44, 3.78 Hz, 1H), 5.10-5.28 (m, 1H), 6.73 (dddd, J=9.15, 7.69, 2.93, 1.71 Hz, 1H), 6.77-6.85 (m, 1H), 6.87-6.98 (m, 1H), 7.04-7.14 (m, 1H), 7.28-7.36 (m, 1H), 8.26-8.34 (m, 1H), 8.54-8.62 (m, 1H), 9.56-9.68 (m, 1H), 10.20 (s, 1H).

Example 288: N-(5-cyano-2-(4-(1-(4-fluorophenyl)ethyl)piperazin-1-yl)phenyl)-2-methoxynicotinamide

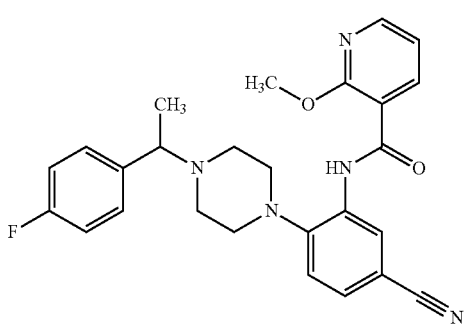 [SMILES: COc1ncccc1C(=O)Nc1cc(C#N)ccc1N1CCN(C(C)c2ccc(F)cc2)CC1]

¹H NMR (500 MHz, CDCl₃) δ ppm 1.42 (d, J=6.35 Hz, 3H), 1.52-1.60 (m, 1H), 2.63 (br s, 4H), 2.98 (t, J=4.39 Hz, 4H), 4.02 (s, 3H), 7.04 (s, 2H), 7.11-7.24 (m, 2H), 7.27 (s, 2H), 7.37-7.43 (m, 1H), 8.36 (dd, J=4.88, 1.95 Hz, 1H), 8.58-8.66 (m, 1H), 8.84 (d, J=1.95 Hz, 1H), 10.35-10.50 (m, 1H); ESI-MS m/z [M+H]⁺ 460.3.

Example 290: N-(5-cyano-2-(4-((3,5-difluoropyridin-2-yl)methyl)piperazin-1-yl)phenyl-2-methoxynicotinamide

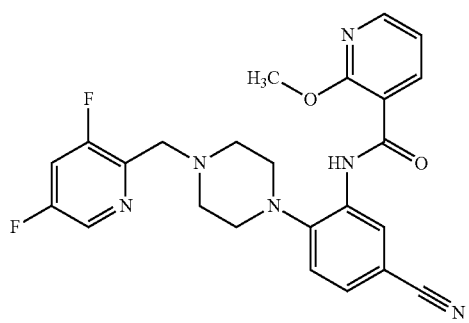 [SMILES: COc1ncccc1C(=O)Nc1cc(C#N)ccc1N1CCN(Cc2ncc(F)cc2F)CC1]

¹H NMR (500 MHz, CDCl₃) δ ppm 2.65-2.90 (m, 4H), 2.93-3.12 (m, 4H), 3.76-3.99 (m, 2H), 4.09-4.27 (m, 3H), 7.12-7.31 (m, 4H), 7.40 (dd, J=8.30, 1.95 Hz, 1H), 8.37 (dd, J=4.64, 2.20 Hz, 2H), 8.59-8.68 (m, 1H), 8.84 (d, J=1.46 Hz, 1H), 10.44 (br s, 1H).

Example 291: N-(5-cyano-2-(4-(2-cyano-4-fluorobenzyl)piperazin-1-yl)phenyl)-2-methoxynicotinamide

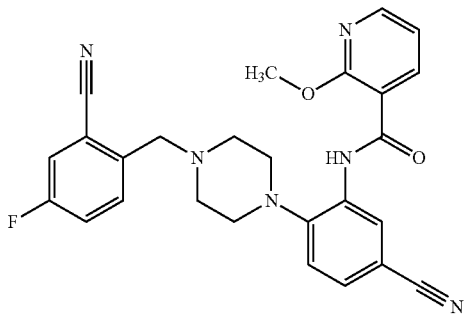 [SMILES: COc1ncccc1C(=O)Nc1cc(C#N)ccc1N1CCN(Cc2ccc(F)cc2C#N)CC1]

$^1$H NMR (500 MHz, CDCl$_3$) δ ppm 2.67-2.83 (m, 4H), 2.96-3.08 (m, 4H), 3.73-3.84 (m, 2H), 4.28 (s, 3H), 7.13-7.25 (m, 2H), 7.31 (td, J=8.18, 2.68 Hz, 1H), 7.35-7.45 (m, 2 H), 7.56 (br s, 1H), 8.38 (dd, J=4.64, 2.20 Hz, 1H), 8.59-8.67 (m, 1H), 8.84 (d, J=1.95 Hz, 1H), 10.45 (s, 1H).

Example 292: N-(5-cyano-2-(4-((2,5-difluoropyridin-3-yl)oxy)piperidin-1-yl)phenyl)-1-methyl-2-oxo-1,2-dihydropyridine-3-carboxamide

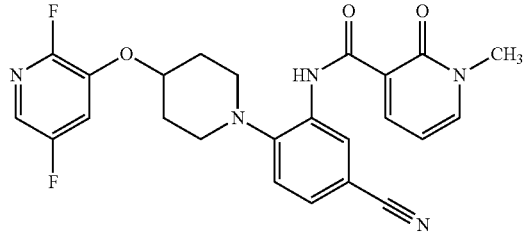 [SMILES: Cn1cccc(C(=O)Nc2cc(C#N)ccc2N2CCC(Oc3cc(F)cnc3F)CC2)c1=O]

$^1$H NMR (500 MHz, DMSO-d$_6$) δ ppm 2.02-2.11 (m, 2H), 2.18-2.28 (m, 2H), 2.91 (ddd, J=11.59, 7.93, 3.42 Hz, 2H), 3.10 (ddd, J=11.23, 7.32, 3.42 Hz, 2H), 3.64 (s, 3H), 4.75-4.85 (m, 1H), 6.61 (dd, J=7.32, 6.35 Hz, 1H), 7.38 (d, J=8.79 Hz, 1H), 7.56 (dd, J=8.30, 1.95 Hz, 1H), 7.76 (t, J=2.68 Hz, 1H), 7.90-7.97 (m, 1H), 8.18 (dd, J=6.59, 2.20 Hz, 1H), 8.49 (dd, J=7.32, 2.44 Hz, 1H), 8.83 (d, J=1.95 Hz, 1H), 12.46 (s, 1H); ESI-MS m/z [M+H]$^+$ 466.

Example 293: N-(5-cyano-2-(4-((3,5-difluoropyridin-2-yl)oxy)piperidin-1-yl)phenyl)-1-methyl-2-oxo-1,2-dihydropyridine-3-carboxamide

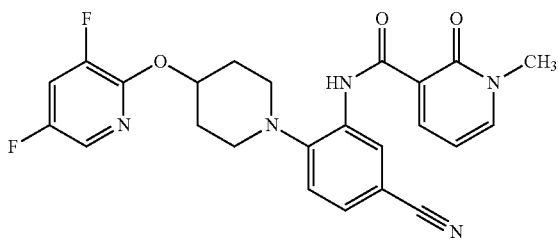 [SMILES: Cn1cccc(C(=O)Nc2cc(C#N)ccc2N2CCC(Oc3ncc(F)cc3F)CC2)c1=O]

$^1$H NMR (500 MHz, DMSO-d$_6$) δ ppm 2.11 (td, J=8.30, 4.39 Hz, 2H), 2.20-2.28 (m, 2H), 2.87-2.96 (m, 2H), 3.08-3.17 (m, 2H), 3.65 (s, 3H), 5.24 (dt, J=7.81, 3.91 Hz, 1H), 6.60 (dd, J=7.32, 6.35 Hz, 1H), 7.40 (d, J=8.30 Hz, 1H), 7.55 (dd, J=8.30, 1.95 Hz, 1H), 7.97 (ddd, J=10.62, 8.18, 2.68 Hz, 1H), 8.07 (d, J=2.44 Hz, 1H), 8.18 (dd, J=6.59, 2.20 Hz, 1H), 8.49 (dd, J=7.32, 2.44 Hz, 1H), 8.83 (d, J=1.95 Hz, 1H), 12.47 (s, 1H); ESI-MS m/z [M+H]$^+$ 466.

Biological Assay Data

Table 1 lists biological assay data (in vitro inhibition of cAMP) for some of the compounds shown in the examples, where larger pEC$_{50}$ values represent higher activity or potency. All of the compounds shown in Table 1 were tested in accordance with a cell-based assay which measures the ability of test compounds to inhibit the constitutive cAMP activity of GPR6 receptor expressed in CHO-K$_1$ cells (reported as pEC$_{50}$). The assay is described in the specification under the heading "In vitro inhibition of cAMP (EC$_{50}$)."

TABLE 1

| In vitro inhibition of cAMP (EC50) | |
|---|---|
| Ex. | pEC50 |
| 1 | 7.2 |
| 2 | 7.0 |
| 3 | 7.5 |
| 4 | 6.7 |
| 5 | 7.4 |
| 6 | 7.3 |
| 7 | 7.4 |
| 8 | 6.9 |
| 9 | 6.1 |
| 10 | 6.9 |
| 11 | 6.7 |
| 12 | 6.4 |
| 13 | 6.3 |
| 14 | 5.7 |
| 15 | 7.1 |
| 16 | 6.6 |
| 17 | 7.2 |
| 18 | 6.8 |
| 19 | 6.7 |
| 20 | 6.9 |
| 21 | 7.4 |
| 22 | 7.1 |
| 23 | 6.3 |
| 24 | 6.2 |
| 25 | 7.0 |
| 26 | 6.4 |
| 27 | 7.4 |
| 28 | 6.6 |
| 29 | 7.3 |
| 30 | 7.2 |
| 31 | 7.1 |
| 32 | 7.0 |
| 33 | 7.2 |
| 34 | 7.0 |
| 35 | 7.4 |
| 36 | 7.0 |
| 37 | 7.1 |
| 38 | 6.8 |
| 39 | 7.3 |
| 40 | 6.2 |
| 41 | 6.4 |
| 42 | 6.9 |
| 43 | 6.1 |
| 44 | 6.2 |
| 45 | 6.6 |
| 46 | 7.2 |
| 47 | 7.2 |
| 48 | 6.8 |
| 49 | 6.5 |
| 50 | 6.2 |
| 51 | 6.8 |
| 52 | 6.2 |

TABLE 1-continued

In vitro inhibition of cAMP (EC50)

| Ex. | pEC50 |
|---|---|
| 53 | 6.3 |
| 54 | 7.4 |
| 55 | 7.3 |
| 56 | 7.2 |
| 57 | 7.3 |
| 58 | 7.4 |
| 59 | 7.3 |
| 60 | 7.3 |
| 61 | 6.4 |
| 62 | 7.3 |
| 63 | 7.1 |
| 64 | 7.0 |
| 65 | 7.3 |
| 66 | 7.3 |
| 67 | 7.0 |
| 68 | 6.6 |
| 69 | 6.7 |
| 70 | 6.4 |
| 71 | 6.5 |
| 72 | 6.6 |
| 73 | 6.5 |
| 74 | 7.1 |
| 75 | 7.3 |
| 76 | <5.7 |
| 77 | <5.7 |
| 78 | 6.9 |
| 79 | 6.8 |
| 80 | 6.3 |
| 81 | 6.9 |
| 82 | 7.0 |
| 83 | 6.9 |
| 84 | 6.6 |
| 85 | 7.2 |
| 86 | 6.8 |
| 87 | 7.2 |
| 88 | 6.4 |
| 89 | 6.3 |
| 90 | 7.2 |
| 91 | 7.1 |
| 92 | 7.3 |
| 93 | 6.3 |
| 94 | <5.7 |
| 95 | 6.2 |
| 96 | 6.5 |
| 97 | 6.4 |
| 98 | 6.4 |
| 99 | 6.1 |
| 100 | 6.8 |
| 101 | 5.9 |
| 102 | 6.1 |
| 103 | 6.5 |
| 104 | <5.7 |
| 105 | 7.0 |
| 106 | 6.5 |
| 107 | 6.6 |
| 108 | 7.0 |
| 109 | 6.7 |
| 110 | 6.3 |
| 111 | 5.5 |
| 112 | 6.4 |
| 113 | 6.9 |
| 114 | 6.1 |
| 115 | 6.6 |
| 116 | 5.9 |
| 117 | 6.3 |
| 118 | 6.4 |
| 119 | <5.7 |
| 120 | 7.4 |
| 121 | 6.7 |
| 122 | 6.1 |
| 123 | 6.5 |
| 124 | 6.9 |
| 125 | 6.7 |
| 126 | 6.3 |
| 127 | 6.1 |
| 128 | 6.6 |
| 129 | 7.2 |
| 130 | 7.1 |
| 131 | 7.0 |
| 132 | 5.6 |
| 133 | 7.1 |
| 134 | 5.8 |
| 135 | 6.8 |
| 136 | 6.8 |
| 137 | 7.1 |
| 138 | <4.5 |
| 139 | <4.5 |
| 140 | 5.7 |
| 141 | 7.2 |
| 142 | 6.2 |
| 143 | 6.8 |
| 144 | 6.9 |
| 145 | 6.6 |
| 146 | 6.6 |
| 147 | 6.9 |
| 148 | 7.2 |
| 149 | 5.8 |
| 150 | <5.7 |
| 151 | 6.3 |
| 152 | 7.1 |
| 153 | 6.4 |
| 154 | 6.5 |
| 155 | 6.3 |
| 156 | 6.4 |
| 157 | 6.7 |
| 158 | 6.3 |
| 159 | 6.0 |
| 160 | 6.5 |
| 161 | 6.5 |
| 162 | 6.6 |
| 163 | 6.7 |
| 164 | 6.5 |
| 165 | 6.7 |
| 166 | 6.1 |
| 167 | 6.5 |
| 168 | 6.4 |
| 169 | 6.4 |
| 170 | 6.5 |
| 171 | 6.6 |
| 172 | 7.1 |
| 173 | 6.8 |
| 174 | 7.1 |
| 175 | 7.0 |
| 176 | 6.5 |
| 177 | 5.7 |
| 178 | 6.8 |
| 179 | 6.2 |
| 180 | 5.8 |
| 181 | 6.4 |
| 182 | 6.3 |
| 183 | 5.9 |
| 184 | 6.8 |
| 185 | 6.4 |
| 186 | 6.4 |
| 187 | 6.6 |
| 188 | 6.4 |
| 189 | 5.8 |
| 190 | 6.5 |
| 191 | 6.8 |
| 192 | 6.3 |
| 193 | 5.9 |
| 194 | 6.3 |
| 195 | 5.9 |
| 196 | 6.7 |
| 197 | 6.7 |
| 198 | 6.4 |
| 199 | 5.9 |
| 200 | 6.9 |
| 201 | 6.8 |
| 202 | 6.3 |
| 203 | 5.6 |
| 204 | 4.9 |

TABLE 1-continued

In vitro inhibition of cAMP (EC50)

| Ex. | pEC50 |
|---|---|
| 205 | 6.0 |
| 206 | 5.1 |
| 207 | 6.8 |
| 208 | 6.9 |
| 209 | 6.1 |
| 210 | 7.3 |
| 211 | 6.7 |
| 212 | <4.5 |
| 213 | 6.8 |
| 214 | 5.5 |
| 215 | 5.5 |
| 216 | 6.4 |
| 217 | 6.7 |
| 218 | 6.8 |
| 219 | 6.3 |
| 220 | 5.8 |
| 221 | <4.5 |
| 222 | 6.7 |
| 223 | 5.6 |
| 224 | 7.3 |
| 225 | 6.4 |
| 226 | 7.0 |
| 227 | 5.8 |
| 228 | 7.2 |
| 229 | 7.3 |
| 230 | 7.1 |
| 231 | 6.3 |
| 232 | 6.4 |
| 233 | 6.4 |
| 234 | <4.5 |
| 235 | 7.1 |
| 236 | 7.1 |
| 237 | 6.7 |
| 238 | 5.0 |
| 239 | 6.9 |
| 240 | 6.8 |
| 241 | 6.0 |
| 242 | 6.8 |
| 243 | 6.5 |
| 244 | 6.3 |
| 245 | 7.0 |
| 246 | 7.1 |
| 247 | 5.9 |
| 248 | 6.9 |
| 249 | 6.4 |
| 250 | 6.0 |
| 251 | 6.8 |
| 252 | 7.0 |
| 253 | 6.8 |
| 254 | 7.2 |
| 255 | 7.3 |
| 256 | 6.7 |
| 257 | 7.0 |
| 258 | 4.9 |
| 259 | 5.3 |
| 260 | 4.9 |
| 261 | 7.2 |
| 262 | 7.3 |
| 263 | 7.1 |
| 264 | 6.8 |
| 265 | 6.7 |
| 266 | 6.8 |
| 267 | 6.4 |
| 268 | 6.9 |
| 269 | 6.9 |
| 270 | 6.9 |
| 271 | 7.1 |
| 272 | 7.4 |
| 273 | 7.3 |
| 274 | 7.0 |
| 275 | 6.5 |
| 276 | 7.3 |
| 277 | 6.5 |
| 278 | 7.4 |
| 279 | 7.0 |
| 280 | 7.1 |
| 281 | 6.4 |
| 282 | 7.2 |
| 283 | 6.8 |
| 284 | 6.6 |
| 285 | 6.9 |
| 286 | 6.7 |
| 287 | 6.2 |
| 288 | 6.0 |
| 289 | 6.9 |
| 290 | 6.5 |
| 291 | 6.9 |
| 292 | 6.6 |
| 293 | 6.6 |

Table 2 shows the ability of GPR6 modulators representative compounds to reverse haloperidol-induced catalepsy. The example compounds listed in Table 2 were tested in accordance with the assay described herein under the heading "In vivo Parkinson's disease model—Haloperidol-induced Catalepsy."

TABLE 2

Biological Efficacy Data in Mouse Catalepsy Model

| Example | Dose (mpk) | Route | Time (minutes) | % reversal |
|---|---|---|---|---|
| 18 | 1 | PO | 30 | 53 |
| 18 | 1 | PO | 90 | 37 |
| 31 | 1 | PO | 60 | 47 |
| 283 | 3 | PO | 60 | 47 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:

1. A compound of Formula 1,

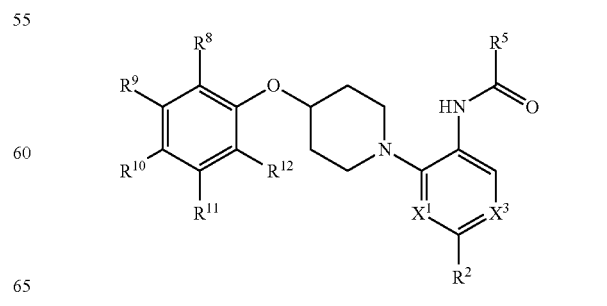

or a pharmaceutically acceptable salt thereof in which:

$X^1$ is selected from N and $CR^1$, and $X^3$ is selected from N and $CR^3$, provided:
(a) if $X^1$ is $CR^1$, $X^3$ is $CR^3$ and $R^1$, $R^2$ and $R^3$ are each hydrogen, then $R^5$ cannot be 2-phenylthiazol-4-yl, and
(b) if $X^1$ is $CR^1$, $X^3$ is $CR^3$ and $R^1$ and $R^3$ are each hydrogen, then $R^2$ cannot be Cl, and
(d) if $X^1$ is N, $X^3$ is $CR^3$ and $R^2$ and $R^3$ are each hydrogen, then $R^5$ cannot be benzo[d][1,3]dioxol-5-yl;

$R^1$ and $R^3$ are each independently selected from hydrogen, cyano, $C_{1-6}$ alkyl, $-(CH_2)_mOR^a$, $-(CH_2)_mN(R^a)R^b$, $-(CH_2)_mN(R^a)C(O)R^b$, $-(CH_2)_mNHC(O)NR^a R^b$, $-(CH_2)_mNR^aC(O)NHR^b$, $-(CH_2)_mC(O)R^a$, $-(CH_2)_mC(O)N(R^a)R^b$, $-(CH_2)_mN(R^a)S(O)_2R^c$, $-(CH_2)_mSR^a$, $-(CH_2)_mS(O)R^c$, $-(CH_2)_mS(O)_2R^c$, and $-(CH_2)_mS(O)_2N(R^a)R^b$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and m is selected from 0, 1, 2, 3, and 4;

$R^2$ is selected from hydrogen, halo, cyano, $C_{1-6}$ alkyl optionally substituted with 1 to 3 halo, $-(CH_2)_nOR^d$, $-(CH_2)_nN(R^d)R^e$, $-(CH_2)_nN(R^d)C(O)R^e$, $-(CH_2)_nNHC(O)NR^dR^e$, $-(CH_2)_nNR^dC(O)NHR^e$, $-(CH_2)_nC(O)R^d$, $-(CH_2)_nC(O)N(R^d)R^e$, $-(CH_2)_nN(R^d)S(O)_2R$, $-(CH_2)_nSR^d$, $-(CH_2)_nS(O)R^f$, $-(CH_2)_nS(O)_2R$, and $-(CH_2)_nS(O)_2N(R^d)R^e$, wherein $R^d$ and $R^e$ are each independently selected from hydrogen, $C_{1-4}$ alkyl, and $C_{2-6}$ heterocyclyl, $R^f$ is selected from $C_{1-4}$ alkyl and $C_{2-6}$ heterocyclyl, and n is selected from 0, 1, 2, 3, and 4, provided if $R^2$ is halo then no more than one of $R^1$ and $R^3$ is hydrogen;

$R^5$ is selected from phenyl and $C_{1-9}$ heteroaryl, wherein phenyl is optionally substituted with from 1 to 3 substituents independently selected from:
(a) amino optionally substituted with 1 or 2 $C_{1-4}$ alkyl;
(b) halo, hydroxy, $C_{3-6}$ cycloalkyl, and $C_{2-6}$ heterocyclyl;
(c) $C_{1-6}$ alkyl optionally substituted with:
 (i) from 1 to 3 substituents independently selected from halo, oxo, $C_{1-4}$ alkoxy, and amino optionally substituted with 1 or 2 $C_{1-4}$ alkyl; or
 (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo; and wherein $C_{1-9}$ heteroaryl is optionally substituted with from 1 to 3 substituents independently selected from:
(a) amino optionally substituted with 1 or 2 $C_{1-4}$ alkyl;
(b) halo, hydroxy, oxo, $C_{3-6}$ cycloalkyl, and $C_{2-6}$ heterocyclyl;
(c) $C_{1-6}$ alkyl optionally substituted with:
 (i) from 1 to 3 substituents independently selected from halo, oxo, $C_{1-4}$ alkoxy, and amino optionally substituted with 1 or 2 $C_{1-4}$ alkyl; or
 (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;

$R^8$, $R^9$, $R^{10}$, $R^{11}$, and $R^{12}$ are each independently selected from hydrogen, halo, cyano, $C_{1-6}$ alkyl optionally substituted with from 1 to 3 halo, and $C_{1-6}$ alkoxy optionally substituted with from 1 to 3 halo;

wherein each of the above-mentioned heteroaryl and heterocyclyl moieties independently has 1 to 3 heteroatoms as ring members, each of the heteroatoms independently selected from N, O, and S.

2. The compound or pharmaceutically acceptable salt according to claim 1, wherein:
(A) $X^1$ is $CR^1$, $X^3$ is $CR^3$, and at least one of $R^1$, $R^2$ and $R^3$ is not hydrogen; or
(B) X is $CR^1$, and $X^3$ is N; or
(C) $X^1$ is N, and $X^3$ is $CR^3$; or
(D) $X^1$ is N, and $X^3$ is N.

3. The compound or pharmaceutically acceptable salt according to claim 1, wherein $R^1$ is selected from hydrogen, cyano, $C_{1-6}$ alkyl, $-(CH_2)_mOR^a$, $-(CH_2)_mN(R^a)C(O)R^b$, $-(CH_2)_mC(O)N(R^a)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and m is selected from 0 and 1.

4. The compound or pharmaceutically acceptable salt according to claim 1, wherein $R^2$ is selected from hydrogen, halo, cyano, $C_{1-6}$ alkyl optionally substituted with 1 to 3 halo, $-(CH_2)_nOR^d$, $-(CH_2)_nC(O)N(R^d)R^e$, and $-(CH_2)_nS(O)_2R$, wherein $R^d$ and $R^e$ are each independently selected from hydrogen, $C_{1-4}$ alkyl, and $C_{2-6}$ heterocyclyl, $R^f$ is $C_{1-4}$ alkyl, and n is selected from 0 and 1.

5. The compound or pharmaceutically acceptable salt according to claim 1, wherein $R^3$ is selected from hydrogen, cyano, $C_{1-6}$ alkyl, $-(CH_2)_mOR^a$, $-(CH_2)_mN(R^a)C(O)R^b$, $-(CH_2)_mC(O)N(R^a)R^b$, and $-(CH_2)_mS(O)_2R^c$, wherein $R^a$ and $R^b$ are each independently selected from hydrogen and $C_{1-4}$ alkyl, $R^c$ is selected from $C_{1-4}$ alkyl and $C_{2-6}$ heterocyclyl, and m is selected from 0 and 1.

6. The compound or pharmaceutically acceptable salt according to claim 1, wherein $R^5$ is selected from phenyl optionally substituted with from 1 to 3 substituents independently selected from:
(a) amino optionally substituted with 1 or 2 $C_{1-4}$ alkyl;
(b) halo, hydroxy, $C_{2-6}$ heterocyclyl, and phenyl; and
(c) $C_{1-6}$ alkyl and $C_{1-6}$ alkoxy, each optionally substituted with from 1 to 3 halo.

7. The compound or pharmaceutically acceptable salt according to claim 1, wherein $R^8$, $R^9$, $R^{10}$, $R^{11}$, and $R^{12}$ are each independently selected from hydrogen, halo, cyano, $C_{1-4}$ alkyl optionally substituted from 1 to 3 halo, and $C_{1-4}$ alkoxy optionally substituted with from 1 to 3 halo.

8. The compound or pharmaceutically acceptable salt according to claim 1, wherein $R^5$ is $C_{1-9}$ heteroaryl optionally substituted with from 1 to 3 substituents independently selected from:
(a) amino optionally substituted with 1 or 2 $C_{1-4}$ alkyl;
(b) halo, hydroxy, oxo, $C_{3-6}$ cycloalkyl, and $C_{2-6}$ heterocyclyl;
(c) $C_{1-6}$ alkyl optionally substituted with:
 (i) from 1 to 3 substituents independently selected from halo, oxo, $C_{1-4}$ alkoxy, and amino optionally substituted with 1 or 2 $C_{1-4}$ alkyl; or
 (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo.

9. The compound or pharmaceutically acceptable salt according to claim 8, wherein each of the optional substituents on the $R^5$ heteroaryl moiety is independently selected from:

(a) amino optionally substituted with 1 or 2 $C_{1-4}$ alkyl;
(b) halo, hydroxy, oxo, $C_{3-6}$ cycloalkyl, and $C_{3-5}$ heterocyclyl;
(c) $C_{1-6}$ alkyl optionally substituted with:
  (i) from 1 to 3 substituents independently selected from halo, oxo, $C_{1-4}$ alkoxy, and amino optionally substituted with 1 or 2 $C_{1-4}$ alkyl; or
  (ii) a substituent selected from phenyl and pyridinyl, each optionally substituted with from 1 to 3 halo;
(d) $C_{1-6}$ alkoxy optionally substituted with from 1 to 3 halo; and
(e) phenyl optionally substituted with from 1 to 3 halo;
wherein the $C_{3-5}$ heterocyclyl moiety is monocyclic, has 5 or 6 ring members in which 1 or 2 ring members are heteroatoms, and the heteroatoms are independently selected from N, O and S.

10. The compound according to claim 1, which is selected from the following compounds:
- N-(2-(4-(2-fluoro-4-methoxyphenoxy)piperidin-1-yl)-5-(methylsulfonyl)phenyl)-1-(2-fluoroethyl)-3-methoxy-1H-pyrazole-4-carboxamide;
- N-(2-(4-(2-fluoro-4-methoxyphenoxy)piperidin-1-yl)-5-(methylsulfonyl)phenyl)-1-(fluoromethyl)-3-methoxy-1H-pyrazole-4-carboxamide;
- N-(2-(4-(2,4-difluorophenoxy)piperidin-1-yl)-5-(methylsulfonyl)phenyl)-1-methyl-2-oxo-1,2-dihydropyridine-3-carboxamide;
- N-(5-cyano-2-(4-(4-fluorophenoxy)piperidin-1-yl)phenyl)-1-methyl-2-oxo-1,2-dihydropyridine-3-carboxamide;
- N-(2-(4-(2,4-difluorophenoxy)piperidin-1-yl)-5-(methylsulfonyl)phenyl)-2-methoxynicotinamide;
- N-(2-(4-(2,4-difluorophenoxy)piperidin-1-yl)-5-(methylsulfonyl)phenyl)-2-methoxybenzamide;
- N-(2-(4-(2,4-difluorophenoxy)piperidin-1-yl)-5-(methylsulfonyl)phenyl)-4-methoxynicotinamide;
- N-(5-cyano-2-(4-(2-fluorophenoxy)piperidin-1-yl)phenyl)-1-methyl-2-oxo-1,2-dihydropyridine-3-carboxamide;
- N-(5-cyano-2-(4-(2,3-difluorophenoxy)piperidin-1-yl)phenyl)-1-methyl-2-oxo-1,2-dihydropyridine-3-carboxamide;
- N-(2-(4-(2,4-difluorophenoxy)piperidin-1-yl)-5-(methylsulfonyl)phenyl)-3-fluoro-2-methoxybenzamide;
- N-(2-(4-(2,4-difluorophenoxy)piperidin-1-yl)-5-(methylsulfonyl)phenyl)-2-fluoro-6-methoxybenzamide;
- N-(5-cyano-2-(4-(3-fluorophenoxy)piperidin-1-yl)phenyl)-1-methyl-2-oxo-1,2-dihydropyridine-3-carboxamide;
- N-(5-cyano-2-(4-(2,6-difluorophenoxy)piperidin-1-yl)phenyl)-1-methyl-2-oxo-1,2-dihydropyridine-3-carboxamide;
- N-(5-cyano-2-(4-(3,5-difluorophenoxy)piperidin-1-yl)phenyl)-1-methyl-2-oxo-1,2-dihydropyridine-3-carboxamide;
- N-(5-cyano-2-(4-(2,5-difluorophenoxy)piperidin-1-yl)phenyl)-1-methyl-2-oxo-1,2-dihydropyridine-3-carboxamide;
- N-(5-cyano-2-(4-(3,4-difluorophenoxy)piperidin-1-yl)phenyl)-1-methyl-2-oxo-1,2-dihydropyridine-3-carboxamide;
- N-(6-chloro-4-(4-(2,4-difluorophenoxy)piperidin-1-yl)pyridin-3-yl)-1-methyl-2-oxo-1,2-dihydropyridine-3-carboxamide;
- N-(4-(4-(2,4-difluorophenoxy)piperidin-1-yl)-2-methylpyrimidin-5-yl)-2-methoxynicotinamide;
- 4-(4-(2,4-difluorophenoxy)piperidin-1-yl)-5-(2-methoxynicotinamido)-N-methylpicolinamide;
- N-(4-(4-(2,4-difluorophenoxy)piperidin-1-yl)-6-methoxypyridin-3-yl)-2-methoxynicotinamide;
- N-(4-(4-(2,4-difluorophenoxy)piperidin-1-yl)-6-methoxypyridin-3-yl)-4-methoxynicotinamide;
- 4-(4-(2,4-difluorophenoxy)piperidin-1-yl)-5-(2-methoxynicotinamido)-N,N-bis(methyl-d$_3$)picolinamide;
- N-(4-(4-(2,4-difluorophenoxy)piperidin-1-yl)-2-methoxypyrimidin-5-yl)-2-methoxy-6-methylnicotinamide;
- N-(5-cyano-2-(4-(2,4-difluorophenoxy)piperidin-1-yl)phenyl)-1,6-dimethyl-4-oxo-1,4-dihydropyridine-3-carboxamide;
- N-(5-cyano-2-(4-(2,4-difluorophenoxy)piperidin-1-yl)phenyl)-3-methoxyisonicotinamide;
- N-(5-cyano-2-(4-(2,4-difluorophenoxy)piperidin-1-yl)phenyl)-3-methoxypicolinamide;
- N-(5-cyano-2-(4-(2,4-difluorophenoxy)piperidin-1-yl)phenyl)-2,3-dihydrobenzofuran-7-carboxamide;
- N-(5-cyano-2-(4-(2,4-difluorophenoxy)piperidin-1-yl)phenyl)-2-ethoxynicotinamide;
- N-(5-cyano-2-(4-(2-fluoro-4-methoxyphenoxy)piperidin-1-yl)phenyl)-1-methyl-2-oxo-1,2-dihydropyridine-3-carboxamide;
- N-(2-(4-(2,4-difluorophenoxy)piperidin-1-yl)-4-(methylsulfonyl)phenyl)-1-methyl-2-oxo-1,2-dihydropyridine-3-carboxamide;
- 4-(4-(2,4-difluorophenoxy)piperidin-1-yl)-5-(2-methoxynicotinamido)-N,N-dimethylpicolinamide;
- 4-(4-(2,4-difluorophenoxy)piperidin-1-yl)-5-(5-fluoro-2-methoxynicotinamido)-N,N-dimethylpicolinamide;
- N-(2-(4-(2,4-difluorophenoxy)piperidin-1-yl)-5-(hydroxymethyl)pyridin-3-yl)-2-methoxynicotinamide;
- N-(2-(4-(2,4-difluorophenoxy)piperidin-1-yl)-5-methylpyridin-3-yl)-4-methoxynicotinamide;
- N-(2-(4-(2,4-difluorophenoxy)piperidin-1-yl)-5-methylpyridin-3-yl)-3-methoxy-1-methyl-1H-pyrazole-4-carboxamide;
- N-(5-cyano-2-(4-(2,4-difluorophenoxy)piperidin-1-yl)phenyl)-4-methoxypyrimidine-5-carboxamide;
- N-(2-(4-(2,4-difluorophenoxy)piperidin-1-yl)-5-(methylsulfonyl)phenyl)-5,6,7,8-tetrahydropyrazolo[5,1-b][1,3]oxazepine-3-carboxamide;
- N-(5-cyano-2-(4-(2,4-difluorophenoxy)piperidin-1-yl)-4-fluorophenyl)-2-methoxy-6-methylnicotinamide;
- N-(4-(4-(4-cyano-2-fluorophenoxy)piperidin-1-yl)-6-methylpyridin-3-yl)-2-methoxynicotinamide;
- N-(5-cyano-2-(4-(2,4-difluorophenoxy)piperidin-1-yl)phenyl)-5-methylisoxazole-3-carboxamide;
- N-(5-cyano-2-(4-(2,4-difluorophenoxy)piperidin-1-yl)phenyl)-1-methyl-1H-pyrazole-3-carboxamide;
- N-(5-cyano-2-(4-(2,4-difluorophenoxy)piperidin-1-yl)phenyl)-2-methyloxazole-4-carboxamide;
- N-(5-cyano-2-(4-(2,4-difluorophenoxy)piperidin-1-yl)phenyl)pyrazine-2-carboxamide;
- N-(5-cyano-2-(4-(2,4-difluorophenoxy)piperidin-1-yl)phenyl)-1-methyl-1H-imidazole-4-carboxamide;
- N-(5-cyano-2-(4-(2,4-difluorophenoxy)piperidin-1-yl)phenyl)-3-methoxythiophene-2-carboxamide;
- N-(5-cyano-2-(4-(2,4-difluorophenoxy)piperidin-1-yl)phenyl)-4-methoxythiophene-3-carboxamide;
- N-(5-cyano-2-(4-(2,4-difluorophenoxy)piperidin-1-yl)phenyl)pyrrolo[1,2-c]pyrimidine-3-carboxamide;
- N-(5-cyano-2-(4-(2,4-difluorophenoxy)piperidin-1-yl)phenyl)-3,5-difluoropicolinamide;

N-(5-cyano-2-(4-(2,4-difluorophenoxy)piperidin-1-yl)
phenyl)-1-methyl-1H-imidazole-2-carboxamide;
N-(5-cyano-2-(4-(2,4-difluorophenoxy)piperidin-1-yl)
phenyl)-4-methylthiazole-2-carboxamide;
N-(5-cyano-2-(4-(2,4-difluorophenoxy)piperidin-1-yl)
phenyl)-6-hydroxypyridazine-3-carboxamide;
N-(5-cyano-2-(4-(2,4-difluorophenoxy)piperidin-1-yl)
phenyl)-6,7-dihydro-5H-pyrazolo[5,1-b][1,3]oxazine-3-carboxamide;
N-(5-cyano-2-(4-(2,4-difluorophenoxy)piperidin-1-yl)
pyridin-3-yl)-6-methylpicolinamide;
4-chloro-N-(5-cyano-2-(4-(2,4-difluorophenoxy)piperidin-1-yl)pyridin-3-yl)picolinamide;
N-(5-cyano-2-(4-(2,4-difluorophenoxy)piperidin-1-yl)
pyridin-3-yl)-4-fluoro-2-methoxybenzamide;
N-(5-cyano-2-(4-(2,4-difluorophenoxy)piperidin-1-yl)
pyridin-3-yl)-3-fluoro-6-methylpicolinamide;
N-(5-cyano-2-(4-(2,4-difluorophenoxy)piperidin-1-yl)
pyridin-3-yl)-1-methyl-2-oxo-1,2-dihydropyridine-3-carboxamide;
N-(5-cyano-2-(4-(2,4-difluorophenoxy)piperidin-1-yl)
pyridin-3-yl)-3-methylpicolinamide;
N-(5-cyano-2-(4-(2,4-difluorophenoxy)piperidin-1-yl)
pyridin-3-yl)-3-methoxy-1-methyl-1H-pyrazole-4-carboxamide;
N-(5-cyano-2-(4-(2,4-difluorophenoxy)piperidin-1-yl)
pyridin-3-yl)-4-hydroxynicotinamide;
N-(2-(4-(2,4-difluorophenoxy)piperidin-1-yl)-6-methylpyridin-3-yl)-4-methoxynicotinamide;
N-(5-cyano-2-(4-(2,4-difluorophenoxy)piperidin-1-yl)
pyridin-3-yl)-2-methoxynicotinamide;
N-(5-(acetamidomethyl)-2-(4-(2,4-difluorophenoxy)piperidin-1-yl)pyridin-3-yl)-2-methoxynicotinamide;
N-(2-(4-(2,4-difluorophenoxy)piperidin-1-yl)-5-(methoxymethyl)pyridin-3-yl)-2-methoxynicotinamide;
N-(5-cyano-2-(4-(2,4-difluorophenoxy)piperidin-1-yl)
pyridin-3-yl)picolinamide;
N-(2-(4-(2-chloro-5-methylphenoxy)piperidin-1-yl)-5-cyanopyridin-3-yl)picolinamide;
N-(4-(4-(2,4-difluorophenoxy)piperidin-1-yl)-2-methylpyrimidin-5-yl)-2-methoxy-6-methylnicotinamide;
N-(5-cyano-2-(4-(2,4-difluorophenoxy)piperidin-1-yl)
phenyl)-2,6-dimethoxynicotinamide;
N-(5-cyano-2-(4-(2,4-difluorophenoxy)piperidin-1-yl)
phenyl)-1,6-dimethyl-2-oxo-1,2-dihydropyridine-3-carboxamide;
N-(5-cyano-2-(4-(2,4-difluorophenoxy)piperidin-1-yl)
phenyl)-2-methoxy-4,6-dimethylnicotinamide;
N-(4-cyano-2-(4-(2,4-difluorophenoxy)piperidin-1-yl)
phenyl)-4-methoxynicotinamide;
N-(5-cyano-2-(4-(2,4-difluorophenoxy)piperidin-1-yl)
phenyl)-3-methoxypyrazine-2-carboxamide;
N-(5-cyano-2-(4-(2,4-difluorophenoxy)piperidin-1-yl)
phenyl)-2-methylthiazole-4-carboxamide;
N-(5-cyano-2-(4-(2,4-difluorophenoxy)piperidin-1-yl)
phenyl)-5-fluoropicolinamide;
N-(5-cyano-2-(4-(2,4-difluorophenoxy)piperidin-1-yl)
phenyl)-5,6-dihydro-4H-pyrrolo[1,2-b]pyrazole-2-carboxamide;
N-(5-cyano-2-(4-(2,4-difluorophenoxy)piperidin-1-yl)
phenyl)-3-fluoropicolinamide;
N-(5-cyano-2-(4-(2,4-difluorophenoxy)piperidin-1-yl)
phenyl)-4-methoxypicolinamide;
N-(5-cyano-2-(4-(2,4-difluorophenoxy)piperidin-1-yl)
phenyl)-2,5-dimethyloxazole-4-carboxamide;
N-(5-cyano-2-(4-(2,4-difluorophenoxy)piperidin-1-yl)
phenyl)-5-cyclopropyloxazole-4-carboxamide;
N-(5-cyano-2-(4-(2,4-difluorophenoxy)piperidin-1-yl)
phenyl)thiazole-4-carboxamide;
N-(5-cyano-2-(4-(2,4-difluorophenoxy)piperidin-1-yl)
phenyl)-1,5-dimethyl-1H-pyrazole-3-carboxamide;
N-(5-cyano-2-(4-(2,4-difluorophenoxy)piperidin-1-yl)
phenyl)-3,5-dimethylpyrazine-2-carboxamide;
N-(5-cyano-2-(4-(2,4-difluorophenoxy)piperidin-1-yl)
phenyl)-3-methylpyrazine-2-carboxamide;
N-(5-cyano-2-(4-(2,4-difluorophenoxy)piperidin-1-yl)
phenyl)-1,2,3-thiadiazole-4-carboxamide;
N-(5-cyano-2-(4-(2,4-difluorophenoxy)piperidin-1-yl)
phenyl)isoxazole-3-carboxamide;
N-(5-cyano-2-(4-(2,4-difluorophenoxy)piperidin-1-yl)
phenyl)-5-ethylisoxazole-3-carboxamide;
N-(5-cyano-2-(4-(2,4-difluorophenoxy)piperidin-1-yl)
phenyl)-4-methyl-1,2,5-oxadiazole-3-carboxamide;
N-(5-cyano-2-(4-(2,4-difluorophenoxy)piperidin-1-yl)
pyridin-3-yl)-1-ethyl-5-methoxy-1H-pyrazole-4-carboxamide;
N-(5-cyano-2-(4-(2,4-difluorophenoxy)piperidin-1-yl)
pyridin-3-yl)-5-ethoxy-1-methyl-1H-pyrazole-4-carboxamide;
N-(5-cyano-2-(4-(2,4-difluorophenoxy)piperidin-1-yl)
phenyl)oxazole-4-carboxamide;
N-(5-cyano-2-(4-(2,4-difluorophenoxy)piperidin-1-yl)
phenyl)-5-methylpyrazine-2-carboxamide;
N-(5-cyano-2-(4-(2,4-difluorophenoxy)piperidin-1-yl)
phenyl)-5-methylpicolinamide;
N-(5-cyano-2-(4-(2,4-difluorophenoxy)piperidin-1-yl)
phenyl)-5-cyclopropylisoxazole-3-carboxamide;
N-(5-cyano-2-(4-(2,4-difluorophenoxy)piperidin-1-yl)
phenyl)pyridazine-3-carboxamide;
N-(5-cyano-2-(4-(2,4-difluorophenoxy)piperidin-1-yl)
phenyl)-5-methyloxazole-4-carboxamide;
N-(5-cyano-2-(4-(2,4-difluorophenoxy)piperidin-1-yl)
phenyl)isothiazole-3-carboxamide;
N-(5-cyano-2-(4-(2,4-difluorophenoxy)piperidin-1-yl)
phenyl)-6-methoxypyrazine-2-carboxamide;
N-(5-cyano-2-(4-(2,4-difluorophenoxy)piperidin-1-yl)
phenyl)-6-methylpyrazine-2-carboxamide;
N-(5-cyano-2-(4-(2,4-difluorophenoxy)piperidin-1-yl)
phenyl)-4,5-dimethylisoxazole-3-carboxamide;
N-(5-cyano-2-(4-(2,4-difluorophenoxy)piperidin-1-yl)
phenyl)-5-methyl-1,3,4-oxadiazole-2-carboxamide;
N-(5-cyano-2-(4-(2,4-difluorophenoxy)piperidin-1-yl)
phenyl)-5-methoxypicolinamide;
N-(5-cyano-2-(4-(2,4-difluorophenoxy)piperidin-1-yl)
phenyl)-1,2,5-thiadiazole-3-carboxamide;
N-(5-cyano-2-(4-(2,4-difluorophenoxy)piperidin-1-yl)
phenyl)-2,6-dimethylpyrimidine-4-carboxamide;
N-(5-cyano-2-(4-(2,4-difluorophenoxy)piperidin-1-yl)
phenyl)-6-methoxypyridazine-3-carboxamide;
N-(5-cyano-2-(4-(2,4-difluorophenoxy)piperidin-1-yl)
phenyl)-5-fluoro-6-methylpicolinamide;
N-(5-cyano-2-(4-(2,4-difluorophenoxy)piperidin-1-yl)
phenyl)-4-methoxypyrimidine-2-carboxamide;
N-(5-cyano-2-(4-(2,4-difluorophenoxy)piperidin-1-yl)
phenyl)-1,2,5-oxadiazole-3-carboxamide;
N-(5-cyano-2-(4-(2,4-difluorophenoxy)piperidin-1-yl)
phenyl)-5-methyl-1,2,4-oxadiazole-3-carboxamide;
N-(5-cyano-2-(4-(2,4-difluorophenoxy)piperidin-1-yl)
phenyl)-2-methylpyrimidine-4-carboxamide;
N-(4-(4-(2,4-difluorophenoxy)piperidin-1-yl)-6-methylpyridin-3-yl)-5-methoxypyrazine-2-carboxamide;

N-(5-cyano-2-(4-(2,4-difluorophenoxy)piperidin-1-yl)phenyl)-1-ethyl-5-methyl-1H-pyrazole-3-carboxamide;
N-(5-cyano-2-(4-(2,4-difluorophenoxy)piperidin-1-yl)phenyl)-2-methoxypyrimidine-4-carboxamide;
N-(5-cyano-2-(4-(2,4-difluorophenoxy)piperidin-1-yl)phenyl)-1-methyl-1H-1,2,3-triazole-4-carboxamide;
N-(5-cyano-2-(4-(2,4-difluorophenoxy)piperidin-1-yl)phenyl)-6-methylpyridazine-3-carboxamide;
6-(4-(2,4-difluorophenoxy)piperidin-1-yl)-5-(2-methoxy-5-methylnicotinamido)-N,N-dimethylnicotinamide;
6-(4-(2,4-difluorophenoxy)piperidin-1-yl)-5-(2-methoxynicotinamido)-N,N-dimethylnicotinamide;
N-(5-cyano-2-(4-(2,4-difluorophenoxy)piperidin-1-yl)phenyl)-6-methoxypicolinamide;
N-(5-cyano-2-(4-(2,4-difluorophenoxy)piperidin-1-yl)phenyl)-1,4,6-trimethyl-2-oxo-1,2-dihydropyridine-3-carboxamide;
1-benzyl-N-(5-cyano-2-(4-(2,4-difluorophenoxy)piperidin-1-yl)phenyl)-2-oxo-1,2-dihydropyridine-3-carboxamide;
N-(5-cyano-2-(4-(2,4-difluorophenoxy)piperidin-1-yl)phenyl)-4-oxo-4H-pyrido[1,2-a]pyrimidine-3-carboxamide;
1-butyl-N-(5-cyano-2-(4-(2,4-difluorophenoxy)piperidin-1-yl)phenyl)-2-oxo-1,2-dihydropyridine-3-carboxamide;
N-(5-cyano-2-(4-(2,4-difluorophenoxy)piperidin-1-yl)phenyl)-1-cyclohexyl-2-oxo-1,2-dihydropyridine-3-carboxamide;
N-(5-cyano-2-(4-(2,4-difluorophenoxy)piperidin-1-yl)phenyl)-1-isopropyl-2-oxo-1,2-dihydropyridine-3-carboxamide;
5-bromo-N-(5-cyano-2-(4-(2,4-difluorophenoxy)piperidin-1-yl)phenyl)-1-isopropyl-2-oxo-1,2-dihydropyridine-3-carboxamide;
N-(5-cyano-2-(4-(2,4-difluorophenoxy)piperidin-1-yl)phenyl)-1-methyl-6-oxo-2-phenyl-1,6-dihydropyrimidine-5-carboxamide;
N-(5-cyano-2-(4-(2,4-difluorophenoxy)piperidin-1-yl)phenyl)-1,5,6-trimethyl-2-oxo-1,2-dihydropyridine-3-carboxamide;
N-(5-cyano-2-(4-(2,4-difluorophenoxy)piperidin-1-yl)phenyl)-1-methyl-2-oxo-1,2,5,6,7,8-hexahydroquinoline-3-carboxamide;
N-(5-cyano-2-(4-(2,4-difluorophenoxy)piperidin-1-yl)phenyl)-6-isopropyl-1-methyl-2-oxo-1,2-dihydropyridine-3-carboxamide;
N-(5-cyano-2-(4-(2,4-difluorophenoxy)piperidin-1-yl)phenyl)-6-methyl-4-oxo-4H-pyrido[1,2-a]pyrimidine-3-carboxamide;
N-(5-cyano-2-(4-(2,4-difluorophenoxy)piperidin-1-yl)phenyl)-4-(dimethylamino)-2-methoxybenzamide;
N-(5-cyano-2-(4-(2,4-difluorophenoxy)piperidin-1-yl)phenyl)-3,6-difluoro-2-methoxybenzamide;
4,5-dichloro-N-(5-cyano-2-(4-(2,4-difluorophenoxy)piperidin-1-yl)phenyl)-2-methoxybenzamide;
6-chloro-N-(5-cyano-2-(4-(2,4-difluorophenoxy)piperidin-1-yl)phenyl)-2-methoxynicotinamide;
N-(5-cyano-2-(4-(2,4-difluorophenoxy)piperidin-1-yl)phenyl)-2,3-difluoro-6-methoxybenzamide;
5-chloro-N-(5-cyano-2-(4-(2,4-difluorophenoxy)piperidin-1-yl)phenyl)-2-methoxynicotinamide;
N-(5-cyano-2-(4-(2,4-difluorophenoxy)piperidin-1-yl)phenyl)-2-methoxy-4-(trifluoromethyl)benzamide;
5-chloro-N-(5-cyano-2-(4-(2,4-difluorophenoxy)piperidin-1-yl)phenyl)-2-methoxy-3-methylbenzamide;
N-(5-cyano-2-(4-(2,4-difluorophenoxy)piperidin-1-yl)phenyl)-2-methoxy-6,7-dihydro-5H-cyclopenta[b]pyridine-3-carboxamide;
N-(5-cyano-2-(4-(2,4-difluorophenoxy)piperidin-1-yl)phenyl)-9-methyl-4-oxo-4H-pyrido[1,2-a]pyrimidine-3-carboxamide;
N-(5-cyano-2-(4-(2,4-difluorophenoxy)piperidin-1-yl)phenyl)-2,3-dimethyl-5-oxo-5H-thiazolo[3,2-a]pyrimidine-6-carboxamide;
N-(5-cyano-2-(4-(2,4-difluorophenoxy)piperidin-1-yl)phenyl)-1-(3-methoxypropyl)-2-oxo-1,2-dihydropyridine-3-carboxamide;
N-(5-cyano-2-(4-(2,4-difluorophenoxy)piperidin-1-yl)phenyl)-5-oxo-5H-thiazolo[3,2-a]pyrimidine-6-carboxamide;
N-(5-cyano-2-(4-(2,4-difluorophenoxy)piperidin-1-yl)phenyl)-7-methyl-4-oxo-4H-pyrido[1,2-a]pyrimidine-3-carboxamide;
N-(5-cyano-2-(4-(2,4-difluorophenoxy)piperidin-1-yl)phenyl)-1-ethyl-4,6-dimethyl-2-oxo-1,2-dihydropyridine-3-carboxamide;
N-(5-cyano-2-(4-(2,4-difluorophenoxy)piperidin-1-yl)phenyl)-2-oxo-1-(pyridin-2-ylmethyl)-1,2-dihydropyridine-3-carboxamide;
N-(5-cyano-2-(4-(2,4-difluorophenoxy)piperidin-1-yl)phenyl)-1-(2-(dimethylamino)-2-oxoethyl)-2-oxo-1,2-dihydropyridine-3-carboxamide;
N-(5-cyano-2-(4-(2,4-difluorophenoxy)piperidin-1-yl)phenyl)-2,5-dimethoxybenzamide;
3,6-dichloro-N-(5-cyano-2-(4-(2,4-difluorophenoxy)piperidin-1-yl)phenyl)-2-methoxybenzamide;
N-(5-cyano-2-(4-(2,4-difluorophenoxy)piperidin-1-yl)phenyl)-3,5-difluoro-2-methoxybenzamide;
N-(5-cyano-2-(4-(2,4-difluorophenoxy)piperidin-1-yl)phenyl)-2-methoxy-5-(trifluoromethyl)benzamide;
5-(tert-butyl)-N-(5-cyano-2-(4-(2,4-difluorophenoxy)piperidin-1-yl)phenyl)-2-methoxybenzamide;
N-(5-cyano-2-(4-(2,4-difluorophenoxy)piperidin-1-yl)phenyl)-5-fluoro-2-methoxybenzamide;
5-chloro-N-(5-cyano-2-(4-(2,4-difluorophenoxy)piperidin-1-yl)phenyl)-2-methoxybenzamide;
3-chloro-N-(5-cyano-2-(4-(2,4-difluorophenoxy)piperidin-1-yl)phenyl)-2,6-dimethoxybenzamide;
N-(5-cyano-2-(4-(2,4-difluorophenoxy)piperidin-1-yl)phenyl)-2-methoxy-6-(trifluoromethyl)nicotinamide;
N-(5-cyano-2-(4-(2,4-difluorophenoxy)piperidin-1-yl)phenyl)-2-methoxy-3,6-dimethylbenzamide;
N-(5-cyano-2-(4-(2,4-difluorophenoxy)piperidin-1-yl)phenyl)-2-methoxy-5-morpholinobenzamide;
4-(tert-butyl)-N-(5-cyano-2-(4-(2,4-difluorophenoxy)piperidin-1-yl)phenyl)-2-methoxybenzamide;
N-(5-cyano-2-(4-(2,4-difluorophenoxy)piperidin-1-yl)phenyl)-2-methyl-5-oxo-5H-thiazolo[3,2-a]pyrimidine-6-carboxamide;
N-(5-cyano-2-(4-(2,4-difluorophenoxy)piperidin-1-yl)phenyl)-3-methyl-5-oxo-5H-thiazolo[3,2-a]pyrimidine-6-carboxamide;
N-(5-cyano-2-(4-(2,4-difluorophenoxy)piperidin-1-yl)phenyl)-4-methoxy-1-phenyl-1H-pyrazole-3-carboxamide;
1-benzyl-N-(5-cyano-2-(4-(2,4-difluorophenoxy)piperidin-1-yl)phenyl)-5-methoxy-1H-1,2,3-triazole-4-carboxamide;
1-(2-chlorobenzyl)-N-(5-cyano-2-(4-(2,4-difluorophenoxy)piperidin-1-yl)phenyl)-5-methoxy-1H-1,2,3-triazole-4-carboxamide;

3-chloro-N-(5-cyano-2-(4-(2,4-difluorophenoxy)piperidin-1-yl)phenyl)-2-methoxybenzamide;
4-chloro-N-(5-cyano-2-(4-(2,4-difluorophenoxy)piperidin-1-yl)phenyl)-2-methoxynicotinamide;
N-(5-cyano-2-(4-(2,4-difluorophenoxy)piperidin-1-yl)phenyl)-5-fluoro-2-methoxynicotinamide;
5-bromo-N-(5-cyano-2-(4-(2,4-difluorophenoxy)piperidin-1-yl)phenyl)-2-methoxybenzamide;
4-bromo-N-(5-cyano-2-(4-(2,4-difluorophenoxy)piperidin-1-yl)phenyl)-2-methoxybenzamide;
N-(5-cyano-2-(4-(2,4-difluorophenoxy)piperidin-1-yl)phenyl)-2-methoxy-6-methylbenzamide;
4-chloro-N-(5-cyano-2-(4-(2,4-difluorophenoxy)piperidin-1-yl)phenyl)-2-methoxybenzamide;
N-(5-cyano-2-(4-(2,4-difluorophenoxy)piperidin-1-yl)phenyl)-4,5-difluoro-2-methoxybenzamide;
N-(5-cyano-2-(4-(2,4-difluorophenoxy)piperidin-1-yl)phenyl)-2,3-dimethoxybenzamide;
N-(5-cyano-2-(4-(2,4-difluorophenoxy)piperidin-1-yl)phenyl)-2-methoxy-5-(trifluoromethoxy)benzamide;
N-(5-cyano-2-(4-(2,4-difluorophenoxy)piperidin-1-yl)phenyl)-2-methoxy-3-methylbenzamide;
N-(5-cyano-2-(4-(2,4-difluorophenoxy)piperidin-1-yl)phenyl)-3,4-difluoro-2-methoxybenzamide;
3,5-dichloro-N-(5-cyano-2-(4-(2,4-difluorophenoxy)piperidin-1-yl)phenyl)-2-methoxybenzamide;
N-(5-cyano-2-(4-(2,4-difluorophenoxy)piperidin-1-yl)phenyl)-2,4-dimethoxybenzamide;
N-(5-cyano-2-(4-(2,4-difluorophenoxy)piperidin-1-yl)phenyl)-2-methoxy-4-methylbenzamide;
N-(5-cyano-2-(4-(2,4-difluorophenoxy)piperidin-1-yl)phenyl)-2-methoxy-5-methylbenzamide;
N-(5-cyano-2-(4-(2,4-difluorophenoxy)piperidin-1-yl)phenyl)-2,6-dimethoxybenzamide;
(R)-4-(4-(2,4-difluorophenoxy)piperidin-1-yl)-5-(2-methoxynicotinamido)-N-(tetrahydrofuran-3-yl)picolinamide;
4-(4-(2,4-difluorophenoxy)piperidin-1-yl)-N-ethyl-5-(2-methoxynicotinamido)picolinamide;
4-(4-(2,4-difluorophenoxy)piperidin-1-yl)-N-isopropyl-5-(2-methoxynicotinamido)picolinamide;
4-(4-(2,4-difluorophenoxy)piperidin-1-yl)-5-(2-methoxynicotinamido)-N-propylpicolinamide;
N-(6-cyano-2-(4-(2,4-difluorophenoxy)piperidin-1-yl)pyridin-3-yl)-5-fluoro-2-methoxynicotinamide;
N-(6-cyano-2-(4-(2,4-difluorophenoxy)piperidin-1-yl)pyridin-3-yl)-5-methoxy-1-methyl-1H-pyrazole-4-carboxamide;
N-(2-(4-(2,4-difluorophenoxy)piperidin-1-yl)phenyl)-1-methyl-2-oxo-1,2-dihydropyridine-3-carboxamide;
N-(4-(4-(2,4-difluorophenoxy)piperidin-1-yl)-6-methylpyridin-3-yl)-4-methoxynicotinamide;
N-(4-(4-(2,4-difluorophenoxy)piperidin-1-yl)pyridin-3-yl)-2-methoxynicotinamide;
N-(2-(4-(2,4-difluorophenoxy)piperidin-1-yl)-5-(dimethylcarbamoyl)phenyl)-2-methoxynicotinamide;
N-(4-(4-(2,4-difluorophenoxy)piperidin-1-yl)-6-(methoxymethyl)pyridin-3-yl)-2-methoxynicotinamide;
4-(4-(2,4-difluorophenoxy)piperidin-1-yl)-5-(2-methoxynicotinamido)picolinamide;
N-(6-cyano-4-(4-(2,4-difluorophenoxy)piperidin-1-yl)pyridin-3-yl)-2-methoxynicotinamide;
N-(4,5-dicyano-2-(4-(2,4-difluorophenoxy)piperidin-1-yl)phenyl)-2-methoxynicotinamide;
N-(4-cyano-2-(4-(2,4-difluorophenoxy)piperidin-1-yl)-5-(dimethylcarbamoyl)phenyl)-2-methoxynicotinamide;
N-(5-cyano-2-(4-(2,4-difluorophenoxy)piperidin-1-yl)-4-(dimethylcarbamoyl)phenyl)-2-methoxynicotinamide;
N-(5-cyano-2-(4-(2,4-difluorophenoxy)piperidin-1-yl)phenyl)-2-oxo-1,2-dihydropyridine-3-carboxamide;
N-(5-cyano-2-(4-(2,4-difluorophenoxy)piperidin-1-yl)phenyl)-2-hydroxybenzamide;
N-(5-cyano-2-(4-(2,4-difluorophenoxy)piperidin-1-yl)phenyl)-2-(difluoromethoxy)nicotinamide;
N-(5-cyano-2-(4-(2,4-difluorophenoxy)piperidin-1-yl)phenyl)-1-(difluoromethyl)-2-oxo-1,2-dihydropyridine-3-carboxamide;
N-(5-cyano-2-(4-(2,4-difluorophenoxy)piperidin-1-yl)phenyl)-4-methoxy-2-methylpyrimidine-5-carboxamide;
N-(2-(4-(2,4-difluorophenoxy)piperidin-1-yl)-5-(morpholinosulfonyl)pyridin-3-yl)-1-methyl-2-oxo-1,2-dihydropyridine-3-carboxamide;
N-(2-cyano-4-(4-(2,4-difluorophenoxy)piperidin-1-yl)pyrimidin-5-yl)-2-methoxy-6-methylnicotinamide;
4-(4-(2,4-difluorophenoxy)piperidin-1-yl)-5-(2-methoxynicotinamido)-N,N-dimethylpyrimidine-2-carboxamide;
4-(4-(2,4-difluorophenoxy)piperidin-1-yl)-5-(2-methoxy-6-methylnicotinamido)-N,N-dimethylpicolinamide; and
N-(4-(4-(2,4-difluorophenoxy)piperidin-1-yl)-6-(trifluoromethyl)pyridin-3-yl)-2-methoxynicotinamide; or
a pharmaceutically acceptable salt of any one of the aforementioned compounds.

11. N-(4-(4-(2,4-difluorophenoxy)piperidin-1-yl)-2-methylpyrimidin-5-yl)-2-methoxynicotinamide or a pharmaceutically acceptable salt thereof.

12. A pharmaceutical composition comprising:
a compound or pharmaceutically acceptable salt as defined in claim 1; and
a pharmaceutically acceptable excipient.

13. A pharmaceutical composition comprising N-(4-(4-(2,4-difluorophenoxy) piperidin-1-yl)-2-methylpyrimidin-5-yl)-2-methoxynicotinamide or a pharmaceutically acceptable salt thereof; and a pharmaceutically acceptable excipient.

14. A method of treating a disease, disorder or condition in a subject, the method comprising administering to the subject an effective amount of a compound or pharmaceutically acceptable salt as defined in claim 1, wherein the disease, disorder or condition is selected from Parkinson's disease, levodopa-induced dyskinesias, Huntington's disease, drug addiction, eating disorders, cognitive disorders, schizophrenia, bipolar disorder, epilepsy, and depression.

15. A method of treating a disease, disorder or condition in a subject, the method comprising administering to the subject an effective amount of N-(4-(4-(2,4-difluorophenoxy) piperidin-1-yl)-2-methylpyrimidin-5-yl)-2-methoxynicotinamide or a pharmaceutically acceptable salt thereof, wherein the disease, disorder or condition is selected from Parkinson's disease, levodopa-induced dyskinesias, Huntington's disease, drug addiction, eating disorders, cognitive disorders, schizophrenia, bipolar disorder, epilepsy, and depression.

16. A combination, pharmaceutical composition or kit comprising a compound or pharmaceutically acceptable salt as defined in claim 1, and at least one additional pharmacologically active agent.

17. The combination, pharmaceutical composition or kit according to claim 16, wherein the additional pharmacologically active agent is:

(A) selected from levodopa, a DOPA decarboxylase inhibitor, a dopamine agonist, an anticholinergic, a B-selective monoamine oxidase inhibitor, and a catechol O-methyl transferase inhibitor; or
(B) levodopa in combination with a DOPA decarboxylase inhibitor.

* * * * *

UNITED STATES PATENT AND TRADEMARK OFFICE
CERTIFICATE OF CORRECTION

PATENT NO. : 11,426,397 B2
APPLICATION NO. : 16/497967
DATED : August 30, 2022
INVENTOR(S) : Jason Green et al.

It is certified that error appears in the above-identified patent and that said Letters Patent is hereby corrected as shown below:

In the Claims

In Claim 1, Column 277, Lines 28-29, please replace the phrase "-$(CH_2)_nN(R^d)S(O)_2R$" with the phrase -- -$(CH_2)_nN(R^d)S(O)_2R^f$ --.

In Claim 4, Column 278, Line 25, please replace the phrase "-$(CH_2)_nS(O)_2R$" with the phrase -- -$(CH_2)_nS(O)_2R^f$ --.

Signed and Sealed this
Eighth Day of November, 2022

*Katherine Kelly Vidal*

Katherine Kelly Vidal
*Director of the United States Patent and Trademark Office*